US010596209B2

(12) United States Patent
Toledo et al.

(10) Patent No.: US 10,596,209 B2
(45) Date of Patent: Mar. 24, 2020

(54) MICROBIAL COMPOSITIONS AND METHODS FOR TREATING TYPE 2 DIABETES, OBESITY, AND METABOLIC SYNDROME

(71) Applicant: Solarea Bio, Inc., Cambridge, MA (US)

(72) Inventors: Gerardo V. Toledo, Hopkinton, MA (US); Tracy Mincer, Jupiter, FL (US); Jahir Mauricio Gutierrez Bugarin, Montreal (CA); Jillian DeWalt, Salem, NC (US); Eric Schott, Charlestown, MA (US); Maria Juliana Soto Giron, Cambridge, MA (US)

(73) Assignee: Solarea Bio, Inc., Cambridge, MA (US)

( * ) Notice: Subject to any disclaimer, the term of this patent is extended or adjusted under 35 U.S.C. 154(b) by 0 days.

(21) Appl. No.: 16/235,858

(22) Filed: Dec. 28, 2018

(65) Prior Publication Data

US 2019/0269743 A1 Sep. 5, 2019

Related U.S. Application Data

(63) Continuation of application No. PCT/US2018/066088, filed on Dec. 17, 2018.

(60) Provisional application No. 62/599,647, filed on Dec. 15, 2017, provisional application No. 62/607,149, filed on Dec. 18, 2017, provisional application No. 62/727,497, filed on Sep. 5, 2018.

(51) Int. Cl.

*A61K 35/747* (2015.01)
*A61P 3/10* (2006.01)
*A23L 29/00* (2016.01)
*A61P 3/04* (2006.01)
*A61K 35/74* (2015.01)
*A61K 35/741* (2015.01)
*A61K 45/06* (2006.01)

(52) U.S. Cl.

CPC .......... *A61K 35/747* (2013.01); *A23L 29/065* (2016.08); *A61K 35/74* (2013.01); *A61K 35/741* (2013.01); *A61K 45/06* (2013.01); *A61P 3/04* (2018.01); *A61P 3/10* (2018.01)

(58) Field of Classification Search

CPC ........ A61K 35/74; A61K 35/741; A61K 8/97; A61K 39/104; A61K 36/00; A61K 35/66; A23L 29/00; A23L 29/065; C12N 1/20; C12Q 1/68

See application file for complete search history.

(56) References Cited

U.S. PATENT DOCUMENTS 3,048,526 A 8/1962 Boswell
3,108,046 A 10/1963 Harbit
3,536,809 A 10/1970 Applezweig
3,598,123 A 8/1971 Zaffaroni
3,845,770 A 11/1974 Theeuwes et al.
3,916,899 A 11/1975 Theeuwes et al.
4,008,719 A 2/1977 Theeuwes et al.
4,478,822 A 10/1984 Haslam et al.
4,532,126 A 7/1985 Ebert et al.
4,625,494 A 12/1986 Iwatschenko
4,671,953 A 6/1987 Stanley et al.
4,786,505 A 11/1988 Lovgren et al.
4,800,083 A 1/1989 Hom et al.
4,904,479 A 2/1990 Illum
4,919,939 A 4/1990 Baker
4,935,243 A 6/1990 Borkan et al.
4,950,484 A 8/1990 Olthoff et al.
5,013,726 A 5/1991 Ivy et al.
5,059,595 A 10/1991 Grazie
5,073,543 A 12/1991 Marshall et al.
5,120,548 A 6/1992 McClelland et al.

(Continued)

FOREIGN PATENT DOCUMENTS

AU 2008231930 10/2008
EP 1495109 12/2005

(Continued)

OTHER PUBLICATIONS

Gouda et al., "Endophytes: A treasure house of bioactive compounds of medicinal importance", Frontiers in Microbiology, Mini Review, Sep. 29, 2016, vol. 7, article 1538, total pp. 1-8. (Front. Microbiol. 7:1538. doi: 10.3389/fmicb.2016.01538). (Year: 2016).*
Abuajah et al (2015) Functional components and medicinal properties of food: a review. J Food Sci Technol 52(5): 2522-2529.
Alcock et al (2014) Is eating behavior manipulated by the gastrointestinal microbiota? Evolutionary pressures and potential mechanisms. Bioessays 36: 940-949.
Allgeier, RJ et al (1929) A colorimetric method for the determination of butyric acid. J Bacteriol 17(2): 79-87.
Aron-Wisnewsky, J et al (2012) The importance of the gut microbiota after bariatric surgery. Nature 9(10): 590-598.
Arumugam et al (2011) Enterotypes of the human gut microbiome. Nature 473(7346): 174-180.
Backhed et al (2004) The Gut microbiota as an environmental factor that regulates fat storage. PNAS 101(44): 15718-15723.

(Continued)

*Primary Examiner* — Satyendra K Singh
(74) *Attorney, Agent, or Firm* — Goodwin Procter LLP

(57) ABSTRACT

The present invention relates to the identification of a group of microorganisms, which are relatively abundant in the microbial communities associated with fruits and vegetables typically consumed raw and therefore transient or permanent members of the human microbiota. The consumption of mixtures of these microbes at relevant doses will produce a beneficial effect in the host by reducing the propensity to diabetes, obesity and metabolic syndrome mediated in part by production of short chain fatty acids to enhance colonic butyrate production. Therapeutic methods of the invention involve the use of live microorganisms or metabolites derived from said microorganisms to establish a microbial composition in the mammalian host that will improve significantly the ability to control weight, reduce the onset of diabetes, obesity and metabolic syndrome, and improve overall health.

28 Claims, 23 Drawing Sheets

Specification includes a Sequence Listing.

(56) References Cited

U.S. PATENT DOCUMENTS

| | | | |
|---|---|---|---|
| 5,225,202 | A | 7/1993 | Hodges et al. |
| 5,354,556 | A | 10/1994 | Sparks et al. |
| 5,591,767 | A | 1/1997 | Mohr et al. |
| 5,610,184 | A | 3/1997 | Shahinian et al. |
| 5,639,476 | A | 6/1997 | Oshlack et al. |
| 5,674,533 | A | 10/1997 | Santus et al. |
| 5,733,556 | A | 3/1998 | Schrier et al. |
| 5,733,575 | A | 3/1998 | Mehra et al. |
| 5,837,284 | A | 11/1998 | Mehta |
| 5,871,776 | A | 2/1999 | Mehta |
| 5,902,632 | A | 5/1999 | Mehta |
| 6,139,875 | A | 10/2000 | Adams et al. |
| 6,258,380 | B1 | 7/2001 | Overholt |
| 6,420,473 | B1 | 7/2002 | Chittamuru et al. |
| 6,455,052 | B1 | 9/2002 | Marcussen et al. |
| 6,482,435 | B1 | 11/2002 | Stratton et al. |
| 6,544,510 | B2 | 4/2003 | Olshenitsk et al. |
| 6,569,457 | B2 | 5/2003 | Ullah et al. |
| 6,572,871 | B1 | 6/2003 | Church et al. |
| 6,750,331 | B1 | 6/2004 | Takaichi et al. |
| 7,214,370 | B2 | 5/2007 | Naidu et al. |
| 8,318,151 | B2 | 11/2012 | Darimont-Nicolau et al. |
| 8,460,726 | B2 | 6/2013 | Harel et al. |
| 8,802,158 | B2 | 8/2014 | Boileau et al. |
| 8,871,266 | B2 | 10/2014 | Sanguansri et al. |
| 8,877,178 | B2 | 11/2014 | Boileau et al. |
| 9,040,101 | B2 | 5/2015 | Heiman et al. |
| 9,095,604 | B2 | 8/2015 | Ikegami et al. |
| 9,173,910 | B2 | 11/2015 | Kaplan et al. |
| 9,301,983 | B2 | 4/2016 | Huang et al. |
| 9,371,510 | B2 | 6/2016 | Moore et al. |
| 9,386,793 | B2 | 7/2016 | Blaser et al. |
| 9,487,764 | B2 | 11/2016 | Falb et al. |
| 9,549,955 | B2 | 1/2017 | Rittmann et al. |
| 9,636,367 | B2 | 5/2017 | Garcia-Rodenas et al. |
| 9,937,211 | B2 | 4/2018 | Kelly et al. |
| 10,064,895 | B2 | 9/2018 | Vincent et al. |
| 2004/0213828 | A1 | 10/2004 | Smith |
| 2005/0147710 | A1 | 7/2005 | Teckoe et al. |
| 2010/0172874 | A1 | 7/2010 | Turnbaugh et al. |
| 2011/0177976 | A1 | 7/2011 | Gordon et al. |
| 2011/0111094 | A1 | 11/2011 | Lavermicocca et al. |
| 2012/0015075 | A1 | 1/2012 | Davis et al. |
| 2012/0040387 | A1* | 2/2012 | Matsuoka ...................... 435/15 |
| 2014/0044858 | A1* | 2/2014 | Quevedo ................ A23L 1/236 426/655 |
| 2014/0065209 | A1 | 3/2014 | Putaala et al. |
| 2014/0179726 | A1 | 6/2014 | Bajaj et al. |
| 2014/0314719 | A1 | 10/2014 | Smith et al. |
| 2015/0126463 | A1* | 5/2015 | Hsiao et al. ......... A61K 36/424 |
| 2015/0259728 | A1 | 9/2015 | Cutcliffe et al. |
| 2015/0366941 | A1 | 12/2015 | Menear et al. |
| 2016/0081309 | A1 | 3/2016 | Newton et al. |
| 2016/0199424 | A1 | 7/2016 | Berry et al. |
| 2016/0206666 | A1 | 7/2016 | Falb et al. |
| 2016/0235792 | A1 | 8/2016 | Berry et al. |
| 2016/0263166 | A1 | 9/2016 | Elinav et al. |
| 2016/0271189 | A1 | 9/2016 | Cutcliffe et al. |
| 2016/0302464 | A1 | 10/2016 | Egli et al. |
| 2017/0326190 | A1 | 11/2017 | Ansell et al. |

FOREIGN PATENT DOCUMENTS

| | | | |
|---|---|---|---|
| EP | 1794283 | 10/2016 | |
| WO | WO 2004/080200 | 9/2004 | |
| WO | WO 2010/099617 | 9/2010 | |
| WO | WO 2012/098254 | 7/2012 | |
| WO | WO 2012/170047 | 12/2012 | |
| WO | WO 2013/067146 | 10/2013 | |
| WO | WO 2013/176774 | 11/2013 | |
| WO | WO 2014/068338 | 8/2014 | |
| WO | WO2014145958 A2 * | 9/2014 | ............ A61K 39/08 |
| WO | WO 2015/177246 | 11/2015 | |
| WO | WO 2016/065075 | 4/2016 | |
| WO | WO 2016/086205 | 6/2016 | |
| WO | WO 2016/124940 | 8/2016 | |

OTHER PUBLICATIONS

Backhed et al (2007) Mechanisms underlying the resistance to diet-induced obesity in germ-free mice. PNAS 104(3): 979-984.

Bahr et al (2015) Risperidone-induced weight gain is mediated through shifts in the gut microbiome and suppression of energy expenditure. EBioMedicine 2: 1725-1734.

Bai et al (2016) Response of gut microbiota and inflammatory status to bitter melon (*Momordica charantia* L.) in high fat diet induced obese rats. J Ethnopharmacol 194: 717-726.

Bakker-Zierikzee et al (2005) Effects of infant formula containing a mixture of galacto- and fructo-oligosaccharides or viable Bifidobacterium animalis on the intestinal microflora during the first 4 months of life. Br J Nutr 94: 783-790.

Basu, A et al (2010) Blueberries decrease cardiovascular risk factors in obese men and women with metabolic syndrome. J Nutr 140(9):1582-1587.

Berg,G et al (2015) The Edible plant microbiome: importance and health issues. In: Lugtenberg B. (eds) Principles of plant-microbe interactions. Springer, Cham.

Bernini et al (2016) Beneficial effects of Bifidobacterium lactis on lipid profile and cytokines in patients with metabolic syndrome. Nutrition 32: 716-719.

Bleau et al (2015) Crosstalk between intestinal microbiota, adipose tissue and skeletal muscle as an early event in systemic low-grade inflammation and the development of obesity and diabetes. Diabetes Metab Res Rev 31(6): 545-61.

Boden, G (2011) Obesity, Insulin Resistance and Free Fatty Acids. Curr Opin Endocrinol Diabetes Obes 18(2): 139-143.

Brahe, LK et al (2013) Is butyrate the link between diet, intestinal microbiota and obesity-related metabolic diseases? Obes Rev 14: 950-959.

Bron et al (2012) Emerging molecular insights into the interaction between probiotics and the host intestinal mucosa. Nat Rev Microbiol 10: 66-78.

Brunkwell, L and Orho-Melander, M. (2017) The gut microbiome as a target for prevention and treatment of hyperglycaemia in type 2 diabetes: from current human evidence to future possibilities. Diabetalogia 60: 943-951.

Camacho, L et al (2015) Metformin in breast cancer—an evolving mystery. Breast Cancer Res 17(88): 1-4.

Campbell, T.C. et al., “The China Study: The most comprehensive study of nutrition ever conducted and startling implications for diet, weight loss, and long term health,” Benbella, 2006, 1-425.

Cani et al (2006) Improvement of glucose tolerance and hepatic insulin sensitivity by oligofructose requires a functional glucagon-like peptide 1 receptor. Diabetes 55:1484-1490.

Cani et al (2007) Metabolic endotoxemia initiates obesity and insulin resistance. Diabetes 56:1761-1772.

Cani et al (2007) Selective increases of bifidobacteria in gut microflora improve high-fat-diet-induced diabetes in mice through a mechanism associated with endotoxaemia. Diabetologica 50: 2374-2383.

Cani et al (2008) Changes in gut microbiota control metabolic endotoxemia-induced inflammation in high-fat diet-induced obesity and diabetes in mice. Diabetes 57:1470-1481.

Chambers, et al (2015) Effects of targeted delivery of propionate to the human colon on appetite regulation, body weight maintenance and adiposity in overweight adults. Gut 64: 1744-1754.

Chanclud, E and Lacombe, B (2017) Plant hormones: key players in gut microbiota and human diseases? Trends Plant Sci 22(9): 754-758.

Chaudhury et al (2017) Clinical review of antidiabetic drugs: implications for type 2 diabetes mellitus management. Front endocrinol8(6): 1-12.

Chen et al (2015) Metabolism of fructooligosaccharides in Lactobacillus plantarum ST-III via differential gene transcription and alteration of cell membrane fluidity. Appl Environ Microbiol 81(22): 7697-7707.

(56) References Cited

OTHER PUBLICATIONS

Cockburn, DW and Koropatkin, NM (2016) Polysaccharide degradation by the intestinal microbiota and its influence on human health and disease. J Mol Biol 428: 3230-3252.
Codella, R et al (2018) Exercise has the guts: how physical activity may positively modulate gut microbiota in chronic and immune-based diseases. Digest Liv Dis 50: 331-341.
Coyle, C et al (2016) Metformin as an adjuvant treatment for cancer: a systematic review and meta analysis. Ann Onc 27:2184-2195.
Dalby et al (2017) Dietary uncoupling of gut microbiota and energy harvesting from obesity and glucose tolerance in mice. Cell Reports 21: 1521-1533.
Das, S (2013) Prevention of Diabetes—a historical note. IJHS 48.4: 625-642.
David, LA et al (2014) Diet rapidly and reproducibly alters the human gut microbiome. Nature 505: 559-563.
Davies et al (2017) Effect of an oral semaglutide compared with placebo and subcutaneous semaglutide on glycemic control in patients with type 2 diabetes. JAMA 318(15):1460-1470.
De Jesus Raposo et al (2016) Emergent Sources of prebiotics: seaweed and microalgae. Mar. Drugs 14(2): doi: 10.3390/md14020027.
De la Cuesta-Zuluaga (2017) Metformin is associated with higher relative abundance of mucin-degrading Akkermansia muciniphila and several short chain fatty acid-producig microbiota in the gut. Diabetes Care 40:54-62.
De Vadder, F et al (2016) Microbiota-produced succinate improves glucose homeostasis via intestinal gluconeogenesis. Cell Metab 24: 151-157.
Delzenne, NM (2015) Gut microorganisms as promising targets for the management of type 2 diabetes. Diabetalogia 58: 2206-2217.
Derrien, M and van Hylckama Vlieg, JET (2015) Fate, activity, and impact of ingested bacteria within the human gut microbiota. Trends in Microbiol 23(6): 354-366.
Devaraj, S et al (2013) The Human gut microbiome and body metabolism: implications for obesity and diabetes. Clin Chem 59(4): 617-628.
Di Francesco et al (2018) A time to fast. Science 362: 770-775.
Drew, L (2016) Reseeding the gut. Nature 540:s109-s112.
Duncan, SH et al (2004) Contribution of acetate to butyrate formation by human faecal bacteria. Br J Nutr 91: 915-923.
Ericsson et al (2017) Variable colonization after reciprocal fecal microbiota transfer between mice with low and high richness microbiota. Front Microbiol 8(196): 1-13.
Everard et al (2013) Cross-talk between Akkermansia muciniphila and intestinal epithelium controls diet-induced obesity. PNAS 11(22):9066-9071.
Everard et al (2014) Microbiome of prebiotic-treated mice reveals novel targets involved in host response during obesity. ISME 8:2116-2130.
Everard, A and Cani, P (2013) Diabetes, obesity and gut microbiota. Best Pract Res Clin Gastroenterol 27: 73-83.
Famouri et al (2017) Effects of probiotics on nonalcoholic fatty liver disease in obese children and adolescents. JPGN 64(3): 413-417.
Fang et al (2015) Intestinal FXR agonism promotes adipose tissue browning and reduces obesity and insulin resistance. Nature 21(2):159-167.
Forslund et al (2015) Corrigendum: Disentangling type 2 diabetes and metformin treatment signatures in the human gut microbiota. Nature 528: 262-266.
Forslund et al (2015) Disentangling type 2 diabetes and metformin treatment signatures in the human gut microbiota. Nature 528(7581): 262-266.
Frost, G et al (2014) The short-chain fatty acid acetate reduces appetite via a central homeostatic mechanism. Nat Commun. 5(3611): 1-11.
Garidou et al (2015) The Gut microbiota regulates intestinal CD4 T cells expressing RORgammat and controls metabolic disease. Cell metab 22:100-112.
Gentile and Weir (2018) The gut microbiota at the intersection of diet and human health. Science 362: 776-780.
Gibson, G and Roberfroid M (1995) Dietary modulation of the human colonic microbiota: introducing the concept of prebiotics. J Nutr 125(6):1401-1412.
Gonzalez-Garcia, RA et al (2017) Microbial propionic acid production. Fermentation 3(21): 1-20.
Graessler et al (2013) Metagenomic sequencing of the human gut microbiome before and after bariatric surgery in obese patients with type 2 diabetes: correlation with inflammatory and metabolic parameteres. Pharmacogenetics J 13: 514-522.
Gu et al (2017) Analyses of gut microbiota and plasma bile acids enable stratification of patients for antidiabetic treatment. Nature Commun 8:1785.
Guo et al (2017) Secretions of Bifidobacterium infantis and Lactobacillus acidophilus protect intestinal epithelial barrier function. JPGN 64(3): 404-412.
Hacquard et al (2015) Microbiota and host nutrition across plant and animal kingdoms. Cell host & microbe 17: 603-616.
Harley and Karp (2012) Obesity and the gut microbiome: striving for causality. Mol Metab 1: 21-31.
Hehemann et al (2010) Transfer of carbohydrate-active enzymes from marine bacteria to Japanese gut microbiota. Nature 464: 908-914.
Heineken, A et al (2013) Systems-level characterization of a host-microbe metabolic symbiosis in the mammalian gut. Gut microbes 4(1):28-40.
Henao-Mejia et al (2012) Inflammasome-mediated dysbiosis regulates progression of NAFLD and obesity. Nature 482 (7384): 179-185.
Hildebrandt et al (2009) High fat diet determines the composition of the murine gut microbiome independently of obesity. Gastroenterology 137(5): 1716.
Holmes, AJ et al (2017) Diet-Microbiome interactions in health are controlled by intestinal nitrogen source constraints. Cell Metab 25: 140-151.
Hooper et al (2012) Interactions between the microbiota and the immune system. Science 336(6086): 1268-1273.
Ilhan, Ze et al (2017) Distinctive microbiomes and metabolites linked with weight loss after gastric bypass, but not gastric banding. ISME J 11(9): 2047-2058.
Imaoka et al (2008) Anti-inflammatory activity of probiotic Bifidobacterium: enhancement of IL-10 production in peripheral blood mononuclear cells from ulcerative colitis patients and inhibition of IL-8 secretion in HT-29 cells. World J Gastroenterol 14(16): 2511-2516.
Jackson, CR et al (2013) Culture dependent and independent analysis of bacterial communities associated with commercial salad leaf vegetables. BMC Microbiol 13 (274): 1-12.
Jackson, CR et al (2015) Emerging perspectives on the natural microbiome of fresh produce vegetables. Agriculture 5: 170-187.
Jahangir, et al (2017) Type 2 diabetes current and future medications: a short review. Int J Pharm Pharmacol 1(1): 101.
Jain, C et al (2018) High throughput ANI analysis of 90K prokaryotic genomes reveals clear species boundaries. Nat Commun 9(5114): 1-8.
Jain, M. et al. "Nanopore sequencing and assembly of a human genome with ultra-long reads," Nature Biotechnology, 2018, vol. 36, No. 4, p. 338.
Jarvis, KG et al (2018) Microbiomes associated with foods from plant and animal sources. Front Microbiol 9:2540.
Jia, B et al (2017) CARD 2017: expansion and model-centric curation of the comprehensive antibiotic resistance database. Nucleic Acids Res 45: D566-D573.
Kaluzna-Czaplinska et al (2017) Is there a relationship between intestinal microbiota, dietary compounds, and obesity? Trends Food Sci Technol 70: 105-113.
Kapitza et al (2017) Effects of semaglutide on beta cell function and glycaemic control in particpants with type 2 diabetes: a randomized , double-blind , placebo-controlled trial. Diabetalogia 60: 1390-1399.

(56) References Cited

OTHER PUBLICATIONS

Kaplan, H and Hutkins, RW (2000) Fermentation of fructooligosaccharides by lactic acid bacteria and bifidobacteria. Appl Environ Microbiol 66(6): 2682-2684.
Kasubuchi, M et al (2015) Dietary gut microbial metabolites, short-chain fatty acids, and host metabolic regulation. Nutrients 7: 2839-2849.
Kau et al (2011) Human nutrition, the gut microbiome and the immune system. Nature 474: 327-336.
Kimura et al (2013) The Gut microbiota suppresses insulin-mediated fat accumulation via the short-chain fatty acid receptor GPR43. Nat Commun 4(1829): 1-12.
Kishida et al (2017) Effect of miglitol on the suppression of nonalcoholic steatohepatitis development and improvement of thegut environment in a rodent model. J Gastroenterol 52(11): 1180-1191.
Koh et al (2016) From Dietary fiber to host physiology: short chain fatty acids as key bacterial metabolites. Cell 165: 1332-1345.
Kreznar et al (2017) Host genotype and gut microbiome modulate insulin secretion and diet-induced metabolic phenotypes. Cell Rep 18: 1739-1750.
Lang, JM et al (2014) The microbes we eat: abundance and taxonomy of microbes consumed in a day's worth of meals for three diet types. PeerJ 2:e659; doi 10.7717/peerj.659.
Lee and Hase (2014) Gut microbiota-generated metabolites in animal health and disease. Nat Chem Biol 10:416-424.
Lee, H and Ko, G (2014) Effect of Metformin on Metabolic Improvement and Gut Microbiota. Appl Environ Microbiol 80 (19): 59355943.
Lee, S et al (2018) Blueberry supplementation influences the gut microbiota, inflammation, and insulin resistance in high-fat-diet-fed rats. J Nutr 148(2): 209-219.
Ley et al (2005) Obesity alters gut microbial ecology. PNAS 102(31): 11070-11075.
Li et al (2011) Metabolic surgery profoundly influences gut microbial-host metabolic crosstalk. Gut 60(9): 1214-1223.
Li et al (2017) Butyrate reduces appetite and activates brown adipose tissue via the gut-brain neural circuit. Gut 0:1-11.
Li et al (2017) Intermittent fasting promotes white adipose browning and decreases obesity by shaping the gut microbiota. Cell Metab 26: 672-685.
Lin, H et al (2012) Butyrate and propionate protect against diet-induced obesity and regulate gut hormones via free fatty acid receptor 3-independent mechanisms. PLoS ONE 7(4): 1-9.
Lin, H et al (2016) Correlations of fecal metabonomic and microbiomic changes induced by high-fat diet in the pre-obesity state. Sci Rep 6(21618):1-14.
Liu, B et al (2019) VFDB 2019: a comparative pathogenomic platform with an interactive web interface. Nucleic Acids Res 47: D687-D692.
Louis, P and Flint, HJ (2017) Formation of propionate and butyrate by the human colonic microbiota. Environ Microbiol. 19(1): 29-41.
Lu, Y et al (2016) Short chain fatty acids prevent high-gat-diet-induced obesity in mice by regulating G protein coupled receptors and gut microbiota. Sci Rep. 6(37589): 1-13.
Lyu, M et al (2017) Balancing herbal medicine and functional food for prevention and treatment of cardiometabolic diseases through modulating gut microbiota. Front Microbiol 8(2146): 1-21.
Madiraju, A et al (2014) Metformin suppresses gluconeogenesis by inhibiting mitochondrial glycerophosphate dehydrogenase. Nature 510: 542-546.
Magnusdottir, S et al (2017) Generation of genome-scale metabolic reconstructions for 773 members of the human gut microbiota. Nature biotechnol 35(1):81-89.
Maier, L et al (2018) Extensive impact of non-antibiotic drugs on human gut bacteria. Nature 000: 1-6.
Martinez-Lopez et al (2017) System-wide benefits of intermeal fasting by autophagy. Cell Metab 26:856-871.
McCabe, L et al (2018) Exercise prevents high fat diet induced bone loss, marrow adiposity and dysbiosis in male mice. Bone https://doi.org/10.1016/j.bone.2018.03.024.
Meng, D et al (2016) Anti-inflammatory effects of *Bifidobacterium longum* subsp *infantis* secretions on fetal human enterocytes are mediated by TLR-4 receptors. Am J Physiol Gastrointest Liver Physiol 311:G744-G753.
Milani, C et al (2015) Bifidobacteria exhibit social behavior through carbohydrate resource sharing in the gut. Sci Rep 5 (15782): 1-14.
Montandon, S and Jornayvaz, F (2017) Effects of antidiabetic drugs on gut microbiota composition. Genes 8(250): 1-12.
Morrison, D and Preston, T (2016) Formation of short chain fatty acids by the gut microbiota and their impact on human metabolism. Gut Microbes 7(3):189-200.
Moslehi-Jenabian, S et al (2010) Beneficial effects of probiotic and food borne yeasts on human health. Nutrients 2: 449-473.
Napolitano et al (2014) Novel Gut-Based Pharmacology of Metformin in Patients with Type 2 Diabetes Mellitus. PLoS ONE 9(7): e100778.
Ni et al (2015) A Molecular-level landscape of diet-gut microbiome interactions: toward dietary interventions targeting bacterial genes. mBio 6(6): e01263-15.
Okeke, F et al (2014) The role of the gut microbiome in the pathogenesis and treatment of obesity. GAHMJ 3(3): 44-57.
Olar, R et al (2010) Prospects for new antimicrobials based on N,N-dimethylbiguanide complexes as effective agents on both planktonic and adhered strains. Eur J Med Chem 45: 2868-2875.
Olson, O et al (2017) Obesity and the tumor microenvironment. Science 358(6367): 1130-1131.
Ozcan, E et al (2017) A Human gut commensal ferments cranberry carbohydrates to produce formate. Appl Environ Microbiol 83(17): 1-16.
Palacios, T et al (2017) The effect of a novel probiotic on metabolic biomarkers in adults with prediabetes and recently diagnosed type 2 diabetes mellitus: study protocol for a randomized controlled trial. Trials 18(7): 1-8.
Parekh, P et al (2014) The role and influence of gut microbiota in pathogenesis and management of obesity and metabolic syndrome. Front Endocrinol 5(47):1-7.
Perry, R et al (2016) Acetate mediates a microbiome-brain-beta-cell axis to promote metabolic syndrome. Nature 534: 213-217.
Plovier, H et al (2017) A purified membrane protein from Akkermansia muciniphila or the pasteurized bacterium improves metabolism in obese and diabetic mice. Nat. Med. 23(1): 107-113.
Postler, TS and Ghosh, S (2017) Understanding the holobiont: how microbial metabolites affect human health and shape the immune system. Cell 26: 110-130.
Pryor, R and Cabriero, F (2015) Repurposing metformin: an old drug with new tricks in its binding pockets. Biochem J 471: 307-322.
Psichas et al (2015) The short chain fatty acid propionate stimulates GLP-1 and PYY secretion via free fatty acid receptor 2 in rodents. Int J Obes 39: 424-429.
Puertollano, E et al (2014) Biological significance of short-chain fatty acid metabolism by the intestinal microbiome. Curr Opin Clin Nutr Metab Care 17(2): 139-144.
Pyra, K et al (2012) Prebiotic fiber increases hepatic acetyl CoA carboxylase phosphorylation and suppresses glucose-dependent insulinotropic polypeptide secretion more effectively when used with metformin in obese rats. J Nutr 142(2): 213-220.
Qin et al (2010) A human gut microbial gene catalogue established by metagenomic sequencing. Nature 464: 59-65.
Ramirez-Puebla et al (2013) Gut and Root Microbiota Commonalities. App Environ Microbiol 79(1): 2-9.
Rastall RA and Gibson GR (2015) Recent developments in prebiotics to selectively impact beneficial microbes and promote intestinal health. Curr Opin Biotechnol 32: 42-46.
Rastogi, G et al (2012) Leaf microbiota in an agroecosystem: spatiotemporal variation in bacterial community composition on field-grown lettuce. ISME J 6: 1812-1822.
Ravussin et al (2012) Responses of gut microbiota to diet composition and weight loss in lean and obese mice. Obesity 20(4): 738-747.
Reichardt, N et al (2014) Phylogenetic distribution of three pathways for propionate production within the human gut microbiota. ISME J 8:1323-1335.

(56) References Cited

OTHER PUBLICATIONS

Reichold et al (2014) Bifidobacterium adolescentis protects from the development of nonalcoholic steatohepatitis in a mouse model. J Nutr Biochem 25: 118-125.
Rios-Covain, D et al (2015) Enhanced butyrate formation by cross-feeding between Faecalibacterium prausnitzii and Bifidobacterium adolescentis. FEMS Microbiol Lett 362(21): 1-7.
Rodriguez-R, LM and Konstantinidis, KT (2016) The enveomics collection: a toolbox for specialized analyses of microbial genomes and metagenomes. PeerJ Preprints 4: e1900v1.
Rosario, D et al (2018) Gut microbiota dysbiosis in metformin-treated type 2 diabetes patients using genome-scale metabolic modeling. Front Physiol 9: 775.
Rosenbaum, M (2015) The Gut microbiota in human energy homeostasis and obesity. Trends Endocrinol Metab 26(9): 493-501.
Rosenberg and Zilber-Rosenberg (2016) Interaction between the microbiome and diet: the hologenome concept. J Nutr Food Sci 6(5): 1000545.
Rothschild, D et al (2018) Environment dominates over host genetics in shaping human gut microbiota. Nature 000: 1-6.
Round and Mazmanian (2009) The gut microbiota shapes intestinal immune responses during health and disease. Nat Rev Immunol 9: 313-324.
Saltiel, AR (2016) New therapeutic approaches for the treatment of obesity. Sci Transl Med 8 (323): 1-12.
Saltiel, AR and Olefsky JM (2017) Inflammatory mechanisms linking obesity and metabolic disease. J Clin Invest 127 (1): 1-4.
Sam, QH et al (2017) The Fungal mycobiome and its interaction with gut bacteria in the host. Int J Mol Sci 18(330): 1-11.
Samah, S et al (2016) Probiotics for the management of type 2 diabetes mellitus: a systematic review and meta-analysis. Diabetes res clin pract 118: 172-182.
Samuel and Gordon (2006) A Humanized gnotobiotic mouse model of host-archaeal-bacteria mutualism. PNAS 103 (26): 10011-10016.
Samuel et al (2008) Effects of the gut microbiota on host adiposity are modulated by the short-chain fatty-acid binding G protein-coupled receptor, Gpr41. PNAS 105(43): 16767-16772.
Sawin, EA (2015) Glycomacropeptide is a prebiotic that reduces Desulfovibrio bacteria, increases cecal short-chain fatty acids, and is anti-inflammatory in mice. Am J Physiol Gastrointest Liver Physiol 309: G590-G601.
Schirmer et al (2016) Linking the human gut microbiome to inflammatory cytokine production capacity. Cell 167(4): 1125-1136.
Schoch, C.L. et al., "Nuclear ribosomal internal transcribed spacer (ITS) region as a universal DNA barcode marker for Fungi," Proceedings of the National Academy of Sciences, 2012, vol. 109, No. 16, pp. 6241-6246.
Schroeder, B and Backhed, F (2016) Signals from the gut microbiota to distant organs in physiology and disease. Nat Med 22(10): 1079-1089.
Schroeder, B et al (2018) Bifidobacteria or Fiber protects against diet-induced microbiota-mediated colonic mucus deterioration. Cell host microbe 23:27-40.
Scott, KP et al (2015) Manipulating the gut microbiota to maintain health and treat disease. Micro Ecol Health Dis 26 (25877): 1-10.
Serino et al (2012) Metabolic adaptation to a high-fat diet is associated with a change in the gut microbiota. Gut 61: 543-553.
Sheikhi, A (2016) Probiotic yogurt culture *Bifidobacterium animalis* subsp *lactis* BB-12 and Lactobacillus acidophilus LA-5 modulate the cytokine secretion by peripheral blood mononuclear cells from patients with ulcerative colitis. Drug Res 66: 300-305.
Shin et al (2014) An increase in the *Akkermansia* spp population induced by metformin treatment improves glucose homeostasis in diet-induced obese mice. Gut 63: 727-735.
Shoaie, S et al (2015) Quantifying diet-induced metabolic changes of the human gut microbiome. Cell metab 22: 320-331.
Simpson, HL and Campbell, BJ (2015) Review article: dietary fibre-microbiota interactions. Aliment Pharmacol Ther 42: 158-179.
Singer and Lumeng (2017) The initiation of metabolic inflammation in childhood obesity. J Clin Invest 127(1):65-73.
Singh et al (2018) Dysregulated microbial fermentation of soluble fiber induces cholestatic liver cancer. Cell 175: 679-694.
Slavin, J (2013) Fiber and Prebiotics: Mechanisms and health benefits. Nutrients 5: 1417-1435.
Smith, IM et al (2014) Yeast modulation of human dendritic cell cytokine secretion: an in vitro study. PLoS ONE 9(5): 1-14.
Sonnenburg, JL and Backhed, F (2016) Diet-microbiota interactions as moderators of human metabolism. Nature 535: 56-64.
Strorelli et al (2013) Metformin, microbes, and aging. Cell Metab 17: 809-811.
Stull, AJ (2016) Blueberries' impact on insulin resistance and glucose intolerance. Antioxidants 5(44): 1-11.
Stull, AJ et al (2010) Bioactives in blueberries improve insulin sensitivity in obese, insulin-resistant men and women. J Nutr 140(10): 1764-8.
Suez, J et al (2018) Post-antibiotic gut mucosal microbiome reconstitution is impaired by probiotics and improved by autologous FMT. Cell 174: 1406-1423.
Sun, et al (2018) Gut Mirobiota and intestinal fxr mediate the clinical benefits of metformin. Nat Med 24: 1919-1929.
Sweeney, T et al (2014) Metabolic surgery: action via hormonal milieu changes, changes in bile acids or gut microbiota? A summary of the literature. Best Pract Res Clin Gastroenterol 28: 727-740.
Terrapon, N and Henrissat, B (2014) How do gut microbes break down dietary fiber? Trends Biochem Sci 39 (4):156-158.
Tolhurst, G et al (2012) Short-chain fatty acids stimulate glucagon-like peptide-1 secretion via the G-protein-coupled receptor FFAR2. Diabetes 61: 364-371.
Truong, DT et al (2015) MetaPhlAn2 for enhanced metagenomic taxonomic profiling. Nature Methods 12(10): 902-904.
Tuohy, KM et al (2012) Up-regulating the human intestinal microbiome using whole plant foods, polyphenols, and/or fiber. J Agric Food Chem 60: 8776-8782.
Turnbaugh et al (2009) A Core gut microbiome in obese and lean twins. Nature 457(7228): 480-484.
Turnbaugh, PJ et al (2006) An Obesity-associated gut microbiome with increased capacity for energy harvest. Nature 444: 1027-1031.
Turnbaugh, PJ et al (2008) Diet-induced obesity is linked to marked but reversible alterations in the mouse distal gut microbiome. Cell Host Microbe 3: 213-223.
Turnbaugh, PJ et al (2009) Supplement: The effect of diet on the human gut microbiome: a metagenomic analysis in humanized gnotobiotic mice. Sci Transl Med 1(6ra14)1-23.
Turnbaugh, PJ et al (2009) The effect of diet on the human gut microbiome: a metagenomic analysis in humanized gnotobiotic mice. Sci Transl Med 1(6ra14)1-23.
Van Hul et al (2017) Reduced obesity, diabetes and steatosis upon cinnamon and grape pomace are associated with changes in gut microbiota and markers of gut barrier. Am J Physiol Endocrinol Metab 314(4): E3340E352.G.
Vatanen, T et al (2016) Variation in microbiome LPS immunogenicity contributes to autoimmunity in humans. Cell 165: 842-853.
Verma et al (2018) Cell Surface polysaccharides of Bifidobacterium bifidum induce the generation of Foxp3+ regulatory T cells. Sci Immunol 3 , eaat6975.
Vijay-Kumar et al (2010) Metabolic syndrome and altered gut microbiota in mice lacking toll-like receptor 5. Science 328(5975): 228-231.
Vital, M et al (2013) A gene-targeted approach to investigate the intestinal butyrate-producing bacterial community. Microbiome 1(8): 1-14.
Voreades et al (2014) Diet and the development of the human intestinal microbiome. Front Microbiol 5(494): 1-9.
Wahlstrom et al (2016) Intestinal crosstalk between bile acids and microbiota and its impact on host metabolism. Cell Metab 24: 41-50.
Wallace, T et al (2004) Use and abuse of HOMA modeling. Diabetes Care 27(6): 1487-1495.
Wang, J (2015) Modulation of gut microbiota during probiotic-mediated attenuation of metabolic syndrome in high fat diet-fed mice. ISME J 9: 1-15.
Wassermann, B et al (2017) Harnessing the microbiomes of *Brassica* vegetables for health issues. Sci Rep 7:17649.

(56) References Cited

OTHER PUBLICATIONS

Weitkunat, K et al (2017) Short-chain fatty acids and inulin, but not guar gum, prevent diet-induced obesity and insulin resistance through differential mechanisms in mice. Sci Rep 7(6109): 1-13.
White, J (2014) A Brief history of the development of diabetes medications. Diabetes Spectr 27(2): 82-86.
Winer et al (2016) The Intestinal immune system in obesity and insulin resistance. Cell Metab 23: 413-426.
Winer et al (2017) Immunologic impact of the intestine in metabolic disease. J Clin Invest 127(1):33-42.
Woo, S-L et al (2014) Metformin ameliorates hepatic steatosis and inflammation without altering adipose phenotype in diet-induced obesity. PLoS ONE 9(3): e91111.
Wu, H et al (2017) Metformin alters the gut microbiome of individuals with treatment-naïve type 2 diabetes, contributing to the therapeutic effects of the drug. Nat Med. 23(7): 850-858.
Wu, H et al (2017) Metformin alters the gut microbiome of individuals with treatment-naïve type 2 diabetes, contributing to the therapeutic effects of the drug. Nat Med. 23(7): supplement.
Yang, JH et al (2017) Potent anti-inflammatory and antiadipogenic properties of bamboo (*Sasa coreana Nakai*) leaves extract and its major constituent flavonoids. J Agric Food Chem 65: 6665-6673.
Yassour, M et al (2016) Natural history of the infant gut microbiome and impact of antibiotic treatment on bacterial strain diversity and stability. Sci Transl Med 8(343): 1-12.
Yousef, N et al (2017) Metformin: a unique herbal origin medication. GJMR-B: Pharma, Drug Discovery, Toxicology, and Medicine 17(3): 31-37.
Zhang et al (2009) Human gut microbiota in obesity and after gastric bypass. PNAS 106(7): 2365-2370.
Zhang, Q et al (2016) Effect of probiotics on glucose metabolism in patients with type 2 diabetes mellitus: a meta-analysis of randomized controlled trials. Medicina 52: 28-34.
Zhang, X et al (2012) Structural changes of gut microbiota during berberine-mediated prevention of obesity and insulin resistance in high-fat diet-fed rats. PLoS ONE 7(8): e42529.
Zhang, X et al (2015) Modulation of gut microbiota by berberine and metformin during the treatment of high-fat diet-induced obesity in rats. Sci Rep 5(14405): 1-10.
Zhang, X et al (2017) Effects of Acarbose on the gut microbiota of prediabetic patients: a randomized, double-blind, controlled crossover trial. 8: 293-307.
Zhao, L et al (2018) Gut bacteria selectively promoted by dietary fibers alleviate type 2 diabetes. Science 359: 1151-1156.
Zheng, J et al (2018) Prebiotic Mannan-oligosaccharides augment the hypoglycemic effects of metformin in correlation with modulating gut microbiota. J Agric Food Chem 66(23): 5821-5831.
Zmora, N et al (2018) Personalized gut mucosal colonization resistance to empiric probiotics is associated with unique host and microbiome features. Cell 174: 1388-1405.

* cited by examiner

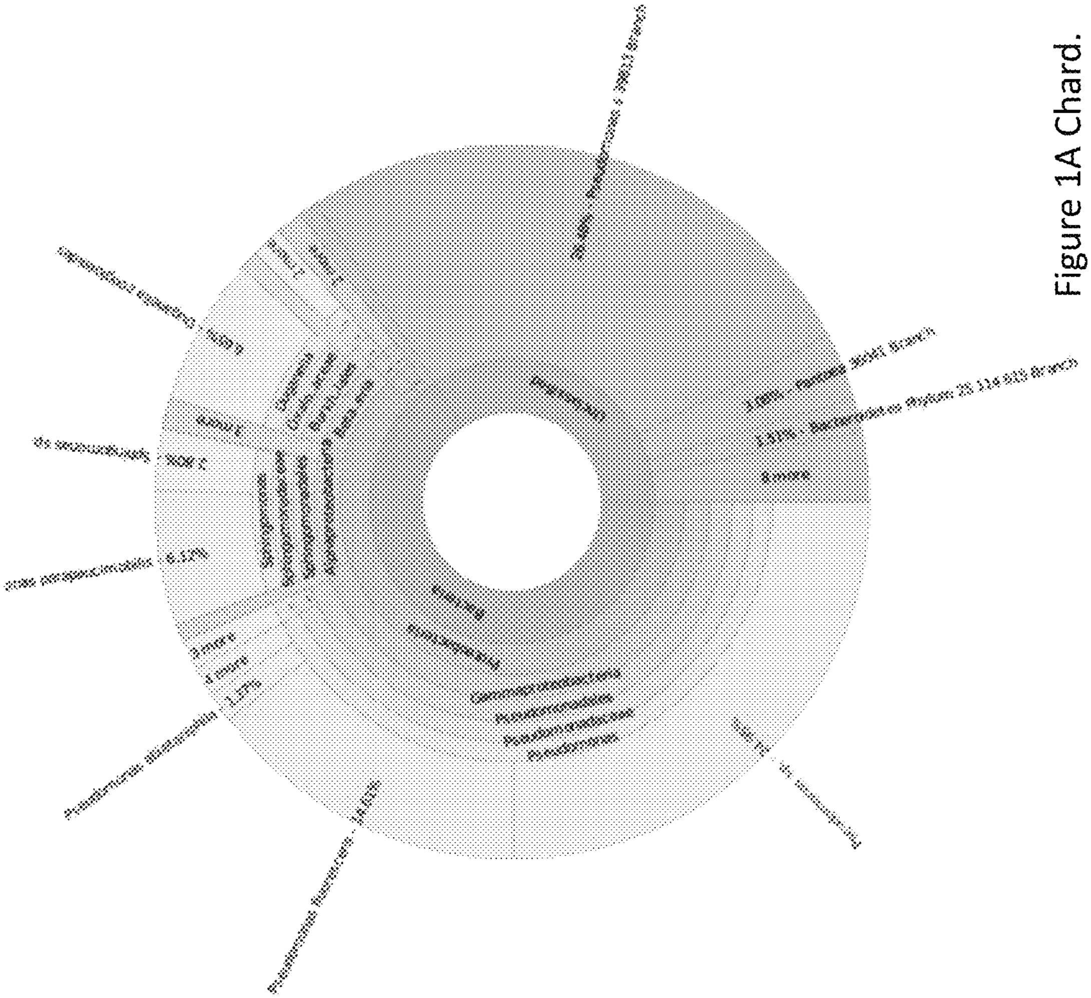
Figure 1A Chard.

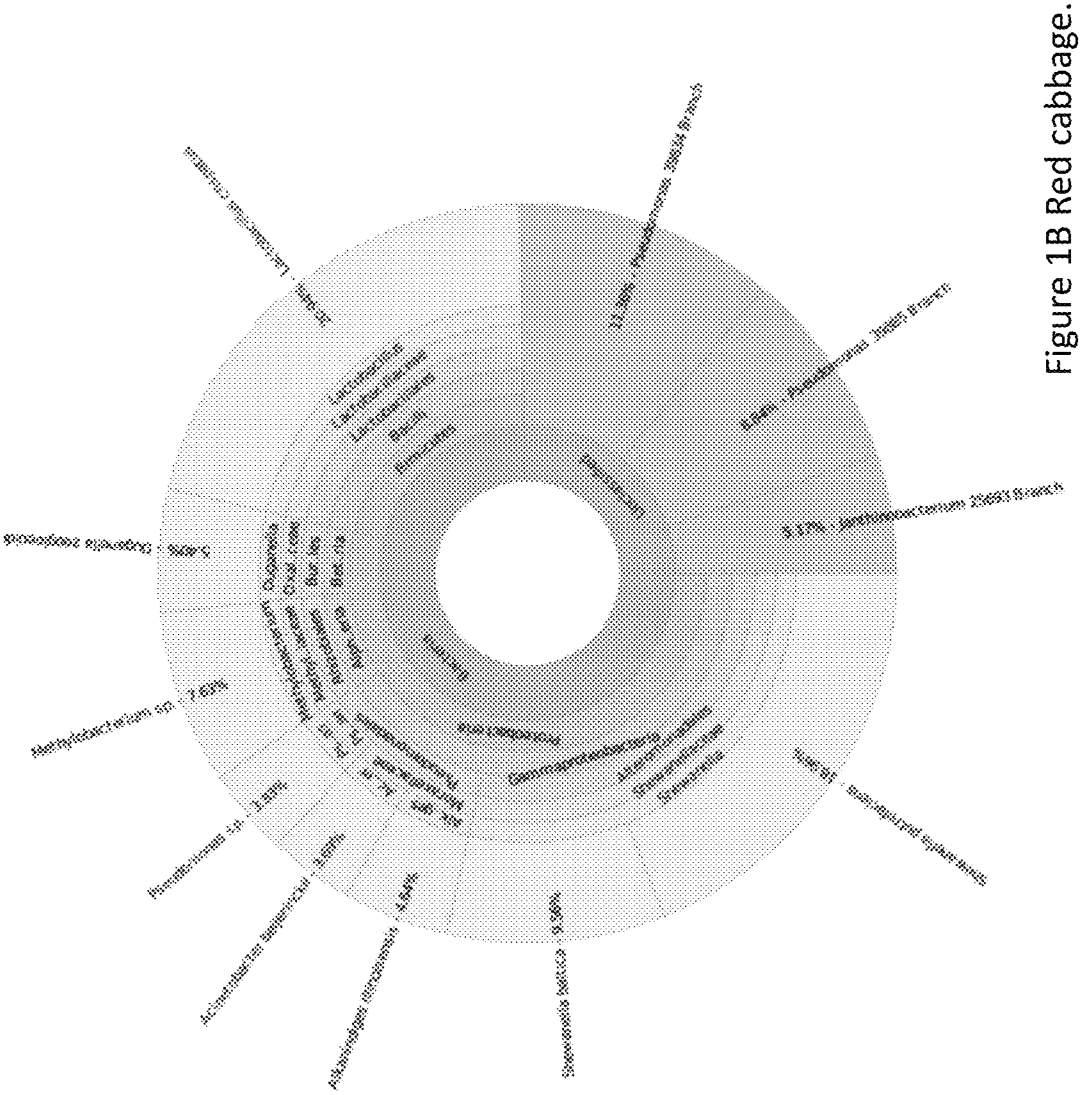
Figure 1B Red cabbage.

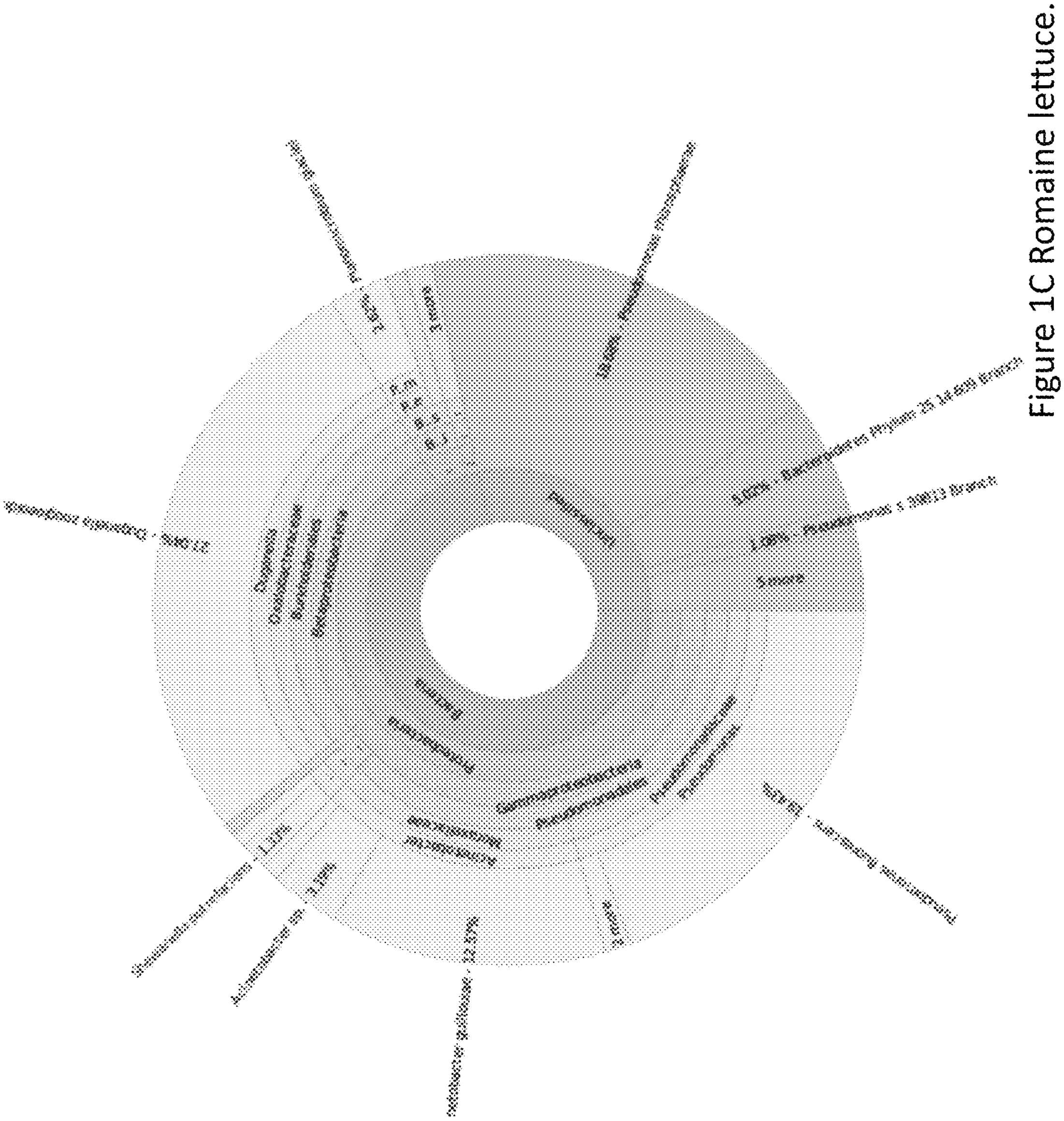
Figure 1C Romaine lettuce.

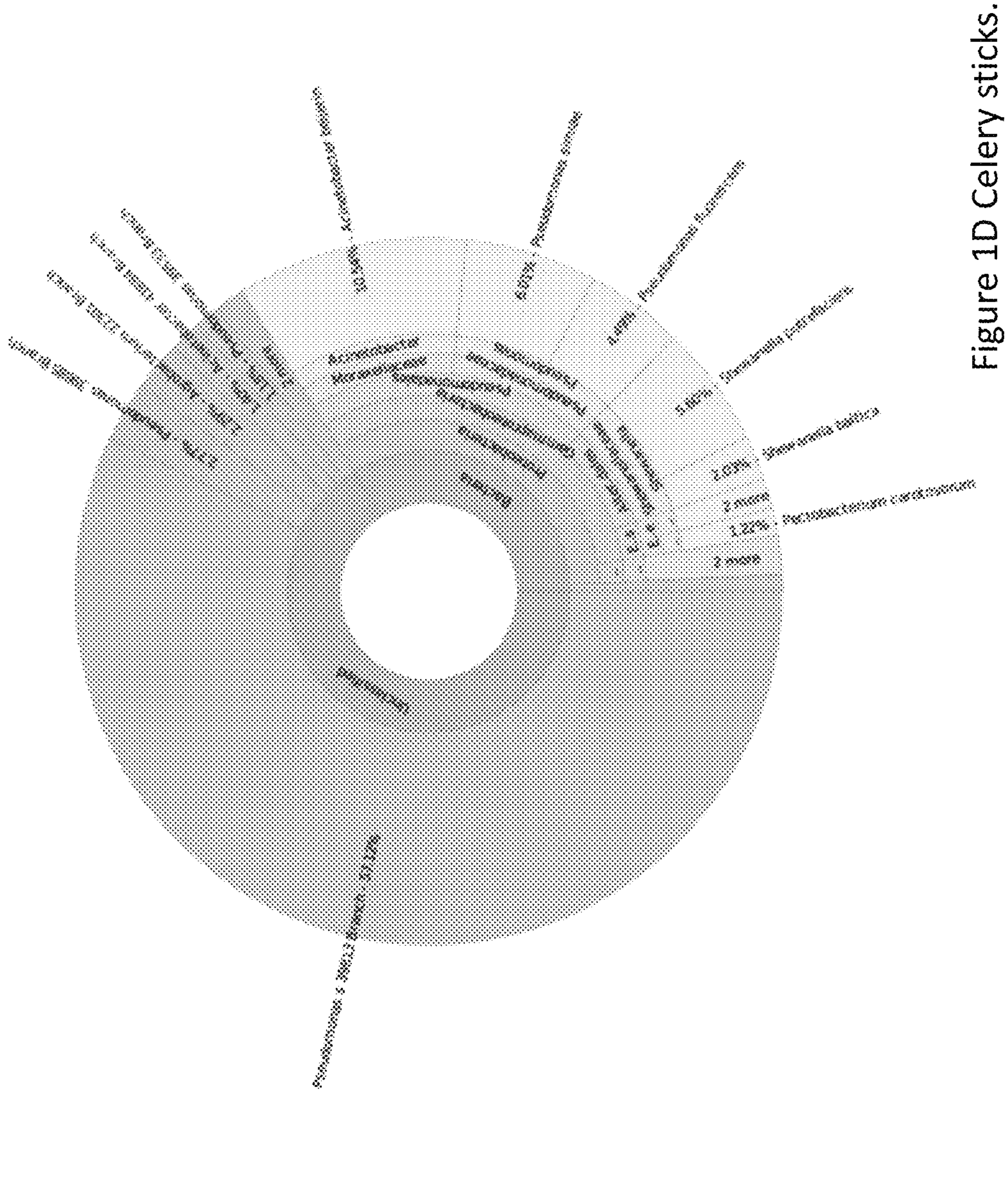
Figure 1D Celery sticks.

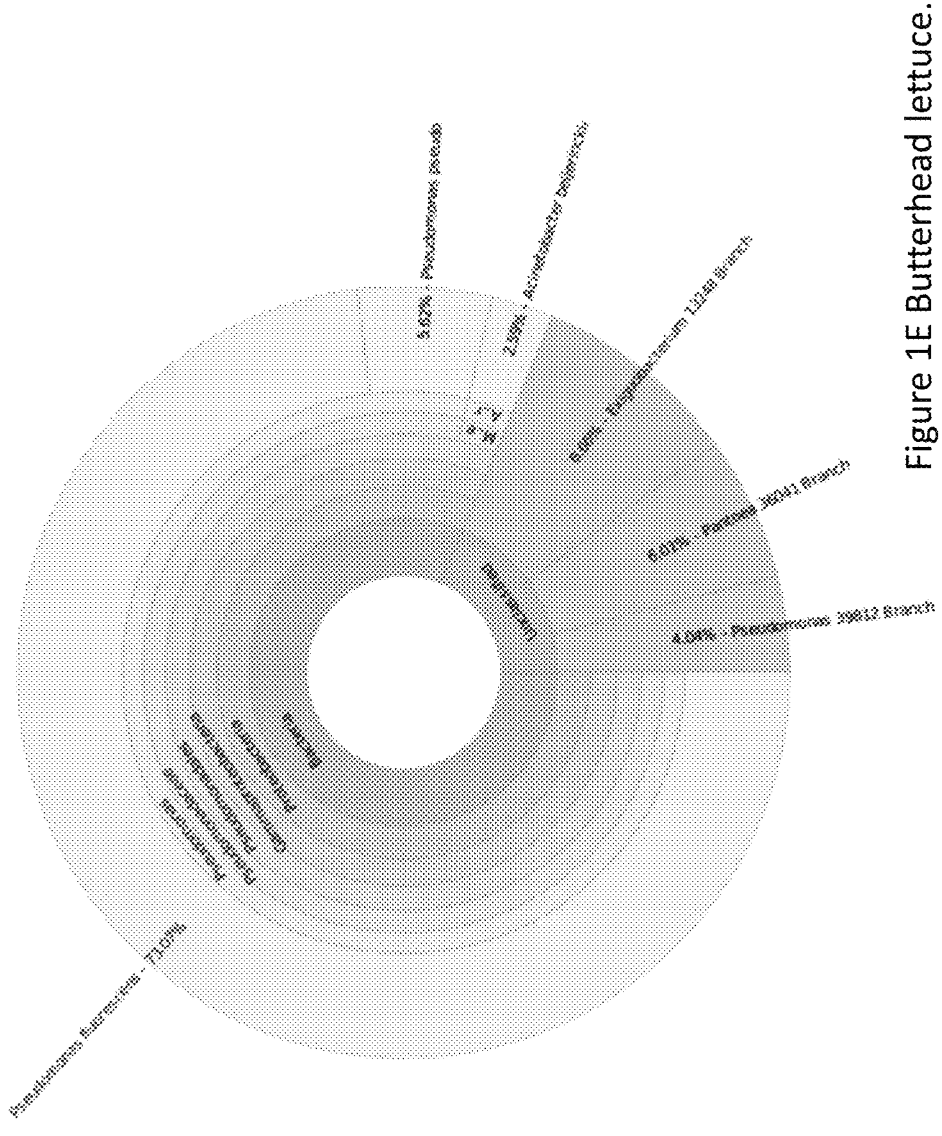
Figure 1E Butterhead lettuce.

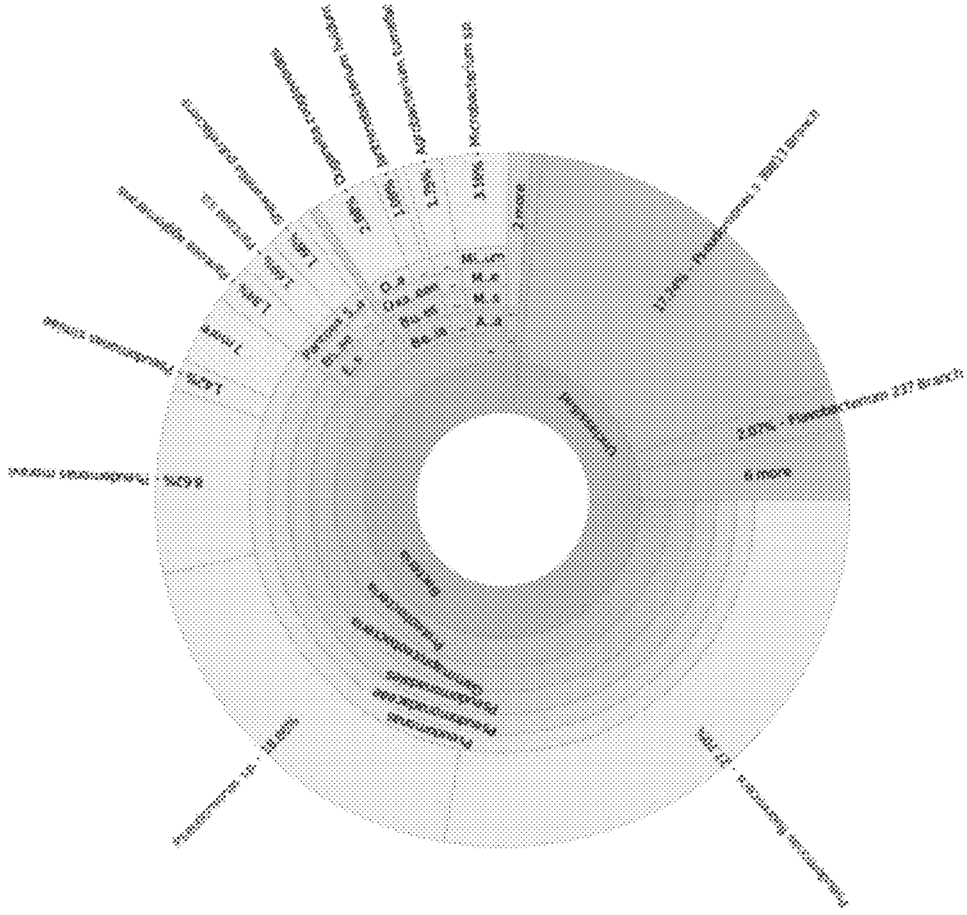
Figure 1F Baby spinach.

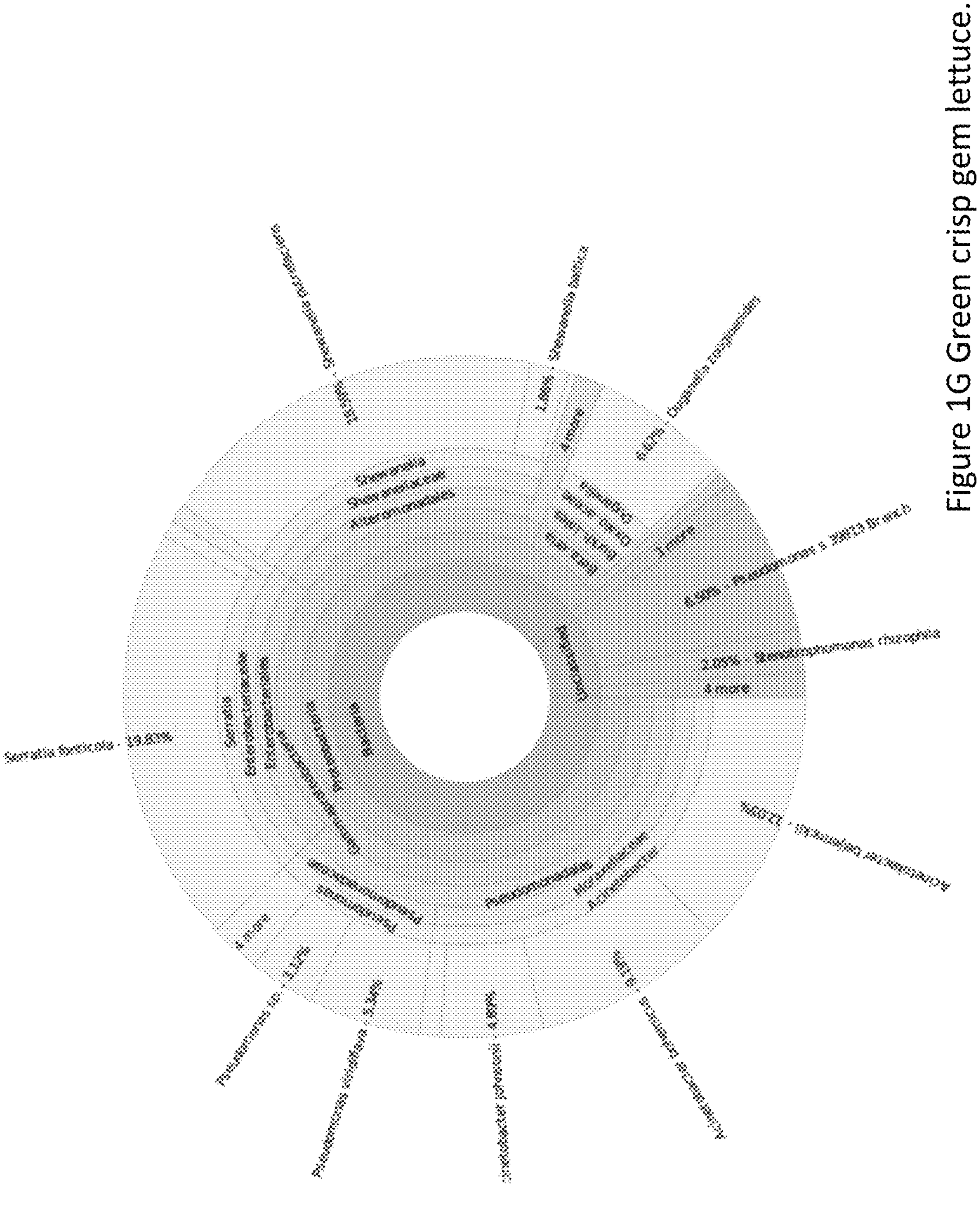
Figure 1G Green crisp gem lettuce.

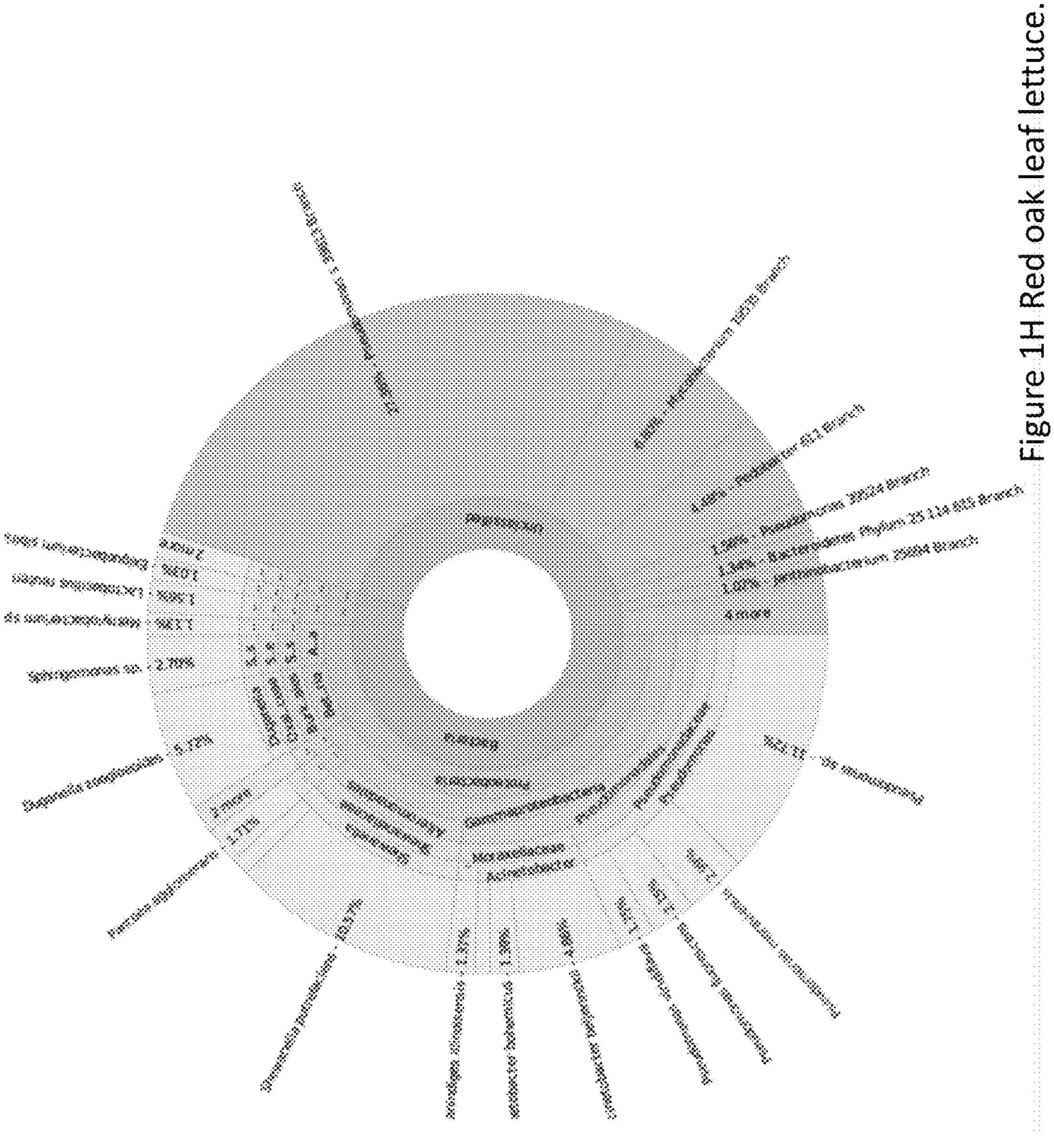
Figure 1H Red oak leaf lettuce.

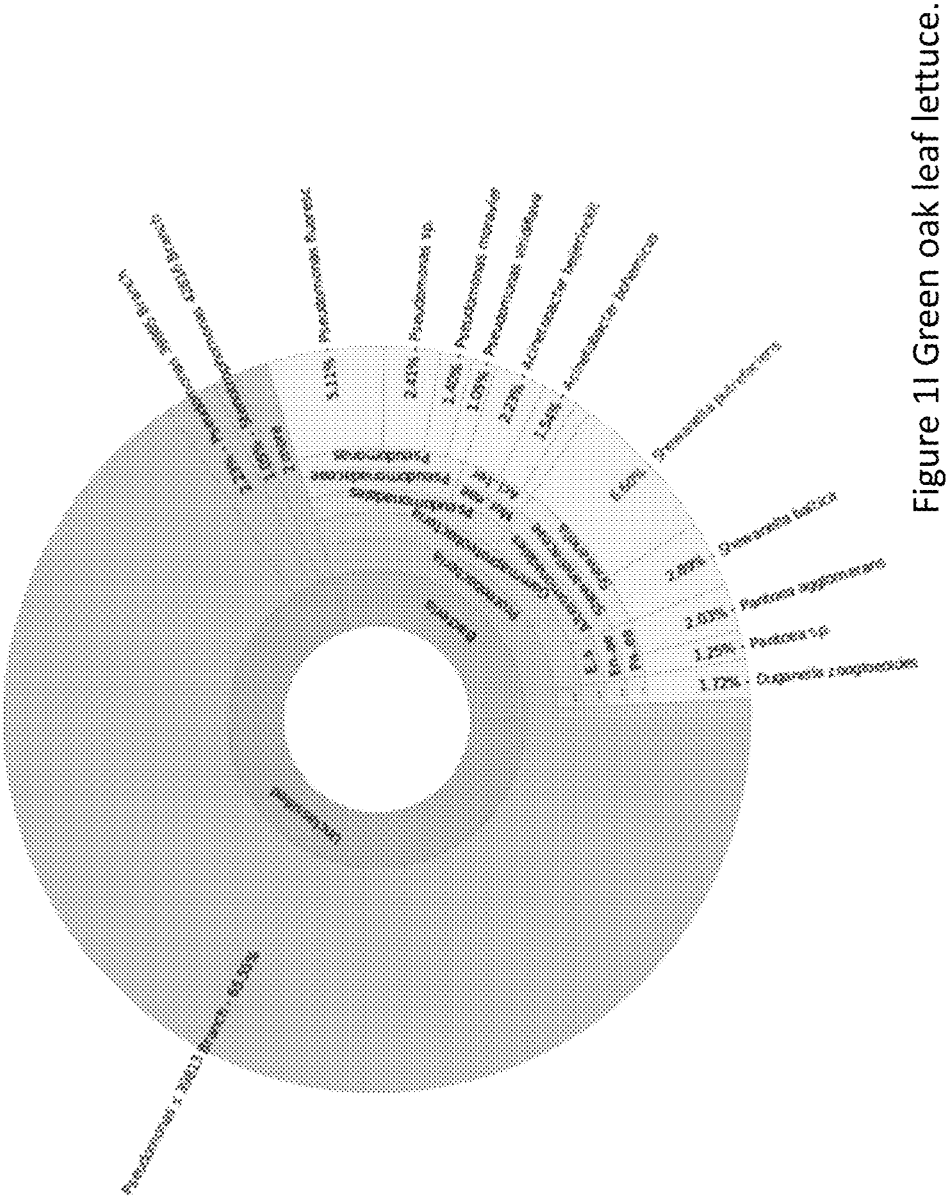
Figure 1I Green oak leaf lettuce.

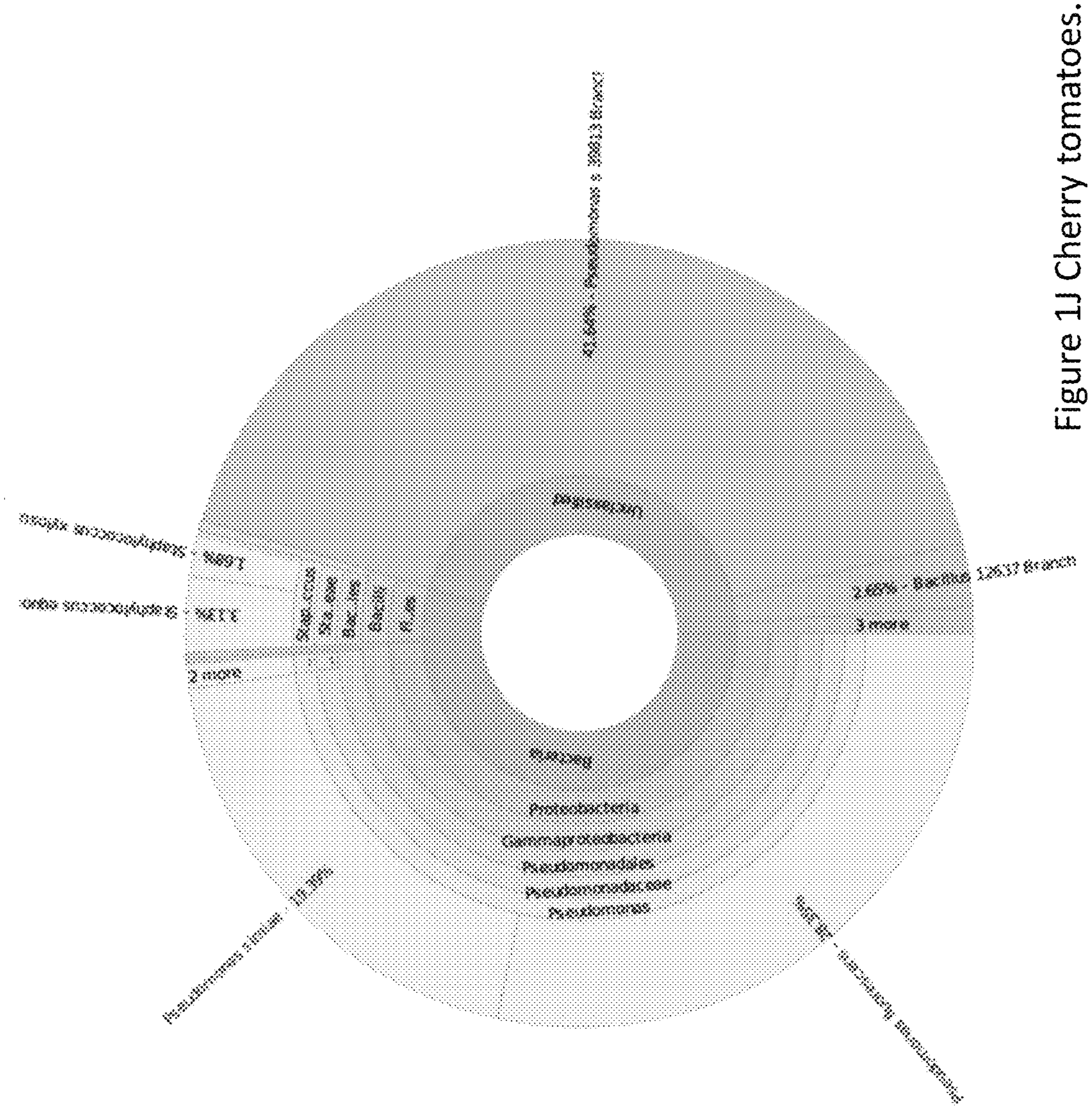
Figure 1J Cherry tomatoes.

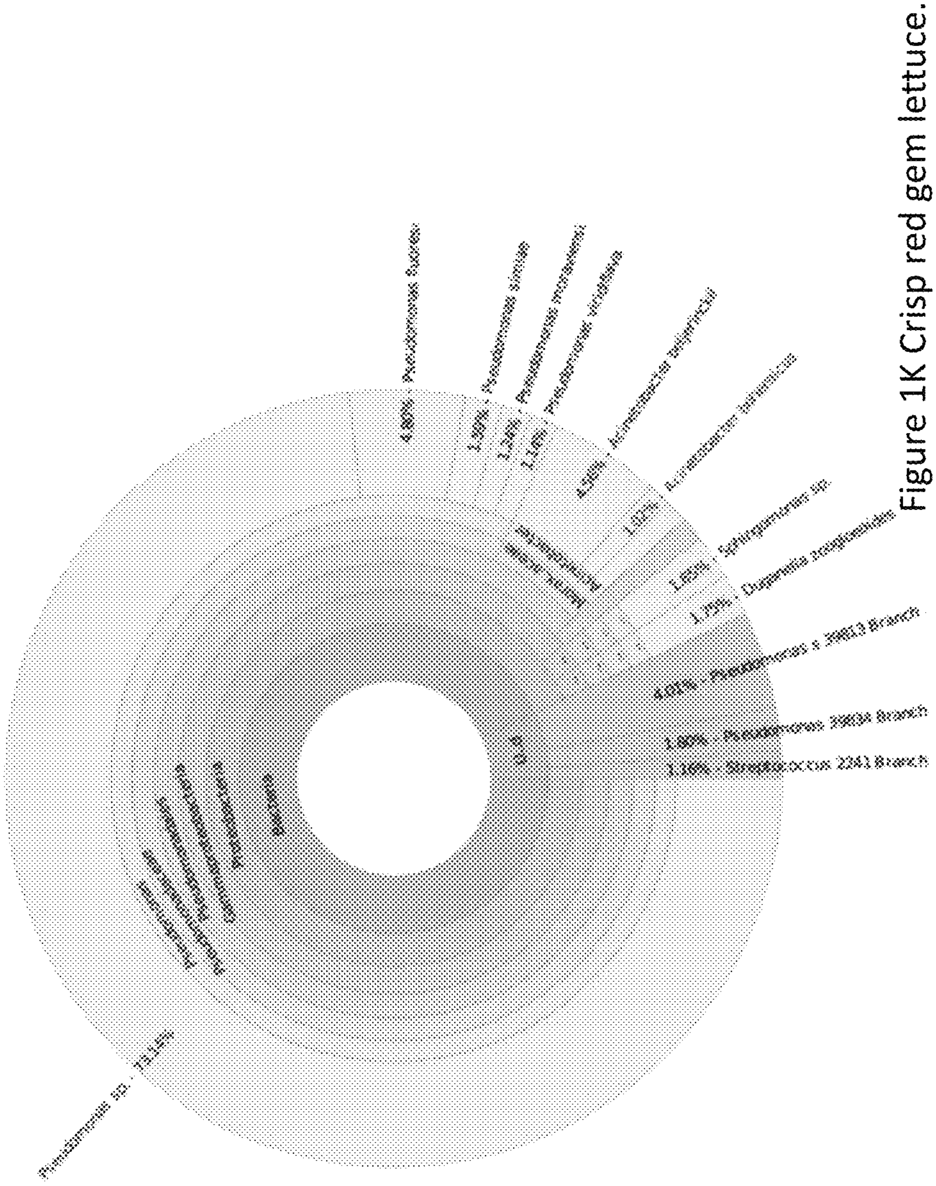
Figure 1K Crisp red gem lettuce.

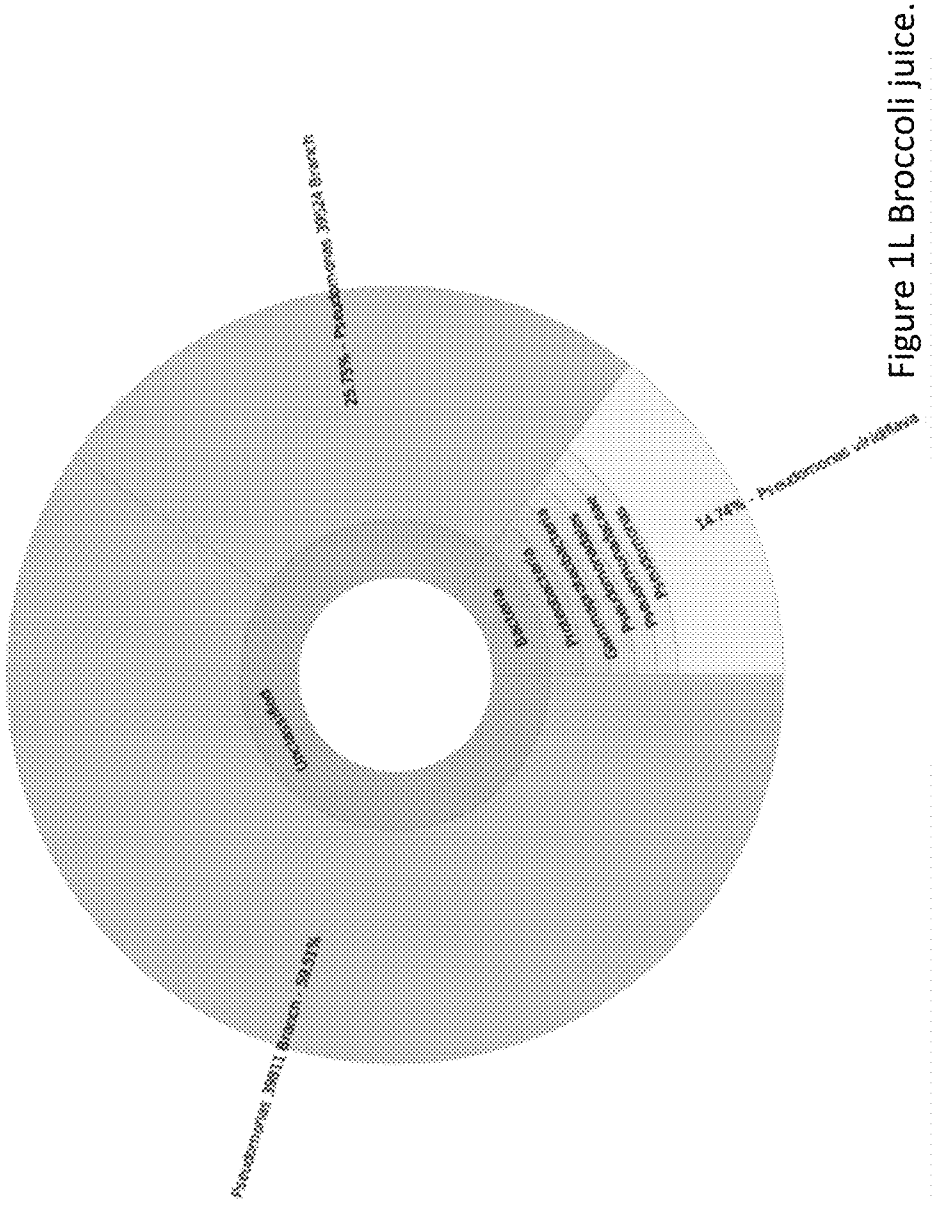
Figure 1L Broccoli juice.

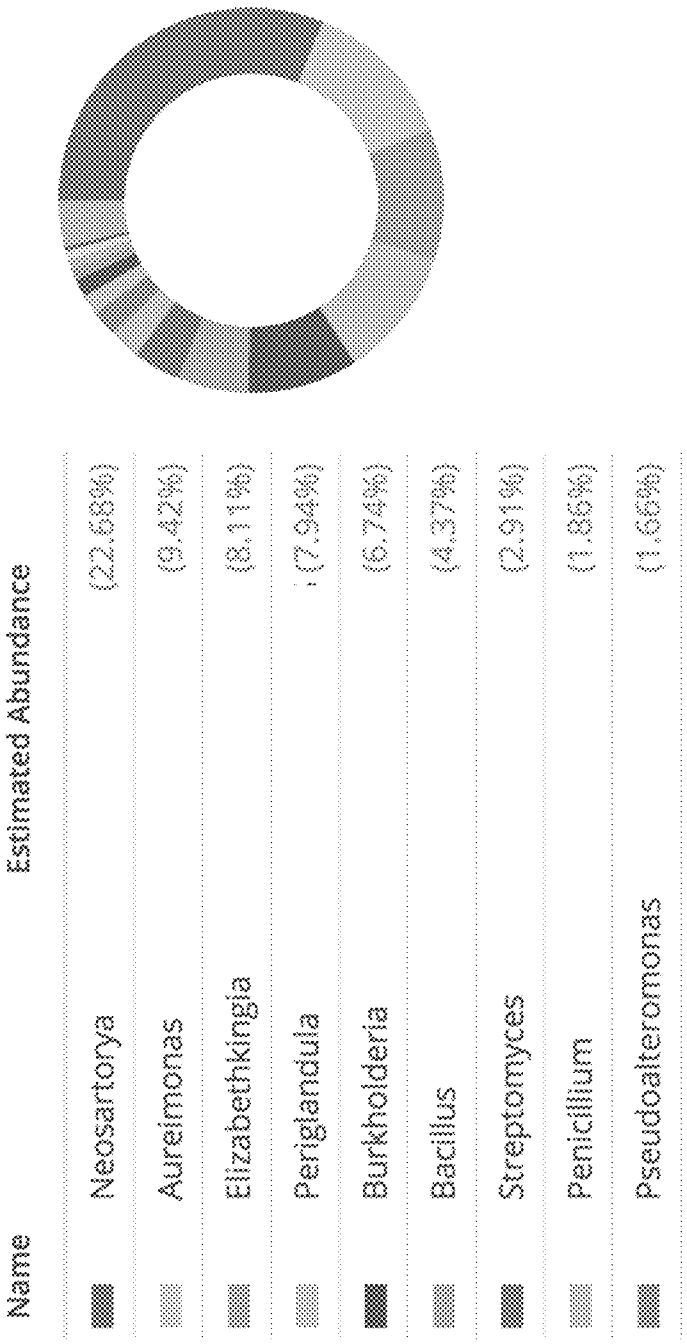
Figure 2A Broccoli head.

| Name | Estimated Abundance |
|---|---|
| Pseudomonas fluorescens | 53.94% |
| Pseudomonas sp. DSM 29167 | 10.99% |
| Propionibacterium acnes | 6.10% |
| Acinetobacter soli | 4.97% |
| Aureobasidium pullulans | 2.96% |
| Pseudomonas syringae | 2.76% |
| Pseudomonas sp. Leaf15 | 1.84% |
| Acinetobacter baumannii | 1.58% |
| Pantoea sp. SL1_M5 | 1.43% |
| Raoultella ornithinolytica | 1.32% |
| Sphingomonas sp. Ant20 | 1.27% |
| Comamonas testosteroni | 1.18% |
| Rahnella sp. WP5 | 1.18% |
| Enterobacter sp. 940_PEND | 1.06% |
| Pseudomonas sp. FH1 | 0.73% |
| Rothia dentocariosa | 0.54% |
| Pectobacterium carotovorum | 0.54% |
| Enhydrobacter aerosaccus | 0.54% |
| Bacillus sp. LL01 | 0.42% |
| Pseudomonas trivialis | 0.39% |

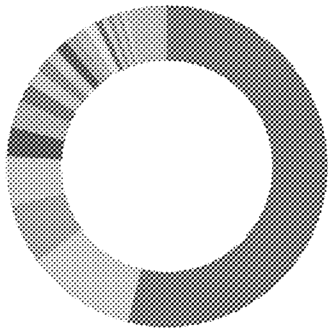

Figure 2B Blueberry.

| Name | Estimated Abundance |
|---|---|
| Lactobacillus acetotolerans | 60.98% |
| Lactobacillus buchneri | 12.34% |
| Pediococcus ethanolidurans | 5.47% |
| Lactobacillus parafarraginis | 4.32% |
| Lactobacillus rapi | 2.91% |
| Lactobacillus plantarum | 1.52% |
| Lactobacillus kefiranofaciens | 1.40% |
| Lactobacillus futsaii | 1.38% |
| Lactobacillus brevis | 1.25% |
| Lactobacillus panis | 1.16% |
| (Remaining) | 7.26% |
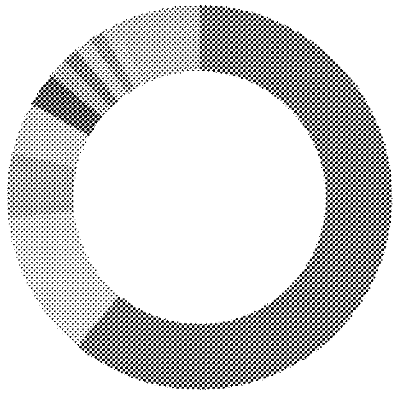
Figure 2C Pickled green olives.

SEQUENCE LISTING

<160> NUMBER OF SEQ ID NOS: 136

<210> SEQ ID NO 1
<211> LENGTH: 1490
<212> TYPE: DNA
<213> ORGANISM: Unknown
<220> FEATURE:
<223> OTHER INFORMATION: Description of Unknown:
      DP1 16S rRNA microbial sequence

<400> SEQUENCE: 1
agtcagacat gcaagtcgag cggtagagag aagcttgctt ctcttgagag cggcggacgg 60
gtgagtaaag cctaggaatc tgcctggtag tgggggataa cgttcggaaa cggacgctaa 120
taccgcatac gtcctacggg agaaagcagg ggaccttcgg gccttgcgct atcagatgag 180
cctaggtcgg attagctagt tggtgaggta atggctcacc aaggcgacga tccgtaactg 240
gtctgagagg atgatcagtc acactggaac tgagacacgg tccagactcc tacgggaggc 300
agcagtgggg aatattggac aatgggcgaa agcctgatcc agccatgccg cgtgtgtgaa 360
gaaggtcttc ggattgtaaa gcactttaag ttgggaggaa gggcattaac ctaatacgtt 420
agtgttttga cgttaccgac agaataagca ccggctaact ctgtgccagc agccgcggta 480
atacagaggg tgcaagcgtt aatcggaatt actgggcgta aagcgcgcgt aggtggtttg 540
ttaagttgga tgtgaaatcc ccgggctcaa cctgggaact gcattcaaaa ctgactgact 600
agagtatggt agagggtggt ggaatttcct gtgtagcggt gaaatgcgta gatataggaa 660
ggaacaccag tggcgaaggc gaccacctgg actaatactg acactgaggt gcgaaagcgt 720
ggggagcaaa caggattaga taccctggta gtccacgccg taaacgatgt caactagccg 780
ttgggagcct tgagctctta gtggcgcagc taacgcatta agttgaccgc ctggggagta 840
cggccgcaag gttaaaactc aaatgaattg acgggggccc gcacaagcgg tggagcatgt 900
ggtttaattc gaagcaacgc gaagaacctt accaggcctt gacatccaat gaactttcta 960
gagatagatt ggtgccttcg ggaacattga gacaggtgct gcatggctgt cgtcagctcg 1020
tgtcgtgaga tgttgggtta agtcccgtaa cgagcgcaac ccttgtcctt agttaccagc 1080
acgtaatggt gggcactcta aggagactgc cggtgacaaa ccggaggaag gtggggatga 1140
cgtcaagtca tcatggccct tacggcctgg gctacacacg tgctacaatg gtcggtacag 1200
agggttgcca agccgcgagg tggagctaat cccataaaac cgatcgtagt ccggatcgca 1260
gtctgcaact cgactgcgtg aagtcggaat cgctagtaat cgcgaatcag aatgtcgcgg 1320
tgaatacgtt cccgggcctt gtacacaccg cccgtcacac catgggagtg ggttgcacca 1380
gaagtagcta gtctaacctt cgggaggacg gttaccacgg tgtgattcat gactggggtg 1440
aagtcgtaac aaggtagccg taggggaacc tgcggctgga tcacctcctt 1490

<210> SEQ ID NO 2
<211> LENGTH: 1115
<212> TYPE: DNA
<213> ORGANISM: Unknown
<220> FEATURE:
<223> OTHER INFORMATION: Description of Unknown:
DP2 ITS microbial sequence
<220> FEATURE:
<221> NAME/KEY: modified_base
<222> LOCATION: (1)..(18)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (79)..(79)
<223> OTHER INFORMATION: a, c, t, g, unknown or other
<220> FEATURE:
<221> NAME/KEY: modified_base
<222> LOCATION: (551)..(551)
<223> OTHER INFORMATION: a, c, t, g, unknown or other
<220> FEATURE:
<221> NAME/KEY: modified_base
<222> LOCATION: (884)..(884)
<223> OTHER INFORMATION: a, c, t, g, unknown or other
<220> FEATURE:
<221> NAME/KEY: modified_base
<222> LOCATION: (894)..(895)
<223> OTHER INFORMATION: a, c, t, g, unknown or other
<220> FEATURE:
<221> NAME/KEY: modified_base
<222> LOCATION: (916)..(917)
<223> OTHER INFORMATION: a, c, t, g, unknown or other
<220> FEATURE:
<221> NAME/KEY: modified_base
<222> LOCATION: (926)..(926)

<223> OTHER INFORMATION: a, c, t, g, unknown or other
<220> FEATURE:
<221> NAME/KEY: modified_base
<222> LOCATION: (940)..(940)
<223> OTHER INFORMATION: a, c, t, g, unknown or other
<220> FEATURE:
<221> NAME/KEY: modified_base
<222> LOCATION: (959)..(960)
<223> OTHER INFORMATION: a, c, t, g, unknown or other
<220> FEATURE:
<221> NAME/KEY: modified_base
<222> LOCATION: (965)..(965)
<223> OTHER INFORMATION: a, c, t, g, unknown or other
<220> FEATURE:
<221> NAME/KEY: modified_base
<222> LOCATION: (967)..(967)
<223> OTHER INFORMATION: a, c, t, g, unknown or other
<220> FEATURE:
<221> NAME/KEY: modified_base
<222> LOCATION: (992)..(992)
<223> OTHER INFORMATION: a, c, t, g, unknown or other
<220> FEATURE:
<221> NAME/KEY: modified_base
<222> LOCATION: (994)..(994)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (1006)..(1006)
<223> OTHER INFORMATION: a, c, t, g, unknown or other
<220> FEATURE:
<221> NAME/KEY: modified_base
<222> LOCATION: (1014)..(1014)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1031)..(1031)
<223> OTHER INFORMATION: a, c, t, g, unknown or other
<220> FEATURE:
<221> NAME/KEY: modified_base
<222> LOCATION: (1036)..(1037)
<223> OTHER INFORMATION: a, c, t, g, unknown or other
<220> FEATURE:
<221> NAME/KEY: modified_base
<222> LOCATION: (1039)..(1039)
<223> OTHER INFORMATION: a, c, t, g, unknown or other
<220> FEATURE:
<221> NAME/KEY: modified_base
<222> LOCATION: (1050)..(1050)
<223> OTHER INFORMATION: a, c, t, g, unknown or other
<220> FEATURE:
<221> NAME/KEY: modified_base
<222> LOCATION: (1052)..(1053)
<223> OTHER INFORMATION: a, c, t, g, unknown or other
<220> FEATURE:
<221> NAME/KEY: modified_base
<222> LOCATION: (1059)..(1059)
<223> OTHER INFORMATION: a, c, t, g, unknown or other
<220> FEATURE:
<221> NAME/KEY: modified_base
<222> LOCATION: (1068)..(1072)
<223> OTHER INFORMATION: a, c, t, g, unknown or other
<220> FEATURE:
<221> NAME/KEY: modified_base
<222> LOCATION: (1076)..(1076)
<223> OTHER INFORMATION: a, c, t, g, unknown or other
<220> FEATURE:
<221> NAME/KEY: modified_base
<222> LOCATION: (1079)..(1081)
<223> OTHER INFORMATION: a, c, t, g, unknown or other
<220> FEATURE:
<221> NAME/KEY: modified_base
<222> LOCATION: (1093)..(1095)
<223> OTHER INFORMATION: a, c, t, g, unknown or other
<220> FEATURE:
<221> NAME/KEY: modified_base
<222> LOCATION: (1101)..(1103)
<223> OTHER INFORMATION: a, c, t, g, unknown or other
<220> FEATURE:
<221> NAME/KEY: modified_base
<222> LOCATION: (1109)..(1109)
<223> OTHER INFORMATION: a, c, t, g, unknown or other
<220> FEATURE:
<221> NAME/KEY: modified_base
<222> LOCATION: (1114)..(1115)
<223> OTHER INFORMATION: a, c, t, g, unknown or other

<400> SEQUENCE: 2
nnnnnnnnnn nnnnnnnntt gttgctcgag ttcttgttta gatcttttac aataatgtgt 60
atctttaatg aagatgngng cttaattgcg ctgctttatt agagtgtcgc agtagaagta 120
gtcttgcttg aatctcagtc aacgtttaca cacattggag tttttttact ttaatttaat 180
tctttctgct ttgaatcgaa aggttcaagg caaaaaacaa acacaaacaa ttttatttta 240
ttataatttt ttaaactaaa ccaaaattcc taacggaaat tttaaaataa tttaaaactt 300
tcaacaacgg atctcttggt tctcgcatcg atgaaaaacg taccgaattg cgataagtaa 360
tgtgaattgc aaatactcgt gaatcattga atttttgaac gcacattgcg cccttgagca 420
ttctcaaggg catgcctgtt tgagcgtcat ttccttctca aaaaataatt ttttattttt 480
tggttgtggg cgatactcag ggttagcttg aaattggaga ctgtttcagt ctttttaat 540 tcaacactta ncttctttgg agacgctgtt ctcgctgtga tgtatttatg gatttattcg 600
ttttacttta caagggaaat ggtaatgtac cttaggcaaa gggttgcttt taatattcat 660
caagtttgac ctcaaatcag gtaggattac ccgctgaact taagcatatc aataagcgga 720
ggaaaagaaa ccaactggga ttaccttagt aacggcgagt gaagcggtaa aagctcaaat 780
ttgaaatctg gtactttcag tgcccgagtt gtaatttgta gaatttgtct ttgattaggt 840
ccttgtctat gttccttgga acaggacgtc atagagggtg agantcccgt ttgnngagga 900
taccttttct ctgtannact ttttcnaaga gtcgagttgn ttgggaatgc agctcaaann 960
gggtngnaaa ttccatctaa agctaaatat tngncnagag accganagcg acantacagn 1020
gatggaaaga ngaaannant tgaaaagaan anngaaaant acgtgaannn nnaaanggnn 1080
nggcatttga tcnnncatgg nnntttttnc atgnn 1115

<210> SEQ ID NO 3
<211> LENGTH: 1547
<212> TYPE: DNA
<213> ORGANISM: Unknown
<220> FEATURE:
<223> OTHER INFORMATION: Description of Unknown:
DP3 16S rRNA microbial sequence

<400> SEQUENCE: 3
attgagagtt tgatcctggc tcaggatgaa cgctggcggc gtgcctaata catgcaagtc 60
gaacgcacag cgaaaggtgc ttgcaccttt caagtgagtg gcgaacgggt gagtaacacg 120
tggacaacct gcctcaaggc tggggataac atttggaaac agatgctaat accgaataaa 180
actcagtgtc gcatgacaca aagttaaaag gcgctttggc gtcacctaga gatggatccg 240
cggtgcatta gttagttggt ggggtaaagg cctaccaaga caatgatgca tagccgagtt 300
gagagactga tcggccacat tgggactgag acacggccca aactcctacg ggaggctgca 360
gtagggaatc ttccacaatg ggcgaaagcc tgatggagca acgccgcgtg tgtgatgaag 420

```
gctttcgggt cgtaaagcac tgttgtacgg gaagaacagc tagaataggg aatgatttta    480

gtttgacggt accataccag aaagggacgg ctaaatacgt gccagcagcc gcggtaatac    540

gtatgtcccg agcgttatcc ggatttattg ggcgtaaagc gagcgcagac ggttgattaa    600

gtctgatgtg aaagcccgga gctcaactcc ggaatggcat tggaaactgg ttaacttgag    660

tgcagtagag gtaagtggaa ctccatgtgt agcggtggaa tgcgtagata tatggaagaa    720

caccagtggc gaaggcggct tactggactg tactgacgtt gaggctcgaa agtgtgggta    780

gcaaacagga ttagataccc tggtagtcca caccgtaaac gatgaacact aggtgttagg    840

aggtttccgc ctcttagtgc cgaagctaac gcattaagtg ttccgcctgg ggagtacgac    900

cgcaaggttg aaactcaaag gaattgacgg ggacccgcac aagcggtgga gcatgtggtt    960

taattcgaag caacgcgaag aaccttacca ggtcttgaca tcctttgaag cttttagaga   1020

tagaagtgtt ctcttcggag acaaagtgac aggtggtgca tggtcgtcgt cagctcgtgt   1080

cgtgagatgt tgggttaagt cccgcaacga gcgcaaccct tattgttagt tgccagcatt   1140

cagatgggca ctctagcgag actgccggtg acaaaccgga ggaaggcggg gacgacgtca   1200

gatcatcatg ccccttatga cctgggctac acacgtgcta caatggcgta tacaacgagt   1260

tgccaacccg cgagggtgag ctaatctctt aaagtacgtc tcagttcgga ttgtagtctg   1320

caactcgact acatgaagtc ggaatcgcta gtaatcgcgg atcagcacgc cgcggtgaat   1380

acgttcccgg gtcttgtaca caccgcccgt cacaccatgg gagtttgtaa tgcccaaagc   1440

cggtggccta accttttagg aaggagccgt ctaaggcagg acagatgact ggggtgaagt   1500

cgtaacaagg tagccgtagg agaacctgcg gctggatcac ctccttt                 1547


<210> SEQ ID NO 4
<211> LENGTH: 1537
<212> TYPE: DNA
<213> ORGANISM: Unknown
<220> FEATURE:
<223> OTHER INFORMATION: Description of Unknown:
      DP4 16S rRNA microbial sequence

<400> SEQUENCE: 4

ttgaagagtt tgatcatggc tcagattgaa cgctggcggc aggcctaaca catgcaagtc     60

gagcggcagc ggaaagtagc ttgctacttt gccggcgagc ggcggacggg tgagtaatgt    120

ctgggaaact gcctgatgga gggggataac tactggaaac ggtagctaat accgcatgac    180

ctcgaaagag caaagtgggg gatcttcgga cctcacgcca tcggatgtgc ccagatggga    240

ttagctagta ggtgaggtaa tggctcacct aggcgacgat ccctagctgg tctgagagga    300

tgaccagcca cactggaact gagacacggt ccagactcct acgggaggca gcagtgggga    360

atattgcaca atgggcgcaa gcctgatgca gccatgccgc gtgtgtgaag aaggccttag    420

ggttgtaaag cactttcagc gaggaggaag gcatcatact taatacgtgt ggtgattgac    480

gttactcgca gaagaagcac cggctaactc cgtgccagca gccgcggtaa tacggagggt    540

gcaagcgtta atcggaatta ctgggcgtaa agcgcacgca ggcggtttgt taagtcagat    600

gtgaaatccc cgcgcttaac gtgggaactg catttgaaac tggcaagcta gagtcttgta    660

gaggggggta gaattccagg tgtagcggtg aaatgcgtag agatctggag gaataccggt    720

ggcgaaggcg gccccctgga caaagactga cgctcaggtg cgaaagcgtg gggagcaaac    780

aggattagat accctggtag tccacgccgt aaacgatgtc gacttggagg ttgttccctt    840

gaggagtggc ttccggagct aacgcgttaa gtcgaccgcc tggggagtac ggccgcaagg    900
```

-continued

```
ttaaaactca aatgaattga cgggggcccg cacaagcggt ggagcatgtg gtttaattcg      960

atgcaacgcg aagaacctta cctactcttg acatccacgg aatttggcag agatgcctta     1020

gtgccttcgg gaaccgtgag acaggtgctg catggctgtc gtcagctcgt gttgtgaaat     1080

gttgggttaa gtcccgcaac gagcgcaacc cttatccttt gttgccagcg attcggtcgg     1140

gaactcaaag gagactgccg gtgataaacc ggaggaaggt ggggatgacg tcaagtcatc     1200

atggccctta cgagtagggc tacacacggc tacaatggcg catacaaaga gaagcgacct     1260

cgcgagagca agcggacctc acaaagtgcg tcgtagtccg gatcggagtc tgcaactcga     1320

ctccgtgaag tcggaatcgc tagtaatcgt ggatcagaat gccacggtga atacgttccc     1380

gggccttgta cacaccgccc gtcacaccat gggagtgggt tgcaaaagaa gtaggtagct     1440

taaccttcgg gagggcgctt accactttgt gattcatgac tggggtgaag tcgtaacaag     1500

gtaaccgtag gggaacctgc ggttggatca cctcctt                              1537
```

```
<210> SEQ ID NO 5
<211> LENGTH: 1157
<212> TYPE: DNA
<213> ORGANISM: Unknown
<220> FEATURE:
<223> OTHER INFORMATION: Description of Unknown:
      DP5 ITS microbial sequence
<220> FEATURE:
<221> NAME/KEY: modified_base
<222> LOCATION: (1)..(17)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (74)..(75)
<223> OTHER INFORMATION: a, c, t, g, unknown or other
<220> FEATURE:
<221> NAME/KEY: modified_base
<222> LOCATION: (1045)..(1045)
<223> OTHER INFORMATION: a, c, t, g, unknown or other
<220> FEATURE:
<221> NAME/KEY: modified_base
<222> LOCATION: (1064)..(1064)
<223> OTHER INFORMATION: a, c, t, g, unknown or other
<220> FEATURE:
<221> NAME/KEY: modified_base
<222> LOCATION: (1072)..(1072)
<223> OTHER INFORMATION: a, c, t, g, unknown or other
<220> FEATURE:
<221> NAME/KEY: modified_base
<222> LOCATION: (1080)..(1080)
<223> OTHER INFORMATION: a, c, t, g, unknown or other
<220> FEATURE:
<221> NAME/KEY: modified_base
<222> LOCATION: (1085)..(1085)
<223> OTHER INFORMATION: a, c, t, g, unknown or other
<220> FEATURE:
<221> NAME/KEY: modified_base
<222> LOCATION: (1088)..(1089)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1105)..(1108)
<223> OTHER INFORMATION: a, c, t, g, unknown or other
<220> FEATURE:
<221> NAME/KEY: modified_base
<222> LOCATION: (1112)..(1113)
<223> OTHER INFORMATION: a, c, t, g, unknown or other
```

<220> FEATURE:
<221> NAME/KEY: modified_base
<222> LOCATION: (1117)..(1118)
<223> OTHER INFORMATION: a, c, t, g, unknown or other
<220> FEATURE:
<221> NAME/KEY: modified_base
<222> LOCATION: (1121)..(1122)
<223> OTHER INFORMATION: a, c, t, g, unknown or other
<220> FEATURE:
<221> NAME/KEY: modified_base
<222> LOCATION: (1126)..(1127)
<223> OTHER INFORMATION: a, c, t, g, unknown or other
<220> FEATURE:
<221> NAME/KEY: modified_base
<222> LOCATION: (1129)..(1131)
<223> OTHER INFORMATION: a, c, t, g, unknown or other
<220> FEATURE:
<221> NAME/KEY: modified_base
<222> LOCATION: (1138)..(1138)
<223> OTHER INFORMATION: a, c, t, g, unknown or other
<220> FEATURE:
<221> NAME/KEY: modified_base
<222> LOCATION: (1148)..(1148)
<223> OTHER INFORMATION: a, c, t, g, unknown or other
<220> FEATURE:
<221> NAME/KEY: modified_base
<222> LOCATION: (1150)..(1152)
<223> OTHER INFORMATION: a, c, t, g, unknown or other
<220> FEATURE:
<221> NAME/KEY: modified_base
<222> LOCATION: (1156)..(1157)
<223> OTHER INFORMATION: a, c, t, g, unknown or other

<400> SEQUENCE: 5
nnnnnnnnnn nnnnnnntgn ngcgcttatt gcgcggcgaa aaaaccttac acacagtgtt 60
ttttgttatt acannaactt ttgctttggt ctggactaga aatagtttgg gccagaggtt 120
actaaactaa acttcaatat ttatattgaa ttgttattta tttaattgtc aatttgttga 180
ttaaattcaa aaaatcttca aaactttcaa caacggatct cttggttctc gcatcgatga 240
agaacgcagc gaaatgcgat aagtaatatg aattgcagat tttcgtgaat catcgaatct 300
ttgaacgcac attgcgccct ctggtattcc agagggcatg cctgtttgag cgtcatttct 360
ctctcaaacc ttcgggtttg gtattgagtg atactcttag tcgaactagg cgtttgcttg 420
aaatgtattg gcatgagtgg tactggatag tgctatatga ctttcaatgt attaggttta 480
tccaactcgt tgaatagttt aatggtatat ttctcggtat tctaggctcg gccttacaat 540
ataacaaaca agtttgacct caaatcaggt aggattaccc gctgaactta agcatatcaa 600
taagcggagg aaaagaaacc aacagggatt gccttagtaa cggcgagtga agcggcaaaa 660
gctcaaattt gaaatctggc accttcggtg tccgagttgt aatttgaaga aggtaacttt 720
ggagttggct cttgtctatg ttccttggaa caggacgtca cagagggtga gaatcccgtg 780
cgatgagatg cccaattcta tgtaaagtgc tttcgaagag tcgagttgtt tgggaatgca 840
gctctaagtg ggtggtaaat tccatctaaa gctaaatatt ggcgagagac cgatagcgaa 900
caagtacagt gatggaaaga tgaaaagaac tttgaaaaga gagtgaaaaa gtacgtgaaa 960
ttgttgaaag ggaaagggct tgagatcaga cttggtattt tgcgatcctt tccttcttgg 1020
ttgggttcct cgcagcttac tgggncagca tcggtttgga tggnaggata angactaagn 1080
aatgnggnnc tacttcgngg agtgnnnnag cnntggnnga nnactnncnn nctaagancg 1140
aggactgngn nntttnn 1157

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 1572
<212> TYPE: DNA
<213> ORGANISM: Unknown
<220> FEATURE:
<223> OTHER INFORMATION: Description of Unknown:
DP9 16S rRNA microbial sequence

<400> SEQUENCE: 9

```
atgagagttt gatcttggct caggatgaac gctggcggcg tgcctaatac atgcaagtcg      60

aacgaacttc cgttaattga ttatgacgta cttgtactga ttgagatttt aacacgaagt     120

gagtggcgaa cgggtgagta acacgtgggt aacctgccca gaagtagggg ataacacctg     180

gaaacagatg ctaataccgt ataacagaga aaaccgcatg gttttctttt aaaagatggc     240

tctgctatca cttctggatg gacccgcggc gtattagcta gttggtgagg caaaggctca     300

ccaaggcagt gatacgtagc cgacctgaga gggtaatcgg ccacattggg actgagacac     360

ggcccagact cctacgggag gcagcagtag ggaatcttcc acaatggacg caagtctgat     420

ggagcaacgc cgcgtgagtg aagaagggtt tcggctcgta aagctctgtt gttaaagaag     480

aacgtgggta agagtaactg tttacccagt gacggtattt aaccagaaag ccacggctaa     540

ctacgtgcca gcagccgcgg taatacgtag gtggcaagcg ttatccggat ttattgggcg     600

taaagcgagc gcaggcggtc ttttaagtct aatgtgaaag ccttcggctc aaccgaagaa     660

gtgcattgga aactgggaga cttgagtgca gaagaggaca gtggaactcc atgtgtagcg     720

gtgaaatgcg tagatatatg gaagaacacc agtggcgaag gcggctgtct ggtctgcaac     780

tgacgctgag gctcgaaagc atgggtagcg aacaggatta gataccctgg tagtccatgc     840

cgtaaacgat gattactaag tgttggaggg tttccgccct tcagtgctgc agctaacgca     900

ttaagtaatc cgcctgggga gtacgaccgc aaggttgaaa ctcaaaagaa ttgacggggg     960

cccgcacaag cggtggagca tgtggtttaa ttcgaagcta cgcgaagaac cttaccaggt    1020

cttgacatct tctgacagtc taagagatta gaggttccct tcggggacag aatgacaggt    1080

ggtgcatggt tgtcgtcagc tcgtgtcgtg agatgttggg ttaagtcccg caacgagcgc    1140

aacccttatt actagttgcc agcattaagt tgggcactct agtgagactg ccggtgacaa    1200

accggaggaa ggtggggacg acgtcaaatc atcatgcccc ttatgacctg ggctacacac    1260

gtgctacaat ggatggtaca acgagtcgcg agaccgcgag gttaagctaa tctcttaaaa    1320

ccattctcag ttcggactgt aggctgcaac tcgcctacac gaagtcggaa tcgctagtaa    1380

tcgcggatca gcatgccgcg gtgaatacgt tcccgggcct tgtacacacc gcccgtcaca    1440

ccatgagagt ttgtaacacc caaagccggt ggggtaacct tttaggagct agccgtctaa    1500

ggtgggacag atgattaggg tgaagtcgta acaaggtagc cgtaggagaa cctgcggctg    1560
```

gatcacctcc tt 1572

<210> SEQ ID NO 10
<211> LENGTH: 1300
<212> TYPE: DNA
<213> ORGANISM: Unknown
<220> FEATURE:
<223> OTHER INFORMATION: Description of Unknown:
DP10 16S rRNA microbial sequence

<400> SEQUENCE: 10
cagatagttg gtgaggtaac ggctcaccaa ggcaacgatg cgtagccgac ctgagagggt 60
gatcggccac actgggactg agacacggcc cagactccta cgggaggcag cagtagggaa 120
tcttccgcaa tggacgaaag tctgacggag caacgccgcg tgagtgatga aggttttcgg 180
atcgtaaagc tctgttgtta gggaagaaca agtgccgttc aaatagggcg gcaccttgac 240
ggtacctaac cagaaagcca cggctaacta cgtgccagca gccgcggtaa tacgtaggtg 300
gcaagcgttg tccggaatta ttgggcgtaa agggctcgca ggcggtttct taagtctgat 360
gtgaaagccc ccggctcaac cggggagggt cattggaaac tggggaactt gagtgcagaa 420
gaggagagtg gaattccacg tgtagcggtg aaatgcgtag agatgtggag gaacaccagt 480
ggcgaaggcg actctctggt ctgtaactga cgctgaggag cgaaagcgtg gggagcgaac 540
aggattagat accctggtag tccacgccgt aaacgatgag tgctaagtgt tagggggttt 600
ccgcccctta gtgctgcagc taacgcatta agcactccgc ctggggagta cggtcgcaag 660
actgaaactc aaaggaattg acgggggccc gcacaagcgg tggagcatgt ggtttaattc 720
gaagcaacgc gaagaacctt accaggtctt gacatcctct gacaatccta gagataggac 780
gtccccttcg ggggcagagt gacaggtggt gcatggttgt cgtcagctcg tgtcgtgaga 840
tgttgggtta agtcccgcaa cgagcgcaac ccttgatctt agttgccagc attcagttgg 900
gcactctaag gtgactgccg gtgacaaacc ggaggaaggt ggggatgacg tcaaatcatc 960
atgcccctta tgacctgggc tacacacgtg ctacaatgga cagaacaaag ggcagcgaaa 1020
ccgcgaggtt aagccaatcc cacaaatctg ttctcagttc ggatcgcagt ctgcaactcg 1080
actgcgtgaa gctggaatcg ctagtaatcg cggatcagca tgccgcggtg aatacgttcc 1140
cgggccttgt acacaccgcc cgtcacacca cgagagtttg taacacccga agtcggtgag 1200
gtaacctttt aggagccagc cgccgaaggt gggacagatg attggggtga agtcgtaaca 1260
aggtagccgt atcggaaggt gcggctggat cacctccttt 1300

<210> SEQ ID NO 11
<211> LENGTH: 1419
<212> TYPE: DNA
<213> ORGANISM: Unknown
<220> FEATURE:
<223> OTHER INFORMATION: Description of Unknown:
DP11 16S rRNA microbial sequence

<400> SEQUENCE: 11
tgaagagttt gatcatggct cagattgaac gctggcggca ggcctaacac atgcaagtcg 60
agcggtagag agaagcttgc ttctcttgag agcggcggac gggtgagtaa tgcctaggaa 120
tctgcctggt agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggcgac gatccgtaac tggtctgaga ggatgatcag 300

```
tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggttgta gattaatact ctgcaatttt gacgttaccg    480

acagaataag caccggctaa ctctgtgcca gcagccgcgg taatacagag ggtgcaagcg    540

ttaatcggaa ttactgggcg taaagcgcgc gtaggtggtt cgttaagttg gatgtgaaag    600

ccccgggctc aacctgggaa ctgcattcaa aactgacgag ctagagtatg gtagagggtg    660

gtggaatttc ctgtgtagcg gtgaaatgcg tagatatagg aaggaacacc agtggcgaag    720

gcgaccacct ggactgatac tgacactgag gtgcgaaagc gtggggagca aacaggatta    780

gataccctgg tagtccacgc cgtaaacgat gtcaactagc cgttggaatc cttgagattt    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga tgggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgttatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgcgaatc agaatgtcgc ggtgaatacg ttcccgggcc   1380

ttgtacacac cgcccgtcac atcccacacg aattgcttg                          1419


<210> SEQ ID NO 12
<211> LENGTH: 1520
<212> TYPE: DNA
<213> ORGANISM: Unknown
<220> FEATURE:
<223> OTHER INFORMATION: Description of Unknown:
      DP12 16S rRNA microbial sequence

<400> SEQUENCE: 12

tacggagagt ttgatcctgg ctcaggatga acgctggcgg cgtgcttaac acatgcaagt     60

cgaacggtga agccaagctt gcttggtgga tcagtggcga acgggtgagt aacacgtgag    120

caacctgccc tggactctgg gataagcgct ggaaacggcg tctaatactg gatatgagcc    180

ttcatcgcat ggtgggggtt ggaaagattt tttggtctgg gatgggctcg cggcctatca    240

gcttgttggt gaggtaatgg ctcaccaagg cgtcgacggg tagccggcct gagagggtga    300

ccggccacac tgggactgag acacggccca gactcctacg ggaggcagca gtggggaata    360

ttgcacaatg ggcgaaagcc tgatgcagca acgccgcgtg agggatgacg gccttcgggt    420

tgtaaacctc ttttagcagg gaagaagcga aagtgacggt acctgcagaa aaagcgccgg    480

ctaactacgt gccagcagcc gcggtaatac gtagggcgca agcgttatcc ggaattattg    540

ggcgtaaaga gctcgtaggc ggtttgtcgc gtctgctgtg aaatcccgag gctcaacctc    600

gggcctgcag tgggtacggg cagactagag tgcggtaggg gagattggaa ttcctggtgt    660

agcggtggaa tgcgcagata tcaggaggaa caccgatggc gaaggcagat ctctgggccg    720

taactgacgc tgaggagcga aagggtgggg agcaaacagg cttagatacc ctggtagtcc    780

accccgtaaa cgttgggaac tagttgtggg gaccattcca cggtttccgt gacgcagcta    840

acgcattaag ttccccgcct ggggagtacg gccgcaaggc taaaactcaa aggaattgac    900
```

ggggacccgc acaagcggcg gagcatgcgg attaattcga tgcaacgcga agaaccttac 960
caaggcttga catacaccag aacgggccag aaatggtcaa ctctttggac actggtgaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtgaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380
cgtcaagtca tgaaagtcgg taacacctga agccggtggc ccaacccttg tggagggagc 1440
cgtcgaaggt gggatcggta attaggacta agtcgtaaca aggtagccgt accggaaggt 1500
gcggctggat cacctccttt 1520

<210> SEQ ID NO 13
<211> LENGTH: 1457
<212> TYPE: DNA
<213> ORGANISM: Unknown
<220> FEATURE:
<223> OTHER INFORMATION: Description of Unknown:
DP13 16S rRNA microbial sequence

<400> SEQUENCE: 13
agttagcggc ggacgggtga gtaacacgtg ggtaacctgc ctataagact gggataactc 60
cgggaaaccg gggctaatac cggataacat tttgcaccgc atggtgcgaa attgaaaggc 120
ggcttcggct gtcacttata gatggacctg cggcgcatta gctagttggt gaggtaacgg 180
ctcaccaagg cgacgatgcg tagccgacct gagagggtga tcggccacac tgggactgag 240
acacggccca gactcctacg ggaggcagca gtagggaatc ttccgcaatg gacgaaagtc 300
tgacggagca acgccgcgtg aacgatgaag gctttcgggt cgtaaagttc tgttgttagg 360
gaagaacaag tgctagttga ataagctggc accttgacgg tacctaacca gaaagccacg 420
gctaactacg tgccagcagc cgcggtaata cgtaggtggc aagcgttatc cggaattatt 480
gggcgtaaag cgcgcgcagg tggtttctta agtctgatgt gaaagcccac ggctcaaccg 540
tggagggtca ttggaaactg ggagacttga gtgcagaaga ggaaagtgga attccatgtg 600
tagcggtgaa atgcgtagag atatggagga acaccagtgg cgaaggcgac tttctggtct 660
gcaactgaca ctgaggcgcg aaagcgtggg gagcaaacag gattagatac cctggtagtc 720
cacgccgtaa acgatgagtg ctaagtgtta gagggtttcc gccctttagt gctgaagtta 780
acgcattaag cactccgcct ggggagtacg gccgcaaggc tgaaactcaa aggaattgac 840
gggggcccgc acaagcggtg gagcatgtgg tttaattcga agcaacgcga agaaccttac 900
caggtcttga catcctctga aaccctaga gatagggctt ccccttcggg ggcagagtga 960
caggtggtgc atggttgtcg tcagctcgtg tcgtgagatg ttgggttaag tcccgcaacg 1020
agcgcaaccc ttgatcttag ttgccatcat taagttgggc actctaaggt gactgccggt 1080
gacaaaccgg aggaaggtgg ggatgacgtc aaatcatcat gccccttatg acctgggcta 1140
cacacgtgct acaatggacg gtacaaagag tcgcaagacc gcgaggtgga gctaatctca 1200
taaaaccgtt ctcagttcgg attgtaggct gcaactcgcc tacatgaagc tggaatcgct 1260
agtaatcgcg gatcagcatg ccgcggtgaa tacgttcccg ggccttgtac acaccgcccg 1320
tcacaccacg agagtttgta acacccgaag tcggtggggt aacctttttgg agccagccgc 1380 ctaaggtggg acagatgatt ggggtgaagt cgtaacaagg tagccgtatc ggaaggtgcg 1440
gctggatcac ctccttt 1457

<210> SEQ ID NO 14
<211> LENGTH: 1525
<212> TYPE: DNA
<213> ORGANISM: Unknown
<220> FEATURE:
<223> OTHER INFORMATION: Description of Unknown:
DP14 16S rRNA microbial sequence

<400> SEQUENCE: 14
tacggagagt ttgatcctgg ctcaggatga acgctggcgg cgtgcttaac acatgcaagt 60
cgaacgatga cttctgtgct tgcacagaat gattagtggc gaacgggtga gtaacacgtg 120
agtaacctgc ccttaacttc gggataagcc tgggaaaccg ggtctaatac cggatacgac 180
ctcctggcgc atgccatggt ggtggaaagc tttagcggtt ttggatggac tcgcggccta 240
tcagcttgtt ggttggggta atggcccacc aaggcgacga cgggtagccg gcctgagagg 300
gtgaccggcc acactgggac tgagacacgg cccagactcc tacgggaggc agcagtgggg 360
aatattgcac aatgggcgaa agcctgatgc agcgacgccg cgtgagggat gacggccttc 420
gggttgtaaa cctctttcag cagggaagaa gcgaaagtga cggtacctgc agaagaagcg 480
ccggctaact acgtgccagc agccgcggta atacgtaggg cgcaagcgtt atccggaatt 540
attgggcgta aagagctcgt aggcggtttg tcgcgtctgc tgtgaaagcc cggggctcaa 600
ccccgggtct gcagtgggta cgggcagact agagtgcagt aggggagact ggaattcctg 660
gtgtagcggt gaaatgcgca gatatcagga ggaacaccga tggcgaaggc aggtctctgg 720
gctgtaactg acgctgagga gcgaaagcat ggggagcgaa caggattaga taccctggta 780
gtccatgccg taaacgttgg gcactaggtg tgggggacat tccacgtttt ccgcgccgta 840
gctaacgcat taagtgcccc gcctggggag tacggccgca aggctaaaac tcaaaggaat 900
tgacgggggc ccgcacaagc ggcggagcat gcggattaat tcgatgcaac gcgaagaacc 960
ttaccaaggc ttgacatgaa ccggtaagac ctggaaacag gtccccccact tgtggccggt 1020 ttacaggtgg tgcatggttg tcgtcagctc gtgtcgtgag atgttgggtt aagtcccgca 1080
acgagcgcaa ccctcgttct atgttgccag cgggttatgc cggggactca taggagactg 1140
ccggggtcaa ctcggaggaa ggtggggacg acgtcaaatc atcatgcccc ttatgtcttg 1200
ggcttcacgc atgctacaat ggccggtaca aagggttgcg atactgtgag gtggagctaa 1260
tcccaaaaag ccggtctcag ttcggattga ggtctgcaac tcgacctcat gaagttggag 1320
tcgctagtaa tcgcagatca gcaacgctgc ggtgaatacg ttcccgggcc ttgtacacac 1380
cgcccgtcaa gtcacgaaag ttggtaacac ccgaagccgg tggcctaacc ccttgtggga 1440
gggagccgtc gaaggtggga ccggcgattg ggacaagtcg taacaaggta gccgtaccgg 1500
aaggtgcggc tggatcacct ccttt 1525

<210> SEQ ID NO 15
<211> LENGTH: 1520
<212> TYPE: DNA
<213> ORGANISM: Unknown
<220> FEATURE:
<223> OTHER INFORMATION: Description of Unknown:
DP15 16S rRNA microbial sequence

<400> SEQUENCE: 15
tacggagagt ttgatcctgg ctcaggacga acgctggcgg cgtgcttaac acatgcaagt 60
cgaacgatga tcaggagctt gctcctgtga ttagtggcga acgggtgagt aacacgtgag 120
taacctgccc ctgactctgg gataagcgtt ggaaacgacg tctaatactg gatatgatca 180
ctggccgcat ggtctggtgg tggaaagatt ttttggttgg ggatggactc gcggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggccttcggg 420
ttgtaaacct cttttagtag ggaagaagcg aaagtgacgg tacctgcaga aaaagcaccg 480
gctaactacg tgccagcagc cgcggtaata cgtagggtgc aagcgttgtc cggaattatt 540
gggcgtaaag agctcgtagg cggtttgtcg cgtctgctgt gaaatcccga ggctcaacct 600
cgggcttgca gtgggtacgg gcagactaga gtgcggtagg ggagattgga attcctggtg 660
tagcggtgga atgcgcagat atcaggagga acaccgatgg cgaaggcaga tctctgggcc 720
gtaactgacg ctgaggagcg aaagcgtggg gagcgaacag gattagatac cctggtagtc 780
cacgccgtaa acgttgggcg ctagatgtag ggacctttcc acggtttctg tgtcgtagct 840
aacgcattaa gcgccccgcc tggggagtac ggccgcaagg ctaaaactca aaggaattga 900
cgggggcccg cacaagcggc ggagcatgcg gattaattcg atgcaacgcg aagaacctta 960
ccaaggcttg acatacaccg gaaacggcca gagatggtcg ccccctgtg gtcggtgtac 1020 aggtggtgca tggttgtcgt cagctcgtgt cgtgagatgt tgggttaagt cccgcaacga 1080
gcgcaaccct cgttctatgt tgccagcgcg ttatggcggg gactcatagg agactgccgg 1140
ggtcaactcg gaggaaggtg gggatgacgt caaatcatca tgccccttat gtcttgggct 1200
tcacgcatgc tacaatggcc ggtacaaagg gctgcgatac cgtaaggtgg agcgaatccc 1260
aaaaagccgg tctcagttcg gattgaggtc tgcaactcga cctcatgaag tcggagtcgc 1320
tagtaatcgc agatcagcaa cgctgcggtg aatacgttcc cgggccttgt acacaccgcc 1380
cgtcaagtca tgaaagtcgg taacacccga agccggtggc ctaacccttg tggaaggagc 1440
cgtcgaaggt gggatcggtg attaggacta agtcgtaaca aggtagccgt accggaaggt 1500
gcggctggat cacctccttt 1520

<210> SEQ ID NO 16

<400> SEQUENCE: 16

000

<210> SEQ ID NO 17
<211> LENGTH: 898
<212> TYPE: DNA
<213> ORGANISM: Unknown
<220> FEATURE:
<223> OTHER INFORMATION: Description of Unknown:
DP17 16S rRNA microbial sequence

<400> SEQUENCE: 17
gtgattgacg ttactcgcag aagaagcacc ggctaactcc gtgccagcag ccgcggtaat 60
acggagggtg caagcgttaa tcggaattac tgggcgtaaa gcgcacgcag gcggtttgtt 120
aagtcagatg tgaaatcccc gcgcttaacg tgggaactgc atttgaaact ggcaagctag 180
agtcttgtag aggggggtag aattccaggt gtagcggtga aatgcgtaga gatctggagg 240
aataccggtg gcgaaggcgg ccccctggac aaagactgac gctcaggtgc gaaagcgtgg 300
ggagcaaaca ggattagata ccctggtagt ccacgctgta aacgatgtcg acttggaggt 360
tgtgcccttg aggcgtggct tccggagcta acgcgttaag tcgaccgcct ggggagtacg 420
gccgcaaggt taaaactcaa atgaattgac gggggcccgc acaagcggtg gagcatgtgg 480
tttaattcga tgcaacgcga agaaccttac ctactcttga catccacgga attcgccaga 540
gatggcttag tgccttcggg aaccgtgaga caggtgctgc atggctgtcg tcagctcgtg 600
ttgtgaaatg ttgggttaag tcccgcaacg agcgcaaccc ttatcctttg ttgccagcac 660
gtaatggtgg gaactcaaag gagactgccg gtgataaacc ggaggaaggt ggggatgacg 720
tcaagtcatc atggccctta cgagtagggc tacacacgtg ctacaatggc atatacaaag 780
agaagcgaac tcgcgagagc aagcggacct cataaagtat gtcgtagtcc ggattggagt 840
ctgcaactcg actccatgaa gtcggaatcg ctagtaatcg tagatcagaa tgctacgg 898

<210> SEQ ID NO 18
<211> LENGTH: 1532
<212> TYPE: DNA
<213> ORGANISM: Unknown
<220> FEATURE:
<223> OTHER INFORMATION: Description of Unknown:
DP18 16S rRNA microbial sequence

<400> SEQUENCE: 18
tgaagagttt gatcatggct cagattgaac gctggcggca ggcctaacac atgcaagtcg 60
agcggatgaa aggagcttgc tcctggattc agcggcggac gggtgagtaa tgcctaggaa 120
tctgcctggt agtgggggac aacgtttcga aaggaacgct aataccgcat acgtcctacg 180
ggagaaagca ggggaccttc gggccttgcg ctatcagatg agcctaggtc ggattagcta 240
gttggtgagg taatggctca ccaaggcgac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcagta aattaatact ttgctgtttt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggtg 660
gtggaatttc ctgtgtagcg gtgaaatgcg tagatatagg aaggaacacc agtggcgaag 720
gcgaccacct ggactgatac tgacactgag gtgcgaaagc gtggggagca aacaggatta 780
gataccctgg tagtccacgc cgtaaacgat gtcaactagc cgttgggagc cttgagctct 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc cagagatgga ttggtgcctt 1020
cgggaacatt gagacaggtg ctgcatggct gtcgtcagct cgtgtcgtga gatgttgggt 1080
taagtcccgt aacgagcgca acccttgtcc ttagttacca gcacgttatg gtgggcactc 1140
taaggagact gccggtgaca aaccggagga aggtggggat gacgtcaagt catcatggcc 1200
cttacggcct gggctacaca cgtgctacaa tggtcggtac aaagggttgc caagccgcga 1260
ggtggagcta atcccataaa accgatcgta gtccggatcg cagtctgcaa ctcgactgcg 1320
tgaagtcgga atcgctagta atcgcgaatc agaatgtcgc ggtgaatacg ttcccgggcc 1380
ttgtacacac cgcccgtcac accatgggag tgggttgcac cagaagtagc tagtctaacc 1440

-continued ttcgggagga cggttaccac ggtgtgattc atgactgggg tgaagtcgta acaaggtagc 1500
cgtaggggaa cctgcggctg gatcacctcc tt 1532

<210> SEQ ID NO 19
<211> LENGTH: 1520
<212> TYPE: DNA
<213> ORGANISM: Unknown
<220> FEATURE:
<223> OTHER INFORMATION: Description of Unknown:
DP19 16S rRNA microbial sequence

<400> SEQUENCE: 19
tacggagagt ttgatcctgg ctcaggacga acgctggcgg cgtgcttaac acatgcaagt 60
cgaacgatga tgcccagctt gctgggtgga ttagtggcga acgggtgagt aacacgtgag 120
taacctgccc ctgactctgg gataagcgtt ggaaacgacg tctaatactg gatacgactg 180
ccggccgcat ggtctggtgg tggaaagatt ttttggttgg ggatggactc gcggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggccttcggg 420
ttgtaaacct cttttagtag ggaagaagcg aaagtgacgg tacctgcaga aaaagcaccg 480
gctaactacg tgccagcagc cgcggtaata cgtagggtgc aagcgttgtc cggaattatt 540
gggcgtaaag agctcgtagg cggtttgtcg cgtctgctgt gaaatcccga ggctcaacct 600
cgggcttgca gtgggtacgg gcagactaga gtgcggtagg ggagattgga attcctggtg 660
tagcggtgga atgcgcagat atcaggagga acaccgatgg cgaaggcaga tctctgggcc 720
gtaactgacg ctgaggagcg aaagcgtggg gagcgaacag gattagatac cctggtagtc 780
cacgccgtaa acgttgggcg ctagatgtag ggacctttcc acggtttctg tgtcgtagct 840
aacgcattaa gcgccccgcc tggggagtac ggccgcaagg ctaaaactca aaggaattga 900
cgggggcccg cacaagcggc ggagcatgcg gattaattcg atgcaacgcg aagaacctta 960
ccaaggcttg acatacaccg gaaacggcca gagatggtcg ccccccttgtg gtcggtgtac 1020 aggtggtgca tggttgtcgt cagctcgtgt cgtgagatgt tgggttaagt cccgcaacga 1080
gcgcaaccct cgttctatgt tgccagcgcg ttatggcggg gactcatagg agactgccgg 1140
ggtcaactcg gaggaaggtg gggatgacgt caaatcatca tgccccttat gtcttgggct 1200
tcacgcatgc tacaatggcc ggtacaaagg gctgcgatac cgtaaggtgg agcgaatccc 1260
aaaaagccgg tctcagttcg gattgaggtc tgcaactcga cctcatgaag tcggagtcgc 1320
tagtaatcgc agatcagcaa cgctgcggtg aatacgttcc cgggccttgt acacaccgcc 1380
cgtcaagtca tgaaagtcgg taacacccga agccggtggc ctaacccttg tggaaggagc 1440
cgtcgaaggt gggatcggtg attaggacta agtcgtaaca aggtagccgt accggaaggt 1500
gcggctggat cacctccttt 1520

<210> SEQ ID NO 20
<211> LENGTH: 1543
<212> TYPE: DNA
<213> ORGANISM: Unknown
<220> FEATURE:
<223> OTHER INFORMATION: Description of Unknown:
DP20 16S rRNA microbial sequence

<400> SEQUENCE: 20
tgaagagttt gatcctggct cagagtgaac gctggcggta ggcctaacac atgcaagtcg 60

```
aacggcagca cagtaagagc ttgctcttat gggtggcgag tggcggacgg gtgaggaata    120

catcggaatc taccttttcg tgggggataa cgtagggaaa cttacgctaa taccgcatac    180

gaccttcggg tgaaagcagg ggaccttcgg gccttgcgcg gatagatgag ccgatgtcgg    240

attagctagt tggcggggta aaggcccacc aaggcgacga tccgtagctg gtctgagagg    300

atgatcagcc acactggaac tgagacacgg tccagactcc tacgggaggc agcagtgggg    360

aatattggac aatgggcgca agcctgatcc agccataccg cgtgggtgaa gaaggccttc    420

gggttgtaaa gcccttttgt tgggaaagaa aagcagtcgg ctaatacccg gttgttctga    480

cggtacccaa agaataagca ccggctaact tcgtgccagc agccgcggta atacgaaggg    540

tgcaagcgtt actcggaatt actgggcgta aagcgtgcgt aggtggttgt ttaagtctgt    600

tgtgaaagcc ctgggctcaa cctgggaatt gcagtggata ctgggcgact agagtgtggt    660

agagggtagt ggaattcccg gtgtagcagt gaaatgcgta gagatcggga ggaacatcca    720

tggcgaaggc agctacctgg accaacactg acactgaggc acgaaagcgt ggggagcaaa    780

caggattaga taccctggta gtccacgccc taaacgatgc gaactggatg ttgggtgcaa    840

tttggcacgc agtatcgaag ctaacgcgtt aagttcgccg cctggggagt acggtcgcaa    900

gactgaaact caaaggaatt gacgggggcc cgcacaagcg gtggagtatg tggtttaatt    960

cgatgcaacg cgaagaacct tacctggtct tgacatgtcg agaactttcc agagatggat   1020

tggtgccttc gggaactcga acacaggtgc tgcatggctg tcgtcagctc gtgtcgtgag   1080

atgttgggtt aagtcccgca acgagcgcaa cccttgtcct tagttgccag cacgtaatgg   1140

tgggaactct aaggagaccg ccggtgacaa accggaggaa ggtggggatg acgtcaagtc   1200

atcatggccc ttacgaccag ggctacacac gtactacaat ggtagggaca gagggctgca   1260

aacccgcgag ggcaagccaa tcccagaaac cctatctcag tccggattgg agtctgcaac   1320

tcgactccat gaagtcggaa tcgctagtaa tcgcagatca gcattgctgc ggtgaatacg   1380

ttcccgggcc ttgtacacac cgcccgtcac accatgggag tttgttgcac cagaagcagg   1440

tagcttaacc ttcgggaggg cgcttgccac ggtgtggccg atgactgggg tgaagtcgta   1500

acaaggtagc cgtatcggaa ggtgcggctg gatcacctcc ttt                     1543
```

<210> SEQ ID NO 21

<400> SEQUENCE: 21

000

<210> SEQ ID NO 22
<211> LENGTH: 1539
<212> TYPE: DNA
<213> ORGANISM: Unknown
<220> FEATURE:
<223> OTHER INFORMATION: Description of Unknown:
DP22 16S rRNA microbial sequence

<400> SEQUENCE: 22

```
ttgaagagtt tgatcatggc tcagattgaa cgctggcggc aggcctaaca catgcaagtc     60

gagcggcagc gggaagtagc ttgctacttt gccggcgagc ggcggacggg tgagtaatgt    120

ctgggaaact gcctgatgga gggggataac tactggaaac ggtagctaat accgcatgac    180

ctcgcaagag caaagtgggg gaccttcggg cctcacgcca tcggatgtgc ccagatggga    240

ttagctagta ggtgaggtaa tggctcacct aggcgacgat ccctagctgg tctgagagga    300
```

-continued tgaccagcca cactggaact gagacacggt ccagactcct acgggaggca gcagtgggga 360
atattgcaca atgggcgcaa gcctgatgca gccatgccgc gtgtgtgaag aaggccttag 420
ggttgtaaag cactttcagc gaggaggaag ggttcagtgt taatagcact gaacattgac 480
gttactcgca gaagaagcac cggctaactc cgtgccagca gccgcggtaa tacggagggt 540
gcaagcgtta atcggaatta ctgggcgtaa agcgcacgca ggcggtttgt taagtcagat 600
gtgaaatccc cgagcttaac ttgggaactg catttgaaac tggcaagcta gagtcttgta 660
gaggggggta gaattccagg tgtagcggtg aaatgcgtag agatctggag gaataccggt 720
ggcgaaggcg gccccctgga caaagactga cgctcaggtg cgaaagcgtg gggagcaaac 780
aggattagat accctggtag tccacgctgt aaacgatgtc gacttggagg ttgtgccctt 840
gaggcgtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctactcttg acatccagag aattcgctag agatagctta 1020
gtgccttcgg gaactctgag acaggtgctg catggctgtc gtcagctcgt gttgtgaaat 1080
gttgggttaa gtcccgcaac gagcgcaacc cttatccttt gttgccagcg agtaatgtcg 1140
ggaactcaaa ggagactgcc ggtgataaac cggaggaagg tggggatgac gtcaagtcat 1200
catggccctt acgagtaggg ctacacacgt gctacaatgg catatacaaa gagaagcaaa 1260
ctcgcgagag caagcggacc tcataaagta tgtcgtagtc cggattggag tctgcaactc 1320
gactccatga agtcggaatc gctagtaatc gtagatcaga atgctacggt gaatacgttc 1380
ccgggccttg tacacaccgc ccgtcacacc atgggagtgg gttgcaaaag aagtaggtag 1440
cttaaccttc gggagggcgc ttaccacttt gtgattcatg actggggtga agtcgtaaca 1500
aggtaaccgt aggggaacct gcggttggat cacctcctt 1539

<210> SEQ ID NO 23
<211> LENGTH: 1536
<212> TYPE: DNA
<213> ORGANISM: Unknown
<220> FEATURE:
<223> OTHER INFORMATION: Description of Unknown:
DP23 16S rRNA microbial sequence

<400> SEQUENCE: 23
ttgaagagtt tgatcatggc tcagattgaa cgctggcggc aggcctaaca catgcaagtc 60
gaacggtagc acagagagct tgctcttggg tgacgagtgg cggacgggtg agtaatgtct 120
gggaaactgc ccgatggagg gggataacta ctggaaacgg tagctaatac cgcataacgt 180
cttcggacca aagtggggga ccttcgggcc tcacaccatc ggatgtgccc agatgggatt 240
agctagtagg tggggtaatg gctcacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatacggtta ataaccgtgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtca agtcagatgt 600
gaaatccccg ggcttaacct gggaactgca tttgaaactg gcaggcttga gtctcgtaga 660
ggggggtaga attccaggtg tagcggtgaa atgcgtagag atctggagga ataccggtgg 720
cgaaggcggc cccctggacg aagactgacg ctcaggtgcg aaagcgtggg gagcaaacag 780
gattagatac cctggtagtc cacgctgtaa acgatgtcga cttggaggtt gtgcccttga 840
ggcgtggctt ccggagctaa cgcgttaagt cgaccgcctg gggagtacgg ccgcaaggtt 900
aaaactcaaa tgaattgacg gggcccgca caagcggtgg agcatgtggt ttaattcgat 960
gcaacgcgaa gaaccttacc tggccttgac atccacagaa ttcggcagag atgccttagt 1020
gccttcggga actgtgagac aggtgctgca tggctgtcgt cagctcgtgt tgtgaaatgt 1080
tgggttaagt cccgcaacga gcgcaaccct tatcctttgt tgccagcgat tcggtcggga 1140
actcaaagga gactgccggt gataaaccgg aggaaggtgg ggatgacgtc aagtcatcat 1200
ggcccttacg gccagggcta cacacgtgct acaatggcgc atacaaagag aagcgacctc 1260
gcgagagcaa gcggacctca taaagtgcgt cgtagtccgg atcggagtct gcaactcgac 1320
tccgtgaagt cggaatcgct agtaatcgta gatcagaatg ctacggtgaa tacgttcccg 1380
ggccttgtac acaccgcccg tcacaccatg ggagtgggtt gcaaaagaag taggtagctt 1440
aaccttcggg agggcgctta ccactttgtg attcatgact ggggtgaagt cgtaacaagg 1500
taaccgtagg ggaacctgcg gttggatcac ctcctt 1536

<210> SEQ ID NO 24
<211> LENGTH: 1315
<212> TYPE: DNA
<213> ORGANISM: Unknown
<220> FEATURE:
<223> OTHER INFORMATION: Description of Unknown:
DP24 16S rRNA microbial sequence

<400> SEQUENCE: 24
agcatttgat tatggtgctt actgattgct atctaggggt ttaacacatg ctagtcaatg 60
atcttttaga ttatggcgta cgggctagga atacttagaa tgataactct atgatcgcag 120
taatagcgta aaaggtataa taccgcatag aggttcgctt cgtatctaat aggtagttgg 180
tgaggtaaag ctcaacaagc cgatgatgag taatattgga tgaaagtctt aaatatagca 240
gtggaaatga aaaagtccac cgttatttat taacgcagca gtggagaatc gtcgtaatgt 300
gcagtattca tttatggata agcatgaacg cgctacctag attcggatag gagatagcat 360
cttctaccga taaaagaact tagaataatg atctagttct cattagtggg tgacaatcgc 420
cgtgccagca tcagcggtaa aacggcttcc gcaagcaata gtaatttaaa ttggtgtaaa 480
gggtacgtag ccggccttat taggctagag ttagatacgg gtaagtacaa tacttggagt 540
agggctgata tcttatgatc ccaaggggag tgctaaaggc gaaggcaact tactggtaat 600
aactgacggt gaggtacgaa ggtcagggca tggaaagaga ttagatacct cattactcct 660
gacagtaaac gatgtagatt aaagattgga ataattctgt cttaacgcta acgcattaaa 720
tctaccacct gtagagtata gtcgcaaggc cgaaatacaa ataattagac ggctctagag 780
caaacggagt gaagcatgtt atttaatacg ataacccgcg taaaatctta ccagttcttg 840
aatcttagac aggtgttgca tggttgtcgt cagctcgtgc taatggtgtc tggttaattc 900
caaataacga gcgcaatcct tacttctagt tttctaggag tctccatttg acatacgtgt 960
caatggttta aggaatatga caaaccctca tggcccttat ggactgggca atagacgtgc 1020
cacaagaatc tagacaaaat gacgcgaaat ggtaacaatg agctaatcat caaagaagat 1080
taatgtacga attatgggct ggaactcgcc catatgaagt aggaattccg agtaatcgcg 1140
tatcagaacg acgcggtgaa catcatctct ggagtgtact aactgctcgt cacgggacga 1200
aagggagtgt attatgaagt ggggctaatt ggttaactcc ggtgagtgtc acgaataatc 1260
cttcccgatt gttctgaagt cgaaacaagg taaccgtaag ggaacttgcg gttga 1315

<210> SEQ ID NO 25
<211> LENGTH: 1520
<212> TYPE: DNA
<213> ORGANISM: Unknown
<220> FEATURE:
<223> OTHER INFORMATION: Description of Unknown:
DP25 16S rRNA microbial sequence

<400> SEQUENCE: 25
tacggagagt ttgatcctgg ctcaggatga acgctggcgg cgtgcttaac acatgcaagt 60
cgaacggtga agccaagctt gcttggtgga tcagtggcga acgggtgagt aacacgtgag 120
caacctgccc tggactctgg gataagcgct ggaaacggcg tctaatactg gatatgagct 180
ccttccgcat ggtgggggtt ggaaagattt ttcggtctgg gatgggctcg cggcctatca 240
gcttgttggt gaggtaatgg ctcaccaagg cgtcgacggg tagccggcct gagagggtga 300
ccggccacac tgggactgag acacggccca gactcctacg ggaggcagca gtggggaata 360
ttgcacaatg ggcggaagcc tgatgcagca acgccgcgtg agggatgacg gccttcgggt 420
tgtaaacctc ttttagcagg gaagaagcga aagtgacggt acctgcagaa aaagcgccgg 480
ctaactacgt gccagcagcc gcggtaatac gtagggcgca agcgttatcc ggaattattg 540
ggcgtaaaga gctcgtaggc ggtttgtcgc gtctgctgtg aaatcccgag gctcaacctc 600
gggcctgcag tgggtacggg cagactagag tgcggtaggg gagattggaa ttcctggtgt 660
agcggtggaa tgcgcagata tcaggaggaa caccgatggc gaaggcagat ctctgggccg 720
taactgacgc tgaggagcga aagggtgggg agcaaacagg cttagatacc ctggtagtcc 780
accccgtaaa cgttgggaac tagttgtggg gaccattcca cggtttccgt gacgcagcta 840
acgcattaag ttccccgcct ggggagtacg gccgcaaggc taaaactcaa aggaattgac 900
ggggacccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggatgacgt caaatcatca tgccccttat gtcttgggct 1200
tcacgcatgc tacaatggcc ggtacaaagg gctgcaatac cgtaaggtgg agcgaatccc 1260
aaaaagccgg tcccagttcg gattgaggtc tgcaactcga cctcatgaag tcggagtcgc 1320
tagtaatcgc agatcagcaa cgctgcggtg aatacgttcc cgggtcttgt acacaccgcc 1380
cgtcaagtca tgaaagtcgg taacacctga agccggtggc ccaacccttg tggagggagc 1440
cgtcgaaggt gggatcggta attaggacta agtcgtaaca aggtagccgt accggaaggt 1500
gcggctggat cacctccttt 1520

<210> SEQ ID NO 26
<211> LENGTH: 1482
<212> TYPE: DNA
<213> ORGANISM: Unknown
<220> FEATURE:
<223> OTHER INFORMATION: Description of Unknown:
DP26 16S rRNA microbial sequence

<400> SEQUENCE: 26
cttgagagtt tgatcctggc tcagagcgaa cgctggcggc aggcttaaca catgcaagtc 60
gagcgggcat cttcggatgt cagcggcaga cgggtgagta acacgtggga acgtaccctt 120
cggttcggaa taacgctggg aaactagcgc taataccgga tacgcccttt tggggaaagg 180
tttactgccg aaggatcggc ccgcgtctga ttagctagtt ggtggggtaa cggcctacca 240
aggcgacgat cagtagctgg tctgagagga tgatcagcca cactgggact gagacacggc 300
ccagactcct acgggaggca gcagtgggga atattggaca atgggcgcaa gcctgatcca 360
gccatgccgc gtgagtgatg aaggccttag ggttgtaaag ctcttttgtc cgggacgata 420
atgacggtac cggaagaata agccccggct aacttcgtgc cagcagccgc ggtaatacga 480
agggggctag cgttgctcgg aatcactggg cgtaaagggc gcgtaggcgg ccattcaagt 540
cgggggtgaa agcctgtggc tcaaccacag aattgccttc gatactgttt ggcttgagta 600
tggtagaggt tggtggaact gcgagtgtag aggtgaaatt cgtagatatt cgcaagaaca 660
ccggtggcga aggcggccaa ctggaccatt actgacgctg aggcgcgaaa gcgtggggag 720
caaacaggat tagataccct ggtagtccac gccgtaaacg atgaatgcca gctgttgggg 780
tgcttgcacc tcagtagcgc agctaacgct ttaagcattc cgcctgggga gtacggtcgc 840
aagattaaaa ctcaaaggaa ttgacggggg cccgcacaag cggtggagca tgtggtttaa 900
ttcgaagcaa cgcgcagaac cttaccatcc cttgacatgg catgttaccc ggagagattc 960
ggggtccact tcggtggcgt gcacacaggt gctgcatggc tgtcgtcagc tcgtgtcgtg 1020
agatgttggg ttaagtcccg caacgagcgc aacccacgtc cttagttgcc atcattcagt 1080
tgggcactct agggagactg ccggtgataa gccgcgagga aggtgtggat gacgtcaagt 1140
cctcatggcc cttacgggat gggctacaca cgtgctacaa tggcggtgac agtgggacgc 1200
gaaggagcga tctggagcaa atccccaaaa accgtctcag ttcagattgc actctgcaac 1260
tcgagtgcat gaaggcggaa tcgctagtaa tcgtggatca gcatgccacg gtgaatacgt 1320
tcccgggcct tgtacacacc gcccgtcaca ccatgggagt tggtcttacc cgacggcgct 1380
gcgccaaccg caaggaggca ggcgaccacg gtagggtcag cgactggggt gaagtcgtaa 1440
caaggtagcc gtaggggaac ctgcggctgg atcacctcct tt 1482

<210> SEQ ID NO 27
<211> LENGTH: 935
<212> TYPE: DNA
<213> ORGANISM: Unknown
<220> FEATURE:
<223> OTHER INFORMATION: Description of Unknown:
DP27 16S rRNA microbial sequence

<400> SEQUENCE: 27
cttgagagtt tgatcctggc tcagaacgaa cgctggcggc atgcctaaca catgcaagtc 60
gaacgatgct ttcgggcata gtggcgcacg ggtgcgtaac gcgtgggaat ctgccctcag 120
gttcggaata acagctggaa acggctgcta ataccggatg atatcgcaag atcaaagatt 180
tatcgcctga ggatgagccc gcgttggatt aggtagttgg tggggtaaag gcctaccaag 240
ccgacgatcc atagctggtc tgagaggatg atcagccaca ctgggactga gacacggccc 300
agactcctac gggaggcagc agtggggaat attggacaat gggcgcaagc ctgatccagc 360
aatgccgcgt gagtgatgaa ggccctaggg ttgtaaagct cttttacccg ggaagataat 420
gactgtaccg ggagaataag ccccggctaa ctccgtgcca gcagccgcgg taatacggag 480
ggggctagcg ttgttcggaa ttactgggcg taaagcgcac gtaggcggct ttgtaagtca 540
gaggtgaaag cctggagctc aactccagaa ctgcctttga gactgcatcg cttgaatcca 600
ggagaggtca gtggaattcc gagtgtagag gtgaaattcg tagatattcg gaagaacacc 660
agtggcgaag gcggctgact ggactggtat tgacgctgag gtgcgaaagc gtggggagca 720
aacaggatta gataccctgg tagtccacgc cgtaaacgat gataactagc tgtccgggca 780
cttggtgctt gggtggcgca gctaacgcat taagttatcc gcctggggag tacggccgca 840
aggttaaaac tcaaaggaat tgacgggggc ctgcacaagc ggtggagcat gtggtttaat 900
tcgaagcaac gcgcagaacc ttaccagcgt ttgac 935

<210> SEQ ID NO 28
<211> LENGTH: 931
<212> TYPE: DNA
<213> ORGANISM: Unknown
<220> FEATURE:
<223> OTHER INFORMATION: Description of Unknown:
DP28 16S rRNA microbial sequence

<400> SEQUENCE: 28
atagtcgggg gcatcagtat tcaattgtca gaggtgaaat tcttggattt attgaagact 60
aactactgcg aaagcatttg ccaaggatgt tttcattaat cagtgaacga aagttagggg 120
atcgaagacg atcagatacc gtcgtagtct taaccataaa ctatgccgac tagggatcgg 180
gcgatgttat cattttgact cgctcggcac cttacgagaa atcaaagtct ttgggttctg 240
gggggagtat ggtcgcaagg ctgaaactta aagaaattga cggaagggca ccaccaggcg 300
tggagcctgc ggcttaattt gactcaacac ggggaaactc accaggtcca gacacaataa 360
ggattgacag attgagagct ctttcttgat tttgtgggtg gtggtgcatg gccgttctta 420
gttggtggag tgatttgtct gcttaattgc gataacgaac gagaccttaa cctgctaaat 480
agcccggccc gctttggcgg gtcgccggct tcttagaggg actatcggct caagccgatg 540
gaagtttgag gcaataacag gtctgtgatg cccttagatg ttctgggccg cacgcgcgct 600
acactgacag agccaacgag ttcatttcct tgcccggaag ggttgggtaa tcttgttaaa 660
ctctgtcgtg ctggggatag agcattgcaa ttattgctct tcaacgagga atgcctagta 720
agcgtacgtc atcagcgtgc gttgattacg tccctgccct ttgtacacac cgcccgtcgc 780
tactaccgat tgaatggctg agtgaggcct tcggactggc ccagggaggt cggcaacgac 840
cacccagggc cggaaagttg gtcaaactcc gtcatttaga ggaagtaaaa gtcgtaacaa 900
ggtttccgta ggtgaacctg cggaaggatc a 931

<210> SEQ ID NO 29
<211> LENGTH: 1002
<212> TYPE: DNA
<213> ORGANISM: Unknown
<220> FEATURE:
<223> OTHER INFORMATION: Description of Unknown:
DP29 16S rRNA microbial sequence

<400> SEQUENCE: 29
tacggagagt ttgatcctgg ctcaggacga acgctggcgg cgtgcttaac acatgcaagt 60
cgaacgatga agcccagctt gctgggttga ttagtggcga acgggtgagt aacacgtgag 120
caacgtgccc ataactctgg gataacctcc ggaaacggtg gctaatactg gatatctaac 180
acgatcgcat ggtctgtgtt tggaaagatt ttttggttat ggatcggctc acggcctatc 240
agcttgttgg tgaggtaatg gctcaccaag gcgacgacgg gtagccggcc tgagagggtg 300
accggccaca ctgggactga gacacggccc agactcctac gggaggcagc agtggggaat 360
attgcacaat gggcgaaagc ctgatgcagc aacgccgcgt gagggatgac ggcattcggg 420

```
ttgtaaacct cttttagtag ggaagaagcg aaagtgacgg tacctgcaga aaaagcaccg    480

gctaactacg tgccagcagc cgctgtaata cgtagggtgc aagcgttgtc cggaattatt    540

gggcgtaaag agctcgtagg cggtttgtcg cgtctgctgt gaaatcccga ggctcaacct    600

cgggtctgca gtgggtacgg gcagactaga gtgtggtagg ggagattgga attcctggtg    660

tagcggtgga atgcgcagat atcaggagga acaccgatgg cgaaggcaga tctctgggcc    720

attactgacg ctgaggagcg aaagcatggg gagcgaacag gattagatac cctggtagtc    780

catgccgtaa acgttgggcg ctagatgtgg ggaccattcc acggtttccg tgtcgtagct    840

aacgcattaa gcgccccgcc tggggagtac ggccgcaagg ctaaaactca aaggaattga    900

cgggggcccg cacaagcggc ggagcatgcg gattaattcg atgcaacgcg aagaacctta    960

ccaaggcttg acatataccg gaaacgttca gaaatgttcg cc                      1002
```

<210> SEQ ID NO 30
<211> LENGTH: 1520
<212> TYPE: DNA
<213> ORGANISM: Unknown
<220> FEATURE:
<223> OTHER INFORMATION: Description of Unknown:
      DP30 16S rRNA microbial sequence

<400> SEQUENCE: 30

```
tacggagagt ttgatcctgg ctcaggatga acgctggcgg cgtgcttaac acatgcaagt     60

cgaacggtga agccaagctt gcttggtgga tcagtggcga acgggtgagt aacacgtgag    120

caacctgccc tggactctgg gataagcgct ggaaacggcg tctaatactg gatatgagac    180

gtgatcgcat ggtcgtgttt ggaaagattt ttcggtctgg gatgggctcg cggcctatca    240

gcttgttggt gaggtaatgg ctcaccaagg cgtcgacggg tagccggcct gagagggtga    300

ccggccacac tgggactgag acacggccca gactcctacg ggaggcagca gtggggaata    360

ttgcacaatg ggcgaaagcc tgatgcagca acgccgcgtg agggatgacg gccttcgggt    420

tgtaaacctc ttttagcagg gaagaagcga aagtgacggt acctgcagaa aaagcgccgg    480

ctaactacgt gccagcagcc gcggtaatac gtagggcgca agcgttatcc ggaattattg    540

ggcgtaaaga gctcgtaggc ggtttgtcgc gtctgctgtg aaatcccgag gctcaacctc    600

gggcctgcag tgggtacggg cagactagag tgcggtaggg gagattggaa ttcctggtgt    660

agcggtggaa tgcgcagata tcaggaggaa caccgatggc gaaggcagat ctctgggccg    720

taactgacgc tgaggagcga aagggtgggg agcaaacagg cttagatacc ctggtagtcc    780

accccgtaaa cgttgggaac tagttgtggg gaccattcca cggtttccgt gacgcagcta    840

acgcattaag ttccccgcct ggggagtacg gccgcaaggc taaaactcaa aggaattgac    900

ggggacccgc acaagcggcg gagcatgcgg attaattcga tgcaacgcga agaaccttac    960

caaggcttga catatacgag aacgggccag aaatggtcaa ctctttggac actcgtaaac   1020

aggtggtgca tggttgtcgt cagctcgtgt cgtgagatgt tgggttaagt cccgcaacga   1080

gcgcaaccct cgttctatgt tgccagcacg taatggtggg aactcatggg atactgccgg   1140

ggtcaactcg gaggaaggtg gggatgacgt caaatcatca tgccccttat gtcttgggct   1200

tcacgcatgc tacaatggcc ggtacaaagg gctgcaatac cgtgaggtgg agcgaatccc   1260

aaaaagccgg tcccagttcg gattgaggtc tgcaactcga cctcatgaag tcggagtcgc   1320

tagtaatcgc agatcagcaa cgctgcggtg aatacgttcc cgggtcttgt acacaccgcc   1380

cgtcaagtca tgaaagtcgg taacacctga agccggtggc ccaacccttg tggagggagc   1440
```

-continued cgtcgaaggt gggatcggta attaggacta agtcgtaaca aggtagccgt accggaaggt 1500
gcggctggat cacctccttt 1520

<210> SEQ ID NO 31
<211> LENGTH: 941
<212> TYPE: DNA
<213> ORGANISM: Unknown
<220> FEATURE:
<223> OTHER INFORMATION: Description of Unknown:
DP31 16S rRNA microbial sequence

<400> SEQUENCE: 31
cagccggggg cattagtatt tgcacgctag aggtgaaatt cttggattgt gcaaagactt 60
cctactgcga aagcatttgc caagaatgtt ttcattaatc aagaacgaag gttagggtat 120
cgaaaacgat tagataccgt tgtagtctta acagtaaact atgccgactc cgaatcggtc 180
gatgctcatt tcactggctc gatcggcgcg gtacgagaaa tcaaagtttt tgggttctgg 240
ggggagtatg gtcgcaaggc tgaaacttaa agaaattgac ggaagggcac caccaggagt 300
ggagcctgcg gcttaatttg actcaacacg ggaaaactca ccgggtccgg acatagtaag 360
gattgacaga ttgatggcgc tttcatgatt ctatgggtgg tggtgcatgg ccgttcttag 420
ttggtggagt gatttgtctg gttaattccg ataacgaacg agaccttgac ctgctaaata 480
gacgggttga cattttgttg gccccttatg tcttcttaga gggacaatcg accgtctagg 540
tgatggaggc aaaaggcaat aacaggtctg tgatgccctt agatgttccg ggctgcacgc 600
gcgctacact gacagagaca acgagtgggg ccccttgtcc gaaatgactg ggtaaacttg 660
tgaaactttg tcgtgctggg gatggagctt tgtaattttt gctcttcaac gaggaattcc 720
tagtaagcgc aagtcatcag cttgcgttga ctacgtccct gccctttgta cacaccgccc 780
gtcgctacta ccgattgaat ggcttagtga ggacttggga gagtacatcg ggagccagc 840 aatggcaccc tgacggctca aactcttaca aacttggtca tttagaggaa gtaaaagtcg 900
taacaaggta tctgtaggtg aacctgcaga tggatcattt c 941

<210> SEQ ID NO 32
<211> LENGTH: 1072
<212> TYPE: DNA
<213> ORGANISM: Unknown
<220> FEATURE:
<223> OTHER INFORMATION: Description of Unknown:
DP32 16S rRNA microbial sequence

<400> SEQUENCE: 32
actgagcatt gacgttactc gcagaagaag caccggctaa ctccgtgcca gcagccgcgg 60
taatacggag ggtgcaagcg ttaatcggaa ttactgggcg taaagcgcac gcaggcggtt 120
tgttaagtca gatgtgaaat ccccgagctt aacttgggaa ctgcatttga aactggcaag 180
ctagagtctt gtagaggggg gtagaattcc aggtgtagcg gtgaaatgcg tagagatctg 240
gaggaatacc ggtggcgaag gcggccccct ggacaaagac tgacgctcag gtgcgaaagc 300
gtggggagca aacaggatta gataccctgg tagtccacgc tgtaaacgat gtcgacttgg 360
aggttgtgcc cttgaggcgt ggcttccgga gctaacgcgt taagtcgacc gcctggggag 420
tacggccgca aggttaaaac tcaaatgaat tgacgggggc ccgcacaagc ggtggagcat 480
gtggtttaat tcgatgcaac gcgaagaacc ttacctactc ttgacatcca gagaattcgc 540
tagagatagc ttagtgcctt cgggaactct gagacaggtg ctgcatggct gtcgtcagct 600
cgtgttgtga aatgttgggt taagtcccgc aacgagcgca acccttatcc tttgttgcca 660
gcgagtaatg tcgggaactc aaaggagact gccggtgata aaccggagga aggtggggat 720
gacgtcaagt catcatggcc cttacgagta gggctacaca cgtgctacaa tggcatatac 780
aaagagaagc gaactcgcga gagcaagcgg acctcataaa gtatgtcgta gtccggattg 840
gagtctgcaa ctcgactcca tgaagtcgga atcgctagta atcgtagatc agaatgctac 900
ggtgaatacg ttcccgggcc ttgtacacac cgcccgtcac accatgggag tgggttgcaa 960
aagaagtagg tagcttaacc ttcgggaggg cgcttaccac tttgtgattc atgactgggg 1020
tgaagtcgta acaaggtaac cgtaggggaa cctgcggttg gatcacctcc tt 1072

<210> SEQ ID NO 33
<211> LENGTH: 853
<212> TYPE: DNA
<213> ORGANISM: Unknown
<220> FEATURE:
<223> OTHER INFORMATION: Description of Unknown:
DP33 16S rRNA microbial sequence

<400> SEQUENCE: 33
ggaggaaggc gtagagatct ggaggaatac cggtggcgaa ggcggccccc tggacaaaga 60
ctgacgctca ggtgcgaaag cgtggggagc aaacaggatt agataccctg gtagtccacg 120
ccgtaaacga tgtcgacttg gaggttgtgc ccttgaggcg tggcttccgg agctaacgcg 180
ttaagtcgac cgcctgggga gtacggccgc aaggttaaaa ctcaaatgaa ttgacggggg 240
cccgcacaag cggtggagca tgtggtttaa ttcgatgcaa cgcgaagaac cttacctggc 300
cttgacatcc acggaattcg gcagagatgc cttagtgcct tcgggaaccg tgagacaggt 360
gctgcatggc tgtcgtcagc tcgtgttgtg aaatgttggg ttaagtcccg caacgagcgc 420
aacccttatc ctttgttgcc agcacgtaat ggtgggaact caaaggagac tgccggtgat 480
aaaccggagg aaggtgggga tgacgtcaag tcatcatggc ccttacggcc agggctacac 540
acgtgctaca atggcgcata caaagagaag cgacctcgcg agagcaagcg gacctcataa 600
agtgcgtcgt agtccggatc ggagtctgca actcgactcc gtgaagtcgg aatcgctagt 660
aatcgtagat cagaatgcta cggtgaatac gttcccgggc cttgtacaca ccgcccgtca 720
caccatggga gtgggttgca aaagaagtag gtagcttaac cttcgggagg gcgcttacca 780
ctttgtgatt catgactggg gtgaagtcgt aacaaggtaa ccgtagggga acctgcggtt 840
ggatcacctc ctt 853

<210> SEQ ID NO 34
<211> LENGTH: 1519
<212> TYPE: DNA
<213> ORGANISM: Unknown
<220> FEATURE:
<223> OTHER INFORMATION: Description of Unknown:
DP34 16S rRNA microbial sequence

<400> SEQUENCE: 34
tacggagagt ttgatcctgg ctcaggacga acgctggcgg cgtgcttaac acatgcaagt 60
cgaacgatga agcccagctt gctgggtgga ttagtggcga acgggtgagt aacacgtgag 120
taacctgccc ttgactctgg gataagcgtt ggaaacgacg tctaataccg gatacgagct 180
tccaccgcat ggtgagttgc tggaaagaat tttggtcaag gatggactcg cggcctatca 240
gcttgttggt gaggtaatgg ctcaccaagg cgacgacggg tagccggcct gagagggtga 300
ccggccacac tgggactgag acacggccca gactcctacg ggaggcagca gtggggaata 360
ttgcacaatg ggcgaaagcc tgatgcagca acgccgcgtg agggacgacg gccttcgggt 420
tgtaaacctc ttttagcagg gaagaagcga aagtgacggt acctgcagaa aaagcaccgg 480
ctaactacgt gccagcagcc gcggtaatac gtagggtgca agcgttgtcc ggaattattg 540
ggcgtaaaga gctcgtaggc ggtttgtcgc gtctgctgtg aaatcccgag gctcaacctc 600
gggtctgcag tgggtacggg cagactagag tgcggtaggg gagattggaa ttcctggtgt 660
agcggtggaa tgcgcagata tcaggaggaa caccgatggc gaaggcagat ctctgggccg 720
ctactgacgc tgaggagcga aagggtgggg agcaaacagg cttagatacc ctggtagtcc 780
accccgtaaa cgttgggcgc tagatgtggg gaccattcca cggtttccgt gtcgtagcta 840
acgcattaag cgccccgcct ggggagtacg gccgcaaggc taaaactcaa aggaattgac 900
gggggcccgc acaagcggcg gagcatgcgg attaattcga tgcaacgcga agaaccttac 960
caaggcttga catatacgag aacgggccag aaatggtcaa ctctttggac actcgtaaac 1020
aggtggtgca tggttgtcgt cagctcgtgt cgtgagatgt tgggttaagt cccgcaacga 1080
gcgcaaccct cgttctatgt tgccagcacg taatggtggg aactcatggg atactgccgg 1140
ggtcaactcg gaggaaggtg gggacgacgt caaatcatca tgccccttat gtcttgggct 1200
tcacgcatgc tacaatggcc agtacaaagg gctgcaatac cgtaaggtgg agcgaatccc 1260
aaaaagctgg tcccagttcg gattgaggtc tgcaactcga cctcatgaag tcggagtcgc 1320
tagtaatcgc agatcagcaa cgctgcggtg aatacgttcc cgggccttgt acacaccgcc 1380
cgtcaagtca tgaaagtcgg taacacccga agccagtggc ctaaccgcaa ggatggagct 1440
gtctaaggtg ggatcggtaa ttaggactaa gtcgtaacaa ggtagccgta ccggaaggtg 1500
cggctggatc acctcctttt 1519

<210> SEQ ID NO 35
<211> LENGTH: 1536
<212> TYPE: DNA
<213> ORGANISM: Unknown
<220> FEATURE:
<223> OTHER INFORMATION: Description of Unknown:
DP35 16S rRNA microbial sequence

<400> SEQUENCE: 35
ttgaagagtt tgatcatggc tcagattgaa cgctggcggc aggcctaaca catgcaagtc 60
ggacggtagc acagagagct tgctcttggg tgacgagtgg cggacgggtg agtaatgtct 120
ggggatctgc ccgatagagg gggataacca ctggaaacgg tggctaatac cgcataacgt 180
cgcaagacca aagaggggga ccttcgggcc tctcactatc ggatgaaccc agatgggatt 240
agctagtagg cggggtaatg gcccacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcgg ggaggaaggc gatgaggtta ataaccgcgt cgattgacgt 480
tacccgcaga agaagcaccg gctaactccg tgccagcagc cgcggtaata cggagggtgc 540
aagcgttaat cggaattact gggcgtaaag cgcacgcagg cggtctgtta agtcagatgt 600
gaaatccccg ggcttaacct gggaactgca tttgaaactg gcaggcttga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gttcccttga 840

-continued

```
ggagtggctt ccggagctaa cgcgttaagt cgaccgcctg gggagtacgg ccgcaaggtt    900

aaaactcaaa tgaattgacg gggcccgca caagcggtgg agcatgtggt ttaattcgat    960

gcaacgcgaa gaaccttacc tactcttgac atccagcgaa cttagcagag atgctttggt   1020

gccttcggga acgctgagac aggtgctgca tggctgtcgt cagctcgtgt tgtgaaatgt   1080

tgggttaagt cccgcaacga gcgcaaccct tatcctttgt tgccagcgat tcggtcggga   1140

actcaaagga gactgccggt gataaaccgg aggaaggtgg ggatgacgtc aagtcatcat   1200

ggcccttacg agtagggcta cacacgtgct acaatggcgc atacaaagag aagcgacctc   1260

gcgagagcaa gcggacctca caaagtgcgt cgtagtccgg atcggagtct gcaactcgac   1320

tccgtgaagt cggaatcgct agtaatcgtg gatcagaatg ccacggtgaa tacgttcccg   1380

ggccttgtac acaccgcccg tcacaccatg ggagtgggtt gcaaaagaag taggtagctt   1440

aaccttcggg agggcgctta ccactttgtg attcattact ggggtgaagt cgtaacaagg   1500

taaccgtagg ggaacctgcg gttggatcac ctcctt                             1536
```

<210> SEQ ID NO 36
<211> LENGTH: 993
<212> TYPE: DNA
<213> ORGANISM: Unknown
<220> FEATURE:
<223> OTHER INFORMATION: Description of Unknown:
DP36 16S rRNA microbial sequence

<400> SEQUENCE: 36

```
ttgaagagtt tgatcatggc tcagattgaa cgctggcggc aggcctaaca catgcaagtc     60

ggacggtagc acagagagct tgctcttggg tgacgagtgg cggacgggtg agtaatgtct    120

ggggatctgc ccgatagagg gggataacca ctggaaacgg tggctaatac cgcataacgt    180

cgcaagacca aagaggggga ccttcgggcc tctcactatc ggatgaaccc agatgggatt    240

agctagtagg cggggtaatg gcccacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcgg ggaggaaggc gatgcggtta ataaccgcgt cgattgacgt    480

tacccgcaga agaagcaccg gctaactccg tgccagcagc cgcggtaata cggagggtgc    540

aagcgttaat cggaattact gggcgtaaag cgcacgcagg cggtctgtta agtcagatgt    600

gaaatccccg ggcttaacct gggaactgca tttgaaactg gcaggcttga gtcttgtaga    660

ggggggtaga attccaggtg tagcggtgaa atgcgtagag atctggagga ataccggtgg    720

cgaaggcggc cccctggaca aagactgacg ctcaggtgcg aaagcgtggg gagcaaacag    780

gattagatac cctggtagtc cacgccgtaa acgatgtcga cttggaggtt gttcccttga    840

ggagtggctt ccggagctaa cgcgttaagt cgaccgcctg gggagtacgg ccgcaaggtt    900

aaaactcaaa tgaattgacg gggcccgca caagcggtgg agcatgtggt ttaattcgat    960

gcaacgcgaa gaaccttacc tactcttgac atc                                993
```

<210> SEQ ID NO 37
<211> LENGTH: 1531
<212> TYPE: DNA
<213> ORGANISM: Unknown
<220> FEATURE:
<223> OTHER INFORMATION: Description of Unknown:
DP37 16S rRNA microbial sequence

<400> SEQUENCE: 37

```
tgaagagttt gatcatggct cagattgaac gctggcggca ggcctaacac atgcaagtcg      60
agcggtagag agaagcttgc ttctcttgag agcggcggac gggtgagtaa tgcctaggaa     120
tctgcctggt agtgggggat aacgttcgga aacgaacgct aataccgcat acgtcctacg     180
ggagaaagca ggggaccttc gggccttgcg ctatcagatg agcctaggtc ggattagcta     240
gttggtgggg taatggctca ccaaggcgac gatccgtaac tggtctgaga ggatgatcag     300
tcacactgga actgagacac ggtccagact cctacgggag gcagcagtgg ggaatattgg     360
acaatgggcg aaagcctgat ccagccatgc cgcgtgtgtg aagaaggtct tcggattgta     420
aagcacttta agttgggagg aagggccatt acctaatacg tgatggtttt gacgttaccg     480
acagaataag caccggctaa ctctgtgcca gcagccgcgg taatacagag ggtgcaagcg     540
ttaatggaat tactgggcgt aaagcgcgcg taggtggttt gttaagttgg atgtgaaatc     600
cccgggctca acctgggaac tgcattcaaa actgactgac tagagtatgg tagagggtgg     660
tggaatttcc tgtgtagcgg tgaaatgcgt agatatagga aggaacacca gtggcgaagg     720
cgaccacctg gactgatact gacactgagg tgcgaaagcg tggggagcaa acaggattag     780
ataccctggt agtccacgcc gtaaacgatg tcaactagcc gttgggagcc ttgagctctt     840
agtggcgcag ctaacgcatt aagttgaccg cctggggagt acggccgcaa ggttaaaact     900
caaatgaatt gacgggggcc cgcacaagcg gtggagcatg tggtttaatt cgaagcaacg     960
cgaagaacct taccaggcct tgacatccaa tgaactttct agagatagat tggtgccttc    1020
gggaacattg agacaggtgc tgcatggctg tcgtcagctc gtgtcgtgag atgttgggtt    1080
aagtcccgta acgagcgcaa cccttgtcct tagttaccag cacgtaatgg tgggcactct    1140
aaggagactg ccggtgacaa accggaggaa ggtggggatg acgtcaagtc atcatggccc    1200
ttacggcctg ggctacacac gtgctacaat ggtcggtaca gagggttgcc aagccgcgag    1260
gtggagctaa tcccataaaa ccgatcgtag tccggatcgc agtctgcaac tcgactgcgt    1320
gaagtcggaa tcgctagtaa tcgcgaatca gaatgtcgcg gtgaatacgt tcccgggcct    1380
tgtacacacc gcccgtcaca ccatgggagt gggttgcacc agaagtagct agtctaacct    1440
tcggggggac ggttaccacg gtgtgattca tgactggggt gaagtcgtaa caaggtagcc    1500
gtaggggaac ctgcggctgg atcacctcct t                                   1531
```

<210> SEQ ID NO 38
<211> LENGTH: 1517
<212> TYPE: DNA
<213> ORGANISM: Unknown
<220> FEATURE:
<223> OTHER INFORMATION: Description of Unknown:
DP38 16S rRNA microbial sequence

<400> SEQUENCE: 38

```
tacggagagt ttgatcctgg ctcaggacga acgctggcgg cgtgcttaac acatgcaagt      60
cgagcggtaa ggcctttcgg ggtacacgag cggcgaacgg gtgagtaaca cgtgggtgat     120
ctgccctgca ctctgggata agcttgggaa actgggtcta ataccggata tgaccacagc     180
atgcatgtgt tgtggtggaa agatttatcg gtgcaggatg ggcccgcggc ctatcagctt     240
gttggtgggg taatggccta ccaaggcgac gacgggtagc cgacctgaga gggtgaccgg     300
ccacactggg actgagacac ggcccagact cctacgggag gcagcagtgg ggaatattgc     360
acaatgggcg gaagcctgat gcagcgacgc cgcgtgaggg atgaaggcct tcgggttgta     420
aacctctttc agcagggacg aagcgtgagt gacggtacct gcagaagaag caccggctaa     480
```

ctacgtgcca gcagccgcgg taatacgtag ggtgcgagcg ttgtccggaa ttactgggcg 540
taaagagttc gtaggcggtt tgtcgcgtcg tttgtgaaaa cccggggctc aacttcgggc 600
ttgcaggcga tacgggcaga cttgagtgtt tcaggggaga ctggaattcc tggtgtagcg 660
gtgaaatgcg cagatatcag gaggaacacc ggtggcgaag gcgggtctct gggaaacaac 720
tgacgctgag gaacgaaagc gtgggtagca aacaggatta gataccctgg tagtccacgc 780
cgtaaacggt gggcgctagg tgtgggttcc ttccacggga tctgtgccgt agctaacgca 840
ttaagcgccc cgcctgggga gtacggccgc aaggctaaaa ctcaaaggaa ttgacggggg 900
cccgcacaag cggcggagca tgtggattaa ttcgatgcaa cgcgaagaac cttacctggg 960
tttgacatac accggaaaac cgtagagata cggtccccct tgtggtcggt gtacaggtgg 1020
tgcatggctg tcgtcagctc gtgtcgtgag atgttgggtt aagtcccgca acgagcgcaa 1080
cccttgtctt atgttgccag cacgtaatgg tggggactcg taagagactg ccggggtcaa 1140
ctcggaggaa ggtggggacg acgtcaagtc atcatgcccc ttatgtccag ggcttcacac 1200
atgctacaat ggccagtaca gagggctgcg agaccgtgag gtggagcgaa tcccttaaag 1260
ctggtctcag ttcggatcgg ggtctgcaac tcgaccccgt gaagtcggag tcgctagtaa 1320
tcgcagatca gcaacgctgc ggtgaatacg ttcccgggcc ttgtacacac cgcccgtcac 1380
gtcatgaaag tcggtaacac ccgaagccgg tggcctaacc ccttacgggg agggagccgt 1440
cgaaggtggg atcggcgatt gggacgaagt cgtaacaagg tagccgtacc ggaaggtgcg 1500
gctggatcac ctccttt 1517

<210> SEQ ID NO 39
<211> LENGTH: 1482
<212> TYPE: DNA
<213> ORGANISM: Unknown
<220> FEATURE:
<223> OTHER INFORMATION: Description of Unknown:
DP39 16S rRNA microbial sequence

<400> SEQUENCE: 39
cttgagagtt tgatcctggc tcagaacgaa cgctggcggc aggcttaaca catgcaagtc 60
gaacgccccg caaggggagt ggcagacggg tgagtaacgc gtgggaatct accgtgccct 120
gcggaatagc tccgggaaac tggaattaat accgcatacg ccctacgggg gaaagattta 180
tcggggtatg atgagcccgc gttggattag ctagttggtg gggtaaaggc ctaccaaggc 240
gacgatccat agctggtctg agaggatgat cagccacatt gggactgaga cacggcccaa 300
actcctacgg gaggcagcag tggggaatat tggacaatgg gcgcaagcct gatccagcca 360
tgccgcgtga gtgatgaagg ccttagggtt gtaaagctct ttcaccggag aagataatga 420
cggtatccgg agaagaagcc ccggctaact tcgtgccagc agccgcggta atacgaaggg 480
ggctagcgtt gttcggaatt actgggcgta aagcgcacgt aggcggatat ttaagtcagg 540
ggtgaaatcc cagagctcaa ctctggaact gcctttgata ctgggtatct tgagtatgga 600
agaggtaagt ggaattccga gtgtagaggt gaaattcgta gatattcgga ggaacaccag 660
tggcgaaggc ggcttactgg tccattactg acgctgaggt gcgaaagcgt ggggagcaaa 720
caggattaga taccctggta gtccacgccg taaacgatga atgttagccg tcgggcagta 780
tactgttcgg tggcgcagct aacgcattaa acattccgcc tggggagtac ggtcgcaaga 840
ttaaaactca aaggaattga cgggggcccg cacaagcggt ggagcatgtg gtttaattcg 900
aagcaacgcg cagaacctta ccagctcttg acattcgggg tttgggcagt ggagacattg 960
tccttcagtt aggctggccc cagaacaggt gctgcatggc tgtcgtcagc tcgtgtcgtg 1020
agatgttggg ttaagtcccg caacgagcgc aaccctcgcc cttagttgcc agcatttagt 1080
tgggcactct aaggggactg ccggtgataa gccgagagga aggtggggat gacgtcaagt 1140
cctcatggcc cttacgggct gggctacaca cgtgctacaa tggtggtgac agtgggcagc 1200
gagacagcga tgtcgagcta atctccaaaa gccatctcag ttcggattgc actctgcaac 1260
tcgagtgcat gaagttggaa tcgctagtaa tcgcagatca gcatgctgcg gtgaatacgt 1320
tcccgggcct tgtacacacc gcccgtcaca ccatgggagt tggttttacc cgaaggtagt 1380
gcgctaaccg caaggaggca gctaaccacg gtagggtcag cgactggggt gaagtcgtaa 1440
caaggtagcc gtaggggaac ctgcggctgg atcacctcct tt 1482

<210> SEQ ID NO 40
<211> LENGTH: 903
<212> TYPE: DNA
<213> ORGANISM: Unknown
<220> FEATURE:
<223> OTHER INFORMATION: Description of Unknown:
DP40 16S rRNA microbial sequence

<400> SEQUENCE: 40
ttgacgttac ccgcagaaga agcaccggct aactccgtgc cagcagccgc ggtaatacgg 60
agggtgcaag cgttaatcgg aattactggg cgtaaagcgc acgcaggcgg tctgttaagt 120
cagatgtgaa atccccgggc ttaacctggg aactgcattt gaaactggca ggcttgagtc 180
ttgtagaggg gggtagaatt ccaggtgtag cggtgaaatg cgtagagatc tggaggaata 240
ccggtggcga aggcggcccc ctggacaaag actgacgctc aggtgcgaaa gcgtggggag 300
caaacaggat tagataccct ggtagtccac gccgtaaacg atgtcgactt ggaggttgtt 360
cccttgagga gtggcttccg gagctaacgc gttaagtcga ccgcctgggg agtacggccg 420
caaggttaaa actcaaatga attgacgggg gcccgcacaa gcggtggagc atgtggttta 480
attcgatgca acgcgaagaa ccttacctac tcttgacatc cagagaactt tccagagatg 540
gattggtgcc ttcgggaact ctgagacagg tgctgcatgg ctgtcgtcag ctcgtgttgt 600
gaaatgttgg gttaagtccc gcaacgagcg caacccttat cctttgttgc cagcgcgtga 660
tggcgggaac tcaaaggaga ctgccggtga taaaccggag gaaggtgggg atgacgtcaa 720
gtcatcatgg cccttacgag tagggctaca cacgtgctac aatggcgcat acaaagagaa 780
gcgacctcgc gagagcaagc ggacctcaca aagtgcgtcg tagtccggat cggagtctgc 840
aactcgactc cgtgaagtcg gaatcgctag taatcgtgga tcagaatgcc acggtgaata 900
cgt 903

<210> SEQ ID NO 41
<211> LENGTH: 1457
<212> TYPE: DNA
<213> ORGANISM: Unknown
<220> FEATURE:
<223> OTHER INFORMATION: Description of Unknown:
DP41 16S rRNA microbial sequence

<400> SEQUENCE: 41
gtggagagtt tgatcctggc tcaggatgaa cgctggcggc gtgcttaaca catgcaagtc 60
gaacggaaag gcccaagctt gcttgggtac tcgagtggcg aacgggtgag taacacgtgg 120
gtgatctgcc ctgcacttcg ggataagcct gggaaactgg gtctaatacc ggataggacg 180

-continued atggtttgga tgccattgtg gaaagttttt tcggtgtggg atgagctcgc ggcctatcag 240
cttgttggtg gggtaatggc ctaccaaggc gtcgacgggt agccggcctg agagggtgta 300
cggccacatt gggactgaga tacggcccag actcctacgg gaggcagcag tggggaatat 360
tgcacaatgg gcgcaagcct gatgcagcga cgccgcgtgg gggatgacgg ccttcgggtt 420
gtaaactcct ttcgctaggg acgaagcgtt ttgtgacggt acctggagaa gaagcaccgg 480
ctaactacgt gccagcagcc gcggtaatac gtagggtgcg agcgttgtcc ggaattactg 540
ggcgtaaaga gctcgtaggt ggtttgtcgc gtcgtttgtg taagcccgca gcttaactgc 600
gggactgcag gcgatacggg cataacttga gtgctgtagg ggagactgga attcctggtg 660
tagcggtgga atgcgcagat atcaggagga acaccgatgg cgaaggcagg tctctgggca 720
gtaactgacg ctgaggagcg aaagcatggg tagcgaacag gattagatac cctggtagtc 780
catgccgtaa acggtgggcg ctaggtgtga gtcccttcca cggggttcgt gccgtagcta 840
acgcattaag cgccccgcct ggggagtacg gccgcaaggc taaaactcaa aggaattgac 900
gggggcccgc acaagcggcg gagcatgtgg attaattcga tgcaacgcga agaaccttac 960
ctgggcttga catacaccag atcgccgtag agatacggtt tccctttgtg gttggtgtac 1020
aggtggtgca tggttgtcgt cagctcgtgt cgtgagatgt tgggttaagt cccgcaacga 1080
gcgcaaccct tgtcttatgt tgccagcacg tgatggtggg gactcgtgag agactgccgg 1140
ggttaactcg gaggaaggtg gggatgacgt caaatcatca tgccccttat gtccagggct 1200
tcacacatgc tacaatggtc ggtacaacgc gcatgcgagc ctgtgagggt gagcgaatcg 1260
ctgtgaaagc cggtcgtagt tcggattggg gtctgcaact cgaccccatg aagtcggagt 1320
cgctagtaat cgcagatcag caacgctgcg gtgaatacgt tcccgggcct tgtacacacc 1380
gcccgtcaca ccatgggagt gggttgcaaa agaagtaggt agcttaacct tcgggagggc 1440
gcttaccact ttgtgat 1457

<210> SEQ ID NO 42
<211> LENGTH: 1532
<212> TYPE: DNA
<213> ORGANISM: Unknown
<220> FEATURE:
<223> OTHER INFORMATION: Description of Unknown:
DP42 16S rRNA microbial sequence

<400> SEQUENCE: 42
tgaagagttt gatcatggct cagattgaac gctggcggca ggcctaacac atgcaagtcg 60
agcggtagag aggtgcttgc acctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcatta acctaatacg ttagtgtctt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggta 660
gtggaatttc ctgtgtagcg gtgaaatgcg tagatatagg aaggaacacc agtggcgaag 720

```
gcgactacct ggactgatac tgacactgag gtgcgaaagc gtggggagca aacaggatta    780

gataccctgg tagtccacgc cgtaaacgat gtcaactagc cgttgggaac cttgagttct    840

tagtggcgca gctaacgcat taagttgacc gcctggggag tacggccgca aggttaaaac    900

tcaaatgaat tgacgggggc ccgcacaagc ggtggagcat gtggtttaat tcgaagcaac    960

gcgaagaacc ttaccaggcc ttgacatcca atgaactttc cagagatgga ttggtgcctt   1020

cgggaacatt gagacaggtg ctgcatggct gtcgtcagct cgtgtcgtga gatgttgggt   1080

taagtcccgt aacgagcgca acccttgtcc ttagttacca gcacgtaatg gtgggcactc   1140

taaggagact gccggtgaca aaccggagga aggtggggat gacgtcaagt catcatggcc   1200

cttacggcct gggctacaca cgtgctacaa tggtcggtac aaagggttgc caagccgcga   1260

ggtggagcta atcccataaa accgatcgta gtccggatcg cagtctgcaa ctcgactgcg   1320

tgaagtcgga atcgctagta atcgtgaatc agaatgtcac ggtgaatacg ttcccgggcc   1380

ttgtacacac cgcccgtcac accatgggag tgggttgcac cagaagtagc tagtctaacc   1440

ctcgggagga cggttaccac ggtgtgattc atgactgggg tgaagtcgta acaaggtagc   1500

cgtaggggaa cctgcggctg gatcacctcc tt                                 1532
```

<210> SEQ ID NO 43
<211> LENGTH: 1525
<212> TYPE: DNA
<213> ORGANISM: Unknown
<220> FEATURE:
<223> OTHER INFORMATION: Description of Unknown:
DP43 16S rRNA microbial sequence

<400> SEQUENCE: 43

```
ctgagtttga tcctggctca gattgaacgc tggcggcatg ccttacacat gcaagtcgaa     60

cggcagcacg gagcttgctc tggtggcgag tggcgaacgg gtgagtaata tatcggaacg    120

taccctggag tgggggataa cgtagcgaaa gttacgctaa taccgcatac gatctaagga    180

tgaaagtggg ggatcgcaag acctcatgct cgtggagcgg ccgatatctg attagctagt    240

tggtagggta aaagcctacc aaggcatcga tcagtagctg gtctgagagg acgaccagcc    300

acactggaac tgagacacgg tccagactcc tacgggaggc agcagtgggg aattttggac    360

aatgggcgaa agcctgatcc agcaatgccg cgtgagtgaa gaaggccttc gggttgtaaa    420

gctcttttgt cagggaagaa acggtgagag ctaatatctc ttgctaatga cggtacctga    480

agaataagca ccggctaact acgtgccagc agccgcggta atacgtaggg tgcaagcgtt    540

aatcggaatt actgggcgta aagcgtgcgc aggcggtttt gtaagtctga tgtgaaatcc    600

ccgggctcaa cctgggaatt gcattggaga ctgcaaggct agaatctggc agaggggggt    660

agaattccac gtgtagcagt gaaatgcgta gatatgtgga ggaacaccga tggcgaaggc    720

agccccctgg gtcaagattg acgctcatgc acgaaagcgt ggggagcaaa caggattaga    780

taccctggta gtccacgccc taaacgatgt ctactagttg tcgggtctta attgacttgg    840

taacgcagct aacgcgtgaa gtagaccgcc tggggagtac ggtcgcaaga ttaaaactca    900

aaggaattga cggggacccg cacaagcggt ggatgatgtg gattaattcg atgcaacgcg    960

aaaaacctta cctacccttg acatggctgg aatccttgag agatcaggga gtgctcgaaa   1020

gagaaccagt acacaggtgc tgcatggctg tcgtcagctc gtgtcgtgag atgttgggtt   1080

aagtcccgca acgagcgcaa cccttgtcat tagttgctac gaaagggcac tctaatgaga   1140

ctgccggtga caaaccggag gaaggtgggg atgacgtcaa gtcctcatgg cccttatggg   1200
```

tagggcttca cacgtcatac aatggtacat acagagcgcc gccaacccgc gagggggagc 1260
taatcgcaga aagtgtatcg tagtccggat tgtagtctgc aactcgactg catgaagttg 1320
gaatcgctag taatcgcgga tcagcatgtc gcggtgaata cgttcccggg tcttgtacac 1380
accgcccgtc acaccatggg agcgggtttt accagaagta ggtagcttaa ccgtaaggag 1440
ggcgcttacc acggtaggat tcgtgactgg ggtgaagtcg taacaaggta gccgtatcgg 1500
aaggtgcggc tggatcacct ccttt 1525

<210> SEQ ID NO 44
<211> LENGTH: 1497
<212> TYPE: DNA
<213> ORGANISM: Unknown
<220> FEATURE:
<223> OTHER INFORMATION: Description of Unknown:
DP44 16S rRNA microbial sequence

<400> SEQUENCE: 44
tggcggcatg ccttacacat gcaagtcgaa cggcagcata ggagcttgct cctgatggcg 60
agtggcgaac gggtgagtaa tatatcggaa cgtgccctag agtgggggat aactagtcga 120
aagactagct aataccgcat acgatctacg gatgaaagtg ggggatcgca agacctcatg 180
ctcctggagc ggccgatatc tgattagcta gttggtgggg taaaagctca ccaaggcgac 240
gatcagtagc tggtctgaga ggacgaccag ccacactggg actgagacac ggcccagact 300
cctacgggag gcagcagtgg ggaattttgg acaatggggg caaccctgat ccagcaatgc 360
cgcgtgagtg aagaaggcct tcgggttgta aagctctttt gtcagggaag aaacggttct 420
ggataatacc taggactaat gacggtacct gaagaataag caccggctaa ctacgtgcca 480
gcagccgcgg taatacgtag ggtgcaagcg ttaatcggaa ttactgggcg taaagcgtgc 540
gcaggcggtt gtgtaagtca gatgtgaaat ccccgggctc aacctgggaa ttgcatttga 600
gactgcacgg ctagagtgtg tcagaggggg gtagaattcc acgtgtagca gtgaaatgcg 660
tagatatgtg gaggaatacc gatggcgaag gcagcccct gggataacac tgacgctcat 720
gcacgaaagc gtggggagca aacaggatta gataccctgg tagtccacgc cctaaacgat 780
gtctactagt tgtcgggtct taattgactt ggtaacgcag ctaacgcgtg aagtagaccg 840
cctggggagt acggtcgcaa gattaaaact caaaggaatt gacggggacc cgcacaagcg 900
gtggatgatg tggattaatt cgatgcaacg cgaaaaacct tacctaccct tgacatggat 960
ggaatcccga agagatttgg gagtgctcga aagagaacca tcacacaggt gctgcatggc 1020
tgtcgtcagc tcgtgtcgtg agatgttggg ttaagtcccg caacgagcgc aacccttgtc 1080
attagttgct acgaaagggc actctaatga gactgccggt gacaaaccgg aggaaggtgg 1140
ggatgacgtc aagtcctcat ggcccttatg ggtagggctt cacacgtcat acaatggtac 1200
atacagaggg ccgccaaccc gcgagggggga gctaatccca gaaagtgtat cgtagtccgg 1260
attggagtct gcaactcgac tccatgaagt tggaatcgct agtaatcgcg gatcagcatg 1320
tcgcggtgaa tacgttcccg ggtcttgtac acaccgcccg tcacaccatg ggagcgggtt 1380
ttaccagaag tgggtagcct aaccgcaagg agggcgctca ccacggtagg attcgtgact 1440
ggggtgaagt cgtaacaagg tagccgtatc ggaaggtgcg gctggatcac ctcctttt 1497

<210> SEQ ID NO 45
<211> LENGTH: 1522
<212> TYPE: DNA
<213> ORGANISM: Unknown
<220> FEATURE:

<223> OTHER INFORMATION: Description of Unknown:
DP45 16S rRNA microbial sequence

<400> SEQUENCE: 45
tacggagagt ttgatcctgg ctcaggacga acgctggcgg cgtgcttaac acatgcaagt 60
cgaacggtga cgctagagct tgctctggtt gatcagtggc gaacgggtga gtaacacgtg 120
agtaacctgc ccttgactct gggataactc cgggaaaccg gggctaatac cggatacgag 180
acgcgaccgc atggtcggcg tctggaaagt ttttcggtca aggatggact cgcggcctat 240
cagcttgttg gtgaggtaat ggctcaccaa ggcgtcgacg ggtagccggc ctgagagggc 300
gaccggccac actgggactg agacacggcc cagactccta cgggaggcag cagtggggaa 360
tattgcacaa tgggcgaaag cctgatgcag cgacgccgcg tgagggatga aggccttcgg 420
gttgtaaacc tctttcagta gggaagaagc gaaagtgacg gtacctgcag aagaagcgcc 480
ggctaactac gtgccagcag ccgcggtaat acgtagggcg caagcgttgt ccggaattat 540
tgggcgtaaa gagctcgtag gcggtttgtc gcgtctggtg tgaaaactca aggctcaacc 600
ttgagcttgc atcgggtacg ggcagactag agtgtggtag ggtgactgg aattcctggt 660 gtagcggtgg aatgcgcaga tatcaggagg aacaccgatg gcgaaggcag gtcactgggc 720
cactactgac gctgaggagc gaaagcatgg ggagcgaaca ggattagata ccctggtagt 780
ccatgccgta aacgttgggc actaggtgtg gggctcattc cacgagttcc gcgccgcagc 840
taacgcatta agtgccccgc ctggggagta cggccgcaag gctaaaactc aaaggaattg 900
acgggggccc gcacaagcgg cggagcatgc ggattaattc gatgcaacgc gaagaacctt 960
accaaggctt gacatacacc ggaatcatgc agagatgtgt gcgtcttcgg actggtgtac 1020
aggtggtgca tggttgtcgt cagctcgtgt cgtgagatgt tgggttaagt cccgcaacga 1080
gcgcaaccct cgtcctatgt tgccagcacg ttatggtggg gactcatagg agactgccgg 1140
ggtcaactcg gaggaaggtg gggatgacgt caaatcatca tgccccttat gtcttgggct 1200
tcacgcatgc tacaatggcc ggtacaaagg gctgcgatac cgcgaggtgg agcgaatccc 1260
aaaaagccgg tctcagttcg gattggggtc tgcaactcga ccccatgaag tcggagtcgc 1320
tagtaatcgc agatcagcaa cgctgcggtg aatacgttcc cgggccttgt acacaccgcc 1380
cgtcaagtca cgaaagtcgg taacacccga agccggtggc ctaacccctt gtgggatgga 1440
gccgtcgaag gtgggattgg cgattgggac taagtcgtaa caaggtagcc gtaccggaag 1500
gtgcggctgg atcacctcct tt 1522

<210> SEQ ID NO 46
<211> LENGTH: 830
<212> TYPE: DNA
<213> ORGANISM: Unknown
<220> FEATURE:
<223> OTHER INFORMATION: Description of Unknown:
DP46 16S rRNA microbial sequence

<400> SEQUENCE: 46
ttgaagagtt tgatcatggc tcagattgaa cgctggcggc aggcctaaca catgcaagtc 60
ggacggtagc acagaggagc tgctccttgg gtgacgagtg gcggacgggt gagtaatgtc 120
tggggatctg cccgatagag gggggataacc actggaaacg gtggctaata ccgcataacg 180
tcgcaagacc aaagaggggg accttcgggc ctctcactat cggatgaacc cagatgggat 240
tagctagtag gcggggtaat ggcccaccta ggcgacgatc cctagctggt ctgagaggat 300
gaccagccac actggaactg agacacggtc cagactccta cgggaggcag cagtggggaa 360
tattgcacaa tgggcgcaag cctgatgcag ccatgccgcg tgtatgaaga aggccttcgg 420
gttgtaaagt actttcagcg gggaggaagg cgacagggtt aataaccctg tcgattgacg 480
ttacccgcag aagaagcacc ggctaactcc gtgccagcag ccgcggtaat acggagggtg 540
caagcgttaa tcggaattac tgggcgtaaa gcgcacgcag gcggtctgtt aagtcagatg 600
tgaaatcccc gggcttaacc tgggaactgc atttgaaact ggcaggcttt agtcttgtag 660
agtggggtag aattccaggt gtagcggtga aatgcgtaga gatgtggagg aacaccagtg 720
gcgaaggcgg ctttttggtc tgtaactgac gctgaggcgc gaaagcgtgg ggagcaaaca 780
ggattagata ccctggtagt ccacgccgta aacgatgagt gctaagtgtt 830

<210> SEQ ID NO 47
<211> LENGTH: 960
<212> TYPE: DNA
<213> ORGANISM: Unknown
<220> FEATURE:
<223> OTHER INFORMATION: Description of Unknown:
DP47 16S rRNA microbial sequence

<400> SEQUENCE: 47
agggtgcaag cgttaatcgg aattactggg cgtaaagcgc gcgtaggtgg tttgttaagt 60
tgaatgtgaa atccccgggc tcaacctggg aactgcattt gaaactggca agctagagtc 120
tcgtagaggg gggtagaatt ccaggtgtag cggtgaaatg cgtagagatc tggaggaata 180
ccggtggcga aggcggcccc ctggacgaag actgacgctc aggtgcgaaa gcgtggggag 240
caaacaggat tagataccct ggtagtccac gccgtaaacg atgtcaacta gccgttggaa 300
gccttgagct tttagtggcg cagctaacgc attaagttga ccgcctgggg agtacggccg 360
caaggttaaa actcaaatga attgacgggg gcccgcacaa gcggtggagc atgtggttta 420
attcgaagca acgcgaagaa ccttaccagg ccttgacatc caatgaactt tctagagata 480
gattggtgcc ttcgggaaca ttgagacagg tgctgcatgg ctgtcgtcag ctcgtgtcgt 540
gagatgttgg gttaagtccc gcaacgagcg caacccttgt cctgtgttgc cagcgcgtaa 600
tggcggggac tcgcaggaga ctgccggggt caactcggag gaaggtgggg atgacgtcaa 660
atcatcatgc cccttatgtc ttgggcttca cgcatgctac aatggccggt acaaagggct 720
gcaataccgt gaggtggagc gaatcccaaa aagccggtcc cagttcggat tgaggtctgc 780
aactcgacct catgaagtcg gagtcgctag taatcgcaga tcagcaacgc tgcggtgaat 840
acgttcccgg gtcttgtaca caccgcccgt caagtcatga aagtcggtaa cacctgaagc 900
cggtggccca acccttgtgg agggagccgt cgaaggtggg atcggtaatt aggactaagt 960

<210> SEQ ID NO 48
<211> LENGTH: 1548
<212> TYPE: DNA
<213> ORGANISM: Unknown
<220> FEATURE:
<223> OTHER INFORMATION: Description of Unknown:
DP48 16S rRNA microbial sequence

<400> SEQUENCE: 48
catggagagt ttgatcctgg ctcaggacga acgctggcgg cgtgcctaat acatgcaagt 60
cgagcggaca gatgggagct tgctccctga tgttagcggc ggacgggtga gtaacacgtg 120
ggtaacctgc ctgtaagact gggataactc cgggaaaccg gggctaatac cggatgcttg 180
attgaaccgc atggttcaat tataaaaggt ggcttttagc taccacttac agatggaccc 240
gcggcgcatt agctagttgg tgaggtaacg gctcaccaag gcaacgatgc gtagccgacc 300
tgagagggtg atcggccaca ctgggactga gacacggccc agactcctac gggaggcagc 360
agtagggaat cttccgcaat ggacgaaagt ctgacggagc aacgccgcgt gagtgatgaa 420
ggttttcgga tcgtaaaact ctgttgttag ggaagaacaa gtaccgttcg aatagggcgg 480
taccttgacg gtacctaacc agaaagccac ggctaactac gtgccagcag ccgcggtaat 540
acgtaggtgg caagcgttgt ccggaattat tgggcgtaaa gcgcgcgcag gcggtttctt 600
aagtctgatg tgaaagcccc cggctcaacc ggggagggtc attggaaact ggggaacttg 660
agtgcagaag aggagagtgg aattccacgt gtagcggtga aatgcgtaga gatgtggagg 720
aacaccagtg gcgaaggcga ctctctggtc tgtaactgac gctgaggcgc gaaagcgtgg 780
ggagcgaaca ggattagata ccctggtagt ccacgccgta aacgatgagt gctaagtgtt 840
agagggtttc cgccctttag tgctgcagca aacgcattaa gcactccgcc tggggagtac 900
ggtcgcaaga ctgaaactca aaggaattga cgggggcccg cacaagcggt ggagcatgtg 960
gtttaattcg aagcaacgcg aagaacctta ccaggtcttg acatcctctg acaaccctag 1020
agatagggct tccccttcgg gggcagagtg acaggtggtg catggttgtc gtcagctcgt 1080
gtcgtgagat gttgggttaa gtcccgcaac gagcgcaacc cttgatctta gttgccagca 1140
ttcagttggg cactctaagg tgactgccgg tgacaaaccg gaggaaggtg gggatgacgt 1200
caaatcatca tgccccttat gacctgggct acacacgtgc tacaatgggc agaacaaagg 1260
gcagcgaagc cgcgaggcta agccaatccc acaaatctgt tctcagttcg gatcgcagtc 1320
tgcaactcga ctgcgtgaag ctggaatcgc tagtaatcgc ggatcagcat gccgcggtga 1380
atacgttccc gggccttgta cacaccgccc gtcacaccac gagagtttgt aacacccgaa 1440
gtcggtgagg taacctttg gagccagccg ccgaaggtgg gacagatgat tggggtgaag 1500
tcgtaacaag gtagccgtat cggaaggtgc ggctggatca cctccttt 1548

<210> SEQ ID NO 49
<211> LENGTH: 1551
<212> TYPE: DNA
<213> ORGANISM: Unknown
<220> FEATURE:
<223> OTHER INFORMATION: Description of Unknown:
DP49 16S rRNA microbial sequence

<400> SEQUENCE: 49
tatggagagt ttgatcctgg ctcaggacga acgctggcgg cgtgcctaat acatgcaagt 60
cgagcggacg tttttgaagc ttgcttcaaa aacgttagcg gcggacgggt gagtaacacg 120
tgggcaacct gccttatcga ctgggataac tccgggaaac cggggctaat accggataat 180
atctagcacc tcctggtgca agattaaaag agggccttcg ggctctcacg gtgagatggg 240
cccgcggcgc attagctagt tggagaggta atggctcccc aaggcgacga tgcgtagccg 300
acctgagagg gtgatcggcc acactgggac tgagacacgg cccagactcc tacgggaggc 360
agcagtaggg aatcttccgc aatggacgaa agtctgacgg agcaacgccg cgtgagtgat 420
gaagggtttc ggctcgtaaa gctctgttat gagggaagaa cacgtaccgt tcgaataggg 480
cggtaccttg acggtacctc atcagaaagc cacggctaac tacgtgccag cagccgcggt 540
aatacgtagg tggcaagcgt tgtccggaat tattgggcgt aaagcgcgcg caggcggcct 600
tttaagtctg atgtgaaatc ttgcggctca accgcaagcg gtcattggaa actgggaggc 660
ttgagtacag aagaggagag tggaattcca cgtgtagcgg tgaaatgcgt agatatgtgg 720
aggaacacca gtggcgaagg cgactctctg gtctgtaact gacgctgagg cgcgaaagcg 780
tggggagcaa acaggattag ataccctggt agtccacgcc gtaaacgatg agtgctaggt 840
gttaggggtt tcgatgcccg tagtgccgaa gttaacacat taagcactcc gcctggggag 900
tacggccgca aggctgaaac tcaaaggaat tgacgggggc ccgcacaagc agtggagcat 960
gtggtttaat tcgaagcaac gcgaagaacc ttaccaggtc ttgacatcct ttgaccactc 1020
tggagacaga gcttcccctt cgggggcaaa gtgacaggtg gtgcatggtt gtcgtcagct 1080
cgtgtcgtga gatgttgggt taagtcccgc aacgagcgca acccttgacc ttagttgcca 1140
gcatttagtt gggcactcta aggtgactgc cggtgacaaa ccggaggaag gtggggatga 1200
cgtcaaatca tcatgcccct tatgacctgg gctacacacg tgctacaatg gatggtacaa 1260
agggttgcga agccgcgagg tgaagccaat cccataaagc cattctcagt tcggattgta 1320
ggctgcaact cgcctgcatg aagctggaat tgctagtaat cgcggatcag catgccgcgg 1380
tgaatacgtt cccgggcctt gtacacaccg cccgtcacac cacgagagtt tgtaacaccc 1440
gaagtcggtg aggtaacctt ttggagccag ccgccgaagg tgggacagat gattggggtg 1500
aagtcgtaac aaggtagccg tatcggaagg tgcggctgga tcacctcctt t 1551

<210> SEQ ID NO 50
<211> LENGTH: 1536
<212> TYPE: DNA
<213> ORGANISM: Unknown
<220> FEATURE:
<223> OTHER INFORMATION: Description of Unknown:
DP50 16S rRNA microbial sequence

<400> SEQUENCE: 50
ttgaagagtt tgatcatggc tcagattgaa cgctggcggc aggcctaaca catgcaagtc 60
gaacggtagc acagagagct tgctcttggg tgacgagtgg cggacgggtg agtaatgtct 120
gggaaactgc ccgatggagg gggataacta ctggaaacgg tagctaatac cgcataacgt 180
cgcaagacca aagtggggga ccttcgggcc tcacaccatc ggatgtgccc agatgggatt 240
agctagtagg tggggtaatg gctcacctag gcgacgatcc ctagctggtc tgagaggatg 300
accagccaca ctggaactga gacacggtcc agactcctac gggaggcagc agtggggaat 360
attgcacaat gggcgcaagc ctgatgcagc catgccgcgt gtatgaagaa ggccttcggg 420
ttgtaaagta ctttcagcga ggaggaaggc attgtggtta ataaccgcag tgattgacgt 480
tactcgcaga agaagcaccg gctaactccg tgccagcagc cgcggtaata cggagggtgc 540
aagcgttaat cggaattact gggcgtaaag cgcacgcagg cggtctgtca agtcggatgt 600
gaaatccccg ggctcaacct gggaactgca ttcgaaactg gcaggctaga gtcttgtaga 660
ggggggtaga attccaggtg tagcggtgaa atgcgtagag atctggagga ataccggtgg 720
cgaaggcggc cccctggaca aagactgacg ctcaggtgcg aaagcgtggg gagcaaacag 780
gattagatac cctggtagtc cacgccgtaa acgatgtcga cttggaggtt gtgcccttga 840
ggcgtggctt ccggagctaa cgcgttaagt cgaccgcctg gggagtacgg ccgcaaggtt 900
aaaactcaaa tgaattgacg ggggcccgca caagcggtgg agcatgtggt ttaattcgat 960
gcaacgcgaa gaaccttacc tactcttgac atccacggaa tttagcagag atgctttagt 1020
gccttcggga accgtgagac aggtgctgca tggctgtcgt cagctcgtgt tgtgaaatgt 1080
tgggttaagt cccgcaacga gcgcaaccct tatcctttgt tgccagcggt tcggccggga 1140
actcaaagga gactgccagt gataaactgg aggaaggtgg ggatgacgtc aagtcatcat 1200

```
ggcccttacg agtagggcta cacacgtgct acaatggcat atacaaagag aagcgacctc   1260

gcgagagcaa gcggacctca taaagtatgt cgtagtccgg atcggagtct gcaactcgac   1320

tccgtgaagt cggaatcgct agtaatcgta gatcagaatg ctacggtgaa tacgttcccg   1380

ggccttgtac acaccgcccg tcacaccatg ggagtgggtt gcaaaagaag taggtagctt   1440

aaccttcggg agggcgctta ccactttgtg attcatgact ggggtgaagt cgtaacaagg   1500

taaccgtagg ggaacctgcg gttggatcac ctcctt                              1536
```

<210> SEQ ID NO 51
<211> LENGTH: 1537
<212> TYPE: DNA
<213> ORGANISM: Unknown
<220> FEATURE:
<223> OTHER INFORMATION: Description of Unknown:
DP51 16S rRNA microbial sequence

<400> SEQUENCE: 51

```
ttgaagagtt tgatcatggc tcagattgaa cgctggcggc aggcctaaca catgcaagtc     60

gagcggtagc acagggagct tgctcctggg tgacgagcgg cggacgggtg agtaatgtct    120

gggaaactgc ctgatggagg gggataacta ctggaaacgg tagctaatac cgcataacgt    180

cgcaagacca aagaggggga ccttcgggcc tcttgccatc agatgtgccc agatgggatt    240

agctagtagg tgaggtaatg gctcacctag gcgacgatcc ctagctggtc tgagaggatg    300

accagccaca ctggaactga gacacggtcc agactcctac gggaggcagc agtggggaat    360

attgcacaat gggcgcaagc ctgatgcagc catgccgcgt gtatgaagaa ggccttcggg    420

ttgtaaagta ctttcagcga ggaggaaggc attaaggtta ataaccttgg tgattgacgt    480

tactcgcaga agaagcaccg gctaactccg tgccagcagc cgcggtaata cgggggggtgc    540

aagcgttaat cggaattact gggcgtaaag cgcacgcagg cggtttgtca agtcggatgt    600

gaaatccccg ggctcaacct gggaactgca ttcgaaacgg gcaagctaga gtcttgtaga    660

ggggggtaga attccaggtg tagcggtgaa atgcgtagag atctggagga ataccggtgg    720

cgaaggcggc cccctggaca aagactgacg ctcaggtgcg aaagcgtggg gagcaaacag    780

gattagatac cctggtagtc cacgccgtaa acgatgtcga cttggaggtt gtgcccttga    840

ggcgtggctt ccggagctaa cgcgttaagt cgaccgcctg gggagtacgg ccgcaaggtt    900

aaaactcaaa tgaattgacg ggggcccgca caagcggtgg agcatgtggt ttaattcgat    960

gcaacgcgaa gaaccttacc tactcttgac atccagagaa ctttccagag atggattggt   1020

gccttcggga actctgagac aggtgctgca tggctgtcgt cagctcgtgt tgtgaaatgt   1080

tgggttaagt cccgcaacga gcgcaaccct tatcctttgt tgccagcgag taatgtcggg   1140

aactcaaagg agactgccag tgacaaactg gaggaaggtg gggatgacgt caagtcatca   1200

tggcccttac gagtagggct acacacgtgc tacaatggca tatacaaaga gaagcgacct   1260

cgcgagagca agcggacctc acaaagtatg tcgtagtccg gatcggagtc tgcaactcga   1320

ctccgtgaag tcggaatcgc tagtaatcgt agatcagaat gctacggtga atacgttccc   1380

gggccttgta cacaccgccc gtcacaccat gggagtgggt tgcaaaagaa gtaggtagct   1440

taaccttcgg gagggcgctt accactttgt gattcatgac tggggtgaag tcgtaacaag   1500

gtaaccgtag gggaacctgc ggttggatca cctcctt                             1537
```

<210> SEQ ID NO 52
<211> LENGTH: 1517
<212> TYPE: DNA

<213> ORGANISM: Unknown
<220> FEATURE:
<223> OTHER INFORMATION: Description of Unknown:
DP52 16S rRNA microbial sequence

<400> SEQUENCE: 52
acggagagtt tgatcctggc tcaggatgaa cgctggcggc gtgcttaaca catgcaagtc 60
gaacgatgat cccagcttgc tgggggatta gtggcgaacg ggtgagtaac acgtgagtaa 120
cctgcccttg actctgggat aagcctggga aactgggtct aataccggat atgactgtct 180
gacgcatgtc aggtggtgga aagcttttgt ggttttggat ggactcgcgg cctatcagct 240
tgttggtggg gtaatggcct accaaggcga cgacgggtag ccggcctgag agggtgaccg 300
gccacactgg gactgagaca cggcccagac tcctacggga ggcagcagtg gggaatattg 360
cacaatgggc gcaagcctga tgcagcgacg ccgcgtgagg gatgacggcc ttcgggttgt 420
aaacctcttt cagtagggaa gaagcgaaag tgacggtacc tgcagaagaa gcgccggcta 480
actacgtgcc agcagccgcg gtaatacgta gggcgcaagc gttatccgga attattgggc 540
gtaaagagct cgtaggcggt ttgtcgcgtc tgctgtgaaa gaccggggct caactccggt 600
tctgcagtgg gtacgggcag actagagtgc agtaggggag actggaattc ctggtgtagc 660
ggtgaaatgc gcagatatca ggaggaacac cgatggcgaa ggcaggtctc tgggctgtaa 720
ctgacgctga ggagcgaaag catggggagc gaacaggatt agataccctg gtagtccatg 780
ccgtaaacgt tgggcactag gtgtggggga cattccacgt tttccgcgcc gtagctaacg 840
cattaagtgc cccgcctggg gagtacggcc gcaaggctaa aactcaaagg aattgacggg 900
ggcccgcaca agcggcggag catgcggatt aattcgatgc aacgcgaaga accttaccaa 960
ggcttgacat gaaccggtaa tacctggaaa caggtgcccc gcttgcggtc ggtttacagg 1020
tggtgcatgg ttgtcgtcag ctcgtgtcgt gagatgttgg gttaagtccc gcaacgagcg 1080
caaccctcgt tctatgttgc cagcgcgtta tggcggggac tcataggaga ctgccggggt 1140
caactcggag gaaggtgggg acgacgtcaa atcatcatgc cccttatgtc ttgggcttca 1200
cgcatgctac aatggccggt acaaagggtt gcgatactgt gaggtggagc taatcccaaa 1260
aagccggtct cagttcggat tggggtctgc aactcgaccc catgaagtcg gagtcgctag 1320
taatcgcaga tcagcaacgc tgcggtgaat acgttcccgg gccttgtaca caccgcccgt 1380
caagtcacga aagttggtaa cacccgaagc cggtggccta acccttgtgg ggggagccgt 1440
cgaaggtggg accggcgatt gggactaagt cgtaacaagg tagccgtacc ggaaggtgcg 1500
gctggatcac ctccttt 1517

<210> SEQ ID NO 53
<211> LENGTH: 1405
<212> TYPE: DNA
<213> ORGANISM: Unknown
<220> FEATURE:
<223> OTHER INFORMATION: Description of Unknown:
DP53 16S rRNA microbial sequence

<400> SEQUENCE: 53
tgaagagttt gatcatggct cagattgaac gctggcggca ggcctaacac atgcaagtcg 60
agcggtagag agaagcttgc ttctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300

```
tcacactgga actgagacac ggtccagact cctacgggag gcagcagtgg ggaatattgg    360

acaatgggcg aaagcctgat ccagccatgc cgcgtgtgtg aagaaggtct tcggattgta    420

aagcacttta agttgggagg aagggcagtt acctaatacg tgattgtctg acgttaccga    480

cagaataagc accggctaac tctgtgccag cagccgcggt aatacagagg gtgcaagcgt    540

taatcggaat tactgggcgt aaagcgcgcg taggtggttt gttaagttga atgtgaaatc    600

cccgggctca acctgggaac tgcatccaaa actggcaagc tagagtatgg tagagggtag    660

tggaatttcc tgtgtagcgg tgaaatgcgt agatatagga aggaacacca gtggcgaagg    720

cgactacctg gactgatact gacactgagg tgcgaaagcg tggggagcaa acaggattag    780

ataccctggt agtccacgcc gtaaacgatg tcaactagcc gttgggagtc ttgaactctt    840

agtggcgcag ctaacgcatt aagttgaccg cctggggagt acggccgcaa ggttaaaact    900

caaatgaatt gacgggggcc cgcacaagcg gtggagcatg tggtttaatt cgaagcaacg    960

cgaagaacct taccaggcct tgacatccaa tgaactttct agagatagat tggtgccttc   1020

gggaacattg agacaggtgc tgcatggctg tcgtcagctc gtgtcgtgag atgttgggtt   1080

aagtcccgta acgagcgcaa cccttgtcct tagttaccag cacgtaatgg tgggcactct   1140

aaggagactg ccggtgacaa accggaggaa ggtggggatg acgtcaagtc atcatggccc   1200

ttacggcctg ggctacacac gtgctacaat ggtcggtaca aagggttgcc aagccgcgag   1260

gtggagctaa tcccataaaa ccgatcgtag tccggatcgc agtctgcaac tcgactgcgt   1320

gaagtcggaa tcgctagtaa tcgtgaatca gaatgtcacg gtgaatacgt tcccgggcct   1380

tgtacacacc gcccgtcaca ccatg                                         1405
```

```
<210> SEQ ID NO 54
<211> LENGTH: 1136
<212> TYPE: DNA
<213> ORGANISM: Unknown
<220> FEATURE:
<223> OTHER INFORMATION: Description of Unknown:
      DP54 16S rRNA microbial sequence

<400> SEQUENCE: 54
```

```
cttgagagtt tgatcctggc tcagagcgaa cgctggcggc aggcttaaca catgcaagtc     60

gagcgggcac cttcgggtgt cagcggcaga cgggtgagta acacgtggga acgtaccctt    120

cggttcggaa taacgctggg aaactagcgc taataccgga tacgcccttt tggggaaagg    180

tttactgccg aaggatcggc ccgcgtctga ttagctagtt ggtggggtaa cggcctacca    240

aggcgacgat cagtagctgg tctgagagga tgatcagcca cactgggact gagacacggc    300

ccagactcct acgggaggca gcagtgggga atattggaca atgggcgcaa gcctgatcca    360

gccatgccgc gtgagtgatg aaggccttag ggttgtaaag ctcttttgtc cgggacgata    420

atgacggtac cggaagaata agccccggct aacttcgtgc cagcagccgc ggtaatacga    480

agggggctag cgttgctcgg aatcactggg cgtaaagggc gcgtaggcgg ccattcaagt    540

cgggggtgaa agcctgtggc tcaaccacag aattgccttc gatactgttt ggcttgagtt    600

tggtagaggt tggtggaact gcgagtgtag aggtgaaatt cgtagatatt cgcaagaaca    660

ccagtggcga aggcggccaa ctggaccaat actgacgctg aggcgcgaaa gcgtggggag    720

caaacaggat tagataccct ggtagtccac gccgtaaacg atgaatgcta gctgttgggg    780

tgcttgcacc tcagtagcgc agctaacgct ttaagcattc cgcctgggga gtacggtcgc    840

aagattaaaa ctcaaaggaa ttgacggggg cccgcacaag cggtggagca tgtggtttaa    900
```

ttcgaagcaa cgcgcagaac cttaccatcc cttgacatgt cgtgccatcc ggagagatcc 960
ggggttccct tcggggacgc gaacacaggt gctgcatggc tgtcgtcagc tcgtgtcgtg 1020
agatgttggg ttaagtcccg caacgagcgc aacccacgtc cttagttgcc atcatttagt 1080
tgggcactct agggagactg ccggtgataa gccgcgagga aggtgtggat gacgtc 1136

<210> SEQ ID NO 55
<211> LENGTH: 1373
<212> TYPE: DNA
<213> ORGANISM: Unknown
<220> FEATURE:
<223> OTHER INFORMATION: Description of Unknown:
DP55 16S rRNA microbial sequence

<400> SEQUENCE: 55
tcggagagtt tgatcctggc tcaggatgaa cgctggcggc gtgcctaata catgcaagtc 60
gagcgaactg attagaagct tgcttctatg acgttagcgg cggacgggtg agtaacacgt 120
gggcaacctg cctgtaagac tgggataact tcgggaaacc gaactaatac cggataggat 180
cttctccttc atgggagatg attgaaagat ggtttcggct atcacttaca gatgggcccg 240
cggtgcatta gctagttggt gaggtaacgg ctcaccaagg caacgatgca tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gctttcgggt cgtaaaactc tgttgttagg gaagaacaag tacaagagta actgcttgta 480
ccttgacggt acctaaccag aaagccacgg ctaactacgt gccagcagcc gcggtaatac 540
gtaggtggca agcgttatcc ggaattattg ggcgtaaagc gcgcgcaggc ggtttcttaa 600
gtctgatgtg aaagcccacg gctcaaccgt ggagggtcat tggaaactgg ggaacttgag 660
tgcagaagag aaaagcggaa ttccacgtgt agcggtgaaa tgcgtagaga tgtggaggaa 720
caccagtggc gaaggcggct ttttggtctg taactgacgc tgaggcgcga aagcgtgggg 780
agcaaacagg attagatacc ctggtagtcc acgccgtaaa cgatgagtgc taagtgttag 840
agggtttccg ccctttagtg ctgcagctaa cgcattaagc actccgcctg gggagtacgg 900
tcgcaagact gaaactcaaa ggaattgacg ggggcccgca caagcggtgg agcatgtggt 960
ttaattcgaa gcaacgcgaa gaaccttacc aggtcttgac atcctctgac aactctagag 1020
atagagcgtt ccccttcggg ggacagagtg acaggtggtg catggttgtc gtcagctcgt 1080
gtcgtgagat gttgggttaa gtcccgcaac gagcgcaacc cttgatctta gttgccagca 1140
tttagttggg cactctaagg tgactgccgg tgacaaaccg gaggaaggtg gggatgacgt 1200
caaatcatca tgccccttat gacctgggct acacacgtgc tacaatggat ggtacaaagg 1260
gctgcaagac cgcgaggtca agccaatccc ataaaaccat tctcagttcg gattgtaggc 1320
tgcaactcgc ctacatgaag ctggaatcgc tagtaatcgc ggatcagcat gct 1373

<210> SEQ ID NO 56
<211> LENGTH: 1554
<212> TYPE: DNA
<213> ORGANISM: Unknown
<220> FEATURE:
<223> OTHER INFORMATION: Description of Unknown:
DP56 16S rRNA microbial sequence

<400> SEQUENCE: 56
attggagagt ttgatcctgg ctcaggacga acgctggcgg cgtgcctaat acatgcaagt 60

-continued

```
cgagcggacc tgatggagtg cttgcactcc tgatggttag cggcggacgg gtgagtaaca    120
cgtaggcaac ctgccctcaa gactgggata actaccggaa acggtagcta ataccggata    180
atttatttca cagcattgtg gaataatgaa agacggagca atctgtcact tggggatggg    240
cctgcggcgc attagctagt tggtggggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc caaggaagaa cgtcttctag agtaactgct    480
aggagagtga cggtacttga gaagaaagcc ccggctaact acgtgccagc agccgcggta    540
atacgtaggg ggcaagcgtt gtccggaatt attgggcgta aagcgcgcgc aggcggttct    600
ttaagtctgg tgtttaaacc cgaggctcaa cttcgggtcg cactggaaac tggggaactt    660
gagtgcagaa gaggagagtg gaattccacg tgtagcggtg aaatgcgtag atatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
taggggtttc gatacccttg gtgccgaagt taacacatta agcattccgc ctggggagta    900
cggtcgcaag actgaaactc aaaggaattg acggggaccc gcacaagcag tggagtatgt    960
ggtttaattc gaagcaacgc gaagaacctt accaagtctt gacatccctc tgaatcctct   1020
agagatagag gcggccttcg ggacagaggt gacaggtggt gcatggttgt cgtcagctcg   1080
tgtcgtgaga tgttgggtta agtcccgcaa cgagcgcaac ccttgatttt agttgccagc   1140
acatcatggt gggcactcta gaatgactgc cggtgacaaa ccggaggaag gcggggatga   1200
cgtcaaatca tcatgcccct tatgacttgg gctacacacg tactacaatg gctggtacaa   1260
cgggaagcga agccgcgagg tggagccaat cctataaaag ccagtctcag ttcggattgc   1320
aggctgcaac tcgcctgcat gaagtcggaa ttgctagtaa tcgcggatca gcatgccgcg   1380
gtgaatacgt tcccgggtct tgtacacacc gcccgtcaca ccacgagagt ttacaacacc   1440
cgaagtcggt ggggtaaccc gcaagggagc cagccgccga aggtggggta gatgattggg   1500
gtgaagtcgt aacaaggtag ccgtatcgga aggtgcggct ggatcacctc cttt         1554
```

<210> SEQ ID NO 57
<211> LENGTH: 1550
<212> TYPE: DNA
<213> ORGANISM: Unknown
<220> FEATURE:
<223> OTHER INFORMATION: Description of Unknown:
DP57 16S rRNA microbial sequence

<400> SEQUENCE: 57

```
attggagagt ttgatcctgg ctcaggatga acgctggcgg cgtgcctaat acatgcaagt     60
cgagcgaatg gattaagagc ttgctcttat gaagttagcg gcggacgggt gagtaacacg    120
tgggtaacct gcccataaga ctgggataac tccgggaaac cggggctaat accggataac    180
attttgcacc gcatggtgcg aaattcaaag gcggcttcgg ctgtcactta tggatggacc    240
cgcgtcgcat tagctagttg gtgaggtaac ggctcaccaa ggcaacgatg cgtagccgac    300
ctgagagggt gatcggccac actgggactg agacacggcc cagactccta cgggaggcag    360
cagtagggaa tcttccgcaa tggacgaaag tctgacggag caacgccgcg tgagtgatga    420
aggctttcgg gtcgtaaaac tctgttgtta gggaagaaca agtgctagtt gaataagctg    480
gcaccttgac ggtacctaac cagaaagcca cggctaacta cgtgccagca gccgcggtaa    540
```

tacgtaggtg gcaagcgtta tccggaatta ttgggcgtaa agcgcgcgca ggtggtttct 600
taagtctgat gtgaaagccc acggctcaac cgtggagggt cattggaaac tgggagactt 660
gagtgcagaa gaggaaagtg gaattccatg tgtagcggtg aaatgcgtag agatatggag 720
gaacaccagt ggcgaaggcg actttctggt ctgtaactga cactgaggcg cgaaagcgtg 780
gggagcaaac aggattagat accctggtag tccacgccgt aaacgatgag tgctaagtgt 840
tagagggttt ccgcccttta gtgctgaagt taacgcatta agcactccgc ctggggagta 900
cggccgcaag gctgaaactc aaaggaattg acgggggccc gcacaagcgg tggagcatgt 960
ggtttaattc gaagcaacgc gaagaacctt accaggtctt gacatcctct gacaacccta 1020
gagatagggc ttccccttcg gggcagagt gacaggtggt gcatggttgt cgtcagctcg 1080
tgtcgtgaga tgttgggtta agtcccgcaa cgagcgcaac ccttgatctt agttgccatc 1140
attaagttgg gcactctaag gtgactgccg gtgacaaacc ggaggaaggt ggggatgacg 1200
tcaaatcatc atgcccctta tgacctgggc tacacacgtg ctacaatgga cggtacaaag 1260
agctgcaaga ccgcgaggtg gagctaatct cataaaaccg ttctcagttc ggattgtagg 1320
ctgcaactcg cctacatgaa gctggaatcg ctagtaatcg cggatcagca tgccgcggtg 1380
aatacgttcc cgggccttgt acacaccgcc cgtcacacca cgagagtttg taacacccga 1440
agtcggtggg gtaacctttt tggagccagc cgcctaaggt gggacagatg attggggtga 1500
agtcgtaaca aggtagccgt atcggaaggt gcggctggat cacctccttt 1550

<210> SEQ ID NO 58
<211> LENGTH: 1060
<212> TYPE: DNA
<213> ORGANISM: Unknown
<220> FEATURE:
<223> OTHER INFORMATION: Description of Unknown:
DP58 16S rRNA microbial sequence

<400> SEQUENCE: 58
aatgacggta cctgaagaat aagcaccggc taactacgtg ccagcagccg cggtaatacg 60
tagggtgcaa gcgttaatcg gaattactgg gcgtaaagcg tgcgcaggcg gttttgtaag 120
tctgatgtga aatccccggg ctcaacctgg gaattgcatt ggagactgca aggctagaat 180
ctggcagagg ggggtagaat tccacgtgta gcagtgaaat gcgtagatat gtggaggaac 240
accgatggcg aaggcagccc cctgggtcaa gattgacgct catgcacgaa agcgtgggga 300
gcaaacagga ttagataccc tggtagtcca cgccctaaac gatgtctact agttgtcggg 360
tcttaattga cttggtaacg cagctaacgc gtgaagtaga ccgcctgggg agtacggtcg 420
caagattaaa actcaaagga attgacgggg acccgcacaa gcggtggatg atgtggatta 480
attcgatgca acgcgaaaaa ccttacctac ccttgacatg gctggaatcc tcgagagatt 540
ggggagtgct cgaaagagaa ccagtacaca ggtgctgcat ggctgtcgtc agctcgtgtc 600
gtgagatgtt gggttaagtc ccgcaacgag cgcaaccctt gtcattagtt gctacgaaag 660
ggcactctaa tgagactgcc ggtgacaaac cggaggaagg tggggatgac gtcaagtcct 720
catggccctt atgggtaggg cttcacacgt catacaatgg tacatacaga gcgccgccaa 780
cccgcgaggg ggagctaatc gcagaaagtg tatcgtagtc cggattgtag tctgcaactc 840
gactgcatga agttggaatc gctagtaatc gcggatcagc atgtcgcggt gaatacgttc 900
ccgggtcttg tacacaccgc ccgtcacacc atgggagcgg gttttaccag aagtaggtag 960
cttaaccgta aggagggcgc ttaccacggt aggattcgtg actggggtga agtcgtaaca 1020
aggtagccgt atcggaaggt gcggctggat cacctccttt 1060

<210> SEQ ID NO 59
<211> LENGTH: 1538
<212> TYPE: DNA
<213> ORGANISM: Unknown
<220> FEATURE:
<223> OTHER INFORMATION: Description of Unknown:
DP59 16S rRNA microbial sequence

<400> SEQUENCE: 59
ttgaagagtt tgatcatggc tcagattgaa cgctggcggc aggcctaaca catgcaagtc 60
gaacggtaac aggaagcagc ttgctgcttt gctgacgagt ggcggacggg tgagtaatgt 120
ctgggaaact gcctgatgga gggggataac tactggaaac ggtagctaat accgcataac 180
gtcgcaagac caaagagggg gaccttcggg cctcttgcca tcagatgtgc ccagatggga 240
ttagctagta ggtggggtaa cggctcacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtatgaag aaggccttcg 420
ggttgtaaag tactttcagc ggggaggaag gcgatgcggt taataaccgc gtcgattgac 480
gttacccgca gaagaagcac cggctaactc cgtgccagca gccgcggtaa tacggagggt 540
gcaagcgtta atcggaatta ctgggcgtaa agcgcacgca ggcggtctgt caagtcggat 600
gtgaaatccc cgggctcaac ctgggaactg catccgaaac tggcaggctt gagtctcgta 660
gaggggggta gaattccagg tgtagcggtg aaatgcgtag agatctggag gaataccggt 720
ggcgaaggcg gccccctgga cgaagactga cgctcaggtg cgaaagcgtg gggagcaaac 780
aggattagat accctggtag tccacgccgt aaacgatgtc gacttggagg ttgtgccctt 840
gaggcgtggc ttccggagct aacgcgttaa gtcgaccgcc tggggagtac ggccgcaagg 900
ttaaaactca aatgaattga cgggggcccg cacaagcggt ggagcatgtg gtttaattcg 960
atgcaacgcg aagaacctta cctggtcttg acatccacag aacttggcag agatgccttg 1020
gtgccttcgg gaactgtgag acaggtgctg catggctgtc gtcagctcgt gttgtgaaat 1080
gttgggttaa gtcccgcaac gagcgcaacc cttatccttt gttgccagcg gttaggccgg 1140
gaactcaaag gagactgcca gtgataaact ggaggaaggt ggggatgacg tcaagtcatc 1200
atggccctta cgaccagggc tacacacgtg ctacaatggc gcatacaaag agaagcgatc 1260
tcgcgagagc cagcggacct cataaagtgc gtcgtagtcc ggattggagt ctgcaactcg 1320
actccatgaa gtcggaatcg ctagtaatcg tgaatcagaa tgtcacggtg aatacgttcc 1380
cgggccttgt acacaccgcc cgtcacacca tgggagtggg ttgcaaaaga agtaggtagc 1440
ttaaccttcg ggagggcgct taccactttg tgattcatga ctggggtgaa gtcgtaacaa 1500
ggtaaccgta ggggaacctg cggttggatc acctcctt 1538

<210> SEQ ID NO 60
<211> LENGTH: 1547
<212> TYPE: DNA
<213> ORGANISM: Unknown
<220> FEATURE:
<223> OTHER INFORMATION: Description of Unknown:
DP60 16S rRNA microbial sequence

<400> SEQUENCE: 60
tcggagagtt tgatcctggc tcaggacgaa cgctggcggc gtgcctaata catgcaagtc 60
gagcgaatcg atgggagctt gctccctgag attagcggcg gacgggtgag taacacgtgg 120
gcaacctgcc tataagactg ggataacttc gggaaaccgg agctaatacc ggatacgttc 180
ttttctcgca tgagagaaga tggaaagacg gttttgctgt cacttataga tgggcccgcg 240
gcgcattagc tagttggtga ggtaatggct caccaaggcg acgatgcgta gccgacctga 300
gagggtgatc ggccacactg ggactgagac acggcccaga ctcctacggg aggcagcagt 360
agggaatctt ccgcaatgga cgaaagtctg acggagcaac gccgcgtgaa cgaagaaggc 420
cttcgggtcg taaagttctg ttgttaggga agaacaagta ccagagtaac tgctggtacc 480
ttgacggtac ctaaccagaa agccacggct aactacgtgc cagcagccgc ggtaatacgt 540
aggtggcaag cgttgtccgg aattattggg cgtaaagcgc gcgcaggtgg ttccttaagt 600
ctgatgtgaa agcccacggc tcaaccgtgg agggtcattg gaaactgggg aacttgagtg 660
cagaagagga aagtggaatt ccaagtgtag cggtgaaatg cgtagagatt tggaggaaca 720
ccagtggcga aggcgacttt ctggtctgta actgacactg aggcgcgaaa gcgtggggag 780
caaacaggat tagataccct ggtagtccac gccgtaaacg atgagtgcta agtgttagag 840
ggtttccgcc ctttagtgct gcagctaacg cattaagcac tccgcctggg gagtacggcc 900
gcaaggctga aactcaaagg aattgacggg ggcccgcaca agcggtggag catgtggttt 960
aattcgaagc aacgcgaaga accttaccag gtcttgacat cctctgacaa ccctagagat 1020
agggcgttcc ccttcggggg acagagtgac aggtggtgca tggttgtcgt cagctcgtgt 1080
cgtgagatgt tgggttaagt cccgcaacga gcgcaaccct tgatcttagt tgccagcatt 1140
cagttgggca ctctaaggtg actgccggtg acaaaccgga ggaaggtggg gatgacgtca 1200
aatcatcatg ccccttatga cctgggctac acacgtgcta caatggatgg tacaaagggc 1260
tgcaaacctg cgaaggtaag cgaatcccat aaagccattc tcagttcgga ttgtaggctg 1320
caactcgcct acatgaagcc ggaatcgcta gtaatcgcgg atcagcatgc cgcggtgaat 1380
acgttcccgg gccttgtaca caccgcccgt cacaccacga gagtttgtaa cacccgaagt 1440
cggtgaggta acctttatgg agccagccgc ctaaggtggg acagatgatt ggggtgaagt 1500
cgtaacaagg tagccgtatc ggaaggtgcg gctggatcac ctccttt 1547

<210> SEQ ID NO 61
<211> LENGTH: 962
<212> TYPE: DNA
<213> ORGANISM: Unknown
<220> FEATURE:
<223> OTHER INFORMATION: Description of Unknown:
DP61 16S rRNA microbial sequence

<400> SEQUENCE: 61
ggaaggcggt ctgtcaagtc ggatgtgaaa tccccgggct caacctggga actgcattcg 60
aaactggcag gctagagtct tgtagagggg ggtagaattc caggtgtagc ggtgaaatgc 120
gtagagatct ggaggaatac cggtggcgaa ggcggccccc tggacaaaga ctgacgctca 180
ggtgcgaaag cgtggggagc aaacaggatt agataccctg gtagtccacg ccgtaaacga 240
tgtcgacttg gaggttgttc ccttgaggag tggcttccgg agctaacgcg ttaagtcgac 300
cgcctgggga gtacggccgc aaggttaaaa ctcaaatgaa ttgacggggg cccgcacaag 360
cggtggagca tgtggtttaa ttcgatgcaa cgcgaagaac cttacctact cttgacatcc 420
acggaattta gcagagatgc tttagtgcct tcgggaaccg tgagacaggt gctgcatggc 480
tgtcgtcagc tcgtgttgtg aaatgttggg ttaagtcccg caacgagcgc aacccttatc 540
ctttgttgcc agcggtccgg ccgggaactc aaaggagact gccagtgata aactggagga 600

```
aggtggggat gacgtcaagt catcatggcc cttacgagta gggctacaca cgtgctacaa    660

tggcgcatac aaagagaagc gacctcgcga gagcaagcgg acctcataaa gtgcgtcgta    720

gtccggatcg gagtctgcaa ctcgactccg tgaagtcgga atcgctagta atcgtagatc    780

agaatgctac ggtgaatacg ttcccgggcc ttgtacacac cgcccgtcac accatgggag    840

tgggttgcaa aagaagtagg tagcttaacc ttcgggaggg cgcttaccac tttgtgattc    900

atgactgggg tgaagtcgta acaaggtaac cgtaggggaa cctgcggttg gatcacctcc    960

tt                                                                    962
```

```
<210> SEQ ID NO 62
<211> LENGTH: 876
<212> TYPE: DNA
<213> ORGANISM: Unknown
<220> FEATURE:
<223> OTHER INFORMATION: Description of Unknown:
      DP62 16S rRNA microbial sequence

<400> SEQUENCE: 62

tggctcagat tgaacgctgg cggcaggcct aacacatgca agtcgaacgg tagcacagag     60

gagcttgctc cttgggtgac gagtggcgga cgggtgagta atgtctggga aactgcccga    120

tggagggggga taactactgg aaacggtagc taataccgca taacgtcttc ggaccaaagt    180

gggggacctt cgggcctcac accatcggat gtgcccagat gggattagct agtaggtggg    240

gtaatggctc acctaggcga cgatccctag ctggtctgag aggatgacca gccacactgg    300

aactgagaca cggtccagac tcctacggga ggcagcagtg gggaatattg cacaatgggc    360

gcaagcctga tgcagccatg ccgcgtgtat gaagaaggcc ttcgggttgt aaagtacttt    420

cagtggggag gaaggcgtta aggttaataa ccttggcgat tgacgttacc cgcagaagaa    480

gcaccggcta actccgtgcc agcagccgcg gtaatacgga gggtgcaagc gttaatcgga    540

attactgggc gtaaagcgca cgcaggcggt ctgtcaagtc ggatgtgaaa tccccgggct    600

caacctggga actgcattcg aaactggcag gctagagtct tgtagagggg ggtagaattc    660

caggtgtagc ggtgaaatgc gtagagatct ggaggaatac cggtggcgaa ggcggccccc    720

tggacaaaga ctgacgctca ggtgcgaaag cgtggggagc aaacaggatt agataccctg    780

gtagtccacg ccgtaaacga tgtcgacttg gaggttgttc ccttgaggag tggcttccgg    840

agctaacgcg ttaagtcgac cgcctgggga gtacgg                              876
```

```
<210> SEQ ID NO 63
<211> LENGTH: 1532
<212> TYPE: DNA
<213> ORGANISM: Unknown
<220> FEATURE:
<223> OTHER INFORMATION: Description of Unknown:
      DP63 16S rRNA microbial sequence

<400> SEQUENCE: 63

tgaagagttt gatcatggct cagattgaac gctggcggca ggcctaacac atgcaagtcg     60

agcggtagag agaagcttgc ttctcttgag agcggcggac gggtgagtaa tgcctaggaa    120

tctgcctggt agtgggggat aacgttcgga aacggacgct aataccgcat acgtcctacg    180

ggagaaagca ggggaccttc gggccttgcg ctatcagatg agcctaggtc ggattagcta    240

gttggtgagg taatggctca ccaaggcgac gatccgtaac tggtctgaga ggatgatcag    300

tcacactgga actgagacac ggtccagact cctacgggag gcagcagtgg ggaatattgg    360
```

acaatgggcg aaagcctgat ccagccatgc cgcgtgtgtg aagaaggtct tcggattgta 420
aagcacttta agttgggagg aagggttgta gattaatact ctgcaatttt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg gatgtgaaat 600
ccccgggctc aacctgggaa ctgcattcaa aactgactga ctagagtatg gtagagggtg 660
gtggaatttc ctgtgtagcg gtgaaatgcg tagatatagg aaggaacacc agtggcgaag 720
gcgaccacct ggactaatac tgacactgag gtgcgaaagc gtggggagca aacaggatta 780
gataccctgg tagtccacgc cgtaaacgat gtcaactagc cgttggaagc cttgagcttt 840
tagtggcgca gctaacgcat taagttgacc gcctggggag tacggccgca aggttaaaac 900
tcaaatgaat tgacgggggc ccgcacaagc ggtggagcat gtggtttaat tcgaagcaac 960
gcgaagaacc ttaccaggcc ttgacatcca atgaactttc tagagataga ttggtgcctt 1020
cgggaacatt gagacaggtg ctgcatggct gtcgtcagct cgtgtcgtga gatgttgggt 1080
taagtcccgt aacgagcgca acccttgttc ttagttacca gcacgttatg gtgggcactc 1140
taaggagact gccggtgaca aaccggagga aggtggggat gacgtcaagt catcatggcc 1200
cttacggcct gggctacaca cgtgctacaa tggtcggtac agagggttgc caagccgcga 1260
ggtggagcta atcccataaa accgatcgta gtccggatcg cagtctgcaa ctcgactgcg 1320
tgaagtcgga atcgctagta atcgcgaatc agaatgtcgc ggtgaatacg ttcccgggcc 1380
ttgtacacac cgcccgtcac accatgggag tgggttgcac cagaagtagc tagtctaacc 1440
ttcgggagga cggttaccac ggtgtgattc atgactgggg tgaagtcgta acaaggtagc 1500
cgtaggggaa cctgcggctg gatcacctcc tt 1532

<210> SEQ ID NO 64
<211> LENGTH: 1649
<212> TYPE: DNA
<213> ORGANISM: Unknown
<220> FEATURE:
<223> OTHER INFORMATION: Description of Unknown:
DP64 ITS microbial sequence

<400> SEQUENCE: 64
tccgtaggtg aacctgcgga aggatcatta aataatcaat aattttggct tgtccattat 60
tatctattta ctgtgaactg tattattact tgacgcttga gggatgctcc actgctataa 120
ggataggcgg tggggatgtt aaccgagtca tagtcaagct taggcttggt atcctattat 180
tatttaccaa aagaattcag aattaatatt gtaacataga cctaaaaaat ctataaaaca 240
acttttaaca acggatctct tggttctcgc atcgatgaag aacgtagcaa agtgcgataa 300
ctagtgtgaa ttgcatattc agtgaatcat cgagtctttg aacgcaactt gcgctcattg 360
gtattccaat gagcacgcct gtttcagtat caaaacaaac cctctattca atatttttgt 420
tgaataggaa tactgagagt ctcttgatct tttctgatct cgaacctctt gaaatgtaca 480
aaggcctgat cttgtttgaa tgcctgaact ttttttaat ataaagagaa gctcttgcgg 540
taaactgtgc tggggcctcc caaataatac tctttttaaa tttgatctga aatcaggcgg 600
gattacccgc tgaacttaag catatcaata agcggaggaa aagaaaataa caatgatttc 660
cctagtaacg gcgagtgaag aggaaagagc tcaaagttgg aaactgtttg gcttagctaa 720
accgtattgt aaactgtaga aacattttcc tggcacgccg gattaataag tcctttggaa 780
caaggcatca tggagggtga gaatcccgtc tttgatccga gtagttgtct tttgtgatat 840

-continued

```
gttttcaaag agtcaggttg tttgggaatg cagcctaaat tgggtggtaa atctcaccta    900

aagctaaata tttgcgagag accgatagcg aacaagtacc gtgagggaaa gatgaaaaga    960

actttgaaaa gagagttaaa cagtatgtga aattgttaaa agggaaccgt ttggagccag   1020

actggtttga ctgtaatcaa cctagaattc gttctgggtg cacttgcagt ctatacctgc   1080

caacaacagt ttgatttgga ggaaaaaatt agtaggaatg tagcctctcg aggtgttata   1140

gcctactatc atactctgga ttggactgag gaacgcagcg aatgccatta ggcgagattg   1200

ctgggtgctt tcgctaataa atgttagaat ttctgcttcg ggtggtgcta atgtttaaag   1260

gaggaacaca tctagtatat tttttattcg cttaggttgt tggcttaatg actctaaatg   1320

acccgtcttg aaacacggac caaggagtcc accataagtg caagtatttg agtgacaaac   1380

tcatatgcgt aaggaaactg attgatacga aatcttttga tggcagtatc acccggcgtt   1440

gacgttttat actgaactga ccgaggtaaa gcacttatga tgggacccga aagatggtga   1500

actatgcctg aatagggtga agccagagga aactctggtg gaggctcgta gcgattctga   1560

cgtgcaaatc gatcgtcaaa tttgggtata ggggcgaaag actaatcgaa ccatctagta   1620

gctggttcct gccgaagttt ccctcagga                                     1649
```

<210> SEQ ID NO 65
<211> LENGTH: 1498
<212> TYPE: DNA
<213> ORGANISM: Unknown
<220> FEATURE:
<223> OTHER INFORMATION: Description of Unknown:
DP65 ITS microbial sequence

<400> SEQUENCE: 65

```
tccgtaggtg aacctgcgga aggatcatta ttgaaaacaa gggtgtccaa tttaacttgg     60

aacccgaact tctcaattct aactttgtgc atctgtatta tggcgagcag tcttcggatt    120

gtgagccttc acttataaac actagtctat gaatgtaaaa tttttataac aaataaaaac    180

tttcaacaac ggatctcttg gctctcgcat cgatgaagaa cgcagcgaaa tgcgatacgt    240

aatgtgaatt gcagaattca gtgaatcatc gaatctttga acgcatcttg cgctctctgg    300

tattccggag agcatgtctg tttgagtgtc atgaattctt caacccaatc ttttcttgta    360

atcgattggt gtttggattt tgagcgctgc tggcttcggc ctagctcgtt cgtaatacat    420

tagcatccct aatacaagtt tggattgact tggcgtaata gactattcgc taaggattcg    480

gtggaaacat cgagccaact tcattaagga agctcctaat ttaaaagtct accttttgat    540

tagatctcaa atcaggcagg attacccgct gaacttaagc atatcaataa gcggaggaaa    600

agaaactaac aaggattccc ctagtagcgg cgagcgaagc gggaaaagct caaatttgta    660

atctggcgtc ttcgacgtcc gagttgtaat ctcgagaagt gttttccgtg atagaccgca    720

tacaagtctc ttggaacaga gcgtcatagt ggtgagaacc cagtacacga tgcggatgcc    780

tattactttg tgatacactt tcgaagagtc gagttgtttg ggaatgcagc tcaaattggg    840

tggtaaattc catctaaagc taaatattgg cgagagaccg atagcgaaca agtaccgtaa    900

gggaaagatg aaaagcactt tggaaagaga gttaacagta cgtgaaattg ttggaaggga    960

aacacatgca gtgatacttg ctattcgggg caactcgatt ggcaggcccg catcagtttt   1020

tcggggcgga aaagcgtaga gagaaggtag caatttcggt tgtgttatag ctctttactg   1080

gattcgccct gggggactga ggaacgcagc gtgcttttag caattccttc gggaattcca   1140

cgcttaggat gcgggtttat ggctgtatat gacccgtctt gaaacacgga ccaaggagtc   1200
```

taacatgctt gcgagtattt gggtgtcaaa cccggatgcg caatgaaagt gaatggaggt 1260
gggaagcgca agctgcacca tcgaccgatc tggatttttt aagatggatt tgagtaagag 1320
caagtatgtt gggacccgaa agatggtgaa ctatgcctga atagggcgaa gccagaggaa 1380
actctggtgg aggctcgtag cggttctgac gtgcaaatcg atcgtcaaat ttgggtatag 1440
gggcgaaaga ctaatcgaac catctagtag ctggttcctg ccgaagtttc cctcagga 1498

<210> SEQ ID NO 66
<211> LENGTH: 1340
<212> TYPE: DNA
<213> ORGANISM: Unknown
<220> FEATURE:
<223> OTHER INFORMATION: Description of Unknown:
DP66 ITS microbial sequence

<400> SEQUENCE: 66
tccgtaggtg aacctgcgga aggatcatta ctgtgattta tccaccacac tgcgtgggcg 60
acacgaaaca ccgaaaccga acgcacgccg tcaagcaaga aatccacaaa actttcaaca 120
acggatctct tggttctcgc atcgatgaag agcgcagcga aatgcgatac ctagtgtgaa 180
ttgcagccat cgtgaatcat cgagttcttg aacgcacatt gcgcccgctg gtattccggc 240
gggcatgcct gtctgagcgt cgtttccttc ttggagcgga gcttcagacc tggcgggctg 300
tctttcggga cggcgcgccc aaagcgaggg gccttctgcg cgaactagac tgtgcgcgcg 360
gggcggccgg cgaacttata ccaagctcga cctcagatca ggcaggagta cccgctgaac 420
ttaagcatat caataagcgg aggaaaagaa accaacaggg attgccccag tagcggcgag 480
tgaagcggca aaagctcaga tttggaatcg cttcggcgag ttgtgaattg caggttggcg 540
cctctgcggc ggcggcggtc caagtccctt ggaacagggc gccattgagg gtgagagccc 600
cgtgggaccg tttgcctatg ctctgaggcc cttctgacga gtcgagttgt ttgggaatgc 660
agctctaagc gggtggtaaa ttccatctaa ggctaaatac tggcgagaga ccgatagcga 720
acaagtactg tgaaggaaag atgaaaagca ctttgaaaag agagtgaaac agcacgtgaa 780
attgttgaaa gggaagggta ttgcgcccga catggagcgt gcgcaccgct gcccctcgtg 840
ggcggcgctc tgggcgtgct ctgggccagc atcggttttt gccgcgggag aagggcggcg 900
ggcatgtagc tcttcggagt gttatagcct gccgccggcg ccgcgagcgg ggaccgagga 960
ctgcgacttt tgtctcggat gctggcacaa cggcgcaaca ccgcccgtct tgaaacatgg 1020
accaaggagt ctaacgtcta tgcgagtgtt tgggtgtgaa accccgggcg cgtaatgaaa 1080
gtgaacgtag gtcggaccgc tcctctcggg gggcgggcac gatcgaccga tcctgatgtc 1140
ttcggatgga tttgagtaag agcatagctg ttgggacccg aaagatggtg aactatgcct 1200
gaatagggtg aagccagagg aaactctggt ggaggctcgt agcggttctg acgtgcaaat 1260
cgatcgtcga atttgggtat aggggcgaaa gactaatcga accatctagt agctggttcc 1320
tgccgaagtt tccctcagga 1340

<210> SEQ ID NO 67
<211> LENGTH: 1698
<212> TYPE: DNA
<213> ORGANISM: Unknown
<220> FEATURE:
<223> OTHER INFORMATION: Description of Unknown:
DP53 Glutamine--tRNA ligase microbial sequence

<400> SEQUENCE: 67
atgagcaagc ccactgtcga ccccactctg aatccaaagg ctggccctgc tgtcccggct 60

```
aacttcctgc gtccaatcgt tcaggcggac ctagactcgg gtaaatacac acagatcgtg    120

acccgctttc cgccggagcc aaacggctat ctgcacatcg gtcatgccaa atccatttgt    180

gtgaactttg ggctggctca agagtttggc ggcgtgacgc atttgcgttt tgacgacacc    240

aacccggcaa aagaagacca ggaatacatc gacgccatcg aaagcgacgt caagtggctg    300

ggcttcgagt gggccggtga agtgcgttac gcgtcgcaat acttcgatca actgcacgag    360

tgggcgattt acctgatcaa agaaggcaag gcctacgtct gcgacctgac gcccgagcaa    420

gccaaggaat accgtggcag cctgaccgag cccggcaaga acagcccgtt ccgcgaccgt    480

agcgttgaag agaacctgga tctgttcgcc cgcatgaccg ccggtgagtt tgaagacggc    540

aagcgtgtgc tgcgcgccaa gatcgacatg acctcgccga acatgaacct gcgcgacccg    600

atcatgtacc gcatccgtca tgcccatcac caccagaccg gtgacaagtg gtgcatctac    660

cccaactatg acttcaccca cggtcagtcg gatgccattg aaggcatcac ccattcgatc    720

tgcaccctgg agttcgaaag ccatcgtccg ctgtacgaat ggttcctgga cagcctgcca    780

gtaccggcgc gcccgcgtca gtacgagttc agccgtctga acctcaacta caccatcacc    840

agcaagcgca agctcaagca gctggtcgat gaaaagcacg tcaacggctg ggatgacccg    900

cgcatgtcga cgctgtcggg tttccgccgt cgcggttaca cgcctaaatc gattcgtaat    960

ttctgtgaca tggtcggcac caaccgttct gacggtgttg ttgacttcgg catgctggaa   1020

ttcagcattc gtgacgattt ggaccacagc gcgccgcgcg ccatgtgcgt gctgcgtcca   1080

ttgaaggtga ttattaccaa ctacccggaa ggtcaggtcg aaaacctcga gctgccttgc   1140

cacccgaaag aagacatggg tgtgcgggtg ttgccgtttg cccgtgaaat ctacatcgac   1200

cgtgaagact tcatggaaga gccgccaaaa ggctacaagc gtcttgagcc tgcgggcgaa   1260

gtgcgtttgc gcggcagcta tgtgatccgt gccgacgaag cgatcaagga tgccgatggc   1320

aacatcgttg aactgcattg ctcgtacgat ccgctgaccc tgggtaaaaa ccctgaaggt   1380

cgcaaggtca agggtgttgt gcactgggtg ccggcggcgg ccagcgtcga atgcgaagtg   1440

cgtttgtatg atcgtctgtt ccgctcgccg aaccctgaaa aggccgaaga cggcgcgggc   1500

ttcctggaaa acatcaaccc tgactcgctg caggtactga ccggttgtcg tgctgaaccc   1560

tcgctgggca atgcacagcc ggaagaccgt ttccagttcg agcgcgaagg ctacttctgc   1620

gcagatatca aggactcgaa acccggtcac ccggtattca accgtaccgt gaccctgcgt   1680

gattcgtggg gccagtga                                                 1698
```

<210> SEQ ID NO 68
<211> LENGTH: 2418
<212> TYPE: DNA
<213> ORGANISM: Unknown
<220> FEATURE:
<223> OTHER INFORMATION: Description of Unknown:
DP53 DNA gyrase subunit B microbial sequence

<400> SEQUENCE: 68

```
ttgagcgaag aaaacacgta cgactcaacg agcattaaag tgctgaaagg ccttgatgcc     60

gtacgcaaac gtcccggtat gtacattggt gatactgacg atggcagcgg tctgcaccac    120

atggtgttcg aagtagtcga caactccatc gacgaagcgc tggctggcca ttgcgacgac    180

atcaccatca cgatccaccc ggacgagtcc atcaccgtgc gcgataacgg ccgcggtatt    240

ccggttgacg tgcataaaga agaaggcgta tctgcagccg aggtcatcat gaccgtgctg    300

cacgccggcg gtaagttcga tgacaactcc tacaaagtat ccggcggctt gcacggtgta    360
```

```
ggtgtttcgg tggtaaacgc cctgtccgaa ctgctggtct tgactgtacg ccgcagcggc    420
aagatctggg aacagaccta cgtccacggt gttcctcagg cgcctatggc tattgtgggt    480
gaaagcgaaa ccacgggtac gcagatccac ttcaagcctt cggctgaaac cttcaagaat    540
atccacttta gctgggacat cctggccaag cggattcgtg aactgtcctt cctgaactcc    600
ggtgtgggta tcgtcctcaa ggacgagcgc agcggcaagg aggagctgtt caagtacgaa    660
ggtggcctgc gtgcattcgt tgattacctg aacaccaaca agaacgctgt gaaccaggtg    720
ttccacttca atgttcagcg tgaagacggc atcggcgtag aaatcgccct gcagtggaac    780
gacagcttca acgagaacct gttgtgcttc accaacaaca ttccacagcg cgatggtggc    840
acgcacttgg tgggcttccg ctctgccctg acgcgtaacc tcaacacgta catcgaagct    900
gaaggcctgg ccaagaagca caaggtcgcc accaccggtg atgacgcccg tgaaggcttg    960
accgcgatca tctcggtgaa agtgccggat ccaaagttca gctcgcagac taaagacaag   1020
ctggtgtctt ccgaagtgaa gaccgctgtt gaacaggaaa tgggcaagtt cttctccgac   1080
ttcctgctgg aacacccgaa cgaagccaag ttgattgtcg gcaagatgat cgacgcagcc   1140
cgtgctcgtg aagctgcacg taaagcccgt gagatgaccc gtcgtaaagg cgcgttggac   1200
atcgcgggct tgccgggcaa gctggctgac tgccaggaaa aagaccctgc tctgtccgaa   1260
ctgtacctgg tggaaggtga ctctgctggc ggctccgcca agcagggtcg caaccgtcgt   1320
acccaagcca tcctgccgtt gaaaggtaaa atcctcaacg tcgagaaagc ccgttttgac   1380
aagatgatct cttcgcaaga agtcggcacc ttgatcactg cgctgggctg tggcatcggc   1440
cgcgaagagt acaacatcga caaactgcgc tatcacaaca tcatcatcat gaccgatgct   1500
gacgttgacg gttcgcacat ccgtaccctg ctgctgacct tcttcttccg tcagttgccg   1560
gagctgatcg agcgtggcta catctacatc gcccagccac cgttgtacaa agtgaaaaag   1620
ggcaagcaag agcagtacat caaagacgac gaggccatgg aagagtacat gacccagtcg   1680
gctcttgaag atgccagcct gcacttgaac gaagatgccc ctggcatctc cggtgaggca   1740
ctggagcgtc tggtgtacga cttccgcatg gtgatgaaga ccctcaagcg tttgtcgcgc   1800
ctgtaccctc aggagctgac cgagcacttc atctacctgc cggctgtaag ccttgagcag   1860
ttgggtgacc acgctgccat gcaggactgg atggccaagt ttgaagagcg tctgcgtctg   1920
gttgagaaat cgggcctggt ctacaaagcc agcctgcgtg aagaccgtga gcgtaatgtc   1980
tggttgccag aggtcgaact gatctcccac ggccactcga cgttcatcac cttcaaccgc   2040
gacttcttcg gcagcaacga ttacaaaacc gttgtgaccc tgggcgctca actgagcacc   2100
ctgctggatg aaggcgccta tatccagcgt ggcgaacgtc gcaagcaagt gaccgagttc   2160
aaagaagcac tggactggtt gatggctgaa agcaccaagc gtcacaccat ccagcgctac   2220
aaaggactgg gtgaaatgaa cccggatcag ctctgggaaa ccacgatgga cccaagcgtg   2280
cgtcgcatgc tgaaagtcac catcgaagac gcgatcggcg ccgatcagat cttcaacacc   2340
ttgatgggcg atgctgtaga accacgtcgt gaattcatcg agagcaacgc actggcagtg   2400
tccaacctgg atttctga                                                 2418
```

<210> SEQ ID NO 69
<211> LENGTH: 2832
<212> TYPE: DNA
<213> ORGANISM: Unknown
<220> FEATURE:
<223> OTHER INFORMATION: Description of Unknown:
DP53 Isoleucine--tRNA ligase microbial sequence

<400> SEQUENCE: 69

```
atgaccgact acaaagccac gctaaacctc ccggacaccg ccttcccaat gaaggccggc      60
ctgccacagc gcgaaccgca aattttgcag cgctgggaca gcattggcct gtacgggaag     120
ttgcgcgaga ttggcaagga tcgtccgaag ttcgtacttc acgacggtcc tccgtacgcc     180
aacggcacta tccatatcgg tcatgcgctg aacaagattc tgaaagacat gatcatccgc     240
tccaagaccc tgtcgggttt tgacgcgccg tatgtgccgg gctgggattg ccatggtttg     300
ccgattgaac acaaggtcga agtgacccac ggtaaaaacc tgagcgcgga taaaacccgc     360
gagctgtgcc gtgcctacgc caccgagcag atcgaggggc agaagtccga gttcatccgt     420
ctgggtgtgc tgggtgattt cgccaacccg tacaagacca tggacttcaa aaacgaagcc     480
ggtgaaatcc gtgctttggc tgagatcgtc aagggcggtt ttgtgttcaa gggcctcaag     540
ccggtgaact ggtgcttcga ttgcggttcg gccctggctg aagctgaagt tgaataccag     600
gacaagaagt ctgcggccat cgacgttgcc ttcccggttg ccgacgaggc caagctggcc     660
gaggcctttg gtctggcggc actgagcaaa cctgcttcga tcgtgatctg gaccaccacc     720
ccgtggacca ttccggccaa ccaggcgctt aacgtacacc cggaattcac ctacgcgctg     780
gtcgacgtgg gcgacaagtt gctggtactg gctgaagaac tggtcgaatc gagtctggcg     840
cgttacaacc tgcagggttc ggtcatcgcc accaccactg gctcagcgct tgaactaatc     900
aacttccgtc acccgttcta tgaccgtctg tcgcctgttt atctggccga ctacgttgag     960
ctgggtgctg gcactggtgt ggttcactcg gctccagcct acggcgtaga cgacttcgtg    1020
acctgcaaag cctatggcat ggtcaacgac gacatcatca acccggtgca aagcaatggc    1080
gtttacgtgc cgtcgctgga gttcttcggt ggccagttca tctggaaggc caaccagaac    1140
atcatcgaca agctgatcga agtcggttcg ctgatgttca ccgagaccat cagccacagc    1200
tatatgcact gctggcgcca caagacgccg ctgatctacc gtgccaccgc ccagtggttt    1260
atcggtatgg acaagcagcc gactgatggc gataccttgc gcacccgtgc gctgcaagcg    1320
atcgaagaca cccagttcgt tccggcctgg ggtcaggcgc gcctgcactc gatgatcgcc    1380
aaccgcccgg actggtgcat ctcgcgtcaa cgcaactggg gcgtgccgat cccgtttttc    1440
ctgaacaagg aaagcggcga gctgcacccg cgcaccgtcg aaatgatgga agaagtggcc    1500
aagcgcgttg aagtcgaagg catcgaggcg tggttcaagc tggatgctgc cgagctgctg    1560
ggcgacgaag cgccgctgta cgacaagatc agcgataccc tcgacgtctg gttcgattcg    1620
ggcaccacgc actggcatgt ccttcgcggt tcgcacccga tgggtcatga aaccggccca    1680
cgcgctgatc tctaccttga aggctccgac cagcaccgtg gctggttcca ctcgtcgttg    1740
ctgaccggtt gcgccatcga caaccacgcg ccgtaccgcg agctgctgac ccacggtttt    1800
accgtggacg aagcgggccg caagatgtcc aagtcgctgg gcaacgtgat tgcaccgcaa    1860
aaggtcaacg acaccctggg cgccgacatc atgcgtctgt gggttgcttc gaccgactac    1920
tcgggcgaaa tcgcggtttc cgaccagatc ctgcagcgca gtgcggacgc ctaccgacgt    1980
atccgcaata ccgcacgctt cctgctgtcg aacctgaccg gtttcaatcc agccaccgac    2040
atcctgcctg ccgaagaaat gctggcactg gaccgctggg cggtggatcg tgcgttgctg    2100
ctgcaacgtg agctggagct gcattacggc gaataccgtt tctggaacgt gtactccaag    2160
gtgcacaact tctgcgttca ggagctgggc ggtttctatc tcgacatcat caaggaccgc    2220
cagtacacca ccggcgccaa cagcaaggct cgccgttcgt gccagaccgc gctgttccac    2280
```

-continued

```
atctctgaag cgctggtgcg ctggatcgct ccgatcctgg cgttcaccgc tgatgagttg   2340

tggcagtacc tgccgggcga gcgcaacgaa tcggtcatgc tcaacacctg gtacgaaggc   2400

ctgactgaac tgccggaagg caccgaactg gatcgcgcct actgggagcg aatcatggcg   2460

gtcaaggttg cggtcaacaa ggaaatggaa aacttgcgcg cagccaaggc cattggcggt   2520

aacttgcaag cagaagtgac cttgttcgcc gaagatcagc tggctgctga tttgtccaag   2580

ttgagcaacg aactgcgttt cgtgttgatc acctccactg ccagcgttgc gccttttgcg   2640

caggctccag cagatgccgt ggttaccgaa gtggctggcc tcaaactcaa ggtggtcaag   2700

tcggcccatg ccaagtgcgc ccgttgctgg cactgccgtg aagacgtcgg cgttaacccc   2760

gagcaccctg aaatctgcgg tcgttgtgta gacaatatca gcggcgctgg tgaggtacgt   2820

cactatgcct aa                                                        2832
```

<210> SEQ ID NO 70
<211> LENGTH: 1785
<212> TYPE: DNA
<213> ORGANISM: Unknown
<220> FEATURE:
<223> OTHER INFORMATION: Description of Unknown:
DP53 NADH-quinone oxidoreductase subunit C/D
microbial sequence

<400> SEQUENCE: 70

```
atgactgcag gctccgctct gtacatcccg ccttacaagg ctgacgacca agatgtggtt     60

gtcgaactca atacccgttt tggccctgag gcgttcaccg cccaggccac gcgcaccggc    120

atgccggtgc tttgggttag ccgcgcaaaa ctggtcgaag tactgacctt cctgcgcaac    180

ctgccaaaac cctacgtcat gctctatgac ctgcacggtg tggacgaacg tctgcgtacc    240

aagcgtcagg gcctgccatc gggtgcagac ttcaccgtct tctaccacct gatgtcgctg    300

gaacgtaaca gcgacgtcat gatcaaggtg gccctgtctg aaaaagacct gagtgtccct    360

accgtgaccg gtatctggcc gaacgccaac tggtacgagc gtgaagtctg ggacatgttc    420

ggcatcgatt tcaaaggcca cccgcacctg tcgcgcatca tgatgccgcc gacctgggaa    480

ggtcacccgc tgcgcaagga cttcccggcc cgtgccacag agttcgatcc gtacagcctg    540

accctggcca aggtgcagct ggaagaggaa gccgcgcgct tccgcccgga agactggggc    600

atgaaacgct ccggtgaaaa cgaggactac atgttcctca acctgggccc taaccaccct    660

tcggctcacg gtgccttccg catcatcctg cagctggacg gtgaagagat cgtcgactgc    720

gtgcctgacg tcggttacca ccaccgtggc gccgagaaaa tggccgaacg ccagtcctgg    780

cacagtttca tcccgtacac cgaccggatc gattacctcg gcggagtgat gaacaacctg    840

ccgtacgtgc tctcggtcga gaagctggcc ggtatcaaag tgccggatcg ggtcgacacc    900

atccgcatca tgatggccga attcttccgt atcaccagcc acctgctgtt cctgggtacc    960

tatatccagg acgtgggcgc catgaccccg gtgttcttca cgttcaccga ccgtcagcgc   1020

gcttacaagg tgatcgaggc catcaccggt ttccgtctgc acccggcctg gtaccgcatc   1080

ggcggcgttg cccacgacct gccgaacggc tgggatcgcc tggtcaagga attcatcgac   1140

tggatgccca agcgtctgga cgagtaccag aaagccgctc tggacaacag catcctgcgt   1200

ggtcgtacca tcggcgttgc cgcctacaac accaaagagg ccctggaatg gggcgtcacc   1260

ggtgccggcc tgcgctccac cggttgtgac ttcgatatcc gcaaggcgcg cccgtattcc   1320

ggctacgaga acttcgaatt cgaagtcccg ctggcagcca acggcgatgc ctacgatcgt   1380

tgcatcgtgc gcgtcgaaga aatgcgccag agcctgaaaa tcatcgagca gtgcatgcgc   1440
```

aacatgccgg ccggcccgta caaggcggat cacccgctga ccacgccgcc gcctaaagaa 1500
cgcacgctgc agcatatcga gaccttgatc acgcacttcc tgcaagtttc gtggggcccg 1560
gtgatgccgg ccaacgaatc cttccagatg atcgaagcga ccaagggcat caacagttat 1620
tacctgacga gcgatggcgg caccatgagc taccgcaccc ggattcgcac cccaagcttc 1680
ccgcacctgc aacagatccc ttcggtgatc aaaggtgaaa tggtcgcgga cttgattgcg 1740
tacctgggta gtatcgattt cgttatggcc gacgtggacc gctaa 1785

<210> SEQ ID NO 71
<211> LENGTH: 1119
<212> TYPE: DNA
<213> ORGANISM: Unknown
<220> FEATURE:
<223> OTHER INFORMATION: Description of Unknown:
DP53 Protein RecA microbial sequence

<400> SEQUENCE: 71
atggacgaca acaagaagaa agccttggct gcggccctgg gtcagatcga acgtcaattc 60
ggcaagggtg ccgtgatgct gatgggcgac caggagcgtc aggcagtccc ggcgatctcc 120
accggctccc tgggtctgga catcgcactg ggcattggcg gtctgccaaa aggccgtatt 180
gttgaaatct acggccctga gtcgtcgggt aaaaccacac tgaccctgtc cgtgattgcc 240
caggcgcaaa aggccggtgc tacctgcgcc ttcgtcgatg ccgagcacgc ccttgatcct 300
gagtacgctg ccaaactggg cgtaaacgtt gatgacctgc tggtttcaca gcctgacacc 360
ggcgaacagg cactggaaat caccgatatg ctggtgcgtt ccaatgcggt tgacgtgatc 420
atcatcgact ccgttgctgc actgacgcca aaagctgaaa tcgaaggcga catgggcgat 480
acccacgttg gcctgcaagc ccgtctgatg tcgcaagcgc tgcgtaaaat caccggtaac 540
atcaagaacg ccaactgcct ggttatcttc atcaaccaga tccgcatgaa aatcggcgtg 600
atgttcggca gccctgaaac caccaccggt ggtaacgcac tgaagttcta cgcttcggta 660
cgtctggata tccgccgcac cggcgccgta aaagaaggcg atgtggtggt gggtagcgaa 720
acccgcgtga aagtggtcaa gaacaaggtg gcaccaccgt tccgtcaggc tgaattccag 780
atcctgtacg gcaagggtat ctacctgaac ggtgaaatga ttgacctggg cgtactgcat 840
ggctttgttg aaaaagctgg cgcctggtac agctacaacg gcagcaaaat cggtcagggc 900
aaggccaact ccgccaagtt cctggacgat aacccggaca tcaaggatgc gctggagaag 960
cagctgcgtg agaagttgct cgggccaaaa accgatgccg aactggcagc gacggactgc 1020
aatggacctg ctcgcgcgac gcgagcacgg tcgagtcgag ctgacgcgca agttgcgtca 1080
gcgcggcgct tgccccgaca tgatcgacgc tgcccttga 1119

<210> SEQ ID NO 72
<211> LENGTH: 1848
<212> TYPE: DNA
<213> ORGANISM: Unknown
<220> FEATURE:
<223> OTHER INFORMATION: Description of Unknown:
DP53 RNA polymerase sigma factor RpoD microbial sequence

<400> SEQUENCE: 72
atgtccggaa aagcgcaaca gcagtctcgt atcaaagagt tgatcaccct cggccgtgag 60
cagaagtatc tgacttacgc agaggtcaac gaccacctgc ccgaagatat ttcagatccg 120
gagcaagtgg aagacatcat ccgcatgatt aatgacatgg ggatccccgt acacgagagt 180
gctccggatg cggacgccct tatgttggcc gatgccgaca ccgacgaagc agcagctgaa 240
gaagcggctg cagcgttggc ggcagtagag accgacattg gtcgtactac cgaccctgtg 300
cgcatgtata tgcgtgaaat gggcacggta gaactgctga cacgtgaagg cgaaatcgaa 360
atcgccaagc gtatcgaaga aggcatccgt gaagtgatgg gcgcaatcgc gcacttccct 420
ggcacggttg accatattct ctccgagtac actcgcgtca ccaccgaagg tggccgcctg 480
tccgacgttc tgagcggtta tatcgacccg gacgacggta ttgcgccgcc cgcagccgaa 540
gtacctcctc ctgtcgacac caaggtgaaa gccgaaggtg atgacgaaga ggacgacaag 600
gaagattccg gcgaagacga ggaagaggtc gaaagcggcc ctgatccgat catcgcggcc 660
cagcgctttg gcgctgtttt cgatcagatg gaaatcgctc gcaaggccct gaaaaagcac 720
ggtcgcggca gcaagcaggc aattgccgag ctggttgcac tggctgagct gttcatgccg 780
atcaaactgg ttccgaagca attcgaaggc ctggttgagc gtgttcgcag cgccctggag 840
cgtctgcgtg cacaagagcg cgcaatcatg cagctgtgtg tacgtgatgc acgcatgccg 900
cgcaccgatt tcctgcgtct gttcccgggc aacgaagtcg acgaaagctg gagcgatgcg 960
ctggccaaag gcaaaagcaa atatgctgaa gccattggtc gcctgcaacc ggacatcatc 1020
cgttgccagc aaaagctctc tgctctggaa gcagaaaccg gcttgaagat tgccgagatc 1080
aaggacatca accgtcgcat gtcgatcggc gaggccaagg cccgccgcgc gaagaaagaa 1140
atggttgaag ccaacttgcg tctggtgatc tccatcgcca agaagtacac caaccgtggc 1200
ctgcagttcc tcgatctgat ccaggaaggc aacatcggct tgatgaaagc ggtagacaag 1260
tttgaatacc gccgcggcta caaattctcg acttatgcca cctggtggat ccgtcaggcg 1320
atcactcgct cgatcgccga ccaggcccgc accatccgta ttccggtgca catgatcgag 1380
acgatcaaca agctcaaccg tatttcccgt cagatgttgc aggaaatggg ccgtgaaccg 1440
accccggaag agctgggcga acgcatggaa atgcctgagg ataaaatccg caaggtattg 1500
aagatcgcta aagagccgat ctccatggaa accccgatcg gtgatgacga agactcccat 1560
ctgggtgact tcatcgaaga ctcgaccatg cagtcgccaa tcgatgttgc taccgttgag 1620
agccttaaag aagcgacacg cgacgtactc ggcggcctca cagcccgtga agccaaggta 1680
ctgcgcatgc gtttcggtat cgacatgaat accgaccaca cccttgagga ggttggtaaa 1740
cagttcgacg ttacccgtga gcggattcgt cagatcgaag ccaaggcgct gcgcaagctg 1800
cgccacccga cgagaagcga gcatttgcgc tccttcctcg acgagtga 1848

<210> SEQ ID NO 73
<211> LENGTH: 4073
<212> TYPE: DNA
<213> ORGANISM: Unknown
<220> FEATURE:
<223> OTHER INFORMATION: Description of Unknown:
DP53 DNA-directed RNA polymerase subunit beta
microbial sequence

<400> SEQUENCE: 73
atggcttact catatactga gaaaaaacgt atccgcaagg actttagcaa gttgccggac 60
gtcatggatg tgccgtatct cttggcaatc cagctggatt cgtatcgtga attcttgcag 120
gcgggagcga ctaaagatca gttccgcgac gtgggcctgc atgcggcctt caaatccgtt 180
ttcccgatca tcagctactc cggcaatgct gcgctggagt acgtcggtta tcgcttgggc 240
gaaccggcat ttgatgtcaa agaatgcgtg ttgcgtggcg taacgtacgc cgtacctttg 300
cgggtaaaag ttcgtttgat cattttcgac aaagaatcgt cgaacaaagc gatcaaggac 360

```
atcaaagagc aagaagtcta catgggtgaa atccccctga tgactgaaaa cggtaccttc    420
gtaatcaacg gtaccgagcg tgtaattgtt tcccagctgc accgttcccc gggcgtgttc    480
tttgccacga ccgcggcaag acgcacagct ccggtaagct gctttattcc gcgcgtatca    540
ttccttaccg tggttcgtgg ctcgacttcg agttcgaccc gaaagactgc gtgttcgtgc    600
gtattgaccg tcgtcgcaag ctgcctgcat cggtattgct gcgcgcgctg ggttatacca    660
ctgagcaagt gctggacgcg ttctacacca ccaacgtgtt ccacgttcag ggtgagagca    720
tcagcctgga gctggttcca cagcgtctgc gcggtgaaat cgcggccatc gacattaccg    780
atgacaaagg caaggtgatt gttgagcagg gtcgtcgtat cactgctcgt catatcaacc    840
agctggaaaa agccggtgtc aaagagctcg ttatgcctct ggactatgtc ctgggtcgca    900
caacggccaa ggctatcgtg catccggcta ctggcgaaat cattgctgag tgcaacaccg    960
agctgaccac tgaaatcctg gcaaaagttg ccaagggcca ggttgttcgc atcgaaacgt   1020
tgtacaccaa cgatatcgac tgcggtccgt tcgtctccga cacgctgaag atcgactcca   1080
ccagcaacca actggaagcg ctggtcgaaa tctatcgcat gatgcgtcca ggcgagccgc   1140
caaccaaaga cgctgccgag actctgttca acaacctgtt cttcagccct gagcgctatg   1200
acctgtctgc ggtcggccgg atgaagttca accgtcgtat cggtcgtacc gagatcgaag   1260
gttcgggcgt gttgtgcaaa gaagacatcg ttgccgtgct gaagaccctg gtcgacatcc   1320
gtaacggtaa aggcatcgtc gatgacatcg accacctggg taaccgtcgt gttcgctgtg   1380
taggcgaaat ggccgagaac cagttccgcg ttggcctggt acgtgttgag cgtgcggtca   1440
aagagcgtct gtcgatggct gaaagcgaag gcctgatgcc gcaagacctg atcaacgcca   1500
agcctgtggc tgcggcggtg aaagagttct tcggttccag ccagctgtcc cagttcatgg   1560
accagaacaa ccctctgtcc gagatcaccc acaagcgccg tgtttctgca ctgggcccgg   1620
gcggtctgac gcgtgagcgt gcgggctttg aagttcgtga cgtacacccg actcactacg   1680
gccgtgtttg ccctattgag acgccggaag gtccgaacat cggtctgatc aactccctgg   1740
ctgcctatgc gcgcaccaac cagtacggct tcctcgagag cccgtaccgt gtagtgaaag   1800
acgcactggt aactgacgag atcgttttcc tgtccgccat cgaagaagct gatcacgtga   1860
tcgctcaggc ctcggccacg atgaacgaca agaaagtgct gatcgacgag ctggttgctg   1920
ttcgtcactt gaacgaattc accgtcaagg cgccggaaga cgtcaccttg atggacgttt   1980
cgccgaagca ggttgtttcg gttgcagcgt cgctgatccc gttcctggaa cacgatgacg   2040
ccaaccgtgc gttgatgggt tccaacatgc agcgtcaagc tgtaccaacc ctgcgcgctg   2100
acaagccgct ggtaggtacc ggcatggagc gtaacgtagc tcgtgactcc ggcgtttgcg   2160
tcgtggctcg tcgtggcggc gtgatcgact ctgttgatgc cagccgtatc gtggttcgtg   2220
ttgctgatga cgaagttgaa actggcgaag ccggtgtcga catctacaac ctgaccaaat   2280
acacccgttc caaccagaac acttgcatca accagcgtcc gctggtgcgc aagggtgacc   2340
gtgtacagcg tagcgacatc atggctgacg gcccgtccac cgatatgggt gaactggcgc   2400
tgggtcaaaa catgcgcatc gcgttcatgg cctggaacgg ttacaacttc gaagactcca   2460
tctgcttgtc ggaacgagtt gttcaagaag accgctttac cacgatccac attcaggaac   2520
tgacctgtgt ggcacgtgac accaagcttg ggcctgaaga gatcactgca gacatcccta   2580
acgtgggtga agctgcactg aacaaactgg acgaagccgg tatcgtttac gtaggtgctg   2640
aagttggcgc cggcgacatt ctggtaggta aggtcactcc gaaaggcgag acccagctga   2700
```

ctccggaaga gaagctgttg cgtgccatct tcggtgaaaa agccagcgac gttaaagaca 2760
cctccctgcg cgtacctacc ggtaccaaag gtactgttat cgacgtgcag gtcttcaccc 2820
gtgacggcgt tgagcgtgat gctcgtgcac tgtcgatcga gaagacccag ctggacgaga 2880
tccgcaagga tctgaacgaa gagttccgta tcgttgaagg cgctaccttc gaacgtctgc 2940
gctctgctct ggttggccgc attgccgaag gtggtgccgg tctgaagaaa ggtcaggaaa 3000
tcaccaatga aatcctggac ggtcttgagc atggtcagtg gttcaaactg cgcatggctg 3060
aagatgctct gaacgagcag cttgaaaagg ctcaggctta catcatcgat cgccgtcgtc 3120
tgctggacga caagttcgaa gacaagaagc gcaaactgca gcagggcgat gacctggctc 3180
caggcgtgct gaaaatcgtc aaggtttacc tggcaatccg ccgtcgcatc cagccgggtg 3240
acaagatggc cggtcgtcac ggtaacaagg gtgtggtctc cgtgatcatg ccggttgaag 3300
acatgccgta cgatgccaat ggcaccccgg ttgatgtggt cctcaacccg ttgggcgtac 3360
cttcgcgtat gaacgttggt cagattctcg aaactcacct gggcctcgcg gccaaaggtc 3420
tgggcgagaa gatcaacctc atgattgaag aacaacgcaa ggtcgctgac ctgcgtaagt 3480
tcctgcatga gatctacaac gaaattggcg gtcgtcaaga aagcctggat gacttctccg 3540
atcaggaaat cctggatctg gcgaagaacc ttcgcggcgg tgtgccaatg gctaccccgg 3600
tgttcgacgg tgccaaggaa agcgaaatca aggcaatgct tcgtttggca gacctgccag 3660
acagcggcca gatggtgctg actgatggtc gtaccggcaa caagttcgag cgtccggtta 3720
ccgttggcta catgtacatg ctgaagctga accacttggt agacgacaag atgcacgctc 3780
gttctaccgg ttcttacagc ctggttaccc agcagccgct gggtggtaag gcgcagttcg 3840
gtggtcagcg tttcggggag atggaggtct gggcgctgga agcctacggc gcggcataca 3900
ctctgcaaga aatgctcaca gtgaagtcgg acgatgtgaa cggccgtacc aagatgtaca 3960
aaaacatcgt ggacggcgat caccgtatgg agccgggcat gcccgagtcc ttcaacgtgt 4020
tgatcaaaga aattcgttcc ctcggcatcg atatcgatct ggaaaccgaa taa 4073

<210> SEQ ID NO 74
<211> LENGTH: 2073
<212> TYPE: DNA
<213> ORGANISM: Unknown
<220> FEATURE:
<223> OTHER INFORMATION: Description of Unknown:
DP9 Glycine--tRNA ligase beta subunit microbial sequence

<400> SEQUENCE: 74
atggcacata attatttact agaaattgga ttggaagaaa ttccggccca tgttgtaact 60
ccaagtatca aacagttagt acaaaaagta acagccttct taaaagaaaa tcgcttaaca 120
tacgactcaa ttgatcattt ttcaactcct cgtcgtttgg caattcgaat caatgggtta 180
ggcgaccaac aacctgatat tgaagaagat gctaaaggcc ctgctcgtaa aattgctcaa 240
gatgctgatg gaaattggac taaggctgca attggcttta cacgtggaca aggtcttacg 300
gttgacgata ttacttttaa aacaatcaaa ggtacggact atgtgtacgt ccataagtta 360
atcaaaggaa agatgactaa ggaaatcctt acggggataa aagaagttgt tgaatcaatt 420
aatttcccaa caatgatgaa gtgggctaac tttgatttta aatatgtacg cccaattcgt 480
tggctggttt ctattctaga tgaagaagtc cttcctttta gtatcttaga cgtaactgcg 540
ggacgccgaa cagaaggaca tcgtttctta ggtgaagctg tcgaactggc taatgctgaa 600
gaatatgaag caaaattaca cgatcaattt gtgattgttg atgccgacga gcgtaaacaa 660

-continued ttaatttcaa accaaattaa agcaattgct gaaagcaatc gttggaacgt taccccctaac 720 ccaggtcttt tagaagaggt taacaatttg gttgagtggc caaccgcttt taatggggga 780
tttgatgaaa agtatttagc tattccagaa gaggtattga taacatcaat gcgtgaccac 840
caacgcttct tctttgtccg cgaccaagct ggaaagctat tgccaaactt catctccgta 900
cgaaatggga atgaagaatt tattgaaaat gttgttcgtg gaaatgaaaa agttttaact 960
gcacgtttag aagacgctgc tttcttctac gaagaagatc aaaaacatga tattaattat 1020
tatgttgacc gacttaaaaa ggttagtttc catgataaga ttggttcaat gtacgaaaaa 1080
atgcaacgag ttaattctat tgctaaagtt attggaaaca ccttaaatct taatcaaacg 1140
gaacttgatg atatcgatcg cgctacaatg atttataaat ttgatttggt aactggtatg 1200
gttggtgagt tctcagaatt acaaggagta atgggtgaaa aatatgctca acttaatggt 1260
gaaaaccaag cagtagccca agccattcgc gaacattaca tgccaaatag cgcagaaggt 1320
gatttgcctg aaagtgtaac gggcgcggta gtcgcattag ctgataagtt tgataacatc 1380
tttagttttt tctcagctgg tatgattcca agtggttcaa acgatccata tgcattacgc 1440
cgacatgcat atggaattgt tagaatctta aatagccgtg attggcaatt agatttaaat 1500
caattcaaat cacaatttaa gactgaatta gcggagaatg gcacagcgtt tggtgtggat 1560
gtcgatcaaa actttgacca agtacttaac ttctttaatg accgtattaa acaattgctt 1620
gatcatcaaa agattagtca tgatatcgtt gaaacggtgc ttacaggtaa taatcatgat 1680
gttacggaaa ttatcgaagc tgcccaagta ctagcagatg ctaaagcgag ctctacattt 1740
aaagatgata ttgaagcttt aacacgagtt caaagaattg ctacaaagaa tgaagaaagt 1800
ggagaactta atgtagatcc acaattattt aataatgctt ctgaaggcga actttttgat 1860
caaattatta aaattgaagc tgcaaataat ttgacaatga gccaactatt tgctaaatta 1920
tgcgagttga ctcctgcgat tagcaagtac tttgacgcaa cgatggtcat ggacaaagac 1980
gaaaatatta agtgtaatcg tttgaatatg atgagtcggt tagctaattt aattctaaaa 2040
attggggatc taactaacgt acttgtaaaa taa 2073

<210> SEQ ID NO 75
<211> LENGTH: 1341
<212> TYPE: DNA
<213> ORGANISM: Unknown
<220> FEATURE:
<223> OTHER INFORMATION: Description of Unknown:
DP9 Glutamine synthetase microbial sequence

<400> SEQUENCE: 75
atggcaaaga aaaattattc gcaagcagat attcgtcaga tggcaaagga tgaaaatgta 60
cgttttctcc gattaatgtt tacagatctt tttggaataa ttaagaacgt tgaagtacca 120
attagtcaat tggacaaact attagataat aaattgatgt ttgatggttc ctcaattgac 180
gggtttgttc ggattgaaga aagtgacatg tatttatacc cagatctttc tacttggatg 240
gttttcccat ggggaagcga acatggcaag gtggctcgca ttatttgtga agtatactca 300
aatgatcgta aaccattcgt gggtgatcca cgtaacaatt taattcgagt actccaagag 360
atgaaggatg caggatttac tgattttaat atcggacctg aacctgagtt tttcttgttg 420
aaattagatg aaaatggtaa accaaccact aatttaaatg ataaaggtag ttactttgat 480
ttagctcctg ttgatttagg tgaaaactgc cgtcgtgata ttgttttgga acttgaaaat 540
atgggctttg atgttgaagc ttctcatcat gaagttgctc caggacaaca cgaaattgac 600

-continued

```
tttaaatacg ccgatgcttt gaccgctgcc gataacattc aaacctttaa gttggttgtt    660

aagacagttg cccgtaaata taacctgcat gctacattta tgcctaaacc tatggatgga    720

atcaatggtt cagggatgca tttaaacatg tcacttttca ataaggaagg caatgctttc    780

tatgacgaaa agggtgactt acaactttct caaaatgctt actggttcct tggtggacta    840

ttgaagcatg ctcgtagtta tacggccgta tgtaacccaa ttgttaactc gtacaaacgt    900

ttagttcctg gatatgaagc tccagtatac gttgcttggt caggttcaaa tcgttcacca    960

cttattcgcg ttccttcaag taagggactc tcaactcgtt ttgaagttcg aagcgtcgat   1020

ccagctgcta acccatactt agcaattgca tcagtattgg aagcaggctt agatggcatt   1080

agaaacaaga ttgaaccaga agattccgtt gatcgtaata tctatcgaat gaacattcaa   1140

gaacgtaatg aagagcatat tacagatcta ccttcaacat tacacaatgc tttgaaggaa   1200

ttccaaaatg atgatgtaat gcgtaaggca ttaggagatc acattttcca aagcttcctc   1260

gaagctaaga agttagaatg ggcttcttac cgtcaagaag tgacacaatg ggaacgtgat   1320

caatatctcg aaatgttcta g                                             1341
```

<210> SEQ ID NO 76
<211> LENGTH: 1947
<212> TYPE: DNA
<213> ORGANISM: Unknown
<220> FEATURE:
<223> OTHER INFORMATION: Description of Unknown:
      DP9 DNA gyrase subunit B microbial sequence

<400> SEQUENCE: 76

```
ttggcagacg aaaaagaaac gaaagcagaa ttagccagag aatatgatgc gagtcaaatt     60

caggttttag aggggctcga agcagttcgt aaacgcccag gaatgtatat tgggtcgact    120

agttctcaag gactacacca tttggtttgg gaaattattg ataatggtat tgatgaagct    180

cttgcaggat ttgcagacaa aattgatgtg atcgttgaaa aagacaatag tattaccgtc    240

actgataatg gacgtgggat tccggttgat atccaaaaga aaactggaaa accagcttta    300

gaaacagtct ttacggtcct acatgccgga ggtaaattcg gcggtggcgg ttataaagtt    360

tctggaggat tgcatggtgt gggcgcatcc gttgtaaatg cgttatcaac ggaattagat    420

gcgcgcgtca tgaaggacgg taaaatctat tacattgatt ttgcgctagg aaaagtaaaa    480

acaccgatga aaacgattgg tgatactgaa catcctgacg atcatggaac tattgttcat    540

ttcgttccag atccagatat tttccaagaa actaccacat acgacattaa tatcttaaaa    600

acacgaattc gtgaattagc ctttttgaac aaaggtctac ggattacttt gaaggatatg    660

cgtcctgaaa agccaactga agacgacttc ttgtatgaag gtgggattcg ccactacgtt    720

gaatatctaa acgaaggcaa agaagtaatt ttccctgaac ctatctatgt tgaaggggtt    780

acaaaaggta tcactgttga agtagctatg caatatatcg aaggttatca aagtaaattg    840

ttaactttta ctaacaatat tcatacttac gaaggcggta cccacgaaga aggtttcaaa    900

cgtgctttaa cacgagttat taacgattac gctaaaaaca acaatatttt aaaagaaaat    960

gatgataaat tgtctggtga tgatgttcga gaaggtttga cggcagtagt cagcgttaag   1020

catcctgatc ctcaattcga aggacaaacg aaaacaaaat tgggtaactc agatgctcgg   1080

acagctgtta acgaagtgtt tgctgaaact ttcaataaat tcttattgga aaatcctaag   1140

gttgcacgtc aaattgttga taagggaatc ttggcagcaa aagcaagagt cgccgctaaa   1200

cgagctcgtg aagttacgcg taagaagagt ggcctagaac tcaataatct tcctggtaaa   1260
```

-continued ttagctgata atacttctaa ggatccttca attagtgaat tattcattgt cgagggtgat 1320
tctgccggtg gtagtgctaa gtcgggacgt tcgcgtctca cacaagctat tttgccaatt 1380
cgtgggaaga ttttgaacgt tgaaaaagcc actttggatc gggttttggc caatgaagaa 1440
attcgttcac tctttacagc gctcggaact ggatttggtg aggactttga tgtaagtaaa 1500
gccaactatc ataaattgat tatcatgacc gatgccgatg tcgatggtgc tcatattcgg 1560
acactattat tgacgctgtt ctatcgttac atgcgtccaa tgattgatgc aggatttgtt 1620
tacattgctc aaccaccgct ctaccaagta cgtcaaggta agatgattca atatatcgat 1680
tctgatgaag aattagaaac agtacttgga caattgtcac catcaccaaa acctgtaatt 1740
caacgttata aaggtcttgg tgaaatggat gctgagcaac tttgggaaac aaccatgaat 1800
ccagaaaatc gacgcttgtt acgagtttca gccgaagatg ctgatgctgc aagtggtgat 1860
tttgaaatgt tgatgggtga caaggttgaa ccacgtcgta aattcattga agagaacgct 1920
gtgtttgtta aaaacttgga tatctaa 1947

<210> SEQ ID NO 77
<211> LENGTH: 2418
<212> TYPE: DNA
<213> ORGANISM: Unknown
<220> FEATURE:
<223> OTHER INFORMATION: Description of Unknown:
DP9 Leucine--tRNA ligase microbial sequence

<400> SEQUENCE: 77
atggcttata atcataaaga tatcgaacag aagtggcagc aattctggag cgacaatgag 60
acttttaaga cggtcgaaga tgcagacaaa cccaaatatt atgcattaga catgttccct 120
tatccatcag gtcaaggact ccatgtgggc catcctgaag gatatacagc aacagatatt 180
atgtcacgaa tgaaacggat gcaaggttac aaagtacttc atccaatggg atgggatgct 240
tttggtcttc cagcagaaca atatgcgatg aagacgggta acaatccgcg tgattttaca 300
gctaagaata ttcaaaactt taagcgtcaa atccaatcac ttggtttttc ttatgactgg 360
tcgcgagaag ttaatacaac tgatccagct tactacaagt ggactcaatg gatttttgag 420
caactctaca agaagggctt agcttatgaa aaagaaacgc tggtaaactg ggctcctgat 480
ttaatgggtg gaacggtagt tgctaacgaa gaagttgtgg atggtaagac agaacgtggt 540
gggttccccg tttatcgtaa accaatgaaa caatggattc ttaaaattac agcttacgcc 600
gaccgtttga ttgacgattt ggacctggta gattggcccg atagtattaa agaaatgcaa 660
aaaaactgga ttggtcgttc agtgggggct agcgtcttct ttaatgttga agatagcgaa 720
aaacaaattg aagtatttac aacgcgtcca gatacattat ttggcgcaac atacttggta 780
atttcaccag aacatgacct cgttgaccaa attacaactc cagaaagtaa agctgccgtt 840
gaagaataca agaaagctgt tgcaactaaa tcagatcttg aacggacgga tttgagtaaa 900
gataagacgg gagtctttac gggagcatac gcggttaacc ctgttaatgg taagaaaatt 960
ccagtttgga ttagtgatta cgtattggct tcatacggaa ctggagcagt gatggctgtt 1020
cctgctcatg atggccgtga ctacgaattt gctaagaaat tcaagataga tatggtgcca 1080
gtttatgaag gtggcaatct tgaagatgga gtattggaca gcgaaggcgg gctaattaac 1140
tctggattcc tagatgggat ggataagcag acggctattg ataccatgat tagctggttg 1200
gaagaacatg gagttggtca taagaaggtt aactatcgtc ttcgtgactg ggtcttctct 1260
cgccaacgct actggggtga accaatccct gtaattcatt gggaagatgg agaaacaact 1320
ttgattcctg aagatgaatt gccattgaga ctcccggctg caactgacat tcgtccttcc 1380
ggtaccggag aaagcccatt agctaaccta gatgattggg taaacgtagt tgatgaaaat 1440
ggtcgtaagg gtcgccggga aactaataca atgccacaat gggcgggtag ttcatggtac 1500
ttcctccgtt acgttgatcc taagaatgat caaaagattg ctgacgaaga tttacttaaa 1560
gaatggttac cagtcgactt atatgttggt ggagctgaac atgcggtact tcatttactt 1620
tatgcacgtt tctggcacaa agttttatat gatctaggag ttgtaccaac taaggaacca 1680
ttccaaaaat tggtcaacca agggatgatt ctcggtagca atcatgagaa gatgtctaag 1740
tcaaaaggga acgtggttaa tccagatgat attgttgagc gctttggagc ggatacttta 1800
cgattatacg aaatgttcat gggacctctg acagaatcag tcgcctggag tgaagatggg 1860
cttaacggaa gtcgtaagtg gattgaccgc gtctggcgct tgatgattga cgacgaaaac 1920
caattgcgtg atcatattgt tactgaaaat gatggcagtt tggatatgat ttataaccaa 1980
actgttaaga aggtaactga tgattatgaa aacatgcgct ttaacacggc tatttcacaa 2040
atgatggtct ttgttaatga agcatacaag gctgataaac ttccagcagt atatatggaa 2100
ggattagtta agatgttagc tccaattatt ccgcacgttg ctgaagaact ttggagtttg 2160
ctaggtcacg aaggtggtat ttcatacgct gaatggccaa catatgatga aagtaagtta 2220
gtagaagcta cagttcaagt cattctacaa gttaatggta aagttcggag taaaattacc 2280
gttgacaagg atatcgccaa agaagaactt gaaaaattag cgttagctga tgctaagatt 2340
caacaatgga cggcagataa gactgttcgt aaggtaattg ttattcctaa caagattgtt 2400
aatatcgtag taggctaa 2418

<210> SEQ ID NO 78
<211> LENGTH: 1350
<212> TYPE: DNA
<213> ORGANISM: Unknown
<220> FEATURE:
<223> OTHER INFORMATION: Description of Unknown:
DP9 Glucose-6-phosphate isomerase microbial sequence

<400> SEQUENCE: 78
atggcacata tttcatttga cagttctaat gttgcagatt ttgtacatga aaacgaactt 60
gcagaaatcc aaccacttgt tacagctgct gatcagattt tacgtgatgg ctctggcgct 120
ggtagtgatt tccgtggatg gatcgattta ccatcaaatt atgataagga cgaatttgcc 180
cgtatcaaga aagccgctga taagatccgc aatgactcag aagtattcgt tgctatcggt 240
attggtggtt catatttggg tgctcgtgca gccattgatt tcttgaacaa cactttctac 300
aatcttctta ctaaagaaca acgtaatggt gctcctcaag taatcttcgc tggtaactca 360
attagttcaa cttaccttgc tgacgtattg aacttaatcg ggaccgtgaa cttctcaatt 420
aacgtaattt ctaagtcagg tacaactaca gaaccagcta ttgcattccg tgttcttaaa 480
gaaaaactaa tcaagaagta cggtgaagaa gaagctaaga aacgtatcta tgcaacaact 540
gaccgtgcta aaggcgccct aaagacagaa gctgatgcag aaaactatga agaattcgta 600
gttcctgatg acattggtgg tcgtttctct gttctttcag ctgttggttt attaccaatc 660
gcggttgccg gtggcgatat tgaccaattg atgaagggtg ctgaagatgc aagcaacgaa 720
tacaaggatg ctgatgttac aaagaacgaa gcatacaagt acgctgcttt acgtaacatc 780
ctttatcgta agggctacac aacagaactt cttgaaaact acgaaccaac acttcaatac 840
ttcggcgaat ggtggaagca attgatgggt gaatcagaag gtaaagatca aaagggtatc 900

-continued tacccatctt ctgctaactt ctcaactgac ttacattcac taggacaata catccaagaa 960
ggtcgtcgca atttaatgga aacagttatc aatgttgaaa agcctaacca tgacatcgac 1020
attcctaagg ctgaccaaga ccttgatgga ttacgttatc tcgaaggtcg cacaatggac 1080
gaagttaaca agaaagctta ccaaggtgta actcttgctc ataacgacgg tggtgttcca 1140
gttatgacgg ttaacattcc tgatcaaaca gcttacacat taggctatat gatttacttc 1200
ttcgaagcag ctgttgctgt atctggttac ttgaacggaa ttaatccatt caaccaacca 1260
ggtgttgaag catacaagtc aaatatgttt gcattacttg gtaaaccagg ttatgaagat 1320
aagacagctg aattaaacgc tcgtctataa 1350

<210> SEQ ID NO 79
<211> LENGTH: 1725
<212> TYPE: DNA
<213> ORGANISM: Unknown
<220> FEATURE:
<223> OTHER INFORMATION: Description of Unknown:
DP9 Phosphoglucomutase microbial sequence

<400> SEQUENCE: 79
atgagttggg aagattctgt caaagaatgg caagattatg cagatttaga ttttaattta 60
aaaaaagaat tagcaacttt agctgaagat aaagatgctt taaaagaagc cttttatgct 120
ccaatggaat ttggtacagc aggaatgcgt ggcgtaatgg gccctggtat caaccggatg 180
aatatctata cggttcgtca agcaacagaa ggtttagcta attttatgga taccttagat 240
tttactgata agaaacgggg agtggcgatc agttttgatt cccgctatca ctcacaagag 300
tttgctttag cagcagctgg tgttttaggt aagcatggta ttccaagttt tgtttttgat 360
agtatgcgtc ccactccaga attatcatat acagtacgtg agttaaacac ttatgctgga 420
atcatgatta ctgctagtca taatcctaaa caatataatg gatataagat ttatggtcct 480
gatggcggac aaatgccacc aatggaatct gataagatta cagaatatat tcgccaagta 540
actgacatct ttggtgttga agctcttact caaagtgaat taagagctaa gggcttaatg 600
accattattg gtgaagacat tgacctcaag tatcttgagg aagttaagac ggtatcaatt 660
aatcatgaac taatccagcg ctttggtgca gacatgaagt tgatctactc accattacat 720
ggtactggaa aagtagttgg tggacgtgcg ttagaaaatg ctggttttaa ggattacact 780
atggtccctg aacaagcaat tgctgaccca gaatttatta caacgccatt ccctaaccca 840
gaattcccac aaacttttga tttggctatt gaattaggta aaaagcaaga tgctgacctt 900
ttgattgcca ctgatccgga tgccgatcgt ttgggagctg ccgttcgttt accaaatggt 960
gactacaaat tattgacagg gaaccaaatt gcagccttga tgttagaata catcttaact 1020
gcgcatgatg cagcaggtga cttgccaggt aacgcagctg ccgttaagtc aattgtttct 1080
agtgaactag caaccagaat tgccgaagcc catcatgtag aaatgattaa cgttctaact 1140
gggtttaagt acattgctga ccaaattaaa cattacgaag aaaatggcga ccataccttt 1200
atgtttggtt tcgaagaaag ttatggctat cttgttcggc catttgttcg cgataaagat 1260
gccatccaag gaattgtcct attggctgaa attgctgctt attatcgtag taaggggcaa 1320
accttatatg acggtcttca aaacttattt actacttacg gatatcatga agaaaagacc 1380
atttcaaaag atttccctgg agttgacggt aaagaaaaaa tggctgccat tatggaaaag 1440
gttcgtgaag aacgcccaag tcaatttgat cagtacaagg tattagaaac tgaagacttc 1500
ttagctcaaa ctaagtatga agcagatgga tctacccaag ctatcaaatt accaaaagcg 1560

```
gatgttttga aatttacatt agatgatggt acttggattg caattcgtcc ttctggaaca   1620

gaaccaaaaa ttaaattcta tattggtaca gttggcgaag atgaaaaaga tgctttgaat   1680

aagattgatg tttttgaaac agctattaat gaacttataa aataa                   1725


<210> SEQ ID NO 80
<211> LENGTH: 3426
<212> TYPE: DNA
<213> ORGANISM: Unknown
<220> FEATURE:
<223> OTHER INFORMATION: Description of Unknown:
      DP9 2-oxoglutarate carboxylase small subunit
      microbial sequence

<400> SEQUENCE: 80

atgcaccgta ttttaattgc caaccgaggc gaaattgcga cccgaattat tcgggcaacg     60

catgaactcg gaaaaacagc tgtagcaatt tatgctaaag cggatgaatt ttctatgcat    120

cgttttaaag cagatgaagc ttaccaagtt ggtgaagata gtgatccaat tggagcatat    180

ttaaatattg atgacattat tcgtattgca aaagaaaata atattgatgc aattcacccc    240

ggctatggat tttgtcgga aaatgctgta tttgcgcgag cagttgaagc agctgggatt     300

aagttcattg gacctcgacc cgaattacta gaaatgtttg gtgataaatt acaagctaaa    360

aatgcagcca ttaaggccgg tgtaccaact attccgggaa cggaaaaacc agttaaagat    420

gtcgatgacg cgctaaattt tgcagagcaa tttggctatc ctatatttgt taagtcagcg    480

gcaggtggcg gcggaaaagg gatgcggatt gtacatcatc aacaagagat gcgcgaagca    540

tttaagatgg ctcagtcaga agcttcttcg tcttttggtg acgatgaaat ttacttagaa    600

cgttacttag ttgatccaat ccatattgag gttcaagtag ttgcggatga acacggtgag    660

atggttcatt tgtatgaacg aaattcatcg attcagcgac gccatcaaaa aatcattgaa    720

tttgctccag cagtgggaat ttctgccacc gtccgtgatc aaataagaaa agctgcttta    780

aaattattga agtcggtcaa ttatagtaac gctgcaacca ttgagttttt ggtagaaggt    840

aatcaatttt actttatgga agtgaatcca cgaattcagg ttgaacatac agttaccgaa    900

gaagtcacgg gaatcgatat tgtgcaaacc caaattaagg ttgctgaagg tcaaagatta    960

cacgaagaaa tcggtgttcc tcaacaagcc caaattgaag ctgtgggagt ggcaattcaa   1020

gcccgaatta ccactgaaga tccaatgaat aactttattc cagatgtcgg tagaatccag   1080

acgtatcgtt cacctggtgg aacaggtgtg agattggatg ctggaaatgc ctttgctgga   1140

gccattgtaa ctccgcatta tgattcactt ctgaccaagg caattgtcca tgcgccaacc   1200

tttgacgaag ccttggtaaa gatggatcga gtgctcaatg aatttgtaat tgctggggtt   1260

aaaactaata ttccattttt aaagaaatta attcatcatc ctatttttag atcggaatta   1320

gctccgacaa cctttgtgga tgagacacca gaactctttg atttaaaagc tgaaactccg   1380

gtagttactc aacttttgag ttacattgct aatactacta tcaatggtta tccaggctta   1440

gaaaagcaga atccagtagt gttaactcgg ccagtccgtc cacattttga agcacaagta   1500

ccgcatgaaa atgcgaaaca gatcttggat agtaagggac ctgatgccat gatcaattgg   1560

ctgttaaaac aaaagcaggt cttgctaacc gatacgacca tgcgggatgc ccatcaatca   1620

ttatttgcta cgcgaatgcg gaccaaagac atggtagaaa ttgccgatca agtccagaaa   1680

ggtctgccta acctattttc agctgaagtt tggggcggtg cgacctttga tgttgcttat   1740

cggttcctag gtgaggatcc atgggaaaga ctccaacaat tgcgggctaa aatgccaaat   1800

acgatgctcc aaatgctttt acgtgggtca aatgcagtag ggtatcaaaa ttatccagac   1860
```

aacgccattg acgaatttat tcgattggct gccaaaaatg gaattgatgt tttccgaatc 1920
tttgattctc ttaattgggt gccacagctt gaagaatcta tccaacgggt gcgtgataat 1980
ggaaaagtgg ctgaagcagc catggcatat actggcgata ttttagatac taatcgtact 2040
aaatataatt tgaaatatta tgtggatttg gctcaagaac tccaagcagc aggtgctcat 2100
attattggaa tcaaagatat gtcaggaatt ttaaaaccac aagctgctta tgcattaatt 2160
tcagagttaa aaaatcatct ggatgtgcca attcatttgc atacgcacga tactacaggc 2220
aacggcattt tcttatattc tgaagcaata cgagctggag ttgatgtggt cgacgttgcc 2280
acttctgcgc tagcgggaac gacttctcag ccttcaatgc agtctcttta ctatgcgttg 2340
tctaataacc agcgccaacc agatttagat attcaaaaag cagaaaaact agatgaatat 2400
tggggcggaa ttcgaccata ttacgaagga tttggcaccc aattaaatgg accacaaact 2460
gaaatttatc gaattgaaat gcctggtgga cagtatacca accttcgcca gcaagctaac 2520
gcagtccatt tgggtaagcg ttgggatgag attaaggaaa tgtacgcaac cgtcaatcaa 2580
atgtttggcg atattccaaa ggttacgcct tcttctaaag tagttggcga tatggcacta 2640
ttcatggtcc aaaatgattt gacgcctgaa atggtaatga acgataaggg acaattaagt 2700
tttcccgaat cagtggtaaa ctttttccgt ggtgatttag gacaaccggc gggtggtttt 2760
ccaaaacagc tccaaaaggt gattctaaaa gagcaagccc cattgacagt acgaccagga 2820
gctttagccg atccagttga ttttgatcaa gttcgtaaac aggcaactaa ggttttaggt 2880
caccaagcaa gtgatgaaga agttatgtcg tttattatgt atccagatgt gatgaccgaa 2940
tacattcaac gtcaaaatga atatggtcca gtaccattat tagatactcc aatctttttc 3000
caaggcatgc atattggcca acgcattgat ttacaattgg gacgcggaaa atcggtcatt 3060
attgtccttc gagaaattag tgaagcagat gaggcgggcc aaaggtcact tttctttgat 3120
ataaatggac aaagtgaaga agtgattgtt tatgatgtta atgcgcaggt aacgaaagta 3180
aagaagatta aagctgatcc gactaaagcc gaacagattg gcgctactat ggcgggctcg 3240
gtcattgaag tccaagtaga agcgggccaa aaggtccagc gaggtgataa cttaattgtc 3300
actgaggcga tgaaaatgga gaccgcgtta agagcacctt tcgacgcaac cattaagaag 3360
atttatgcta cccctgaaat gcaaatcgag acgggggatt tattgattga actagaaaag 3420
gagtaa 3426

<210> SEQ ID NO 81
<211> LENGTH: 2058
<212> TYPE: DNA
<213> ORGANISM: Unknown
<220> FEATURE:
<223> OTHER INFORMATION: Description of Unknown:
DP3 Glycine--tRNA ligase beta subunit microbial sequence

<400> SEQUENCE: 81
atgtcaacat ttttattaga aattggactt gaagaaatac cagctcattt ggtaaccagt 60
tcagagaatc agttaattga aagaactaaa aagttcttat cagagcatcg tttaacagta 120
ggtgatatta aaccatattc aacaccgcga cgtctggctg tcgttttgac agatgttgct 180
gaaacatcag aaagtttaag cgaagaaaag cgtggaccat ctgttgaccg tgcacaagac 240
gaaaacggta attggacaaa ggcagcatta ggttttgcac gtggtcaagg tgctaatcct 300
gaagcatttg aaattaaaga tggatatgtt tggctaacaa aacgtactgc tggtgtagcc 360
gcgaatgaaa ttttagctaa aattggtgat gaagttgtcg cccaaatgaa attttcaact 420
tatatgaagt gggctaatca cagctttttg tatgttcgac ctattcgttg gctcgtagca 480
cttcttgata gtgaagtcat ttctttcaac gtgttagata ttaccacaga tcgtttcaca 540
cgtggtcatc gttttttgtc ttcagaacat gttgaaatat cttctgcaga taattatgta 600
acgactttgc agggtgctaa cgtggttgtt gatgctacag tgcgcaaaaa tgaaattcga 660
tcgcagttga atgcaattgc tgaagctaat ggttgggttc tgcaacttga gaccgatgcg 720
gcgcaagatt tgttggaaga agttaataac attgttgagt ggccaacagc gtttgctggc 780
agtttcgatg agaaatattt agaaatacca gatgaagttt tgattacatc aatgcgcgaa 840
catcagcgtt tcttctttgt gacgaatgaa aaaggacaat tattgccaca ctttttgtca 900
ataagaaatg gtaaccgtga gcatctaaac aacgttattg ctggaaatga aaaagtattg 960
gtagcaaggt tagaagatgc cgaattcttc tatcatgaag accaaaccaa atcaatttct 1020
gattacatga ctaaagttaa aaagttagtc ttccatgaaa aaattggtac ggtgtatgaa 1080
cacatgcaac gcactggtgc tttggcttca gcaatggcgg tggttttgaa gtttgatgaa 1140
gtacaacagg ctgatttgac ccgtgcatca gaaatttata aatttgattt gatgaccggt 1200
atggttggtg aatttgatga acttcaaggc attatgggtg agcattatgc caagcttttt 1260
ggcgaagatg atgcggttgc aacagccatt cgagagcatt atatgccaac ttcagctaat 1320
ggtgaggttg cgcaatctga aattggtgct ttgttggccg ttgcggataa acttgatagc 1380
attgtgacgt tttttgctgc tggattaata ccaagtggtt ctaatgatcc ttatggctta 1440
cgacgtgcag ctactggcat cgtgcgtaca ttggtggata aaaaatggca tattgatttg 1500
cggcctttgc tagctgattt tgtgcaacag caaggtaagg taactgacac cgatttaacg 1560
acatttgttg atttcatgtt ggatcgtgtt cgtaaattat cgttggatgc tggaatacgt 1620
caagatattg tcattgctgg attaggcaac gttgatagag ctgatatcgt atatattagt 1680
cagcgagtcg aagttttgtc ccaacatagt ggtgatggca atttccgaga tgtaattgag 1740
gcactgactc gtgtggatcg cttagccgta aagcaagtaa ctaatgcaac ggttgatcct 1800
gctaagtttg aaaatcaatc tgaaaaggac ctatatcaag caacgttaac gcttgattta 1860
aatactttga tgcatgacgg tgcagaaaat ctctacatgg ccttagcaaa tttgcaaaaa 1920
ccaattgcgg cttattttga tgaaaccatg gttaacgctg aagatgaatc tgttaaagat 1980
aatcgatatg cgcagctgaa cgtcatacaa cgactaacca acggattagg agatttgacg 2040
caaatcgtca ttaagtaa 2058

<210> SEQ ID NO 82
<211> LENGTH: 1347
<212> TYPE: DNA
<213> ORGANISM: Unknown
<220> FEATURE:
<223> OTHER INFORMATION: Description of Unknown:
DP3 Glutamine synthetase microbial sequence

<400> SEQUENCE: 82
atggctcgta aaacatttac caaagaagaa attaaacaaa ttgttgttga tgaaaatgta 60
gaattcattc gtgtaacatt cactgatgtc ttaggtgcga ttaaaaacgt tgaagtacca 120
acttctcaat tagataaggt gcttgacaac aatttaatgt ttgacggttc atcaatcgag 180
ggatttgttc gtatcaatga atcagatatg tatctttacc ccgatttatc aacatttatg 240
attttcccat gggcaacgga tggtcatggt ggtaaagtgg cccgcttgat tgccgacatt 300
tatactgctg atcgtgagcc atttgctgga gaccccccgtc atgcgttacg ttcggtactc 360

```
gctgacgcgc gtgaagctgg gtttacggcg tttaatgtcg ggacagaacc tgaatttttc    420

ttgtttaaac ttgatgaaaa aggcaaccca accacagagt taaacgacaa aggtggttat    480

tttgacctag caccattgga tatgggtgaa aatgttcgtc gtgaaattgt tttgactttg    540

gaaaaaatgg gctttgaaat tgaagctgct caccacgaag ttgccgaagg acagcatgaa    600

gtagacttta aatacgcttc agctcttgaa gccgctgaca acattcagac gtttaagttg    660

gttgttaaaa ccatcgcacg caagaatggt tactatgcta cctttatgcc aaagcctgtt    720

gcaggtatta acggatccgg tatgcacaca aacatgtcat tatttacaaa agatggtaac    780

gcatttgttg atacatcgga tgaaatgggc ttgtcaaaaa cagcatataa cttcttgggt    840

ggtattttag aacatgcgac tgcgtttaca gcgcttgcaa acccaacagt taactcatac    900

aagcgcttga caccaggatt cgaagcacct gtttatgttg catggtcagc atcaaatcgt    960

tcaccaatgg ttcgagttcc ggcctcacgt ggtaattcaa cacgtttgga acttcgttca   1020

gttgacccaa cagctaatcc ttatactgca ttggcagcca ttttggcttc aggactggat   1080

gggatcaagc gtgaattaga gcctttggcc tcagttgata aaaatattta tttgatggat   1140

gaggtcgaac gggaaaaggc aggcattaca gacttaccag atactctgtt ggctgcagtt   1200

cgtgagttgg cggctgatga tgttgttcgt tcagctattg gagaacatat tgctgataag   1260

tttattgaag caaagaagat tgaatacaca tcatatcgtc agtttgtttc tgaatgggaa   1320

acagattctt atcttgaaaa ttactaa                                       1347
```

<210> SEQ ID NO 83
<211> LENGTH: 2049
<212> TYPE: DNA
<213> ORGANISM: Unknown
<220> FEATURE:
<223> OTHER INFORMATION: Description of Unknown:
DP3 DNA gyrase subunit B microbial sequence

<400> SEQUENCE: 83

```
gtgttcgcag attatatctg ttcacacgct aataatatgg cagagaatat cgaaaatgaa     60

gcattggaga acattgatgg catcgtaacc gatgataccg aaatccgtca agcaagcacc    120

gttcatgcag cagcaggcgc ttacaatgct gatcagattc aagttttgga aggattggaa    180

gctgtccgca aacgccctgg catgtacatt ggtacgacca cagcgcaagg cttgcaccat    240

ttggtatggg aaattgttga taacgggatt gatgaggcat tagcagggtt tgcgtcacat    300

attacggtca caatcgaaaa ggataactca atcacggtaa ccgatgacgg ccgtggtatt    360

cctgtcgaca ttcaaactaa aacgggtaag ccagctcttg aaactgtctt tacggtatta    420

cacgccggtg gtaaatttgg cggtggcggt tataaagtat ctggtggatt acacggtgtt    480

ggagcttctg ttgtcaatgc cttgtcaacg gatttggacg ttagagttgt tcgtgataat    540

actgtttatt acatggactt caaagtggga cgcgtcaaca caccgatgaa acaattgacg    600

gaaaagccca ctattgagcg tggtacaatt gttcatttta agcccgatgc agatattttc    660

cgtgaaacaa cagtttataa ctacaacaca ttactaacac gtgtgcgcga attggccttt    720

ttgaataaag gtttgcgcat ttcgattaca gataatcgac ctgaagaagc tgtttctgaa    780

agctttcatt ttgaaggtgg gattaaagaa tacgtcagct atttgaataa ggacaagact    840

gctattttcc ctgaacctgt ttacgttgag ggtgaagaaa atggcattgt agtggaagct    900

gccttacagt acactaccga tattaaagac aatctgcgga cgtttactaa caatatcaat    960

acctatgaag gtgggacgca cgaaactggc tttaaaacag ccttaacacg tgtaatcaat   1020
```

gattacgctc gtaaaaatgg tcagctcaaa gataatgcag aaagtttgac aggggaagat 1080
gtgcgcgaag gcatgactgc tatcgtgtca atcaagcacc cagatccaca atttgaagga 1140
caaaccaaaa ctaaattagg taactccgat gcacgtcaag caacggatcg gatgttctca 1200
gaaacgttca gtcgtttcat gatggaaaat ccagcagttg ccaagcaaat tgttgaaaaa 1260
ggtgtcttag cccaaaaagc acgattggct gccaagcgtg cacgcgaaat gacacgcaaa 1320
caatctggtt tggaaattgg taatttgcca ggtaaattag ctgataatac ctcaaatgat 1380
cctgaaattt cagaattatt tattgttgag ggtgattcag ccggtggttc agctaagcaa 1440
ggacgtaacc gtttgacgca agctattttg ccaattcgag gcaaaatttt aaatgttggg 1500
aaagcctcat tggatcgggt gttagccaac gaagaaattc gatcattgtt tacagcaatg 1560
ggaactggat ttggtgagga ctttaatgtt gaaaaagcca attatcacaa agtcattatt 1620
atgacagatg ccgatgtcga tggcgcccat attcgaacac tattgttaac gctattttat 1680
cgttatatgc gaccacttgt tgacgcaggc tatatttata ttgcgcagcc accgctttac 1740
ggtgttgcct taggcaataa taaatcaatg acgtacattg attctgatga agaacttgaa 1800
gactatttgt cacaattgcc atctaatatt aaaccaaaag ttcaacgtta taagggacta 1860
ggggaaatgg attacgatca actagcagat acaaccatgg atccgcagaa tcgtcgtttg 1920
ctacgtgttg acccaactga tgctgaagaa gccgaagcag ttattgatat gttaatgggt 1980
ggggatgtac caccacgtcg taagtttatt gaagacaatg ctgtctttgt tgagaacttg 2040
gatatttaa 2049

<210> SEQ ID NO 84
<211> LENGTH: 375
<212> TYPE: DNA
<213> ORGANISM: Unknown
<220> FEATURE:
<223> OTHER INFORMATION: Description of Unknown:
DP3 Leucine--tRNA ligase microbial sequence

<400> SEQUENCE: 84
atgattttcg tcaacgaagc ttacaaaacc gatgctgtgc cgaaagcggc ggcggaaaac 60
ttcgtacaga tgctgtcccc actggcaccg catttggcag aagaactgtg ggaacgactt 120
ggtcataccg atacgattac gtatgaacca tggccaacgt acgatgaggc ttggaccata 180
gaatccgaag tggaaatcgt cgtgcaagtg aacggcaaaa tcgtagaacg cacgaaaatt 240
tccaaagacc tggatcaagc agcgatgcaa gaacacagct taagcctgcc gaatgttcag 300
caggctgtgg ctgggaagac gatccgcaaa gtgattgcgg tgccaggcaa gctggtgaat 360
atcgtcgttg gataa 375

<210> SEQ ID NO 85
<211> LENGTH: 1353
<212> TYPE: DNA
<213> ORGANISM: Unknown
<220> FEATURE:
<223> OTHER INFORMATION: Description of Unknown:
DP3 Glucose-6-phosphate isomerase microbial sequence

<400> SEQUENCE: 85
atggcacaca ttacatttga cacaaagaac attgagaatt ttgttgcacc atacgaattg 60
gacgaaatgc aaccattaat tacgatggct gaccaacaat tgcgcaatcg tacgggcgct 120
ggtgcagaat attctgattg gttgactcta cctactgatt acgacaagga agaatttgca 180

```
cgtattcaaa aggcggcgca acaaattcaa tctgattcaa agattttggt tgtcattggt    240

attggtggtt catatttggg cgcgaagatg gcggttgatt tcttgaatcc aatgtttaat    300

aatgaattgt cggatgacca acgtcaaggt gttaaaattt attttgctgg taactcaact    360

tctgcagctt acttaaatga tttagttcgt gtcattggtg atcaagactt ttctgtcaac    420

gttatctcaa agtctggcac aacaacggaa ccatcaatcg ctttccgtgt gtttaaacaa    480

ttgttagaga aaaagtatgg ttctgatgct gctaagaagc gtatctatgc cacaacagat    540

gccaatcgtg gtgctttgca cgatgaagca gcggcttcag gttatgaaac attcacaatt    600

cctgatggtg tcggtggtcg cttctctgtt ttgacagctg ttggcttgtt gccaattgct    660

gcttcaggcg ctgatatcca aaaattgatg gacggcgctc gtgatgcgca aaacgaatat    720

actgattctg atttgaaaaa gaacgaggca tataaatatg cagccgttcg tcgtattttg    780

tatgataagg gttatacaac agaattgttg attaactggg aaccttcaat gcaatatttg    840

tcagagtggt ggaagcaatt gatgggcgag tctgaaggta aaaatcaaaa gggtatctat    900

ccatcttcag ctaacttctc aaccgacttg cactcacttg gacaatatat tcaagaagga    960

cgccgtgatt tgtttgagac ggtggttaag ttagacaatc ctgtatctaa tttggaccta   1020

ccacatgaag aaggcaacaa tgatggtttg caatatttgg aaggtatcac gatcgatgaa   1080

gtgaacacca aagcatctca aggggttact ttggctcacg ttgatggtgg tgtgcctaac   1140

ttggctgttc acttgccagc acaagatgct tattcactcg gttacatgat ttacttcttt   1200

gaaatggctg ttggggcgtc tggttatacg tttggtatta acccattcaa ccaaccgggt   1260

gtcgaagcct ataagacagc tatgtttgca ctattaggta agcctggcta tgaggaagcg   1320

acaaaagcat tccgtgcccg cttagacaaa taa                                1353
```

<210> SEQ ID NO 86
<211> LENGTH: 672
<212> TYPE: DNA
<213> ORGANISM: Unknown
<220> FEATURE:
<223> OTHER INFORMATION: Description of Unknown:
DP3 Beta-phosphoglucomutase microbial sequence

<400> SEQUENCE: 86

```
atgactaaat tttcagatat taaaggtttt gcctttgatt tagatggggt tattgctgat     60

acggcgcgtt tccatggtga agcttggcat caaacagctg atgaggttgg cacaacttgg    120

acaccagaat tggctgaagg tttgaagggc attagtcgta tggcttcctt gcaaatgatt    180

ttggatgctg ggatcatgc cgatgatttt tcgcaagcag ataaagaagc attagcagaa    240

aagaaaaatc ataattatca acaacttatt tcaacattga cggaagatga tattttgcct    300

ggcatgaaag attttattca atcagccaag gcagccggct atacaatgtc ggtggcatca    360

gcttctaaaa acgcaccaat gattctagat catttgggat tgaccaagta ttttgtcggc    420

attgttgatc ccgccacttt gacaaaggga aaacctgatc ctgaaatctt cgttcgtgct    480

gcggaagtct tacatttaaa tccagaaaat gttattggat tggaagattc agctgctggt    540

attgtgtcaa tcaatggcgc aggtgagaca tcactagcca ttggtaacgc agatgttttg    600

tcaggagcgg acttgaattt tgcgtctact tcagaagtga ccttagcaaa tattgaagct    660

aaaatgcaat ag                                                        672
```

<210> SEQ ID NO 87
<211> LENGTH: 1377
<212> TYPE: DNA

<213> ORGANISM: Unknown
<220> FEATURE:
<223> OTHER INFORMATION: Description of Unknown:
DP3 2-oxoglutarate carboxylase small subunit
microbial sequence

<400> SEQUENCE: 87

```
atgtttaaaa aagtgcttgt tgctaatcgt ggtgaaattg cggttcgcat cattcgaacg     60
ctcaaagaaa tggggattgc ttcagtcgct atttactcga cagccgataa agatagttta    120
cacgtacaaa tcgctgacga agcgattgct gtggggggac cgaaacctaa agattcatac    180
ttaaatatga aaaatatttt aagtgcagcc ctgctgtcgg gagcagaggc aattcatcca    240
ggatatggct ttttagctga aaatacattg tttgctgaaa tggttggcga agttggtatt    300
aaatggattg ggcctaggcc agaaacaatt gagttaatgg gtaacaaagc taacgcacgt    360
gaagaaatgc ggcgtgccgg cgtaccagta attccaggtt cagagggatt tatccgtgat    420
tttcatgaag caaaaacggt tgctgataaa attggctatc ctttgttgct aaaagctgcc    480
gctggtggtg gtggtaaagg catgcgtttt gtttacggtg aggatgagtt atcagataaa    540
tttgatgatg ctcaaaacga agcgcgtgct tcgtttggcg atgatcacat gtatattgaa    600
aaagttatgt cacgtgttcg ccacattgaa atgcaagtgt ttcgtgatga gaatggtcat    660
gttgtttact tgccagaacg aaattgctca ttgcaacgca ataatcaaaa ggtgattgaa    720
gaatcaccag ctacgggtgt aacgcctgaa atgcgtgcgc atcttggcga aattgttact    780
aaagccgcaa aagcattggc gtatgaaaat actggaacca ttgaattttt gcaagatcgc    840
gatggtcatt tctactttat ggaaatgaac acacgtattc aagtagaaca tccagtttct    900
gaaatggtaa cgggattaga tttaattaag ttacaaattc aagttgctgc aggcttagat    960
ttaccggtgg ttcaagatga cgtgatcgtt caaggccact ctatcgaagt acgtttgacg   1020
gctgagcagc cagaaaaaca ctttgcacct agtgctggaa cgattgattt tgttttttttg   1080
ccaactggtg gaccgggtgt tcgtattgat tcagccttat ttaatggcga taaaattcaa   1140
ccattttacg attctatgat tggcaaatta attgttaagg ccgatgatcg tgaaacagcc   1200
atgagaaaga ttcaacgtgt ggttgatgaa actgttgtac gtggtgtagc aacgagccgt   1260
aattttcaaa aagctctgtt agctgatcca caggttcaac gtggcgaatt tgacacacgt   1320
tatttggaaa ctgaattttt accgagatgg acacaaacat tgccagataa tcaataa      1377
```

<210> SEQ ID NO 88
<211> LENGTH: 1701
<212> TYPE: DNA
<213> ORGANISM: Unknown
<220> FEATURE:
<223> OTHER INFORMATION: Description of Unknown:
DP1 Glutamine--tRNA ligase microbial sequence

<400> SEQUENCE: 88

```
atgagcaagc ccactgtcga ccctacctcg aattccaagg ccggacctgc cgtcccggtc     60
aatttcctgc gcccgatcat ccaggcggac ctggattcgg gcaagcatac gcagatcgtc    120
acccgcttcc cgccagagcc caacggctac ctgcacatcg gtcatgccaa gtcgatttgt    180
gtgaacttcg gcctggctca ggagttcggt ggcgttacgc acctgcgttt cgacgacacc    240
aacccggcca aggaagacca ggaatacatc gacgccatcg aaagcgacat caagtggctg    300
ggcttcgaat ggtccggtga agtgcgctat gcatccaagt atttcgacca gctgttcgac    360
tgggccgtcg agttgatcaa ggccggcaag gcctacgttg acgacctgac ccccgagcaa    420
```

gccaaggaat accgtggcag cctgaccgag ccgggcaaga acagcccgtt ccgcgaccgt 480
tcggtcgaag agaacctcga ctggttcaac cgcatgcgcg ccggtgagtt cccggacggc 540
gcccgcgtgc tgcgcgccaa gatcgacatg gcctcgccga acatgaacct gcgcgacccg 600
atcatgtacc gcattcgcca tgcccatcac caccagaccg gtgacaagtg gtgcatctac 660
cccaactacg acttcaccca cggtcagtcg gacgccatcg aaggcatcac ccactccatc 720
tgcaccctgg agttcgaaag ccatcgccct ctgtacgaat ggttcctgga cagcctgccg 780
gtgccggcgc acccgcgtca gtacgaattc agccgcctga acctgaacta caccatcacc 840
agcaagcgca agctcaagca actggtcgat gaaaagcacg tgcatggctg ggacgacccg 900
cgcatgtcga cgctctcggg tttccgtcgt cgtggctaca ccccggcgtc gatccgcaat 960
ttctgcgaca tggtcggcac caaccgttct gacggtgtgg tcgattacgg catgcttgag 1020
ttcagcatcc gtcaggatct ggacgcgaac gcgccgcgcg ccatgtgcgt gctgcgtccg 1080
ttgaaagtcg tgatcaccaa ctacccggaa gacaaggtcg accaccttga gctgccgcgt 1140
cacccgcaga aagaagagct gggcgtgcgc aagctgccgt tcgcgcgcga aatctacatc 1200
gaccgtgacg acttcatgga agagccgccg aagggttaca agcgcctgga gccgaacggc 1260
gaagtgcgcc tgcgtggcag ctacgtgatc cgcgccgacg aagcaatcaa ggacgccgaa 1320
ggcaacatcg tcgaactgcg ctgctcgtac gatccggaaa cactcggcaa gaaccctgaa 1380
ggccgtaagg tcaagggcgt gatccactgg gtgccggccg ctgccagcat cgagtgcgaa 1440
gtgcgtctgt acgatcgtct gttccgatcg ccgaacccgg agaaggccga agacagcgcc 1500
agcttcctgg acaacatcaa ccctgactcg ctgcaagtgc ttacaggttg tcgtgctgag 1560
ccatcgcttg gcgacgcaca gccggaagac cgtttccagt tcgagcgcga aggttacttc 1620
tgcgcggata tcaaggactc gaaacccggt gctccggtat tcaaccgtac cgtgaccttg 1680
cgtgattcgt ggggccagtg a 1701

<210> SEQ ID NO 89
<211> LENGTH: 2418
<212> TYPE: DNA
<213> ORGANISM: Unknown
<220> FEATURE:
<223> OTHER INFORMATION: Description of Unknown:
DP1 DNA gyrase subunit B microbial sequence

<400> SEQUENCE: 89
atgagcgaag aaaacacgta cgactcgacc agcattaaag tgctgaaagg tttggatgcc 60
gtacgcaaac gtcccggtat gtacatcggc gacaccgatg atggtagcgg tctgcaccac 120
atggtgttcg aggtggtcga caactccatc gacgaagctt tggccggtca ctgcgacgac 180
atcagcatta tcatccaccc ggatgagtcc atcacggtgc gcgacaacgg tcgcggcatt 240
ccggtcgatg tgcacaaaga agaaggcgtt tcggcggctg aggtcatcat gaccgtgctg 300
cacgccggcg gtaagttcga tgacaactct tataaagtct ccggcggtct gcacggtgta 360
ggtgtgtcgg tagtgaacgc actgtccgaa gagctgatcc tgaccgttcg ccgtagcggc 420
aagatttggg agcagacgta cgtccatggt gtgccacaag agccgatgaa aatcgttggc 480
gacagtgaat ccacgggtac gcagatccac ttcaagccat cggctgaaac cttcaagaac 540
atccacttta gctgggacat cctggccaag cggattcgcg aactgtcctt cctcaactcc 600
ggtgtgggta tcgtcctcaa ggacgagcgc agcggcaagg aagaactgtt caagtacgaa 660
ggcggtctgc gcgcgttcgt tgaatacctg aacaccaata agaccgcggt caaccaggtg 720
ttccacttca acattcagcg tgaagacggc atcggcgtgg aaatcgccct gcagtggaac 780
gacagcttca acgagaactt gttgtgcttc accaacaaca ttccacagcg cgatggcggt 840
actcacttgg tgggtttccg ttccgcactg acgcgtaacc tgaacactta catcgaagcc 900
gaaggcttgg ccaagaagca caaagtcgcc accaccggtg acgatgcgcg tgaaggcctg 960
accgcgatta tctcggtgaa agtgccggat cccaagttca gctcccagac caaagacaag 1020
ctggtttctt ccgaggtgaa gaccgccgtg gaacaggaga tgggcaagta cttctccgac 1080
ttcctgctgg agaacccgaa cgaagccaag ctggtcgtcg gcaagatgat cgacgctgca 1140
cgtgctcgcg aagcggcgcg taaagcccgt gagatgaccc gtcgtaaagg cgcgctggat 1200
attgctggct tgcctggcaa gttggctgac tgccaggaga aggacccagc gctctccgag 1260
ctatatcttg tggaaggtga ctctgctggc ggttccgcca agcagggtcg taaccgtcgc 1320
acccaggcga tcctgccgtt gaaaggcaag attctcaacg tagagaaggc ccgcttcgac 1380
aagatgattt cctcccagga agtcggcacc ttgattacgg cgttgggttg cggcattggc 1440
cgcgatgagt acaacatcga caagctgcgc taccacaaca tcatcatcat gaccgatgct 1500
gacgtcgacg gttcgcacat ccgtaccttg ctgctgacct tcttcttccg tcagttgcct 1560
gagctgattg agcgtggcta catctatatc gcgcagccgc cgttgtacaa agtgaaaaag 1620
ggcaagcaag agcagtacat caaagacgac gacgccatgg aagagtacat gacgcagtcg 1680
gccctggaag atgcaagcct gcacttgaac gacgaagcac cgggtatctc cggtgaggcg 1740
ttggagcgtc tggttaacga cttccgtatg gtgatgaaga ccctcaagcg tctatcgcgt 1800
ctgtaccctc aggaactgac cgagcacttc atctacctgc cggccgtcag tctggagcag 1860
ttgggtgatc atgcagcgat gcaagagtgg ctggctcagt acgaagtacg cctgcgcact 1920
gttgagaagt ctggcctggt gtacaaagcc agtctgcgtg aagaccgtga acgtaacgtg 1980
tggctgccgg aggttgagtt gatctcccac ggcctgtcga attacgtcac cttcaaccgc 2040
gacttcttcg gcagtaatga ctacaagacg gtcgtgaccc tcggcgcgca gttgagcacc 2100
ttgctggatg atggtgctta cattcaacgt ggcgagcgta agaaagcggt caaggagttc 2160
aaggaagcct tggactggct gatggcggaa agcaccaagc gtcataccat tcagcgatac 2220
aaaggtctgg gcgagatgaa ccctgatcag ttgtgggaaa ccaccatgga tccagcacag 2280
cgtcgcatgc tgcgcgtgac catcgaagac gccattggcg cagatcagat cttcaacacc 2340
ctgatgggtg atgcggtcga acctcgccgt gacttcatcg agagcaatgc cttggcggtg 2400
tccaacctgg acttctga 2418

<210> SEQ ID NO 90
<211> LENGTH: 1632
<212> TYPE: DNA
<213> ORGANISM: Unknown
<220> FEATURE:
<223> OTHER INFORMATION: Description of Unknown:
DP1 Isoleucine--tRNA ligase microbial sequence

<400> SEQUENCE: 90
atgaccgact ataaagccac gctaaacctt ccggacaccg ccttcccaat gaaggccggc 60
ctgccacagc gcgaaccgca gatcctgcag cgctgggaca gtattggcct gtacggaaag 120
ttgcgcgaaa ttggcaagga tcgtccgaag ttcgtcctgc acgacggccc tccttatgcc 180
aacggcacga ttcacatcgg tcatgcgctg aacaaaattc tcaaggacat gatcctgcgc 240
tcgaaaaccc tgtcgggttt tgacgcgccg tatgtcccgg gctgggactg ccatggcctg 300
ccgatcgaac acaaagtcga agtgacctac ggcaaaaacc tgggcgcgga taaaacccgc 360
gaactgtgcc gtgcctacgc cactgagcag atcgaagggc agaagtccga attcatccgc 420
ctgggcgtgc tgggcgagtg ggacaacccg tacaagacca tgaacttcaa gaacgaggcc 480
ggtgaaatcc gtgccttggc tgaaatcgtc aaaggcggtt ttgtgttcaa gggcctcaag 540
cccgtgaact ggtgcttcga ctgcggttcg gccctggctg aggcggaagt cgaatacgaa 600
gacaagaagt cctcgaccat cgacgtggcc ttcccgatcg ccgacgacgc caagttggcc 660
caggctttcg gcctggcaag cctgagcaag ccggcggcca tcgtgatctg gaccaccacc 720
ccgtggacca tcccggccaa ccaggcgctg aacgtgcacc cggaattcac ctacgccctg 780
gtggacgtcg gtgatcgcct gctggtgctg gccgaggaaa tggtcgaggc ctgtctggcg 840
cgctacgaac tgcaaggttc ggtgatcgcc accaccaccg gctccgcgct ggaactgatc 900
aacttccgtc acccgttcta tgaccgcctg tcgccggttt acctggctga ctacgtcgaa 960
ctgggttcgg gtacgggtgt ggttcactcc gcaccggcct acggcgttga cgacttcgtg 1020
acctgcaaag cctacggtat ggtcaacgat gacatcctca acccggtgca gagcaatggt 1080
gtgtacgcgc catcgctgga gttcttcggc ggccagttca tcttcaaggc taacgagccg 1140
atcatcgaca aactgcgtga agtcggtgcg ctgctgcaca ccgaaaccat caagcacagc 1200
tacatgcact gctggcgcca caaaaccccg ctgatctacc gcgccaccgc gcagtggttt 1260
atcggcatgg acaaagagcc gaccagcggc gacaccctgc gtgtgcgctc gctcaaagcc 1320
atcgaagaca ccaagttcgt cccggcctgg ggccaggcgc gcctgcactc gatgatcgcc 1380
aatcgtccgg actggtgcat ctcccgccag cgtaactggg gcgtaccgat cccgttcttc 1440
ctgaacaagg aaagcggcga gctgcaccca cgcaccgtcg agctgatgga agccgtggcc 1500
ttgcgcgttg aacaggaagg catcgaagcc tggttcaagc tggacgccgc cgagctgctg 1560
ggcgacgaag cgccgctgta cgacaagaag gctcggacca acaccgtggc tggttccact 1620
cgtcgctgct ga 1632

<210> SEQ ID NO 91
<211> LENGTH: 1784
<212> TYPE: DNA
<213> ORGANISM: Unknown
<220> FEATURE:
<223> OTHER INFORMATION: Description of Unknown:
DP1 NADH-quinone oxidoreductase subunit C/D microbial sequence

<400> SEQUENCE: 91
atgactacag gcagtgctct gtacatcccg ccttataagg cagacgacca ggatgtggtt 60
gtcgaactca ataaccgttt tggccctgac gcctttaccg cccaggccac acgtaccggc 120
atgccggtgc tgtgggtggc gcgcgccagg ctcgtcgaag tcctgacctt cctgcgcaac 180
ctgcccaagc cgtacgtcat gctctatgac ctgcatggcg tggacgagcg tctgcggacc 240
aagcgccagg gcctgccgag cggcgccgat ttcaccgtgt tctatcacct gctgtcgatc 300
gaacgtaaca gcgacgtgat gatcaaggtc gccctctccg aaagcgacct gagcgtcccg 360
accgtgaccg gcatctggcc caacgccagt tggtacgagc gtgaagtctg ggacatgttc 420
ggtatcgact tccctggcca cccgcacctg acgcgcatca tgatgccgcc gacctgggaa 480
ggtcacccgc tgcgcaagga cttccctgcg cgcgccaccg aattcgaccc gttcagcctg 540
aacctcgcca agcaacagct tgaagaagag gctgcacgct tccggccgga agactggggc 600
atgaaacgct ccggcaccaa cgaggactac atgttcctca acctgggccc gaaccaccct 660

```
tcggcgcacg gtgccttccg tatcatcctg caactggacg gcgaagaaat cgtcgactgc    720

gtgccggaca tcggttacca ccaccgtggt gccgagaaga tggccgagcg ccagtcgtgg    780

cacagcttca tcccgtacac cgaccgtatc gactacctcg gcggcgtgat gaacaatctg    840

ccgtacgtgc tctcggtcga gaagctggcc ggtatcaagg tgccggaccg cgtcgacacc    900

atccgcatca tgatggccga gttcttccgg atcaccagcc acctgctgtt cctgggtacc    960

tacatccagg acgtcggcgc catgaccccg gtgttcttca ccttcaccga ccgtcagcgc   1020

gcctacaagg tcatcgaagc catcaccggc ttccgcctgc acccggcctg gtaccgcatc   1080

ggcggtgtcg cgcacgacct gccaaatggc tgggaacgcc tggtcaagga attcatcgac   1140

tggatgccca agcgtctgga cgagtaccag aaagccgccc tggacaacag catcctcaag   1200

ggccggacca ttggggtcgc ggcctacaac accaaagagg ccctggaatg ggcgtcacc    1260

ggtgctggcc tgcgttccac cggttgcgat ttcgacctgc gtaaagcgcg cccgtactcc   1320

ggctacgaga acttcgaatt cgaagtgccg ttggcggcca atggcgatgc ctacgaccgt   1380

tgcatcgtgc gcgtcgaaga aatgcgccag agcctgaaga tcatcgagca atgcatgcgc   1440

aacatccggc aggcccgtac aaggcggacc acccgctgac cacgccgccg ccgaaagagc   1500

gcacgctgca acacatcgaa accctgatca cgcacttcct gcaggtttcg tggggcccgg   1560

tgatgccggc caacgaatcc ttccagatga tcgaagcgac caagggtatc aacagttatt   1620

acctgacgag cgatggcggc accatgagct accgcacccg gattcgcact ccaagcttcc   1680

cgcacctgca gcagatccct tcggtgatca aaggtgaaat ggtcgcggac ttgattgcgt   1740

acctgggtag tatcgatttc gttatggccg acgtggaccg ctaa                    1784
```

<210> SEQ ID NO 92
<211> LENGTH: 1059
<212> TYPE: DNA
<213> ORGANISM: Unknown
<220> FEATURE:
<223> OTHER INFORMATION: Description of Unknown:
      DP1 Protein RecA microbial sequence

<400> SEQUENCE: 92

```
atggacgaca acaagaagaa agccttggct gcggccctgg gtcagatcga acgtcaattc     60

ggcaagggtg ccgtaatgcg tatgggcgat cacgaccgtc aggcgatccc ggctatttcc    120

actggctctc tgggtctgga catcgcactc ggcattggcg gcctgccaaa aggccgtatc    180

gttgaaatct acggccctga atcttccggt aaaaccaccc tgaccctgtc ggtgattgcc    240

caggcgcaaa aaatgggcgc cacttgtgcg ttcgtcgatg ccgagcacgc tcttgaccct    300

gaatacgccg gcaagctggg cgtcaacgtt gacgacctgc tggtttccca accggacacc    360

ggtgagcaag ccttggaaat caccgacatg ctggtgcgct ccaacgccat cgacgtgatc    420

gtggtcgact ccgtggctgc cctggtgccg aaagctgaaa tcgaaggcga aatgggcgac    480

atgcacgtgg gcctgcaagc ccgtctgatg tcccaggcgc tgcgtaaaat caccggtaac    540

atcaagaacg ccaactgcct ggtgatcttc atcaaccaga tccgtatgaa gattggcgtg    600

atgttcggca gcccggaaac caccaccggt ggtaacgcgt tgaagttcta cgcttcggtc    660

cgtctggata tccgccgtac tggcgcggtg aaggaaggcg acgaggtggt gggtagcgaa    720

acccgcgtta aagttgtgaa gaacaaggtg gccccgccat tccgtcaggc tgagttccag    780

attctctacg gcaagggtat ctacctgaac ggcgagatga tcgacctggg cgtactgcac    840

ggtttcgtcg agaagtccgg tgcctggtat gcctacaacg gcagcaagat cggtcagggc    900
```

aaggccaact cggccaagtt cctggcggac aacccggata tcgctgccac gcttgagaag 960
cagattcgcg acaagctgct gaccccggca ccagacgtga aagctgctgc caaccgcgag 1020
ccggttgaag aagtagaaga agtcgacact gacatctga 1059

<210> SEQ ID NO 93
<211> LENGTH: 1161
<212> TYPE: DNA
<213> ORGANISM: Unknown
<220> FEATURE:
<223> OTHER INFORMATION: Description of Unknown:
DP1 RNA polymerase sigma factor RpoD microbial sequence

<400> SEQUENCE: 93
atggaaatca cccgcaaggc tctgaaaaag cacggtcgcg gcaacaagct ggcaattgcc 60
gagctggtgg ccctggctga gctgttcatg ccaatcaagc tggtgccgaa gcaatttgaa 120
ggcctggttg agcgtgtgcg cagtgctctt gagcgtctgc gtgcccaaga gcgcgcaatc 180
atgcagctct gcgtacgtga tgcacgcatg ccgcgtgccg acttcctgcg ccagttcccg 240
ggcaacgaag tggatgaaag ctggaccgac gcactggcca aaggcaaggc gaagtacgcc 300
gaagccattg gtcgcctgca gccggacatc atccgttgcc agcagaagct gaccgcgctt 360
caaaccgaaa ccggtctgac gattgctgag atcaaggaca tcaaccgtcg catgtcgatc 420
ggtgaggcca aggcccgccg cgcgaagaaa gagatggttg aagcgaactt gcgtctggtg 480
atctccatcg ccaagaagta caccaaccgt ggcctgcaat tcctcgatct gatccaggaa 540
ggcaacatcg gcttgatgaa ggctgtggac aagttcgaat accgtcgcgg ctacaagttc 600
tcgacttatg ccacctggtg gatccgtcag gcgatcactc gctcgatcgc agaccaggcc 660
cgcaccatcc gtattccggt gcacatgatc gagaccatca acaagctcaa ccgtatttcc 720
cggcagatgt tgcaggaaat gggtcgcgaa ccgacgccgg aagagctggg cgaacgcatg 780
gaaatgcctg aggataaaat ccgtaaggta ttgaagatcg ctaaagagcc gatctccatg 840
gaaacgccga ttggtgatga cgaagactcc catctgggtg acttcatcga agactcgacc 900
atgcagtcgc ccatcgatgt ggctaccgtt gagagcctta aagaagcgac tcgcgacgta 960
ctgtccggcc tcactgcccg tgaagccaag gtactgcgca tgcgtttcgg catcgacatg 1020
aataccgacc acacccttga ggaagtcggt aagcagtttg acgtgacccg tgaacggatc 1080
cgtcagatcg aagccaaggc actgcgcaag ttgcgccacc cgacgcgaag cgagcatcta 1140
cgctccttcc tcgacgagtg a 1161

<210> SEQ ID NO 94
<211> LENGTH: 4074
<212> TYPE: DNA
<213> ORGANISM: Unknown
<220> FEATURE:
<223> OTHER INFORMATION: Description of Unknown:
DP1 DNA-directed RNA polymerase subunit beta
microbial sequence

<400> SEQUENCE: 94
atggcttact catatactga gaaaaaacgt atccgcaagg actttagcaa gttgccggac 60
gtcatggatg tcccgtacct tctggctatc cagctggatt cgtatcgtga attcttgcaa 120
gcgggagcga ctaaagatca gttccgcgac gtgggcctgc atgcggcctt caaatccgtt 180
ttcccgatca tcagctactc cggcaatgct gcgctggagt acgtgggtta tcgcctgggc 240
gaaccggcat ttgatgtcaa agaatgcgtg ttgcgcggtg ttacgtacgc cgtacctttg 300
cgggtaaaag tccgtctgat cattttcgac aaagaatcgt cgaacaaagc gatcaaggac 360
atcaaagagc aagaagtcta catgggcgaa atcccattga tgactgaaaa cggtaccttc 420
gttatcaacg gtaccgagcg cgttatcgtt tcccagctgc accgttcccc gggcgtgttc 480
ttcgaccacg accgcggcaa gacgcacagc tccggtaagc tcctgtactc cgcgcggatc 540
attccgtacc gcggctcgtg gttggacttc gagttcgacc cgaaagactg cgtgttcgtg 600
cgtatcgacc gtcgtcgtaa gctgccggcc tcggtactgc tgcgcgcgct cggctatacc 660
actgagcaag tgcttgatgc tttctacacc accaacgtat tcagcctgaa ggatgaaacc 720
ctcagcctgg aactgattgc ttcgcgtctg cgtggtgaaa ttgccgtcct ggatatccag 780
gatgaaaacg gcaaggtcat cgttgaagct ggccgccgta ttaccgcgcg ccacatcaac 840
cagatcgaaa aagccggtat caagtcgctg gacgtgccgc tggactacgt cctgggtcgc 900
accactgcca aggtcatcgt tcacccggct acaggcgaaa tcctggctga gtgcaacacc 960
gagctgaaca ccgagatcct ggcaaaaatc gccaaggccc aggttgttcg catcgagacc 1020
ctgtacacca acgacatcga ctgcggtccg ttcatctccg acacgctgaa gatcgactcc 1080
accagcaacc aattggaagc gctggtcgag atctatcgca tgatgcgtcc tggtgagcca 1140
ccgaccaaag acgctgccga gaccctgttc aacaacctgt tcttcagccc tgagcgctat 1200
gacctgtctg cggtcggccg gatgaagttc aaccgtcgta tcggtcgtac cgagatcgaa 1260
ggttcgggcg tgctgtgcaa ggaagacatc gtcgcggtac tgaagacctt ggtcgacatc 1320
cgtaacggta aaggcatcgt cgatgacatc gaccacttgg gtaaccgtcg tgttcgctgc 1380
gtaggcgaaa tggccgagaa ccagttccgc gttggcctgg tacgtgttga gcgtgcggtc 1440
aaagagcgtc tgtcgatggc tgaaagcgaa ggcctgatgc cgcaagatct gatcaacgcc 1500
aagccagtgg ctgcggcggt gaaagagttc ttcggttcca gccagctctc gcagttcatg 1560
gaccagaaca acccgctctc cgagatcacc cacaagcgcc gtgtttccgc actgggcccg 1620
ggcggtctga cccgtgagcg tgcaggcttt gaagttcgtg acgtacaccc aacgcactac 1680
ggtcgtgttt gcccgatcga aacgccggaa ggtccgaaca tcggtctgat caactccctt 1740
gccgcttatg cacgcactaa ccagtacggc ttcctcgaga gcccgtaccg tgtagtgaaa 1800
gatgcactgg tcaccgacga gatcgtgttc ctgtccgcca tcgaagaagc cgatcacgtg 1860
atcgctcagg cttcggccac gatgaacgac aagaaagtcc tgatcgacga gctggtagct 1920
gttcgtcact tgaacgagtt caccgttaag gcgccggaag acgtcacctt gatggacgtt 1980
tcgccgaagc aggtagtttc ggttgcagcg tcgctgatcc cgttcctgga gcacgatgac 2040
gccaaccgtg cgttgatggg ttccaacatg cagcgtcaag ctgtacccac cctgcgtgcc 2100
gacaagccgc tggtaggtac cggcatggag cgtaacgtag cccgtgactc cggcgtttgc 2160
gtcgtggctc gtcgtggcgg cgtgatcgac tctgttgatg ccagccgtat cgtggttcgt 2220
gttgccgatg acgaagttga gactggcgaa gccggtgtcg acatctacaa cctgaccaaa 2280
tacacccgct cgaaccagaa cacctgcatc aaccagcgcc cgctggtgag caagggtgat 2340
cgcgttcagc gtagcgacat catggccgac ggcccgtcca ccgatatggg tgagctggca 2400
ctgggtcaga acatgcgcat cgcgttcatg gcatggaacg gcttcaactt cgaagactcc 2460
atctgcctgt ccgagcgtgt tgttcaagaa gaccgcttca ccacgatcca cattcaggag 2520
ctgacctgtg tggcgcgtga caccaagctt gggccagagg aaatcactgc agacatcccg 2580
aacgtgggtg aagctgcact gaacaaactg gacgaagccg gtatcgttta cgtaggtgct 2640
gaagttggcg caggcgacat cctggttggt aaggtcactc cgaaaggcga gacccaactg 2700

```
actccggaag agaagctgtt gcgtgccatc ttcggtgaaa aagccagcga cgttaaagac   2760
acttccctgc gcgtacctac cggtaccaag ggtactgtca tcgacgtaca ggtcttcacc   2820
cgtgacggcg ttgagcgtga tgctcgtgca ctgtccatcg agaagactca actcgacgag   2880
atccgcaagg acctgaacga agagttccgt atcgttgaag gcgcgacctt cgaacgtctg   2940
cgttccgctc tggtaggcca caaggctgaa ggcggcgcag gtctgaagaa aggtcaggac   3000
atcaccgacg aaatcctcga cggtcttgag cacggccagt ggttcaaact gcgcatggct   3060
gaagacgctc tgaacgagca gctcgagaag gcccaggcct atatcgttga tcgccgccgt   3120
ctgctggacg acaagttcga agacaagaag cgcaaactgc agcagggcga tgacctggct   3180
ccaggcgtgc tgaaaatcgt caaggtttac ctggcaatcc gtcgccgcat tcagccgggc   3240
gacaagatgg ccggtcgtca cggtaacaag ggtgtggtct ccgtgatcat gccggttgaa   3300
gacatgccgc acgatgccaa tggcaccccg gtcgacgtcg tcctcaaccc gttgggcgta   3360
ccttcgcgta tgaacgttgg tcagatcctt gaaacccacc tgggcctcgc ggccaaaggt   3420
ctgggcgaga agatcaaccg tatgatcgaa gagcagcgca aggtcgcaga cctgcgtaag   3480
ttcctgcacg agatctacaa cgagatcggc ggtcgcaacg aagagctgga caccttctcc   3540
gaccaggaaa tcctggatct ggcgaagaac ctgcgcggcg gcgttccaat ggctaccccg   3600
gtattcgacg gtgccaagga aagcgaaatc aaggccatgc tgaaactggc agacctgccg   3660
gaaagtggcc agatgcagct gttcgacggc cgtaccggca acaagtttga gcgcccggtt   3720
actgttggct acatgtacat gctgaagctg aaccacttgg tagacgacaa gatgcacgct   3780
cgttctaccg gttcgtacag cctggttacc cagcagccgc tgggtggtaa ggctcagttc   3840
ggtggtcagc gtttcgggga gatggaggtc tgggcactgg aagcatacgg tgctgcttac   3900
actctgcaag aaatgctcac agtgaagtcg gacgatgtga acggtcggac caagatgtac   3960
aaaaacatcg tggacggcga tcaccgtatg gagccgggca tgcccgagtc cttcaacgtg   4020
ttgatcaaag aaattcgttc cctcggcatc gatatcgatc tggaaaccga ataa         4074
```

```
<210> SEQ ID NO 95
<211> LENGTH: 1671
<212> TYPE: DNA
<213> ORGANISM: Unknown
<220> FEATURE:
<223> OTHER INFORMATION: Description of Unknown:
      DP22 Glutamine--tRNA ligase microbial sequence

<400> SEQUENCE: 95
```

```
atgagtgagg ctgaagcccg cccaacaaat tttatccgtc agattattga tgaagatctg     60
gcgaccggga aacacaatac cgttcatacc cgtttcccgc ctgagccaaa tggctatctg    120
catatcggtc atgcgaaatc tatctgcctg aacttcggca ttgcgcaaga ctatcagggg    180
cagtgcaacc tgcgttttga cgataccaac ccggcaaaag aagacatcga attcgttgag    240
tcgatcaaac acgacgtcca gtggttaggt ttcgactgga gcggtgatat tcactactct    300
tcagactatt ttgatcaact gcacgcttat gcgctggaac tgatcaacaa aggtctggcg    360
tacgttgacg aactgtcacc ggatcagatc cgtgaatacc gcggctcgct gacgtctccg    420
ggcaaaaaca gcccgtaccg tgaccgttca gtggaagaga acatcgcgct gtttgagaaa    480
atgcgtaacg gtgaatttgc cgaaggcgct gcctgtctgc gtgcaaaaat cgatatggcg    540
tcgcctttct tcgtgatgcg cgatccggtt ctgtaccgta ttaagtttgc agaacaccac    600
cagaccggca aaaaatggtg catctatccg atgtacgatt tcacccactg catttccgat    660
```

gcgctggaag ggatcaccca ttcgctgtgt acgctggaat tccaggacaa ccgccgtctg 720
tacgactggg ttctggataa catctccatt ccatgccacc cgcgtcagta cgagttctcc 780
cgtctgaatc tcgagtactc catcatgtct aagcgtaagc tgaaccagct ggtgaccgag 840
aagattgtgg aaggctggga cgacccgcgt atgccgactg tttcaggtct gcgtcgtcgt 900
ggttacaccg ccgcgtctat ccgtgaattc tgccgtcgta tcggcgtcac caagcaagac 960
aacaacgtcg aaatgatggc gctggaatcc tgtatccgtg acgatctgaa cgaaaatgca 1020
ccgcgcgcca tggcggtgat caacccggtt aaagtgatca ttgaaaactt taccggtgat 1080
gacgtgcaga gggtgaaaat gccgaaccac ccgagcaaac cggaaatggg cacccgcgaa 1140
gtgccattta cccgtgagat ttatatcgat caggcagatt tccgcgaaga agcgaacaag 1200
caatacaagc gtctggtgct cggcaaagaa gtgcgtctgc gcaatgcgta tgtgatcaaa 1260
gcagaacgta tcgagaaaga tgcagaaggc aatatcacca cgatcttctg ttcttacgat 1320
atcgatacac tgagcaaaga tcctgccgat ggccgcaagg tgaaaggcgt gatccactgg 1380
gtttcggcgt cagaaggcaa accggcggag ttccgcctgt atgaccgtct gttcagcgtc 1440
gccaacccgg gtcaggcaga agatttcctg accaccatca acccggaatc tctggtgatt 1500
tcccacggtt tcgtggagcc atcactggtg gctgcacagg ctgaaatcag cctgcagttc 1560
gagcgtgaag gttacttctg cgccgacagc cgctactcaa gcgctgaaca tctggtgttt 1620
aaccgtaccg ttggcctgcg cgatacctgg gaaagcaaac ccgtcgtgta a 1671

<210> SEQ ID NO 96
<211> LENGTH: 2415
<212> TYPE: DNA
<213> ORGANISM: Unknown
<220> FEATURE:
<223> OTHER INFORMATION: Description of Unknown:
DP22 DNA gyrase subunit B microbial sequence

<400> SEQUENCE: 96
atgtcgaatt cttatgactc ctcaagtatc aaggtattaa aagggctgga cgcggtgcgt 60
aagcgccccg gcatgtatat cggcgatacc gatgacggca ctggtctgca ccacatggta 120
ttcgaggttg tggacaacgc tatcgacgaa gccctcgcgg gccactgtaa agagattcag 180
gtcacgatcc atgcggataa ctctgtgtcc gtacaggatg atggtcgtgg cattccgacc 240
ggtattcatg aagaagaggg cgtttctgct gctcaggtca tcatgaccgt tcttcacgcc 300
ggcggtaaat ttgacgataa ctcgtataaa gtctccggcg gtctgcatgg cgtgggtgtt 360
tccgtcgtta acgccctgtc agaaaaactg gaactggtta tccgccgcga aggcaaagtg 420
cacacccaga cttacgtgca tggcgaacct caggatccgc tgaaagtgat tggcgatact 480
gacgtgaccg gtaccacggt acgtttctgg ccaagcttca acaccttcac caatcacact 540
gaattcgagt atgacattct ggcgaaacgc ctgcgtgaac tgtcattcct gaactccggc 600
gtggcgatcc gcctgctgga taaacgtgat ggtaaaaacg atcacttcca ttatgaaggc 660
ggtatcaaag ctttcgtgga atatctgaac aaaaacaaaa ccccaatcca tccgaccgta 720
ttctatttct ccacggtcaa agatgacatt ggcgttgaag tggcgttgca gtggaacgac 780
ggtttccagg aaaacattta ctgcttcacc aacaacattc cacagcgcga tggcgggact 840
cacttagccg gtttccgttc ggcaatgacc cgtaccctga acgcgtacat ggataaagaa 900
ggctacagca agaaatccaa aatcagcgcc accggtgatg atgcccgtga aggcctgatt 960
gctgtggtgt cggtgaaggt gccggatcct aagttctctt ctcagaccaa agacaaactg 1020
gtgtcttctg aagtgaaaac agcggttgaa acgctgatga acgagaagct ggtggattac 1080
ctgatggaaa acccgtcaga cgccaaaatc gttgtcggta aaatcatcga cgcagcgcgt 1140
gcccgtgaag cagcacgtaa agcgcgtgaa atgacccgcc gtaaaggcgc gctggatctg 1200
gctggcttgc caggcaaact ggcggactgt caggaacgcg atccggcaca ttccgaactg 1260
tacttagtgg aaggggactc agcgggcggc tctgcaaaac aaggccgtaa ccgtaagaac 1320
caggcgattc tgccgttgaa aggtaaaatc ctcaacgtgg agaaagcgcg cttcgacaaa 1380
atgctctctt ctcaggaagt ggcaacgctg attacagcac tcggttgcgg cattggccgt 1440
gacgaataca acccggacaa actgcgctat cacagcatca tcatcatgac cgatgccgac 1500
gtcgatggtt cgcacatccg taccctgttg ctgacattct tctaccgtca gatgcctgaa 1560
attgtagaac gtggccacgt gtttatcgcc cagccgccgt tgtacaaagt gaaaaaaggc 1620
aagcaggaac agtacattaa agatgacgaa gcgatggatc agtatcagat ttccattgcg 1680
atggacgggg caacgttaca cgccaacgct catgcgccag ccctggcggg tgaaccgctg 1740
gagaaactgg tcgctgaaca tcacagcgtg cagaaaatga ttggccgcat ggaacgtcgt 1800
tatccgcgtg cgctgctgaa taacctgatc tatcagccga ccctgccggg tgcagatctg 1860
gccgatcagg cgaaagtgca ggcctggatg gaatcgctgg tggcgcgtct caacgagaaa 1920
gagcagcacg gcagttctta cagcgcgatc gtgcgtgaaa accgcgaaca tcagctgttc 1980
gaaccggttc tgcgtatccg cacccacggt gttgataccg attacgatct ggatgccgac 2040
ttcatcaaag gcggcgaata ccgcaaaatc tgtgcgctgg gtgaacagct gcgcggcctg 2100
atcgaagaag atgccttcat cgaacgtggc gaacgccgtc agcccgtcac cagcttcgaa 2160
caggcgctgg aatggctggt gaaagagtcc cgtcgtggtc tgtcgattca gcgatacaaa 2220
ggtctgggtg aaatgaaccc tgaacagctg tgggaaacca ccatggatcc tgagcaacgt 2280
cgcatgttac gtgtgaccgt gaaggatgcc atcgccgctg accagttgtt cacgacgctg 2340
atgggcgatg cggttgaacc gcgccgcgcc tttatcgaag agaacgccct gaaagccgcc 2400
aatatcgata tctga 2415

<210> SEQ ID NO 97
<211> LENGTH: 2733
<212> TYPE: DNA
<213> ORGANISM: Unknown
<220> FEATURE:
<223> OTHER INFORMATION: Description of Unknown:
DP22 Isoleucine--tRNA ligase microbial sequence

<400> SEQUENCE: 97
atgagtgact acaagaacac cctgaatttg ccggaaacag ggttcccgat gcgtggcgat 60
ctggccaagc gtgaacctga catgctgaaa aattggtatg accaggatct gtacgggatt 120
attcgtgctg ccaagaaagg caaaaaaacc tttattttgc atgacggccc tccgtatgcg 180
aacggcagca ttcatattgg tcactcagta aacaaaattc ttaaagacat gattatcaag 240
tccaaaggac ttgcgggctt tgatgcgccg tatgtgccgg gctgggattg tcatggtctg 300
ccgatcgagc tgaaagtcga acaactgatc ggtaagccgg gcgagaaagt tacggcggcg 360
gaattccgtg aagcctgccg taaatatgcc gcagaacagg ttgaaggcca gaagaaagac 420
ttcatccgtc tgggcgtgct gggcgactgg gatcatccgt acctgacgat ggatttcaaa 480
accgaagcca acatcatccg tgcgctgggc aaaatcatcg gtaacggcca cctgcataaa 540
ggcgccaagc cggtgcactg gtgtacagat tgcggttcgt cgctggccga agccgaagtc 600
gaatattacg acaaagcctc gccttctatt gatgtggcgt tcaacgcgac ggatgccgca 660
gccgtggcag cgaaatttgg cgttactgcc tttaatggcc cgatctcgct ggttatctgg 720
accacaacac cgtggactat gcccgctaac cgcgccattt cactgaatcc tgagtttgct 780
tatcagctgg ttcaggtcga aggtcagtgt ctgatcctgg caaccgatct ggttgaaagc 840
gtcatgaaac gtgccggtat tgccggatgg accgttctgg gcgagtgcaa aggcgcagac 900
ctcgaactgc tgcgcttcaa acacccgttc ctcggtttcg acgttccggc gatcctgggc 960
gatcacgtga cgctcgatgc gggtaccggt gccgtgcata ccgcaccagg ccacggccct 1020
gacgactttg ttatcggcca gaaatacggt ctggaagtgg cgaatccggt agggccgaac 1080
ggttgctacc tgccgggcac ttacccgacg ctggacggta aatttgtctt taaagccaac 1140
gacctgatcg ttgagttgct gcgtgaaaaa ggcgcattgc tgcacgttga gaaaatcacg 1200
cacagctatc cttgctgctg gcgccacaaa acgccaatca tcttccgcgc gacgccgcaa 1260
tggttcatca gcatggatca gaagggcctg cgtcagcagt cgctggaaga gatcaaaggc 1320
gtgcagtgga tcccggactg ggtcaggca cgtatcgaaa acatggtcgc taaccgtcct 1380
gactggtgta tctcccgtca gcgtacctgg ggcgtgccga tgtctctgtt cgttcacaaa 1440
gacactgagc agctgcatcc gcgcagcctt gagctgatgg aagaagtggc gaaacgtgtt 1500
gaggtggatg gcattcaggc gtggtgggat ctgaatccgg aagacattct gggtgcagac 1560
gccgcagatt acgtcaaagt accggacacg ctggacgtct ggtttgactc cggttcaacg 1620
cattcttccg ttgtggatgt gcgtcctgag ttcaacgggc attctcctga tctgtatctg 1680
gaaggttctg accagcatcg cggctggttc atgtcttccc tgatgatttc gacggcaatg 1740
aaaggcaaag cgccttacaa acaagtgctg actcacggtt tcaccgtgga tggtcagggc 1800
cgcaaaatgt ctaaatccat cggcaatacc atcgcgccgc aagacgtgat gaacaagctg 1860
ggtggcgaca ttctgcgtct gtgggtcgcg tcgacggatt acaccggcga aatcgccgtg 1920
tccgacgaaa tcctcaaacg tgctgctgat tcttaccgcc gtatccgtaa caccgcgcgc 1980
ttcctgctgg cgaaccttaa cggtttcgat ccggcgctgc acagcgtggc tccggaagac 2040
atggtggtgc tggaccgctg ggcggttggc cgtgcgaaag ccgctcagga agaaatcatt 2100
gctgcgtatg aagcctatga tttccatggc gttgttcagc gtctgatgca gttctgctcg 2160
atcgaaatgg gttccttcta tctggatatc attaaagatc gtcagtacac cgcgaaaagc 2220
gacagcgttg cacgtcgcag ctgtcagacc gcgctgtatc acatcagtga agcgctggtt 2280
cgctggatgg caccgatcat gtcgttcaca gccgatgaaa tctgggcgga actgccggga 2340
agccgtgaga aattcgtctt caccgaagag tggtacgacg gtctgttcgg tctcgcaggc 2400
aacgaatcca tgaacgatgc gttctgggat gaactgctga aagtgcgtgg cgaagtgaac 2460
aaagtgatcg aacaggcgcg tgcggataaa cgtctgggcg gttctctgga agcagcggtt 2520
acgctgtttg ctgatgatgc gctggcaaca gacctgcgtt ctctgggcaa tgaactgcgc 2580
tttgtgctgc tgacgtcagg ggcgaaagtt gccgcactga gtgatgcaga tgacgcggct 2640
cagtcgagtg aattgctgaa aggcctgaag attggtctgg cgaaagcaga aggcgacaag 2700
tgcccgcgct gctggcatta cactaccgat taa 2733

<210> SEQ ID NO 98
<211> LENGTH: 1800
<212> TYPE: DNA
<213> ORGANISM: Unknown
<220> FEATURE:

<223> OTHER INFORMATION: Description of Unknown:
      DP22 NADH-quinone oxidoreductase subunit C/D
      microbial sequence

<400> SEQUENCE: 98
atgacagatt tgacgacgca agattccgcc ctgccagcat ggcataccg tgatcatctc 60 gatgatccgg ttatcggcga attgcgtaac cgttttgggc cagaggcctt tactgtccag 120
gcaacccgca ccggaattcc cgtggtgtgg ttcaagcgtg aacagttact ggaagcgatt 180 accttttac gaaaacagcc aaaaccttac gtcatgcttt tcgatttgca tggctttgat 240
gagcgtttac gtacacaccg cgacggttta ccggctgcgg atttttccgt tttctaccac 300
ctgatctccg tcgagcgtaa ccgcgacatc atgatcaaag tggcgttgtc agaaaacgat 360
cttcatgttc cgacgatcac caaagtgttc ccgaacgcta actggtacga acgcgaaaca 420
tgggaaatgt tcggtattac cttcgacggc catccgcacc tgacgcgcat catgatgccg 480
cagacctggg aagggcatcc gctgcgtaaa gactatccgg cgcgcgccac cgagttcgat 540
ccttatgagc tgactaagca aaaagaagaa ctcgagatgg aatcgctgac cttcaagccg 600
gaagactggg gcatgaagcg cggtaccgat aacgaggact ttatgttcct caacctcggt 660
cctaaccacc cgtcagcgca tggtgcattc cgtattatcc tgcagctgga tggcgaagag 720
attgtcgact gcgtgcctga cgtcggttac caccaccgtg gtgcggagaa aatgggcgaa 780
cgccagtcat ggcacagcta cattccgtat actgaccgta tcgaatatct cggcggttgt 840
gttaacgaaa tgccttacgt gctggctgtt gaaaaactcg ccggtatcgt gacgccggat 900
cgcgttaaca ccatccgtgt gatgctgtct gaactgttcc gtatcaacag ccatctgctg 960
tacatctcta cgtttattca ggacgtgggt gcgatgacgc cggtattctt cgcctttacc 1020
gatcgtcaga aaatttacga tctggtggaa gcgatcaccg gtttccgtat gcacccggcc 1080
tggttccgta tcggtggcgt agcgcatgac ctgccgaaag gctgggaccg cctgctgcgt 1140
gaattccttg actggatgcc agcccgtttg gattcctacg tcaaagcggc gctgagaaac 1200
accattctga ttggccgttc caaaggcgtg gccgcgtata acgccgacga cgcactggcc 1260
tggggcacca ccggtgctgg cctgcgcgca acgggtatcc cgttcgatgt gcgtaaatgg 1320
cgtccgtatt caggttatga aaactttgac tttgaagtgc cgaccggtga tggcgtcagt 1380
gactgctatt cccgcgtgat gctgaaagtg gaagaacttc gtcagagcct gcgcattctg 1440
gaacagtgct acaaaaacat gccggaaggc ccgttcaagg cggatcaccc gctgaccacg 1500
ccgccaccga aagagcgcac gctgcaacac atcgagaccc tgatcacgca cttcctgcaa 1560
gtgtcgtggg ggccggtcat gcctgcacaa gaatctttcc agatggttga agcaaccaaa 1620
gggatcaaca gctactacct gaccagtgac ggcagcacca tgagctaccg cacccgtgtc 1680
cgtacgccga gcttcccgca tttgcagcag atcccgtccg taatccgtgg cagcctggta 1740
tccgacctga tcgtgtatct gggcagtatc gattttgtaa tgtcagatgt ggaccgctaa 1800

<210> SEQ ID NO 99
<211> LENGTH: 1065
<212> TYPE: DNA
<213> ORGANISM: Unknown
<220> FEATURE:
<223> OTHER INFORMATION: Description of Unknown:
      DP22 Protein RecA microbial sequence

<400> SEQUENCE: 99
atggctattg atgagaacaa gcaaaaagcg ttagctgcag cactgggcca gattgaaaag 60

-continued

```
caattcggta aaggctccat catgcgtctg ggtgaagatc gctccatgga cgttgaaacg    120

atctctaccg gctctttgtc tctggatatc gcgttaggtg ccggcggttt gccaatgggc    180

cgtatcgttg agatctatgg cccggaatct tccggtaaaa caacgctgac cttgcaagtt    240

atcgcggctg cacagcgtga aggcaaaacc tgtgcgttca tcgatgcaga acacgccctg    300

gacccgatct acgctaaaaa actgggcgtg gatatcgata acctgctgtg ttctcagcca    360

gataccggcg aacaggctct ggaaatctgt gacgcgctga cccgttcagg cgctgttgac    420

gtgatcatcg ttgactccgt tgccgcactg acaccgaaag cggaaatcga aggcgaaatt    480

ggtgactctc acatgggcct cgcggcacgt atgatgagcc aggcgatgcg taagctggcc    540

ggtaacctga aaaacgccaa caccttgctg atcttcatca accagatccg tatgaaaatt    600

ggtgtgatgt tcggtaaccc ggaaaccacc accggcggta acgccctgaa attctacgct    660

tctgtgcgtc tggatatccg ccgtatcggc gcgatcaaag aaggcgatgt ggttgtcggt    720

agcgaaacgc gtgtgaaagt ggtgaagaac aaaatcgctg cgccatttaa acaagctgaa    780

ttccagatca tgtacggcga aggcatcaat atcaacggcg agctgattga tctcggcgtg    840

aagcacaagc tgatcgaaaa agccggtgca tggtatagct acaacggtga gaagattggt    900

cagggtaaag cgaactcctg caacttcctg aaagaaaacc cgaaagtggc tgccgagctg    960

gataaaaaac tgcgtgatat gctgttgagc ggtaccggtg aactgagtgc tgcgaccacg   1020

gctgaagatg ctgacgacaa catggaaacc agcgaagagt tttaa                   1065
```

<210> SEQ ID NO 100
<211> LENGTH: 1839
<212> TYPE: DNA
<213> ORGANISM: Unknown
<220> FEATURE:
<223> OTHER INFORMATION: Description of Unknown:
DP22 RNA polymerase sigma factor RpoD microbial sequence

<400> SEQUENCE: 100

```
atggagcaaa acccgcagtc acagcttaag ctacttgtca cccgtggtaa ggagcaaggc     60

tatctgacct atgctgaggt caatgaccat ctgccggaag atatcgtcga ttccgaccag    120

atcgaagaca tcatccagat gattaacgac atgggcatcc aggtacttga agaagcaccg    180

gacgccgatg atttgatgct ggccgaaaac cgccctgata ccgatgaaga cgctgcagaa    240

gccgcggcgc aggtgctttc cagcgttgaa tccgaaattg gccgtaccac cgaccctgtg    300

cgtatgtata tgcgcgagat gggtaccgtt gagttgctga cccgtgaagg cgaaatcgac    360

atcgccaaac gtatcgaaga cggtatcaat caggtccagt gctccgttgc tgaatatcct    420

gaagctatca cttatttgtt agagcaatat gaccgtgtgg aagcaggcga agtacgtctg    480

tctgacctga tcaccggttt tgttgacccg aacgccgaag aagaaatcgc accaactgcg    540

actcacgtgg gttctgaact gaccactgaa gagcagaatg atgacgacga agacgaagat    600

gaagacgacg acgctgaaga cgacaacagc atcgatccgg aactggctcg ccagaagttc    660

accgaactgc gtgaacagca tgaagcgacg cgtctggtca tcaagaaaaa cggccgtagt    720

cacaagagcg cagcagaaga aatcctgaag ctgtccgatg tgttcaaaca gttccgtctg    780

gtgccaaaac agttcgattt cctggttaac agcatgcgtt ccatgatgga tcgcgttcgt    840

gctcaggaac gtctgatcat gaaagtgtgc gttgaacagt gcaaaatgcc gaagaaaaac    900

ttcgtcaatc tgttcgccgg taacgaaacc agcgatacct ggtttgatgc cgctctggca    960

atgggtaaac catggtccga gaagctgaaa gaagtcaccg aagacgtgca acgcggcctg   1020
```

atgaaactgc gtcagatcga agaagaaacc ggcctgacta tcgaacaggt taaagacatc 1080
aaccgtcgca tgtcgatcgg cgaagcgaaa gcccgtcgcg cgaagaaaga gatggttgaa 1140
gcaaacttac gtctggttat ttctatcgcc aagaaataca ccaaccgtgg tctgcagttc 1200
cttgacctga tccaggaagg taacatcggc ctgatgaaag ccgttgataa gtttgaatat 1260
cgccgtggtt ataagttctc aacttatgcg acctggtgga tccgtcaggc tatcacccgc 1320
tccatcgccg accaggcgcg taccatccgt atcccggtac atatgattga gacgatcaac 1380
aaactcaacc gtatctcccg tcagatgctg caagagatgg gccgcgaacc gacaccggaa 1440
gagctggctg agcgtatgtt gatgccggaa gacaaaatcc gcaaagtgct gaaaattgcc 1500
aaagagccaa tctccatgga aacgccaatc ggcgacgatg aagattcgca tctgggcgat 1560
ttcatcgagg ataccaccct cgagctgcca ctggattctg cgacgtctga aagcctgcgt 1620
tctgcaacgc atgacgttct ggctggcctg actgcacgtg aagcgaaagt tctgcgtatg 1680
cgtttcggta tcgatatgaa cactgaccac acgctggaag aagtgggcaa acagttcgac 1740
gtgacccgtg agcgtatccg tcagatcgaa gcgaaagcgt tgcgtaaact gcgccacccg 1800
agccgctccg aagtactgcg cagcttcctg gacgattaa 1839

<210> SEQ ID NO 101
<211> LENGTH: 4221
<212> TYPE: DNA
<213> ORGANISM: Unknown
<220> FEATURE:
<223> OTHER INFORMATION: Description of Unknown:
      DP22 DNA-directed RNA polymerase subunit beta'
      microbial sequence

<400> SEQUENCE: 101
gtgaaagact tactaaagtt tctgaaagcg caaactaaga ccgaagagtt tgatgcgatc 60
aaaattgctc tggcatcgcc agacatgatc cgttcttggt cttttggtga agttaagaag 120
ccagaaacca ttaactaccg tacgttcaaa ccagaacgtg acggcctttt ctgtgcccgt 180
attttcggac cagtaaaaga ctacgaatgc ctgtgcggta agtacaagcg tttaaaacat 240
cgcggcgtga tctgcgagaa gtgcggcgtt gaagtgaccc agactaaagt acgccgtgag 300
cgtatgggcc acatcgaact ggcttccccg actgcacaca tctggttcct gaaatcgctg 360
ccatcgcgca tcggtttgct gctggatatg ccactgcgtg acatcgaacg tgttctgtac 420
ttcgaatcct atgtggttat cgaaggcggc atgactaacc tcgaaaaacg ccagatcctg 480
actgaagagc agtatctgga tgcgttggaa gagtttggtg atgagttcga cgcgaagatg 540
ggtgcggaag ctattcaggc cctgttgaaa aacatggatc tggaagcaga gtgcgagcaa 600
ctgcgtgaag agttgaacga aaccaactcc gaaaccaaac gtaagaagct gaccaagcgt 660
atcaagctgc tggaagcgtt cgttcagtct ggtaacaaac cagagtggat gatcctgact 720
gtgctgccgg tactgccacc agacttgcgt ccattggttc cgttggacgg cggccgtttc 780
gcaacgtcgg atctgaacga tctgtatcgt cgcgtgatca accgtaacaa ccgtctgaaa 840
cgcctgctgg atctggctgc gccagacatc atcgtacgta acgaaaaacg tatgctgcaa 900
gaagcggtag atgctttgct ggataacggc cgtcgcggtc gtgctatcac cggctctaac 960
aagcgtccgc tgaaatctct ggcagacatg attaaaggta aacagggtcg tttccgtcag 1020
aacttgctgg gtaaacgtgt cgactactct ggtcgttccg ttatcaccgt aggtccatac 1080
ctgcgtctgc accagtgtgg tctgccgaag aaaatggcac tggaactgtt caaaccgttc 1140
atctacggca agctggaact gcgtggcctg gccaccacca tcaaagccgc gaagaaaatg 1200
gttgagcgcg aagaagctgt cgtttgggac atcctggacg aagttatccg cgaacacccg 1260
gtactgctga accgtgcacc aaccctgcac cgtttgggta tccaggcgtt tgaaccggtt 1320
ctgatcgaag gtaaagcaat ccagctgcac ccgctggttt gtgcggcata taacgccgac 1380
ttcgatggtg accagatggc tgttcacgta ccgttgacgc tggaagccca gctggaagcg 1440
cgtgcgttga tgatgtctac caacaacatc ctgtcacctg cgaacggcga gccaatcatc 1500
gttccttctc aggacgttgt attgggtctg tactacatga cccgtgactg tgttaacgcc 1560
aaaggcgaag gcatggttct gaccggtcct aaagaagctg agcgtattta ccgcgccggt 1620
ttggcctctc tgcatgcgcg tgtcaaagtg cgtattacag aagagatcaa aaataccgaa 1680
ggcgaagtta cgcacaagac gtcgattatc gacacgacag ttggtcgcgc catcctttgg 1740
atgatcgtac ctaaaggtct gccgttctct atcgtcaacc agcctctggg caaaaaagct 1800
atctccaaaa tgctgaacac ctgttaccgc attttgggcc tgaagccgac cgttattttt 1860
gctgaccaga tcatgtacac cggttttgct tacgctgccc gttcaggcgc gtcagtaggt 1920
atcgatgaca tggtaatccc tgcgaagaaa gcagagatca tcgaagaagc agaaaccgaa 1980
gttgctgaaa tccaggaaca gttccagtct ggtctggtca ctgctggcga acgctataac 2040
aaagtgatcg acatctgggc tgcggccaac gaacgtgttg ctaaggcaat gatggaaaac 2100
ttgtctgttg aagacgtcgt caaccgtgac ggtgttgttg aacagcaggt ttccttcaac 2160
agtatcttta tgatggccga ctccggtgcg cgtggttctg ctgcacagat tcgtcagctg 2220
gccggtatgc gtggcctgat ggcgaaacca gatggttcca tcattgaaac gccaatcacc 2280
gcgaacttcc gtgaaggtct gaacgtactc cagtacttca tctctactca cggtgctcgt 2340
aaaggtttgg cggataccgc acttaaaacg gctaactccg gttatctgac ccgtcgtctg 2400
gttgacgtcg cgcaggatct ggttgtgacc gaagacgact gtgggactca cgaaggcatc 2460
atgatgactc cggtcatcga aggtggcgac gttaaagaac cactgcgtga gcgtgtactg 2520
ggtcgtgtga ctgcagaaga tatcctcaag ccgggtacgg cggatatcct ggttccacgt 2580
aacaccctgc ttcacgagaa gacgtgtgat ctgttagaag agaactcagt cgacagcgtg 2640
aaagtacgtt cagtcgtaag ttgcgaaacc gactttggtg tgtgtgcaaa ctgctacggt 2700
cgcgacctgg cacgtggtca catcatcaac aaaggtgaag cgatcggtgt tattgcagca 2760
cagtccatcg gtgagccggg tacccagctg acgatgcgta cgttccacat cggtggtgcg 2820
gcatctcgtg cggcagcgga atccagcatc caggttaaga acactggtac cattaaactg 2880
agcaaccaca agcacgttag caactctaac ggcaaactgg tgatcacttc ccgtaacact 2940
gagctgaaat tgatcgacga attcggtcgt accaaagaaa gctataaagt gccttacggt 3000
tccgtgatgg gcaaaggcga tggcgcatca gttaacggcg gcgaaaccgt tgctaactgg 3060
gatccgcaca ccatgccagt tatcagtgaa gtgagtggtt tcattcgctt tgccgatatg 3120
gtggatactc agaccatcac acgccagacc gacgacctga ccggtttgtc ttctctggtt 3180
gttctggact ctgcagagcg taccggtagc ggtaaagacc tgcgtccggc actgaaaatc 3240
gttgacgcta aaggcgacga cgtattgatt ccaggtactg atatgcctgc tcaatacttc 3300
ctgccaggta aagcgattgt tcagctggaa gatggtactc agatccactc tggtgacacc 3360
ctggcgcgta ttcctcagga atccggcggt accaaggaca tcaccggtgg tctgccacgc 3420
gttgctgacc tgttcgaagc acgtcgtccg aaagagcctg caatccttgc tgaaatcagc 3480
gggatcatct ccttcggtaa agaaaccaaa ggcaaacgtc gtctggtaat ttctccgtta 3540
gatggcagcg atgcttacga agaaatgatc cctaaatggc gtcagctgaa cgtgttcgaa 3600
ggcgaagttg tggaacgtgg tgacgtcgta tccgacggcc ctgagtctcc gcacgacatc 3660
ttgcgtttac gtggtgttca cgcggttacc cgctacatca ccaacgaagt gcaggaagtt 3720
taccgtctgc aaggcgttaa gattaacgat aagcacatcg aagttatcgt tcgtcagatg 3780
ttgcgtaaag gcaccatcgt tagcgctggt ggcactgact tcctggaagg cgagcaggca 3840
gaaatgtctc gcgttaaaat cgctaaccgt aagctggaag ctgaaggcaa aatcacggca 3900
acattcagcc gtgacctgct cggtatcacc aaggcatccc tggcgaccga atccttcatc 3960
tctgcagcgt cgttccagga aaccacgcgt gttcttaccg aagcggctgt tgccggtaaa 4020
cgtgatgaac tgcgtggcct gaaagagaac gttatcgttg gccgtctgat cccagccggt 4080
accggttacg cttatcatca ggatcgtgca cgccgtaaag cacaaggcga agtgccagtt 4140
gtaccgcaag tcagcgcgga tgaagcaacg gctaacctgg ctgaactgct gaacgcaggt 4200
ttcggtaaca gcgacgatta a 4221

<210> SEQ ID NO 102
<211> LENGTH: 1668
<212> TYPE: DNA
<213> ORGANISM: Unknown
<220> FEATURE:
<223> OTHER INFORMATION: Description of Unknown:
DP67 Glutamine--tRNA ligase microbial sequence

<400> SEQUENCE: 102
atgagtgagg ctgaagcccg cccaactaac tttattcgtc agattatcga cgaagatctg 60
gcgaacggta agcacagttc agtgcacacc cgcttcccgc ctgagccgaa tggctatctg 120
catattggcc atgcgaaatc aatctgcctg aactttggta tcgctcagga ttatcagggg 180
cagtgtaacc tgcgctttga tgacactaac ccggtgaaag aagatctgga gtttgttgaa 240
tcaatcaagc gtgatgtgca gtggctgggc tttaagtgga gtggtgacgt acgctactca 300
tctgactatt tcgagcaact gcacaattat gccgttgagc tgattagtaa agggctggcg 360
tacgttgatg aactgtcacc ggagcagatc cgtgaatacc gtggcagcct gacctcagcg 420
ggtaaaaaca gccccttccg cgatcgcagc gtggacgaaa accttgcgct ctttgcaaaa 480
atgcgcgcgg gcggctttgc cgagggcacc gcgtgtttac gagccaaaat tgatatggct 540
tccaacttta tcgttctgcg cgatccggtg atctaccgca tcaaatttgc cgaacatcat 600
cagaccggca ataagtggtg catctatccg atgtatgact ttacccactg catctctgat 660
gcgctggaag gcattactca ctcactgtgt acgctggaat tccaggataa ccgtcgcctg 720
tacgactggg tgctggataa catcaccatt ccggttcatc cgcgtcagta tgaattctct 780
cgcctgaatc ttgaatatgc catcatgtcc aagcgtaagt tgagtcagtt ggtgaccgag 840
aacgtggtgg aaggttggga tgatccccgt atgctgactg tttcgggttt gcgccgccgt 900
ggctacactg cggaatccat ccgtgaattc tgccgccgca ttggggtgac caagcaggac 960
aatattgttg aaatggccgc tctggaatcc tgtatccgtg acgacctcaa tgagaatgcc 1020
ccgcgtgcca tggcagtgat ggatccggta aaagtggtga tagaaaatct gcctgcgcat 1080
cacgatgagg tgatcaccat gccgaatcat ccgagcaagc cggaaatggg tacccgcgaa 1140
gtcccgttca gtcgtgagat ctacatcgat cgtgctgact tccgtgagga agcaaacaag 1200
cagtacaagc ggctggtgct gggcaaagaa gtgcgtctgc gtaacgctta tgtgatcaaa 1260
gccgagcgcg tggcaaagga cgatgaaggc aacattacct gcctgttctg tacctgtgat 1320

```
gtggatactc tgagcaagga tccggccgac gggcgtaaag tgaagggcgt tatccactgg   1380

gtgtcagctg ttcatgccct tccggcagag ttccgtctgt acgatcggct gttcagcgta   1440

ccgaatccgg gggcggcaga agacttcctg gccagcatca acccggaatc tctggtgatc   1500

cgtcagggct tcgtggagcc cgggatgcag caggcggagg cgtcagcccc gtatcagttt   1560

gagcgtgaag gctacttctg cgctgacagt gtctactcca gtgccagcaa tctggtgttc   1620

aaccgcaccg ttggcctgcg tgacacctgg gcgaaagtcg gcgagtaa                1668
```

<210> SEQ ID NO 103
<211> LENGTH: 2409
<212> TYPE: DNA
<213> ORGANISM: Unknown
<220> FEATURE:
<223> OTHER INFORMATION: Description of Unknown:
DP67 DNA gyrase subunit B microbial sequence

<400> SEQUENCE: 103

```
atgtcgaatt cttatgactc ctccagtatc aaagttctga aagggctcga tgctgtacgc     60

aaacgcccgg gtatgtatat cggcgatacg gatgacggta ccggtctgca tcacatggta    120

tttgaggtcg tggataacgc cattgacgaa gcgctcgccg gtcactgttc cgatattctt    180

gtcactattc atgccgataa ctctgtttcc gttgtggatg atggccgtgg tattccgacc    240

ggtattcacg aagaagaagg catctcagcc gctgaagtga tcatgaccgt gctgcacgcc    300

ggcggtaagt tcgacgataa ctcttataaa gtctccggcg gcctgcacgg cgtgggcgtg    360

tcagtggtga acgccctgtc ggaaaaactg gagctgacca ttcgtcgcga agggaaagtt    420

caccagcaga cttacgtcca cggcgtgcca caggccccgt tgagtgtgag cggtgaaact    480

gacctgacgg gaacgcgcgt gcgtttctgg cccagccatc agacgttcac taacgtcgtg    540

gagttcgagt acgaaatttt ggcaaagcgc ctgcgtgagc tgtcgttcct gaactccggt    600

gtatcaatca agctggaaga taagcgcgac ggtaaaagcg accattacca ctatgaaggt    660

ggtatcaagg cgtttgttga gtacctcaac aagaacaaaa ccccgatcca cccgaatgtg    720

ttctatttct caaccgagaa agacggcatt ggtgtggaag tggcgctgca gtggaacgat    780

ggtttccagg aaaatatcta ctgctttacc aacaacatcc cacagcggga tgggggcacg    840

cacctcgttg gtttccgtac cgcgatgacc cgtaccctga atgcctacat ggataaagaa    900

ggctacagca agaaagccaa agtcagcgcc accggtgacg acgcgcgtga aggcctgatt    960

gctgtggtgt cggtgaaagt gccggatccg aaattctctt cacagaccaa agataaactg   1020

gtctcttctg aagtgaaaac cgccgttgag cagcagatga acgagctgct ggcagaatac   1080

ctgctggaaa acccgaccga tgccaaaatc gtcgtcggta aaatcattga tgcggcccgc   1140

gcccgtgaag cggcccgtcg tgcacgtgaa atgacccgcc gtaaaggcgc gctggatctg   1200

gcaggcctgc cgggcaaact ggcggactgc caggagcgtg atccggctct gtccgaaatt   1260

tacctggtgg aaggggactc tgcgggcggc tctgccaagc agggacgtaa ccgtaaaaac   1320

caggccatcc tgccgctgaa gggtaaaatc ctcaacgtcg agaaggcgcg ctttgacaag   1380

atgctcgcgt cgcaggaagt cgctacgctg atcaccgcgc tgggctgtgg tatcggtcgt   1440

gatgagtaca accccgacaa actgcgctat cacagcatca ttatcatgac cgatgccgac   1500

gtggatggct cgcatatccg taccctgctg ctgaccttct tctaccgtca gatgccagaa   1560

atcattgagc gtggtcatgt ctatattgcc cagccaccgc tgtacaaggt gaaaaaaggc   1620

aagcaggagc agtatattaa agacgacgat gcgatggatc agtaccagat cgccatcgcg   1680
```

ctggacggtg ccacgctgca tgcgaacgcc agcgccccgg cccttggcgg taagccactg 1740
gaagatctgg tgtctgagtt caacagcacg cgcaagatga tcaagcgcat ggagcgccgt 1800
tacccggtgg ccttgctgaa tgcgctggtc tacaacccga ccctgagcga tttgaccgcc 1860
gaagcgccgg tacagagctg gatggatgtg ctggtgaagt atctgaacga caacgaccag 1920
cacggcagca cctacagcgg tctggtacgc gaaaatctgg agctgcatat ctttgagccg 1980
gtactgcgta tcaaaaccca cggcgtggat accgattatc cgctcgacag cgagtttatg 2040
ctcggcggcg aataccgtaa gctctgcgcg ctgggtgaga agctgcgtgg cctgatcgaa 2100
gaagacgcgt tcatcgaacg tggtgagcgg cgtcagccga ttgccagctt tgagcaggcg 2160
atggagtggc tggttaaaga gtcacgccgt ggcctgacgg ttcagcgtta taaaggtctg 2220
ggcgagatga acccggatca gctgtgggaa accaccatgg atccggacag ccgccgtatg 2280
ctgcgcgtga ccatcaaaga tgccgtggcc gccgaccagc tgttcaccac cctgatgggg 2340
gatgcggtag agccccgtcg tgcctttatt gaagagaacg ccctgcgcgc ggcaaacatc 2400
gatatctga 2409

<210> SEQ ID NO 104
<211> LENGTH: 2817
<212> TYPE: DNA
<213> ORGANISM: Unknown
<220> FEATURE:
<223> OTHER INFORMATION: Description of Unknown:
DP67 Isoleucine--tRNA ligase microbial sequence

<400> SEQUENCE: 104
atgagtgact ataaatctac cctgaatttg ccggaaacgg ggttcccgat gcgtggcgat 60
ctggccaaac gcgaaccggg tatgctgcaa cgttggtatg atgacaagct gtacggcatc 120
attcgcgaag ccaagaaagg gaaaaaaacc tttatcctgc acgatggccc tccttacgcc 180
aacggcagca ttcatattgg tcactccgtt aacaagattc tgaaagacat tatcgttaag 240
tcgaaaggca tggcgggcta tgactcgcct tatgtaccgg gttgggactg ccacggtctg 300
cctatcgagc ataaagttga gcagatgatc ggtaagccgg gagagaaagt cagcgccgct 360
gagttccgtg ctgcctgccg caaatacgct gccgagcagg tggaagggca gaaagccgac 420
tttatccgtc tgggtgtgtt gggtgactgg gatcgtccgt atctgacaat gaacttccag 480
accgaagcca atattatccg tgcgctgggt aaaatcatcg gtaacgggca cctgcacaaa 540
ggggccaagc cggtacactg gtgcctggac tgccgttctg ccctggctga ggcggaagtg 600
gagtactacg ataaaacctc tccgtctatc gatgtcatgt tcaatgcgac tgataaagag 660
ggggtacagg ccaaatttgc ggcaacgaat gttgacggcc cgatctcgct ggtgatctgg 720
actaccacgc cgtggaccat gccggctaac cgcgctatct cactgcatcc tgaattcgac 780
taccagctgg tacagattga aggccgtgct ctgatcctcg ccaaagagat ggttgagagc 840
gtgatgcagc gcgttggtgt tgccgcctgg accgtgctgg gcgaagcgaa aggggcagac 900
ctggagctga tgggcttcca gcatccgttc ctcgaccata cctctccggt tgtgctgggt 960
gagcatgtca cgctggaagc cggtaccggt gcggtccata ccgcaccagg ccatggcccg 1020
gacgactatg ttatcggtca gaaatacggt atcgaagtgg ctaacccggt cggcccggat 1080
ggctgctacc tgccgggaac ctacccgacg ctggatggtg tgaacgtctt taaagccaac 1140
gatatgatcg ttgaactgct gcgtgaaaag ggtgctctgc tgcacgttga gaaactgttc 1200
cacagctatc cacactgctg gcgtcataaa acgcccatca tcttccgcgc tacgccacag 1260

```
tggtttatca gcatggatca gaagggcctg cgtgcgcagt cgctgaaaga gatcaagggc   1320
gtgcagtgga tcccggactg ggtcaggca cgtattgaat cgatggtcgc gaaccgtcct   1380
gactggtgta tttcccgtca gcgtacctgg ggcgtgccga tggcgctgtt cgtccataaa   1440
gacaccgaac agctgcaccc ggattcgctg gagctgatgg agaaagtggc gaagcgggtt   1500
gagcaggacg gcattcaggc atggtgggat cttgatgccc gcgacctgat gggcgccgat   1560
gctgacaact acgttaaagt cccggatacc ctggacgtct ggtttgactc cggttcaacc   1620
agctactcgg tcgtcgatgc ccgccctgaa tttgacggca atgcccctga cctgtatctg   1680
gaaggatcgg atcagcaccg cggctggttt atgtcctcac tgatgatctc gaccgcgatg   1740
aaaggcaaag cgccttaccg tcaggtactg acgcacggct tcaccgtcga tggtcagggc   1800
cgtaagatgt ccaagtcact gggcaatact gtcagcccgc aggatgtgat gaacaaactg   1860
ggcgccgata ttctgcgcct gtgggtcgcc tctacggact actccggtga gatcgccgta   1920
tccgacgaga tccttaaacg ctctgccgac agctatcgcc gcatccgtaa caccgcacgt   1980
ttcctgctgg caaaccttgc cggttttaat ccggaaaccg atagggtgaa accggaagag   2040
atggtggtgg tggatcgctg ggccgttggc cgtgcgctgg cggcacagaa tgatatcgta   2100
gcctcgtatg aagcttatga cttccatgaa gtcgtgcagc gtctgatgca gttctgttcg   2160
gttgagatgg gctccttcta cctggatatc atcaaggatc gtcagtacac cgcgaaggcc   2220
gatggcctgg cgcgtcgcag ctgtcagacg gcgctgtggt atatcgtgga agcgctggtg   2280
cgctggatgg caccgattat gtccttcact gccgatgaaa tctggggtta cctgccgggt   2340
aaacgcagcc agtatgtctt taccgaagag tggtttgacg ggctgttcag cctggaggac   2400
aatcagccga tgaacgacag ttactgggca gaactgctga aagtacgcgg tgaagtcaac   2460
aaggtgatcg agcaggcccg cgctgataag cggattggcg ggtctctgga agccagcgtg   2520
acgctgtatg ctgacgcaga cctggccgcg aagctgacca gcctgggtga ggagctgcgc   2580
tttgtgttgc tgacttccgg ggcgcaggtt gcggattatg cgcaggccac cgctgatgca   2640
cagcaaagcg aaggggtaaa aggtctgaaa attgccctga gcaaagcgga aggcgagaag   2700
tgcccgcgct gctggcatta cactaacgat atcggccaga atgctgaaca cgctgacgtg   2760
tgcggccgtt gtgtcactaa cgtcgcgggc agcggcgaac agcgtaagtt tgcatga      2817
```

<210> SEQ ID NO 105
<211> LENGTH: 1731
<212> TYPE: DNA
<213> ORGANISM: Unknown
<220> FEATURE:
<223> OTHER INFORMATION: Description of Unknown:
      DP67 NADH-quinone oxidoreductase subunit C/D
      microbial sequence

<400> SEQUENCE: 105

```
gtgatcggcg agctgcgtaa tcgttttggg cctgatgcct ttacagtaca agcgacccgt     60
accggcgtgc cggtggtctg ggtaaaacgt gagcagttgc ttgagattat tgagttcctg    120
cgcaagctgc ctaaacccta tgtgatgctg tatgacctgc atggcatgga tgagcgcctg    180
cgtactcacc gtgccggttt accggcggcg gatttttccg ttttctatca cttcatctcc    240
attgaacgta accgcgacat catgctcaag gtggcgttgt ctgaaaacga tttgaatgtg    300
cccaccatca ccaaaatttt cccgaatgcc aactggtatg agcgtgaaac ctgggagatg    360
tttggtatca atgttgaagg ccacccgcac ctgacgcgca ttatgatgcc gcagagctgg    420
gaagggcatc cgctgcgcaa agattaccct gcgcgtgcga ccgagttcga tccgtttgaa    480
```

ctgaccaagc agaaagaaga tctggagatg gaatctctga ccttcaagcc tgaagactgg 540
ggcatgaagc gttcgaccaa caatgaggac ttcatgttcc tcaacctggg cccgaaccac 600
ccttctgcgc acggcgcgtt ccgtatcatc ctgcaactgg acggtgaaga gatcgtcgac 660
tgcgtgccgg atatcggata ccaccatcgt ggtgccgaaa aaatgggtga acgccagtcc 720
tggcacagct acattccgta taccgaccgt attgagtatc tcggcggctg cgtaaacgaa 780
atgccgtacg tgctggcggt agaaaagctg gctggtatca aagtccctga gcgcgtggaa 840
gtcattcgcg tgatgctatc agagctgttc cgtataaaca gccacctgct gtacatctct 900
acgtttatcc aggacgtcgg tgctatgtcc ccggtgttct ttgcctttac tgaccgccag 960
aaaatttacg acgtggtaga agccattacc ggcttccgta tgcatccggc ctggttccgc 1020
attggtggcg tggcgcatga tctgcctaaa ggctgggagc gcctgctgcg tgagttcctg 1080
gattggatgc ctaagcgtct gaaagcctat gagcagaccg cactgaaaaa ctccgtgctt 1140
attgcccgtt ccaaaggggt ttctgcctat aacatggaag aagcactggc ctggggcacg 1200
acgggggctg gcctgcgtgg taccggtctg gactttgatg tgcgtaaatg gcgtccatat 1260
tccggttatg aaaacttcga tttcgaagtg ccaatcggag atggcgtaag ctgtgcttac 1320
acccgtgtca tgctgaagat ggaagagatg cgccagagta tgcgcatcct ggaacagtgc 1380
ctgaagaaca tgccagcagg cccgttcaag gctgaccatc cgctgaccac gccgccgccg 1440
aaagagcgca cgctgcagca tatcgaaacc ctgatcactc acttcctgca ggtttcgtgg 1500
ggcccggtaa tgccggcaaa cgaatccttc cagatgattg aagcgaccaa agggatcaac 1560
agttactacc tgaccagtga tggcagcacg atgagctacc gcacccgcgt gcgtacgccg 1620
agcttcccgc atttgcaaca gatcccatcg gtgatcaacg gcagcctggt atccgatctg 1680
atcgtatacc tcggtagtat cgattttgtt atgtcagacg tggaccgcta a 1731

<210> SEQ ID NO 106
<211> LENGTH: 1062
<212> TYPE: DNA
<213> ORGANISM: Unknown
<220> FEATURE:
<223> OTHER INFORMATION: Description of Unknown:
DP67 Protein RecA microbial sequence

<400> SEQUENCE: 106
atggctatcg acgaaaacaa gcaaaaagca ctggcagcag cgctgggcca gattgaaaag 60
cagtttggta aaggctccat catgcgcctg ggtgaagacc gcaccatgga tgtggaaacc 120
atctcaaccg gttctttatc actggatatc gcgctgggtg ccggtggttt accaatgggc 180
cgtatcgttg aaatctatgg cccggagtct tccggtaaaa ccaccctgac gctgcaggtt 240
atcgcttctg cacagcgtaa agggaaaacc tgtgcattta tcgatgccga gcatgctctg 300
gacccggtct acgctaaaaa actgggcgtg gatatcgata acttgctgtg ttctcagccg 360
gataccggtg agcaggcgct ggaaatctgt gatgcgctgg cccgttccgg tgcggttgac 420
gtcatcatcg tcgactccgt agcggcgttg acaccaaaag cagaaatcga aggtgaaatc 480
ggtgactctc atatgggcct tgcggcacgt atgatgagcc aggcgatgcg taagctggcc 540
ggtaacctga agaactccgg tacgctgctg atctttatca accagatccg tatgaaaatt 600
ggcgtgatgt tcggtaaccc ggaaaccact accggtggta acgctctgaa attctacgct 660
tctgtccgtc tggatattcg ccgcatcggc gcgatcaaag agggtgatga agtggtgggt 720
agcgaaaccc gcgttaaagt ggtgaaaaac aaaatcgcag caccgtttaa acaggctgag 780
ttccagatca tgtacggcga aggtatcaac gtttacggtg agctggtcga cctgggcgtg 840
aagcacaagc tgatcgaaaa agccggtgcc tggtacagct ataacggtga caagattggt 900
cagggtaaag ccaactcagg taacttcctg aaagagaacc cggctatcgc taacgaaatc 960
gaagcaaaac tgcgtgaaat gctgttgaac agcccggacg ataagcctga ttttgttccg 1020
gctccgcatg aagccgatag tgaagttaac gaagatatct aa 1062

<210> SEQ ID NO 107
<211> LENGTH: 1842
<212> TYPE: DNA
<213> ORGANISM: Unknown
<220> FEATURE:
<223> OTHER INFORMATION: Description of Unknown:
RNA polymerase sigma factor RpoD microbial sequence

<400> SEQUENCE: 107
atggagcaaa acccgcagtc acagcttaag ctacttgtca cccgtggtaa ggagcaaggc 60
tatctgacct atgccgaggt caatgaccat ctgccggaag atatcgtcga ctccgatcag 120
attgaagaca tcattcagat gatcaacgac atgggcattc aggttgtaga agaagcgcct 180
gatgccgatg atttgatgct gaatgagaac aacaacgaca cggacgaaga cgctgccgaa 240
gcggctgctc aggtattatc cagcgtagaa tctgaaatcg gacgtaccac cgacccggtg 300
cgcatgtaca tgcgcgaaat ggggacggtt gaactgctga cgcgtgaagg cgagatcgat 360
atcgccaaac gcatcgaaga gggtatcaac caggtacagt gttccgttgc tgaatatcct 420
gaagcgatta cttacctgct tgagcaatat gaccgtgttg aagcgggcga agcgcgcctg 480
tcggatctga tcaccggttt tgtcgacccg aatgccgaag cagagatcgc ccctactgcg 540
actcacgtgg gttcagaact ttccgctgaa gagcgtgatg acgaagaaga agacgaagag 600
tctgacgacg acagctcgga tgatgacaac agcatcgatc cggaactggc gcgggaaaaa 660
ttcaacgacc tgcgcgttca gtacgaaacc acccgtaccg ttatcaaagc gaaaagccgc 720
agccacgctg atgccatcgc tgagatccag aatctgtccg acgtgttcaa gcagttccgc 780
ctggtgccga agcagttcga cttcctggtg aacagcatgc gcaccatgat ggatcgcgtc 840
cgtactcagg aacgcctgat cctcaagctg tgcgtagaaa tctgtaagat gccgaagaag 900
aacttcatta ccctgttcac cggtaatgaa accagcgaaa cctggttcaa agcggcactg 960
gcaatgaata agccgtggtc agagaagctg aacgatgtgt cagatgacgt acaccgtagc 1020
ctgatgaagc tgcagcagat cgaaacggaa actggcctga cgattgaaca ggtaaaagac 1080
atcaaccgtc gtatgtcgat cggcgaagcg aaagcgcgcc gtgcgaagaa agagatggtt 1140
gaggctaacc tgcgtctggt tatctctatc gccaagaagt acaccaaccg tggcctgcag 1200
ttcctggatc tgattcagga aggtaacatc ggtctgatga aagcggtgga taagtttgaa 1260
tatcgccgtg gttataagtt ctcgacttat gccacctggt ggatccgtca ggcgatcacc 1320
cgttcaatcg ctgaccaggc gcgtaccatc cgtattccgg tgcacatgat tgagacgatt 1380
aacaagctca accgtatttc ccgccagatg ctgcaagaga tgggccgtga gccgacgccg 1440
gaagagctgg ccgagcgtat gctgatgccg gaagataaga tccgtaaggt gctgaaaatt 1500
gccaaagagc cgatctctat ggagacgccg attggtgatg atgaagattc acatctgggt 1560
gattttatcg aagacaccac gctggagctg ccgctggact ccgcgacgtc agagagcctg 1620
cgttctgcca cgcacgacgt gctggccggt ctgaccgcgc gtgaagccaa agtactgcgt 1680
atgcgtttcg gtatcgatat gaataccgac cacacgctgg aagaagtggg caaacagttc 1740
gacgtaacgc gtgagcgtat tcgtcagatt gaggcgaaag cgctgcgtaa gctgcgtcac 1800
ccaagccgct ctgaagtgct gcgcagcttc ctcgacgatt aa 1842

<210> SEQ ID NO 108
<211> LENGTH: 4029
<212> TYPE: DNA
<213> ORGANISM: Unknown
<220> FEATURE:
<223> OTHER INFORMATION: Description of Unknown:
DNA-directed RNA polymerase subunit beta microbial sequence

<400> SEQUENCE: 108
atggtttact cctataccga gaaaaaacgt attcgtaagg attttggaaa gcgtccacaa 60
gttctggaca ttccatatct cctttctatc cagcttgact cgttccagaa gttcatcgag 120
caagatccgg aaggtcaata tggtctggaa gcagcattcc gctccgtatt tccaatccaa 180
agctatagcg gtaattctga gctgcagtac gtcagctacc gtttaggcga acccgtcttt 240
gatgtgaaag agtgtcagat tcgtggcgtc acgtattctg ctcctctgcg cgtaaaactg 300
cgcctggtga tctacgagcg cgaagcgccg gaaggcaccg ttaaagacat caaagaacaa 360
gaagtttaca tgggcgaaat tccgctcatg acggataacg gtacctttgt tatcaacggt 420
actgagcgcg ttatcgtttc tcagctccac cgtagtcctg gtgtcttctt cgacagcgat 480
aagggtaaaa cccactcgtc cggtaaagtg ctgtataacg cacgtatcat cccttaccgt 540
ggttcatggc tggacttcga gttcgacccg aaagacaacc tgttcgtccg tattgaccgt 600
cgccgtaaac tgccagcgac catcattctg cgcgcgttga attacaccac tgaacagatc 660
ctcgacctgt tcttcgataa agtggtttac caaattcgcg acaacaagct gcagatggag 720
cttattcctg agcgcctgcg tggtgagacc gcttcatttg atattgaagc gaacggcacc 780
gtttacgtcg aaaaaggccg ccgtattact gcgcgccata ttcgccagct tgagaaagat 840
gctgttgccc acatcgaagt gccggttgag tatattgccg gtaaagtggt cgctaaagac 900
tacgttgatg agagcaccgg tgaactgctg atcgcagcga acatggaact gtcactggat 960
ctgctggcta aactcagcca gtccggtcac aagcgcattg aaaccctgtt caccaacgat 1020
ctggatcacg gtgcgtacat gtctgagacg gtacgtgtcg acccaaccag cgatcgcctg 1080
agcgctctgg ttgagatcta ccgcatgatg cgtcctggtg agccaccaac gcgtgaagcg 1140
gctgaaaacc tgtttgagaa cctgttcttc tctgaagacc gctatgatct gtctgcggtt 1200
ggtcgtatga agttcaaccg ttctctgctg cgcgacgaga tcgaaggttc cggtatcctg 1260
agcaaagacg acatcattca ggtgatgaag aagctcatcg gtatccgtaa cggtattggc 1320
gaagtggatg atatcgacca cctcggcaac cgtcgtatcc gttccgttgg cgaaatggct 1380
gaaaaccagt tccgtgttgg ccttgtgcgc gtagagcgtg cggtgaaaga gcgtctgtcc 1440
ctgggcgatc tggataccct gatgccacag gacatgatca acgccaagcc aatttctgcg 1500
gcagtgaaag agttcttcgg ctccagccag ctgtcacagt ttatggacca gaacaacccg 1560
ttgtctgaga tcacgcataa gcgtcgtatc tctgcactgg gtccgggcgg tctgacgcgt 1620
gagcgtgcag gcttcgaagt tcgagacgta cacccgacgc actacggtcg cgtatgtcca 1680
atcgaaacgc cggaaggtcc aaacatcggt ctgatcaact ccttgtctgt gtatgcacag 1740
accaatgagt acggtttcct ggaaacccca taccgtcgcg ttcgcgaagg cgtggtgacc 1800
gacgaaattc attacctctc tgctattgaa gagggtaact acgttatcgc tcaggcaaac 1860
accaatctcg acgacgaagg tcacttcgta gacgacctgg tcacctgccg tagcaaaggc 1920
gaatcgagtc tcttcaaccg cgatcaagtt gactacatgg acgtttccac ccagcaggtg 1980
gtttccgtcg gtgcgtcact gatcccgttc ctggagcacg atgacgccaa ccgcgcattg 2040
atgggtgcaa acatgcaacg tcaggcggtt cctactctgc gtgctgataa gccgctggta 2100
ggtaccggta tggagcgtgc ggttgcggtt gactccggtg ttactgccgt agcgaaacgt 2160
ggtggtaccg tgcagtacgt ggatgcatcc cgtatcgtta ttaaagttaa cgaagacgaa 2220
atgtatccgg gcgaagccgg tatcgacatt tacaacctga ccaaatatac ccgttctaac 2280
cagaacacct gcatcaacca gatgccttgc gtgaacctgg gtgagccaat cgaacgtggt 2340
gatgtgctgg ctgatggccc ttcaaccgat ctcggcgaac tggcactcgg tcagaacatg 2400
cgcgtcgcgt tcatgccgtg gaacggctac aacttcgaag actccattct ggtctcggag 2460
cgcgttgttc aggaagatcg cttcaccact atccacattc aggaactggc gtgtgtgtct 2520
cgtgacacca agctggggcc agaagagatc accgctgaca tccctaacgt gggtgaagct 2580
gcgctctcta aactggatga gtccggtatc gtgtatatcg gtgcggaagt gaccggtggg 2640
gacattctgg ttggtaaggt aacacctaaa ggtgaaaccc agctgacgcc agaagagaaa 2700
ctgctgcgtg cgatcttcgg tgaaaaagcg tctgacgtta aagactcttc tctgcgcgta 2760
ccaaacggtg tgtcagggac aatcatcgac gttcaggtct ttacccgcga tggcgtggaa 2820
aaagacaagc gtgcgctgga aatcgaagag atgcagctga agcaggcgaa gaaagacctg 2880
tctgaagaat tgcagatcct cgaagccggc ttgttcagcc gtattaacta cctgctggtt 2940
gccggcggtg ttgaagcgga aaaactggag aagctgccac gtgagcgctg gctcgaactg 3000
ggcctgaccg acgaagagaa gcaaaatcag ctggaacagc tggccgagca gtacgacgag 3060
ctgaagcacg agtttgagaa aaaacttgaa gccaagcgcc gtaaaatcac tcagggcgat 3120
gacctggcac ctggcgtgct gaaaatcgtg aaagtgtatc tggccgttaa acgtcagatc 3180
cagcctggtg acaaaatggc aggtcgtcac gggaacaaag gtgttatctc caagatcaac 3240
ccgatcgaag atatgccata cgatgagttc ggtacgccgg tcgacatcgt actgaacccg 3300
ctgggcgttc catcacgtat gaacattggt cagattcttg aaacccacct gggtatggct 3360
gcgaaaggca ttggcgagaa aattaacgct atgcttaaga agcaggaaga agtgtccaag 3420
ctgcgtgaat tcattcagcg tgcttacgat ctgggcagcg atctgcgtca gaaagttgac 3480
ctgaacacct tcaccgatga cgaagtgctg cgcctggcag agaatctgaa aaaaggtatg 3540
ccaattgcaa caccagtgtt tgacggcgcg aaagagagcg aaatcaaaga gctgttacag 3600
ctcggcggcc tgccttcttc tggccagatc acgctgtttg atggtcgtac cggtgagcag 3660
ttcgaacgtc aggttaccgt tggctacatg tacatgctga agctgaacca cctggttgat 3720
gacaaaatgc atgcgcgttc taccggttct tacagcctcg ttactcagca gccgctgggt 3780
ggtaaggcgc agttcggtgg tcagcgcttc ggtgagatgg aagtgtgggc actggaagca 3840
tacggtgccg cgtataccct gcaggaaatg ctgaccgtga agtctgatga cgttaacggc 3900
cgtaccaaga tgtataaaaa catcgttgac ggcaaccatc agatggaacc gggcatgccg 3960
gaatctttca acgtactgtt gaaagagatc cgctcgctgg gtatcaacat cgagctggaa 4020
gacgagtaa 4029

<210> SEQ ID NO 109
<211> LENGTH: 1700
<212> TYPE: DNA
<213> ORGANISM: Unknown
<220> FEATURE:

<223> OTHER INFORMATION: Description of Unknown:
DP68 Glutamine--tRNA ligase microbial sequence

<400> SEQUENCE: 109

```
atgagcaagc ccactgtcga ccctacctcg aattccaagg ccggacctgc cgtcccggtc     60
aatttcctgc gcccgatcat ccaggcggac ctggattcgg gcaagcacac gcagatcgtc    120
acccgcttcc cgccagagcc caacggctac ctgcacatcg gtcacgccaa gtcgatctgt    180
gtgaacttcg gcctggccca ggagttcggt ggcgtcacgc acctgcgttt cgacgacacc    240
aacccggcca aggaagacca ggaatacatc gacgccatcg aaagcgacat caagtggctg    300
ggcttcgaat ggtccggtga agtgcgctat gcgtccaagt atttcgacca gttgttcgac    360
tgggccgtcg agctgatcaa ggccggcaag gcctacgtcg acgacctgac cccggagcag    420
gccaaggaat accgtggcac gctgaccgag ccgggcaaga acagcccgtt ccgtgaccgt    480
tcggtagaag agaacctcga ctggttcaac cgcatgcgcg ccggtgagtt cccggacggc    540
gcccgcgtgc tgcgcgccaa gatcgacatg gcctcgccga acatgaacct gcgcgacccg    600
atcatgtacc gcatccgcca cgcccatcac caccagaccg gtgacaagtg gtgcatctac    660
ccgaactatg acttcaccca cggtcagtcg gacgccatcg aaggcatcac ccactccatc    720
tgcaccctgg agttcgaaag ccatcgcccg ctgtatgagt ggttcctcga cagcctgccg    780
gttccggcgc acccgcgtca gtacgagttc agccgcctga acctgaacta caccatcacc    840
agcaagcgca agctcaagca gttggtggac gaaaagcacg tgcatggctg ggatgacccg    900
cgcatgtcca ccctgtcggg tttccgccgt cgcggctaca ccccggcgtc gatccgcagc    960
ttctgcgaca tggtcggcac caaccgctcc gacggcgtgg tcgattacgg catgctcgag   1020
ttcagcatcc gtcaggacct ggacgccaac gcgccgcgtg ccatgtgcgt attgcgcccg   1080
ttgaaagtcg tgatcaccaa ctatccggaa gacaaggtcg accacctcga actgccgcgt   1140
cacccgcaga aagaagaact tggcgtgcgc aagctgccgt tcgcgcgtga aatctacatc   1200
gaccgtgatg acttcatgga agagccgccg aaaggctaca agcgcctgga gcctaacggc   1260
gaagtgcgcc tgcgcggcag ctacgtgatc cgtgccgatg aagcgatcaa ggacgccgat   1320
ggcaacatcg tcgaactgcg atgctcctac gacccggaaa ccctgggcaa gaaccctgaa   1380
ggccgcaagg tcaaaggcgt cgttcactgg gtgccggctg ctgccagcat cgagtgcgaa   1440
gtgcgcctgt acgatcgtct gttccgttcg ccgaaccctg agaaggctga agacagcgcc   1500
agcttcctgg acaacatcaa ccctgactcc ctgcaagttc tcacgggttg tcgtgccgag   1560
ccatcgcttg gcgacgcaca gccggaagac cgtttccagt tcgagcgcga aggttacttc   1620
tgcgcggata tcaaggactc caaacctggt catccggtct tcaaccgtac cgtgaccttg   1680
cgtgattcgt ggggccagtg                                                 1700
```

<210> SEQ ID NO 110
<211> LENGTH: 2418
<212> TYPE: DNA
<213> ORGANISM: Unknown
<220> FEATURE:
<223> OTHER INFORMATION: Description of Unknown:
DP68 DNA gyrase subunit B microbial sequence

<400> SEQUENCE: 110

```
atgagcgaag aaaacacgta cgactcgacc agcattaaag tgctgaaagg tttggatgcc     60
gtacgcaaac gtcccggtat gtacatcggc gacaccgatg atggtagcgg tctgcaccac    120
atggtgttcg aggtggtcga caactccatc gacgaagctt tggccggtca ctgcgacgac    180
```

```
atcagcatta tcatccaccc ggatgagtcc atcaccgtgc gcgacaacgg tcgcggtatt    240
ccggtcgatg tgcacaaaga agaaggcgta tcggcggcag aggtcatcat gaccgtgctt    300
cacgccggcg gtaagttcga cgacaactcc tataaagttt ccggcggttt gcacggtgta    360
ggtgtgtcgg tggtgaacgc tctgtccgaa gagcttatcc tgactgttcg ccgtagcggc    420
aagatctggg aacagaccta cgtgcatggt gttccacaag aaccgatgaa aatcgttggc    480
gacagtgaat ccaccggtac gcagatccac ttcaagcctt cggcagaaac cttcaagaat    540
atccacttca gttgggacat cctggccaag cgtattcgtg aactgtcgtt ccttaactcc    600
ggtgtgggta tcgtcctcaa ggacgagcgc agcggcaagg aagagttgtt caagtacgaa    660
ggcggcttgc gtgcgttcgt tgagtacctg aacaccaaca agactgcggt caaccaggtg    720
ttccacttca acatccagcg tgaagacggt atcggcgttg aaatcgccct gcagtggaac    780
gacagcttca acgagaacct gttgtgcttc accaacaaca ttccacagcg cgacggcggt    840
actcacttgg tgggtttccg ttccgcactg acgcgtaacc tgaacaccta catcgaagcg    900
gaaggcttgg ccaagaagca caaagtggcc actaccggtg acgatgcgcg tgaaggcctg    960
acggcgatta tctcggtgaa agtgccggat ccaaagttca gctcccagac caaagacaag   1020
ctggtgtctt ccgaagtgaa gaccgcagtg gaacaggaga tgggcaagta cttctccgac   1080
ttcctgctgg aaaacccgaa cgaagccaag ttggttgtcg gcaagatgat cgacgcggcg   1140
cgtgcccgtg aagcggcgcg taaagcccgt gagatgaccc gccgtaaagg cgcgttggat   1200
atcgccggcc tgccgggcaa actggctgac tgccaggaga aggaccctgc cctctccgaa   1260
ctgtacctgg tggaaggtga ctctgctggc ggttccgcca agcagggtcg taaccgtcgc   1320
acccaggcta tcctgccgtt gaagggtaag atcctcaacg tcgagaaggc ccgcttcgac   1380
aagatgattt cctctcagga agtcggcacc ttgatcacgg cgttgggctg cggtattggc   1440
cgcgatgagt acaacatcga caaactgcgt taccacaaca tcatcatcat gaccgatgct   1500
gacgtcgacg gttcgcacat ccgtaccctg ctgctgacct tcttcttccg tcagttgccg   1560
gagctgatcg agcgtggcta catctacatc gctcagccgc cgttgtacaa agtgaaaaag   1620
ggcaagcaag agcagtacat caaagacgac gacgccatgg aagagtacat gacgcagtcg   1680
gccctggaag atgccagcct gcacttgaac gacgaagccc cgggcatttc cggtgaggcg   1740
ctggagcgtt tggttaacga cttccgcatg gtaatgaaga ccctcaagcg tctgtcgcgc   1800
ctgtaccctc aggagctgac cgagcacttc atctacctgc cttccgtgag cctggagcag   1860
ttgggcgatc acgcccacat gcagaattgg ctggctcagt acgaagtacg tctgcgcacc   1920
gtcgagaagt ctggcctggt ttacaaagcc agcttgcgtg aagaccgtga acgtaacgtg   1980
tggctgccgg aggttgaact gatctcccac ggcctgtcga actacgtcac cttcaaccgc   2040
gacttcttcg gcagcaacga ctacaagacc gtggttaccc tcggcgcgca attgagcacc   2100
ctgttggacg acggtgctta catccagcgt ggcgagcgta agaaagcggt caaggagttc   2160
aaggaagccc tggactggtt gatggctgaa agcaccaagc gccacaccat ccagcgatac   2220
aaaggtctgg gcgagatgaa cccggatcaa ctgtgggaaa ccaccatgga tcctgctcag   2280
cgtcgcatgc tacgcgtgac catcgaagac gccattggcg cagaccagat cttcaacacc   2340
ctgatgggtg atgcggtcga gcctcgccgt gacttcatcg agagcaacgc cttggcggtg   2400
tctaacctgg atttctga                                                 2418
```

<210> SEQ ID NO 111

<211> LENGTH: 2832
<212> TYPE: DNA
<213> ORGANISM: Unknown
<220> FEATURE:
<223> OTHER INFORMATION: Description of Unknown:
DP68 Isoleucine--tRNA ligase microbial sequence

<400> SEQUENCE: 111
atgaccgact ataaagccac gctaaacctt ccggacaccg ccttcccaat gaaggccggc 60
ctgccacagc gcgaaccgca gatcctgcag cgctgggaca gtattggcct gtacggaaag 120
ttgcgcgaaa ttggcaagga tcgtccgaag ttcgtcctgc acgacggccc tccttatgcc 180
aacggcacga ttcacatcgg tcatgcgctg aacaaaattc tcaaggacat gatcctgcgt 240
tcgaaaaccc tgtcgggctt cgacgcgcct tatgttccgg gctgggactg ccacggcctg 300
ccgatcgaac acaaagtcga agtgacctac ggcaagaacc tgggcgcgga taaaacccgc 360
gaactgtgcc gtgcctacgc caccgagcag atcgaagggc agaagtccga attcatccgc 420
ctgggcgtgc tgggcgagtg ggacaacccg tacaagacca tgaacttcaa gaacgaggcc 480
ggtgaaatcc gtgccttggc tgaaatcgtc aaaggcggtt tcgtgttcaa gggcctcaag 540
cccgtgaact ggtgcttcga ctgcggttcg gccctggctg aagcggaagt cgagtacgaa 600
gacaagaagt cctcgaccat cgacgtggcc ttcccgatcg ccgacgacga caagctggct 660
caagcctttg gcctgtccag cctgccaaag cctgcagcca tcgtgatctg gaccaccacc 720
ccgtggacca tcccggccaa ccaggcgctg aacgtgcacc cggaattcac ctacgccctg 780
gtggacgtcg gtgatcgcct gctggtgctg gctgaagaaa tggtcgaggc ctgcctggcg 840
cgctacgagc tgcaaggttc ggtcatcgcc accaccaccg gcactgcgct ggagctgatc 900
aatttccgtc acccgttcta tgaccgtctg tcgccggtgt acctggctga ctacgtagag 960
ctgggttcgg gtactggtgt ggttcactcc gcgccggcct acggcgttga tgactttgtg 1020
acctgcaaag cctacggcat ggtcaacgat gacatcctca acccggtgca gagcaatggc 1080
gtgtacgcgc cgtcgctgga gttctttggc ggccagttca tcttcaaggc caacgagccg 1140
atcatcgaca aactgcgtga agtcggttcg ctgctgcaca ccgaaaccat caagcacagc 1200
tacatgcact gctggcgtca caagaccccg ctgatctacc gcgctaccgc gcagtggttt 1260
atcggcatgg acaaagagcc gaccagcggc gacaccctgc gtgtgcgctc gctcaaagcg 1320
atcgaagaga ccaagtttgt cccggcctgg ggccaggcgc gcctgcactc gatgatcgcc 1380
aaccgcccgg actggtgcat ctcccgccag cgcaactggg gcgtgccgat tccgttcttc 1440
ctgaacaagg aaagcggcga gctgcaccca cgtaccgttg aactgatgga agcagtggcg 1500
ctgcgcgttg agcaggaagg catcgaagcc tggttcaagc tggacgccgc cgaactgctg 1560
ggcgacgaag cgccgctgta cgacaagatc agcgacaccc tcgacgtgtg gttcgactcg 1620
ggtaccaccc actggcacgt gctgcgcggt tcgcacccga tgggtcacgc caccggcccg 1680
cgtgccgacc tgtacctgga aggctcggac caacaccgtg gctggttcca ctcgtcgttg 1740
ctgaccggct gcgccatcga caaccacgcg ccgtaccgcg aactgctgac ccacggcttc 1800
accgtcgacg agacgggccg caagatgtcc aagtcgctga aaaacgtgat cgagccgaaa 1860
aagatcaacg acaccctggg cgccgatatc atgcgtctgt gggtcgcctc gaccgattac 1920
tcgggcgaaa tcgccgtgtc ggaccagatc ctggcccgta gcgccgatgc ctaccgccgt 1980
atccgtaata ccgcacgctt cctgctgtcg aacctgaccg gtttcaaccc ggccaccgac 2040
atcctgccgg ccgaggacat gctcgccctg gaccgttggg ccgtggaccg tacgctgttg 2100

-continued ctgcagcgcg agttgcagga acactacggc gaataccgtt tctggaacgt gtactccaag 2160
atccacaact tctgcgtgca ggagctgggt ggtttctacc tcgatatcat caaggaccgc 2220
cagtacacca ccggcgccaa cagcaaggcg cgccgctcgg cgcagaccgc gctgtaccac 2280
atctctgaag cgctggtgcg ctggatcgca ccgatcctgg ccttcaccgc tgacgaactg 2340
tgggaatacc tgccgggcga gcgtaacgaa tcggtgatgc tcaacacctg gtacgaaggc 2400
ctgaccgaat tgccggccaa cttcgaactg ggccgcgagt actgggaagg cgtgatggcc 2460
gtcaaggttg cggtgaacaa ggagctggaa gttcagcgcg cggccaaggc cgtcggtggc 2520
aacctgcaag ccgaagtcac cctgtttgcc gaggaaggcc tgaccgccga cctggccaag 2580
ctgagcaacg aactgcgctt cgtactgatc acctcgaccg cgagcctggc accgtttgcc 2640
caggcacctg cggacgcagt ggccaccgaa gtgccgggcc tcaagctcaa agtggtcaag 2700
tcggcctttc ctaagtgcgc ccgttgctgg cactgccgtg aagacgtcgg cgtgaaccca 2760
gagcatccgg aaatctgcgg tcgttgcgtc gacaacatca gcggtgctgg cgaggttcgc 2820
cactatgcct aa 2832

<210> SEQ ID NO 112
<211> LENGTH: 1785
<212> TYPE: DNA
<213> ORGANISM: Unknown
<220> FEATURE:
<223> OTHER INFORMATION: Description of Unknown:
DP68 NADH-quinone oxidoreductase subunit C/D
microbial sequence

<400> SEQUENCE: 112
atgactacag gcagtgctct gtacatcccg ccttacaagg cagacgacca ggatgtggtt 60
gtcgaactca ataaccgttt tggccctgac gccttcaccg cccaggccac acgcaccggt 120
atgccggtgc tgtgggtggc gcgcgccaag ctcgtcgaag tcctgagctt cctgcgcaac 180
ctgcccaagc cgtacgtcat gctttatgac ctgcatggcg tggacgagcg tctgcgcacc 240
aagcgtcaag gtttgccgag cggtgccgat ttcaccgtgt tctaccactt gatgtcgctg 300
gaacgtaaca gcgacgtgat gatcaaggtc gcgctgtccg aaagcgactt gagcatcccg 360
accgtcaccg gtatctggcc gaatgccagc tggtacgagc gcgaagtttg ggacatgttc 420
ggtatcgact tcccgggcca cccgcacctg acgcgcatca tgatgccgcc gacctgggaa 480
ggtcacccgc tgcgcaagga ctttcctgcc cgcgcaaccg aattcgaccc gttcagcctc 540
aacctcgcca agcagcagct tgaagaagaa gctgcacgct tccgtccgga agactggggc 600
atgaaacgct ccggcaccaa cgaggactac atgttcctca acctgggccc gaaccaccct 660
tcggctcacg gtgccttccg tatcatcctg caactggacg gcgaagaaat cgtcgactgt 720
gtgccggaca tcggttacca ccaccgtggt gccgagaaga tggccgagcg ccagtcctgg 780
cacagcttca tcccgtacac cgaccgtatc gactacctcg gcggcgtgat gaacaacctg 840
ccgtacgtgc tgtcggtcga gaagctggcc ggtatcaagg tgccggaccg cgtcgacacc 900
atccgcatca tgatggccga gttcttccgc atcaccagcc acctgctgtt cctgggtacc 960
tatatccagg acgttggcgc catgaccccg gtgttcttca ccttcaccga ccgtcaacgc 1020
gcctacaagg tgatcgaagc catcaccggt ttccgcctgc acccggcctg gtatcgcatc 1080
ggcggcgtgg cgcacgacct gccgaacggc tgggagcgcc tggtcaagga attcatcgac 1140
tggatgccca agcgtctgga cgagtaccaa aaggctgcgc tggacaacag catcctcaag 1200
ggtcgtacca tcggcgtcgc gcagtacaac accaaagaag ccctggaatg gggcgtcact 1260
ggtgccggcc tgcgttcgac cggctgcgac ttcgacctgc gtaaagcacg gccgtactcg 1320
ggctacgaga acttcgagtt cgaagtgccg ctggccgcca atggcgatgc ctacgaccgg 1380
tgcatcgtgc gcgttgaaga aatgcgccag agcctgaaga tcatcgagca gtgcatgcgc 1440
aacatgccgg ctggcccgta caaggcggat catccgctga ccacaccgcc gccgaaagag 1500
cgcacgctgc agcacatcga aaccctgatc acgcacttcc tgcaagtttc gtggggcccg 1560
gtgatgccgg ccaacgaatc cttccagatg atcgaagcga ccaagggtat caacagttat 1620
tacctgacga gcgatggcgg caccatgagc taccgcaccc ggattcgtac cccaagcttt 1680
gcccacttgc agcagatccc ttcggtgatc aaaggcgaga tggtcgcgga cttgattgcg 1740
tacctgggta gtatcgattt cgttatggcc gacgtggacc gctaa 1785

<210> SEQ ID NO 113
<211> LENGTH: 1059
<212> TYPE: DNA
<213> ORGANISM: Unknown
<220> FEATURE:
<223> OTHER INFORMATION: Description of Unknown:
DP68 Protein RecA microbial sequence

<400> SEQUENCE: 113
atggacgaca acaagaagaa agccttggct gcggccctgg gtcagatcga acgtcaattc 60
ggcaagggtg ccgtaatgcg tatgggcgat cacgaccgtc aggcgatccc ggctatttcc 120
actggctctc tgggtctgga catcgcactc ggcattggcg gcctgccaaa aggccgtatc 180
gttgaaatct acggtcctga atcttccggt aaaaccaccc tgaccctgtc ggtgattgcc 240
caggcgcaaa aaatgggcgc cacctgtgcg ttcgtcgacg ccgagcacgc cctggacccg 300
gaatacgccg gtaagctggg cgtcaacgtt gacgacctgc tggtttccca gccggacacc 360
ggtgagcaag ccctggaaat caccgacatg ctggtgcgct ccaacgccat cgacgtgatc 420
gtggtcgact ccgtggctgc cctggtaccg aaagctgaaa tcgaaggcga aatgggcgac 480
atgcacgtgg gcctgcaagc ccgcctgatg tcccaggcgc tgcgtaaaat taccggtaac 540
atcaagaacg ccaactgcct ggtgatcttc atcaaccaga tccgtatgaa gatcggcgta 600
atgttcggca gcccggaaac cactaccggt ggtaacgcgc tgaagttcta cgcttcggtc 660
cgtctggaca tccgccgtac cggcgcggtg aaggaaggtg acgaagttgt tggtagcgaa 720
actcgcgtta aagtcgtgaa gaacaaggtc gctccgcctt tccgtcaggc agagttccag 780
attctctacg gcaagggtat ctacctgaac ggcgagatga ttgacctggg cgtactgcac 840
ggtttcgtcg agaagtccgg tgcctggtat gcctacaacg gcagcaagat cggtcagggc 900
aaggccaact cggccaagtt cctggcagac aacccggata tcgctgccac gcttgagaag 960
cagattcgcg acaagctgct gaccccagcg ccagacgtga aagctgccgc caaccgcgag 1020
ccggttgaag aagtggaaga agctgacact gatatctga 1059

<210> SEQ ID NO 114
<211> LENGTH: 1851
<212> TYPE: DNA
<213> ORGANISM: Unknown
<220> FEATURE:
<223> OTHER INFORMATION: Description of Unknown:
DP68 RNA polymerase sigma factor RpoD microbial sequence

<400> SEQUENCE: 114
atgtccggaa aagcgcaaca acagtctcgt attaaagagt tgatcaccct tggtcgtgag 60
cagaaatatc tgacttacgc agaggtcaac gatcacctgc ctgaggatat ttcagatcct 120
gagcaggtgg aagacatcat ccgcatgatt aatgacatgg ggatccccgt acacgagagt 180
gctccggatg cggacgccct tatgttggcc gactccgata ccgacgaggc agctgctgaa 240
gaagcggctg ctgcgctggc agcggtggag accgacatcg gtcgtacgac tgaccctgtg 300
cgcatgtata tgcgtgaaat gggtaccgtc gagctgctga cacgtgaagg cgaaatcgaa 360
atcgccaaac gtattgaaga gggtatccgt gaagtgatgg gcgcaatcgc gcacttccct 420
ggcacggttg accacattct ctccgagtac actcgcgtca ccaccgaagg tggccgcctg 480
tctgacgttc tgagcggcta catcgacccg gacgacggca ttgcgccgcc tgccgccgaa 540
gtaccgccgc ccgtcgatgc gaaagccgcg aaggctgacg acgacaccga agacgacgat 600
gctgaagcca gcagcgacga cgaagatgaa gttgaaagcg gcccggaccc gatcatcgca 660
gcccagcgtt tcggtgcggt ttccgatcaa atggaaatca cccgcaaggc cctgaaaaag 720
cacggtcgct ccaacaagct ggcgattgcc gagctggtgg ccctggctga gctgttcatg 780
ccgatcaagc tggtaccgaa gcaattcgaa ggcttggttg agcgtgttcg cagtgccctt 840
gaacgtctgc gtgcgcaaga acgcgcaatc atgcagctgt gtgtacgtga tgcacgtatg 900
ccgcgggctg acttcctgcg ccagttcccg ggcaacgaag tagacgaaag ctggaccgac 960
gcactggcca aaggcaaggc gaaatacgcc gaagccattg gtcgcctgca gccggacatc 1020
atccgttgcc agcagaagct gaccgcgctt gagaccgaaa ccggtctgac gattgctgaa 1080
atcaaagaca tcaaccgtcg catgtcgatc ggtgaggcca aggcccgccg cgcgaagaaa 1140
gagatggttg aagcgaactt gcgtctggtg atctcgatcg ccaagaagta caccaaccgt 1200
ggtctgcaat tcctcgatct gatccaggaa ggcaacatcg gcttgatgaa ggcggtggac 1260
aagttcgaat accgtcgcgg ctacaagttc tcgacttatg ccacctggtg gatccgtcag 1320
gcgatcactc gctcgatcgc cgaccaggct cgcaccatcc gtattccggt gcacatgatc 1380
gagacgatca acaagctcaa ccgtatttcc cggcagatgt tgcaggaaat gggtcgcgaa 1440
ccgaccccgg aagagctggg cgaacgcatg gaaatgcctg aggataaaat ccgcaaggta 1500
ttgaagatcg ctaaagagcc gatctccatg gaaacgccga ttggtgatga cgaagactcc 1560
cacctgggtg acttcatcga agactcgacc atgcagtcgc caatcgatgt cgccactgtt 1620
gagagcctta aagaagcgac tcgcgacgta ctgtccggcc tcactgcccg tgaagccaag 1680
gtactgcgca tgcgtttcgg catcgacatg aataccgacc acacccttga ggaagtcggt 1740
aagcagtttg acgtgacccg cgagcggatc cgtcagatcg aagccaaggc gctgcgcaag 1800
ttgcgccacc cgacgcgaag cgagcatctg cgctccttcc tcgacgagtg a 1851

<210> SEQ ID NO 115
<211> LENGTH: 4074
<212> TYPE: DNA
<213> ORGANISM: Unknown
<220> FEATURE:
<223> OTHER INFORMATION: Description of Unknown:
DP68 DNA-directed RNA polymerase subunit beta
microbial sequence

<400> SEQUENCE: 115
atggcttact catatactga gaaaaaacgt atccgcaagg actttagcaa gttgccggac 60
gtcatggatg tcccgtacct tctggctatc cagctggatt cgtatcgtga attcttgcag 120
gcgggagcga ccaaagatca gttccgcgac gtgggcctgc atgcggcctt caaatccgtt 180
ttcccgatca tcagctactc cggcaatgct gcgctggagt acgtgggtta tcgcctgggc 240

```
gaaccggcat ttgatgtcaa agaatgcgtg ttgcgcggtg ttacgtacgc cgtacctttg    300
cgggtaaaag tccgcctgat cattttcgac aaagaatcgt cgaacaaagc gatcaaggac    360
atcaaagagc aagaagtcta catgggcgaa atcccactga tgactgaaaa cggtaccttc    420
gtaatcaacg gtaccgagcg tgttattgtt tcccagctgc accgttcccc gggcgtgttc    480
ttcgaccacg accgcggcaa gacgcacagc tccggtaaac tcctgtactc cgcgcggatc    540
attccgtacc gcggttcgtg gttggacttc gagttcgacc cgaaagactg cgtgttcgtg    600
cgtatcgacc gtcgtcgcaa gctgccggcc tcggtactgc tgcgcgcgct cggttacacc    660
actgagcagg tgctggacgc tttctacacc accaacgtat tcagcctgaa ggatgaaacc    720
ctcagcctgg agctgattgc ttcgcgtctg cgtggtgaaa ttgccgttct ggacattcag    780
gacgaaaacg gcaaagtgat cgttgaagcg ggtcgtcgta ttactgcgcg ccacatcaac    840
cagatcgaaa aagccggcat caagtcgctg gaagtgcctc tggactacgt cctgggtcgc    900
accaccgcca aggttatcgt tcacccggct acaggcgaaa tcctggctga gtgcaacacc    960
gagctgaaca ccgaaatcct ggcaaaaatc gccaaggccc aggttgttcg catcgagacc   1020
ctgtacacca acgacatcga ctgcggtccg ttcatctccg acacactgaa gatcgactcc   1080
accagcaacc aattggaagc gctggtcgag atctatcgca tgatgcgtcc tggtgagcca   1140
ccgaccaaag acgctgccga gaccctgttc aacaacctgt tcttcagccc tgagcgttat   1200
gacctgtctg cggtcggccg gatgaagttc aaccgtcgta tcggtcgtac cgagatcgaa   1260
ggttcgggcg tgctgtgcaa ggaagatatc gtcgcggtac tgaagactct ggtcgacatc   1320
cgtaacggta aaggcatcgt cgatgacatc gaccacctgg gtaaccgtcg tgttcgctgc   1380
gtaggcgaaa tggccgaaaa ccagttccgc gttggccttg tgcgtgttga acgtgcggtc   1440
aaagagcgtc tgtcgatggc tgaaagcgaa ggcctgatgc cgcaagacct gatcaacgcc   1500
aagccagtgg ctgcggcagt gaaagagttc ttcggttcca gccagctttc ccagttcatg   1560
gaccagaaca acccgctctc cgagatcacc cacaagcgcc gtgtttctgc actgggcccg   1620
ggcggtctga cccgtgagcg tgctggcttt gaagttcgtg acgtacaccc gacgcactac   1680
ggtcgtgttt gcccgatcga aacgccggaa ggtccgaaca tcggtctgat caactccctg   1740
gccgcttatg cgcgcaccaa ccagtacggc ttcctcgaga gcccgtaccg cgtggtgaaa   1800
gacgctctgg tcaccgacga gatcgtattc ctgtccgcca tcgaagaagc tgatcacgtg   1860
atcgctcagg cttcggccac gatgaacgac aagaaagtcc tgatcgacga gctggtagct   1920
gttcgtcact tgaacgagtt caccgtcaag gcgccggaag acgtcacctt gatggacgtt   1980
tcgccgaagc aggtagtttc ggttgcagcg tcgctgatcc cgttcctgga acacgatgac   2040
gccaaccgtg cgttgatggg ttccaacatg cagcgtcaag ctgtaccaac cctgcgcgct   2100
gacaagccgc tggtaggtac cggcatggag cgtaacgtag cccgtgactc cggcgtttgc   2160
gtcgtagccc gtcgtggcgg cgtgatcgac tccgttgatg ccagccgtat cgtggttcgt   2220
gttgccgatg atgaagttga aactggcgaa gccggtgtcg acatctacaa cctgaccaaa   2280
tacacccgct cgaaccagaa cacctgcatc aaccagcgtc cgctggtgag caagggtgac   2340
cgcgttcagc gtagcgacat catggccgac ggcccgtcca ctgacatggg tgaactggct   2400
ctgggtcaga acatgcgcat cgcgttcatg gcatggaacg gcttcaactt cgaagactcc   2460
atctgcctgt ccgagcgtgt tgttcaagaa gaccgtttca ccacgatcca cattcaggaa   2520
ctgacctgtg tggcacgtga taccaagctt gggccagagg aaatcactgc agacatcccg   2580
```

-continued aacgtgggtg aagctgcact gaacaagctg gacgaagccg gtatcgttta cgtaggtgct 2640
gaagttggcg caggcgacat cctggtaggt aaggtcactc cgaaaggcga gacccaactg 2700
actccggaag agaagctgct gcgtgccatc ttcggtgaaa aagccagcga cgttaaagac 2760
acctccctgc gtgtacctac cggtaccaag ggtactgtta tcgacgtaca ggtcttcacc 2820
cgtgacggcg ttgagcgtga tgctcgtgca ctgtccatcg agaagactca actcgacgag 2880
atccgcaagg acctgaacga agagttccgt atcgttgaag gcgcgacctt cgaacgtctg 2940
cgttccgctc tggtaggcca caaggctgaa ggcggcgcag gtctgaagaa aggtcaggac 3000
atcaccgacg aagtactcga cggtcttgag cacggccagt ggttcaaact gcgcatggct 3060
gaagatgctc tgaacgagca gctcgagaag gcccaggcct acatcgttga tcgccgtcgt 3120
ctgctggacg acaagttcga agacaagaag cgcaaactgc agcagggcga tgacctggct 3180
ccaggcgtgc tgaaaatcgt caaggtttac ctggcaatcc gtcgccgcat ccagccgggc 3240
gacaagatgg ccggtcgtca cggtaacaaa ggtgtggtct ccgtgatcat gccggttgaa 3300
gacatgccgc acgatgccaa tggcaccccg gtcgacgtcg tcctcaaccc gttgggcgta 3360
ccttcgcgta tgaacgttgg tcagatcctc gaaacccacc tgggcctcgc ggccaaaggt 3420
ctgggcgaga agatcaaccg tatgatcgaa gagcagcgca aggttgctga cctgcgtaag 3480
ttcctgcacg agatctacaa cgagatcggc ggtcgcaacg aagagctgga caccttctcc 3540
gaccaggaaa tcctggactt ggcgaagaac ctgcgcggcg gcgttccaat ggctaccccg 3600
gtgttcgacg gtgccaagga aagcgaaatc aaggccatgc tgaaactggc agacctgccg 3660
gaaagcggcc agatgcagct gttcgacggc cgtaccggca acaagtttga gcgcccggtt 3720
actgttggct acatgtacat gctgaagctg aaccacttgg tagacgacaa gatgcacgct 3780
cgttctaccg gttcgtacag cctggttacc cagcagccgc tgggtggtaa ggctcagttc 3840
ggtggtcagc gtttcgggga gatggaggtc tgggcactgg aagcatacgg tgctgcatac 3900
actctgcaag aaatgctcac agtgaagtcg gacgatgtga acggtcggac caagatgtac 3960
aaaaacatcg tggacggcga tcaccgtatg gagccgggca tgcccgagtc cttcaacgtg 4020
ttgatcaaag aaattcgttc cctcggcatc gatatcgatc tggaaaccga ataa 4074

<210> SEQ ID NO 116
<211> LENGTH: 1674
<212> TYPE: DNA
<213> ORGANISM: Unknown
<220> FEATURE:
<223> OTHER INFORMATION: Description of Unknown:
DP69 Glutamine--tRNA ligase microbial sequence

<400> SEQUENCE: 116
gtgcgcgagg acctggccag cggaaagcac caggcgatca agacccgctt cccgccggag 60
ccgaacggct acctgcacat cggccacgcc aagtcgatct gcctgaactt cggcatcgcc 120
ggtgagttca gcggcgtctg caacctgcgt ttcgacgaca ccaatccggc caaggaagac 180
ccggagtacg tggccgcgat ccaggacgac gtgcgctggc tgggctttga atggaacgag 240
ctgcgccacg cctcggacta cttccagacc tattacctgg ccgccgagaa gctgatcgaa 300
cagggcaagg cctacgtctg cgacctgtcg gccgaggaag tgcgcgccta ccgcggcacc 360
ctgaccgagc cgggccgccc gtcgccgtgg cgtgaccgca gcgtcgagga gaacctcgac 420
ctgttccgcc gcatgcgtgc cggtgaattc cccgatggcg cgcgcaccgt gcgcgccaag 480
atcgacatgg ccagcggcaa catcaacctg cgtgatccgg cgctgtaccg catcaagcac 540
gtcgagcacc agaacaccgg caacgcgtgg ccgatctacc cgatgtacga cttcgcccat 600
gcgctgggcg attcgatcga gggcatcacc cactcgctgt gcacgctgga attcgaagac 660
caccgcccgc tgtacgactg gtgcgtggac aacgtcgact tcgcccacga tgacgcgctg 720
acccagccgc tggtcgacgc cggcctgccg cgcgaagcgg ccaaaccgcg ccagatcgag 780
ttctcgcgcc tgaacatcaa ctacacggtg atgagcaagc gcaagctgat ggcgctggtc 840
accgaacagc tggtggacgg ctgggaagac ccgcgcatgc cgaccctgca gggcctgcgt 900
cgccgtggct acaccccggc agcgatgcgc ctgttcgccg agcgcgtggg catcagcaag 960
cagaattcgc tgatcgattt cagcgtgctg gaaggcgcgc tgcgcgaaga cctggacagc 1020
gccgcaccgc gccgcatggc cgtggtcgac ccggtcaagc tggtgctgac caacctggcc 1080
gaaggccacg aagagcagct gaccttcagc aaccacccga aggacgagag cttcggtacc 1140
cgcgaagtgc cgttcgcacg tgaagtgtgg atcgaccgcg aggacttcgc cgaagtgccg 1200
ccgaagggct ggaagcgcct ggttcccggt ggtgaagtgc gcctgcgcgg cgccggcatc 1260
atccgctgcg acgacgtgat caaggatgcc gacggcacca tcaccgagct gcgcggctgg 1320
ctggatccgg aatcgcgccc gggcatggaa ggcgccaacc gcaaggtcaa gggcaccatc 1380
cactgggtca gcgcggtgca cggtgtgccg gccgagatcc gcctgtatga ccgcctgttc 1440
tcggtgccga acccggacga tgaatcggaa ggcaagacct accgcgacta cctcaatccg 1500
gactcgcgcc gcaccgtcac cggctatgtc gagccggcgg ctgccagcgc tgcgccggaa 1560
cagtcgttcc agttcgagcg caccggctac ttcgttgccg accgccgcga ccacaccgaa 1620
gccaagccgg tgttcaaccg cagcgtgacc ctgcgcgaca cctggtcggc ctga 1674

<210> SEQ ID NO 117
<211> LENGTH: 2460
<212> TYPE: DNA
<213> ORGANISM: Unknown
<220> FEATURE:
<223> OTHER INFORMATION: Description of Unknown:
DP69 DNA gyrase subunit B microbial sequence

<400> SEQUENCE: 117
atgaccgacg aacagaacac cccggcaaac aacggcaact acgacgccaa cagcattacg 60
gccctggaag gcctggaggc tgtccgcaag cgcccaggca tgtacatcgg cgacgtccat 120
gacggcaccg gcctgcatca catggtgttc gaggtcgtcg acaactcaat cgacgaagcc 180
ctcgccggcc atgccgacca cgtctcggtg acgatccatg ccgatggctc ggtaggcgtg 240
tccgacaacg gtcgcggcat cccgacgggc aagcacgagc agatgagcaa gaagctcgac 300
cgcgatgtgt ctgcagccga agtggtgatg acggtcctgc acgcaggcgg caagttcgac 360
gacaacagct acaaggtttc cggcggcctg cacggcgtgg gcgtcagcgt ggtcaacgcg 420
ctgtcgcaga agctggtcct ggatatctac cagggtggct tccactacca gcaggagtac 480
gccgacggcg cagcactgca tccgctgaag cagatcggcc ccagcaccaa gcgcgggacc 540
accctgcgct tctggccctc ggtaaaggct ttccacgaca acgtggaatt ccactacgac 600
atcctggccc ggcgcctgcg cgaactgtcc ttcctcaatt ccggcgtcaa gatcgtgctg 660
gtggacgagc gtggtgatgg ccgccgcgac gacttccatt acgagggcgg catccgcagc 720
ttcgtggagc atctggcgca gttgaagacg ccgttgcacc cgaacgtgat ctcggtgacc 780
ggcgaatcca atggcatcac cgtggaagtg gcgctgcagt ggaccgactc ctaccaggag 840
acgatgtact gcttcaccaa caacattccg cagaaggacg gcggtaccca cctggccggc 900
ttccgtggcg cattgacccg cgtgctcaac aactacatcg agcagaacgg catcgccaag 960
caggccaaga tcaacctgac cggcgatgac atgcgcgaag gcatgatcgc ggtgctgtcg 1020
gtgaaggtgc cggatcccag cttctccagc cagaccaagg aaaagctggt cagctcggat 1080
gtgcgcccgg ccgtggaaag cgcgttcggc cagcgcctgg aagagttcct gcaggaaaac 1140
ccgaacgaag ccaaggccat cgccggcaag atcgtcgacg ctgcccgtgc ccgcgaagcg 1200
gcgcgcaagg cccgcgacct gacccgccgc aagggtgcgc tggatatcgc cggcctgccg 1260
ggcaagctgg ccgactgcca ggaaaaggat ccggcgctgt ccgaactgtt catcgtcgag 1320
ggtgactcgg caggtggttc ggccaagcag ggtcgcaacc gcaagaacca ggcggtgctg 1380
ccgctgcgcg gcaagatcct caacgtggaa cgtgcgcgct tcgaccgcat gctggcgtcc 1440
gaccaggtgg gtacgctgat caccgcgctg ggtaccggca tcggtcgtga cgagtacaac 1500
ccggacaagc tgcggtacca caagatcatc atcatgaccg acgccgacgt cgacggcgcg 1560
cacatccgca ccctgctgct gacgttcttc taccgtcaga tgccggagct gatcgagcgc 1620
ggttatgtct atatcggcct gccgccgttg tacaagatca agcagggcaa gcaggagctg 1680
tacctgaagg acgacccggc gctggacagc tatctggcca gcagcgcggt ggagaacgct 1740
gggctggtgc cggccagcgg cgagccgccg atcgacggcg tggcactgga aaagctgctg 1800
ctcgcctacg ctgccgcgca ggacacgatc aaccgcaata cccaccgcta cgaccgcaac 1860
ctgctcgaag cgctggtcga cttcatgccg ctggagctgg aaaacctgcg cactgcaggt 1920
cctggcgaag gtctggacgc gttggccaag cacctcaacc agggcaacct cggcagcgcc 1980
cgcttcaccc tggaactgca ggaacccaac gagcagcgtc cggcggccgt actggtgacc 2040
cgcagccaca tgggcgaaca gcacatccag gtgctgccgc tgtccgcgct ggaaagcggc 2100
gaactgcgcg gcatccatca ggcagcgcag ctgctgcacg gtctggtccg cgaaggcgcg 2160
gtcatcaccc gtggcgccaa gtcgatcgag atcgactcgt tcgcacaggc ccgcaactgg 2220
ctgttggacg aagccaagcg cggccggcag atccagcgat tcaagggtct gggcgaaatg 2280
aatccggaac agctgtggga taccaccgtc aatcccgata cccgtcgcct gctgcaggtg 2340
cgcatcgaag acgcggtggc cgctgaccag atcttcagca ccctgatggg tgatgtggtc 2400
gaaccgcgtc gtgacttcat cgaagacaac gcgttgaagg tcgccaacct ggatatctga 2460

<210> SEQ ID NO 118
<211> LENGTH: 2835
<212> TYPE: DNA
<213> ORGANISM: Unknown
<220> FEATURE:
<223> OTHER INFORMATION: Description of Unknown:
DP69 Isoleucine--tRNA ligase microbial sequence

<400> SEQUENCE: 118
gtgagccagg actacaagac caccctcaac ctgccggcca ccgaattccc gatgcgcggc 60
gacctgccca agcgcgagcc gggcattctg gcgcgctggg aagagcaggg gctctaccag 120
cagctgcgcg acaacgccgc cggccgcccg ctgttcgtgc tgcatgacgg cccgccgtac 180
gccaatgcgc gcatccacct gggccatgcg gtcaacaaga tcctcaagga catcatcgtc 240
aagtcgcgct acctggccgg cttcgatgcg ccctacgtgc cgggctggga ctgccatggc 300
ctgccgatcg aaatcgcggt ggaaaagaag tggggcaagg tcggggtgaa gctcgatgcg 360
gtcgagttcc ggcagaagtg ccgcgagttc gccgaagaac agatcgacat ccagcgtgcc 420
gacttcaagc gcctgggcgt caccggcgac tgggacaacc cgtacaagac cctaagcttc 480

-continued

```
gatttcgagg ccaacgagat ccgtgcgctg tccaagatcg tggccaacgg ccatctgctg    540
cgtggcgcca agccggtcta ctggtgcttc gactgcggct cggcactggc cgaggccgag    600
atcgagtacc acgagaagac ctcgccggcg atcgacgtgg cctacaccgc gcgtgatccg    660
caggcggtgg cgcaggcgtt cggcgtcagc ctgccggccg atgtcgaagt ggcggtgccg    720
atctggacca ccactccgtg gacgctgccg gcttcgctgg cggtgtcgct gggcgcggac    780
atccgctacg tgctggccga aggcccggcg cacaacggca agcgccgttg gctggtgctg    840
gctgctgcgc tggccgaacg gtcgctgcag cgctacggcg tggacgcggt ggtgctgcac    900
ggtgaagccg aaggttcggc gctggaaaac cagctgctgg cgcacccgtt ctacccggag    960
cgcgagatcc ccgtgctcaa cggcgaacac gtgtccgacg aggacggtac cggtgcggtg   1020
cacactgccc ccggccacgg ccaggaagac tacgtggtca gccagaagta cggcctgctg   1080
gagaagtaca acgccggcca gatcaatccg gtcgacggtg cgggcgtgta cctggcgtcc   1140
accccgcccg ccggtgacct ggtgctggcc ggtacccaca tctggaaggc gcagcagccg   1200
atcatcgaag tgctggccgc cagcggcgcg ctgctcaagg ccgtggagat cgtgcacagt   1260
tatccgcatt gttggcgcca caagaagacc ccgctggtgt tccgcgccac cccgcagtgg   1320
ttcatttcga tggacaaggc caacctgcgc aacgatgcgc tggccgcgat cgataccgtc   1380
ggctggttcc cgagctgggg caaggcgcgc atccaaagca tgatcgacgg ccgcccggac   1440
tggaccatct cgcgccagcg cacctggggc gtgccgatcg cgctgttcac ccaccgccag   1500
accggcgaga tccacccgcg ttcggtggag ctgatgcagc aggtggccga ccgcgttgaa   1560
gccgaaggca tcgacgtgtg gtactcgctg gatgcggctg aactgctggg cgctgaagcg   1620
gccgactacg agaaggtcac cgacatcctc gatgtctggt tcgattccgg cgtgacccac   1680
gaagccgtgc tggctgcccg tggcttcggc aagccggccg atctgtacct ggaaggttcg   1740
gaccagcatc gcggctggtt ccagtcctcg ctgctgaccg gcgtggccat cgacaagcgc   1800
gcgccgtaca agcagtgcct cacccacggt ttcaccgtgg acgagcacgg ccgcaagatg   1860
tccaagtcgc tgggcaacgg catcgaaccg caggaaatca tgaacaagct gggcgcggac   1920
atcctgcgcc tgtggatcgc ctcggccgac tacagcaacg agatgtcgct gtcgcaggaa   1980
atcctcaagc gcaccgccga cgcctaccgc cgcctgcgca acaccgcccg cttcctgctg   2040
ggcaacctgg acggtttcga tccggcccag cacctgcgcc cgctcaacga gatggtcgcg   2100
ctggaccgct ggatcgtgca tcgcgcctgg gagctgcagg agaagatcaa ggcggcgtat   2160
gacaactacg acatggccga gatcgtgcag ttgctgctga acttctgcag cgtggacctg   2220
ggctcgctgt acctggacgt gaccaaggat cgcctgtata cgatgccgac cgattcggat   2280
ggtcgtcgtt cggcgcagag cgcgatgtac cacatcgccg aagcgttcac ccgctgggtg   2340
gcgccgatcc tgaccttcac cgccgacgag ctgtggggct acctgccggg cgatcgtgcc   2400
ggccacgtgc tgttcactac ctggtacgag ggcctggcac cgctgccgac cgatgcacag   2460
ctcaacgctg ccgacttcga tcagctgctg gccgtgcgcg agcaggtggc caaggtgctg   2520
gagccgatgc gcgccaatgg tgcgatcggt gccgcgctgg aagcggagat caccatcgcc   2580
gccagcgaag agcaggccgc gcgctggcag ccgctggccg atgaactgcg tttcctgttc   2640
atcagtggtg acgtgcaggt gcgtccggcg accaccgacg aggtgttcgt cagcgcgcag   2700
ccgacgcaga agtccaagtg cgtgcgctgc tggcaccacc gtgccgacgt tggcagcaat   2760
gccgaccacc cggaactgtg cggccgctgc gtgaccaaca tcgccggtgc cggcgaagcg   2820
cggagctggt tctga                                                    2835
```

<210> SEQ ID NO 119
<211> LENGTH: 2076
<212> TYPE: DNA
<213> ORGANISM: Unknown
<220> FEATURE:
<223> OTHER INFORMATION: Description of Unknown:
DP69 Glycine--tRNA ligase beta subunit microbial sequence

<400> SEQUENCE: 119
atgagccact tgtctcccct gctgattgaa ctgggcaccg aagagttgcc ggtcaaggcg 60
ctgccgggcc tggcccaggc cttcttcgac ggtgttgtcg atggcctgcg caagcgcggc 120
gtcgaactgg agctgggcga tgcccgcccg ctgtcgaccc cgcgccgcct ggccgtgctg 180
ctgccgggcg ttggcctgga acagccggaa caacacagcg aagtgctggg cccgtacctg 240
aacatcgcgc tggacgccga aggccagccg accaaggcgc tgcagggttt cgcggccaag 300
gccgggatcg actggaccgc gctggagaag accaccgaca acaagggtga gcgcttcgtg 360
caccgtgcgg tgactccggg cgcgcgcacc gctgcgctgc tgccggagat cctgcgcgag 420
gccatcgccg gcatgccgat tcccaagccg atgcgctggg gcgaccacag ctggggcttc 480
gcccgcccgg tgcactggct ggtgctgctg catggcggcg acgtggtcga ggccgaactg 540
tttggcctga aggccgaccg catgagccgc ggccaccgct tcctgcacga caagaccgtg 600
tggctgaccc agccgcagga ctatgtcgaa tcgctgcgcg ccgccttcgt gctggtcgat 660
ccggccgagc gccgccggcg catcgttgcc gaagtggaag ccgctgccgc caccgccggt 720
ggcagcgcac gcatcaccga ggacaacctg gagcaggtgg tgaacctggt cgagtggccg 780
gcggcagtgt tgtgcagctt cgagcgcgcg ttcctggcgg taccgcagga agcgctgatc 840
gagacgatgg agatcaacca gaagttcttc ccggtgctgg atgacggcgg caagctgacc 900
gagaagttca tcggcatcgc caacatcgag tccaaggacg tggccgaagt ggccaagggc 960
tacgagcgcg tgatccgccc gcgcttcgcc gatgccaagt tcttcttcga cgaagacctg 1020
aagcagggcc tgcaggcgat gggcgagggc ctgaagacgg tgacctacca ggccaagctg 1080
ggcagcgtgg ccgacaaggt cgcgcgcgtg gcggcgctgg ccgaggtgat cgctgcgcag 1140
gtgggggccg acccggtgct ggccaagcgt gccgcgcagc tggccaagaa cgacctgcag 1200
tcgcgcatgg tcaatgagtt cccggaactg cagggcatcg ctggccgcca ctacgcggtg 1260
gccggtggcg agtcgccgga ggtggcgctg gccatcgacg aggcctacca gccgcgcttc 1320
ggtggcgatg acatcgcgct gtcgccgctg ggcaaggtgc tggcgatcgc cgagcgtgtg 1380
gacacgctgg ccggcggttt cgccgcgggc ctgaagccga ccggcaacaa ggacccgttc 1440
gccctgcgcc gcaacgcgct gggcctggcc cgcacgatta tcgaaagtgg cttcgagctg 1500
gacctgcgcg cgctgctggc cagcgccaat gccgggctga ccgtgcgcaa cgtgcaggcc 1560
gacgtggctg agctgtacga cttcatcctc gaccgcctga agggctacta cagcgacaag 1620
ggcgtgccgg ccagccactt caatgcggtg gctgagctga agccggtctc gctgtacgat 1680
ttcgaccgtc gcctggacgc catcggtatc ttcgcggcgc tgccggaggc cgaggcgctg 1740
gcagcggcca acaagcgcat ccgcaacatc ctgcgcaagg ccgaaggcga tattccgggc 1800
cagatcgatg cggccctgtt gcaggaagat gccgagcgcg cgctggcgga agccgtgact 1860
gcagccatcg acgacaccgg cgccagcctg caccagaagg actacgtggc cgtgctggcg 1920
cgcctggccc gcctgcgtcc gcaggtcgat gcgttcttcg atggggtgat ggtcaatgcc 1980
gaggatccgg cactgcgcgg caaccgcctg gcgctgctga cgatgctggg cgagcgcttg 2040
ggcaaggtcg cggcgatcga gcatctgtcg agctga 2076

<210> SEQ ID NO 120
<211> LENGTH: 1410
<212> TYPE: DNA
<213> ORGANISM: Unknown
<220> FEATURE:
<223> OTHER INFORMATION: Description of Unknown:
DP69 Glutamine synthetase microbial sequence

<400> SEQUENCE: 120
atgtccgtgg aaaccgtaga gaagctgatc aaggacaacc agatcgagtt cgtcgatctg 60
cgcttcgtcg acatgcgtgg tgtcgaacag catgtgacct tcccggtcag catcgtcgag 120
ccgtcgctgt ttgaagaagg caagatgttc gatggcagct cgatcgccgg ctggaagggc 180
atcaacgagt cggacatggt gctgctgccg gacaccgcca gcgcctacgt cgacccgttc 240
tacgccgatc cgaccatcgt gatcagctgc gacatcctcg acccggccac catgcagccg 300
tatggccgtt gcccgcgcgg catcgccaag cgcgccgagt cctacctgaa gtcctcgggc 360
atcgccgaaa ccgcgttctt cggcccggag ccggagttct tcatcttcga ctcggtgcgt 420
ttcgccaatg aaatgggcaa caccttcttc aaggtcgact cggaagaagc ggcgtggaac 480
agcggcgcca agtacgacgg cgccaacagc ggctaccgtc cgggcgtgaa gggcggttat 540
ttccccgttc cgccgaccga caccctgcac gacctgcgtg cggagatgtg caagaccctg 600
gaacaggtcg gcatcgaagt ggaagtgcag caccacgaag tggccaccgc cggccagtgc 660
gagatcggca ccaagttcag caccctggtg cagaaggccg acgaactgct gcggatgaag 720
tacgtcatca agaacgtcgc ccaccgcaac ggcaagaccg tcaccttcat gcccaagccg 780
atcgtcggcg acaacggcag cggcatgcac gtgcaccagt cgctgtccaa gggcggcacc 840
aacctgttct ccggtgacgg ctacggtggc ctgagccaga tggcgctgtg gtacatcggc 900
ggcatcttca agcatgccaa ggcgatcaac gcctttgcca actcgggtac caacagctac 960
aagcgcctgg tgccgggctt cgaagccccg gtgatgctgg cctactcggc gcgcaaccgt 1020
tcggcctcgt gccgcattcc gtgggtgtcc aacccgaagg cgcgtcgcat tgaaatgcgc 1080
ttccccgatc cgatccagtc gggctacctg accttcaccg cgctgatgat ggccggcctg 1140
gacggcatca agaaccagat cgacccgggc gcaccgagcg acaaggatct gtacgacctg 1200
ccgccggaag aagagaagct gattccgcag gtctgctcct cgctggacca ggccctggaa 1260
gcgctggaca aggaccgtga gttcctcaag gccggtggcg tgatgagcga tgacttcatc 1320
gacggctaca tcgcgctgaa gatgcaggaa gtgaccaagt tccgcgcggc gacccacccg 1380
ctggaatacc agttgtacta cgccagctga 1410

<210> SEQ ID NO 121
<211> LENGTH: 1515
<212> TYPE: DNA
<213> ORGANISM: Unknown
<220> FEATURE:
<223> OTHER INFORMATION: Description of Unknown:
DP69 Glucose-6-phosphate isomerase microbial sequence

<400> SEQUENCE: 121
atgacaacga acaacggatt cgactcgctg cattcccacg cccagcgcct gaagggcgca 60
agcatcccca gcctgctcgc cgccgaaccc ggccgcgtac aggacctggc gctgcgggtc 120
ggtccgttgt atgtcaactt cgcccggcag aaatacgatg ccgcggcgtt gcaggcgctg 180
ttggcgctgg ctgccgaacg tgatgtcggc ggcgccatca cgcgcctgtt ccgtggcgag 240
caggtcaatc tgaccgaagg ccgcgccgca ctgcacaccg cactgcgcgg cgacgtggtc 300
gatgcgccgg ttgccgccga ggcctatgcc acggcccgcg aaatccgcca gcgcatgggc 360
gtgctggtgc gcgcactgga agacagtggc gtgaccgatg tggtcagtgt cggcatcggc 420
ggttccgatc tcggtccgcg tctggtcgcc gacgcactgc gtccagtcac tggcgctcgc 480
ctgcgcgtgc atttcgtgtc taacgtggac ggcgctgcca tgcagcgcac gctggccacg 540
ctggatccgg cgaagaccgc cggcatcctc atttccaaga ccttcggtac ccaggaaacc 600
ctgctcaacg gccagatcct gcacgattgg ctgggtggca gcgagcgcct gtacgcggtc 660
agcgccaatc cggaacgcgc cgccaaggcc ttcgccatcg ccgccgagcg cgtgctgccg 720
atgtgggact gggtaggggg gcgctattcg ctgtggtcgg ccgtcggttt cccgatcgca 780
ctggccatcg gcttcgagcg tttcgagcag ttgctggaag gcgccgcgca gatggatgcg 840
catgcgctgg acgcgccgct ggagcgcaac ctgccggtgc tgcacggcct gaccgacatc 900
tggaaccgca atctgctggg ctctgccacg catgcggtga tgacctacga ccagcgcttg 960
gcgctgctgc cggcctacct gcagcagctg gtgatggaaa gcctgggcaa gcgcgtgcag 1020
cgcgatggcc agccggtcac caccgacacc gtgccggtgt ggtggggcgg tgccggcacc 1080
gatgtgcagc acagcttctt ccaggccctg caccagggca ccagcatcat tccggccgat 1140
ttcatcggct gcgtgcacaa cgacgatccg tatacggtca accaccaggc gttgatggcc 1200
aacctgctgg cgcagaccga agcgctggcc aacggccagg gcagtgacga tccgcaccgc 1260
gattatccgg gtggccgccc gagcacgatg atcctgctcg acgcgctcac cccgcaggcg 1320
ctgggcgcct tgatcgcgat gtacgaacac gccgtgtacg tgcagtcggt gatctggaac 1380
atcaacgcct tcgaccagtt cggtgtcgag ctgggcaagc agctggccag tggcctgctg 1440
cccgctctgc agggtgagga tgtcgaggtc aacgacccgc tgacccgtga gctgctggcc 1500
cagctgaagg gctga 1515

<210> SEQ ID NO 122
<211> LENGTH: 2640
<212> TYPE: DNA
<213> ORGANISM: Unknown
<220> FEATURE:
<223> OTHER INFORMATION: Description of Unknown:
DP69 Leucine--tRNA ligase microbial sequence

<400> SEQUENCE: 122
atgaccagcg tcgaacccaa cgtttacgat ccgcagcagg ttgaatccgc cgcccagaag 60
tactgggacg ctacccgtgc cttcgaggtc gatgaagcct cggacaagcc gaagtactac 120
tgcctgtcga tgcttccgta tccgtccggt gcgctgcaca tgggccacgt gcgcaattac 180
acgatcggcg acgtgatcag ccgctacaag cgcatgaccg gccacaacgt gctgcagccg 240
atgggctggg acgcgtttgg cctgccggcg gaaaacgctg cgatcaagaa caagaccgcg 300
ccggccgcct ggacctacaa gaacatcgac cacatgcgca gccagctgca gtcgctgggc 360
tatgccatcg actggtcgcg cgagttcgcc acctgccgcc cggactatta cgtccacgag 420
cagcgcatgt tcacccgcct gatgcgcaag ggcctggcct accgccgcaa cgcggtggtg 480
aactgggacc cggtcgacca gaccgtgctg gccaacgagc aggtcatcga cggccgtggc 540
tggcgctccg gcgcgcttgt ggaaaagcgc gagatcccgc agtggttcct gcgcatcacc 600
gactacgccc aggaactgct ggacggcctg gatgagctgg acggctggcc ggagtcggtc 660
aagaccatgc agcgcaactg gatcggccgc tccgaagggc tggaaatcca gttcgacgtg 720
cgcgacgtcg atggtgccgc actggatccg ctgcgcgtgt tcaccacccg cccggacacc 780
gtgatgggcg tgactttcgt gtcgatcgcg gccgaacatc cgctggcgct gcatgccgcg 840
aagaacaacc cggaactggc tgcgctgctg tcggaaatga agcagggcgg cgtgtccgag 900
gccgagctgg agacccagga aaagcgcggc atggataccg gcctgcgcgc cgtgcatccg 960
gttaccggtg cccaggtgcc ggtgtgggtc gccaacttcg tgctgatggg ctacggcact 1020
ggcgcggtga tggccgtacc gggccacgac cagcgcgaca atgaattcgc caacaagtac 1080
aacctgccga tccgccaggt catcgcgctg aagtcgctgc gcaaggacga aggcgcctac 1140
gacgcgacgc gctggcagga ctggtacggc gacaagaccc gcgagaccga actggtcaac 1200
tccgaagagt tcgacggcct ggacttccag ggcgctttcg aggcgctggc cgaacggttc 1260
gagcgcaagg cccagggaca gcgccgggtg aactaccgcc tgcgcgactg gggcgtgagc 1320
cgccagcgct actggggctg cccgattccg gtgatctact gcgacaagtg tggcgcggta 1380
ccggtgccgg aagaccagct gccggtggtg ctgccggaag acgtggcgtt cgccggtacc 1440
ggttcgccga tcaagaccga tccggaatgg cgcaagacca cctgcccgga ctgcggcggt 1500
gcggccgagc gtgagaccga caccttcgac accttcatgg agtcgagctg gtactacgcc 1560
cgctacacct cgccgggcgc ccgcgatgcg gtcgacaagc gcggcaacta ctggctgccg 1620
gtggaccagt acatcggtgg catcgaacac gcgatcctgc acctgatgta tttccgcttc 1680
taccacaagc tgctgcgcga cgcgcggatg gtggacagca acgaacccgc gcggaacctg 1740
ctgtgccagg gcatggtgat cgctgagacc tactaccgcc cgaacccgga cggctcgaag 1800
gactggatca acccggccga tgtggaagtg cagcgcgacg agcgcggccg catcaccggc 1860
gccaccctga tcgccgacgg tcagccggtg gtggtcggtg gtaccgagaa gatgtccaag 1920
tcgaagaaca acggcgtgga cccgcaggcg atggtcggca agtacggcgc cgataccgtg 1980
cgcctgttct cgatgttcgc tgcaccgccg gaacagtcgc tggaatggaa cgaagccggc 2040
gtggacggca tggcccgctt cctgcgccgc ctgtgggcac aggtgcagaa gcacgctgcc 2100
gagggtgccg caccggcgct cgacgcggcc gcgctggatg ccggccagaa ggccctgcgc 2160
cgcaagaccc acgagaccat cggcaaggtc ggcgacgact acggccgccg ccacagcttc 2220
aacaccgcca ttgccgcggt gatggagctg atgaacgcgc tggccaagtt cgaggacggc 2280
agtgaacagg ggcgcgccgt gcgccaggaa gcactgcagg ccatcgtgct gctgctcaac 2340
ccgatcaccc cgcatgccag ccacgccctg tggcaggtac tgggccatgg cgaaacgctg 2400
ctggaagatc agccgttccc gcaggccgac agcagtgcgc tggtgcgcga tgcgctgact 2460
ttggccgtgc aggtcaatgg caagctgcgt ggcaccatcg aggtcgccgc cgatgccgcg 2520
cgcgagcaga tcgaagcgct ggccctggcc gagccgaacg cggccaagtt cctggaaggc 2580
ctgacggtgc gcaagatcat catcgttccc ggcaagatcg tgaacatcgt cgctgcctga 2640

<210> SEQ ID NO 123
<211> LENGTH: 2070
<212> TYPE: DNA
<213> ORGANISM: Unknown
<220> FEATURE:
<223> OTHER INFORMATION: Description of Unknown:
DP70 Glycine--tRNA ligase beta subunit microbial sequence

<400> SEQUENCE: 123
atgtctaaac atacagtatt gttcgaattg ggctgtgaag aacttccacc taaaagcctc 60

-continued

```
aaaaaattac gtgatgcact gcatgctgaa acggtaaaag gcttaaaaga tgcaggctta    120
gcattcgact caatcgaagc ttatgcagca ccgcgtcgtt tggcacttaa aattgtgaat    180
atcgatggcg ctcagcctga tacacaaaaa cgctttgacg gccctgcaaa agaagcggct    240
tatgatgctg aaggcaaacc aagcaaagca ttagaaggct ttatgcgtgg tcaaggcatc    300
actgcggatc aagtcaccac gttccaagcg ggtaaagttg aaaaggtttg ctatttaaaa    360
gatgttaaag gtcaaagcct tgaggtttta ctgccacaaa ttctacaagc agctttggac    420
aatcttccaa ttgcaaaacg tatgcgttca gcggcaagcc gtactgaatt cgtgcgtcct    480
gtaaaatggg tggtgttgct caaagacaat gatgtgattg cagccactat tcaagatcac    540
aaagcaggca atgtgactta tggtcatcgt ttccatgccc ctgaagcgat tactttggct    600
catgcagatg aatatcttgc caagttaaaa gcggcttatg tggttgctga ctttgcagaa    660
cgccaagcca tcattgacca acaagtcaaa gcgttggctg atgaagttaa tgcgattgcg    720
attgtaccaa gcgacctgcg tgatgaagtg accgcattgg tggaatggcc tgttgcgcta    780
cgtgccagct ttgaggagcg tttccttgct gtaccgcaag aagctttgat taccacgatg    840
caagacaacc aaaaatactt ctgtttggtg aatagtgata acaagctaca gccttatttc    900
attactgttt caaatattga gtctaaagat ccgattcaaa ttattgaagg caatgaaaaa    960
gtggttcgtc cacgtttgtc ggatgctgaa ttcttcttct tgcaagatca aaagcaacca   1020
ctagcttctc gtaaagaaaa actggctaac atggtgttcc aagcacaatt gggtacgctg   1080
tgggataagt cacaacgtat tgcaaaattg gctgtggctt tatcgaacat cacgggtgca   1140
actgcggctg atgctgaaaa agcagcattg ctggcaaaat gtgacttaac ctctgaattg   1200
gtgggtgaat tccctgaact tcaaggcatt gcgggaacct attacgcacg cattgaaggt   1260
gaaaaccatg aagtggctga agctttaggc gaacagtatt tacctaaatt tgcaggcgat   1320
gttttaccgc aaacaaaaac aggcacaacc attgcccttg ccgaccgttt agacacgctc   1380
acgggtattt ttggtattgg tcaagcacct acaggttcta aagatccgtt tgcattacgt   1440
cgttctgcaa tcggtatttt acgtttggtg actgaaaaca atcttgatgt gtcgattgaa   1500
gatttaatcc agctggcatt aaacgcttat ggcgatgttg tagcggatca tgcgaagact   1560
ttagcggatg ctgttgcatt ccttgaaggt cgttaccgtg ccaagtatga agaccaaggc   1620
gttgcagttg atgtgattca agcggttcaa gcattatcac caaaatcacc tttagatttt   1680
gataagcgtg tgactgcggt aaatcatttc cgtgcattgc ctgaagctgc tgcactggct   1740
gctgcaaata agcgtgttgc caacattctt gccaaagaag cagaactaac aggcgcagtg   1800
gttgaagcaa acttggttga agaggctgaa aaagcattat tcgctgtact tgctaaaatt   1860
acgcctgaag ttgaaccatt atttgctgcc aaagattaca ccactgcatt gtctaagctt   1920
gctgctttac gtgcgcctgt ggatgcattc tttgaaggcg tcatggtcat ggcagatgat   1980
gcagaattga aagccaaccg tttacgttta ttggctcaat tacgtggttt gtttacaagt   2040
gttgcggata tttcggtgtt gcagcactaa                                    2070
```

<210> SEQ ID NO 124
<211> LENGTH: 2472
<212> TYPE: DNA
<213> ORGANISM: Unknown
<220> FEATURE:
<223> OTHER INFORMATION: Description of Unknown:
      DP70 DNA gyrase subunit B microbial sequence

<400> SEQUENCE: 124

-continued

```
atgagttcag aagatcaagc tgcttctcaa acagaacaaa ccaatgaaaa ggcttatgat     60
tcctctagta tcaaagtatt acgtggccta gatgctgttc gtaagcgtcc gggtatgtat    120
attggtgata cggacgatgg ttcaggttta catcacatgg tgtttgaggt ggtcgataat    180
gcgattgatg aagccttagc gggtcactgt gatgaaatct tagtcaccat ccatgaagat    240
gagtctgtaa gtgttgcaga taacggtcgt gggattccaa cggatattca ccctgaagaa    300
ggggtatctg ccgctgaagt gattttaacc attttgcatg ctggcggtaa gtttgatgat    360
aatagctata aagtttccgg tggtttacac ggggtaggtg tttctgttgt aaatgccttg    420
tcgagtaaat tattactaaa tattcgtcgt gcaggaaaag tatatgaaca ggaatatcac    480
catggtgatc ctgtctatcc attacgcgcg attggtgata ctgaagaaac cggtaccacc    540
gttcgtttct atccgagtga attaaccttc tctcaaacga tttttaatgt tgatatttta    600
gcgcgtcgtt tgcgcgaact ttcattctta aatgcagggg ttcgtattgt attacgtgat    660
gaacgtatca atgctgaaca tgtatttgat tatgaaggtg gtttgtctga atttgtaaaa    720
tatatcaatc aaggtaaaac ccacttgaat gagatttttc attttaccag tgaagttgtg    780
gaaacaggaa ttactgttga agtagcatta cagtggaatg atacttatca agaaaatgtc    840
cgttgcttta ccaataacat cccacaaaaa gatggtggta cgcatttagc cggtttccgt    900
gccgcgttaa cacggggttt aaaccagtat cttgatagtg aaaatattct taagaaagaa    960
aaagttgctg tcacaggtga tgatgcccgt gaaggtttaa cggcgattgt ttcagtgaaa   1020
gtgcctgatc caaaattctc atcacaaacc aaagaaaaat tggtttccag tgaagtgaaa   1080
actgctgtag agcaggcgat gaacaagtct tttctgaat atcttttaga aaatccacaa    1140
gcggctaaat cgattgccgg caaaattatt gatgctgcac gtgcacgtga tgctgcgcgt   1200
aaagcacgtg aaatgacacg tcgtaagagt gcattagata ttgctggtct gcctggtaaa   1260
ctggcggatt gccaagaaaa agatccagca ttgtctgaac tttacttggt cgaaggtgac   1320
tcggcgggcg gttctgcaaa acagggtcgt aaccgtaaga tgcaagctat tctgccgctt   1380
aaaggtaaaa tcttaaacgt agaacgtgca cgttttgaca aaatgatttc atcgcaagaa   1440
gtgggcacgc tgattactgc actgggctgt ggtattggtc gtgaggaata caatcctgat   1500
aaattgcgtt atcacaaaat cattatcatg accgatgccg acgtcgatgg ttcgcacatt   1560
cgtacgctcc tgttgacctt cttcttccgt caaatgccag aacttgtgga acgtggttat   1620
atttatattg cacagccacc gttgtataag ttgaaaaaag gtaagcaaga gcaatatctt   1680
aaagataatg atgctttaga aacctatctt atttcgaatg ccattgatga gcttgaactg   1740
catattagtg ctgaggcacc tgcgattcgt ggtgaatctt tggctaaagt gattgctgat   1800
tatcaaacct cacaaaaaag tttaaatcgt ttaacgctac gttatcctgc aagcttgctg   1860
gatggtttac ttggtttgga tgcatttaaa cttgatcaaa atcatgatga agattatgta   1920
aaacaatggt ctgaacaatt gcgtgcagca attgaacaac accaaccaag tttgcgtcct   1980
gaaatcacct tagaagcttt tgaaaaagag catgcagatg gtgagaaagt gacgcattat   2040
tggccacgtg taacggtcta tgtacataac ttgccgcatc attatttact tgattctgga   2100
ttattggctt caagtgaata caagcgttta ctgcaaaatt cgaagagttg gttcacattg   2160
cttgaagatg gcgcttattt gcaaaaaggt gagcgtaaaa ttcatgtcgc cactttccat   2220
caagtttggc aacatatttt atccgactcg cgtcgtggca tgatgatcca gcgctataaa   2280
ggtttgggtg agatgaacgc ggaacagctt tgggaaacca ccatggatcc tgaaaaccgt   2340
aacatgttgc aagtcaccat taatgatgcg attgaagcgg atcgtatgtt ctcttgtttg   2400
```

atgggagatg atgtggaacc acgtcgtgcc ttcattgaag aaaatgcttt aaatgcggat 2460
attgacgctt aa 2472

<210> SEQ ID NO 125
<211> LENGTH: 2625
<212> TYPE: DNA
<213> ORGANISM: Unknown
<220> FEATURE:
<223> OTHER INFORMATION: Description of Unknown:
DP70 Leucine--tRNA ligase microbial sequence

<400> SEQUENCE: 125
atgactactt ctcacattga ccctgaatat caagcgagcg cgattgaatc cactgtccaa 60
caagactggg aaactcgcaa agcctttaaa gttgccgaca ctgtagaagg taaacatcgt 120
tatatcctct cgatgttccc ttatccaagt ggcaagctgc atatgggtca tgtgcgtaac 180
tacaccattg gcgacgtgat tagccgtttc caccgtctca aggtgaaac tgtcctacaa 240 ccgatgggtt gggatgcttt tggtctgcct gcggaaaatg cagcgattgc acaccaagtt 300
gcccctgcaa aatggacctt tgaaaacatc gcgtacatgc gtgaccagtt aaaaaaattg 360
ggtctgtcag tcgattggga tcgtgaattt gcgacctgta cgccagagta ttatcactgg 420
gaacaatggt tatttgtaca gctgtataaa aaagggctga tttatcgcaa actttcaacg 480
gtaaactggg atcctgtcga tcagactgta cttgctaatg aacaagttga aaatggtcgt 540
ggttggcgtt cgggtgcatt ggttgaaaaa cgtgatattc caatgtatta cttccgtatt 600
accgattatg cacaagaatt attagacgat ttagattcgc ttaaagatgg ttggccgcaa 660
caagtcttga ccatgcaacg caactggatt ggtcgttcac aaggcatgga aatcaccttt 720
ccatctgcga accctgaaat ctatgcagat gatttaacgg tttataccac acgtggtgac 780
accttgatgg gcgtgacgta tgttgcggtt gccgctgaac atccaatggc gcttaaagcg 840
gctgaaacaa atcccgaatt ggctgcattt attgaagaat gccgtatggg ttcagtggct 900
gaagcagatc ttgccactgc cgagaaaaaa ggcatggcca ctggtttgtc tgtgaagcat 960
cctgtaacgg gtgaagtggt tccagtgtgg attgcgaact atgtattgat gtcatacggt 1020
tcaggtgcgg tgatggcagt tccagcacac gacgaacgtg atttcgaatt tgccaacaaa 1080
tatggtttaa ccctccagca agtgattgat gccaaaggtg cagacgatgc tgaatttttct 1140 gcaactgaat ggcaggaatg gtatggctcg aaagaaggca aactggttaa ttctggcgaa 1200
tttgacggtt tagacttcca agctgcattt gatgcattca ttgcaaaatt agaaccacaa 1260
aaactggcaa atacgaaagt tcagttccgt ctacgtgact ggggtgtttc gcgtcagcgt 1320
tattggggtt gtccaattcc aatgatcaac tgtgaaactt gtggtcaagt acctgtacct 1380
gaagaacaac ttccagtaat tttaccaact gacgtggtgc cagatggttc aggcaatccg 1440
ttaaataaaa tgcctgaatt ttatgaaacc caatgtccat gttgtggtgc aggtgcacgc 1500
cgtgaaaccg atactttgga tacgttcgta gagtcatctt ggtactatgc acgttatgca 1560
tctccagatt tcactggcgg tttagttaaa cctgaagctg caaaatcatg gctaccagtc 1620
aaccaatata ttggcggtgt ggaacatgca attttgcatt tattgtatgc ccgtttcttc 1680
cataaattga tgcgtgatga aggcgtcgtt gaaggcaatg aacctttcgc taacttactg 1740
actcaaggta tggttttagc tgataccttc taccgtgaag ccgaatcagg taagaaaaca 1800
tggtttaatc ctgcggatat tgaattagaa aaagacgaaa aaggtcgtgt tctttctgct 1860
aaatacacag gtgatggcca agaagttgtg gttggcggtc aagaaaaaat gtcgaaatcg 1920
aaaaataatg gcatcgaccc gcaatcgatt attgatcaat acggcgcaga tactgcacgt 1980
gtatttatga tgtttgcggc cccacccgat caatcgcttg aatggtctga tgccggtgtg 2040
gaaggtgcaa accgtttctt gaaacgtgta tggcgtttaa ccacaggttt cttagaaaaa 2100
ggcaaccatg ctgctgtaat tgatgttgcg aatttgtcat cagcggcaca agacttacgt 2160
cgtaaaaccc acgaaaccat tcaaaaagtc ggtgatgaca ttgaacgtcg tcatgccttc 2220
aatactgcca ttgcagcgca aatggaatta ttgaatgctt gcaataaatt tgaagccaaa 2280
gatgataatg acgttgcggt tgaacgcgat gctattgtta gcttactcac tttacttgca 2340
ccatttgcac cacatttaag tcagacccta ttggctcaat tcggtattga gttaactgaa 2400
accttgttcc ctactgtgga tgagtctgcg ctaacccgca acacacaaac tattgtggta 2460
caggtcaatg gtaaacttcg tggcaagttg gaagtgtctg ttgatctctc taaagaagat 2520
attttggatc aagccaaagc attgcctgaa gtacaacaat tcttaaccgg tccaaccaag 2580
aaagaaattg tggtgccgaa taaattggtc aatttggtgg tttaa 2625

<210> SEQ ID NO 126
<211> LENGTH: 1671
<212> TYPE: DNA
<213> ORGANISM: Unknown
<220> FEATURE:
<223> OTHER INFORMATION: Description of Unknown:
DP70 Glucose-6-phosphate isomerase microbial sequence

<400> SEQUENCE: 126
atgaatagta ttgaaaaatt tcccttgcat gatacggatc tgattcagga aaaactaaaa 60
agttttgccc aacaagagca agagattaat ttaaattatt tatttaaaaa aaataaaaaa 120
cgttttgatg aatattccgt tcatgcgggt cagttatgtt ttgattatag taagcaccgt 180
gttgatgagc gtattattaa cgagcttatt tgttatgcgg aatcacaaca tttgggtaac 240
tggattcagc gcttattttc tttagaaaaa attaattaca ctgaaaatcg cgcagcgatg 300
cattgggctt tgcgtttgcc gaagcaagat agtacacatg cagatttggc agcgcaggta 360
catagtcagc ttgatcgtat gtatcaattg gtcgagaaaa ttcatcaggg gcagtatcga 420
ggagctacag gtgaggtcat ccatgatgtg gtcaatattg gtgtcggtgg atcagatctt 480
ggtcctttaa tggtgtctca agcgctgact gattttaaag ttcaaacggc tcaaaaatta 540
aaagtccatt ttgtttcgac gatggatggc agccaacttt cagatctttt acatcagttt 600
cgcccagaaa ccaccttgtt tattatttca tccaagtctt ttggcaccat tgatacgctt 660
tccaatgcac aaacggcaaa atgctggctt gagcaatctt taggaacgtc gaaatcagtt 720
ctaagatgtc actttgttgg tgtttcaacc aagcccgata agatgaccga gtggggaatc 780
agcactgaaa atcaattctt attgtgggat tgggtcggtg ggcgctattc actatggtcg 840
tgtattggtt tgcctattgc attaagtatt ggggtcgagg gctttaaaca gttgcttgct 900
ggtgcttatg aaatggatca gcattttcag aacacaccac ttgaacaaaa tattcctgtg 960
ttgatgggtt tactgggaat atggaataac aacttcctga atattcaaac tcatgcggta 1020
cttccttatg atggtcggct gaaatatttt gcggcttatt tacagcaatt ggaaatggag 1080
tcgaatggta agtcgattca gcgttctggt gaaaaagtcg tattagatac ctgcccaatt 1140
ttatggggtg aagttggacc aaatgcacaa catgcttttt atcagctgct gcatcaaggt 1200
acacatgctg tgagttgtga ctttattgca cctgtgaaac gctataatgc caatcaattt 1260
acctatgttg aaaatgcaga ggctttagtt gaacaacacc atttagcctt atcgaattgt 1320
ttggcacaat cacgtctatt ggcctttggt aatcatgttc tagatccgaa agaagtagaa 1380
agttcaccga aatataaaca atatgcaggc aaccaaccga ccacaacaat tttgttaaaa 1440
gagttgaatc cgcgcagttt aggtatgctc attgcgatgt atgagcacaa ggtatttgtg 1500
caatccgtga tgtggaatat taatccattt gaccaatggg gcgtagaaaa aggtaaagaa 1560
attgccaatc aactgttacc gattctcaat caagagcaag ctgatgtttc tgatcttgat 1620
tcttcaacgc aaggtctatt aagaatttta ctgggaaaag ctgatggcta a 1671

<210> SEQ ID NO 127
<211> LENGTH: 1788
<212> TYPE: DNA
<213> ORGANISM: Unknown
<220> FEATURE:
<223> OTHER INFORMATION: Description of Unknown:
DP70 NADH-quinone oxidoreductase subunit C/D
microbial sequence

<400> SEQUENCE: 127
atggctgaaa ctgacattgc tatgccagaa tcaacgcctg ttgattcacg cccagcattt 60
gcaattgtag aagagctcaa agccaaattt ggtgagaact tctatgtgca agcgactttt 120
gaagattttc caacggtctg ggttgagcgc gcgcgcgtac aagatgtttt aatgttcttg 180
cgtaaagtat cacgtccata cgtgatgctg ttcgacttgt ctgcggtaga tgagcgttta 240
cgtacccacc gtgacggttt acctgcatca gacttcactg tgttttatca tttgttgtcg 300
ctagagcgca acagtgatat tcgtattaaa gttgcgttga gtgagagtga tctcaatctt 360
ccaaccgcaa ccaacatttg gccaaatgcc aactggtacg aacgtgaagc ttacgatatg 420
ttcgggatca atttcgaagg gcatccaatg ctccgtcgta ttttgttgcc aacctattgg 480
gaaggtcacc cactgcgtaa agaatattct gcacgtgcga ctgaatatac accgtatatg 540
cagaaccaag cgaagcagga tttcgagcaa gaacatttac gttttgttcc tgaagattgg 600
ggtctatcac gcggtaatgc cgatgaagat ttcatgttct tgaacttagg tccaaaccat 660
ccatctgcgc acggtgcatt ccgtatcatt ttgcagttgg acggtgaaga agtgaaagac 720
tgtgtgcctg atattggcta tcaccaccgt ggtgtggaaa agatggctga acgtcaaact 780
tggcattcat tcattccata taccgaccgt gttgactact tgggtggttg tgcgcaaaac 840
atgccttatg tgatgggtgt ggagcaaatg gcaggaatta ctgttcctga ccgtgcacaa 900
tgtatccgtg tcatgatgtc tgaattattc cgtatcaata accatttatt gtttattggt 960
actgcaattc aagatgccgg cggtatgacg ccagtcttct atatgtttgc cgatcgtcaa 1020
aagatctatg atgcgattga agcgattaca ggctaccgta tgcatccagc atggttccgt 1080
attggcggga ctgcgcacga ccttccaaac aattggcaac atctgattcg tgaaattctc 1140
gaatggatgc cgaagcgtat gaatgaatac tatacagctg cactacgcaa ctcagtattt 1200
attggtcgta cccgtaatgt tgcacaatac gatgcaaaat ctgcattggc ttggggtgta 1260
acaggtacag gtctacgcgc gacagggatt gatttcgacg tgcgtaaata ccgtccgtat 1320
agcggttatg aaaactacga cttcgacgtg cctttagaat acgaaggcga tgcttacgct 1380
cgtgtgatgg ttcacttccg tgaaattgaa gaatcactga aaattgtgaa gcagtgcttg 1440
gataacatgc catctggtcc atataaagcg gatcatcctt tggctgttcc accaccaaaa 1500
gacaagacat tacaagatat tgaaactttg attacgcact tcttgagcgt gtcatggggt 1560
cctgtgatgc ctgcgggtga agcgtctgta atggctgaag tggtaaaagg tgcatcgaac 1620
tactacttga cttcagacaa gtcaaccatg agttatcgta cccgtattcg tacaccaact 1680
ttcacgcact tacagcaaat gccttctgtg attaatggca gtcttgtatc tgacttgatc 1740
atttatttag cgaccattga cgtcgtaatg gctgacgtgg atcgctag 1788

<210> SEQ ID NO 128
<211> LENGTH: 1044
<212> TYPE: DNA
<213> ORGANISM: Unknown
<220> FEATURE:
<223> OTHER INFORMATION: Description of Unknown:
DP70 Protein RecA microbial sequence

<400> SEQUENCE: 128
atggatgata ataaaagtaa ggcgcttaat gctgccctaa gccagattga aaaacaattt 60
ggtaaaaata ccgtaatgcg tcttggtgat aataccgtat tggccgttga agcggtctct 120
acaggttctt taacactaga cattgcactt ggtattggtg gcttaccaaa aggtcgtatc 180
gttgaaattt acggtcctga atcttctggt aaaaccacaa tgacattgca agcgattgca 240
caatgtcaaa aagccggtgg tacttgtgct tttatcgatg cagaacatgc actcgatcct 300
cagtatgcac gtaagcttgg tgtcgacctt gacaacctgt tggtttctca accagaccac 360
ggtgaacaag cccttgaaat tgcagacatg ttagtccgct ctggtgctat tgacatgatc 420
gttgtcgatt ccgtggctgc actgacacct cgcgctgaaa ttgaaggtga aatgggcgac 480
tcacatatgg gcttacaagc acgtttgatg agtcaggcat tacgtaaaat tactggtaat 540
gcaaaacgct caaactgtat ggtgatcttc attaaccaaa tccgtatgaa gattggtgta 600
atgtttggta gccctgaaac cacaacaggt ggtaatgcac tcaaattcta cgcttctgta 660
cgtttggata tccgtcgtat tggtcaagtg aaagaaggcg atgaaattgt cggttcagaa 720
acccgcgtta aagtcgtaaa aaataaaatg gcacctcctt ttaaggaagc gttattccaa 780
attttatatg gcaaaggtgt caatcaactg ggtgaactgg ttgatcttgc tgttgcgcaa 840
gaactggtac aaaaagcagg tgcttggtat tcatatcaag gcaataaaat tggtcaaggt 900
aaaaacaacg tgatccgcca tttagaggaa aatcctcaaa ttgcacaaga acttgatcgc 960
ctgattcgtg aaaaattgtt gacaccaacg accacgccta ttgaagaaaa agatgaagta 1020
gaaccagact ttctagatgc ttaa 1044

<210> SEQ ID NO 129
<211> LENGTH: 1887
<212> TYPE: DNA
<213> ORGANISM: Unknown
<220> FEATURE:
<223> OTHER INFORMATION: Description of Unknown:
DP70 RNA polymerase sigma factor RpoD microbial sequence

<400> SEQUENCE: 129
atgagcgata tgacttcccc tacttcgcaa gtagcggctc tgattagccg aggcaaagag 60
caaggttact taacttacgc tgaggttaac gatcatctcc cagactcgat cacggaaagc 120
gaacagattg aagacattat tcaaatgctt caagatgtcg gcattccagt gcatgaacgt 180
gcgcctgaat ctgatgacac catgttcgac ggtaacaatg cagaagcaac cgatgaagtc 240
gctgaagaag aagcggcagc tgttcttgct tcagttgaaa gcgaacctgg tcgtaccacc 300
gatccagtac gtatgtacat gcgtgaaatg ggaacggttg aactattaac gcgtgaaggc 360
gaaattagca ttgcaaaacg cattgaagaa ggtattcgtg acgttcttca ttcgattgcg 420
tactggccaa atgcagttga agttgtatta aaagaatata gcgatgttgc tgaaggcgaa 480
cgtcgtcttg ctgatatttt atctggttat ttagacccag aatctgacga agaaattcca 540
gaagttttag aagaagaagc tgaaattgtt gaagatgatg aagcgacgac taaaaccact 600
aaagatgtaa aattggacga tgacgaagaa gaagaatctg aaagtgatga tgattctgaa 660
ggtgagtctg gtccagatcc agaaattgca cgtgttcgtt tcactgaatt agaagatgcg 720
tggaaagtaa ccaaagccac cattgaaaag catggccgta acagcaaaca agcagatgaa 780
gcgcttgaag ctcttgcaac tgtgtttatg atgttcaaat ttacaccacg tttatttgaa 840
atcatttcag aaatgattcg tggcacgcat gaacaaattc gtacagcaga acgtgaagtg 900
atgcgttacg cagttcgtcg tggtcgtatg gaccgtaccc aattccgtac atcgttccca 960
ggccaagagt caaatccagc ttggttagat gaacaaattg ctaaagcacc tgcggatcaa 1020
aaaggttatt tagaaaaagt acgtccagat gttgttgcat tccagcaaaa gattgccgat 1080
atcgaaaaag aattgggctt agatgttaaa gacatcaaag acatttctaa acgtatggct 1140
gtgggtgaag cgaaagcacg tcgcgcgaaa aaagaaatgg ttgaagcaaa cttacgtttg 1200
gtgatttcga ttgcgaaaaa atataccaac cgtggtttac aattccttga cttgattcaa 1260
gaaggtaaca tcggtttgat gaaagccgta gacaagtttg aataccgtcg tggttataaa 1320
ttctcgactt atgcaacttg gtggattcgt caggcgatta cccgttcgat tgccgatcaa 1380
gcacgtacca tccgtattcc agtacacatg atcgaaacca ttaacaagat caaccgtgta 1440
tctcgtcaac ttcttcaaga aatgggccgt gagcctaccc ctgaagaatt aggcgaacgt 1500
ctggaaatgg acgaagttaa agtacgtaaa gtgctgaaaa ttgccaaaga accgatttcg 1560
atggaaacac cgattggtga tgacgaagat tcgcatcttg gtgacttcat tgaagatggt 1620
aacattacct ctccaattga tgccgcgact tctgaaggct taaaagaagc aacacgtgaa 1680
gtgctggaaa acttgaccga acgtgaagcg aaagtcttaa aaatgcgttt tggtattgat 1740
atgccaaccg accatacttt agaagaagtg ggtaaacaat ttgatgtaac acgtgaacgt 1800
attcgtcaga ttgaagccaa agctttacgt aaattacgtc acccttctcg ttctgaacac 1860
ttacgttcat tcctagaaaa tgactaa 1887

<210> SEQ ID NO 130
<211> LENGTH: 1671
<212> TYPE: DNA
<213> ORGANISM: Unknown
<220> FEATURE:
<223> OTHER INFORMATION: Description of Unknown:
DP71 Glutamine--tRNA ligase microbial sequence

<400> SEQUENCE: 130
atgagtgagg ctgaagcccg cccaacaaat tttatccgtc agattattga tgaagatctg 60
gcgaccggga aacacaatac cgttcacacc cgtttcccgc ctgagcctaa tggctatttg 120
catatcggcc atgcgaagtc tatctgcctg aatttcggca ttgcgcaaga ctaccagggt 180
cagtgcaatc tgcgttttga cgatactaac ccggcaaaag aagacatcga attcgttgag 240
tcgatcaaat acgacgtcca gtggctgggc ttcgactgga gcggtgatat tcactactcc 300
tcagactatt tcgatcaact gcacgcatac gcgctggagc taatcaacaa aggtctggcg 360
tacgttgacg aactgtctcc cgatcaaatt cgcgaatacc gtggttcgct gaccgcaccg 420
ggcaaaaaca gcccgtatcg cgatcgcagc gtggaagaaa atatcgcgct gtttgaaaaa 480
atgcgtaacg gtgaattcgc cgaaggtgcc gcttgcctgc gtgccaaaat cgatatggcg 540
tcgccattct tcgtgatgcg cgatccggtc atctaccgta ttaagtttgc cgaacatcat 600
cagactggca caaaatggtg catctacccg atgtacgatt tcactcactg catttccgat 660
gcgctggaag ggatcaccca ttcactgtgt acgctggaat tccaggacaa ccgccgtctg 720
tacgactggg tactggataa catcactatt ccatgccatc cgcgtcagta tgagttctcc 780
cgtctgaatc ttgaatactc catcatgtcc aagcgtaagc tgaacctgct ggtgacggat 840
aagattgtag aaggttggga cgatccgcgt atgccgacgg tttccggtct gcgtcgccgt 900
ggttataccg ccgcgtctat ccgcgaattc tgccgtcgta tcggcgtgac caagcaggac 960
aacaacgttg aaatgatggc gctggaatcc tgtattcgtg acgatctgaa cgaaaacgca 1020
ccgcgcgcca tggccgttat taacccggtt aaagttgtca ttgagaactt caccggtgat 1080
gacgtgcaaa tggtgaaaat gccgaatcat ccgagcaaac cggaaatggg cacccgcgaa 1140
gtgccgttca cccgtgagat ttacatcgat caggctgatt tccgcgaaga agcgaacaaa 1200
cagtacaaac gtctggtgct gggcaaagaa gttcgcctgc gcaatgcgta tgtgatcaaa 1260
gcggaacaca tcgagaaaga cgcggaaggg aatatcacca ccatcttctg ttcttacgat 1320
atcgatacgc tgagcaaaga tcccgctgat ggccgtaagg tgaaaggcgt gattcactgg 1380
gtttctgctt ctgaaggtaa accggcagaa tttcgcctgt atgaccgtct gttcagtgtt 1440
gcgaaccctg gccaggctga agatttcctg accaccatca acccggaatc tctggtgatt 1500
gctcagggct tcgttgagcc gtctctggtc gctgctcagg cagaagtcag tgtgcagttc 1560
gaacgtgaag gttacttctg tgccgacagc cgctattcaa gtgctgagca tctggtgttc 1620
aaccgcaccg tcggccttcg cgacacctgg gaaagcaaac ccgtcgcctg a 1671

<210> SEQ ID NO 131
<211> LENGTH: 2415
<212> TYPE: DNA
<213> ORGANISM: Unknown
<220> FEATURE:
<223> OTHER INFORMATION: Description of Unknown:
DP71 DNA gyrase subunit B microbial sequence

<400> SEQUENCE: 131
atgtcgaatt cttatgactc ctcaagtatc aaggtattaa aagggctgga cgcggtgcgt 60
aagcgccccg gcatgtatat cggcgatacc gatgacggca ctggtctgca ccacatggta 120
ttcgaggttg tggacaacgc tatcgacgaa gccctcgcgg gccactgtaa agagattcag 180
gtcacgatcc atgcggataa ctctgtttcc gtacaggatg atggtcgtgg tattcctacc 240
ggcattcacg aagaagaggg cgtttctgct gctcaggtca tcatgaccgt acttcatgcc 300
ggcggtaaat ttgacgataa ctcgtacaaa gtctccggcg gtctgcatgg cgtgggtgtt 360
tccgtcgtta acgccctgtc ggaaaaactg gagctggtta tccgccgtga aggcaaagtg 420
cacacccaga cttacgtcca cggtgagccg caggatccgc tgaaagtggt tggcgatacc 480
gaggcgaccg gtacgaccgt gcgcttctgg ccaagctacg ccaccttcac caatcaaaca 540
gaattcgagt atgacattct ggcgaaacgc ctccgtgagc tgtcattcct gaactctggt 600
gtggcgatcc gcctgctcga caaacgcgat ggcaagaacg atcacttcca ttatgaaggc 660
ggtatcaaag ctttcgtgga atacctgaac aaaaacaaaa ccccaatcca cccaaccgtg 720
ttctatttct ccaccgtgaa agacgatatc ggtgtggaag tggcgttgca gtggaatgat 780
ggtttccagg aaaatattta ctgctttacc aacaatatcc ctcagcgcga cggcggcacc 840
catctggtag gcttccgttc tgcgatgacc cgtacgctta acgcgtatat ggataaagaa 900
ggctacagca agaaatccaa aatcagcgcc accggtgatg atgcccgtga aggcctgatc 960
gccgtggttt cggtaaaagt gccggatcct aagttctcct ctcagaccaa agacaaactg 1020
gtttcttccg aagtgaagac cgccgttgag tctctgatga acgagaagct ggttgattat 1080
ctgatggaaa acccggccga cgcgaaaatc gttgtcggta aaatcatcga tgcagcccgt 1140
gcgcgtgaag ccgcgcgtaa agcacgtgaa atgacccgtc gtaaaggcgc gctcgatctg 1200
gccggtctgc caggcaaact ggctgactgt caggaacgcg acccggcaca ttccgaactg 1260
tacttagtgg aaggggactc agcgggcggc tctgcaaaac aaggccgtaa ccgtaagaac 1320
caggcgattc tgccgttgaa agggaaaatc ctcaacgttg agaaagcgcg cttcgacaaa 1380
atgctctctt ctcaggaagt ggcgacgctg attaccgcgc tcggttgcgg tatcggccgt 1440
gacgaataca acccggataa actgcgttat cacagcatca tcatcatgac cgatgccgac 1500
gtcgatggtt cgcacatccg taccctgtta ctgacattct tctaccgtca gatgcctgaa 1560
attgtagagc gtggccacgt gtttatcgcg cagcctccgc tgtacaaagt gaaaaaaggc 1620
aaacaggaac agtacattaa agatgatgaa gcgatggatc agtatcaaat ctctatcgcg 1680
atggacgggg caacgttaca cgccaacgcc catgcaccag cactggcggg cgaaccgctg 1740
gagaaactgg tggctgaaca tcacagcgtg cagaaaatga ttggccgtat ggaacgtcgt 1800
tatccgcgtg cgctgctgaa taatctggtc tatcagccaa cgctggcggg tgctgaactt 1860
gccgacgaag cgaaagtgaa ggaatggatt gaaacgctgg tgtctcgtct gaacgagaaa 1920
gagcagcacg gcagcagcta cagtgcgatc gtgcgcgaaa atcttgaaca ccagctgttc 1980
gagccaatcc tgcgcattcg tactcacggt gtggataccg actacgatct cgatgcagac 2040
ttcattcagg gcggcgaata ccgcaaaatc tgtaccctgg gtgaaaaact gcgcggcctg 2100
atcgaagaag atgcttacat cgaacgtggc gaacgccgtc agccagtgac cagcttcgag 2160
caggcgctgg aatggctggt gaaagagtcg cgtcgcggtc tgtcgattca gcgttataaa 2220
ggtctgggtg aaatgaaccc tgagcaattg tgggaaacca cgatggatcc gacacaacgc 2280
cgcatgctgc gcgtgacggt gaaagatgct atcgcggcgg accagctgtt caccacgctg 2340
atgggcgatg cggttgaacc gcgccgcgcc ttcatcgaag agaacgccct taaagctgcc 2400
aatatcgata tctga 2415

<210> SEQ ID NO 132
<211> LENGTH: 2817
<212> TYPE: DNA
<213> ORGANISM: Unknown
<220> FEATURE:
<223> OTHER INFORMATION: Description of Unknown:
DP71 Isoleucine--tRNA ligase microbial sequence

<400> SEQUENCE: 132
atgagtgact acaagaacac cctgaatttg ccggaaacag ggttcccgat gcgtggcgat 60
ctggccaagc gtgaacctga catgctgaag aattggtatg accaggatct gtacgggatt 120
attcgtgctg ccaagaaagg caagaaaacc tttatcttgc atgacggccc tccgtatgcg 180
aacggcagca ttcatattgg tcactcagta aacaaaattc ttaaagacat gatcgttaag 240
tccaaaggac tggcgggctt tgatgcgccg tatgttccgg gctgggattg tcatggtctg 300
ccgattgaac tgaaagttga acagctgatc ggtaagccgg gcgaaaaagt cacggcggcg 360
gaattccgtg aagcctgccg caagtacgct gctgaacagg ttgaaggtca gaagaaagac 420
ttcatccgtc tgggcgtgct cggtgactgg gatcatccgt acctgaccat ggacttcaaa 480
acagaagcca acatcattcg tgccctgggt aaaatcatcg gcaacggtca cctgcataaa 540
ggtgcgaaac ctgttcactg gtgtaccgat tgcggatctt cactggctga agccgaagtc 600
gaatattacg acaaagtgtc tccgtctatc gacgtgacgt ttaatgcgac ggatgccgcc 660
gctgttgctg cgaaattcgg tgccactgct ttcaatggcc cggtttctct ggtcatctgg 720
accaccaccc cgtggaccat gccagctaac cgcgcgattt cactcaacgc tgagttctct 780
tatcagctgg tgcagattga aggtcagtgc ctgatcctgg ctaccgatct ggtagaaagc 840
gtgatgaatc gcgccggtat cgctgagtgg actgtgctgg gcgaatgtaa aggtgcggat 900
cttgaattgc ttcgattcca gcatccgttc ctcggtttcg atgttccggc gatcctcggc 960
gatcacgtta ctctcgatgc cggtaccggt gctgtacata ccgcacctgg ccacggtcct 1020
gatgactttg tcattggcca gaaatacggt ctggaagtcg caaacccggt tggaccgaac 1080
ggctgctacc tgccgggcac ttatccgacg ctggatggca aattcgtctt taaagcgaat 1140
gatctgatcg ttgaattgct gcgtgagaag ggcgcactgc tgcacgttga gaaaatgaac 1200
cacagctatc cgtgctgctg gcgtcacaaa acgccgatca tcttccgcgc tacgccacaa 1260
tggttcatca gcatggatca gaaaggtttg cgtcagaagt ctctggaaga gatcaaaggc 1320
gtgcagtgga tccctgactg ggtcaggcg cgtatcgaaa acatggtcgc taaccgtcct 1380
gactggtgta tctcccgcca gcgtacgtgg ggcgtaccga tgtctctgtt cgtgcataaa 1440
gataccgaac agcttcatcc gcgcagcctt gagctgatgg aagaagtggc aaaacgcgtg 1500
gaagccgatg gcattcaggc atggtgggat ctgaaccctg aagagatttt gggtgcagac 1560
gctgccgatt acgtcaaagt gccggatacg ctggacgtct ggtttgactc cggttccacg 1620
cactcctccg ttgtggatgt gcgccctgag ttcaacggtc attcaccgga tctgtatctg 1680
gaaggttctg accagcatcg cggctggttc atgtcttctc tgatgatttc tacggcgatg 1740
aaaggcaaag cgccttacaa acaagtactg actcacggtt tcaccgtcga tggtcagggc 1800
cgtaaaatgt ctaaatccat cggtaacacc atcgcgcctc aggatgtgat gaataagctg 1860
ggtggcgaca tcctgcgttt gtgggtggca tctacggatt acaccggcga aatcgccgtg 1920
tccgacgaaa tcctcaaacg tgctgccgat tcttatcgcc gtatccgtaa caccgcgcgc 1980
ttcctgctgg cgaaccttaa cggtttcgat ccggcgctgc acagcgtggc accggaagag 2040
atggttgtgc tggatcgctg ggcggttggc cgcgcgaaag ctgcacaaga cgagatcatt 2100
gctgcgtacg aagcctatga tttccacggc gttgttcagc gtctgatgca gttctgctcg 2160
atcgaaatgg gttcgttcta tctggatatc attaaagatc gccagtacac cgcgaagagc 2220
gacagcgttg cgcgccgcag ctgccagacc gcgctgtatc acatctgcga agcactggtt 2280
cgctggatgg cgccaatcat gtccttcact gccgatgaaa tctgggctga actgccaggt 2340
catcgcgaga agttcgtctt tactgaagaa tggtacgacg gtctgtttgg cctgatcggt 2400
aacgaatcca tgaacgatgc gttctgggat gagctgctga aagtgcgtgg tgaagtgaac 2460
aaagtgatcg aacaggcgcg tgctgataaa cgtctgggcg gttctctgga agcagccgtg 2520
accttatatg cagacgacgc gctggcaaca gacctgcgtt ctctgggtaa cgaactgcgc 2580
tttgtgctcc tgacttccgg tgcgaaagtc gccgcgctgt ctgaagctga tgactcagcg 2640
caggccagcg aattgttgaa aggactgaaa attggtctgg cgaaagcaga aggcgagaag 2700
tgcccgcgct gctggcattt caccactgat atcggccaga atgcggaaca cagtgacatc 2760
tgtggccgtt gtgtgactaa cattgccggt gacggcgaag agcgtaagtt tgcataa 2817

<210> SEQ ID NO 133

<211> LENGTH: 1560
<212> TYPE: DNA
<213> ORGANISM: Unknown
<220> FEATURE:
<223> OTHER INFORMATION: Description of Unknown:
DP71 NADH-quinone oxidoreductase subunit C/D
microbial sequence

<400> SEQUENCE: 133
atgtcagaac ttactcatat taatgcttcc ggcgacgccc acatggtgga tgtctccggt 60
aaagacgaca ccgttcgtga agcccgtgcc gaagcctttg ttgaaatggc cgaaagcacg 120
ctggcgatga tcatcggcgg taatcaccat aagggtgacg tgttcgcgac cgcgcggatt 180
gccggtattc aggcagcgaa gaaaacctgg gatctgatcc cgctgtgtca tccgctgttg 240
ctgaccaagg tggaagtgaa tcttgaagcg cagccagaat ttaatcgtgt acgtattgaa 300
tcccgctgcc gcctgagcgg taaaaccggc gtcgagatgg aagcgctgac cttcaagcct 360
gaagactggg gaatgaagcg cggcaccgaa aacgaggact tcatgttcct caacctcgga 420
cctaaccatc cgtctgcgca cggtgcgttc cgcatcatcc tgcagcttga tggcgaagaa 480
attgtcgact gtgtaccgga cgtcggttac caccaccgtg gtgctgagaa gatgggcgag 540
cgccagtcat ggcacagcta cattccatac acggaccgta tcgaatacct cggcggttgc 600
gttaacgaga tgccatacgt actggctgtt gaaaaactgg cgggtatcgt cgtgccggat 660
cgcgttaaca ccatccgcgt gatgctgtct gaactgttcc gtatcaacag ccacctgctg 720
tacatctcta cgtttattca ggacgtgggc gcgatgacgc cagtgttctt cgcctttacc 780
gatcgtcaga aaatttacga tctggtggaa gcgatcaccg gtttccgtat gcacccggcc 840
tggttccgta ttggtggcgt tgcacacgac ctgccgaaag gctgggagcg tctgctgcgt 900
gaattccttg actggatgcc agcccgtctg gattcctacg tcaaggcagc gctgaaaaac 960
accattctga ttggacgttc caaaggcgta gcagcataca acgccgatga tgcgctggcg 1020
tggggcacca ccggtgctgg cctgcgtgcg accgggatcg acttcgatgt ccgcaaatgg 1080
cgtccatatt caggttacga aaacttcgat tttgaagtgc cggtcggcga tggcgtcagt 1140
gattgctatt cccgcgtgat gctaaaagtg gaagagcttc gtcagagcct gcgcattctg 1200
gaacagtgct acaaaaacat gccggaaggc ccgttcaagg cggatcaccc gctgaccacg 1260
ccgccaccga aagagcgtac gctgcaacac atcgaaaccc tgatcactca cttcctgcaa 1320
gtgtcgtggg gtccgatcat gcctgcgcaa gaatctttcc agatggttga agccaccaaa 1380
gggatcaaca gctactacct gaccagtgac ggcagcacca tgagctaccg cacgcgcgtc 1440
cgtacgccaa gcttcccgca tttgcagcag atcccgtccg taatccgtgg cagcctggta 1500
tccgacctga tcgtgtatct gggcagtatc gattttgtaa tgtcagatgt ggaccgctaa 1560

<210> SEQ ID NO 134
<211> LENGTH: 1065
<212> TYPE: DNA
<213> ORGANISM: Unknown
<220> FEATURE:
<223> OTHER INFORMATION: Description of Unknown:
DP71 Protein RecA microbial sequence

<400> SEQUENCE: 134
atggctattg atgagaacaa gcaaaaagcg ttagctgcag cactgggcca gattgaaaag 60
caattcggta aaggctccat catgcgtctg ggtgaagatc gctctatgga cgtggaaacg 120
atctctaccg gctctttgtc tctggatatc gcgttaggcg ccggtggttt gccgatgggc 180

```
cgtatcgttg agatttatgg cccggaatcc tccggtaaaa ctacgctgac ccttcaggtt    240

attgctgccg cacagcgcga aggcaaaacc tgtgcgttca tcgatgcgga acatgcactt    300

gaccctatct acgcgaagaa attgggcgta gatatcgaca acctgttgtg ttctcagccg    360

gataccggcg aacaggctct ggaaatctgt gacgcgctga cccgttcagg cgcggtcgac    420

gttatcatcg tcgactccgt tgctgcactg acgccaaaag cagaaatcga aggcgaaatc    480

ggtgactctc acatgggcct tgcggcacgt atgatgagcc aggcaatgcg taagcttgcc    540

ggtaacctga aaaacgccaa caccttgctg atcttcatca accagatccg tatgaaaatc    600

ggtgtgatgt tcggtaaccc ggaaaccacc accggtggta acgccctgaa attctacgcc    660

tctgtgcgtc tggatatccg ccgcatcggc gctatcaaag aaggcgacgt ggtgatcggc    720

agtgaaacgc gcgtgaaagt tgtgaagaac aaaatcgctg cgcctttcaa acaggctgaa    780

ttccagatcc tatacggcga aggcatcaac attaacggcg agctgatcga tttgggcgtt    840

aagcacaaac tggtcgaaaa agccggtgca tggtacagct acaacggcga gaagattggt    900

cagggtaaat ctaactcctg caactatctg aaagaaaacc cgaaaatcgc tgctgaactg    960

gataaaaaac tgcgtgatat gttgttgagt ggcactggtg aactggccgc tgcaaccaca   1020

gcagaacttg cagacgacga tatggaaacc agcgaagagt tttaa                   1065


<210> SEQ ID NO 135
<211> LENGTH: 1794
<212> TYPE: DNA
<213> ORGANISM: Unknown
<220> FEATURE:
<223> OTHER INFORMATION: Description of Unknown:
      DP71 RNA polymerase sigma factor RpoD microbial sequence

<400> SEQUENCE: 135

ggtaaggagc aaggctatct gacctttgct gaggtcaatg accatctgcc ggaagatatc     60

gtcgactccg accagatcga agacatcatc cagatgatta acgacatggg catccaggtt    120

cttgaagaag cgccggacgc cgatgatttg atgctggccg aaaaccgccc tgataccgat    180

gaagatgctg cagaagcagc ggctcaggtg ctttccagcg ttgaatctga aattggccgt    240

accaccgacc ctgtgcgtat gtatatgcgc gaaatgggta ccgttgagct cctgacccgt    300

gaaggcgaaa tcgacatcgc caaacgtatc gaagacggta tcaatcaggt ccagtgctcc    360

gttgctgaat atcctgaagc tatcacctat ttgttagagc aatatgaccg tgttgaagca    420

ggcgaagcac gtctgtctga tttgatcacc ggttttgttg atccgaacgc cgaagaagaa    480

atcgcgccga ctgcgactca cgtgggttct gaactgacca ctgaagagca aaatgatacc    540

gacgacgatg aagaagacga cgacgatgct gaagacgaca acagcatcga cccggaactg    600

gcgcgtcaga agttcaccga tctgcgtgag caacatgaag cgacccgtgc cgtcatcaag    660

aaaaatggcc gtagccacaa aagcgccgca gaagaaattc tgaagctgtc cgatgtgttt    720

aaacagttcc gtctggtacc aaaacagttc gatttcctgg tgaacagcat gcgctccatg    780

atggatcgcg tccgtactca ggaacgtctg atcatgaaag tgtgcgttga acagtgcaaa    840

atgccgaaga aaaacttcgt caatctgttc gccggtaacg aaaccagcag tacctggttt    900

gatgctgctc tggcaatggg taaaccatgg tctgagaagc tgaaagaagt gaccgaagac    960

gtgcagcgcg gcctgatgaa actgcgccaa atcgaagaag aaactggcct gactatcgaa   1020

caggtaaaag acattaaccg tcgcatgtcg atcggcgaag cgaaagcacg ccgcgcgaag   1080

aaagagatgg ttgaagcgaa cttacgtctg gttatctcta tcgcgaagaa atacaccaac   1140
```

cgtggcttgc agttccttga cctgattcag gaaggtaaca tcggcctgat gaaagccgtt 1200
gataagtttg aatatcgccg tggttataag ttctctactt atgcgacctg gtggatccgt 1260
caggctatca cccgctccat cgccgaccag gcacgtacca tccgtattcc ggtgcatatg 1320
attgagacca tcaacaaact caaccgtatt tcgcgccaga tgttgcagga gatgggccgt 1380
gagccgacgc cggaagagct ggctgaacgc atgctgatgc cggaagacaa gatccgtaaa 1440
gtgctgaaaa ttgctaaaga gccaatctcc atggaaacgc caatcggcga cgatgaagat 1500
tcgcatctgg gtgatttcat cgaggatact accctcgagc tgccgctgga ttctgcgacc 1560
tctgaaagcc tgcgttctgc aacgcacgac gttctggctg gcctgaccgc acgtgaagcg 1620
aaagttctgc gtatgcgttt cggtatcgat atgaacactg accacactct ggaagaagtg 1680
ggcaaacagt tcgacgtaac ccgtgaacgt atccgtcaga tcgaagccaa agcgttgcgt 1740
aaactacgcc acccaagccg ctccgaagtg ctgcgcagct tcctcgacga ctag 1794

<210> SEQ ID NO 136
<211> LENGTH: 2487
<212> TYPE: DNA
<213> ORGANISM: Unknown
<220> FEATURE:
<223> OTHER INFORMATION: Description of Unknown:
DP71 DNA-directed RNA polymerase subunit beta
microbial sequence

<400> SEQUENCE: 136
atggaccaga acaacccgtt gtctgagatc acgcacaaac gtcgtatctc tgcactgggc 60
ccgggcggtt tgacccgtga acgtgctggc tttgaagttc gagacgtaca cccgacgcac 120
tacggtcgcg tatgtccaat cgaaacgcca gaaggtccaa acatcggtct gatcaactca 180
ttatctgtct atgcacagac aaatgagtat ggtttcctgg aaacccctta ccgccgtgtg 240
cgtgaaggta tggttaccga tgaaattaac tacctgtctg ccatcgaaga aggcaacttt 300
gttatcgctc aggcgaactc caacctggat gacgaaggcc acttcctgga agatttagtc 360
acttgtcgta gcaaaggcga atcaagcctg ttcagccgcg accaggttga ctacatggac 420
gtttctaccc agcagatcgt atccgttggt gcttcactga ttccattcct ggaacacgat 480
gacgccaacc gtgcattgat gggtgcgaac atgcaacgtc aggcagttcc tactctgcgt 540
gctgataagc cgctggtagg tactggtatg gaacgtgctg ttgcggttga ctccggtgtt 600
actgccgttg ccaaacgtgg tggtactgtt cagtacgtag atgcatcccg tatcgttatt 660
cgtgttaacg aagaagagat gaatccaggc gaagcaggta tcgacattta taacctgact 720
aagtacaccc gttctaacca gaacacctgc atcaaccaga tgccgtgtgt gaatctgggc 780
gagccaatcg agcgcggcga cgtgctggca gatggtccgt caacagatct gggcgaactg 840
gcactgggtc agaacatgcg tgtcgcgttc atgccttgga acggttacaa cttcgaagac 900
tccatcttgg tctccgaacg tgttgtgcag gaagatcgct tcacgaccat ccatatccag 960
gaactggcat gtgtgtcccg tgacacaaag ttagggcctg aagagatcac tgctgatatc 1020
cctaacgtgg gtgaagctgc gctctccaaa ctggatgagt ccggtattgt gtatatcggt 1080
gctgaagtga ccggtggtga cattctggtc ggtaaagtta cgcctaaagg cgaaacccag 1140
ctgactccag aagagaaact gctgcgtgcg atcttcggtg agaaagcgtc tgacgttaaa 1200
gattcttctc tgcgtgtacc aaacggcgtt tccggtacga ttattgacgt gcaagtcttt 1260
acccgcgatg gcgtggaaaa agataagcgt gcgttagaaa tcgaagaaat gcagctgaaa 1320
caggctaaga aagacctgac tgaagagctg caaattctgg aagctggtct gtttgcacgt 1380

-continued

```
atccagtccg cgctggttgc tggcggtgtt gaagccgata agctgggcaa attgccacgc   1440

gatcgttggc ttgaactgtc actgactgac gaagacaaac agaatcagtt ggaacagctt   1500

gctgaacagt acgacgaact gaaatccgag tttgagaaaa aactcgaagc taaacgtcgt   1560

aaaatcactc agggcgatga cctagcacca ggtgtgctga aaatcgttaa agtgtacctg   1620

gccgttaaac gtcagatcca acctggtgac aaaatggcag gccgccacgg taacaaaggt   1680

gttatctcca agatcaaccc gatcgaagat atgccttacg atgaaaacgg gactcctgtt   1740

gacatcgtac tgaacccgct gggcgttcca tcacgtatga acattggtca gattttagaa   1800

acccacctgg gtatggccgc gaaaggtatt ggtgaaaaaa tcaatgccat gcttaagaaa   1860

catgaagaag tttctaagct gcgcgagttc atccagcgtg cctatgatct gggcgacgac   1920

gtacgtcaga aagttgatct gaccaccttc accgatgatg aagtattgcg tttggctgaa   1980

aacctgaaaa agggtatgcc aattgcaaca ccagtcttcg acggtgcgaa agagacagag   2040

atcaagcaac tgcttgaaat gggcggcgtc ccaacctctg gccagatcac actgtttgac   2100

ggccgtaccg gcgagcaatt cgagcgccag gttaccgtcg gctacatgta catgctgaaa   2160

ctgaaccacc tggttgacga taagatgcat gcgcgttcta ccggttctta cagccttgtt   2220

actcagcagc cgctgggtgg taaagctcag ttcggtggtc agcgcttcgg tgagatggaa   2280

gtgtgggcac tggaagcata cggtgccgct tataccctgc aggaaatgct gactgttaag   2340

tccgatgacg tgaacggccg tactaagatg tataaaaaca tcgtagatgg cgatcaccgg   2400

atggaaccag gcatgccgga atcattcaac gtactgttga aagaaatccg ctctctgggt   2460

atcaacatcg agctggaaga cgagtaa                                       2487
```

MICROBIAL COMPOSITIONS AND METHODS FOR TREATING TYPE 2 DIABETES, OBESITY, AND METABOLIC SYNDROME

CROSS REFERENCE TO RELATED APPLICATIONS

This application is a continuation of PCT Application No. PCT/US2018/066088, filed Dec. 17, 2018, which claims the benefit of U.S. Provisional Application Nos. 62/599,647, filed Dec. 15, 2017; 62/607,149, filed Dec. 18, 2017; and 62/727,497, filed Sep. 5, 2018, each of which is hereby incorporated by reference in its entirety.

SEQUENCE LISTING

The instant application contains a Sequence Listing which has been submitted via EFS-Web and is hereby incorporated by reference in its entirety. Said ASCII copy, created on Apr. 5, 2019, is named 33863-42455_US_SL.txt and is 321,948 bytes in size.

BACKGROUND OF THE INVENTION

The invention relates to methods and compositions useful for treating type 2 diabetes, obesity, and metabolic syndrome.

Daily consumption of fresh fruits, vegetables, seeds and other plant-derived ingredients of salads and juices is recognized as part of a healthy diet and associated with weight loss, weight management and overall healthy life styles. This is demonstrated clinically and epidemiologically in the "China Study" (Campbell, T. C. and Campbell T. M. 2006. The China Study: startling implications for diet, weight loss and long-term health. Benbella books. pp 419) where a lower incidence of cardiovascular diseases, cancer and other inflammatory-related indications were observed in rural areas where diets are whole food plant-based. The benefit from these is thought to be derived from the vitamins, fiber, antioxidants and other molecules that are thought to benefit the microbial flora through the production of prebiotics. These can be in the form of fermentation products from the breakdown of complex carbohydrates and other plant-based polymers. There has been no clear mechanistic association between microbes in whole food plant-based diets and the benefits conferred by such a diet. The role of these microbes as probiotics, capable of contributing to gut colonization and thereby influencing a subject's microbiota composition in response to a plant-based diet, has been underappreciated. In contrast to a plant-based diet, diets deficient in microbes such as the Western diet are associated with chronic inflammation, obesity, metabolic syndrome, type 2 diabetes (T2D) and sequelae.

Type 2 diabetes (T2D) is a systemic inflammatory condition where loss of insulin sensitivity leads to hyperglycemia and dyslipidemia, culminating in cell and tissue damage. Numerous studies have identified dysbiosis of the gut microbiome as a primary factor in the development of obesity and T2D, leading to a robust effort to develop microbiome-based therapeutic candidates for these conditions. In obesity and T2D, the gut microbiome is characterized by reduced microbial diversity and a shift in the equilibrium of *Firmicutes* and *Bacteroidetes*, the two most prevalent bacterial phyla residing in the colon. This altered microbial environment can result in increased energy harvest and intestinal permeability, as well as reduced production of enteroendocrine peptides and short chain fatty acids (SCFA), all of which can promote the inflammation and insulin resistance associated with obesity and T2D. Recent evidence indicates oral anti-diabetic drugs such as metformin may in part exert their effects through modulation of the gut microbiome.

What is needed are compositions and methods that treat T2D, obesity and metabolic syndrome by modulating a subject's microbiota composition away from that associated with a Western diet and toward one conferring the benefits of a plant-based diet.

SUMMARY OF THE INVENTION

In one aspect, provided herein are pharmaceutical compositions comprising a plurality of purified microbes, wherein at least two microbes have at least 97 percent identity to any of Seq ID Nos. 1-66 at the 16S rRNA or fungal ITS locus.

In some embodiments, at least two microbes have 100 percent identity to one of Seq ID Nos 1-66 at the 16S rRNA or fungal ITS locus, or 100 percent identity to a diagnostic sequence thereof.

In some embodiments, the pharmaceutical composition comprises microbial entities DP5 and DP1. In some embodiments, the pharmaceutical composition comprises microbial entities DP9, DP5, and DP22. In some embodiments, the pharmaceutical composition comprises microbial entities DP9, DP2, and DP3. In some embodiments, the pharmaceutical composition comprises microbial entities DP9, DP2, and DP53.

In some embodiments, the pharmaceutical composition comprises microbes with 16S sequences that are individually at least 97% identical to SEQ ID Nos 9, 5, and 22. In some embodiments, the pharmaceutical composition comprises microbes with 16S sequences that are individually at least 98% identical to SEQ ID Nos 9, 5, and 22. In some embodiments, the pharmaceutical composition comprises microbes with 16S sequences that are individually at least 99% identical to SEQ ID Nos 9, 5, and 22. In some embodiments, the pharmaceutical composition comprises microbes with 16S sequences that are individually 100% identical to SEQ ID Nos 9, 5, and 22. In some embodiments, the pharmaceutical composition comprises microbes with 16S sequences that are individually at least 97% identical to SEQ ID Nos 9, 2, and 3. In some embodiments, the pharmaceutical composition comprises microbes with 16S sequences that are individually at least 98% identical to SEQ ID Nos 9, 2, and 3. In some embodiments, the pharmaceutical composition comprises microbes with 16S sequences that are individually at least 99% identical to SEQ ID Nos 9, 2, and 3. In some embodiments, the pharmaceutical composition comprises microbes with 16S sequences that are individually 100% identical to SEQ ID Nos 9, 2, and 3. In some embodiments, the pharmaceutical composition comprises microbes with 16S sequences that are individually at least 97% identical to SEQ ID Nos 9, 2, and 53. In some embodiments, the pharmaceutical composition comprises microbes with 16S sequences that are individually at least 98% identical to SEQ ID Nos 9, 2, and 53. In some embodiments, the pharmaceutical composition comprises microbes with 16S sequences that are at individually least 99% identical to SEQ ID Nos 9, 2, and 53. In some embodiments, the pharmaceutical composition comprises microbes with 16S sequences that are individually 100% identical to SEQ ID Nos 9, 2, and 53. In some embodiments, the pharmaceutical composition comprises microbes with 16S sequences that are individually at least 97% identical to SEQ ID Nos 5 and 1. In some embodiments, the pharmaceutical composition comprises microbes with 16S sequences that are individually at least 98% identical to SEQ ID Nos 5 and 1. In some embodiments, the pharmaceutical composition comprises microbes with 16S sequences that are individually at least 99% identical to SEQ ID Nos 5 and 1. In some embodiments, the pharmaceutical composition comprises microbes with 16S sequences that are individually 100% identical to SEQ ID Nos 5 and 1.

In another aspect, provided herein are pharmaceutical compositions comprising a plurality of purified viable microbes comprising at least one microbial entity classified as a gamma proteobacterium, and at least one prebiotic fiber.

In some embodiments, the pharmaceutical composition further comprising at least one additional probiotic microbial species.

In some embodiments, the pharmaceutical composition further comprising at least one microbial entity classified as a fungus or yeast.

In some embodiments, the prebiotic fiber is oligofructose, or derived from a fiber source yielding a prebiotic fiber rich in oligofructose.

In another aspect, provided herein are methods for treating diabetes or metabolic syndrome, comprising administering to a patient in need thereof the pharmaceutical composition of any of the previous claims in concert with an appropriate regimen of any suitable anti-diabetic therapy.

In another aspect, provided herein are pharmaceutical compositions comprising a plurality of purified viable microbes and a prebiotic fiber, wherein the microbes produce more short chain fatty acids (SCFAs) when grown together than when cultured separately, and wherein growth on the chosen prebiotic sugar results in increased synergy compared to growth on rich medium, and wherein at least one of the microbes has at least 97 percent identity at the 16S rRNA locus or the ITS locus to any of Seq ID No 1-66.

In some embodiments, at least one of the microbes has at least 97 percent identity at the 16S rRNA locus to Seq ID No 1. In some embodiments, at least one of the microbes has at least 97 percent identity at the ITS locus to Seq ID No 2. In some embodiments, at least one of the microbes has at least 97 percent identity at the 16S rRNA to Seq ID No 3. In some embodiments, at least one of the microbes has at least 97 percent identity at the ITS locus to Seq ID No 5. In some embodiments, at least one of the microbes has at least 97 percent identity at the 16S rRNA locus to Seq ID No 9. In some embodiments, at least one of the microbes has at least 97 percent identity at the 16S rRNA locus to Seq ID No 22. In some embodiments, at least one of the microbes has at least 97 percent identity at the 16S rRNA locus to Seq ID No 53. In some embodiments, at least one of the microbes has 100 percent identity at the 16S rRNA locus or the ITS locus to any of Seq ID No 1-63, or 100 percent identity to a diagnostic sequence thereof. In some embodiments, at least one of the microbes has 100 percent identity at the 16S rRNA locus or the ITS locus to any of Seq ID No 1, 2, 3, 5, 9, 22, and 53, or 100 percent identity to a diagnostic sequence thereof.

In another aspect, provided herein are methods for altering relative abundance of microbiota in a subject, comprising administering to the subject an effective dose of a composition consisting of a substantially purified plant-derived microbial assemblage, comprising at least 2 microbes from Table 4 as identified by 16S rRNA sequence or ITS sequence, wherein the subject has a disorder selected from the group consisting of obesity, metabolic syndrome, insulin deficiency, insulin-resistance related disorders, elevated fasting blood glucose, glucose intolerance, diabetes, non-alcoholic fatty liver, and abnormal lipid metabolism.

In another aspect, provided herein are methods to formulate a defined microbial assemblage comprising a purified microbial population isolated from a first plant-based sample selected from samples in Table 3 artificially associated with a purified microbial population isolated from a second plant-based sample from selected from samples Table 3, wherein the purified bacterial population is predicted using a computational simulation and is capable of modulating production of one or more branched chain fatty acids, short chain fatty acids, and/or flavones in a mammalian gut.

In another aspect, provided herein are a defined microbial assemblage comprising a purified microbial population isolated from a first plant-based sample selected from samples in Table 3 artificially associated with a purified microbial population isolated from a second plant-based sample from selected from samples Table 3, wherein the synthetic microbial consortia is capable of modulating the diabetic symptoms of a mammal treated with the synthetic microbial consortia, as compared to a reference mammal.

In another aspect, provided herein are a defined microbial assemblage comprising a purified microbial population that, when combined with an anti-diabetic regimen, lowers fasting blood glucose to levels found in a low fat diet control subject and wherein at least one of the microbes has at least 97 percent identity at the 16S rRNA locus or the ITS locus to any of Seq ID No 1-66.

In another aspect, provided herein are a fermented probiotic composition for the treatment of diabetes comprising a mixture of *Pediococcus pentosaceus* and/or *Leuconostoc mesenteroides* combined with non-lactic acid bacteria from Table 4 or Table 7, the fermented probiotic being in a capsule or microcapsule adapted for enteric delivery.

In another aspect, provided herein are methods for treatment of diabetes in a mammal comprising the steps of administering a composition comprising an effective amount of organisms described in Table 4 to a mammal in need of treatment for diabetes.

In another aspect, provided herein are methods of treating diabetes, comprising administering to a subject a pharmaceutical composition comprising a plurality of purified microbes, wherein at least two microbes have at least 97 percent identity to any of Seq ID Nos. 1-66 at the 16S rRNA or fungal ITS locus.

In another aspect, provided herein are methods of treating diabetes, comprising administering to a subject a pharmaceutical composition comprising a plurality of strains having at least 97 percent identity to DP5 or DP1.

In another aspect, provided herein are methods of treating diabetes, comprising administering to a subject a pharmaceutical composition comprising a plurality of strains having at least 97 percent identity to DP9, DP22, and DP2.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least one of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least two of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI, low inflammatory metabolic indicators, and ameliorated diabetic symptoms, and wherein at least three of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least one of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least two of the microorganisms has a 16S rRNA sequence that is 97 percent identical to one of Seq ID Nos 1-66.

In another aspect, provided herein are pharmaceutical compositions for treatment of diabetes, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms are identified to a whole genome sequence in public databases by using a k-mer method, and wherein at least three of the microorganisms has a 16S rRNA sequence that is 97 percent identical to one of Seq ID Nos 1-66.

In another aspect, provided herein are methods for treating diabetes in a mammal in need thereof comprising administering to the mammal a therapeutically effective amount of a probiotic composition comprising at least one strain classified as gamma proteobacteria by 16S rRNA gene sequence.

In another aspect, provided herein are methods for treating diabetes in a mammal in need thereof comprising administering to the mammal a therapeutically effective amount of a probiotic composition comprising at least two strain classified as gamma proteobacteria by 16S rRNA gene sequence.

In another aspect, provided herein are methods for treating diabetes in a mammal in need thereof comprising administering to the mammal a therapeutically effective amount of a probiotic composition comprising at least three strain classified as gamma proteobacteria by 16S rRNA gene sequence.

In another aspect, provided herein are methods for reducing body weight of a high fat diet subject, comprising administering a probiotic composition, wherein the probiotic bacterial assemblage comprises at least one strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for reducing body weight of a high fat diet subject, comprising administering a probiotic composition, wherein the probiotic bacterial assemblage comprises at least two strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4.

The method of claim 62, wherein the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for reducing body weight of a high fat diet subject, comprising administering a probiotic composition, wherein the probiotic bacterial assemblage comprises at least three strain classified as gamma proteobacteria by 16S rRNA gene sequence, formulated as a defined microbial assemblage with at least one other plant-derived microbe listed in Table 4 or Table 7.

In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods for treatment of diabetes and its complications for a high fat diet subject, comprising administering a probiotic composition, wherein the probiotic bacterial assemblage comprises at least one strain classified as gamma proteobacteria by 16S rRNA gene sequence, and wherein the probiotic is formulated as a defined microbial assemblage with at least one other plant-derived microbe from Table 4 or Table 7. In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, wherein the at least two other plant-derived microbe are listed in Table 7.

In another aspect, provided herein are methods for treatment of diabetes and its complications for a high fat diet subject, comprising administering a probiotic composition, wherein the probiotic bacterial assemblage comprises at least one strain classified as gamma proteobacteria by 16S rRNA gene sequence, and wherein the probiotic is formulated as a defined microbial assemblage with at least two other plant-derived microbe from Table 4 or Table 7. In some embodiments, the at least one other plant-derived microbe is listed in Table 4. In some embodiments, the at least one other plant-derived microbe is listed in Table 7. In some embodiments, the probiotic bacterial assemblage comprises at least one strain classified as gamma proteobacteria by 16S rRNA gene sequence, formulated as a defined microbial assemblage with at least two other plant-derived microbe listed in Table 4 or Table 7. In some embodiments, the at least two other plant-derived microbe are listed in Table 4. In some embodiments, the at least two other plant-derived microbe are listed in Table 7.

In another aspect, provided herein are methods of the treatment of inhibition of the biosynthesis of lipids, high total body fat, high visceral fat, high gonadal fat, high total cholesterol, high triglyceride concentration, or high LDL/HDL ratio for a high fat diet subject, comprising administrating a probiotic composition, wherein the probiotic bacterial assemblage comprises at least one strain classified as gamma proteobacteria by 16S rRNA gene sequence.

In another aspect, provided herein are microbial compositions comprised of bacterial assemblages present in whole food plant-based diets that bear taxonomic resemblance to microbial species present in human microbiome as detected by stool from individuals with desirable phenotypic attributes such as BMI, low levels of inflammatory signaling molecules or diabetic symptoms.

In another aspect, provided herein are microbial compositions comprised of bacterial assemblages present in whole food plant-based diets that bear taxonomic resemblance to microbial species present in companion animal, or livestock microbiome as detected by stool from individuals with desirable phenotypic attributes such as BMI, low levels of inflammatory signaling molecules or diabetes symptoms.

In some embodiments, the composition comprises at least one microbe from Table 4, as determined by 97 percent or higher sequence identity at the 16S rRNA or ITS locus.

In another aspect, provided herein are methods for treating diabetes, the method comprising administration of a known anti-diabetic medication and the microbial composition of any of the preceding claims.

In another aspect, provided herein are methods for treating diabetes comprising administration of metformin and the microbial composition of any of the preceding claims.

In another aspect, provided herein are methods for treating diabetes comprising administration of a known anti-diabetic medication and a composition of metabolites derived from the microbial community of any of the preceding claims.

In another aspect, provided herein are methods for improving the efficacy of a known anti-diabetic drug, said method comprising administration of the anti-diabetic drug along with the microbial composition of any of the preceding claims.

In another aspect, provided herein are methods for treating diabetes, the method comprising administration of a known anti-diabetic medication and the pharmaceutical composition of any of the preceding claims.

In an aspect, the disclosure describes an oral or rectal pharmaceutical composition in a capsule or microcapsule, solution, or slurry adapted for enteric delivery comprising a plurality of viable gammaproteobacteria and other microbes from Table 4 or Table 7, wherein said pharmaceutical comprises between about 10^5 and 10^10 viable microbes. In another aspect, the oral pharmaceutical composition comprises at least *Pseudomonas, Rahnella*, other gammaproteobacteria, or other microbial species. In another aspect, the pharmaceutical composition comprises an isolated population of bacterial cells comprising three or more strains present in whole food plant-based diets, wherein each strain is capable of modulating production of one or more short chain fatty acids. In another aspect, the disclosure describes a pharmaceutical composition for treatment of obesity and obesity related metabolic syndrome, comprising heterologous microorganisms which can colonize the gastrointestinal tract of mammals and reduce free fatty acids absorbed into the body of a host by absorbing the free fatty acids in the gastrointestinal tract of mammals, wherein the heterologous microorganisms comprise genes encoding metabolic functions related to desirable health outcomes such as BMI or low inflammatory metabolic indicators. Metabolic indicators of relevance would be related to microbial production of short chain fatty acids (SCFA) including: Glycoside Hydrolase, Polysaccharide lyase, beta-fructofuranosidase, Phosphotransferase (PTS), Beta-fructofuranosidase (SacA), fructokinase (SacK), pyruvate formate lyase (PFL), Pyruvate Dehydrogenase (PDH), Lactate Dehydrogenase (LDH), Pyruvate Oxidase (PDX), Phosphotransacetylase (PTA), Acetate Kinase (ACK), Butyryl-CoA:Acetate CoA-transferase (But1, But2, But3) Butyrate inase (Buk1, Buk2, Buk3, ect) Phosphotransbutyrylase, propionaldehyde dehydrogenase (pduP) methylmalonyl-CoA (mmdA, mmdB), Lactoyl-CoA (lcdA, lcdB, lcdC), Succinate pathway, and the propanediol pathway.

In another aspect, the pharmaceutical composition comprises a treatment for T2D. In an aspect, the pharmaceutical composition may be administered with an anti-diabetic drug, either simultaneously or according to a sequence.

In another aspect, the disclosed invention pertains to methods of treating diabetes.

BRIEF DESCRIPTION OF THE SEVERAL VIEWS OF THE DRAWINGS

These and other features, aspects, and advantages of the present invention will become better understood with regard to the following description, and accompanying drawings, where:

FIGS. 1A-L show plots depicting the diversity of microbial species detected in samples taken from 12 plants usually consumed raw by humans.

FIGS. 2A-C show graphs depicting the taxonomic composition of microbial samples taken from broccoli heads (FIG. 2A), blueberries (FIG. 2B), and pickled olives (FIG. 2C).

DETAILED DESCRIPTION

Advantages and Utility

Figure 3:
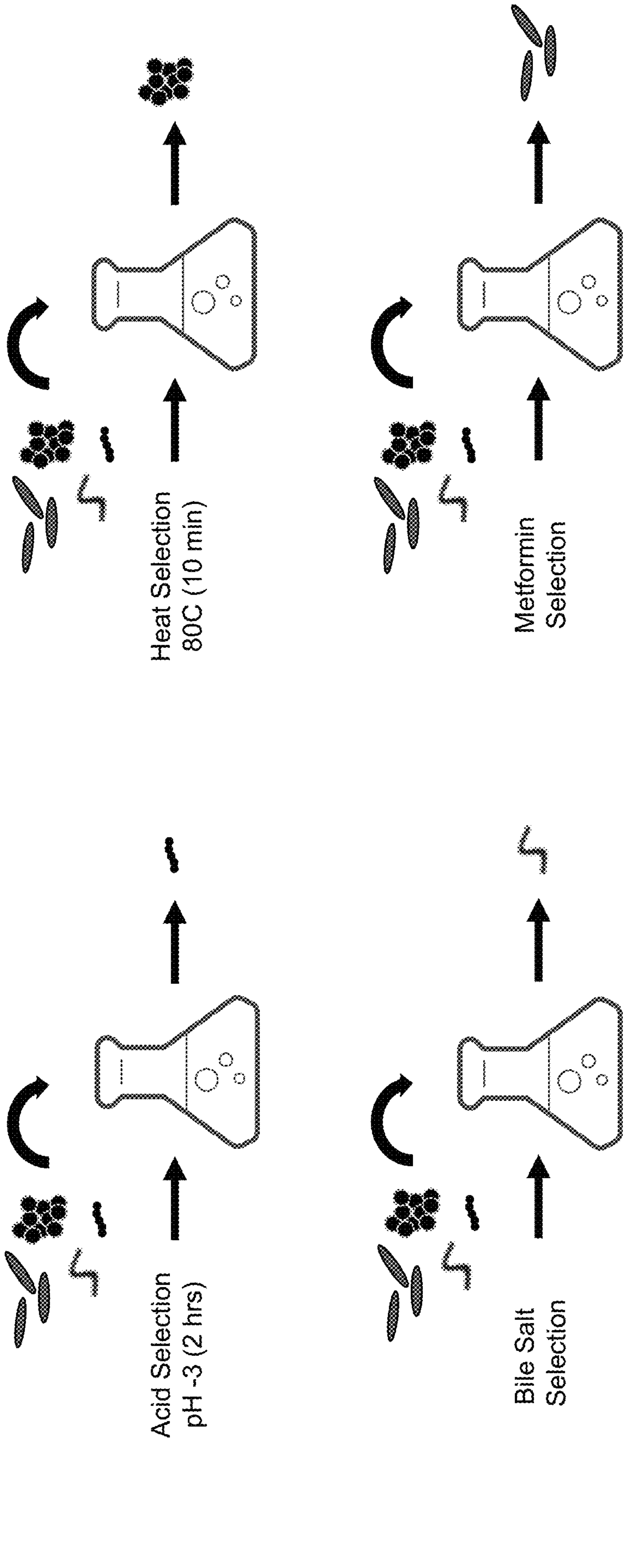
FIG. 3 shows a schematic describing a gut simulator experiment. The experiment comprises an in vitro system that represents various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. Utilizing this system, the impact of various oral anti-diabetic therapies alone or in combination with probiotic cocktails of interest on the microbial ecosystem is tested.

Briefly, and as described in more detail below, described herein are methods and compositions for using microbial agents (probiotics) and agents that promote growth of certain microbes (prebiotics) for management (including prevention and treatment) of T2D, obesity and metabolic syndrome. Diabetes Mellitus is a feared and complex disorder. It has been a most distressing disease that can develop to a seriously life-threatening condition. For ages, society was resigned to accepting various methods and medications that became a standard with no real hope for a cure, or drastic eradication of the disease. In fact, many of the drugs used cause serious side effects.

An important indicator of the ability of the body to deal with the complications of diabetes is the glycated hemoglobin (HbA1c), that gives an integrated reading of the level of blood glucose. While all other known methods and medications help lower the glucose level at limited periods of the day or night time, the HbA1C remains higher than the normal 4.3 to 6.7 range regardless of the insulin dosage and other medicines. No full cure is expected by the present regimens. Thus, in an aspect, the present disclosure provides compositions and methods for treatment of T2D that result in reductions of HbA1C toward more normal levels.

Several features of the current approach should be noted. It is based on development of synergistic combinations of microbes based on those found in fruits and vegetables consumed as part of a plant-based diet. The combinations are based, in part, on analyses of biochemical pathways catalyzed by genes in these microbes and selection of microbial combinations that promote beneficial metabolic changes in a subject through the biochemical reactions they catalyze such as the production of SCFA.

Advantages of this approach are numerous. They include reduction of the morbidity associated with T2D, obesity and metabolic syndrome without the use of traditional drugs, or with lower doses of traditional drugs, and thus reduced levels of the side effects they can sometimes cause. Typical treatment regimens for T2D involve use of drugs such as metformin or acarbose. These drugs can be efficacious but are not without side effects. Prior art approaches are, additionally, not recommended for all patients. The disclosed methods and compositions provided in this application augment the efficacy of traditional drugs and additionally can serve patient populations for whom current methodologies are not recommended, by providing health benefits associated with consumption of a plant-based diet.

Definitions

Terms used in the claims and specification are defined as set forth below unless otherwise specified.

The term "ameliorating" refers to any therapeutically beneficial result in the treatment of a disease state, e.g., a metabolic disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and includes but is not limited to humans, non-human primates, canines, felines, murines, bovines, equines, and porcines.

As used herein, the term "derived from" includes microbes immediately taken from an environmental sample and also microbes isolated from an environmental source and subsequently grown in pure culture.

The term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. In some aspects, percent identity is defined with respect to a region useful for characterizing phylogenetic similarity of two or more organisms, including two or more microorganisms.

Percent identity, in these circumstances can be determined by identifying such sequences within the context of a larger sequence, that can include sequences introduced by cloning or sequencing manipulations such as, e.g., primers, adapters, etc., and analyzing the percent identity in the regions of interest, without including in those analyses introduced sequences that do not inform phylogenetic similarity.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

The term "sufficient amount" means an amount sufficient to produce a desired effect, e.g., an amount sufficient to alter the microbial content of a subject's microbiota.

The term "therapeutically effective amount" is an amount that is effective to ameliorate a symptom of a disease. A therapeutically effective amount can be a "prophylactically effective amount" as prophylaxis can be considered therapy.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, inhibiting substantially, slowing, or reversing the progression of a condition, substantially ameliorating clinical or aesthetical symptoms of a condition.

As used herein, the term "preventing" includes completely or substantially reducing the likelihood or occurrence or the severity of initial clinical or aesthetical symptoms of a condition.

As used herein, the term "about" includes variation of up to approximately +/−10% and that allows for functional equivalence in the product.

As used herein, the term "colony-forming unit" or "cfu" is an individual cell that is able to clone itself into an entire colony of identical cells.

As used herein all percentages are weight percent unless otherwise indicated.

As used herein, "viable organisms" are organisms that are capable of growth and multiplication. In some embodiments, viability can be assessed by numbers of colony-forming units that can be cultured. In some embodiments viability can be assessed by other means, such as quantitative polymerase chain reaction.

The term "derived from" includes material isolated from the recited source, and materials obtained using the isolated materials (e.g., cultures of microorganisms made from microorganisms isolated from the recited source).

"Microbiota" refers to the community of microorganisms that occur (sustainably or transiently) in and on an animal subject, typically a mammal such as a human, including eukaryotes, archaea, bacteria, and viruses (including bacterial viruses i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a gastrointestinal pathogen or may be at risk of developing or transmitting to others an infection due to a gastrointestinal pathogen.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

As used herein "heterologous" designates organisms to be administered that are not naturally present in the same proportions as in the therapeutic composition as in subjects to be treated with the therapeutic composition. These can be organisms that are not normally present in individuals in need of the composition described herein, or organisms that are not present in sufficient proportion in said individuals. These organisms can comprise a synthetic composition of organisms derived from separate plant sources or can comprise a composition of organisms derived from the same plant source, or a combination thereof.

Compositions disclosed herein can be used to treat obesity and metabolic syndrome. As defined herein "obesity" indicates a condition where the subject's body mass index is 30 or higher.

As used herein "metabolic syndrome" indicates a syndrome whose characterizing symptoms include high blood pressure, high blood sugar, excess body fat around the waist, and abnormal cholesterol levels.

As used herein, "diabetes" indicates diabetes mellitus.

Controlled-release refers to delayed release of an agent, from a composition or dosage form in which the agent is released according to a desired profile in which the release occurs after a period of time.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

As used herein GOS indicates one or more galacto-oligosaccharides and FOS indicates one or more fructo-oligosaccharide.

The following abbreviations are used in this specification and/or Figures: ac=acetic acid; but=butyric acid; ppa=propionic acid.

Prebiotic and Probiotic Compositions

In certain embodiments, compositions of the invention comprise probiotic compositions formulated for administration or consumption, with a prebiotic and any necessary or useful excipient. In other embodiments, provided herein are probiotic compositions formulated for consumption without a prebiotic. Probiotic compositions are preferably isolated from foods normally consumed raw and isolated for cultivation. Preferably, microbes are isolated from different foods normally consumed raw, but multiple microbes from the same food source may be used.

It is known to those of skill in the art how to identify microbial strains. Bacterial strains are commonly identified by 16S rRNA gene sequence. Fungal species can be identified by sequence of the internal transcribed space (ITS) regions of rDNA.

One of skill in the art will recognize that the 16S rRNA gene and the ITS region comprise a small portion of the overall genome, and so sequence of the entire genome (whole genome sequence) may also be obtained and compared to known species.

Additionally, multi-locus sequence typing (MLST) is known to those of skill in the art. This method uses the sequences of 7 known bacterial genes, typically 7 housekeeping genes, to identify bacterial species based upon sequence identity of known species as recorded in the publically available PubMLST database. Housekeeping genes are genes involved in basic cellular functions. Examples of MLST gene sequences are provided for DP1, DP3, DP9, DP22, DP53, and DP67-DP71.

In certain embodiments, bacterial entities of the invention are identified by comparison of the 16S rRNA sequence to those of known bacterial species, as is well understood by those of skill in the art. In certain embodiments, fungal species of the invention are identified based upon comparison of the ITS sequence to those of known species (Schoch et al PNAS 2012). In certain embodiments, microbial strains of the invention are identified by whole genome sequencing and subsequent comparison of the whole genome sequence to a database of known microbial genome sequences. While microbes identified by whole genome sequence comparison, in some embodiments, are described and discussed in terms of their closest defined genetic match, as indicated by 16S rRNA sequence, it should be understood that these microbes are not identical to their closest genetic match and are novel microbial entities. This can be shown by examining the Average Nucleotide Identity (ANI) of microbial entities of interest as compared to the reference strain that most closely matches the genome of the microbial entity of interest. ANI is further discussed in example 6.

In other embodiments, microbial entities described herein are functionally equivalent to previously described strains with homology at the 16S rRNA or ITS region. In certain embodiments, functionally equivalent bacterial strains have 95% identity at the 16S rRNA region and functionally equivalent fungal strains have 95% identity at the ITS region. In certain embodiments, functionally equivalent bacterial strains have 96% identity at the 16S rRNA region and functionally equivalent fungal strains have 96% identity at the ITS region. In certain embodiments, functionally equivalent bacterial strains have 97% identity at the 16S rRNA region and functionally equivalent fungal strains have 97% identity at the ITS region. In certain embodiments, functionally equivalent bacterial strains have 98% identity at the 16S rRNA region and functionally equivalent fungal strains have 98% identity at the ITS region. . In certain embodiments, functionally equivalent bacterial strains have 99% identity at the 16S rRNA region and functionally equivalent fungal strains have 99% identity at the ITS region. In certain embodiments, functionally equivalent bacterial strains have 99.5% identity at the 16S rRNA region and functionally equivalent fungal strains have 99.5% identity at the ITS region. In certain embodiments, functionally equivalent bacterial strains have 100% identity at the 16S rRNA region and functionally equivalent fungal strains have 100% identity at the ITS region.

16S rRNA sequences for strains tolerant of metformin (described in table 7) are found in seq ID Nos. 1-63. 16S rRNA is one way to classify bacteria into operational taxonomic units (OTUs). Bacterial strains with 97% sequence identity at the 16S rRNA locus are considered to belong to the same OTU. A similar calculation can be done with fungi using the ITS locus in place of the bacterial 16S rRNA sequence.

In some embodiments, the invention provides a fermented probiotic composition for the treatment of diabetes, obesity, and metabolic syndrome comprising a mixture of *Pediococcus pentosaceus* and/or *Leuconostoc mesenteroides*, combined with non-lactic acid bacteria isolated or identified from samples described in Table 3 or described in Table 4. In some embodiments, the invention provides a fermented probiotic composition for the treatment of diabetes, obesity, and metabolic syndrome comprising a mixture of *Pediococcus pentosaceus* and/or *Leuconostoc mesenteroides* and at least one non-lactic acid bacterium, preferably a bacterium classified as a gamma proteobacterium or a filamentous fungus or yeast. Some embodiments comprise the fermented probiotic being in a capsule or microcapsule adapted for enteric delivery. In some embodiments, the probiotic regimen complements an anti-diabetic regimen.

The compositions disclosed herein are derived from edible plants and can comprise a mixture of microorganisms, comprising bacteria, fungi, archaea, and/or other indigenous or exogenous microorganisms, all of which work together to form a microbial ecosystem with a role for each of its members.

In some embodiments, species of interest are isolated from plant-based food sources normally consumed raw. These isolated compositions of microorganisms from individual plant sources can be combined to create a new mixture of organisms. Particular species from individual plant sources can be selected and mixed with other species cultured from other plant sources, which have been similarly isolated and grown. In some embodiments, species of interest are grown in pure cultures before being prepared for consumption or administration. In some embodiments, the organisms grown in pure culture are combined to form a synthetic combination of organisms.

In some embodiments, the microbial composition comprises proteobacteria or gamma proteobacteria. In some embodiments, the microbial composition comprises several species of *Pseudomonas*. In some embodiments, species from another genus are also present. In some embodiments, a species from the genus *Duganella* is also present. In some embodiments of said microbial composition, the population comprises at least three unique isolates selected from the group consisting of *Pseudomonas, Acinetobacter, Aeromonas, Curtobacterium, Escherichia, Lactobacillus, Leuconostoc, Pediococcus, Serratia, Streptococcus*, and *Stenotrophomonas*. In some embodiments, the bacteria are selected based upon their ability to modulate production of one or more branch chain fatty acids, short chain fatty acids, and/or flavones in a mammalian gut.

In some embodiments, microbial compositions comprise isolates that are capable of modulating production or activity of the enzymes involved in fatty acid metabolism, such as acetolactate synthase I, N-acetylglutamate synthase, acetate kinase, Acetyl-CoA synthetase, acetyl-CoA hydrolase, Glucan 1,4-alpha-glucosidase, or Bile acid symporter Acr3.

In some embodiments, the administered microbial compositions colonize the treated mammal's digestive tract. In some embodiments, these colonizing microbes comprise bacterial assemblages present in whole food plant-based diets. In some embodiments, these colonizing microbes comprise *Pseudomonas* with a diverse species denomination that is present and abundant in whole food plant-based diets. In some embodiments, these colonizing microbes reduce free fatty acids absorbed into the body of a host by absorbing the free fatty acids in the gastrointestinal tract of mammals. In some embodiments, these colonizing microbes comprise genes encoding metabolic functions related to desirable health outcomes such as increased efficacy of anti-diabetic treatments, lowered BMI, lowered inflammatory metabolic indicators, etc.

Some embodiments comprise bacteria that are not completely viable but act by releasing metabolites that act in the gastro-intestinal tract of a patient promoting weight loss, increased efficacy of diabetic regimens, or other desirable outcome. Some embodiments comprise a prebiotic composition derived from metabolites present in whole food plant-based materials, identified and enriched as part of the formula for oral delivery.

Prebiotics

Prebiotics, in accordance with the teachings of this disclosure, comprise compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect a subject's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics help probiotics flourish in the gastrointestinal tract, and accordingly, their health benefits are largely indirect. Metabolites generated by colonic fermentation by intestinal microflora, such as short-chain fatty acids, can play important functional roles in the health of the host. Prebiotics can be useful agents for enhancing the ability of intestinal microflora to provide benefits to their host.

Prebiotics, in accordance with the embodiments of this invention, include, without limitation, mucopolysaccharides, oligosaccharides, polysaccharides, amino acids, vitamins, nutrient precursors, proteins, and combinations thereof.

According to particular embodiments, compositions comprise a prebiotic comprising a dietary fiber, including, without limitation, polysaccharides and oligosaccharides. These compounds have the ability to increase the number of probiotics, and augment their associated benefits. For example, an increase of beneficial *Bifidobacteria* likely changes the intestinal pH to support the increase of *Bifidobacteria*, thereby decreasing pathogenic organisms.

Non-limiting examples of oligosaccharides that are categorized as prebiotics in accordance with particular embodiments include galactooligosaccharides, fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments, compositions comprise a prebiotic comprising an amino acid.

Prebiotics are found naturally in a variety of foods including, without limitation, cabbage, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans). Generally, according to particular embodiments, compositions comprise a prebiotic present in a sweetener composition or functional sweetened composition in an amount sufficient to promote health and wellness.

In particular embodiments, prebiotics also can be added to high-potency sweeteners or sweetened compositions. Non-limiting examples of prebiotics that can be used in this manner include fructooligosaccharides, xylooligosaccharides, galactooligosaccharides, and combinations thereof.

Many prebiotics have been discovered from dietary intake including, but not limited to: antimicrobial peptides, polyphenols, Okara (soybean pulp by product from the manufacturing of tofu), polydextrose, lactosucrose, malto-oligosaccharides, gluco-oligosaccharides (GOS), fructo-oligosaccharides (FOS), xantho-oligosaccharides, soluble dietary fiber in general. Types of soluble dietary fiber include, but are not limited to, psyllium, pectin, or inulin.

Phytoestrogens (plant-derived isoflavone compounds that have estrogenic effects) have been found to have beneficial growth effects of intestinal microbiota through increasing microbial activity and microbial metabolism by increasing the blood testosterone levels, in humans and farm animals. Phytoestrogen compounds include but are not limited to: Oestradiol, Daidzein, Formononetin, Biochainin A, Genistein, and Equol.

Dosage for the compositions described herein are deemed to be "effective doses," indicating that the probiotic or prebiotic composition is administered in a sufficient quantity to alter the physiology of a subject in a desired manner. In some embodiments, the desired alterations include reducing obesity, and or metabolic syndrome, and sequelae associated with these conditions. In some embodiments, the desired alterations are promoting rapid weight gain in livestock. In some embodiments, the prebiotic and probiotic compositions are given in addition to an anti-diabetic regimen.

FOS, GOS, and Other Appropriate Polysaccharide Formulations

Formulations

In an aspect, prebiotic compositions for the treatment of T2D, obesity and metabolic syndrome are provided. In an embodiment a prebiotic composition comprises inulin, FOS, lactulose, GOS, raffinose, stachyose, or a combination thereof. In addition, other plant-derived polysaccharides such as xylan, pectin, isomalto-oligosaccharides, gentio-oligosaccharides, 4-O-methyl glucuronoxylan (GX), neutral arabinoxylan (AX), heteroxylan (HX) can be combined with the probiotics to enhance bacterial metabolic function. Some of these can be derived from plant material found in the plant host from which the probiotics were isolated (i.e., the "cognate" plant). In some embodiments the prebiotics are thus adapted to be assimilated and digested by the accompanying probiotics in a manner that recapitulates the rich complexity and variety of polysaccharides present in the cognate plant and which play a role during digestion following its consumption of an animal.

In an embodiment a prebiotic composition comprises or consists of FOS, GOS, or other appropriate polysaccharide. In another embodiment a prebiotic composition comprises FOS, GOS, or other appropriate polysaccharide, in combination with one or more digestible saccharides. Digestible saccharides are saccharides that are digestible by humans and include, but are not limited to lactose, glucose, and galactose. In an embodiment a prebiotic composition comprises FOS, GOS, or other appropriate polysaccharide, and less than 20% weight/weight of one or more digestible saccharides (e.g. lactose, glucose, or galactose). In an embodiment a prebiotic composition comprises FOS, GOS, or other appropriate polysaccharide, and less than 10% of one or more digestible saccharides. In an embodiment a prebiotic composition comprises FOS, GOS, or other appropriate polysaccharide, and less than 5% of one or more digestible saccharides. In another embodiment a prebiotic composition contains less than 5% lactose. In another embodiment a prebiotic composition contains less than 4% lactose. In another embodiment a prebiotic composition contains less than 3% lactose. In another embodiment a prebiotic composition contains less than 2% lactose. In another embodiment a prebiotic composition contains less than 1% lactose. In another embodiment a prebiotic composition contains less than 0.5% lactose. In another embodiment a prebiotic composition contains less than 0.4% lactose. In another embodiment a prebiotic composition contains less than 0.3% lactose. In another embodiment a prebiotic composition contains less than 0.2% lactose. In another embodiment a prebiotic composition contains less than 0.1% lactose. In another embodiment a prebiotic composition contains less than 0.05% lactose. In another embodiment a prebiotic composition contains less than 0.01% lactose. In another embodiment a prebiotic composition contains less than 0.005% lactose. In an embodiment a prebiotic composition comprises FOS, GOS, or other appropriate polysaccharide, and essentially no lactose. In an embodiment a prebiotic composition does not contain any lactose. In another embodiment a prebiotic composition contains FOS, GOS, or other appropriate polysaccharide, and at least one probiotic bacteria strain. In another embodiment a prebiotic composition comprises FOS, GOS, or other appropriate polysaccharide, and optionally one or more of lactose, at least one probiotic bacteria strain, or a buffer. Additional ingredients include ingredients to improve handling, preservatives, antioxidants, flavorings and the like.

In an embodiment, a prebiotic composition comprises FOS, GOS, or other appropriate polysaccharide, or a probiotic. In other embodiment, a prebiotic composition is in the form of a powder, tablet, capsule, or liquid. In an embodiment, a prebiotic composition can be administered with a dairy product and is in the form of milk or other common dairy product such as a yogurt, shake, smoothie, cheese, and the like.

In embodiments where a prebiotic composition comprises less than 100% by weight of FOS, GOS, or other appropriate polysaccharide, the remaining ingredients can be any suitable ingredients intended for the consumption of the subject in need thereof, e.g., human, including, but not limited to, other prebiotics (e.g., FOS), a buffer, one or more digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings, and the like.

Buffer Components

One or more buffers, optionally with a calcium counter ion, can also be administered in methods and compositions described herein. Any buffer suitable for consumption by the subject being treated, e.g., human, are useful for the compositions herein. The buffer can partially or wholly neutralize stomach acidity, which can, e.g., allow live bacteria to reach the gut. Buffers include citrates, phosphates, and the like. One embodiment utilizes a buffer with a calcium counter ion, such as Calcium Phosphate Tribasic. The calcium can serve to restore the calcium that many lactose intolerant subjects are missing in their diet. Calcium phosphate can protect *Lactobacillus acidophilus* from bile.

In an embodiment, a buffer such as calcium phosphate is given prior to beginning treatment with a prebiotic composition (such as a composition comprising or consisting essentially of FOS, GOS, or other appropriate polysaccharide), optionally in conjunction with administration of bacteria. In an embodiment, a buffer such as calcium phosphate is given in conjunction with treatment with a prebiotic composition (e.g., a composition comprising or consisting essentially of FOS, GOS, or other appropriate polysaccharide), for part or all of the treatment with lactose. Thus, in an embodiment, some or all doses of a prebiotic composition are accompanied by a dose of a buffer such as calcium phosphate. In an embodiment, a buffer such as calcium phosphate is given initially with a prebiotic composition (such as a composition comprising or consisting essentially of FOS, GOS, or other appropriate polysaccharide), but then the buffer use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In an embodiment, a buffer such as calcium phosphate can be given for the first two days of treatment, and then the administration of buffer is discontinued. In an embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e., calcium. In an embodiment a buffer can be used in a dose from about 2 mg to about 2000 mg, or about 4 mg to about 400 mg, or about 4 mg to about 200 mg, or about 4 mg to about 100 mg, or about 8 mg to about 50 mg, or about 10 mg to about 40 mg, or about 20 mg to about 30 mg, or about 20, 21, 22, 23, 24, 25, 26, 27, 28, 29, or 30 mg. In another embodiment a prebiotic composition further comprises an amount of a buffer from 1-50 mg, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg. In an embodiment, buffer is used in a dose of about 25 mg. In an embodiment, calcium phosphate is used in a dose of about 25 mg. The dose can be given in combination with a prebiotic composition (e.g., a composition comprising or consisting essentially of FOS, GOS, or other appropriate polysaccharide). In an embodiment, as a prebiotic composition dose increases, the dose of buffer increases as well. For example, an initial dose of a prebiotic composition can be about 0.6 g to 1.0 g, e.g., 0.8 g, given in combination with about 20-30 mg, e.g., about 25 mg, of buffer, e.g., calcium phosphate. The dose of a prebiotic composition can be increased incrementally by about 0.6 g to 1.0 g, e.g., 0.8 g, and the accompanying dose of buffer, e.g., calcium phosphate, can be increased by about 20-30 mg, e.g., about 25 mg, of buffer, e.g., calcium phosphate.

Compositions Comprising GOS and at Least One Probiotic Bacteria Strain

In an embodiment, a prebiotic composition comprises FOS, GOS, or other appropriate polysaccharide, and at least one probiotic bacteria strain. The FOS, GOS, or other appropriate polysaccharide can comprise more than 1% of the weight of the composition while the at least one probiotic bacteria strain will typically comprise less than about 10%, 5%, 4%, 3%, or 2% by weight of the compositions. For example, the FOS, GOS, or other appropriate polysaccharide can be present at about 1-99.75% by weight and the at least one probiotic bacteria strain at about 0.25-2% by weight, or the FOS, GOS, or other appropriate polysaccharide can be present at about 89-96% by weight and the bacteria at about 1.2-3.7% by weight. In an embodiment, FOS, GOS, or other appropriate polysaccharide are present at about 92% by weight and at least one probiotic bacteria strain, (e.g., *L. mesenteroides, P. pentosaceus*, or other members from Table 4), is present at about 1.5% by weight. In an embodiment, FOS, GOS, or other appropriate polysaccharide are present at about 92% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 93% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 94% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 95% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 96% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 97% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 98% by weight and at least one probiotic bacteria strain, (e.g., *L. mesenteroides, P. pentosaceus*, or other members from Table 4), is present at about 1.5% by weight. In another embodiment, FOS, GOS, or other appropriate polysaccharide are present at about 98.5% by weight and at least one probiotic bacteria strain, (e.g., *L. mesenteroides, P. pentosaceus*, or other members from Table 4), is present at about 1.5% by weight. If the at least one probiotic bacteria strain and FOS, GOS, or other appropriate polysaccharide do not make up 100% by weight of the prebiotic composition, the remaining ingredients can be any suitable ingredients intended for consumption by the subject in need thereof, e.g., human, including, but not limited to, other prebiotics (e.g., FOS), one or more buffers, digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising FOS, GOS, or Other Appropriate Polysaccharide and a Buffer In another embodiment, a prebiotic composition comprises FOS, GOS, or other appropriate polysaccharide and a buffer (e.g., calcium phosphate tribasic). For example, FOS, GOS, or other appropriate polysaccharide can be present at about 1-100% by weight and the buffer at about 0.50-4% by weight, or FOS, GOS, or other appropriate polysaccharide can be present at about 1-96% by weight and the buffer at about 1 to about 3.75% by weight. In an embodiment, FOS, GOS, or other appropriate polysaccharide are present at about 1% by weight and buffer is present at about 3% by weight. In an embodiment, FOS, GOS, or other appropriate polysaccharide are present at about 5% by weight and buffer is present at about 3% by weight. In an embodiment, FOS, GOS, or other appropriate polysaccharide are present at about 10% by weight and buffer is present at about 3% by weight. In an embodiment, FOS, GOS, or other appropriate polysaccharide are present at about 15% by weight and buffer is present at about 15% by weight. In an embodiment, FOS, GOS, or other appropriate polysaccharide are present at about 20% by weight and buffer is present at about 3% by weight. In an embodiment, FOS, GOS, or other appropriate polysaccharide are present at about 25% by weight and buffer is present at about 3% by weight. In an embodiment, FOS, GOS, or other appropriate polysaccharide are present at about 30% by weight and buffer is present at about 3% by weight. In an embodiment, FOS, GOS, or other appropriate polysaccharide are present at about 35% by weight and buffer is present at about 3% by weight. In an embodiment, FOS, GOS, or other appropriate polysaccharide are present at about 40% by weight and buffer is present at about 3% by weight. In an embodiment, FOS, GOS, or other appropriate polysaccharide are present at about 50% by weight and buffer is present at about 3% by weight. In an embodiment, FOS, GOS, or other appropriate polysaccharide are present at about 60% by weight and buffer is present at about 3% by weight. In an embodiment, FOS, GOS, or other appropriate polysaccharide are present at about 70% by weight and buffer is present at about 3% by weight. In another embodiment, FOS, GOS, or other appropriate polysaccharide are present at about 90% by weight and buffer is present at about 3% by weight. In another embodiment, FOS, GOS, or other appropriate polysaccharide are present at about 92% by weight and buffer is present at about 3% by weight. In another embodiment, FOS, GOS, or other appropriate polysaccharide are present at about 93% by weight and buffer is present at about 3% by weight. In another embodiment, FOS, GOS, or other appropriate polysaccharide are present at about 94% by weight and buffer is present at about 3% by weight. In another embodiment, FOS, GOS, or other appropriate polysaccharide are present at about 95% by weight and buffer is present at about 3% by weight. In another embodiment, FOS, GOS, or other appropriate polysaccharide are present at about 96% by weight and buffer is present at about 3% by weight. In another embodiment, FOS, GOS, or other appropriate polysaccharide are present at about 97% by weight and buffer is present at about 2% by weight. In another embodiment, FOS, GOS, or other appropriate polysaccharide are present at about 98% by weight and buffer is present at about 1% by weight. In another embodiment, FOS, GOS, or other appropriate polysaccharide are present at about 99% by weight and buffer is present at about 1% by weight. In another embodiment, FOS, GOS, or other appropriate polysaccharide are present at about 100% by weight and buffer is present at less than about 1% by weight. If the buffer and FOS, GOS, or other appropriate polysaccharide do not make up 100% by weight of the composition, the remaining ingredients can be any suitable ingredients intended for consumption by the subject (e.g., a human) including, but not limited to, probiotics (e.g., beneficial bacteria) or other prebiotics (e.g., FOS), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, a Probiotic Bacteria, and FOS, GOS, or Other Appropriate Polysaccharide In an embodiment, a prebiotic composition comprises a digestible saccharide (e.g. lactose, glucose, or galactose), a probiotic bacteria (e.g., *L. mesenteroides, P. pentosaceus*, or other members from Table 4), and FOS, GOS, or other appropriate polysaccharide. In an embodiment, lactose can be present at about 1-20% by weight, bacteria at about 0.25-20.10% by weight, and FOS, GOS, or other appropriate polysaccharide at about 1-98.75% by weight. In another embodiment lactose can be present at about 5-20% by weight, bacteria at about 0.91-1.95% by weight, and FOS, GOS, or other appropriate polysaccharide at about 1 to about 96% by weight. In another embodiment, lactose is present at about 20% by weight, bacteria at about 1.5% by weight, and FOS, GOS, or other appropriate polysaccharide are present at about 1% by weight. In another embodiment, lactose is present at about 20% by weight, bacteria at about 1.5% by weight, and FOS, GOS, or other appropriate polysaccharide are present at about 50% by weight. In another embodiment, lactose is present at about 20% by weight, bacteria at about 1.5% by weight, and FOS, GOS, or other appropriate polysaccharide are present at about 60% by weight. In another embodiment, lactose is present at about 20% by weight, bacteria at about 1.5% by weight, and FOS, GOS, or other appropriate polysaccharide are present at about 70% by weight. In another embodiment, lactose is present at about 5% by weight, bacteria at about 1.5% by weight, and FOS, GOS, or other appropriate polysaccharide are present at about 90% by weight. In another embodiment, lactose is present at about 5% by weight, bacteria at about 1.5% by weight, and FOS, GOS, or other appropriate polysaccharide are present at about 92% by weight. In another embodiment, lactose is present at about 5% by weight, bacteria at about 1.5% by weight, and FOS, GOS, or other appropriate polysaccharide are present at about 93% by weight. In another embodiment, lactose is present at about 5% by weight, bacteria at about 1% by weight, and FOS, GOS, or other appropriate polysaccharide are present at about 94% by weight. In another embodiment, lactose is present at about 4.5% by weight, bacteria at about 1.5% by weight, and FOS, GOS, or other appropriate polysaccharide are present at about 94% by weight. In another embodiment, lactose is present at about 4.5% by weight, bacteria at about 0.5% by weight, and FOS, GOS, or other appropriate polysaccharide are present at about 95% by weight. In another embodiment, lactose is present at about 3.5% by weight, bacteria at about 0.5% by weight, and FOS, GOS, or other appropriate polysaccharide are present at about 96% by weight. In another embodiment, lactose is present at about 2.5% by weight, bacteria at about 0.5% by weight, and FOS, GOS, or other appropriate polysaccharides are present at about 97% by weight. In another embodiment, lactose is present at about 1.5% by weight, bacteria at about 0.5% by weight, and FOS, GOS, or other appropriate polysaccharide are present at about 98% by weight. In another embodiment, lactose is present at about 0.5% by weight, bacteria at about 0.5% by weight, and FOS, GOS, or other appropriate polysaccharide are present at about 99% by weight. If the bacteria, FOS, GOS, or other appropriate polysaccharide and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising FOS, GOS, or Other Appropriate Polysaccharide, a Probiotic Bacteria, and Buffer In an embodiment, a prebiotic composition comprises FOS, GOS, or other appropriate polysaccharide, a probiotic bacteria strain, and buffer. In an embodiment, FOS, GOS, or other appropriate polysaccharide can be present at about 1-100% by weight, a probiotic bacteria strain at about 0.25-2% by weight, and the buffer at about 0.50-4% by weight. In another embodiment, FOS, GOS, or other appropriate polysaccharide can be present at about 1-95% by weight, a probiotic bacteria strain at about 0.91-1.95% by weight, and the buffer at about 1.2-30.75% by weight. In another embodiment, FOS, GOS, or other appropriate polysaccharide are present at about 1% by weight, a probiotic bacteria strain at about 1.5% by weight, and buffer is present at about 3% by weight. In another embodiment, FOS, GOS, or other appropriate polysaccharide are present at about 5% by weight, a probiotic bacteria strain at about 1.5% by weight, and buffer is present at about 3% by weight. In another embodiment, FOS, GOS, or other appropriate polysaccharide are present at about 10% by weight, a probiotic bacteria strain at about 1.5% by weight, and buffer is present at about 3% by weight. In another embodiment, FOS, GOS, or other appropriate polysaccharide are present at about 15% by weight, a probiotic bacteria strain at about 1.5% by weight, and buffer is present at about 3% by weight. In another embodiment, FOS, GOS, or other appropriate polysaccharide are present at about 20% by weight, a probiotic bacteria strain at about 1.5% by weight, and buffer is present at about 3% by weight. In another embodiment, FOS, GOS, or other appropriate polysaccharide are present at about 25% by weight, a probiotic bacteria strain at about 1.5% by weight, and buffer is present at about 3% by weight. In another embodiment, FOS, GOS, or other appropriate polysaccharide are present at about 30% by weight, a probiotic bacteria strain at about 1.5% by weight, and buffer is present at about 3% by weight. In another embodiment, FOS, GOS, or other appropriate polysaccharide are present at about 35% by weight, a probiotic bacteria strain at about 1.5% by weight, and buffer is present at about 3% by weight. In another embodiment, FOS, GOS, or other appropriate polysaccharide are present at about 40% by weight, a probiotic bacteria strain at about 1.5% by weight, and buffer is present at about 3% by weight. In another embodiment, FOS, GOS, or other appropriate polysaccharide are present at about 50% by weight, a probiotic bacteria strain at about 1.5% by weight, and buffer is present at about 3% by weight. In another embodiment, FOS, GOS, or other appropriate polysaccharide are present at about 60% by weight, a probiotic bacteria strain at about 1.5% by weight, and buffer is present at about 3% by weight. In another embodiment, FOS, GOS, or other appropriate polysaccharide are present at about 70% by weight, a probiotic bacteria strain at about 1.5% by weight, and buffer is present at about 3% by weight. In another embodiment, FOS, GOS, or other appropriate polysaccharide are present at about 90% by weight, a probiotic bacteria strain at about 1.5% by weight, and buffer is present at about 3% by weight. In another embodiment, FOS, GOS, or other appropriate polysaccharide are present at about 92% by weight, a probiotic bacteria strain at about 1.5% by weight, and buffer is present at about 3% by weight. In another embodiment, FOS, GOS, or other appropriate polysaccharide are present at about 93% by weight, a probiotic bacteria strain at about 1.5% by weight, and buffer is present at about 3% by weight. In another embodiment, FOS, GOS, or other appropriate polysaccharide are present at about 94% by weight, a probiotic bacteria strain at about 1.5% by weight, and buffer is present at about 3% by weight. In another embodiment, FOS, GOS, or other appropriate polysaccharide are present at about 95% by weight, a probiotic bacteria strain at about 1.5% by weight, and buffer is present at about 3% by weight. In another embodiment, FOS, GOS, or other appropriate polysaccharide are present at about 96% by weight, a probiotic bacteria strain at about 1.5% by weight, and buffer is present at about 2% by weight. In another embodiment, FOS, GOS, or other appropriate polysaccharide are present at about 97% by weight, a probiotic bacteria strain at about 1.5% by weight, and buffer is present at about 1.5% by weight. In another embodiment, FOS, GOS, or other appropriate polysaccharide are present at about 99% by weight, a probiotic bacteria strain at about 0.5% by weight, and buffer is present at about 0.5% by weight. In another embodiment, FOS, GOS, or other appropriate polysaccharide are present at about 100% by weight, a probiotic bacteria strain at less than about 0.5% by weight, and buffer is present at less than about 0.5% by weight. If the probiotic bacteria strain, buffer, and FOS, GOS, or other appropriate polysaccharide do not make up 100% of the composition, the remaining ingredients can be any suitable ingredients intended for the consumption of a subject (e.g., human) including, but not limited to, other prebiotics (e.g., FOS), digestible saccharides (e.g., lactose, glucose or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, FOS, GOS, or Other Appropriate Polysaccharide, and a Buffer.

In an embodiment, a prebiotic composition comprises a digestible saccharide (e.g. lactose, glucose, or galactose), FOS, GOS, or other appropriate polysaccharide, and a buffer. For example, lactose can be present at about 1-20% by weight, FOS, GOS, or other appropriate polysaccharide at about 1-100% by weight, and the buffer at about 0.50-4% by weight, or the lactose can be present at about 5-20% by weight, FOS, GOS, or other appropriate polysaccharide at about 1-96% by weight, and the buffer at about 1.2-30.75% by weight. In an embodiment, lactose is present at about 20% by weight, FOS, GOS, or other appropriate polysaccharide at about 1% by weight, and buffer is present at about 3% by weight. In an embodiment, lactose is present at about 5% by weight, FOS, GOS, or other appropriate polysaccharide at about 1% by weight, and buffer is present at about 3% by weight. In an embodiment, lactose is present at about 20% by weight, FOS, GOS, or other appropriate polysaccharide at about 10% by weight, and buffer is present at about 3% by weight. In an embodiment, lactose is present at about 20% by weight, FOS, GOS, or other appropriate polysaccharide at about 15% by weight, and buffer is present at about 3% by weight. In an embodiment, lactose is present at about 20% by weight, FOS, GOS, or other appropriate polysaccharide at about 20% by weight, and buffer is present at about 3% by weight. In an embodiment, lactose is present at about 20% by weight, FOS, GOS, or other appropriate polysaccharide at about 25% by weight, and buffer is present at about 3% by weight. In an embodiment, lactose is present at about 20% by weight, FOS, GOS, or other appropriate polysaccharide at about 30% by weight, and buffer is present at about 3% by weight. In an embodiment, lactose is present at about 20% by weight, FOS, GOS, or other appropriate polysaccharide at about 35% by weight, and buffer is present at about 3% by weight. In an embodiment, lactose is present at about 20% by weight, FOS, GOS, or other appropriate polysaccharide at about 40% by weight, and buffer is present at about 3% by weight. In an embodiment, lactose is present at about 20% by weight, FOS, GOS, or other appropriate polysaccharide at about 50% by weight, and buffer is present at about 3% by weight. In an embodiment, lactose is present at about 20% by weight, FOS, GOS, or other appropriate polysaccharide at about 60% by weight, and buffer is present at about 3% by weight. In an embodiment, lactose is present at about 20% by weight, FOS, GOS, or other appropriate polysaccharide at about 70% by weight, and buffer is present at about 3% by weight. In another embodiment, lactose is present at about 5% by weight, FOS, GOS, or other appropriate polysaccharide at about 90% by weight, and buffer is present at about 3% by weight. In another embodiment, lactose is present at about 5% by weight, FOS, GOS, or other appropriate polysaccharide at about 92% by weight, and buffer is present at about 3% by weight. In another embodiment, lactose is present at about 4% by weight, FOS, GOS, or other appropriate polysaccharide at about 93% by weight, and buffer is present at about 3% by weight. In another embodiment, lactose is present at about 3% by weight, FOS, GOS, or other appropriate polysaccharide at about 94% by weight, and buffer is present at about 3% by weight. In another embodiment, lactose is present at about 2% by weight, FOS, GOS, or other appropriate polysaccharide at about 95% by weight, and buffer is present at about 3% by weight. In another embodiment, lactose is present at about 1% by weight, FOS, GOS, or other appropriate polysaccharide at about 96% by weight, and buffer is present at about 3% by weight. If a suitable prebiotic, buffer and lactose do not make up 100% of the composition by weight, the remaining ingredients can be any suitable ingredients intended for consumption by a subject (e.g., human) including, but not limited to, bacteria, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Compositions Comprising a Digestible Saccharide, Bacteria, GOS, and a Buffer

In an embodiment, a composition comprises a digestible saccharide (e.g. lactose, glucose, or galactose), bacteria, FOS, GOS, or other appropriate polysaccharide, and buffer. For example, lactose can be present at about 1-20% by weight, bacteria at about 0.25-2.10% by weight, FOS, GOS, or other appropriate polysaccharide at about 1-100% by weight, and the buffer at about 0.50-4% by weight, or the lactose can be present at about 5-20% by weight, bacteria at about 0.91-1.95% by weight, FOS, GOS, or other appropriate polysaccharide at about 70-95% by weight, and the buffer at about 1.2-30.75% by weight. In an embodiment, lactose is present at about 20% by weight, bacteria at about 1.47% by weight, FOS, GOS, or other appropriate polysaccharide at about 1% by weight, and buffer is present at about 3% by weight. In an embodiment, lactose is present at about 20% by weight, bacteria at about 1.47% by weight, FOS, GOS, or other appropriate polysaccharide at about 10% by weight, and buffer is present at about 3% by weight. In an embodiment, lactose is present at about 20% by weight, bacteria at about 1.47% by weight, FOS, GOS, or other appropriate polysaccharide at about 15% by weight, and buffer is present at about 3% by weight. In an embodiment, lactose is present at about 20% by weight, bacteria at about 1.47% by weight, FOS, GOS, or other appropriate polysaccharide at about 20% by weight, and buffer is present at about 3% by weight. In an embodiment, lactose is present at about 20% by weight, bacteria at about 1.47% by weight, FOS, GOS, or other appropriate polysaccharide at about 25% by weight, and buffer is present at about 3% by weight. In an embodiment, lactose is present at about 20% by weight, bacteria at about 1.47% by weight, FOS, GOS, or other appropriate polysaccharide at about 30% by weight, and buffer is present at about 3% by weight. In an embodiment, lactose is present at about 20% by weight, bacteria at about 1.47% by weight, FOS, GOS, or other appropriate polysaccharide at about 35% by weight, and buffer is present at about 3% by weight. In an embodiment, lactose is present at about 20% by weight, bacteria at about 1.47% by weight, FOS, GOS, or other appropriate polysaccharide at about 40% by weight, and buffer is present at about 3% by weight. In an embodiment, lactose is present at about 20% by weight, bacteria at about 1.47% by weight, FOS, GOS, or other appropriate polysaccharide at about 50% by weight, and buffer is present at about 3% by weight. In an embodiment, lactose is present at about 20% by weight, bacteria at about 1.47% by weight, FOS, GOS, or other appropriate polysaccharide at about 60% by weight, and buffer is present at about 3% by weight. In an embodiment, lactose is present at about 20% by weight, bacteria at about 1.47% by weight, FOS, GOS, or other appropriate polysaccharide at about 70% by weight, and buffer is present at about 3% by weight. In an embodiment, lactose is present at about 5% by weight, bacteria at about 1.47% by weight, FOS, GOS, or other appropriate polysaccharide at about 90% by weight, and buffer is present at about 3% by weight. In an embodiment, lactose is present at about 3% by weight, bacteria at about 1.47% by weight, FOS, GOS, or other appropriate polysaccharide at about 92% by weight, and buffer is present at about 3% by weight. In an embodiment, lactose is present at about 2% by weight, bacteria at about 1.47% by weight, FOS, GOS, or other appropriate polysaccharide at about 93% by weight, and buffer is present at about 3% by weight. In an embodiment, lactose is present at about 1% by weight, bacteria at about 1.47% by weight, FOS, GOS, or other appropriate polysaccharide at about 94% by weight, and buffer is present at about 3% by weight. In an embodiment, lactose is present at about 0.5% by weight, bacteria at about 1.47% by weight, FOS, GOS, or other appropriate polysaccharide at about 95% by weight, and buffer is present at about 3% by weight. If the bacteria, FOS, GOS, or other, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

Additional Ingredients

Additional ingredients include ingredients to improve handling, preservatives, antioxidants, flavorings and the like. For example, in an embodiment, a prebiotic composition in powdered form can include flavorings such that when mixed in a liquid (e.g., water), the powder can flavor the liquid with various flavors such as grape, strawberry, lime, lemon, chocolate, and the like. In an embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

Methods of Use

Included within the scope of this disclosure are methods for treatment of diabetes, obesity, and/or metabolic syndrome.

These methods include treatment with a prebiotic composition (e.g., a composition comprising or consisting of FOS, GOS, or other appropriate polysaccharide), optionally in conjunction with a probiotic composition, one or more digestible saccharides (e.g. lactose, glucose, or galactose), a buffer, or a combination thereof. These methods optionally are used in combination with other treatments to reduce diabetes, obesity, and/or metabolic syndrome. Any suitable treatment for the reduction of diabetes, obesity and/or metabolic syndrome can be used. In some embodiments the additional treatment is administered before, during, or after treatment with a prebiotic composition, or any combination thereof. In an embodiment, when diabetes, obesity and/or metabolic syndrome are not completely or substantially completely eliminated by treatment with a prebiotic composition, the additional treatment is administered after prebiotic treatment is terminated. The additional treatment is used on an as-needed basis.

In an embodiment, treating diabetes further involves administration of any one or combination of known anti-diabetic medications. These include, but are not limited to, metformin, Acarbose, Miglitol, Voglibose, Sitagliptin, Saxagliptin, Liraglutide, Pioglitazone, dipeptidyl peptidase-4 (DPP4)-inhibitors, glucagon-like peptide-1 (GLP-1) receptor analogs, alpha glucosidase inhibitors, thiazolidinedione, and sodium/glucose cotransporter 2 (SGLT2) inhibitors.

In an embodiment a subject to be treated for one or more symptoms of obesity and/or metabolic syndrome is a human. In an embodiment the human subject is a preterm newborn, a full-term newborn, an infant up to one year of age, a young child (e.g., 1 yr to 12 yrs), a teenager, (e.g., 13-19 yrs), an adult (e.g., 20-64 yrs), a pregnant woman, or an elderly adult (65 yrs and older).

The administration of the microbial composition can be accomplished orally or rectally, although administration is not limited to these methods. In some embodiments, the microbial composition is administered orally. In some embodiments, the microbial composition is delivered rectally. In some embodiments, the administration of the microbial composition occurs at regular intervals. In some embodiments, the administration occurs daily.

The microbial composition can be administered via typical pharmacological means, such as slurries, capsules, microcapsules, or solutions, although means of administration are not limited to these methods. In some embodiments, an enteric capsule or enteric microcapsule is used. In some embodiments the pharmaceutical composition involving the microbial composition described herein will be fresh or frozen prior to application. In some embodiments, said pharmaceutical composition will be lyophilized or otherwise treated to increase stability or otherwise obtain a benefit from said treatment.

In some embodiments, the microbial composition is administered with an effective amount of an anti-diabetic drug or along with an effective anti-diabetic drug regimen.

Timing and Dose of Probiotics and Prebiotics

In an embodiment, probiotic bacteria, such as *Lactobacillus, Leuconostoc*, or *Pediococcus* are given prior to beginning treatment with a prebiotic. In an embodiment, probiotic bacteria, such as *L. mesenteroides*, are given in conjunction with treatment with a prebiotic (e.g., comprising or consisting essentially of FOS, GOS, or other appropriate polysaccharide), for part or all of the duration of treatment with the prebiotic. Thus, in an embodiment, some or all doses of a prebiotic (e.g., comprising or consisting essentially of FOS, GOS, or other appropriate polysaccharide) are accompanied by a dose of bacteria, e.g., live cultured bacteria, e.g., *L. mesenteroides*. In an embodiment, bacteria, e.g., *L. mesenteroides*, are given initially with a prebiotic (e.g., comprising or consisting essentially of FOS, GOS, or other appropriate polysaccharide), but then use of the bacteria is discontinued. For example, the initial one, two, three, four, five, six, seven, eight, nine, ten, or more than ten days of treatment with a prebiotic (e.g., comprising or consisting essentially of FOS, GOS, or other appropriate polysaccharide) further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with a prebiotic (comprising or consisting essentially of FOS, GOS, or other appropriate polysaccharide) is terminated. The bacteria can be taken for any suitable period after the termination of treatment with prebiotic and can be taken daily or at regular or irregular intervals. Doses can be as described below.

Any suitable amount of probiotic per serving can be used that allows an effective microbiota in the GI as demonstrated by a reduction in weight or amelioration of other signs of metabolic syndrome measured by insulin resistance, HbA1c, body mass index (BMI), visceral adiposity, and dyslipidemia. Typically, probiotics are given as live cultured bacteria. Herein measurement is mg indicate dry weight of purified bacteria. The dose can be about 0.001 mg to about 1 mg, or about 0.5 mg to about 5 mg, or about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 50 mg to about 200 mg, or about 200 mg to about 1000 mg, or about 10, 11, 12, 12.5, 13, 14, or 15 mg per serving. In an embodiment, *L. mesenteroides* used in a dose of about 12.5 mg per serving. The probiotic bacteria can also be about 0.5% w/w to about 20% w/w of the final composition. The dose of probiotics can be given in combination with one or more prebiotics. Another common way of specifying the amount of probiotics is as a colony forming unit (cfu). In an embodiment, one or more strains of probiotic bacteria are ingested in an amount of about 1×10^6 to about 1×10^9 cfu's, or about 1×10^6 cfu's to about 1×10^9 cfu's, or about 10×10^6 cfu's to about 0.5×10^9 cfu's, or about 113×10^5 cfu's to about 113×10^6 cfu's, or about 240×10^5 cfu's to about 240×10^6 cfu's, or about 0.3×10^9 cfu's per serving. In another embodiment, one or more strains of probiotic bacteria are administered as part of a dairy product. In an embodiment, a typical serving size for a dairy product such as fluid milk is about 240 g. In other embodiments, a serving size is about 245 g, or about 240 g to about 245 g, or about 227 to about 300 g. In an embodiment the dairy product is yogurt. Yogurt can have a serving size of about 4 oz, or about 6 oz, or about 8 oz, or about 4 oz to 10 oz, or about half cup, or about 1 cup, or about 113 g, or about 170 g, or about 227 g, or about 245 g or about 277 g, or about 100 g to about 350 g.

In an embodiment, probiotic bacteria are given as live cultured bacteria, e.g., in combination with a prebiotic (e.g., comprising or consisting essentially of FOS, GOS, or other appropriate polysaccharide) and, optionally, other substances. The dose can be about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 10, 11, 12, 12.5, 13, 14, or 15 mg of probiotic bacterial cell culture dry weight. In an embodiment, *Lactobacillus* (i.e. *L. acidophilus*), *Leuconostoc* (i.e. *L. mes-*

*enteroides*), or *Pediococcus* (i.e. *P. pentosaceus*), is used in a dose of about 12.5 mg. In an embodiment, as the administration of a prebiotic (e.g., comprising or consisting essentially of FOS, GOS, or other appropriate polysaccharide) dose to a subject increases, the dose of bacteria increases as well. For example, an initial dose of a prebiotic (e.g., comprising or consisting essentially of FOS, GOS, or other appropriate polysaccharides) can be about 0.6 g to 1.0 g, e.g., 0.8 g, given in combination with about 10-15 mg, e.g., about 12.5 mg, of *L. mesenteroides*. The dose of a prebiotic (e.g., comprising or consisting essentially of FOS, GOS, or other appropriate polysaccharide) can be increased incrementally by about 0.6 g to 1.0 g, e.g., 0.8 g, and the accompanying dose of *L. mesenteroides* can be increased by about 10-15 mg, e.g., about 12.5 mg, of *L. mesenteroides*.

Timing and Dosage of Probiotic and Anti-Diabetic Drugs

In an embodiment, probiotic bacteria, such as *L. mesenteroides, P. pentosaceus*, are given prior to beginning treatment with an anti-diabetic drug. In an embodiment, probiotic bacteria, such as *L. mesenteroides, P. pentosaceus*, are given in conjunction with treatment with an anti-diabetic drug, such as metformin, for part or all of the treatment with the anti-diabetic drug. Thus, in an embodiment, some or all doses of an anti-diabetic drug are accompanied by a dose of bacteria, e.g., live cultured bacteria, e.g., *L. mesenteroides, P. pentosaceus*. In an embodiment, bacteria, e.g., *L. mesenteroides, P. pentosaceus*, are given initially with an anti-diabetic therapy, but then use of the bacteria is discontinued. For example, the initial one, two, three, four, five, six, seven, eight, nine, ten, or more than ten days of treatment with an anti-diabetic drug further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with an anti-diabetic drug is terminated. The bacteria can be taken for any suitable period after the termination of treatment with the anti-diabetic drug and can be taken daily or at regular or irregular intervals. Doses can be as described below. Any suitable amount of probiotic per serving can be used that allows an effective microbiota in the GI as demonstrated by a reduction in weight or amelioration of other signs of metabolic syndrome measured by one or more of: insulin resistance, HbA1c, body mass index (BMI), visceral adiposity, and dyslipidemia.

Examples of antidiabetic combination partners are metformin; sulphonylureas such as glibenclamide, tolbutamide, glimepiride, glipizide, gliquidon, glibornuride and gliclazide; nateglinide; repaglinide; thiazolidinediones such as rosiglitazone and pioglitazone; PPAR gamma modulators such as metaglidases; PPAR-gamma agonists such as GI 262570; PPAR-gamma antagonists; PPAR-gamma/alpha modulators such as tesaglitazar, muraglitazar, aleglitazar, indeglitazar, AVE0897 and KRP297; PPAR-gamma/alpha/delta modulators; AMPK-activators such as AICAR; acetyl-CoA carboxylase (ACC1 and ACC2) inhibitors; diacylglycerol-acetyltransferase (DGAT) inhibitors; pancreatic beta cell GPCR agonists other than GPR119 agonists; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin zinc suspension and insulin glargin; Gastric inhibitory Peptide (GIP); pramlintide, davalintide; amylin and amylin analogues or GLP-1 and GLP-1 analogues such as Exendin-4, e.g. exenatide, exenatide LAR, liraglutide, taspoglutide, AVE-0010, LY-2428757, LY-2189265, semaglutide or albiglutide; SGLT2-inhibitors such as KGT-1251; inhibitors of protein tyrosine-phosphatase (e.g., trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors, such as e.g. dapagliflozin, sergliflozin, atigliflozin, larnagliflozin or canagliflozin (or compound of formula (I-S) or (I-K) from WO 2009/035969); KV 1.3 channel inhibitors; GPR40 modulators; SCD-1 inhibitors; dopamine receptor agonists (bromocriptine mesylate [Cycloset]); and CCR-2 antagonists.

Metformin is usually given in doses varying from about 250 mg to 3000 mg, particularly from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day.

Particular dosage strengths may be 250, 500, 625, 750, 850 and 1000 mg of metformin hydrochloride.

Dosage Forms

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

In an embodiment, compositions described herein comprise one or more excipients. In an embodiment, the one or more excipients comprise one or more antiadherents, one or more binders, one or more coatings, one or more disintegrants, one or more fillers, one or more flavors, one or more colors, one or more lubricants, one or more glidants, one or more sorbents, one or more preservatives, one or more sweeteners, or a combination thereof. In an embodiment, the antiadherent is magnesium stearate. In an embodiment, the one or more binders are cellulose, microcrystalline cellulose, hydroxypropyl cellulose, xylitol, sorbitol, maltitiol, gelatin, polyvinylpyrrolidone, polyethylene glycol, methyl cellulose, hydroxypropyl methylcellulose, or a combination thereof. In an embodiment, the one or more coatings are a hydroxypropyl methylcellulose film, shellac, corn protein zein, gelatin, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, stearic acid, or a combination thereof. In an embodiment, the one or more disintegrants are crosslinked polyvinylpyrrolidone (crospovidone), crosslinked sodium carboxymethyl cellulose (croscarmellose sodium), sodium starch glycolate, or a combination thereof. In an embodiment, the one or more fillers are calcium carbonate, magnesium stearate, dibasic calcium phosphate, cellulose, vegetable oil, vegetable fat, or a combination thereof. In an embodiment, the one or more flavors are mint, cherry, anise, peach, apricot, licorice, raspberry, vanilla, or a combination thereof. In an embodiment, the one or more lubricants are talc, silica, vegetable stearin, magnesium stearate, stearic acid, or a combination thereof. In an embodiment, the one or more glidants are fumed silica, talc, magnesium carbonate, or a combination thereof. In an embodiment, the one or more sorbents are fatty acids, waxes, shellac, plastics, plant fibers, or a combination thereof. In an embodiment, the one or more preservatives are vitamin A, vitamin E, vitamin C, retinyl palmitate, selenium, cysteine, methionine, citric acid, sodium citrate, methyl paraben, propyl paraben, or a combination thereof. In an embodiment, the one or more sweeteners are stevia, sparame, sucralose, neotame, acesulfame potassium, saccharin or a combination thereof.

Oral Dosage Forms and Components

In one aspect provided herein are methods and compositions formulated for oral delivery to a subject in need thereof. In an embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof.

1. Forms

In an embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients including freeze-dried plant material serving both as prebiotic and as a filler. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents.

In an embodiment, a provided composition includes a softgel formulation. A softgel can contain a gelatin-based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In an embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach, but rather, travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel®, Aquacoat® ECD, and Metolose®); polyvinylacetate phthalate (trade name Sureteric®); and methacrylic acid (trade name Eudragit®).

In an embodiment, an enteric coated prebiotic composition is administered to a subject. In another embodiment, an enteric coated probiotic composition is administered to a subject. In another embodiment, an enteric coated probiotic and prebiotic composition is administered to a subject. In an embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In an embodiment a prebiotic composition is provided as a tablet, capsule, or caplet with an enteric coating. In an embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In an embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In an embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In an embodiment, the dosage form is a gelatin capsule having a size indicated in Table 1.

Gel Cap Sizes Allowable For Human Consumption

Empty Gelatin Capsule Physical Specifications. Note: Sizes and Volumes are Approximate.

TABLE 1

| Outer Diameter Size (mm) | Height or Locked Length (mm) | Actual Volume (ml) |
|---|---|---|
| 9.97 | 26.14 | 1.37 |
| 8.53 | 23.30 | 0.95 |
| 7.65 | 21.7 | 0.68 |
| 6.91 | 19.4 | 0.50 |
| 6.35 | 18.0 | 0.37 |
| 5.82 | 15.9 | 0.3 |
| 5.31 | 14.3 | 0.21 |
| 4.91 | 11.1 | 0.13 |

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment the prebiotic mixture is a plant or plant extract, either in solid or liquid form.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In an embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In an embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example, a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In an embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In an embodiment, compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc. New York, N.Y., 2002; Vol. 126, which is herein incorporated by reference in its entirety).

In an embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In an embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, about 1 g to about 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In an embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam-jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In an embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In an embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In an embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

When present in a controlled-release oral dosage form, the compositions described herein can be administered at a substantially lower daily dosage level than immediate-release forms.

In an embodiment, the controlled-release layer is capable of releasing about 30 to about 40% of the one or more active agents (e.g., prebiotic and/or probiotic) contained therein in the stomach of a subject in need thereof in about 5 to about 10 minutes following oral administration. In another embodiment, the controlled-release layer is capable of releasing about 90% of the one or more active agents (e.g., prebiotic and/or probiotic) is released in about 40 minutes after oral administration.

In some embodiments, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In an embodiment, a controlled release formulation weighs between about 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In an embodiment citric acid and sodium bicarbonate are used.

In another aspect the dosage form can be in a candy form (e.g., matrix), such as a lollipop or lozenge. In an embodiment an effective amount of a prebiotic is dispersed within a candy matrix. In an embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartames, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In an embodiment a candy mass is prepared that comprises one or more layers which can comprise different amounts or rates of dissolution of the prebiotic. In an embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In an embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In an embodiment the pharmaceutical particles have a final size of 3-1000 04, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μM. In another embodiment the pharmaceutical particles have a final size of 10-500 μM. In another embodiment the pharmaceutical particles have a final size of 50-600 μM. In another embodiment the pharmaceutical particles have a final size of 100-800 μM.

In an embodiment an oral dosage form (such as a powder, tablet, or capsule) is provided comprising a prebiotic composition comprising about 0.7 g of FOS, GOS, or other FOS, GOS, or other appropriate polysaccharide, about 0.2 g of lactose, about 0.01 g of glucose, about 0.01 g of galactose, about 0.1-0.2 g of a binder, about 0.1-0.2 g of a dispersant, about 0.1-0.2 g of a solubilizer, wherein the FOS, GOS, or other FOS, GOS, or other appropriate polysaccharide are composed of about 1-25% disaccharides, about 1-25% trisaccharides, about 1-25% tetrasaccharides, and about 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising about 1-99.9% by weight of FOS, GOS, or other FOS, GOS, or other appropriate polysaccharide about 0.5-20% by weight of lactose, about 0.1-2% by weight of glucose, about 0.1-2% by weight of galactose, about 0.05-2% by weight of a binder, about 0.05-2% by weight of a dispersant, about 0.05-2% by weight of a solubilizer, wherein the FOS, GOS, or other FOS, GOS, or other appropriate polysaccharide are composed of about 1-25% by weight disaccharides, about 1-25% by weight trisaccharides, about 1-25% by weight tetrasaccharides, and about 1-25% by weight pentasaccharides.

In another embodiment an oral dosage form (such as a powder, tablet, or capsule) is provided comprising a prebiotic composition comprising about 1, 10, 20, 30, 40, 50, 60, 70, 80, 90, 95, 99.5, 100% by weight of FOS, GOS, or other FOS, GOS, or other appropriate polysaccharide about 0, 5, 10, 15, or 20% by weight of lactose, about 0.1, 0.5, 1, or 2% by weight of glucose, about 0.1, 0.5, 1, or 2% by weight of galactose, about 0.05, 0.1, 0.5, 1, or 2% by weight of a binder, about 0.05, 0.1, 0.5, 1, or 2% by weight of a dispersant, about 0.05, 0.1, 0.5, 1, or 2% by weight of a solubilizer, wherein the FOS, GOS, or other FOS, GOS, or other appropriate polysaccharide are composed of about 1, 5, 10, 15, 20, or 25% by weight disaccharides, about 1, 5, 10, 15, 20, or 25% by weight trisaccharides, about 1, 5, 10, 15, 20, or 25% by weight tetrasaccharides, and about 1, 5, 10, 15, 20, or 25% by weight pentasaccharides.

In another embodiment, an oral dosage form is provided comprising a prebiotic composition, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a prebiotic composition. The solid can be, for example, about 1-96%, 10-96%, 20-96%, 30-96%, 40-96%, 50-96%, 60-96%, 70-96%, 80-96%, or 90-96% prebiotic composition. The solid can be, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96% prebiotic composition. In an embodiment a prebiotic composition comprises FOS, GOS, or other FOS, GOS, or other appropriate polysaccharide. In another embodiment a prebiotic composition comprises FOS, GOS, or other FOS, GOS, or other appropriate polysaccharide and another prebiotic. In another embodiment a prebiotic composition comprises FOS, GOS or other and inulin or GOS and FOS.

In an embodiment, the softgel capsule is about 0.25 mL, 0.5 mL, 1.0 mL, 1.25 mL, 1.5 mL, 1.75 mL, or 2.0 mL. In another embodiment, a softgel capsule comprises about 0.1 g to 2.0 g of prebiotic composition. In another embodiment, a softgel capsule comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In an embodiment the prebiotic composition comprises FOS, GOS, or other FOS, GOS, or other appropriate polysaccharide. In another embodiment the prebiotic composition consists essentially of FOS, GOS, or other FOS, GOS, or other appropriate polysaccharide. In another embodiment, a softgel capsule comprises FOS, GOS, or other FOS, GOS, or other appropriate polysaccharide and inulin or FOS.

In another embodiment, the prebiotic composition is delivered in a gelatin capsule containing an amount of FOS, GOS, or other FOS, GOS, or other appropriate polysaccharide within the ranges listed in Table 2. In another embodiment, the number of pills taken per day is within the ranges listed in Table 2.

TABLE 2

Exemplary GOS Dosing Units
Exemplary GOS Composition
Dosages in Gel Caps

| Size | GOS/Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In an embodiment a prebiotic composition comprising FOS, GOS, or other FOS, GOS, or other appropriate polysaccharide does not contain a preservative or an antioxidant.

In another embodiment, a prebiotic composition is formulated as a viscous fluid. In another embodiment, a prebiotic composition is formulated such that its water content is low enough that it does not support microbial growth. In an embodiment, this composition is an intermediate-moisture food, with a water activity between 0.6 and 0.85; in another embodiment this composition is a low-moisture food, with a water activity less than 0.6. Low-moisture foods limit microbial growth significantly and can be produced by one of ordinary skill in the art. For example, these products could be produced similarly to a liquid-centered cough drop. In another embodiment, a prebiotic composition is formulated as a viscous fluid without a preservative in a gel capsule. In another embodiment, a prebiotic composition comprising FOS, GOS, or other FOS, GOS, or other appropriate polysaccharide is a viscous fluid. In another embodiment, a prebiotic composition comprises a high percentage of FOS, GOS, or other FOS, GOS, or other appropriate polysaccharide that does not support microbial growth. In another embodiment, the prebiotic composition comprises FOS, GOS, or other FOS, GOS, or other appropriate polysaccharide and inulin or FOS.

In another embodiment, an oral dosage form is provided comprising a prebiotic composition, wherein the oral dosage form is a softgel. In an embodiment the softgel comprises a syrup. In an embodiment the syrup comprises a prebiotic composition. In an embodiment the prebiotic composition comprises FOS, GOS, or other FOS, GOS, or other appropriate polysaccharide. In another embodiment the prebiotic composition comprises more than 80% FOS, GOS, or other FOS, GOS, or other appropriate polysaccharide. In another embodiment the prebiotic composition comprises between 80-99.9% FOS, GOS, or other. In another embodiment the prebiotic composition comprises more than 80% FOS, GOS, or other FOS, GOS, or other appropriate polysaccharide. In another embodiment the prebiotic composition comprises about 80, 81, 82, 83, 84, 85, 86, 87, 88, 89, 90, 91, 92, 93, 94, 95, 96, 97, 98, 99, or 99.9% FOS, GOS, or other FOS, GOS, or other appropriate polysaccharide.

In an embodiment a FOS, GOS, or other FOS, GOS, or other appropriate polysaccharide composition is formulated for delivery in a soft gel capsule. In an embodiment a FOS, GOS, or other FOS, GOS, or other appropriate polysaccharide composition formulated for delivery in a soft gel capsule is a high percentage FOS, GOS, or other FOS, GOS, or other appropriate polysaccharide composition, such as a 90-100% FOS, GOS, or other FOS, GOS, or other appropriate polysaccharide composition (e.g., 90, 91, 92, 93, 94, 95, 96, 97, 98, 99 or 100% FOS, GOS, or other FOS, GOS, or other appropriate polysaccharide composition by weight). In another embodiment a FOS, GOS, or other FOS, GOS, or other appropriate polysaccharide composition formulated for delivery in a soft gel capsule comprises about 95% FOS, GOS, or other FOS, GOS, or other appropriate polysaccharide. In another embodiment a FOS, GOS, or other FOS, GOS, or other appropriate polysaccharide composition formulated for delivery in a soft gel capsule comprises about 96% FOS, GOS, or other FOS, GOS, or other appropriate polysaccharide. In another embodiment, the FOS, GOS, or other FOS, GOS, or other appropriate polysaccharide composition is formulated such that its water content is low enough that it does not support microbial growth. In another embodiment, the FOS, GOS, or other FOS, GOS, or other appropriate polysaccharide composition is formulated as a viscous fluid without a preservative in a gel capsule. In another embodiment, the FOS, GOS, or other FOS, GOS, or other appropriate polysaccharide composition is formulated as a viscous fluid without an antioxidant in a gel capsule. In another embodiment the soft gel capsule comprises about 0.1-2 g of a FOS, GOS, or other FOS, GOS, or other appropriate polysaccharide composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber (e.g., cellulose or lignin), or a neutralizing component. In an embodiment a prebiotic composition can be in the form of a chewable tablet.

In an embodiment a foaming component can be at least one member selected from the group consisting of sodium hydrogencarbonate, sodium carbonate, and calcium carbonate. In an embodiment a neutralizing component can be at least one member selected from the group consisting of citric acid, L-tartaric acid, fumaric acid, L-ascorbic acid, DL-malic acid, acetic acid, lactic acid, and anhydrous citric acid. In an embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatine, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and stevia, saccharin, and like sweeteners. The amounts of these additives can be properly selected based on their relation to other components and properties of the preparation, production method, etc.

In an embodiment, a FOS, GOS, or other FOS, GOS, or other appropriate polysaccharide composition is a chewable oral dosage formulation. In an embodiment the chewable formulation can comprises between about 1-99.9% FOS, GOS, or other FOS, GOS, or other appropriate polysaccharide. In an embodiment, a FOS, GOS, or other FOS, GOS, or other appropriate polysaccharide composition comprises about 80% FOS, GOS, or other FOS, GOS, or other appropriate polysaccharide about 5% L-ascorbic acid, about 2% anhydrous citric acid, about 3% sodium hydrogencarbonate, about 3% calcium carbonate, about 2% sucrose fatty acid, about 3% fruit juice powder, and about 2% potassium carbonate.

In another embodiment, a FOS, GOS, or other FOS, GOS, or other appropriate polysaccharide composition comprises about 85% FOS, GOS, or other FOS, GOS, or other appropriate polysaccharide, about 5% L-ascorbic acid, about 3% sodium hydrogencarbonate, about 2% sodium carbonate, about 2% sucrose fatty acid ester, about 2% fruit juice powder, and about 1% potassium carbonate.

In another embodiment, a FOS, GOS, or other FOS, GOS, or other appropriate polysaccharide composition comprises about 90% FOS, GOS, or other FOS, GOS, or other appropriate polysaccharide, about 2% L-ascorbic acid, about 1% anhydrous citric acid, about 2% sodium hydrogencarbonate, about 2% sodium carbonate, about 2% sucrose fatty acid ester, and about 1% potassium carbonate.

In another embodiment, a FOS, GOS, or other FOS, GOS, or other appropriate polysaccharide composition comprises about 95% FOS, GOS, or other FOS, GOS, or other appropriate polysaccharide, about 2% L-ascorbic acid, about 1% sodium hydrogencarbonate, and about 2% fruit juice powder. In another embodiment, a FOS, GOS, or other FOS, GOS, or other appropriate polysaccharide composition comprises about 95% FOS, GOS, or other FOS, GOS, or other appropriate polysaccharide and about 5% of L-ascorbic acid, anhydrous citric acid, sodium hydrogencarbonate, calcium carbonate, sucrose fatty acid, fruit juice powder, or potassium carbonate.

In another embodiment, a FOS, GOS, or other FOS, GOS, or other appropriate polysaccharide composition comprises about 95% FOS, GOS, or other FOS, GOS, or other appropriate polysaccharide and about 5% of L-ascorbic acid, anhydrous citric acid, sodium hydrogencarbonate, calcium carbonate, sucrose fatty acid, fruit juice powder, and potassium carbonate.

Medical Foods

An alternate embodiment of the present invention is a formulation as a medical food.

The consuming public has come to understand that foods possess more than basic nutrition (protein, carbohydrate, fat, etc). For example, 95% of consumers agree that "certain foods have health benefits that go beyond basic nutrition and may reduce the risk of disease or other health concerns." More than 50% of consumers believe that foods can replace the use of drugs. Replacing the use of drugs may have the benefit of reducing the incidence of adverse side effects suffered by patients following a pharmaceutical drug treatment regimen. In fact, medical foods are assumed to be generally safe, as people have historically consumed these foods safely in non-medical contexts.

The compositions of the invention may be administered under the supervision of a medical specialist, or may be self-administered. Medical foods could take the form of nutritional shakes or other liquids or meal replacements. Medical foods of the present invention could also take the form of a powder capable of being consumed upon addition to suitable food or liquid.

For treatment of metabolic syndrome, obesity or diabetes under clinical supervision it is possible to combine the nutritional approach with conventional pharmaceutical therapies such as weight-control drugs or diabetes medicines. For example, the composition of the invention may be provided in the form of a kit for separate, sequential or simultaneous administration in conjunction with weight-control drugs or diabetes medicines as defined hereinabove.

A medical food formulation of the present invention could confer benefits of a synthetic composition of microbes isolated from nutritionally beneficial plants, as well as the benefits of prebiotics, or other nutritionally beneficial inclusions, but not consumed to obtain nutrition from them but rather to provide a metabolic function different than a foodstuff. For example, medical foods of the invention may also include at least one vitamin, or vitamin precursor. Preferred vitamins possess antioxidant properties and include vitamins A, C and F, and/or their biochemical precursors. Another embodiment of the medical foods of the invention also includes at least one trace element, preferably selected from the group consisting of zinc, manganese and selenium. Medical foods of the invention also may include at least one additional antioxidant selected from the group consisting of carotenoids, N-acetylcysteine and L-glutamine. It is known to those of skill in the art how to construct medical foods containing these elements.

Medical foods of the present invention would include effective doses of microbes deemed useful for the indication and effective doses of any vitamin, prebiotic, or other beneficial additive not consumed to obtain nutrition but to add a therapeutic benefit mediated by the production of SCFA or other immuno-stimulant molecules when passing through the GI tract.

Typically, the dietary supplements and medical foods of the present invention are consumed at least once daily, and preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals.

Anyone perceived to be at risk from metabolic syndrome, obesity, T2D, or already suffering from these or associated disorders, can potentially benefit from ingesting the compositions of the invention. According to the invention it is believed to be possible to effectively ameliorate symptoms and conditions associated with T2D, metabolic syndrome, or obesity with natural compounds, which do not show any severe side effects. Furthermore, the present methods are expected to be well-tolerated, for example without causing any discomfort or nausea, and simple to apply.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Microbial Preparations and Metagenomic Analyses

A sample set of 15 vegetables typically eaten raw was selected to analyze the microbial communities by whole genome shotgun sequencing and comparison to microbial databases. The 15 fruits and vegetable samples are shown in Table 3 and represent ingredients in typical salads or eaten fresh. The materials were sourced at the point of distribution in supermarkets selling both conventional and organic farmed vegetables, either washed and ready to eat or without washing.

The samples were divided into 50 g portions, thoroughly rinsed with tap water and blended for 30 seconds on phosphate buffer pH 7.4 (PBS) in a household blender. The resulting slurry was strained by serial use of a coarse household sieve and then a fine household sieve followed by filtration through a 40 μm sieve. The cell suspension containing the plant microbiota, chloroplasts and plant cell debris was centrifuged at slow speed (100×g) 5 minutes for removing plant material and the resulting supernatant centrifuged at high speed (4000×g) 10 minutes to pellet microbial cells. The pellet was resuspended in a plant cell lysis buffer containing a chelator such as EDTA 10 mM to reduce divalent cation concentration to less than, and a non-ionic detergent to lyse the plant cells without destroying the bacterial cells. The lysed material was washed by spinning down the microbial cells at 4000×g for 10 minutes, and then resuspended in PBS and repelleted as above. For sample #12 (broccoli) the cell pellet was washed and a fraction of the biomass separated and only the top part of the pellet collected. This was deemed "broccoli juice" for analyses. The resulting microbiota prep was inspected under fluorescence microscopy with DNA stains to visualize plant and microbial cells based on cell size and DNA structure (nuclei for plants) and selected for DNA isolation based on a minimum ratio of 9:1 microbe to plant cells. The DNA isolation was based on the method reported by Marmur (Journal of Molecular Biology 3, 208-218; 1961), or using commercial DNA extraction kits based on magnetic beads such as Thermo Charge Switch resulting in a quality suitable for DNA library prep and free of PCR inhibitors.

The DNA was used to construct a single read 150 base pair libraries and a total of 26 million reads sequenced per sample according to the standard methods done by CosmosID (www.cosmosid.com) for samples #1 to #12 or 300 base pair-end libraries and sequenced in an Illumina NextSeq instrument covering 4 Gigabases per sample for samples #13 to #15. The unassembled reads were then mapped to the CosmosID for first 12 samples or OneCodex for the last 3 samples databases containing 36,000 reference bacterial genomes covering representative members from diverse taxa. The mapped reads were tabulated and represented using a "sunburst" plot to display the relative abundance for each genome identified corresponding to that bacterial strain and normalized to the total of identified reads for each sample. In addition, phylogenetic trees were constructed based on the classification for each genome in the database with a curated review. There are genomes that have not been updated in the taxonomic classifier and therefore reported as unclassified here but it does not reflect a true lack of clear taxonomic position, it reflects only the need for manual curation and updating of those genomes in the taxonomic classifier tool.

Figure 4:
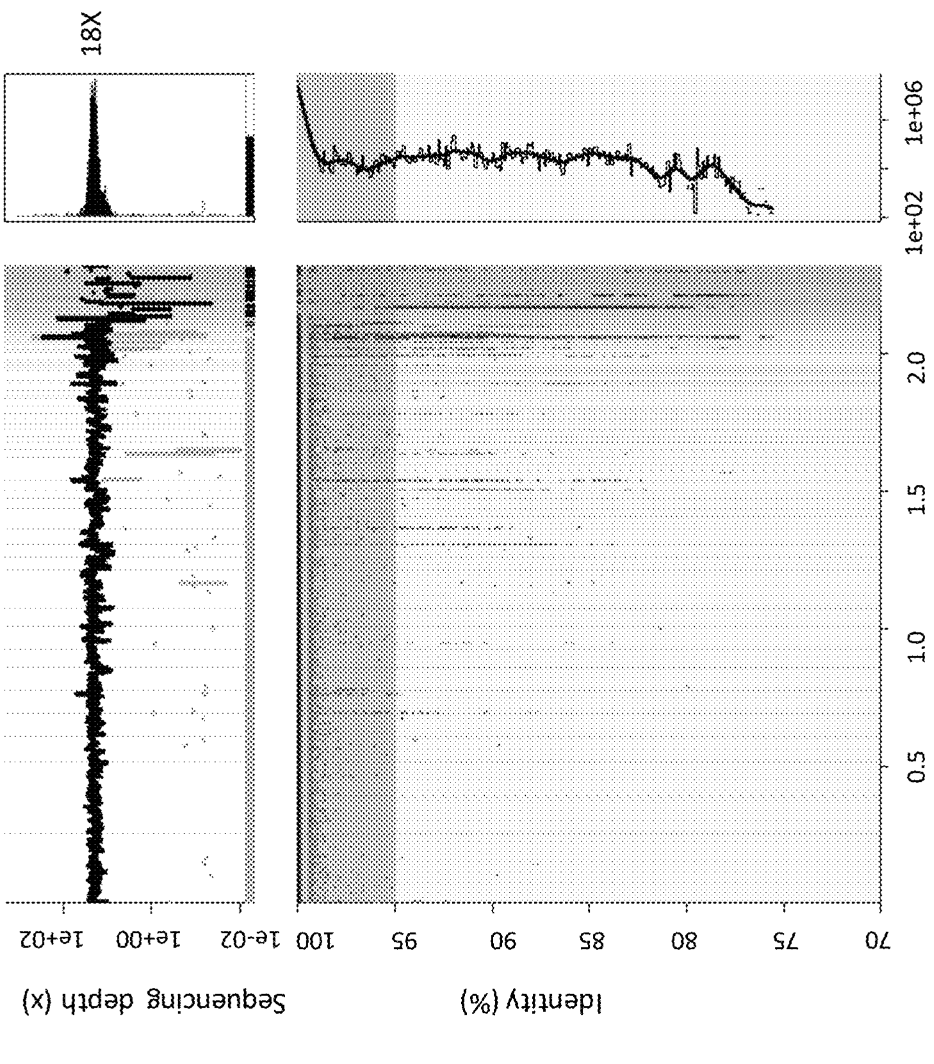
FIG. 4. Shows a fragment recruitment plot sample for the shotgun sequencing on sample 22 (fermented cabbage) comparing to the reference genome of strain DP3 *Leuconostoc mesenteroides*-like and the 18× coverage indicating the isolated strain is represented in the environmental sample and it is relatively clonal.

FIG. 4 shows a fragment recruitment plot sample for the shotgun sequencing on sample 22 (fermented cabbage) comparing to the reference genome of strain DP3 *Leuconostoc mesenteroides*-like and the 18× coverage indicating the isolated strain is represented in the environmental sample and it is relatively clonal.

In addition to the shotgun metagenomics survey relevant microbes were isolated from fruits and vegetables listed in Table 3 using potato dextrose agar or nutrient agar and their genomes sequenced to cover 50× and analyzed their metabolic potential by using genome-wide models. For example, a yeast isolated from blueberries was sequenced and its genome showed identity to *Aureobasidium subglaciale* assembled in contigs with an N50 of 71 Kb and annotated to code for 10, 908 genes. Similarly, bacterial genomes from the same sample were sequenced and annotated for strains with high identity to *Pseudomonas* and *Rahnella.*

The microbial cocktail with the combined individual strains is then adjusted to the correct dose to be fed to mice to validate the efficacy using a laboratory animal model to demonstrate the biological effect in obesity, or metabolic syndrome. For this, a mouse model recapitulating the onset and symptoms on obesity and prediabetes are generated by either feeding a high fat diet to lean mice to induce weight gain and sequelae. This is observed by insulin resistance and increase on BMI. In addition, other mice models such as ob/ob, db/db recapitulating some of the late stages in diabetes seen as hyperglycemia, and observed in the islet cells, β-cells and insulin resistance or not producing insulin at all. For the diet-induced obese and pre-diabetic mice the test animals are subject to a 12-week high fat diet to observe an approximate doubling in weight vs low fat diet control. The subject arm of the mice cohort is then fed with a high fat, diet simulating the Western diet and a range of doses with the candidate assemblage fed daily. The high fat diet is 60% kcal of fat (lard), 20% protein, and 20% carb (https://researchdiets.com/formulas/d12492). The low fat diet control is 10% kcal from fat, 20% protein, and 70% carbohydrate (https://researchdiets.com/formulas/d12450J).

The mice response is measured daily during the treatment period of 4 weeks for acetate in blood, insulin response, weight, BMI and other chronic inflammation indicators.

The optimal dose for the feeding experiment is determined experimentally by providing a range between 10^8 and 10^11 CFU per gram of chow in a feeding experiment that will elicit a response in the mice. The dose, once determined in the animal model is then normalized to a person on an equivalent biomass and food intake.

TABLE 3

Samples analyzed.

| Sample # | Figure 1 Legend | Description |
|---|---|---|
| 1 | 1A | Chard |
| 2 | 1B | Red cabbage |
| 3 | 1C | Organic romaine |
| 4 | 1D | Organic celery |
| 5 | 1E | Butterhead organic lettuce |
| 6 | 1F | Organic baby spinach |
| 7 | 1G | Crisp green gem lettuce |
| 8 | 1H | Red oak leaf lettuce |
| 9 | 1I | Green oak leaf lettuce |
| 10 | 1J | Cherry tomato |
| 11 | 1K | Crisp red gem lettuce |
| 12 | 1L | Broccoli juice |
| 13 | 2A | Broccoli head |
| 14 | 2B | blueberries |
| 15 | 2C | Pickled olives |

Results

For most samples, bacterial abundances of fresh material contain 10^7 to 10^8 microbes per gram of vegetable as estimated by direct microscopy counts. Diverse cell morphologies were observed including rods, elongated rods, cocci and fungal hyphae. Microorganisms were purified from host cells, DNA was isolated and sequenced using a shotgun approach mapping reads to 35,000 bacterial genomes using a k-mer method. All samples were dominated by gamma proteobacteria, primarily *Pseudomonadacea*, presumably largely endophytes as some samples were triple washed before packaging. *Pseudomonas* cluster was the dominant genera for several samples with 10-90% of the bacterial relative abundance detected per sample and mapped to a total of 27 different genomes indicating it is a diverse group. A second relevant bacterial strain identified was *Duganella zoogloeoides* ATCC 25935 as it was present in almost all the samples ranging from 1-6% of the bacterial relative abundance detected per sample or can reach 29% of the bacterial relative abundance detected per sample in organic romaine. Red cabbage was identified to contain a relatively large proportion of lactic acid bacteria as it showed 22% *Lactobacillus crispatus*, a species commercialized as probiotic and recognized relevant in vaginal healthy microbial community. Another vegetable containing lactic acid bacteria was red oak leaf lettuce containing 1.5% of the bacterial relative abundance detected per sample *Lactobacillus reuteri*. Other bacterial species recognized as probiotics included *Bacillus, Bacteroidetes, Propionibacterium* and *Streptococcus*. A large proportion of the abundant taxa in most samples was associated with plant microbiota and members recognized to act as biocontrol agents against fungal diseases or growth promoting agents such as *Pseudomonas fluorescens*. The aggregated list of unique bacteria detected by the k-mer method is 318 (Table 4).

Blueberries contain a mixture of bacteria and fungi dominated by *Pseudomonas* and *Propionibacterium* but the yeast *Aureobasidium* was identified as a relevant member of the community. A lesser abundant bacterial species was *Rahnella*. Pickled olives are highly enriched in lactic acid bacteria after being pickled in brine allowing the endogenous probiotic populations to flourish by acidifying the environment and eliminating most of the acid-sensitive microbes including bacteria and fungi. This resulted in a large amount of *Lactobacillus* species and *Pediococcus* recognized as probiotics and related to obesity treatment.

The shotgun sequencing method allows for the analysis of the metagenome including genes coding for metabolic reactions involved in the assimilation of nutrient, fermentative processes to produce short chain fatty acids, flavonoids and other relevant molecules in human nutrition.

TABLE 4

Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Acinetobacter baumannii* | — | |
| *Acinetobacter soli* | — | |
| *Acinetobacter* 41764 Branch | — | |
| *Acinetobacter* 41930 Branch | — | |
| *Acinetobacter* 41981 Branch | — | |
| *Acinetobacter* 41982 Branch | — | |
| *Acinetobacter baumannii* 348935 | — | |
| *Acinetobacter baumannii* 40298 Branch | — | |
| *Acinetobacter beijerinckii* 41969 Branch | — | |
| *Acinetobacter beijerinckii* CIP 110307 | CIP 110307 | WFCC |
| *Acinetobacter bohemicus* ANC 3994 | — | |
| *Acinetobacter guillouiae* 41985 Branch | — | |
| *Acinetobacter guillouiae* 41986 Branch | — | |
| *Acinetobacter gyllenbergii* 41690 Branch | — | |
| *Acinetobacter haemolyticus* TG19602 | — | |
| *Acinetobacter harbinensis* strain HITLi 7 | — | |
| *Acinetobacter johnsonii* 41886 Branch | — | |
| *Acinetobacter johnsonii* ANC 3681 | — | |
| *Acinetobacter junii* 41994 Branch | — | |
| *Acinetobacter lwoffii* WJ10621 | — | |
| *Acinetobacter* sp 41945 Branch | — | |
| *Acinetobacter* sp 41674 Branch | — | |
| *Acinetobacter* sp 41698 Branch | — | |
| *Acinetobacter* sp ETR1 | — | |
| *Acinetobacter* sp NIPH 298 | — | |
| *Acinetobacter tandoii* 41859 Branch | — | |
| *Acinetobacter tjernbergiae* 41962 Branch | — | |
| *Acinetobacter towneri* 41848 Branch | — | |
| *Acinetobacter venetianus* VE C3 | — | |
| *Actinobacterium* LLX17 | — | |
| *Aeromonas bestiarum* strain CECT 4227 | CECT 4227 | CECT |
| *Aeromonas caviae* strain CECT 4221 | CECT 4221 | CECT |
| *Aeromonas hydrophila* 4AK4 | — | |
| *Aeromonas media* 37528 Branch | — | |
| *Aeromonas media* strain ARB 37524 Branch | — | |
| *Aeromonas salmonicida* subsp 37538 Branch | — | |
| *Aeromonas* sp ZOR0002 | — | |
| *Agrobacterium* 22298 Branch | — | |
| *Agrobacterium* 22301 Branch | — | |
| *Agrobacterium* 22313 Branch | — | |
| *Agrobacterium* 22314 Branch | — | |
| *Agrobacterium* sp ATCC 31749 | ATCC 31749 | ATCC |
| *Agrobacterium tumefaciens* 22306 Branch | | |
| *Agrobacterium tumefaciens* strain MEJ076 | — | |
| *Agrobacterium tumefaciens* strain S2 | — | |
| *Alkanindiges illinoisensis* DSM 15370 | DSM 15370 | WFCC |
| *alpha proteobacterium* L41A | — | |
| *Arthrobacter* 20515 Branch | — | |
| *Arthrobacter arilaitensis* Re117 | — | |
| *Arthrobacter chlorophenolicus* A6 | — | |
| *Arthrobacter nicotinovorans* 20547 Branch | — | |
| *Arthrobacter phenanthrenivorans* Sphe3 | — | |
| *Arthrobacter* sp 20511 Branch | — | |
| *Arthrobacter* sp PAO19 | — | |
| *Arthrobacter* sp W1 | — | |
| *Aureimonas* sp. Leaf427 | — | |
| *Aureobasidium pullulans* | — | |
| *Bacillaceae* Family 24410112691 Branch | — | |
| *Bacillus* sp. LL01 | — | |
| *Bacillus* 12637 Branch | — | |
| *Bacillus aerophilus* strain C772 | — | |
| *Bacillus thuringiensis* serovar 12940 Branch | — | |
| *Brevundimonas nasdae* strain TPW30 | — | |
| *Brevundimonas* sp 23867 Branch | — | |

TABLE 4-continued

Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Brevundimonas* sp EAKA | — | |
| *Buchnera aphidicola* str 28655 Branch | — | |
| *Burkholderiales* Order 156136 Node 25777 | — | |
| *Buttiauxella agrestis* 35837 Branch | — | |
| *Candidatus Burkholderia verschuerenii* | — | |
| *Carnobacterium* 5833 Branch | — | |
| *Carnobacterium maltaromaticum* ATCC 35586 | ATCC 35586 | ATCC |
| *Chryseobacterium* 285 Branch | — | |
| *Chryseobacterium daeguense* DSM 19388 | DSM 19388 | WFCC |
| *Chryseobacterium formosense* | — | |
| *Chryseobacterium* sp YR005 | — | |
| *Clavibacter* 20772 Branch | — | |
| *Clostridium diolis* DSM 15410 | DSM 15410 | WFCC |
| *Comamonas* sp B 9 | — | |
| *Curtobacterium flaccumfaciens* 20762 Branch | — | |
| *Curtobacterium flaccumfaciens* UCD AKU | — | |
| *Curtobacterium* sp UNCCL17 | — | |
| *Deinococcus aquatilis* DSM 23025 | DSM 23025 | WFCC |
| *Debaromyces hansenii* ATCC 36239 | ATCC 25935 | ATCC |
| *Duganella zoogloeoides* ATCC 25935 | | |
| *Dyadobacter* 575 Branch | — | |
| *Elizabethkingia anophelis* | — | |
| *Empedobacter falsenii* strain 282 | — | |
| *Enterobacter* sp 638 | — | |
| *Enterobacteriaceae* Family 9 3608 Node 35891 | — | |
| *Enterobacteriaceae* Family 9 593 Node 36513 | — | |
| *Epilithonimonas lactis* | — | |
| *Epilithonimonas tenax* DSM 16811 | DSM 16811 | WFCC |
| *Erwinia* 35491 Branch | — | |
| *Erwinia amylovora* 35816 Branch | — | |
| *Erwinia pyrifoliae* 35813 Branch | — | |
| *Erwinia tasmaniensis* Et1 99 | DSM 17950 | WFCC |
| *Escherichia coli* ISC11 | — | |
| *Exiguobacterium* 13246 Branch | — | |
| *Exiguobacterium* 13260 Branch | — | |
| *Exiguobacterium sibiricum* 25515 | DSM 17290 | WFCC |
| *Exiguobacterium* sp 13263 Branch | — | |
| *Exiguobacterium undae* 13250 Branch | — | |
| *Exiguobacterium undae* DSM 14481 | DSM 14481 | WFCC |
| *Flavobacterium* 237 Branch | — | |
| *Flavobacterium aquatile* LMG 4008 | LMG 4008 | WFCC |
| *Flavobacterium chungangense* LMG 26729 | LMG 26729 | WFCC |
| *Flavobacterium daejeonense* DSM 17708 | DSM 17708 | WFCC |
| *Flavobacterium hibernum* strain DSM 12611 | DSM 12611 | WFCC |
| *Flavobacterium hydatis* | — | |
| *Flavobacterium johnsoniae* UW101 | ATCC 17061D-5 | ATCC |
| *Flavobacterium reichenbachii* | — | |
| *Flavobacterium soli* DSM 19725 | DSM 19725 | WFCC |
| *Flavobacterium* sp 238 Branch | — | |
| Flavobacterium sp EM1321 | — | |
| Flavobacterium sp MEB061 | — | |
| *Hanseniaspora uvarum* ATCC 18859 | — | |
| *Hanseniaspora occidentalis* ATCC 32053 | | |
| *Herminiimonas arsenicoxydans* | | |
| *Hymenobacter swuensis* DY53 | — | |
| *Janthinobacterium* 25694 Branch | — | |
| *Janthinobacterium agaricidamnosum* NBRC 102515 DSM 9628 | DSM 9628 | WFCC |
| *Janthinobacterium lividum* strain RIT308 | — | |
| *Janthinobacterium* sp RA13 | — | |
| *Kocuria* 20614 Branch | — | |
| *Kocuria rhizophila* 20623 Branch | — | |
| *Lactobacillus acetotolerans* | — | |
| *Lactobacillus brevis* | — | |
| *Lactobacillus buchneri* | — | |
| *Lactobacillus futsaii* | — | |
| *Lactobacillus kefiranofaciens* | — | |
| *Lactobacillus panis* | — | |
| *Lactobacillus parafarraginis* | — | |
| *Lactobacillus plantarum* | — | |
| *Lactobacillus rapi* | — | |

TABLE 4-continued

Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Lactobacillus crispatus* 5565 Branch | — | |
| *Lactobacillus plantarum* WJL | — | |
| *Lactobacillus reuteri* 5515 Branch | — | |
| *Leuconostoc mesenteroides* ATCC 8293 | — | |
| *Luteibacter* sp 9135 | | |
| *Massilia timonae* CCUG 45783 | — | |
| *Methylobacterium extorquens* 23001 Branch | — | |
| *Methylobacterium* sp 22185 Branch | — | |
| *Methylobacterium* sp 285MFTsu51 | — | |
| *Methylobacterium* sp 88A | — | |
| *Methylotenera versatilis* 7 | — | |
| *Microbacterium laevaniformans* OR221 | — | |
| *Microbacterium oleivorans* | — | |
| *Microbacterium* sp MEJ108Y | — | |
| *Microbacterium* sp UCD TDU | — | |
| *Microbacterium testaceum* StLB037 | — | |
| *Micrococcus luteus* strain RIT304 | NCTC 2665 | NCTC |
| *Mycobacterium abscessus* 19573 Branch | — | |
| *Neosartorya fischeri* | — | |
| *Oxalobacteraceae bacterium* AB 14 | — | |
| *Paenibacillus* sp FSL 28088 Branch | — | |
| *Paenibacillus* sp FSL H7 689 | — | |
| *Pantoea* sp. SL1 M5 | — | |
| *Pantoea* 36041 Branch | — | |
| *Pantoea agglomerans* strain 4 | — | |
| *Pantoea agglomerans* strain 4 | — | |
| *Pantoea agglomerans* strain LMAE 2 | — | |
| *Pantoea agglomerans* Tx10 | — | |
| *Pantoea* sp 36061 Branch | — | |
| *Pantoea* sp MBLJ3 | — | |
| *Pantoea* sp SL1 M5 | — | |
| *Paracoccus* sp PAMC 22219 | — | |
| *Patulibacter minatonensis* DSM 18081 | DSM 18081 | WFCC |
| *Pectobacterium carotovorum* subsp *carotovorum* strain 28625 Branch | — | |
| *Pediococcus ethanolidurans* | — | |
| *Pediococcus pentosaceus* ATCC 33314 | — | |
| *Pedobacter* 611 Branch | | |
| *Pedobacter agri* PB92 | — | |
| *Pedobacter borealis* DSM 19626 | DSM 19626 | WFCC |
| *Pedobacter kyungheensis* strain KACC 16221 | — | |
| *Pedobacter* sp R2019 | — | |
| *Periglandula ipomoeae* | — | |
| *Planomicrobium glaciei* CHR43 | — | |
| *Propionibacterium acnes* | — | |
| *Propionibacterium* 20955 Branch | — | |
| *Propionibacterium acnes* 21065 Branch | — | |
| *Pseudomonas fluorescens* | — | |
| *Pseudomonas* sp. DSM 29167 | — | |
| *Pseudomonas* sp. Leaf15 | — | |
| *Pseudomonas syringae* | — | |
| *Pseudomonas* 39524 Branch | — | |
| *Pseudomonas* 39642 Branch | — | |
| *Pseudomonas* 39733 Branch | — | |
| *Pseudomonas* 39744 Branch | — | |
| *Pseudomonas* 39791 Branch | — | |
| *Pseudomonas* 39821 Branch | — | |
| *Pseudomonas* 39834 Branch | — | |
| *Pseudomonas* 39875 Branch | — | |
| *Pseudomonas* 39880 Branch | — | |
| *Pseudomonas* 39889 Branch | — | |
| *Pseudomonas* 39894 Branch | — | |
| *Pseudomonas* 39913 Branch | — | |
| *Pseudomonas* 39931 Branch | — | |
| *Pseudomonas* 39942 Branch | — | |
| *Pseudomonas* 39979 Branch | — | |
| *Pseudomonas* 39996 Branch | — | |
| *Pseudomonas* 40058 Branch | — | |
| *Pseudomonas* 40185 Branch | — | |
| *Pseudomonas abietamphila* strain KF717 | — | |
| *Pseudomonas chlororaphis* strain EA105 | — | |

TABLE 4-continued

Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Pseudomonas cremoricolorata* DSM 17059 | DSM 17059 | WFCC |
| *Pseudomonas entomophila* L48 | — | |
| *Pseudomonas extremaustralis* 143 substr 143b | — | |
| *Pseudomonas fluorescens* BBc6R8 | — | |
| *Pseudomonas fluorescens* BS2 | ATCC 12633 | ATCC |
| *Pseudomonas fluorescens* EGD AQ6 | — | |
| *Pseudomonas fluorescens* strain AU 39831 Branch | — | |
| *Pseudomonas fluorescens* strain AU10973 | — | |
| *Pseudomonas fluorescens* strain AU14440 | — | |
| *Pseudomonas fragi* B25 | NCTC 10689 | NCTC |
| *Pseudomonas frederiksbergensis* strain SI8 | — | |
| *Pseudomonas fulva* strain MEJ086 | — | |
| *Pseudomonas fuscovaginae* 39768 Branch | — | |
| *Pseudomonas gingeri* NCPPB 3146 | NCPPB 3146 | NCPPB |
| *Pseudomonas lutea* | — | |
| *Pseudomonas luteola* XLDN49 | — | |
| *Pseudomonas mandelii* JR 1 | — | |
| *Pseudomonas moraviensis* R28 S | — | |
| *Pseudomonas mosselii* SJ10 | — | |
| *Pseudomonas plecoglossicida* NB 39639 Branch | — | |
| *Pseudomonas poae* RE*1114 | — | |
| *Pseudomonas pseudoalcaligenes* AD6 | — | |
| *Pseudomonas psychrophila* HA 4 | — | |
| *Pseudomonas putida* DOT T1E | — | |
| *Pseudomonas putida* strain KF703 | — | |
| *Pseudomonas putida* strain MC4 5222 | — | |
| *Pseudomonas rhizosphaerae* | — | |
| *Pseudomonas rhodesiae* strain FF9 | — | |
| *Pseudomonas* sp 39813 Branch | — | |
| *Pseudomonas simiae* strain 2 36 | — | |
| *Pseudomonas simiae* strain MEB105 | — | |
| *Pseudomonas* sp 1112A | — | |
| *Pseudomonas* sp 2922010 | — | |
| *Pseudomonas* sp CF149 | — | |
| *Pseudomonas* sp Eur1 941 | — | |
| *Pseudomonas* sp LAMO17WK12 I2 | — | |
| *Pseudomonas* sp PAMC 25886 | — | |
| *Pseudomonas* sp PTA1 | — | |
| *Pseudomonas* sp R62 | — | |
| *Pseudomonas* sp WCS374 | — | |
| *Pseudomonas synxantha* BG33R | — | |
| *Pseudomonas synxantha* BG33R | — | |
| *Pseudomonas syringae* 39550 Branch | — | |
| *Pseudomonas syringae* 39596 Branch | — | |
| *Pseudomonas syringae* 40123 Branch | — | |
| *Pseudomonas syringae* CC 39499 Branch | — | |
| *Pseudomonas syringae* pv panici str LMG 2367 | — | |
| *Pseudomonas syringae* strain mixed | — | |
| *Pseudomonas tolaasii* 39796 Branch | — | |
| *Pseudomonas tolaasii* PMS117 | — | |
| *Pseudomonas veronii* 1YdBTEX2 | — | |
| *Pseudomonas viridiflava* CC1582 | — | |
| *Pseudomonas viridiflava* strain LMCA8 | — | |
| *Pseudomonas viridiflava* TA043 | — | |
| *Pseudomonas viridiflava* UASWS0038 | — | |
| *Rahnella* 35969 Branch | — | |
| *Rahnella* 35970 Branch | — | |
| *Rahnella* 35971 Branch | — | |
| *Rahnella aquatilis* HX2 | — | |
| *Rahnella* sp WP5 | — | |
| *Raoultella ornithinolytica* | — | |
| *Rhizobiales* Order 22324 Branch | — | |
| *Rhizobium* sp YR528 | — | |
| *Rhodococcus fascians* A76 | — | |
| *Rhodococcus* sp BS 15 | — | |
| *Saccharomyces cerevisiae* | DSM 10542 | WFCC |
| *Sanguibacter keddieii* DSM 10542 | | |
| *Serratia fonticola* AU 35657 Branch | — | |
| *Serratia fonticola* AU AP2C | — | |
| *Serratia liquefaciens* ATCC 27592 | ATCC 27592 | ATCC |
| *Serratia* sp H 35589 Branch | — | |

TABLE 4-continued

Bacteria identified in a 15 sample survey identified by whole genome matching to reference genomes. The fruits and vegetables were selected based on their recognition as part of the whole food plant based diet and some antidiabetic and obesogenic properties. There is general recognition of microbes in these vegetables relevant for plant health but not previously recognized for their use in human health. Strains were identified by k-mer based on entire genome

| Strain | Strain number | Collection |
|---|---|---|
| *Shewanella* 37294 Branch | — | |
| *Shewanella baltica* 37301 Branch | — | |
| *Shewanella baltica* 37315 Branch | — | |
| *Shewanella baltica* OS 37308 Branch | — | |
| *Shewanella baltica* OS 37312 Branch | — | |
| *Shewanella baltica* OS185 | — | |
| *Shewanella baltica* OS223 | — | |
| *Shewanella baltica* OS678 | — | |
| *Shewanella oneidensis* MR 1 | — | |
| *Shewanella putrefaciens* HRCR 6 | — | |
| *Shewanella* sp W3181 | — | |
| *Sphingobacterium* sp ML3W | — | |
| *Sphingobium japonicum* BiD32 | — | |
| *Sphingobium xenophagum* 24443 Branch | — | |
| *Sphingomonas echinoides* ATCC 14820 | ATCC 14820 | ATCC |
| *Sphingomonas parapaucimobilis* NBRC 15100 | ATCC 51231 | ATCC |
| *Sphingomonas paucimobilis* NBRC 13935 | ATCC 29837 | ATCC |
| *Sphingomonas phyllosphaerae* 52 | — | |
| *Sphingomonas* sp 23777 Branch | — | |
| *Sphingomonas* sp STIS62 | — | |
| *Staphylococcus* 6317 Branch | — | |
| *Staphylococcus equorum* UMC CNS 924 | — | |
| *Staphylococcus* sp 6275 Branch | — | |
| *Staphylococcus* sp 6240 Branch | — | |
| *Staphylococcus* sp OJ82 | — | |
| *Staphylococcus xylosus* strain LSR 02N | — | |
| *Stenotrophomonas* 14028 Branch | — | |
| *Stenotrophomonas* 42816 Branch | — | |
| *Stenotrophomonas maltophilia* 42817 Branch | — | |
| *Stenotrophomonas maltophilia* PML168 | — | |
| *Stenotrophomonas maltophilia* strain ZBG7B | — | |
| *Stenotrophomonas rhizophila* | — | |
| *Stenotrophomonas* sp RIT309 | — | |
| *Streptococcus gallolyticus* subsp *gallolyticus* TX20005 | — | |
| *Streptococcus infantarius* subsp *infantarius* 2242 Branch | — | |
| *Streptococcus infantarius* subsp *infantarius* ATCC BAA 102 | ATCC BAA 102 | ATCC |
| *Streptococcus macedonicus* ACA DC 198 | ATCC BAA-249 | ATCC |
| *Streptomyces olindensis* | — | |
| *Variovorax paradoxus* 110B | — | |
| *Variovorax paradoxus* ZNC0006 | — | |
| *Variovorax* sp CF313 | — | |
| *Vibrio fluvialis* 44473 Branch | — | |
| *Xanthomonas campestris* 37936 Branch | — | |
| *Xanthomonas campestris* pv *raphani* 756C | — | |

FIG. 1 shows bacterial diversity observed in a set of 12 plant-derived samples as seen by a community reconstruction based on mapping the reads from a shotgun sequencing library into the full genomes of a database containing 36,000 genomes by the k-mer method (CosmosID). The display corresponds to a sunburst plot constructed with the relative abundance for each corresponding genome identified and their taxonomic classification. The genomes identified as unclassified have not been curated in the database with taxonomic identifiers and therefore not assigned to a group. This does not represent novel taxa and it is an artifact of the database updating process.

More specifically, FIG. 1A shows bacterial diversity observed in a green chard. The dominant group is gamma proteobacteria with different *Pseudomonas* species. The members of the group "unclassified" are largely gamma proteobacteria not included in the hierarchical classification as an artifact of the database annotation.

FIG. 1B shows bacterial diversity in red cabbage. There is a large abundance of *Lactobacillus* in the sample followed by a variety of *Pseudomonas* and *Shewanella.*

FIG. 1C shows bacterial diversity in romaine lettuce. *Pseudomonas* and *Duganella* are the dominant groups. A member of the *Bacteroidetes* was also identified.

FIG. 1D shows bacterial diversity in celery sticks. This sample was dominated by a *Pseudomonas* species that was not annotated yet into the database and therefore appeared as "unclassified" same for *Agrobacterium* and *Acinetobacter.*

FIG. 1E shows bacterial diversity observed in butterhead lettuce grown hydroponically. The sample contains relatively low bacterial complexity dominated by *Pseudomonas fluorescens* and other groups. Also, there is a 9% abundance of *Exiguobacterium.*

FIG. 1F shows bacterial diversity in organic baby spinach. The samples were triple-washed before distribution at the point of sale and therefore it is expected that must of the bacteria detected here are endophytes. Multiple *Pseudomonas* species observed in this sample including *P. fluorescens* and other shown as "unclassified."

FIG. 1G shows bacterial diversity in green crisp gem lettuce. This variety of lettuce showed clear dominance of gamma proteobacteria and with *Pseudomonas, Shewanella, Serratia* as well as other groups such as *Duganella.*

FIG. 1H shows bacterial diversity in red oak leaf lettuce. There is a relative high diversity represented in this sample with members of *Lactobacillus, Microbacterium, Bacteroidetes, Exiguobacterium* and a variety of *Pseudomonas.*

FIG. 1I shows bacterial diversity in green oak leaf lettuce. It is dominated by a single *Pseudomonas* species including *fluorescens* and mostly gamma proteobacteria.

FIG. 1J shows bacterial diversity in cherry tomatoes. It is dominated by 3 species of *Pseudomonas* comprising more than 85% of the total diversity on which *P. fluorescens* comprises 28% of bacterial diversity.

FIG. 1K shows bacterial diversity in crisp red gem lettuce. Dominance by a single *Pseudomonas* species covering 73% of the bacterial diversity, on which *P. fluorescens* comprises 5% of bacterial diversity.

FIG. 1L shows bacterial diversity in broccoli juice. The sample is absolutely dominated by 3 varieties of *Pseudomonas.*

FIG. 2 shows taxonomic composition of blueberries, pickled olives and broccoli head. More specifically, FIG. 2A shows taxonomic composition of broccoli head showing a diversity of fungi and bacteria distinct from the broccoli juice dominated by few *Pseudomonas* species.

FIG. 2B shows taxonomic composition of blueberries including seeds and pericarp (peel) as seen by shotgun sequencing showing dominance of *Pseudomonas* and strains isolated and sequenced.

FIG. 2C shows taxonomic composition of pickled olives showing a variety of lactic acid bacteria present and dominant. Some of the species are recognized as probiotics.

Example 2: In Silico Modeling Outputs for Different Assemblages and DMA Formulation To generate in silico predictions for the effect of different microbial assemblages with a human host a genome-wide metabolic analysis was performed with formulated microbial communities selected from the Agora collection (Magbustoddir et al. (2016) Generation of genome-scale metabolic reconstructions for 773 members of the human gut microbiota. Nat. Biotech. 35, 81-89) and augmented with the genomes of bacterial members detected in the present survey. These simulations predict the "fermentative power" of each assemblage when simulated under different nutritional regimes including relatively high carbon availability (carbon replete) or carbon limited conditions when using plant fibers such as inulin, oligofructose and others as carbon source. The method used for DNA sequencing the sample-associated microbiomes enabled to search for genes detected in the different vegetables related to propionate, butyrate, acetate and bile salt metabolism. This was done by mapping the reads obtained in the samples to reference genes selected for their intermediate role in the synthesis or degradation of these metabolites. There were organisms present in some of the 15 analyzed samples that matched the target pathways indicating their metabolic potential to produce desirable metabolites. Table 5 shows Metabolites in samples.

TABLE 5

Metabolites in samples.

| Name of enzyme | Associated metabolite | Gene symbol | Pathway | E.C. number | Comments |
|---|---|---|---|---|---|
| Acetolactate synthase I | (s)-2-acetolactate | | Butanoate metabolism | 2.2.1.6 | Butyrate production |
| Acetate kinase | Propionate | Acka | Propanoate metabolism | 2.7.2.1 | Propionate |
| Acetyl-coa synthetase | Propionate | Aacs | Propanoate metabolism | 6.2.1.1 | Propionate |
| Acetyl-coa hydrolase | Acetate | | Pyruvate metabolism | 3.1.2.1 | Acetate |
| Bile salt transporter | Bile salts | Acr3 | Bile salt transport | | Bile salt tolerance |

DMA Formulation

Microbes in nature interact with multiple other groups and form consortia that work in synergy exchanging metabolic products and substrates resulting in thermodynamically favorable reactions as compared to the individual metabolism. For example, in the human colon, the process for plant fiber depolymerization, digestion and fermentation into butyrate is achieved by multiple metabolic groups working in concert. This metabolic synergy is reproduced in the DMA concept where strains are selected to be combined based on their ability to synergize to produce an increased amount of SCFA when grown together and when exposed to substrates such as plant fibers.

To illustrate this process, a set of 40 bacterial and fungal strains were isolated from food sources and their genomes were sequenced. The assembled and annotated genomes were then used to formulate in silico assemblages considering the human host as one of the metabolic members. Assuming a diet composed of lipids, different carbohydrates and proteins the metabolic fluxes were predicted using an unconstrained model comparing the individual strain production of acetate, propionate and butyrate and compared to the metabolic fluxes with the assemblage.

In the first model, 4 strains were combined into a DMA. Strains 1-4 are predicted to produce acetate as single cultures but the combination into a DMA predicts the flux will increase when modeled on replete media and the flux decreases when modeled on plant fibers. Strain 4 is predicted to utilize the fibers better than the other 3 to produce acetate. Strain 1 is the only member of the assemblage predicted to produce propionate and when modeled with the other 3 strains the predicted flux doubles in replete media and quadruples in the fiber media illustrating the potential metabolic synergy from the assemblage. Strain 3 is the only member of the assemblage predicted to produce butyrate and when modeled with the other 3 strains the predicted flux increase slightly in replete media and doubled in the fiber media illustrating the potential metabolic synergy from the assemblage.

TABLE 6

| Strains from first DMA model. | |
|---|---|
| # | Strain |
| Strain 1 | DP6 *Bacillus cereus*-like |
| Strain 2 | DP9 *Pediococcus pentosaceus*-like |
| Strain 3 | *Clostridium butyricum* DSM 10702 |
| Strain 4 | DP1 *Pseudomonas fluorescens*-like |

Figure 5:
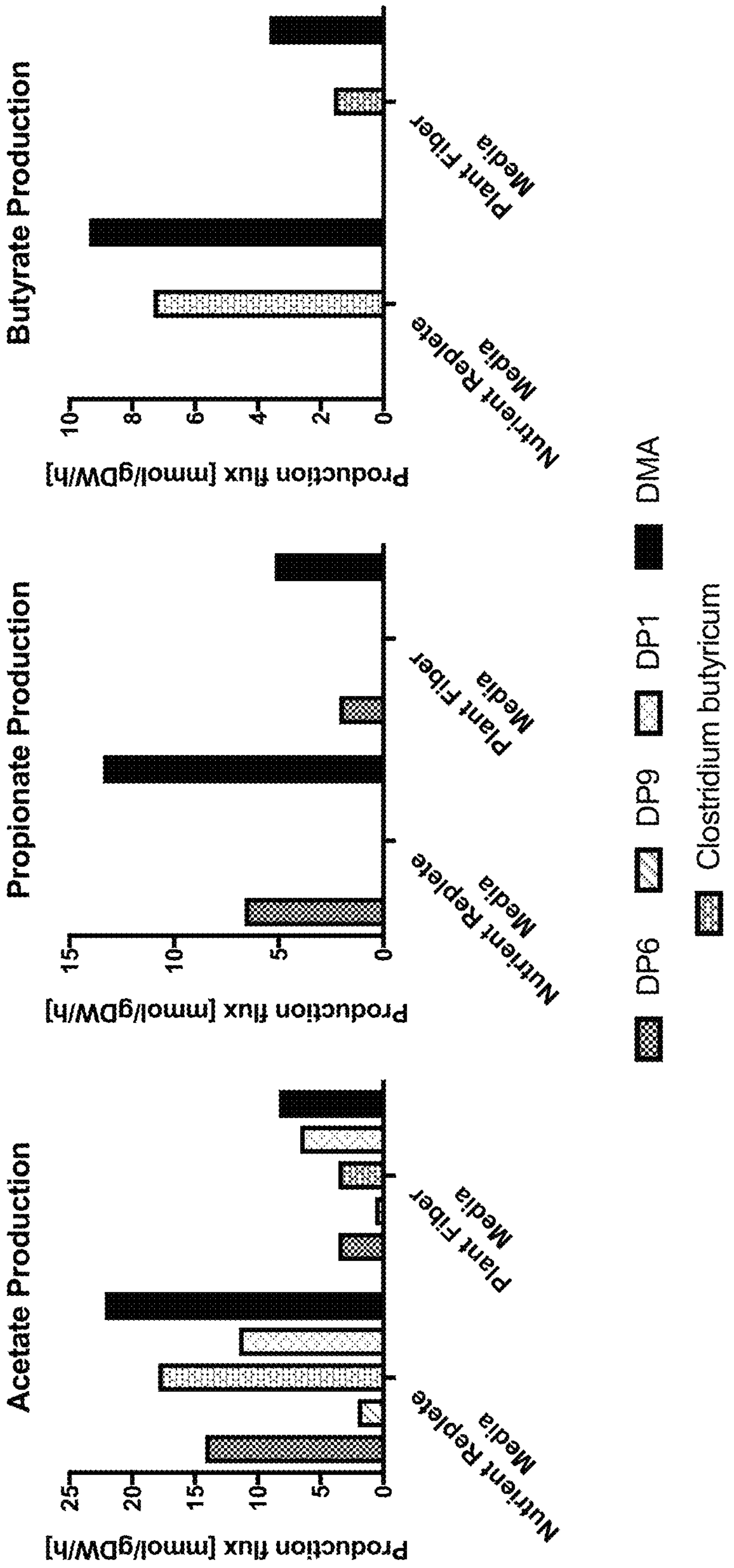
FIG. 5. Genome-wide metabolic model for a DMA formulated in silico with 3 DP strains and one genome from a reference in NCBI. The predicted fluxes for acetate, propionate and butyrate under a nutrient-replete and plant fiber media are indicated.

Substrate availability plays an important role in the establishment of synergistic interactions. Carbon limitation in presence of plant fibers favors fiber depolymerization and fermentation to produce SCFA. Conversely carbon replete conditions will prevent the establishment of synergistic metabolism to degrade fibers as it is not favored thermodynamically when the energy available from simple sugars is available. To illustrate this, we formulated a DMA containing two strains of lactic acid bacteria and run a metabolic prediction assuming a limited media with plant fibers. According to the model, *Leuconostoc* predicted flux is higher than *Pediococcus* and the DMA flux increases five times on the combined strains. When tested in the lab and measured by gas chromatography, the acetate production increases 3 times compared to the single strains (FIG. 5). However, when grown on carbon replete media with available simple sugars, acetate production is correspondingly higher compared to the plant fiber media but there is no benefit of synergistic acetate production when the two strains are grown together into a DMA.

Figure 6:
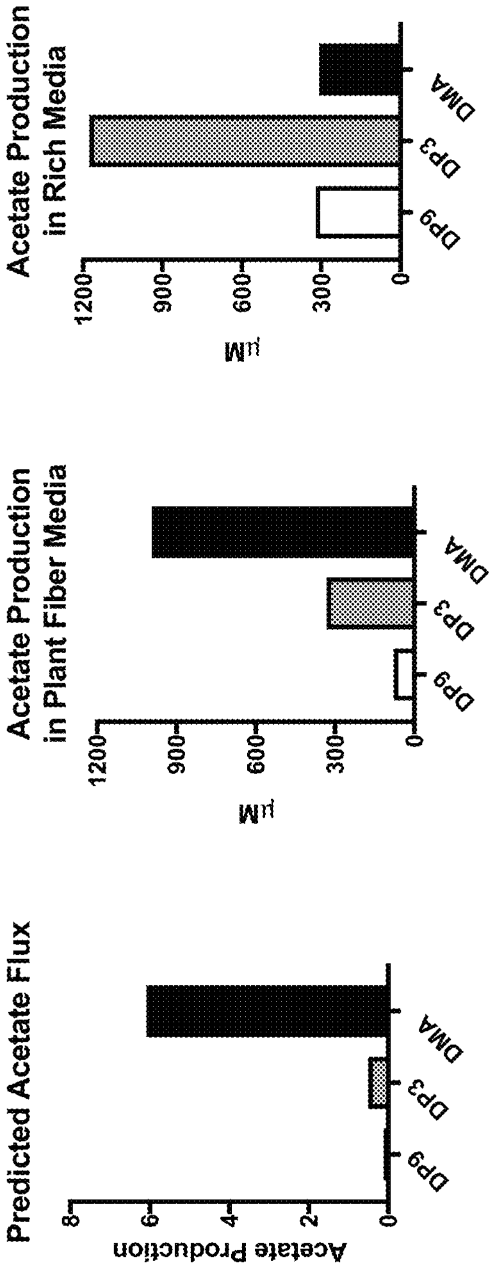
FIG. 6. DMA experimental validation for a combination of strains DP3 and DP9 under nutrient replete and plant fiber media showing that the strains show synergy for increased SCFA production only under plant fiber media but not under rich media.

In addition to acetate, propionate, and butyrate some strains produce other isomers. For example, strains SBI0189 related to *Pseudomonas fluorescens* and SBI0319 related to *Debaromyces hansenii* (yeast) produce isobutyrate when grown in carbon-replete media as single strains, however there is metabolic synergy when tested together as DMA measured as an increase in the isobutyric acid production (FIG. 6).

To describe experimentally the process of DMA validation the following method can be applied to find other candidates applicable to other products:

1. Define a suitable habitat where microbes are with the desirable attributes are abundant based on ecological hypotheses. For example, fresh vegetables are known to have anti-inflammatory effects when consumed in a whole-food plant based diet, and therefore, it is likely they harbor microbes that can colonize the human gut.
2. Apply a selection filter to isolate and characterize only those microbes capable of a relevant gut function. For example, tolerate acid shock, bile salts and low oxygen. In addition, strains need to be compatible with target therapeutic drugs. In type 2 diabetes metformin is a common first line therapy.

3. Selected strains are then cultivated in vitro and their genomes sequenced at 100× coverage to assemble, annotate and use in predictive genome-wide metabolic models.
4. Metabolic fluxes are generated with unconstrained models that consider multiple strains and the human host to determine the synergistic effects from multiple strains when it is assumed they are co-cultured under a simulated substrate conditions.
5. Predicted synergistic combinations are then tested in the laboratory for validation.

Single strains are grown to produce a biomass and the spent growth media removed after reaching late log phase. The washed cells are then combined in Defined Microbial Assemblages with 2-10 different strains per DMA and incubated using a culture media with plant fibers as substrates to produce short chain fatty acids to promote gut health.

6. The DMAs are then analyzed by gas chromatography to quantify the short chain fatty acid production where the synergistic effect produces an increased production in the combined assemblage as compared to the individual contributions.

Example 3: Meformin Resistance Experiments

To assess the effect of metformin in the microbiota, metformin is used as a selection agent by applying to a variety of growth media from a filter sterilized metformin stock at 100 mg/ml by adding 20 μL into 4 ml of liquid media for a final concentration of 500 μg/mL. The media tested is potato dextrose broth in liquid, 0.5× R2A liquid media or both formulations in solid media by the addition of 2% agar. Samples containing microbiomes are plated and spread onto solid media and colonies isolated and propagated as pure cultures. DNA is extracted from these strains and sequenced using Illumina's NGS protocols.

A total of 234 strains were isolated using solid 0.5× R2A and their genomes were sequenced. In addition, enrichments in liquid media using the conditions listed above were set up to generate a consortium capable of growing with metformin and to develop its potential therapeutic activity.

The results of the metformin resistance experiments are shown below in Table 7.

Example 4: Gut Simulation Experiments

The experiment comprises an in vitro, system that mimics various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. A schematic of the gut simulator experiments is shown in FIG. 3. Utilizing this system, the impact of various oral anti-diabetic therapies alone or in combination with probiotic cocktails of interest on the microbial ecosystem can be tested. Representative isolates are shown in Table 7.

TABLE 7

Strains resistant to metformin, listed with heat shock tolerance, acid shock tolerance, and isolation temperature.

| Strain number | Heat shock | Isolation temperature | Acid shock (pH 3) 2 hr | Genus | species |
|---|---|---|---|---|---|
| DP1 | No | 25 | No | *Pseudomonas* | *fluorescens* |
| DP2 | No | 37 | No | *Hanseniaspora* | *occidentalis* |
| DP3 | No | 25 | No | *Leuconostoc* | *mesenteroides* |
| DP4 | No | 25 | No | *Aureobasidium* | *pullanans* |
| DP5 | No | 37 | No | *Debaromyces* | *hansenii* |
| DP6 | Yes | 25 | No | *Bacillus* | *cereus* |
| DP7 | No | 25 | No | *Pichia* | *fermentans* |
| DP8 | No | 25 | No | *Hanseniaspora* | *opuntiae* |
| DP9 | No | 25 | No | *Pediococcus* | *pentosauceus* |
| DP10 | Yes | 25 | No | *Bacillus* | *velezensis* |
| DP11 | No | 25 | No | *Pseudomonas* | *putida* |
| DP12 | No | 25 | Yes | *Microbacterium* | sp. |
| DP13 | No | 25 | Yes | *Bacillus* | *mycoides* |
| DP14 | No | 25 | Yes | *Arthrobacter* | *luteolus* |
| DP15 | No | 25 | No | *Curtobacterium* | sp. |
| DP16 | No | 25 | No | *Cryptococcus* | *laurentii* |
| DP17 | No | 25 | No | *Rahnella* | *aquatilis* |
| DP18 | No | 25 | No | *Pseudomonas* | sp. |
| DP19 | No | 25 | No | *Curtobacterium* | *pusillum* |
| DP20 | No | 25 | No | *Stenotrophomonas* | *rhizophila* |
| DP21 | No | 25 | No | *Candida* | *santamariae* |
| DP22 | No | 25 | No | *Rahnella* | sp. |
| DP23 | No | 25 | No | *Erwinia* | *billingiae* |
| DP24 | No | 25 | No | *Filobasidium* | *globisporum* |
| DP25 | No | 25 | No | *Penicillium* | *solitum* |
| DP26 | No | 25 | No | *Methylobacterium* | sp. |
| DP27 | No | 25 | No | *Sphingomonas* | sp. |
| DP28 | No | 25 | Yes | *Aureobasidium* | *pullulans* |
| DP29 | No | 25 | Yes | *Pseudoclavibacter* | *helvolus* |
| DP30 | No | 25 | Yes | *Microbacterium* | *testaceum* |
| DP31 | No | 25 | Yes | *Sporisorium* | *reilianum* |
| DP32 | No | 25 | No | *Hafnia* | *paralvei* |
| DP33 | No | 25 | No | *Erwinia* | *persicinus* |
| DP34 | No | 25 | Yes | *Plantibacter* | *flavus* |
| DP35 | No | 25 | Yes | *Pantoea* | *ananatis* |
| DP36 | No | 25 | Yes | *Pantoea* | *vagans* |
| DP37 | No | 25 | No | *Pseudomonas* | *rhodesiae* |
| DP38 | No | 25 | No | *Rhodococcus* | sp. |
| DP39 | No | 25 | No | *Agrobacterium* | *tumefaciens* |
| DP40 | No | 37 | No | *Pantoea* | sp. |
| DP41 | Yes | 37 | No | *Corynebacterium* | *mucifaciens* |
| DP42 | No | 37 | No | *Pseudomonas* | *lundensis* |
| DP43 | No | 25 | No | *Janthinobacterium* | sp. |
| DP44 | No | 25 | No | *Herbaspirillum* | sp. |
| DP45 | No | 25 | No | *Sanguibacter* | *keddieii* |
| DP46 | No | 25 | Yes | *Pantoea* | *agglomerans* |
| DP47 | No | 25 | Yes | *Cronobacter* | *dublinensis* |
| DP48 | Yes | 25 | No | *Bacillus* | *paralicheniformis* |
| DP49 | Yes | 25 | No | *Bacillus* | *gibsonii* |
| DP50 | No | 25 | No | *Enterobacter* | sp. |
| DP51 | No | 25 | No | *Klebsiella* | *aerogenes* |
| DP52 | No | 25 | No | *Arthrobacter* | sp. |
| DP53 | No | 25 | No | *Pseudomonas* | *fragi* |
| DP54 | No | 25 | No | *Methylobacterium* | *adhaesivum* |
| DP55 | Yes | 25 | No | *Bacillus* | *megaterium* |
| DP56 | Yes | 25 | No | *Paenibacillus* | *lautus* |
| DP57 | Yes | 25 | No | *Bacillus* | *mycoides* |
| DP58 | No | 25 | No | *Janthinobacterium* | *svalbardensis* |
| DP59 | No | 25 | No | *Kosakonia* | *cowanii* |
| DP60 | Yes | 25 | No | *Bacillus* | *simplex* |
| DP61 | No | 25 | No | *Lelliottia* | sp. |
| DP62 | No | 25 | No | *Erwinia* | sp. |
| DP63 | No | 25 | Yes | *Pseudomonas* | *azotoformans* |
| DP64 | No | 25 | No | *Saccharomycetaceae* | |
| DP65 | No | 25 | No | *Sporobolomyces* | *carnicolor* |
| DP66 | No | 25 | No | *Pichia* | |

Example 5: Preclinical Experiments

Figure 7:
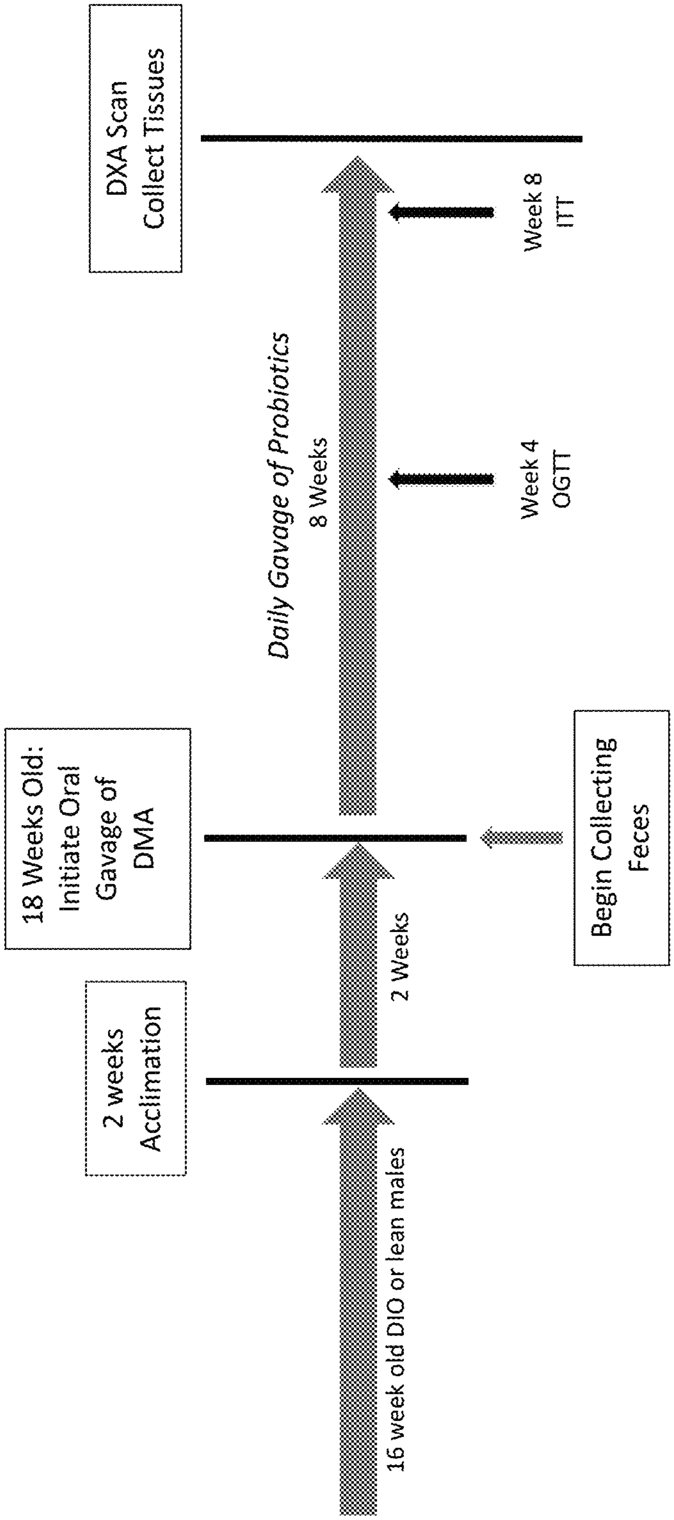
FIG. 7 shows a schematic detailing the experimental procedure for a pre-clinical model testing the disclosed methods. To test the translational viability of enhancing the effects of oral anti-diabetic drugs such as metformin, the diet-induced obesity mouse model, a highly-accepted, clinically relevant animal model of type 2 diabetes (T2D) is used.

To test the effect of the therapeutic compositions disclosed in this application prior to studies in the clinic, experiments are conducted in a mouse model of dietary-induced obesity. FIG. 7 provides a schematic detailing the experimental procedure for this pre-clinical experiment.

DIO Preclinical Study

Male diet induced obese (DIO) and low-fat diet control C57BL/6J mice were purchased from the Jackson Laboratories (Jax) at 16 weeks of age and were singly housed in individually ventilated cages (IVCs) (Allentown Inc) in a room with a 12-hour light/dark schedule at Invivotek (Trenton, N.J.). At Jax, mice were placed on either a low-fat diet (10% kcal, D12450B) or high-fat diet (60% kcal, D12492) (Open Source Diets; Research Diets Inc.) at 5-weeks of age and remained on those respective diets for the duration of the experiment. Mice were allowed to acclimate for 2-weeks at Invivotek prior to the experimental commencement. At 18-weeks of age, test articles were provided to the mice via oral gavage as indicated in Table 1. Control groups were provided sterile water at a dose of 5 mL/kg body weight. Metformin treatment was provided at a dose of 100 mg/kg body weight either independently, or in combination with various Defined Microbial Assemblages (DMAs). DMAs were provided at a dose of $8\times10^{10}$ CFUs/kg body weight. Mice were gavaged with test articles daily for 8-weeks. Here, mice are placed at 5 weeks of age on either a low-fat (10% kcal fat) or high-fat (60% kcal fat) diet. At 16 weeks of age, the mice are delivered to the facility and allowed to acclimate for 2 weeks. After 13 weeks of diet, mice receive a daily oral gavage of saline (control), metformin, probiotic cocktail of interest, or probiotic cocktail in combination with metformin, to quantify the ability of the probiotic cocktail to improve metformin efficacy. Daily gavages continue for 8 weeks, at which point glucose tolerance tests and insulin tolerance tests are performed to evaluate the metabolic health of each mouse. Each week, mice are weighed, and fecal samples are collected to evaluate changes in the microbial composition over time. At sacrifice, adipose tissue depots, blood, liver, small intestine, and colonic tissue from each mouse are collected for downstream mechanistic analysis.

Oral Glucose Tolerance Test (OGTT)

After 4 weeks of dosing mice with test article, an OGTT was performed. Here, mice were fasted for 6 hours after which fasting blood glucose levels were measured via tail vein blood using a glucometer (One-Touch Ultra II). Mice were then dosed with an oral glucose bolus (2 g/kg) via oral gavage, and blood glucose was measured at 20, 40, 60, and 120 minutes post gavage.

Insulin Tolerance Test (ITT)

8 weeks after the first dose of test material, mice were fasted for 4-hours and a baseline blood glucose level measurement was recorded using a glucometer (One-Touch Ultra II). Following baseline measurements, mice received an intraperitoneal (IP) injection of insulin (10 mL/kg at a concentration of 0.1 U/mL). After injection, blood glucose was measured at 15, 30, 60, 90, and 120 minutes via tail vein blood.

Body composition

Body fat percentage was determined using Dual Energy x-ray Absorptiometry (DEXA) scan (PIXImus2 Mouse Densitometer; GE) 8 weeks after initiation of DMA treatment. Prior to DEXA scans, mice were anesthetized via intraperitoneal injection of ketamine (60 mg/kg) and xylazine (4 mg/kg).

TABLE 8

| Group | Diet | Treatment | Gender |
|---|---|---|---|
| 1 | Low Fat | Vehicle (Water) | Male |
| 2 | High Fat | Vehicle (Water) | Male |
| 3 | High Fat | Metformin | Male |
| 4 | High Fat | DMA buffer | Male |
| 5 | High Fat | DMA #2 | Male |
| 6 | High Fat | DMA #3 | Male |
| 7 | High Fat | DMA #4 | Male |
| 8 | High Fat | DMA #5 | Male |
| 9 | High Fat | Metformin + DMA buffer | Male |
| 10 | High Fat | Metformin + DMA #2 | Male |
| 11 | High Fat | Metformin + DMA #3 | Male |
| 12 | High Fat | Metformin + DMA #4 | Male |
| 13 | High Fat | Metformin + DMA #5 | Male |

Table 9. List of single strains and combinations into DMAs for preclinical experiments. The DMAs were selected based on their ability to produce SCFA synergistically, their growth compatibility, tolerance to metformin, ability to grown on plant fibers and tolerance to cryopreservation.

TABLE 9

| Isolate | Genus | Species | Sample origin |
|---|---|---|---|
| DP1 | *Psuedomonas* | *fluorescens* | Cherry tomato |
| DP5 | *Debaryomyces* | *hansenii* | Red cabbage |
| DP2 | *Hanseniaspora* | *uvarum* | Lime |
| DP3 | *Leuconostoc* | *mesenteroides* | Fermented tomatoes |
| DP9 | *Pediococcus* | *pentosaceus* | Fermented cabbage |
| DP22 | *Rahenlla* | Sp. | pomegranate |
| DP53 | *Psuedomonas* | *fragi* | arugula |

DMAs

#2-DP9:DP2:DP53

#3-DP9:DP2:DP3

#4-DP9:DP2:DP22

#5-DP5:DP1

At sacrifice blood is collected from each mouse for downstream mechanistic analysis. This assay, as with the assays described above can be carried out with metformin or any appropriate anti-diabetic therapy. Additionally, adipose tissue depots, blood, liver, small intestine, and colonic tissue are collected from each mouse for subsequent analysis.

Figure 8:
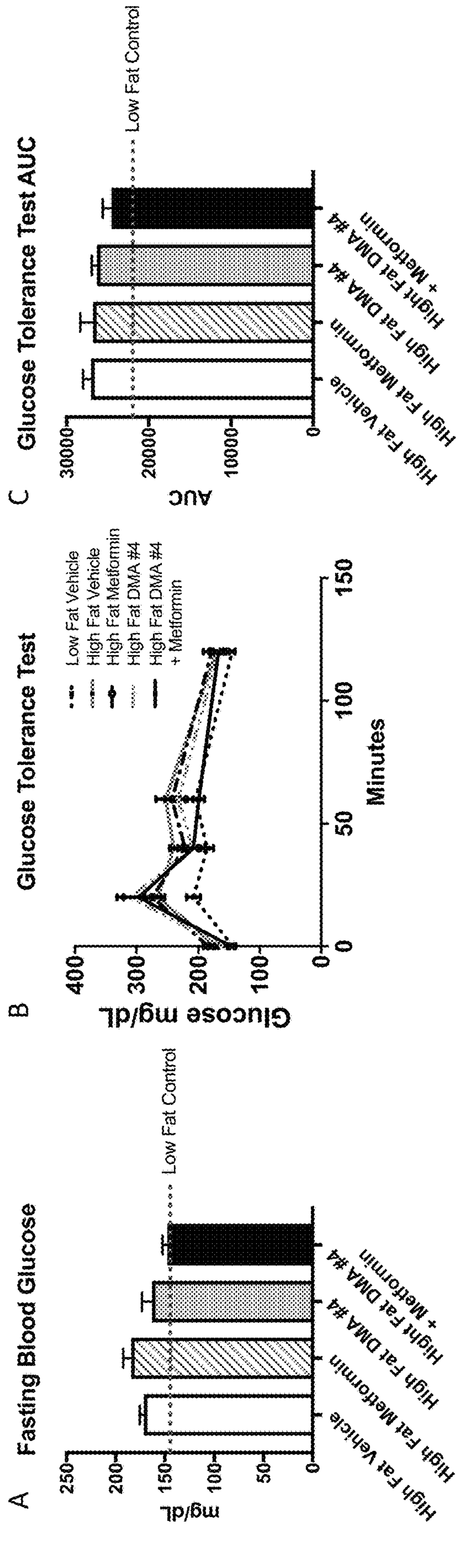
FIG. 8. Glucose tolerance test conducted with mice receiving the formulated DMA4 showing benefit when combined with metformin to reduce fasting glucose, and a rapid glucose clearance after 20 minutes of receiving a glucose dose.

Glucose tolerance test revealed that combination of DMA #4 and metformin led to an improved fasting blood glucose and glucose tolerance compared to either high-fat diet control, metformin monotherapy treated, or DMA #4 monotherapy treated mice. As observed in FIG. 8A, obese mice treated with the combination therapy had a fasting blood glucose identical to low fat control mice, indicative of normal glycemic health despite consuming a high-fat diet. Further, glucose tolerance tests (FIG. 8B) indicate that mice treated with the combination of DMA #4 and Metformin also had improved capacity to respond to a glucose challenge and absorb the glucose from the blood stream compared to either high-fat diet control, metformin monotherapy treated, or DMA #4 monotherapy treated mice. This is observed in (FIG. 8B) where despite a larger increase in blood glucose following challenge compared to lean mice at 15 minutes, the glucose was rapidly absorbed and returned to normal levels by 60 minutes while high-fat diet control, metformin monotherapy treated, or DMA #4 monotherapy treated mice all remained elevated. This effect is also observed by the area under the curve (AUC) in (FIG. 8C).

Figure 9:
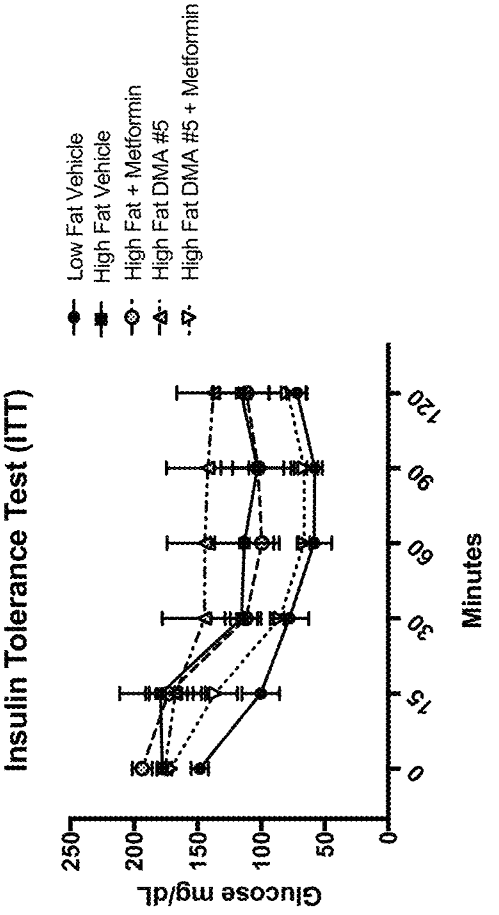
FIG. 9. Insulin tolerance test for mice receiving DMA5 and metformin showing a rapid insulin sensitivity response similar to that of lean mice grown under a low fat diet.

Combination therapy of DMA #5 and metformin improves insulin tolerance in Obese mice (FIG. 9). After 7 weeks of therapeutic intervention, mice received an insulin tolerance test. Here, we found that a combination of DMA #5 and metformin led to a significantly improved response to insulin, as indicated by the rapid clearance of glucose from the blood stream following intraperitoneal injection with insulin. The response to insulin was improved compared to obese controls. In fact, the response was exactly the same as the lean control mice, indicating that these obese mice have the same insulin sensitivity as a healthy mouse even after consuming a high fat diet for 20 weeks. Further, when controlling for the initial elevated fasting blood glucose in obese mice by normalizing to baseline, the significant improvement remained. DMA #5 is comprised of DP5 *Debaromyces hansenii*-like and DP1 *Pseudomonas fluorescens*-like isolates (Table 9).

Example 6: Computation of Microbial Entity Average Nucleotide Identity (ANI)

Microbial whole-genome sequencing has become an important tool for effectively and rapidly analyzing hundreds of bacterial genomes from different environments and with special relevance for human health. The study of bacterial genomes from multiple isolation sources has increased our knowledge of their ecological roles in different ecosystems, led to the identification of novel species, and the tracking of disease outbreaks. However, most of microbes remain uncultured, hampering its characterization and thus the identification of microbial key players and their participation in modulating host homeostasis is still far from complete.

Remarkable advances over the last decade in the human gut microbiome through the Human Microbiome Project (HMP) and the Metagenomics of the Human Intestinal Tract project (MetaHIT) have allowed to describe the baseline diversity found in the gut flora in a healthy and sick host. However, the amount of novel genetic diversity of microbial communities from complex environments such as soil, vegetables, and marine environments, remains essentially unknown.

16S rRNA gene sequencing is a cultured-independent method commonly used to classify bacterial genomes at the species level. However, because of its high sequence conservation, this method offers insufficient genetic resolution to capture intraspecific variation, limiting our knowledge. Alternative methods based on a set of maker genes or universally conserved genes often provide insufficient resolution because these genes show higher sequence conservation than the genome average sequence.

In view of the foregoing limitations, we applied a whole-genome based method, the average nucleotide identity (ANI), to estimate the genetic relatedness among bacterial genomes and profile hundreds of microbial species at a higher resolution taxonomic level (i.e., species- and strain-level classification). ANI is based on the average of the nucleotide identity of all orthologous genes shared between a genome pair. Genomes of the same species present ANI values above 95% and of the same genus values above 80% (Jain et al. 2018).

Taxonomic annotation of the strains combined into DMAs using ANI and the NCBI RefSeq database indicated that these microbes represent species not present in the database and most likely are new bacterial species even when the nucleotide identity based on the 16S rRNA gene is 99%.

TABLE 10

Comparative predictive power of 16S rRNA sequence analysis and Average Nucleotide Identity (ANI) analysis. While 16S rRNA sequence percentage indicates a high degree of homology, ANI analysis demonstrates that the overall genome sequence of the microbial entities isolated from plants and described herein as compared to reference strains is different enough in many cases to qualify as a different species.

| ID | NCBI match | 16S rRNA gene (%) | Closest Reference genome at NCBI | ANI (%) |
|---|---|---|---|---|
| DP3 | *Leuconostoc mesenteroides* (NR_074957.1.) | 99 | *Leuconostoc pseudomesenteroides* (JDVA01000001.1.) | 91.77 |
| DP9 | *Pediococcus pentosauceus* (NR_042058.1.) | 99 | *Pediococcus pentosauceus* (NC_022780.1.) | 99.6 |
| DP53 | *Pseudomonas helleri* (NR_148763.1.) | 99 | *Pseudomonas psychrophile* (NZ_LT629795.1.) | 86.82 |
| DP1 | *Pseudomonas fluorescens* (NR_115715.1.) | 99 | *Pseudomonas antarctica* (NZ_CP015600.1.) | 94.48 |
| DP22 | *Rahnella aquatilis* (NR_025337.1) | 98 | *Rahnella* sp. (NC_015061.1.) | 88.31 |

Example 7: Monitoring the Effect of DMAs on Microbial Flora of a Mammal

Alterations of the gut microbiota have been linked with changes in the host homeostasis such as metabolic diseases. In order to evaluate alterations in the gut microbiota composition in obese individuals, fecal samples were collected from DIO and lean mice and the gut microbiota was characterized. Briefly, DNA was extracted using the Zymo Quick-DNA Fecal/Soil Microbe Kit and quantified using a Qubit 2.0 flurometer with the dsDNA HS assay kit. Metagenomic libraries were prepared using the Illumina Nextera XT DNA library prep kit and an equimolar mixture of the libraries was sequenced on an Illumina NextSeq instrument on a 2×150 bp paired end run. Raw reads from the sequencing run were analyzed using SolexaQA (Cox et al. 2010) for trimming and removing of Illumina adaptors using a Phred score cutoff of 20 and minimum fragment length of 50 bp. Taxonomic classification of the short-read metagenomes was determined using MetaPhlan2, which uses Glade-specific marker genes from approximately 17,000 reference genomes to estimate the relative abundance of microbial members present in the sample (Troung et al. 2015).

Figure 10:
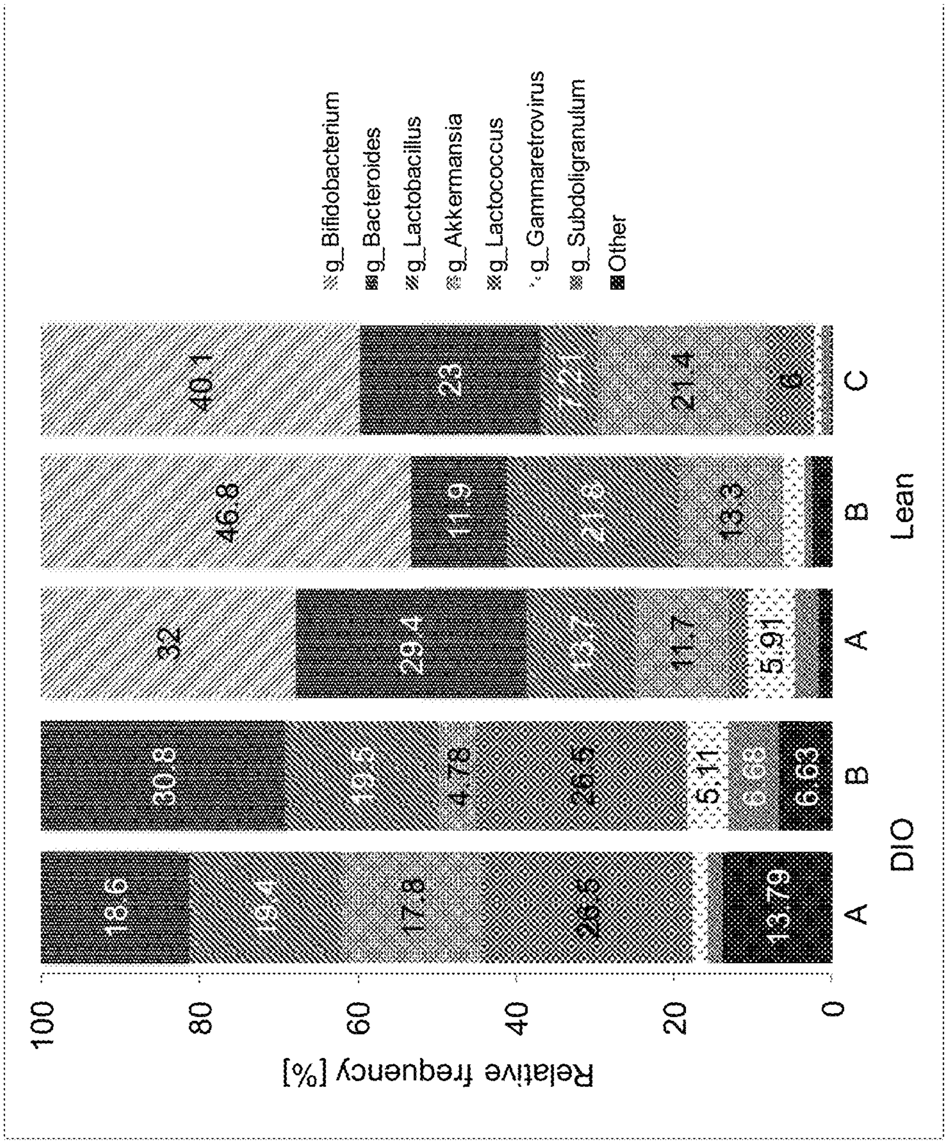
FIG. 10. Stool microbiome baseline for mice grown under high or low fat diet indicating the differences primarily seen as a lack of *Bifidobacteria* under high fat diet.

FIG. 10 shows the composition of the gut microbial community of DIO and lean mice. Overall, the genus *Bifidobacterium* was the most prevalent taxon detected in lean mice encompassing on average 40% of the total community followed by *Bacteorides* with 21.4% on average, and Akkermansia with 14.2% on average. In the case of the DIO mice, *Lactococcus* was the most abundant genus with 26.5% on average followed by *Bacteroides* with 24.6% and *Lactobacillus* with 19.4%.

All references, issued patents and patent applications cited within the body of the instant specification are hereby incorporated by reference in their entirety, for all purposes.

SEQUENCE LISTING
Seq ID No.
Description
Sequence

1
DP1 16S rRNA
AGTCAGACATGCAAGTCGAGCGGTAGAGAGAAGCTTGCTTCTCTTGAGAGCGGCGGACGGGTGAG
TAAAGCCTAGGAATCTGCCTGGTAGTGGGGGATAACGTTCGGAAACGGACGCTAATACCGCATACGT
CCTACGGGAGAAAGCAGGGGACCTTCGGGCCTTGCGCTATCAGATGAGCCTAGGTCGGATTAGCTAG
TTGGTGAGGTAATGGCTCACCAAGGCGACGATCCGTAACTGGTCTGAGAGGATGATCAGTCACACTG
GAACTGAGACACGGTCCAGACTCCTACGGGAGGCAGCAGTGGGGAATATTGGACAATGGGCGAAAG
CCTGATCCAGCCATGCCGCGTGTGTGAAGAAGGTCTTCGGATTGTAAAGCACTTTAAGTTGGGAGGA
AGGGCATTAACCTAATACGTTAGTGTTTTGACGTTACCGACAGAATAAGCACCGGCTAACTCTGTGCC
AGCAGCCGCGGTAATACAGAGGGTGCAAGCGTTAATCGGAATTACTGGGCGTAAAGCGCGCGTAGGT
GGTTTGTTAAGTTGGATGTGAAATCCCCGGGCTCAACCTGGGAACTGCATTCAAAACTGACTGACTAG
AGTATGGTAGAGGGTGGTGGAATTTCCTGTGTAGCGGTGAAATGCGTAGATATAGGAAGGAACACCA
GTGGCGAAGGCGACCACCTGGACTAATACTGACACTGAGGTGCGAAAGCGTGGGGAGCAAACAGGA
TTAGATACCCTGGTAGTCCACGCCGTAAACGATGTCAACTAGCCGTTGGGAGCCTTGAGCTCTTAGTG
GCGCAGCTAACGCATTAAGTTGACCGCCTGGGGAGTACGGCCGCAAGGTTAAAACTCAAATGAATTG
ACGGGGGCCCGCACAAGCGGTGGAGCATGTGGTTTAATTCGAAGCAACGCGAAGAACCTTACCAGGC
CTTGACATCCAATGAACTTTCTAGAGATAGATTGGTGCCTTCGGGAACATTGAGACAGGTGCTGCATG
GCTGTCGTCAGCTCGTGTCGTGAGATGTTGGGTTAAGTCCCGTAACGAGCGCAACCCTTGTCCTTAGT
TACCAGCACGTAATGGTGGGCACTCTAAGGAGACTGCCGGTGACAAACCGGAGGAAGGTGGGGATG
ACGTCAAGTCATCATGGCCCTTACGGCCTGGGCTACACACGTGCTACAATGGTCGGTACAGAGGGTT
GCCAAGCCGCGAGGTGGAGCTAATCCCATAAAACCGATCGTAGTCCGGATCGCAGTCTGCAACTCGA
CTGCGTGAAGTCGGAATCGCTAGTAATCGCGAATCAGAATGTCGCGGTGAATACGTTCCCGGGCCTT
GTACACACCGCCCGTCACACCATGGGAGTGGGTTGCACCAGAAGTAGCTAGTCTAACCTTCGGGAGG
ACGGTTACCACGGTGTGATTCATGACTGGGGTGAAGTCGTAACAAGGTAGCCGTAGGGGAACCTGCG
GCTGGATCACCTCCTT

2
DP2 ITS sequence
NNNNNNNNNNNNNNNNNNTTGTTGCTCGAGTTCTTGTTTAGATCTTTTACAATAATGTGTATCTTT
AATGAAGATGNGNGCTTAATTGCGCTGCTTTATTAGAGTGTCGCAGTAGAAGTAGTCTTGCTTGAATC
TCAGTCAACGTTTACACACATTGGAGTTTTTTTACTTTAATTTAATTCTTTCTGCTTTGAATCGAAAGG
TTCAAGGCAAAAAACAAACACAAACAATTTTATTTTATTATAATTTTTTAAACTAAACCAAAATTCCT
AACGGAAATTTTAAAATAATTTAAAACTTTCAACAACGGATCTCTTGGTTCTCGCATCGATGAAAAAC
GTACCGAATTGCGATAAGTAATGTGAATTGCAAATACTCGTGAATCATTGAATTTTTGAACGCACATT
GCGCCCTTGAGCATTCTCAAGGGCATGCCTGTTTGAGCGTCATTTCCTTCTCAAAAAATAATTTTTTAT
TTTTTGGTTGTGGGCGATACTCAGGGTTAGCTTGAAATTGGAGACTGTTTCAGTCTTTTTTAATTCAAC
ACTTANCTTCTTTGGAGACGCTGTTCTCGCTGTGATGTATTTATGGATTTATTCGTTTTACTTTACAAG
GGAAATGGTAATGTACCTTAGGCAAAGGGTTGCTTTTAATATTCATCAAGTTTGACCTCAAATCAGGT
AGGATTACCCGCTGAACTTAAGCATATCAATAAGCGGAGGAAAAGAAACCAACTGGGATTACCTTAG
TAACGGCGAGTGAAGCGGTAAAAGCTCAAATTTGAAATCTGGTACTTTCAGTGCCCGAGTTGTAATTT
GTAGAATTTGTCTTTGATTAGGTCCTTGTCTATGTTCCTTGGAACAGGACGTCATAGAGGGTGAGANT
CCCGTTTGNNGAGGATACCTTTTCTCTGTANNACTTTTTCNAAGAGTCGAGTTGNTTGGGAATGCAGC
TCAAANNGGGTNGNAAATTCCATCTAAAGCTAAATATTNGNCNAGAGACCGANAGCGACANTACAG
NGATGGAAAGANGAAANNANTTGAAAAGAANANNGAAAANTACGTGAANNNNNAAANGGNNNGGC
ATTTGATCNNNCATGGNNNTTTTTNCATGNN 3
DP3 16S rRNA
ATTGAGAGTTTGATCCTGGCTCAGGATGAACGCTGGCGGCGTGCCTAATACATGCAAGTCGAACG
CACAGCGAAAGGTGCTTGCACCTTTCAAGTGAGTGGCGAACGGGTGAGTAACACGTGGACAACCTGC
CTCAAGGCTGGGGATAACATTTGGAAACAGATGCTAATACCGAATAAAACTCAGTGTCGCATGACAC
AAAGTTAAAAGGCGCTTTGGCGTCACCTAGAGATGGATCCGCGGTGCATTAGTTAGTTGGTGGGGTA
AAGGCCTACCAAGACAATGATGCATAGCCGAGTTGAGAGACTGATCGGCCACATTGGGACTGAGACA
CGGCCCAAACTCCTACGGGAGGCTGCAGTAGGGAATCTTCCACAATGGGCGAAAGCCTGATGGAGCA
ACGCCGCGTGTGTGATGAAGGCTTTCGGGTCGTAAAGCACTGTTGTACGGGAAGAACAGCTAGAATA
GGGAATGATTTTAGTTTGACGGTACCATACCAGAAAGGGACGGCTAAATACGTGCCAGCAGCCGCGG
TAATACGTATGTCCCGAGCGTTATCCGGATTTATTGGGCGTAAAGCGAGCGCAGACGGTTGATTAAGT
CTGATGTGAAAGCCCGGAGCTCAACTCCGGAATGGCATTGGAAACTGGTTAACTTGAGTGCAGTAGA
GGTAAGTGGAACTCCATGTGTAGCGGTGGAATGCGTAGATATATGGAAGAACACCAGTGGCGAAGGC
GGCTTACTGGACTGTACTGACGTTGAGGCTCGAAAGTGTGGGTAGCAAACAGGATTAGATACCCTGG
TAGTCCACACCGTAAACGATGAACACTAGGTGTTAGGAGGTTTCCGCCTCTTAGTGCCGAAGCTAACG
CATTAAGTGTTCCGCCTGGGGAGTACGACCGCAAGGTTGAAACTCAAAGGAATTGACGGGGACCCGC
ACAAGCGGTGGAGCATGTGGTTTAATTCGAAGCAACGCGAAGAACCTTACCAGGTCTTGACATCCTTT
GAAGCTTTTAGAGATAGAAGTGTTCTCTTCGGAGACAAAGTGACAGGTGGTGCATGGTCGTCGTCAG
CTCGTGTCGTGAGATGTTGGGTTAAGTCCCGCAACGAGCGCAACCCTTATTGTTAGTTGCCAGCATTC
AGATGGGCACTCTAGCGAGACTGCCGGTGACAAACCGGAGGAAGGCGGGGACGACGTCAGATCATC
ATGCCCCTTATGACCTGGGCTACACACGTGCTACAATGGCGTATACAACGAGTTGCCAACCCGCGAG
GGTGAGCTAATCTCTTAAAGTACGTCTCAGTTCGGATTGTAGTCTGCAACTCGACTACATGAAGTCGG
AATCGCTAGTAATCGCGGATCAGCACGCCGCGGTGAATACGTTCCCGGGTCTTGTACACACCGCCCGT -continued

| SEQUENCE LISTING<br>Seq ID No.<br>Description<br>Sequence |
|---|

CACACCATGGGAGTTTGTAATGCCCAAAGCCGGTGGCCTAACCTTTTAGGAAGGAGCCGTCTAAGGC
AGGACAGATGACTGGGGTGAAGTCGTAACAAGGTAGCCGTAGGAGAACCTGCGGCTGGATCACCTCC
TTT

4
DP4 16S rRNA
TTGAAGAGTTTGATCATGGCTCAGATTGAACGCTGGCGGCAGGCCTAACACATGCAAGTCGAGCG
GCAGCGGAAAGTAGCTTGCTACTTTGCCGGCGAGCGGCGGACGGGTGAGTAATGTCTGGGAAACTGC
CTGATGGAGGGGGATAACTACTGGAAACGGTAGCTAATACCGCATGACCTCGAAAGAGCAAAGTGG
GGGATCTTCGGACCTCACGCCATCGGATGTGCCCAGATGGGATTAGCTAGTAGGTGAGGTAATGGCT
CACCTAGGCGACGATCCCTAGCTGGTCTGAGAGGATGACCAGCCACACTGGAACTGAGACACGGTCC
AGACTCCTACGGGAGGCAGCAGTGGGGAATATTGCACAATGGGCGCAAGCCTGATGCAGCCATGCCG
CGTGTGTGAAGAAGGCCTTAGGGTTGTAAAGCACTTTCAGCGAGGAGGAAGGCATCATACTTAATAC
GTGTGGTGATTGACGTTACTCGCAGAAGAAGCACCGGCTAACTCCGTGCCAGCAGCCGCGGTAATAC
GGAGGGTGCAAGCGTTAATCGGAATTACTGGGCGTAAAGCGCACGCAGGCGGTTTGTTAAGTCAGAT
GTGAAATCCCCGCGCTTAACGTGGGAACTGCATTTGAAACTGGCAAGCTAGAGTCTTGTAGAGGGGG
GTAGAATTCCAGGTGTAGCGGTGAAATGCGTAGAGATCTGGAGGAATACCGGTGGCGAAGGCGGCCC
CCTGGACAAAGACTGACGCTCAGGTGCGAAAGCGTGGGGAGCAAACAGGATTAGATACCCTGGTAGT
CCACGCCGTAAACGATGTCGACTTGGAGGTTGTTCCCTTGAGGAGTGGCTTCCGGAGCTAACGCGTTA
AGTCGACCGCCTGGGGAGTACGGCCGCAAGGTTAAAACTCAAATGAATTGACGGGGGCCCGCACAA
GCGGTGGAGCATGTGGTTTAATTCGATGCAACGCGAAGAACCTTACCTACTCTTGACATCCACGGAAT
TTGGCAGAGATGCCTTAGTGCCTTCGGGAACCGTGAGACAGGTGCTGCATGGCTGTCGTCAGCTCGTG
TTGTGAAATGTTGGGTTAAGTCCCGCAACGAGCGCAACCCTTATCCTTTGTTGCCAGCGATTCGGTCG
GGAACTCAAAGGAGACTGCCGGTGATAAACCGGAGGAAGGTGGGGATGACGTCAAGTCATCATGGC
CCTTACGAGTAGGGCTACACACGGCTACAATGGCGCATACAAAGAGAAGCGACCTCGCGAGAGCAA
GCGGACCTCACAAAGTGCGTCGTAGTCCGGATCGGAGTCTGCAACTCGACTCCGTGAAGTCGGAATC
GCTAGTAATCGTGGATCAGAATGCCACGGTGAATACGTTCCCGGGCCTTGTACACACCGCCCGTCACA
CCATGGGAGTGGGTTGCAAAAGAAGTAGGTAGCTTAACCTTCGGGAGGGCGCTTACCACTTTGTGAT
TCATGACTGGGGTGAAGTCGTAACAAGGTAACCGTAGGGGAACCTGCGGTTGGATCACCTCCTT

5
DP5 ITS sequence
NNNNNNNNNNNNNNNNNTGNNGCGCTTATTGCGCGGCGAAAAAACCTTACACACAGTGTTTTTTG
TTATTACANNAACTTTTGCTTTGGTCTGGACTAGAAATAGTTTGGGCCAGAGGTTACTAAACTAAACT
TCAATATTTATATTGAATTGTTATTTATTTAATTGTCAATTTGTTGATTAAATTCAAAAAATCTTCAAA
ACTTTCAACAACGGATCTCTTGGTTCTCGCATCGATGAAGAACGCAGCGAAATGCGATAAGTAATAT
GAATTGCAGATTTTCGTGAATCATCGAATCTTTGAACGCACATTGCGCCCTCTGGTATTCCAGAGGGC
ATGCCTGTTTGAGCGTCATTTCTCTCTCAAACCTTCGGGTTTGGTATTGAGTGATACTCTTAGTCGAAC
TAGGCGTTTGCTTGAAATGTATTGGCATGAGTGGTACTGGATAGTGCTATATGACTTTCAATGTATTA
GGTTTATCCAACTCGTTGAATAGTTTAATGGTATATTTCTCGGTATTCTAGGCTCGGCCTTACAATATA
ACAAACAAGTTTGACCTCAAATCAGGTAGGATTACCCGCTGAACTTAAGCATATCAATAAGCGGAGG
AAAAGAAACCAACAGGGATTGCCTTAGTAACGGCGAGTGAAGCGGCAAAAGCTCAAATTTGAAATCT
GGCACCTTCGGTGTCCGAGTTGTAATTTGAAGAAGGTAACTTTGGAGTTGGCTCTTGTCTATGTTCCTT
GGAACAGGACGTCACAGAGGGTGAGAATCCCGTGCGATGAGATGCCCAATTCTATGTAAAGTGCTTT
CGAAGAGTCGAGTTGTTTGGGAATGCAGCTCTAAGTGGGTGGTAAATTCCATCTAAAGCTAAATATTG
GCGAGAGACCGATAGCGAACAAGTACAGTGATGGAAAGATGAAAAGAACTTTGAAAAGAGAGTGAA
AAAGTACGTGAAATTGTTGAAAGGGAAAGGGCTTGAGATCAGACTTGGTATTTTGCGATCCTTTCCTT
CTTGGTTGGGTTCCTCGCAGCTTACTGGGNCAGCATCGGTTTGGATGGNAGGATAANGACTAAGNAA
TGNGGNNCTACTTCGNGGAGTGNNNNAGCNNTGGNNGANNACTNNCNNNCTAAGANCGAGGACTGN
GNNNTTTNN 6
DP6 16S rRNA 7
DP7 16S rRNA 8
DP8 16S rRNA 9
DP9 16S rRNA
ATGAGAGTTTGATCTTGGCTCAGGATGAACGCTGGCGGCGTGCCTAATACATGCAAGTCGAACGA
ACTTCCGTTAATTGATTATGACGTACTTGTACTGATTGAGATTTTAACACGAAGTGAGTGGCGAACGG
GTGAGTAACACGTGGGTAACCTGCCCAGAAGTAGGGGATAACACCTGGAAACAGATGCTAATACCGT
ATAACAGAGAAAACCGCATGGTTTTCTTTTAAAAGATGGCTCTGCTATCACTTCTGGATGGACCCGCG
GCGTATTAGCTAGTTGGTGAGGCAAAGGCTCACCAAGGCAGTGATACGTAGCCGACCTGAGAGGGTA
ATCGGCCACATTGGGACTGAGACACGGCCCAGACTCCTACGGGAGGCAGCAGTAGGGAATCTTCCAC
AATGGACGCAAGTCTGATGGAGCAACGCCGCGTGAGTGAAGAAGGGTTTCGGCTCGTAAAGCTCTGT
TGTTAAAGAAGAACGTGGGTAAGAGTAACTGTTTACCCAGTGACGGTATTTAACCAGAAAGCCACGG
CTAACTACGTGCCAGCAGCCGCGGTAATACGTAGGTGGCAAGCGTTATCCGGATTTATTGGGCGTAA
AGCGAGCGCAGGCGGTCTTTTAAGTCTAATGTGAAAGCCTTCGGCTCAACCGAAGAAGTGCATTGGA
AACTGGGAGACTTGAGTGCAGAAGAGGACAGTGGAACTCCATGTGTAGCGGTGAAATGCGTAGATAT
ATGGAAGAACACCAGTGGCGAAGGCGGCTGTCTGGTCTGCAACTGACGCTGAGGCTCGAAAGCATGG -continued

| SEQUENCE LISTING Seq ID No. Description Sequence |
|---|

GTAGCGAACAGGATTAGATACCCTGGTAGTCCATGCCGTAAACGATGATTACTAAGTGTTGGAGGGT
TTCCGCCCTTCAGTGCTGCAGCTAACGCATTAAGTAATCCGCCTGGGGAGTACGACCGCAAGGTTGAA
ACTCAAAAGAATTGACGGGGGCCCGCACAAGCGGTGGAGCATGTGGTTTAATTCGAAGCTACGCGAA
GAACCTTACCAGGTCTTGACATCTTCTGACAGTCTAAGAGATTAGAGGTTCCCTTCGGGGACAGAATG
ACAGGTGGTGCATGGTTGTCGTCAGCTCGTGTCGTGAGATGTTGGGTTAAGTCCCGCAACGAGCGCA
ACCCTTATTACTAGTTGCCAGCATTAAGTTGGGCACTCTAGTGAGACTGCCGGTGACAAACCGGAGG
AAGGTGGGGACGACGTCAAATCATCATGCCCCTTATGACCTGGGCTACACACGTGCTACAATGGATG
GTACAACGAGTCGCGAGACCGCGAGGTTAAGCTAATCTCTTAAAACCATTCTCAGTTCGGACTGTAG
GCTGCAACTCGCCTACACGAAGTCGGAATCGCTAGTAATCGCGGATCAGCATGCCGCGGTGAATACG
TTCCCGGGCCTTGTACACACCGCCCGTCACACCATGAGAGTTTGTAACACCCAAAGCCGGTGGGGTA
ACCTTTTAGGAGCTAGCCGTCTAAGGTGGGACAGATGATTAGGGTGAAGTCGTAACAAGGTAGCCGT
AGGAGAACCTGCGGCTGGATCACCTCCTT

10
DP10 16S rRNA
CAGATAGTTGGTGAGGTAACGGCTCACCAAGGCAACGATGCGTAGCCGACCTGAGAGGGTGATCG
GCCACACTGGGACTGAGACACGGCCCAGACTCCTACGGGAGGCAGCAGTAGGGAATCTTCCGCAATG
GACGAAAGTCTGACGGAGCAACGCCGCGTGAGTGATGAAGGTTTTCGGATCGTAAAGCTCTGTTGTT
AGGGAAGAACAAGTGCCGTTCAAATAGGGCGGCACCTTGACGGTACCTAACCAGAAAGCCACGGCT
AACTACGTGCCAGCAGCCGCGGTAATACGTAGGTGGCAAGCGTTGTCCGGAATTATTGGGCGTAAAG
GGCTCGCAGGCGGTTTCTTAAGTCTGATGTGAAAGCCCCCGGCTCAACCGGGGAGGGTCATTGGAAA
CTGGGGAACTTGAGTGCAGAAGAGGAGAGTGGAATTCCACGTGTAGCGGTGAAATGCGTAGAGATGT
GGAGGAACACCAGTGGCGAAGGCGACTCTCTGGTCTGTAACTGACGCTGAGGAGCGAAAGCGTGGG
GAGCGAACAGGATTAGATACCCTGGTAGTCCACGCCGTAAACGATGAGTGCTAAGTGTTAGGGGGTT
TCCGCCCCTTAGTGCTGCAGCTAACGCATTAAGCACTCCGCCTGGGGAGTACGGTCGCAAGACTGAA
ACTCAAAGGAATTGACGGGGGCCCGCACAAGCGGTGGAGCATGTGGTTTAATTCGAAGCAACGCGAA
GAACCTTACCAGGTCTTGACATCCTCTGACAATCCTAGAGATAGGACGTCCCCTTCGGGGGCAGAGTG
ACAGGTGGTGCATGGTTGTCGTCAGCTCGTGTCGTGAGATGTTGGGTTAAGTCCCGCAACGAGCGCA
ACCCTTGATCTTAGTTGCCAGCATTCAGTTGGGCACTCTAAGGTGACTGCCGGTGACAAACCGGAGGA
AGGTGGGGATGACGTCAAATCATCATGCCCCTTATGACCTGGGCTACACACGTGCTACAATGGACAG
AACAAAGGGCAGCGAAACCGCGAGGTTAAGCCAATCCCACAAATCTGTTCTCAGTTCGGATCGCAGT
CTGCAACTCGACTGCGTGAAGCTGGAATCGCTAGTAATCGCGGATCAGCATGCCGCGGTGAATACGT
TCCCGGGCCTTGTACACACCGCCCGTCACACCACGAGAGTTTGTAACACCCGAAGTCGGTGAGGTAA
CCTTTTAGGAGCCAGCCGCCGAAGGTGGGACAGATGATTGGGGTGAAGTCGTAACAAGGTAGCCGTA
TCGGAAGGTGCGGCTGGATCACCTCCTTT

11
DP11 16S rRNA
TGAAGAGTTTGATCATGGCTCAGATTGAACGCTGGCGGCAGGCCTAACACATGCAAGTCGAGCGG
TAGAGAGAAGCTTGCTTCTCTTGAGAGCGGCGGACGGGTGAGTAATGCCTAGGAATCTGCCTGGTAG
TGGGGGATAACGTTCGGAAACGGACGCTAATACCGCATACGTCCTACGGGAGAAAGCAGGGGACCTT
CGGGCCTTGCGCTATCAGATGAGCCTAGGTCGGATTAGCTAGTTGGTGAGGTAATGGCTCACCAAGG
CGACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGTTGTAGATTAATACTCTGCAATT
TTGACGTTACCGACAGAATAAGCACCGGCTAACTCTGTGCCAGCAGCCGCGGTAATACAGAGGGTGC
AAGCGTTAATCGGAATTACTGGGCGTAAAGCGCGCGTAGGTGGTTCGTTAAGTTGGATGTGAAAGCC
CCGGGCTCAACCTGGGAACTGCATTCAAAACTGACGAGCTAGAGTATGGTAGAGGGTGGTGGAATTT
CCTGTGTAGCGGTGAAATGCGTAGATATAGGAAGGAACACCAGTGGCGAAGGCGACCACCTGGACTG
ATACTGACACTGAGGTGCGAAAGCGTGGGGAGCAAACAGGATTAGATACCCTGGTAGTCCACGCCGT
AAACGATGTCAACTAGCCGTTGGAATCCTTGAGATTTTAGTGGCGCAGCTAACGCATTAAGTTGACCG
CCTGGGGAGTACGGCCGCAAGGTTAAAACTCAAATGAATTGACGGGGGCCCGCACAAGCGGTGGAG
CATGTGGTTTAATTCGAAGCAACGCGAAGAACCTTACCAGGCCTTGACATCCAATGAACTTTCCAGAG
ATGGATGGGTGCCTTCGGGAACATTGAGACAGGTGCTGCATGGCTGTCGTCAGCTCGTGTCGTGAGAT
GTTGGGTTAAGTCCCGTAACGAGCGCAACCCTTGTCCTTAGTTACCAGCACGTTATGGTGGGCACTCT
AAGGAGACTGCCGGTGACAAACCGGAGGAAGGTGGGGATGACGTCAAGTCATCATGGCCCTTACGG
CCTGGGCTACACACGTGCTACAATGGTCGGTACAAAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGCGAATCAGAATGTCGCGGTGAATACGTTCCCGGGCCTTGTACACACCGCCCGTCACATCCCACAC
GAATTGCTTG

12
DP12 16S rRNA
TACGGAGAGTTTGATCCTGGCTCAGGATGAACGCTGGCGGCGTGCTTAACACATGCAAGTCGAAC
GGTGAAGCCAAGCTTGCTTGGTGGATCAGTGGCGAACGGGTGAGTAACACGTGAGCAACCTGCCCTG
GACTCTGGGATAAGCGCTGGAAACGGCGTCTAATACTGGATATGAGCCTTCATCGCATGGTGGGGGT
TGGAAAGATTTTTTGGTCTGGGATGGGCTCGCGGCCTATCAGCTTGTTGGTGAGGTAATGGCTCACCA
AGGCGTCGACGGGTAGCCGGCCTGAGAGGGTGACCGGCCACACTGGGACTGAGACACGGCCCAGAC
TCCTACGGGAGGCAGCAGTGGGGAATATTGCACAATGGGCGAAAGCCTGATGCAGCAACGCCGCGTG
AGGGATGACGGCCTTCGGGTTGTAAACCTCTTTTAGCAGGGAAGAAGCGAAAGTGACGGTACCTGCA
GAAAAAGCGCCGGCTAACTACGTGCCAGCAGCCGCGGTAATACGTAGGGCGCAAGCGTTATCCGGAA
TTATTGGGCGTAAAGAGCTCGTAGGCGGTTTGTCGCGTCTGCTGTGAAATCCCGAGGCTCAACCTCGG
GCCTGCAGTGGGTACGGGCAGACTAGAGTGCGGTAGGGGAGATTGGAATTCCTGGTGTAGCGGTGGA
ATGCGCAGATATCAGGAGGAACACCGATGGCGAAGGCAGATCTCTGGGCCGTAACTGACGCTGAGG

-continued

| SEQUENCE LISTING<br>Seq ID No.<br>Description<br>Sequence |
|---|

AGCGAAAGGGTGGGGAGCAAACAGGCTTAGATACCCTGGTAGTCCACCCCGTAAACGTTGGGAACTA
GTTGTGGGGACCATTCCACGGTTTCCGTGACGCAGCTAACGCATTAAGTTCCCCGCCTGGGGAGTACG
GCCGCAAGGCTAAAACTCAAAGGAATTGACGGGGACCCGCACAAGCGGCGGAGCATGCGGATTAAT
TCGATGCAACGCGAAGAACCTTACCAAGGCTTGACATACACCAGAACGGGCCAGAAATGGTCAACTC
TTTGGACACTGGTGAACAGGTGGTGCATGGTTGTCGTCAGCTCGTGTCGTGAGATGTTGGGTTAAGTC
CCGCAACGAGCGCAACCCTCGTTCTATGTTGCCAGCACGTAATGGTGGGAACTCATGGGATACTGCC
GGGGTCAACTCGGAGGAAGGTGGGGATGACGTCAAATCATCATGCCCCTTATGTCTTGGGCTTCACG
CATGCTACAATGGCCGGTACAAAGGGCTGCAATACCGTGAGGTGGAGCGAATCCCAAAAAGCCGGTC
CCAGTTCGGATTGAGGTCTGCAACTCGACCTCATGAAGTCGGAGTCGCTAGTAATCGCAGATCAGCA
ACGCTGCGGTGAATACGTTCCCGGGTCTTGTACACACCGCCCGTCAAGTCATGAAAGTCGGTAACACC
TGAAGCCGGTGGCCCAACCCTTGTGGAGGGAGCCGTCGAAGGTGGGATCGGTAATTAGGACTAAGTC
GTAACAAGGTAGCCGTACCGGAAGGTGCGGCTGGATCACCTCCTTT

13
DP13 16S rRNA
AGTTAGCGGCGGACGGGTGAGTAACACGTGGGTAACCTGCCTATAAGACTGGGATAACTCCGGGA
AACCGGGGCTAATACCGGATAACATTTTGCACCGCATGGTGCGAAATTGAAAGGCGGCTTCGGCTGT
CACTTATAGATGGACCTGCGGCGCATTAGCTAGTTGGTGAGGTAACGGCTCACCAAGGCGACGATGC
GTAGCCGACCTGAGAGGGTGATCGGCCACACTGGGACTGAGACACGGCCCAGACTCCTACGGGAGGC
AGCAGTAGGGAATCTTCCGCAATGGACGAAAGTCTGACGGAGCAACGCCGCGTGAACGATGAAGGC
TTTCGGGTCGTAAAGTTCTGTTGTTAGGGAAGAACAAGTGCTAGTTGAATAAGCTGGCACCTTGACGG
TACCTAACCAGAAAGCCACGGCTAACTACGTGCCAGCAGCCGCGGTAATACGTAGGTGGCAAGCGTT
ATCCGGAATTATTGGGCGTAAAGCGCGCGCAGGTGGTTTCTTAAGTCTGATGTGAAAGCCCACGGCTC
AACCGTGGAGGGTCATTGGAAACTGGGAGACTTGAGTGCAGAAGAGGAAAGTGGAATTCCATGTGTA
GCGGTGAAATGCGTAGAGATATGGAGGAACACCAGTGGCGAAGGCGACTTTCTGGTCTGCAACTGAC
ACTGAGGCGCGAAAGCGTGGGGAGCAAACAGGATTAGATACCCTGGTAGTCCACGCCGTAAACGAT
GAGTGCTAAGTGTTAGAGGGTTTCCGCCCTTTAGTGCTGAAGTTAACGCATTAAGCACTCCGCCTGGG
GAGTACGGCCGCAAGGCTGAAACTCAAAGGAATTGACGGGGGCCCGCACAAGCGGTGGAGCATGTG
GTTTAATTCGAAGCAACGCGAAGAACCTTACCAGGTCTTGACATCCTCTGAAAACCCTAGAGATAGG
GCTTCCCCTTCGGGGGCAGAGTGACAGGTGGTGCATGGTTGTCGTCAGCTCGTGTCGTGAGATGTTGG
GTTAAGTCCCGCAACGAGCGCAACCCTTGATCTTAGTTGCCATCATTAAGTTGGGCACTCTAAGGTGA
CTGCCGGTGACAAACCGGAGGAAGGTGGGGATGACGTCAAATCATCATGCCCCTTATGACCTGGGCT
ACACACGTGCTACAATGGACGGTACAAAGAGTCGCAAGACCGCGAGGTGGAGCTAATCTCATAAAAC
CGTTCTCAGTTCGGATTGTAGGCTGCAACTCGCCTACATGAAGCTGGAATCGCTAGTAATCGCGGATC
AGCATGCCGCGGTGAATACGTTCCCGGGCCTTGTACACACCGCCCGTCACACCACGAGAGTTTGTAAC
ACCCGAAGTCGGTGGGGTAACCTTTTGGAGCCAGCCGCCTAAGGTGGGACAGATGATTGGGGTGAAG
TCGTAACAAGGTAGCCGTATCGGAAGGTGCGGCTGGATCACCTCCTTT

14
DP14 16S rRNA
TACGGAGAGTTTGATCCTGGCTCAGGATGAACGCTGGCGGCGTGCTTAACACATGCAAGTCGAAC
GATGACTTCTGTGCTTGCACAGAATGATTAGTGGCGAACGGGTGAGTAACACGTGAGTAACCTGCCC
TTAACTTCGGGATAAGCCTGGGAAACCGGGTCTAATACCGGATACGACCTCCTGGCGCATGCCATGG
TGGTGGAAAGCTTTAGCGGTTTTGGATGGACTCGCGGCCTATCAGCTTGTTGGTTGGGGTAATGGCCC
ACCAAGGCGACGACGGGTAGCCGGCCTGAGAGGGTGACCGGCCACACTGGGACTGAGACACGGCCC
AGACTCCTACGGGAGGCAGCAGTGGGGAATATTGCACAATGGGCGAAAGCCTGATGCAGCGACGCC
GCGTGAGGGATGACGGCCTTCGGGTTGTAAACCTCTTTCAGCAGGGAAGAAGCGAAAGTGACGGTAC
CTGCAGAAGAAGCGCCGGCTAACTACGTGCCAGCAGCCGCGGTAATACGTAGGGCGCAAGCGTTATC
CGGAATTATTGGGCGTAAAGAGCTCGTAGGCGGTTTGTCGCGTCTGCTGTGAAAGCCCGGGGCTCAA
CCCCGGGTCTGCAGTGGGTACGGGCAGACTAGAGTGCAGTAGGGGAGACTGGAATTCCTGGTGTAGC
GGTGAAATGCGCAGATATCAGGAGGAACACCGATGGCGAAGGCAGGTCTCTGGGCTGTAACTGACGC
TGAGGAGCGAAAGCATGGGGAGCGAACAGGATTAGATACCCTGGTAGTCCATGCCGTAAACGTTGGG
CACTAGGTGTGGGGGACATTCCACGTTTTCCGCGCCGTAGCTAACGCATTAAGTGCCCCGCCTGGGGA
GTACGGCCGCAAGGCTAAAACTCAAAGGAATTGACGGGGGCCCGCACAAGCGGCGGAGCATGCGGA
TTAATTCGATGCAACGCGAAGAACCTTACCAAGGCTTGACATGAACCGGTAAGACCTGGAAACAGGT
CCCCCACTTGTGGCCGGTTTACAGGTGGTGCATGGTTGTCGTCAGCTCGTGTCGTGAGATGTTGGGTT
AAGTCCCGCAACGAGCGCAACCCTCGTTCTATGTTGCCAGCGGGTTATGCCGGGGACTCATAGGAGA
CTGCCGGGGTCAACTCGGAGGAAGGTGGGGACGACGTCAAATCATCATGCCCCTTATGTCTTGGGCTT
CACGCATGCTACAATGGCCGGTACAAAGGGTTGCGATACTGTGAGGTGGAGCTAATCCCAAAAAGCC
GGTCTCAGTTCGGATTGAGGTCTGCAACTCGACCTCATGAAGTTGGAGTCGCTAGTAATCGCAGATCA
GCAACGCTGCGGTGAATACGTTCCCGGGCCTTGTACACACCGCCCGTCAAGTCACGAAAGTTGGTAA
CACCCGAAGCCGGTGGCCTAACCCCTTGTGGGAGGGAGCCGTCGAAGGTGGGACCGGCGATTGGGAC
AAGTCGTAACAAGGTAGCCGTACCGGAAGGTGCGGCTGGATCACCTCCTTT

15
DP15 16S rRNA
TACGGAGAGTTTGATCCTGGCTCAGGACGAACGCTGGCGGCGTGCTTAACACATGCAAGTCGAAC
GATGATCAGGAGCTTGCTCCTGTGATTAGTGGCGAACGGGTGAGTAACACGTGAGTAACCTGCCCCT
GACTCTGGGATAAGCGTTGGAAACGACGTCTAATACTGGATATGATCACTGGCCGCATGGTCTGGTG
GTGGAAAGATTTTTTGGTTGGGGATGGACTCGCGGCCTATCAGCTTGTTGGTGAGGTAATGGCTCACC
AAGGCGACGACGGGTAGCCGGCCTGAGAGGGTGACCGGCCACACTGGGACTGAGACACGGCCCAGA
CTCCTACGGGAGGCAGCAGTGGGGAATATTGCACAATGGGCGAAAGCCTGATGCAGCAACGCCGCGT
GAGGGATGACGGCCTTCGGGTTGTAAACCTCTTTTAGTAGGGAAGAAGCGAAAGTGACGGTACCTGC
AGAAAAAGCACCGGCTAACTACGTGCCAGCAGCCGCGGTAATACGTAGGGTGCAAGCGTTGTCCGGA

-continued

SEQUENCE LISTING
Seq ID No.
Description
Sequence

ATTATTGGGCGTAAAGAGCTCGTAGGCGGTTTGTCGCGTCTGCTGTGAAATCCCGAGGCTCAACCTCG
GGCTTGCAGTGGGTACGGGCAGACTAGAGTGCGGTAGGGGAGATTGGAATTCCTGGTGTAGCGGTGG
AATGCGCAGATATCAGGAGGAACACCGATGGCGAAGGCAGATCTCTGGGCCGTAACTGACGCTGAG
GAGCGAAAGCGTGGGGAGCGAACAGGATTAGATACCCTGGTAGTCCACGCCGTAAACGTTGGGCGCT
AGATGTAGGGACCTTTCCACGGTTTCTGTGTCGTAGCTAACGCATTAAGCGCCCCGCCTGGGGAGTAC
GGCCGCAAGGCTAAAACTCAAAGGAATTGACGGGGGCCCGCACAAGCGGCGGAGCATGCGGATTAA
TTCGATGCAACGCGAAGAACCTTACCAAGGCTTGACATACACCGGAAACGGCCAGAGATGGTCGCCC
CCTTGTGGTCGGTGTACAGGTGGTGCATGGTTGTCGTCAGCTCGTGTCGTGAGATGTTGGGTTAAGTC
CCGCAACGAGCGCAACCCTCGTTCTATGTTGCCAGCGCGTTATGGCGGGGACTCATAGGAGACTGCC
GGGGTCAACTCGGAGGAAGGTGGGGATGACGTCAAATCATCATGCCCCTTATGTCTTGGGCTTCACG
CATGCTACAATGGCCGGTACAAAGGGCTGCGATACCGTAAGGTGGAGCGAATCCCAAAAAGCCGGTC
TCAGTTCGGATTGAGGTCTGCAACTCGACCTCATGAAGTCGGAGTCGCTAGTAATCGCAGATCAGCA
ACGCTGCGGTGAATACGTTCCCGGGCCTTGTACACACCGCCCGTCAAGTCATGAAAGTCGGTAACAC
CCGAAGCCGGTGGCCTAACCCTTGTGGAAGGAGCCGTCGAAGGTGGGATCGGTGATTAGGACTAAGT
CGTAACAAGGTAGCCGTACCGGAAGGTGCGGCTGGATCACCTCCTTT

16
DP16 16S rRNA

17
DP17 16S rRNA
GTGATTGACGTTACTCGCAGAAGAAGCACCGGCTAACTCCGTGCCAGCAGCCGCGGTAATACGGA
GGGTGCAAGCGTTAATCGGAATTACTGGGCGTAAAGCGCACGCAGGCGGTTTGTTAAGTCAGATGTG
AAATCCCCGCGCTTAACGTGGGAACTGCATTTGAAACTGGCAAGCTAGAGTCTTGTAGAGGGGGGTA
GAATTCCAGGTGTAGCGGTGAAATGCGTAGAGATCTGGAGGAATACCGGTGGCGAAGGCGGCCCCCT
GGACAAAGACTGACGCTCAGGTGCGAAAGCGTGGGGAGCAAACAGGATTAGATACCCTGGTAGTCC
ACGCTGTAAACGATGTCGACTTGGAGGTTGTGCCCTTGAGGCGTGGCTTCCGGAGCTAACGCGTTAAG
TCGACCGCCTGGGGAGTACGGCCGCAAGGTTAAAACTCAAATGAATTGACGGGGGCCCGCACAAGCG
GTGGAGCATGTGGTTTAATTCGATGCAACGCGAAGAACCTTACCTACTCTTGACATCCACGGAATTCG
CCAGAGATGGCTTAGTGCCTTCGGGAACCGTGAGACAGGTGCTGCATGGCTGTCGTCAGCTCGTGTTG
TGAAATGTTGGGTTAAGTCCCGCAACGAGCGCAACCCTTATCCTTTGTTGCCAGCACGTAATGGTGGG
AACTCAAAGGAGACTGCCGGTGATAAACCGGAGGAAGGTGGGGATGACGTCAAGTCATCATGGCCCT
TACGAGTAGGGCTACACACGTGCTACAATGGCATATACAAAGAGAAGCGAACTCGCGAGAGCAAGC
GGACCTCATAAAGTATGTCGTAGTCCGGATTGGAGTCTGCAACTCGACTCCATGAAGTCGGAATCGCT
AGTAATCGTAGATCAGAATGCTACGG

18
DP18 16S rRNA
TGAAGAGTTTGATCATGGCTCAGATTGAACGCTGGCGGCAGGCCTAACACATGCAAGTCGAGCGG
ATGAAAGGAGCTTGCTCCTGGATTCAGCGGCGGACGGGTGAGTAATGCCTAGGAATCTGCCTGGTAG
TGGGGGACAACGTTTCGAAAGGAACGCTAATACCGCATACGTCCTACGGGAGAAAGCAGGGGACCTT
CGGGCCTTGCGCTATCAGATGAGCCTAGGTCGGATTAGCTAGTTGGTGAGGTAATGGCTCACCAAGG
CGACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGCAGTAAATTAATACTTTGCTGTT
TTGACGTTACCGACAGAATAAGCACCGGCTAACTCTGTGCCAGCAGCCGCGGTAATACAGAGGGTGC
AAGCGTTAATCGGAATTACTGGGCGTAAAGCGCGCGTAGGTGGTTTGTTAAGTTGAATGTGAAATCC
CCGGGCTCAACCTGGGAACTGCATCCAAAACTGGCAAGCTAGAGTATGGTAGAGGGTGGTGGAATTT
CCTGTGTAGCGGTGAAATGCGTAGATATAGGAAGGAACACCAGTGGCGAAGGCGACCACCTGGACTG
ATACTGACACTGAGGTGCGAAAGCGTGGGGAGCAAACAGGATTAGATACCCTGGTAGTCCACGCCGT
AAACGATGTCAACTAGCCGTTGGGAGCCTTGAGCTCTTAGTGGCGCAGCTAACGCATTAAGTTGACC
GCCTGGGGAGTACGGCCGCAAGGTTAAAACTCAAATGAATTGACGGGGGCCCGCACAAGCGGTGGA
GCATGTGGTTTAATTCGAAGCAACGCGAAGAACCTTACCAGGCCTTGACATCCAATGAACTTTCCAGA
GATGGATTGGTGCCTTCGGGAACATTGAGACAGGTGCTGCATGGCTGTCGTCAGCTCGTGTCGTGAGA
TGTTGGGTTAAGTCCCGTAACGAGCGCAACCCTTGTCCTTAGTTACCAGCACGTTATGGTGGGCACTC
TAAGGAGACTGCCGGTGACAAACCGGAGGAAGGTGGGGATGACGTCAAGTCATCATGGCCCTTACGG
CCTGGGCTACACACGTGCTACAATGGTCGGTACAAAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGCGAATCAGAATGTCGCGGTGAATACGTTCCCGGGCCTTGTACACACCGCCCGTCACACCATGGG
AGTGGGTTGCACCAGAAGTAGCTAGTCTAACCTTCGGGAGGACGGTTACCACGGTGTGATTCATGAC
TGGGGTGAAGTCGTAACAAGGTAGCCGTAGGGGAACCTGCGGCTGGATCACCTCCTT

19
DP19 16S rRNA
TACGGAGAGTTTGATCCTGGCTCAGGACGAACGCTGGCGGCGTGCTTAACACATGCAAGTCGAAC
GATGATGCCCAGCTTGCTGGGTGGATTAGTGGCGAACGGGTGAGTAACACGTGAGTAACCTGCCCCT
GACTCTGGGATAAGCGTTGGAAACGACGTCTAATACTGGATACGACTGCCGGCCGCATGGTCTGGTG
GTGGAAAGATTTTTTGGTTGGGGATGGACTCGCGGCCTATCAGCTTGTTGGTGAGGTAATGGCTCACC
AAGGCGACGACGGGTAGCCGGCCTGAGAGGGTGACCGGCCACACTGGGACTGAGACACGGCCCAGA
CTCCTACGGGAGGCAGCAGTGGGGAATATTGCACAATGGGCGAAAGCCTGATGCAGCAACGCCGCGT
GAGGGATGACGGCCTTCGGGTTGTAAACCTCTTTTAGTAGGGAAGAAGCGAAAGTGACGGTACCTGC
AGAAAAAGCACCGGCTAACTACGTGCCAGCAGCCGCGGTAATACGTAGGGTGCAAGCGTTGTCCGGA
ATTATTGGGCGTAAAGAGCTCGTAGGCGGTTTGTCGCGTCTGCTGTGAAATCCCGAGGCTCAACCTCG
GGCTTGCAGTGGGTACGGGCAGACTAGAGTGCGGTAGGGGAGATTGGAATTCCTGGTGTAGCGGTGG

-continued

| SEQUENCE LISTING<br>Seq ID No.<br>Description<br>Sequence |
|---|

AATGCGCAGATATCAGGAGGAACACCGATGGCGAAGGCAGATCTCTGGGCCGTAACTGACGCTGAG
GAGCGAAAGCGTGGGGAGCGAACAGGATTAGATACCCTGGTAGTCCACGCCGTAAACGTTGGGCGCT
AGATGTAGGGACCTTTCCACGGTTTCTGTGTCGTAGCTAACGCATTAAGCGCCCCGCCTGGGGAGTAC
GGCCGCAAGGCTAAAACTCAAAGGAATTGACGGGGGCCCGCACAAGCGGCGGAGCATGCGGATTAA
TTCGATGCAACGCGAAGAACCTTACCAAGGCTTGACATACACCGGAAACGGCCAGAGATGGTCGCCC
CCTTGTGGTCGGTGTACAGGTGGTGCATGGTTGTCGTCAGCTCGTGTCGTGAGATGTTGGGTTAAGTC
CCGCAACGAGCGCAACCCTCGTTCTATGTTGCCAGCGCGTTATGGCGGGGACTCATAGGAGACTGCC
GGGGTCAACTCGGAGGAAGGTGGGGATGACGTCAAATCATCATGCCCCTTATGTCTTGGGCTTCACG
CATGCTACAATGGCCGGTACAAAGGGCTGCGATACCGTAAGGTGGAGCGAATCCCAAAAAGCCGGTC
TCAGTTCGGATTGAGGTCTGCAACTCGACCTCATGAAGTCGGAGTCGCTAGTAATCGCAGATCAGCA
ACGCTGCGGTGAATACGTTCCCGGGCCTTGTACACACCGCCCGTCAAGTCATGAAAGTCGGTAACAC
CCGAAGCCGGTGGCCTAACCCTTGTGGAAGGAGCCGTCGAAGGTGGGATCGGTGATTAGGACTAAGT
CGTAACAAGGTAGCCGTACCGGAAGGTGCGGCTGGATCACCTCCTTT

20
DP20 16S rRNA
TGAAGAGTTTGATCCTGGCTCAGAGTGAACGCTGGCGGTAGGCCTAACACATGCAAGTCGAACGG
CAGCACAGTAAGAGCTTGCTCTTATGGGTGGCGAGTGGCGGACGGGTGAGGAATACATCGGAATCTA
CCTTTTCGTGGGGGATAACGTAGGGAAACTTACGCTAATACCGCATACGACCTTCGGGTGAAAGCAG
GGGACCTTCGGGCCTTGCGCGGATAGATGAGCCGATGTCGGATTAGCTAGTTGGCGGGGTAAAGGCC
CACCAAGGCGACGATCCGTAGCTGGTCTGAGAGGATGATCAGCCACACTGGAACTGAGACACGGTCC
AGACTCCTACGGGAGGCAGCAGTGGGGAATATTGGACAATGGGCGCAAGCCTGATCCAGCCATACCG
CGTGGGTGAAGAAGGCCTTCGGGTTGTAAAGCCCTTTTGTTGGGAAAGAAAAGCAGTCGGCTAATAC
CCGGTTGTTCTGACGGTACCCAAAGAATAAGCACCGGCTAACTTCGTGCCAGCAGCCGCGGTAATAC
GAAGGGTGCAAGCGTTACTCGGAATTACTGGGCGTAAAGCGTGCGTAGGTGGTTGTTTAAGTCTGTTG
TGAAAGCCCTGGGCTCAACCTGGGAATTGCAGTGGATACTGGGCGACTAGAGTGTGGTAGAGGGTAG
TGGAATTCCCGGTGTAGCAGTGAAATGCGTAGAGATCGGGAGGAACATCCATGGCGAAGGCAGCTAC
CTGGACCAACACTGACACTGAGGCACGAAAGCGTGGGGAGCAAACAGGATTAGATACCCTGGTAGTC
CACGCCCTAAACGATGCGAACTGGATGTTGGGTGCAATTTGGCACGCAGTATCGAAGCTAACGCGTT
AAGTTCGCCGCCTGGGGAGTACGGTCGCAAGACTGAAACTCAAAGGAATTGACGGGGGCCCGCACA
AGCGGTGGAGTATGTGGTTTAATTCGATGCAACGCGAAGAACCTTACCTGGTCTTGACATGTCGAGA
ACTTTCCAGAGATGGATTGGTGCCTTCGGGAACTCGAACACAGGTGCTGCATGGCTGTCGTCAGCTCG
TGTCGTGAGATGTTGGGTTAAGTCCCGCAACGAGCGCAACCCTTGTCCTTAGTTGCCAGCACGTAATG
GTGGGAACTCTAAGGAGACCGCCGGTGACAAACCGGAGGAAGGTGGGGATGACGTCAAGTCATCAT
GGCCCTTACGACCAGGGCTACACACGTACTACAATGGTAGGGACAGAGGGCTGCAAACCCGCGAGG
GCAAGCCAATCCCAGAAACCCTATCTCAGTCCGGATTGGAGTCTGCAACTCGACTCCATGAAGTCGG
AATCGCTAGTAATCGCAGATCAGCATTGCTGCGGTGAATACGTTCCCGGGCCTTGTACACACCGCCCG
TCACACCATGGGAGTTTGTTGCACCAGAAGCAGGTAGCTTAACCTTCGGGAGGGCGCTTGCCACGGT
GTGGCCGATGACTGGGGTGAAGTCGTAACAAGGTAGCCGTATCGGAAGGTGCGGCTGGATCACCTCC
TTT

21 DP21 16S rRNA

22 DP22 16S rRNA
TTGAAGAGTTTGATCATGGCTCAGATTGAACGCTGGCGGCAGGCCTAACACATGCAAGTCGAGCG
GCAGCGGGAAGTAGCTTGCTACTTTGCCGGCGAGCGGCGGACGGGTGAGTAATGTCTGGGAAACTGC
CTGATGGAGGGGGATAACTACTGGAAACGGTAGCTAATACCGCATGACCTCGCAAGAGCAAAGTGG
GGGACCTTCGGGCCTCACGCCATCGGATGTGCCCAGATGGGATTAGCTAGTAGGTGAGGTAATGGCT
CACCTAGGCGACGATCCCTAGCTGGTCTGAGAGGATGACCAGCCACACTGGAACTGAGACACGGTCC
AGACTCCTACGGGAGGCAGCAGTGGGGAATATTGCACAATGGGCGCAAGCCTGATGCAGCCATGCCG
CGTGTGTGAAGAAGGCCTTAGGGTTGTAAAGCACTTTCAGCGAGGAGGAAGGGTTCAGTGTTAATAG
CACTGAACATTGACGTTACTCGCAGAAGAAGCACCGGCTAACTCCGTGCCAGCAGCCGCGGTAATAC
GGAGGGTGCAAGCGTTAATCGGAATTACTGGGCGTAAAGCGCACGCAGGCGGTTTGTTAAGTCAGAT
GTGAAATCCCCGAGCTTAACTTGGGAACTGCATTTGAAACTGGCAAGCTAGAGTCTTGTAGAGGGGG
GTAGAATTCCAGGTGTAGCGGTGAAATGCGTAGAGATCTGGAGGAATACCGGTGGCGAAGGCGGCCC
CCTGGACAAAGACTGACGCTCAGGTGCGAAAGCGTGGGGAGCAAACAGGATTAGATACCCTGGTAGT
CCACGCTGTAAACGATGTCGACTTGGAGGTTGTGCCCTTGAGGCGTGGCTTCCGGAGCTAACGCGTTA
AGTCGACCGCCTGGGGAGTACGGCCGCAAGGTTAAAACTCAAATGAATTGACGGGGGCCCGCACAA
GCGGTGGAGCATGTGGTTTAATTCGATGCAACGCGAAGAACCTTACCTACTCTTGACATCCAGAGAAT
TCGCTAGAGATAGCTTAGTGCCTTCGGGAACTCTGAGACAGGTGCTGCATGGCTGTCGTCAGCTCGTG
TTGTGAAATGTTGGGTTAAGTCCCGCAACGAGCGCAACCCTTATCCTTTGTTGCCAGCGAGTAATGTC
GGGAACTCAAAGGAGACTGCCGGTGATAAACCGGAGGAAGGTGGGGATGACGTCAAGTCATCATGG
CCCTTACGAGTAGGGCTACACACGTGCTACAATGGCATATACAAAGAGAAGCAAACTCGCGAGAGCA
AGCGGACCTCATAAAGTATGTCGTAGTCCGGATTGGAGTCTGCAACTCGACTCCATGAAGTCGGAAT
CGCTAGTAATCGTAGATCAGAATGCTACGGTGAATACGTTCCCGGGCCTTGTACACACCGCCCGTCAC
ACCATGGGAGTGGGTTGCAAAAGAAGTAGGTAGCTTAACCTTCGGGAGGGCGCTTACCACTTTGTGA
TTCATGACTGGGGTGAAGTCGTAACAAGGTAACCGTAGGGGAACCTGCGGTTGGATCACCTCCTT

23
DP23 16S rRNA
TTGAAGAGTTTGATCATGGCTCAGATTGAACGCTGGCGGCAGGCCTAACACATGCAAGTCGAACG
GTAGCACAGAGAGCTTGCTCTTGGGTGACGAGTGGCGGACGGGTGAGTAATGTCTGGGAAACTGCCC
GATGGAGGGGGATAACTACTGGAAACGGTAGCTAATACCGCATAACGTCTTCGGACCAAAGTGGGG
ACCTTCGGGCCTCACACCATCGGATGTGCCCAGATGGGATTAGCTAGTAGGTGGGGTAATGGCTCAC

-continued

| SEQUENCE LISTING<br>Seq ID No.<br>Description<br>Sequence |
|---|

CTAGGCGACGATCCCTAGCTGGTCTGAGAGGATGACCAGCCACACTGGAACTGAGACACGGTCCAGA
CTCCTACGGGAGGCAGCAGTGGGGAATATTGCACAATGGGCGCAAGCCTGATGCAGCCATGCCGCGT
GTATGAAGAAGGCCTTCGGGTTGTAAAGTACTTTCAGCGGGGAGGAAGGCGATACGGTTAATAACCG
TGTCGATTGACGTTACCCGCAGAAGAAGCACCGGCTAACTCCGTGCCAGCAGCCGCGGTAATACGGA
GGGTGCAAGCGTTAATCGGAATTACTGGGCGTAAAGCGCACGCAGGCGGTCTGTCAAGTCAGATGTG
AAATCCCCGGGCTTAACCTGGGAACTGCATTTGAAACTGGCAGGCTTGAGTCTCGTAGAGGGGGGTA
GAATTCCAGGTGTAGCGGTGAAATGCGTAGAGATCTGGAGGAATACCGGTGGCGAAGGCGGCCCCCT
GGACGAAGACTGACGCTCAGGTGCGAAAGCGTGGGGAGCAAACAGGATTAGATACCCTGGTAGTCC
ACGCTGTAAACGATGTCGACTTGGAGGTTGTGCCCTTGAGGCGTGGCTTCCGGAGCTAACGCGTTAAG
TCGACCGCCTGGGGAGTACGGCCGCAAGGTTAAAACTCAAATGAATTGACGGGGGCCCGCACAAGCG
GTGGAGCATGTGGTTTAATTCGATGCAACGCGAAGAACCTTACCTGGCCTTGACATCCACAGAATTCG
GCAGAGATGCCTTAGTGCCTTCGGGAACTGTGAGACAGGTGCTGCATGGCTGTCGTCAGCTCGTGTTG
TGAAATGTTGGGTTAAGTCCCGCAACGAGCGCAACCCTTATCCTTTGTTGCCAGCGATTCGGTCGGGA
ACTCAAAGGAGACTGCCGGTGATAAACCGGAGGAAGGTGGGGATGACGTCAAGTCATCATGGCCCTT
ACGGCCAGGGCTACACACGTGCTACAATGGCGCATACAAAGAGAAGCGACCTCGCGAGAGCAAGCG
GACCTCATAAAGTGCGTCGTAGTCCGGATCGGAGTCTGCAACTCGACTCCGTGAAGTCGGAATCGCT
AGTAATCGTAGATCAGAATGCTACGGTGAATACGTTCCCGGGCCTTGTACACACCGCCCGTCACACCA
TGGGAGTGGGTTGCAAAAGAAGTAGGTAGCTTAACCTTCGGGAGGGCGCTTACCACTTTGTGATTCAT
GACTGGGGTGAAGTCGTAACAAGGTAACCGTAGGGGAACCTGCGGTTGGATCACCTCCTT

24
DP24 16S rRNA
AGCATTTGATTATGGTGCTTACTGATTGCTATCTAGGGGTTTAACACATGCTAGTCAATGATCTTTT
AGATTATGGCGTACGGGCTAGGAATACTTAGAATGATAACTCTATGATCGCAGTAATAGCGTAAAAG
GTATAATACCGCATAGAGGTTCGCTTCGTATCTAATAGGTAGTTGGTGAGGTAAAGCTCAACAAGCC
GATGATGAGTAATATTGGATGAAAGTCTTAAATATAGCAGTGGAAATGAAAAAGTCCACCGTTATTT
ATTAACGCAGCAGTGGAGAATCGTCGTAATGTGCAGTATTCATTTATGGATAAGCATGAACGCGCTA
CCTAGATTCGGATAGGAGATAGCATCTTCTACCGATAAAAGAACTTAGAATAATGATCTAGTTCTCAT
TAGTGGGTGACAATCGCCGTGCCAGCATCAGCGGTAAAACGGCTTCCGCAAGCAATAGTAATTTAAA
TTGGTGTAAAGGGTACGTAGCCGGCCTTATTAGGCTAGAGTTAGATACGGGTAAGTACAATACTTGG
AGTAGGGCTGATATCTTATGATCCCAAGGGGAGTGCTAAAGGCGAAGGCAACTTACTGGTAATAACT
GACGGTGAGGTACGAAGGTCAGGGCATGGAAAGAGATTAGATACCTCATTACTCCTGACAGTAAACG
ATGTAGATTAAAGATTGGAATAATTCTGTCTTAACGCTAACGCATTAAATCTACCACCTGTAGAGTAT
AGTCGCAAGGCCGAAATACAAATAATTAGACGGCTCTAGAGCAAACGGAGTGAAGCATGTTATTTAA
TACGATAACCCGCGTAAAATCTTACCAGTTCTTGAATCTTAGACAGGTGTTGCATGGTTGTCGTCAGC
TCGTGCTAATGGTGTCTGGTTAATTCCAAATAACGAGCGCAATCCTTACTTCTAGTTTTCTAGGAGTCT
CCATTTGACATACGTGTCAATGGTTTAAGGAATATGACAAACCCTCATGGCCCTTATGGACTGGGCAA
TAGACGTGCCACAAGAATCTAGACAAAATGACGCGAAATGGTAACAATGAGCTAATCATCAAAGAA
GATTAATGTACGAATTATGGGCTGGAACTCGCCCATATGAAGTAGGAATTCCGAGTAATCGCGTATC
AGAACGACGCGGTGAACATCATCTCTGGAGTGTACTAACTGCTCGTCACGGGACGAAAGGGAGTGTA
TTATGAAGTGGGGCTAATTGGTTAACTCCGGTGAGTGTCACGAATAATCCTTCCCGATTGTTCTGAAG
TCGAAACAAGGTAACCGTAAGGGAACTTGCGGTTGA

25
DP25 16S rRNA
TACGGAGAGTTTGATCCTGGCTCAGGATGAACGCTGGCGGCGTGCTTAACACATGCAAGTCGAAC
GGTGAAGCCAAGCTTGCTTGGTGGATCAGTGGCGAACGGGTGAGTAACACGTGAGCAACCTGCCCTG
GACTCTGGGATAAGCGCTGGAAACGGCGTCTAATACTGGATATGAGCTCCTTCCGCATGGTGGGGGT
TGGAAAGATTTTTCGGTCTGGGATGGGCTCGCGGCCTATCAGCTTGTTGGTGAGGTAATGGCTCACCA
AGGCGTCGACGGGTAGCCGGCCTGAGAGGGTGACCGGCCACACTGGGACTGAGACACGGCCCAGAC
TCCTACGGGAGGCAGCAGTGGGGAATATTGCACAATGGGCGGAAGCCTGATGCAGCAACGCCGCGTG
AGGGATGACGGCCTTCGGGTTGTAAACCTCTTTTAGCAGGGAAGAAGCGAAAGTGACGGTACCTGCA
GAAAAAGCGCCGGCTAACTACGTGCCAGCAGCCGCGGTAATACGTAGGGCGCAAGCGTTATCCGGAA
TTATTGGGCGTAAAGAGCTCGTAGGCGGTTTGTCGCGTCTGCTGTGAAATCCCGAGGCTCAACCTCGG
GCCTGCAGTGGGTACGGGCAGACTAGAGTGCGGTAGGGGAGATTGGAATTCCTGGTGTAGCGGTGGA
ATGCGCAGATATCAGGAGGAACACCGATGGCGAAGGCAGATCTCTGGGCCGTAACTGACGCTGAGG
AGCGAAAGGGTGGGGAGCAAACAGGCTTAGATACCCTGGTAGTCCACCCCGTAAACGTTGGGAACTA
GTTGTGGGGACCATTCCACGGTTTCCGTGACGCAGCTAACGCATTAAGTTCCCCGCCTGGGGAGTACG
GCCGCAAGGCTAAAACTCAAAGGAATTGACGGGGACCCGCACAAGCGGCGGAGCATGCGGATTAAT
TCGATGCAACGCGAAGAACCTTACCAAGGCTTGACATATACGAGAACGGGCCAGAAATGGTCAACTC
TTTGGACACTCGTAAACAGGTGGTGCATGGTTGTCGTCAGCTCGTGTCGTGAGATGTTGGGTTAAGTC
CCGCAACGAGCGCAACCCTCGTTCTATGTTGCCAGCACGTAATGGTGGGAACTCATGGGATACTGCC
GGGGTCAACTCGGAGGAAGGTGGGGATGACGTCAAATCATCATGCCCCTTATGTCTTGGGCTTCACG
CATGCTACAATGGCCGGTACAAAGGGCTGCAATACCGTAAGGTGGAGCGAATCCCAAAAAGCCGGTC
CCAGTTCGGATTGAGGTCTGCAACTCGACCTCATGAAGTCGGAGTCGCTAGTAATCGCAGATCAGCA
ACGCTGCGGTGAATACGTTCCCGGGTCTTGTACACACCGCCCGTCAAGTCATGAAAGTCGGTAACACC
TGAAGCCGGTGGCCCAACCCTTGTGGAGGGAGCCGTCGAAGGTGGGATCGGTAATTAGGACTAAGTC
GTAACAAGGTAGCCGTACCGGAAGGTGCGGCTGGATCACCTCCTTT

26
DP26 16S rRNA
CTTGAGAGTTTGATCCTGGCTCAGAGCGAACGCTGGCGGCAGGCTTAACACATGCAAGTCGAGCG
GGCATCTTCGGATGTCAGCGGCAGACGGGTGAGTAACACGTGGGAACGTACCCTTCGGTTCGGAATA
ACGCTGGGAAACTAGCGCTAATACCGGATACGCCCTTTTGGGGAAAGGTTTACTGCCGAAGGATCGG

-continued

| SEQUENCE LISTING Seq ID No. Description Sequence |
|---|

CCCGCGTCTGATTAGCTAGTTGGTGGGGTAACGGCCTACCAAGGCGACGATCAGTAGCTGGTCTGAG
AGGATGATCAGCCACACTGGGACTGAGACACGGCCCAGACTCCTACGGGAGGCAGCAGTGGGGAAT
ATTGGACAATGGGCGCAAGCCTGATCCAGCCATGCCGCGTGAGTGATGAAGGCCTTAGGGTTGTAAA
GCTCTTTTGTCCGGGACGATAATGACGGTACCGGAAGAATAAGCCCCGGCTAACTTCGTGCCAGCAG
CCGCGGTAATACGAAGGGGGCTAGCGTTGCTCGGAATCACTGGGCGTAAAGGGCGCGTAGGCGGCCA
TTCAAGTCGGGGGTGAAAGCCTGTGGCTCAACCACAGAATTGCCTTCGATACTGTTTGGCTTGAGTAT
GGTAGAGGTTGGTGGAACTGCGAGTGTAGAGGTGAAATTCGTAGATATTCGCAAGAACACCGGTGGC
GAAGGCGGCCAACTGGACCATTACTGACGCTGAGGCGCGAAAGCGTGGGGAGCAAACAGGATTAGA
TACCCTGGTAGTCCACGCCGTAAACGATGAATGCCAGCTGTTGGGGTGCTTGCACCTCAGTAGCGCAG
CTAACGCTTTAAGCATTCCGCCTGGGGAGTACGGTCGCAAGATTAAAACTCAAAGGAATTGACGGGG
GCCCGCACAAGCGGTGGAGCATGTGGTTTAATTCGAAGCAACGCGCAGAACCTTACCATCCCTTGAC
ATGGCATGTTACCCGGAGAGATTCGGGGTCCACTTCGGTGGCGTGCACACAGGTGCTGCATGGCTGTC
GTCAGCTCGTGTCGTGAGATGTTGGGTTAAGTCCCGCAACGAGCGCAACCCACGTCCTTAGTTGCCAT
CATTCAGTTGGGCACTCTAGGGAGACTGCCGGTGATAAGCCGCGAGGAAGGTGTGGATGACGTCAAG
TCCTCATGGCCCTTACGGGATGGGCTACACACGTGCTACAATGGCGGTGACAGTGGGACGCGAAGGA
GCGATCTGGAGCAAATCCCCAAAAACCGTCTCAGTTCAGATTGCACTCTGCAACTCGAGTGCATGAA
GGCGGAATCGCTAGTAATCGTGGATCAGCATGCCACGGTGAATACGTTCCCGGGCCTTGTACACACC
GCCCGTCACACCATGGGAGTTGGTCTTACCCGACGGCGCTGCGCCAACCGCAAGGAGGCAGGCGACC
ACGGTAGGGTCAGCGACTGGGGTGAAGTCGTAACAAGGTAGCCGTAGGGGAACCTGCGGCTGGATC
ACCTCCTTT

27
DP27 16S rRNA
CTTGAGAGTTTGATCCTGGCTCAGAACGAACGCTGGCGGCATGCCTAACACATGCAAGTCGAACG
ATGCTTTCGGGCATAGTGGCGCACGGGTGCGTAACGCGTGGGAATCTGCCCTCAGGTTCGGAATAAC
AGCTGGAAACGGCTGCTAATACCGGATGATATCGCAAGATCAAAGATTTATCGCCTGAGGATGAGCC
CGCGTTGGATTAGGTAGTTGGTGGGGTAAAGGCCTACCAAGCCGACGATCCATAGCTGGTCTGAGAG
GATGATCAGCCACACTGGGACTGAGACACGGCCCAGACTCCTACGGGAGGCAGCAGTGGGGAATATT
GGACAATGGGCGCAAGCCTGATCCAGCAATGCCGCGTGAGTGATGAAGGCCCTAGGGTTGTAAAGCT
CTTTTACCCGGGAAGATAATGACTGTACCGGGAGAATAAGCCCCGGCTAACTCCGTGCCAGCAGCCG
CGGTAATACGGAGGGGGCTAGCGTTGTTCGGAATTACTGGGCGTAAAGCGCACGTAGGCGGCTTTGT
AAGTCAGAGGTGAAAGCCTGGAGCTCAACTCCAGAACTGCCTTTGAGACTGCATCGCTTGAATCCAG
GAGAGGTCAGTGGAATTCCGAGTGTAGAGGTGAAATTCGTAGATATTCGGAAGAACACCAGTGGCGA
AGGCGGCTGACTGGACTGGTATTGACGCTGAGGTGCGAAAGCGTGGGGAGCAAACAGGATTAGATA
CCCTGGTAGTCCACGCCGTAAACGATGATAACTAGCTGTCCGGGCACTTGGTGCTTGGGTGGCGCAGC
TAACGCATTAAGTTATCCGCCTGGGGAGTACGGCCGCAAGGTTAAAACTCAAAGGAATTGACGGGGG
CCTGCACAAGCGGTGGAGCATGTGGTTTAATTCGAAGCAACGCGCAGAACCTTACCAGCGTTTGAC

28
DP28 16S rRNA
ATAGTCGGGGGCATCAGTATTCAATTGTCAGAGGTGAAATTCTTGGATTTATTGAAGACTAACTAC
TGCGAAAGCATTTGCCAAGGATGTTTTCATTAATCAGTGAACGAAAGTTAGGGGATCGAAGACGATC
AGATACCGTCGTAGTCTTAACCATAAACTATGCCGACTAGGGATCGGGCGATGTTATCATTTTGACTC
GCTCGGCACCTTACGAGAAATCAAAGTCTTTGGGTTCTGGGGGGAGTATGGTCGCAAGGCTGAAACT
TAAAGAAATTGACGGAAGGGCACCACCAGGCGTGGAGCCTGCGGCTTAATTTGACTCAACACGGGGA
AACTCACCAGGTCCAGACACAATAAGGATTGACAGATTGAGAGCTCTTTCTTGATTTTGTGGGTGGTG
GTGCATGGCCGTTCTTAGTTGGTGGAGTGATTTGTCTGCTTAATTGCGATAACGAACGAGACCTTAAC
CTGCTAAATAGCCCGGCCCGCTTTGGCGGGTCGCCGGCTTCTTAGAGGGACTATCGGCTCAAGCCGAT
GGAAGTTTGAGGCAATAACAGGTCTGTGATGCCCTTAGATGTTCTGGGCCGCACGCGCGCTACACTG
ACAGAGCCAACGAGTTCATTTCCTTGCCCGGAAGGGTTGGGTAATCTTGTTAAACTCTGTCGTGCTGG
GGATAGAGCATTGCAATTATTGCTCTTCAACGAGGAATGCCTAGTAAGCGTACGTCATCAGCGTGCGT
TGATTACGTCCCTGCCCTTTGTACACACCGCCCGTCGCTACTACCGATTGAATGGCTGAGTGAGGCCT
TCGGACTGGCCCAGGGAGGTCGGCAACGACCACCCAGGGCCGGAAAGTTGGTCAAACTCCGTCATTT
AGAGGAAGTAAAAGTCGTAACAAGGTTTCCGTAGGTGAACCTGCGGAAGGATCA

29
DP29 16S rRNA
TACGGAGAGTTTGATCCTGGCTCAGGACGAACGCTGGCGGCGTGCTTAACACATGCAAGTCGAAC
GATGAAGCCCAGCTTGCTGGGTTGATTAGTGGCGAACGGGTGAGTAACACGTGAGCAACGTGCCCAT
AACTCTGGGATAACCTCCGGAAACGGTGGCTAATACTGGATATCTAACACGATCGCATGGTCTGTGTT
TGGAAAGATTTTTTGGTTATGGATCGGCTCACGGCCTATCAGCTTGTTGGTGAGGTAATGGCTCACCA
AGGCGACGACGGGTAGCCGGCCTGAGAGGGTGACCGGCCACACTGGGACTGAGACACGGCCCAGAC
TCCTACGGGAGGCAGCAGTGGGGAATATTGCACAATGGGCGAAAGCCTGATGCAGCAACGCCGCGTG
AGGGATGACGGCATTCGGGTTGTAAACCTCTTTTAGTAGGGAAGAAGCGAAAGTGACGGTACCTGCA
GAAAAAGCACCGGCTAACTACGTGCCAGCAGCCGCTGTAATACGTAGGGTGCAAGCGTTGTCCGGAA
TTATTGGGCGTAAAGAGCTCGTAGGCGGTTTGTCGCGTCTGCTGTGAAATCCCGAGGCTCAACCTCGG
GTCTGCAGTGGGTACGGGCAGACTAGAGTGTGGTAGGGGAGATTGGAATTCCTGGTGTAGCGGTGGA
ATGCGCAGATATCAGGAGGAACACCGATGGCGAAGGCAGATCTCTGGGCCATTACTGACGCTGAGGA
GCGAAAGCATGGGGAGCGAACAGGATTAGATACCCTGGTAGTCCATGCCGTAAACGTTGGGCGCTAG
ATGTGGGGACCATTCCACGGTTTCCGTGTCGTAGCTAACGCATTAAGCGCCCCGCCTGGGGAGTACGG
CCGCAAGGCTAAAACTCAAAGGAATTGACGGGGGCCCGCACAAGCGGCGGAGCATGCGGATTAATT
CGATGCAACGCGAAGAACCTTACCAAGGCTTGACATATACCGGAAACGTTCAGAAATGTTCGCC

-continued

| SEQUENCE LISTING Seq ID No. Description Sequence |
|---|
| 30<br>DP30 16S rRNA<br>TACGGAGAGTTTGATCCTGGCTCAGGATGAACGCTGGCGGCGTGCTTAACACATGCAAGTCGAAC<br>GGTGAAGCCAAGCTTGCTTGGTGGATCAGTGGCGAACGGGTGAGTAACACGTGAGCAACCTGCCCTG<br>GACTCTGGGATAAGCGCTGGAAACGGCGTCTAATACTGGATATGAGACGTGATCGCATGGTCGTGTT<br>TGGAAAGATTTTTCGGTCTGGGATGGGCTCGCGGCCTATCAGCTTGTTGGTGAGGTAATGGCTCACCA<br>AGGCGTCGACGGGTAGCCGGCCTGAGAGGGTGACCGGCCACACTGGGACTGAGACACGGCCCAGAC<br>TCCTACGGGAGGCAGCAGTGGGGAATATTGCACAATGGGCGAAAGCCTGATGCAGCAACGCCGCGTG<br>AGGGATGACGGCCTTCGGGTTGTAAACCTCTTTTAGCAGGGAAGAAGCGAAAGTGACGGTACCTGCA<br>GAAAAAGCGCCGGCTAACTACGTGCCAGCAGCCGCGGTAATACGTAGGGCGCAAGCGTTATCCGGAA<br>TTATTGGGCGTAAAGAGCTCGTAGGCGGTTTGTCGCGTCTGCTGTGAAATCCCGAGGCTCAACCTCGG<br>GCCTGCAGTGGGTACGGGCAGACTAGAGTGCGGTAGGGGAGATTGGAATTCCTGGTGTAGCGGTGGA<br>ATGCGCAGATATCAGGAGGAACACCGATGGCGAAGGCAGATCTCTGGGCCGTAACTGACGCTGAGG<br>AGCGAAAGGGTGGGGAGCAAACAGGCTTAGATACCCTGGTAGTCCACCCCGTAAACGTTGGGAACTA<br>GTTGTGGGGACCATTCCACGGTTTCCGTGACGCAGCTAACGCATTAAGTTCCCCGCCTGGGGAGTACG<br>GCCGCAAGGCTAAAACTCAAAGGAATTGACGGGGACCCGCACAAGCGGCGGAGCATGCGGATTAAT<br>TCGATGCAACGCGAAGAACCTTACCAAGGCTTGACATATACGAGAACGGGCCAGAAATGGTCAACTC<br>TTTGGACACTCGTAAACAGGTGGTGCATGGTTGTCGTCAGCTCGTGTCGTGAGATGTTGGGTTAAGTC<br>CCGCAACGAGCGCAACCCTCGTTCTATGTTGCCAGCACGTAATGGTGGGAACTCATGGGATACTGCC<br>GGGGTCAACTCGGAGGAAGGTGGGGATGACGTCAAATCATCATGCCCCTTATGTCTTGGGCTTCACG<br>CATGCTACAATGGCCGGTACAAAGGGCTGCAATACCGTGAGGTGGAGCGAATCCCAAAAAGCCGGTC<br>CCAGTTCGGATTGAGGTCTGCAACTCGACCTCATGAAGTCGGAGTCGCTAGTAATCGCAGATCAGCA<br>ACGCTGCGGTGAATACGTTCCCGGGTCTTGTACACACCGCCCGTCAAGTCATGAAAGTCGGTAACACC<br>TGAAGCCGGTGGCCCAACCCTTGTGGAGGGAGCCGTCGAAGGTGGGATCGGTAATTAGGACTAAGTC<br>GTAACAAGGTAGCCGTACCGGAAGGTGCGGCTGGATCACCTCCTTT |
| 31<br>DP31 16S rRNA<br>CAGCCGGGGGCATTAGTATTTGCACGCTAGAGGTGAAATTCTTGGATTGTGCAAAGACTTCCTACT<br>GCGAAAGCATTTGCCAAGAATGTTTTCATTAATCAAGAACGAAGGTTAGGGTATCGAAAACGATTAG<br>ATACCGTTGTAGTCTTAACAGTAAACTATGCCGACTCCGAATCGGTCGATGCTCATTTCACTGGCTCG<br>ATCGGCGCGGTACGAGAAATCAAAGTTTTTGGGTTCTGGGGGGAGTATGGTCGCAAGGCTGAAACTT<br>AAAGAAATTGACGGAAGGGCACCACCAGGAGTGGAGCCTGCGGCTTAATTTGACTCAACACGGGAA<br>AACTCACCGGGTCCGGACATAGTAAGGATTGACAGATTGATGGCGCTTTCATGATTCTATGGGTGGTG<br>GTGCATGGCCGTTCTTAGTTGGTGGAGTGATTTGTCTGGTTAATTCCGATAACGAACGAGACCTTGAC<br>CTGCTAAATAGACGGGTTGACATTTTGTTGGCCCCTTATGTCTTCTTAGAGGGACAATCGACCGTCTA<br>GGTGATGGAGGCAAAAGGCAATAACAGGTCTGTGATGCCCTTAGATGTTCCGGGCTGCACGCGCGCT<br>ACACTGACAGAGACAACGAGTGGGGCCCCTTGTCCGAAATGACTGGGTAAACTTGTGAAACTTTGTC<br>GTGCTGGGGATGGAGCTTTGTAATTTTTGCTCTTCAACGAGGAATTCCTAGTAAGCGCAAGTCATCAG<br>CTTGCGTTGACTACGTCCCTGCCCTTTGTACACACCGCCCGTCGCTACTACCGATTGAATGGCTTAGTG<br>AGGACTTGGGAGAGTACATCGGGGAGCCAGCAATGGCACCCTGACGGCTCAAACTCTTACAAACTTG<br>GTCATTTAGAGGAAGTAAAAGTCGTAACAAGGTATCTGTAGGTGAACCTGCAGATGGATCATTTC |
| 32<br>DP32 16S rRNA<br>ACTGAGCATTGACGTTACTCGCAGAAGAAGCACCGGCTAACTCCGTGCCAGCAGCCGCGGTAATA<br>CGGAGGGTGCAAGCGTTAATCGGAATTACTGGGCGTAAAGCGCACGCAGGCGGTTTGTTAAGTCAGA<br>TGTGAAATCCCCGAGCTTAACTTGGGAACTGCATTTGAAACTGGCAAGCTAGAGTCTTGTAGAGGGG<br>GGTAGAATTCCAGGTGTAGCGGTGAAATGCGTAGAGATCTGGAGGAATACCGGTGGCGAAGGCGGC<br>CCCCTGGACAAAGACTGACGCTCAGGTGCGAAAGCGTGGGGAGCAAACAGGATTAGATACCCTGGTA<br>GTCCACGCTGTAAACGATGTCGACTTGGAGGTTGTGCCCTTGAGGCGTGGCTTCCGGAGCTAACGCGT<br>TAAGTCGACCGCCTGGGGAGTACGGCCGCAAGGTTAAAACTCAAATGAATTGACGGGGGCCCGCACA<br>AGCGGTGGAGCATGTGGTTTAATTCGATGCAACGCGAAGAACCTTACCTACTCTTGACATCCAGAGA<br>ATTCGCTAGAGATAGCTTAGTGCCTTCGGGAACTCTGAGACAGGTGCTGCATGGCTGTCGTCAGCTCG<br>TGTTGTGAAATGTTGGGTTAAGTCCCGCAACGAGCGCAACCCTTATCCTTTGTTGCCAGCGAGTAATG<br>TCGGGAACTCAAAGGAGACTGCCGGTGATAAACCGGAGGAAGGTGGGGATGACGTCAAGTCATCAT<br>GGCCCTTACGAGTAGGGCTACACACGTGCTACAATGGCATATACAAAGAGAAGCGAACTCGCGAGAG<br>CAAGCGGACCTCATAAAGTATGTCGTAGTCCGGATTGGAGTCTGCAACTCGACTCCATGAAGTCGGA<br>ATCGCTAGTAATCGTAGATCAGAATGCTACGGTGAATACGTTCCCGGGCCTTGTACACACCGCCCGTC<br>ACACCATGGGAGTGGGTTGCAAAAGAAGTAGGTAGCTTAACCTTCGGGAGGGCGCTTACCACTTTGT<br>GATTCATGACTGGGGTGAAGTCGTAACAAGGTAACCGTAGGGGAACCTGCGGTTGGATCACCTCCTT |
| 33<br>DP33 16S rRNA<br>GGAGGAAGGCGTAGAGATCTGGAGGAATACCGGTGGCGAAGGCGGCCCCCTGGACAAAGACTGA<br>CGCTCAGGTGCGAAAGCGTGGGGAGCAAACAGGATTAGATACCCTGGTAGTCCACGCCGTAAACGAT<br>GTCGACTTGGAGGTTGTGCCCTTGAGGCGTGGCTTCCGGAGCTAACGCGTTAAGTCGACCGCCTGGGG<br>AGTACGGCCGCAAGGTTAAAACTCAAATGAATTGACGGGGGCCCGCACAAGCGGTGGAGCATGTGGT<br>TTAATTCGATGCAACGCGAAGAACCTTACCTGGCCTTGACATCCACGGAATTCGGCAGAGATGCCTTA<br>GTGCCTTCGGGAACCGTGAGACAGGTGCTGCATGGCTGTCGTCAGCTCGTGTTGTGAAATGTTGGGTT<br>AAGTCCCGCAACGAGCGCAACCCTTATCCTTTGTTGCCAGCACGTAATGGTGGGAACTCAAAGGAGA<br>CTGCCGGTGATAAACCGGAGGAAGGTGGGGATGACGTCAAGTCATCATGGCCCTTACGGCCAGGGCT<br>ACACACGTGCTACAATGGCGCATACAAAGAGAAGCGACCTCGCGAGAGCAAGCGGACCTCATAAAG<br>TGCGTCGTAGTCCGGATCGGAGTCTGCAACTCGACTCCGTGAAGTCGGAATCGCTAGTAATCGTAGAT |

-continued

| SEQUENCE LISTING Seq ID No. Description Sequence |
|---|

CAGAATGCTACGGTGAATACGTTCCCGGGCCTTGTACACACCGCCCGTCACACCATGGGAGTGGGTT
GCAAAAGAAGTAGGTAGCTTAACCTTCGGGAGGGCGCTTACCACTTTGTGATTCATGACTGGGGTGA
AGTCGTAACAAGGTAACCGTAGGGGAACCTGCGGTTGGATCACCTCCTT

34
DP34 16S rRNA
TACGGAGAGTTTGATCCTGGCTCAGGACGAACGCTGGCGGCGTGCTTAACACATGCAAGTCGAAC
GATGAAGCCCAGCTTGCTGGGTGGATTAGTGGCGAACGGGTGAGTAACACGTGAGTAACCTGCCCTT
GACTCTGGGATAAGCGTTGGAAACGACGTCTAATACCGGATACGAGCTTCCACCGCATGGTGAGTTG
CTGGAAAGAATTTTGGTCAAGGATGGACTCGCGGCCTATCAGCTTGTTGGTGAGGTAATGGCTCACCA
AGGCGACGACGGGTAGCCGGCCTGAGAGGGTGACCGGCCACACTGGGACTGAGACACGGCCCAGAC
TCCTACGGGAGGCAGCAGTGGGGAATATTGCACAATGGGCGAAAGCCTGATGCAGCAACGCCGCGTG
AGGGACGACGGCCTTCGGGTTGTAAACCTCTTTTAGCAGGGAAGAAGCGAAAGTGACGGTACCTGCA
GAAAAAGCACCGGCTAACTACGTGCCAGCAGCCGCGGTAATACGTAGGGTGCAAGCGTTGTCCGGAA
TTATTGGGCGTAAAGAGCTCGTAGGCGGTTTGTCGCGTCTGCTGTGAAATCCCGAGGCTCAACCTCGG
GTCTGCAGTGGGTACGGGCAGACTAGAGTGCGGTAGGGGAGATTGGAATTCCTGGTGTAGCGGTGGA
ATGCGCAGATATCAGGAGGAACACCGATGGCGAAGGCAGATCTCTGGGCCGCTACTGACGCTGAGGA
GCGAAAGGGTGGGGAGCAAACAGGCTTAGATACCCTGGTAGTCCACCCCGTAAACGTTGGGCGCTAG
ATGTGGGGACCATTCCACGGTTTCCGTGTCGTAGCTAACGCATTAAGCGCCCCGCCTGGGGAGTACGG
CCGCAAGGCTAAAACTCAAAGGAATTGACGGGGGCCCGCACAAGCGGCGGAGCATGCGGATTAATT
CGATGCAACGCGAAGAACCTTACCAAGGCTTGACATATACGAGAACGGGCCAGAAATGGTCAACTCT
TTGGACACTCGTAAACAGGTGGTGCATGGTTGTCGTCAGCTCGTGTCGTGAGATGTTGGGTTAAGTCC
CGCAACGAGCGCAACCCTCGTTCTATGTTGCCAGCACGTAATGGTGGGAACTCATGGGATACTGCCG
GGGTCAACTCGGAGGAAGGTGGGGACGACGTCAAATCATCATGCCCCTTATGTCTTGGGCTTCACGC
ATGCTACAATGGCCAGTACAAAGGGCTGCAATACCGTAAGGTGGAGCGAATCCCAAAAAGCTGGTCC
CAGTTCGGATTGAGGTCTGCAACTCGACCTCATGAAGTCGGAGTCGCTAGTAATCGCAGATCAGCAA
CGCTGCGGTGAATACGTTCCCGGGCCTTGTACACACCGCCCGTCAAGTCATGAAAGTCGGTAACACCC
GAAGCCAGTGGCCTAACCGCAAGGATGGAGCTGTCTAAGGTGGGATCGGTAATTAGGACTAAGTCGT
AACAAGGTAGCCGTACCGGAAGGTGCGGCTGGATCACCTCCTTT

35
DP35 16S rRNA
TTGAAGAGTTTGATCATGGCTCAGATTGAACGCTGGCGGCAGGCCTAACACATGCAAGTCGGACG
GTAGCACAGAGAGCTTGCTCTTGGGTGACGAGTGGCGGACGGGTGAGTAATGTCTGGGGATCTGCCC
GATAGAGGGGGATAACCACTGGAAACGGTGGCTAATACCGCATAACGTCGCAAGACCAAAGAGGGG
GACCTTCGGGCCTCTCACTATCGGATGAACCCAGATGGGATTAGCTAGTAGGCGGGGTAATGGCCCA
CCTAGGCGACGATCCCTAGCTGGTCTGAGAGGATGACCAGCCACACTGGAACTGAGACACGGTCCAG
ACTCCTACGGGAGGCAGCAGTGGGGAATATTGCACAATGGGCGCAAGCCTGATGCAGCCATGCCGCG
TGTATGAAGAAGGCCTTCGGGTTGTAAAGTACTTTCAGCGGGGAGGAAGGCGATGAGGTTAATAACC
GCGTCGATTGACGTTACCCGCAGAAGAAGCACCGGCTAACTCCGTGCCAGCAGCCGCGGTAATACGG
AGGGTGCAAGCGTTAATCGGAATTACTGGGCGTAAAGCGCACGCAGGCGGTCTGTTAAGTCAGATGT
GAAATCCCCGGGCTTAACCTGGGAACTGCATTTGAAACTGGCAGGCTTGAGTCTTGTAGAGGGGGGT
AGAATTCCAGGTGTAGCGGTGAAATGCGTAGAGATCTGGAGGAATACCGGTGGCGAAGGCGGCCCCC
TGGACAAAGACTGACGCTCAGGTGCGAAAGCGTGGGGAGCAAACAGGATTAGATACCCTGGTAGTCC
ACGCCGTAAACGATGTCGACTTGGAGGTTGTTCCCTTGAGGAGTGGCTTCCGGAGCTAACGCGTTAAG
TCGACCGCCTGGGGAGTACGGCCGCAAGGTTAAAACTCAAATGAATTGACGGGGGCCCGCACAAGCG
GTGGAGCATGTGGTTTAATTCGATGCAACGCGAAGAACCTTACCTACTCTTGACATCCAGCGAACTTA
GCAGAGATGCTTTGGTGCCTTCGGGAACGCTGAGACAGGTGCTGCATGGCTGTCGTCAGCTCGTGTTG
TGAAATGTTGGGTTAAGTCCCGCAACGAGCGCAACCCTTATCCTTTGTTGCCAGCGATTCGGTCGGGA
ACTCAAAGGAGACTGCCGGTGATAAACCGGAGGAAGGTGGGGATGACGTCAAGTCATCATGGCCCTT
ACGAGTAGGGCTACACACGTGCTACAATGGCGCATACAAAGAGAAGCGACCTCGCGAGAGCAAGCG
GACCTCACAAAGTGCGTCGTAGTCCGGATCGGAGTCTGCAACTCGACTCCGTGAAGTCGGAATCGCT
AGTAATCGTGGATCAGAATGCCACGGTGAATACGTTCCCGGGCCTTGTACACACCGCCCGTCACACC
ATGGGAGTGGGTTGCAAAAGAAGTAGGTAGCTTAACCTTCGGGAGGGCGCTTACCACTTTGTGATTC
ATTACTGGGGTGAAGTCGTAACAAGGTAACCGTAGGGGAACCTGCGGTTGGATCACCTCCTT

36
DP36 16S
rRNATTGAAGAGTTTGATCATGGCTCAGATTGAACGCTGGCGGCAGGCCTAACACATGCAAGTCGGAC
GGTAGCACAGAGAGCTTGCTCTTGGGTGACGAGTGGCGGACGGGTGAGTAATGTCTGGGGATCTGCC
CGATAGAGGGGGATAACCACTGGAAACGGTGGCTAATACCGCATAACGTCGCAAGACCAAAGAGGG
GGACCTTCGGGCCTCTCACTATCGGATGAACCCAGATGGGATTAGCTAGTAGGCGGGGTAATGGCCC
ACCTAGGCGACGATCCCTAGCTGGTCTGAGAGGATGACCAGCCACACTGGAACTGAGACACGGTCCA
GACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGCGATGCGGTTAATAAC
CGCGTCGATTGACGTTACCCGCAGAAGAAGCACCGGCTAACTCCGTGCCAGCAGCCGCGGTAATACG
GAGGGTGCAAGCGTTAATCGGAATTACTGGGCGTAAAGCGCACGCAGGCGGTCTGTTAAGTCAGATG
TGAAATCCCCGGGCTTAACCTGGGAACTGCATTTGAAACTGGCAGGCTTGAGTCTTGTAGAGGGGGG
TAGAATTCCAGGTGTAGCGGTGAAATGCGTAGAGATCTGGAGGAATACCGGTGGCGAAGGCGGCCCC
CTGGACAAAGACTGACGCTCAGGTGCGAAAGCGTGGGGAGCAAACAGGATTAGATACCCTGGTAGTC
CACGCCGTAAACGATGTCGACTTGGAGGTTGTTCCCTTGAGGAGTGGCTTCCGGAGCTAACGCGTTAA
GTCGACCGCCTGGGGAGTACGGCCGCAAGGTTAAAACTCAAATGAATTGACGGGGGCCCGCACAAGC
GGTGGAGCATGTGGTTTAATTCGATGCAACGCGAAGAACCTTACCTACTCTTGACATC

-continued

| SEQUENCE LISTING<br>Seq ID No.<br>Description<br>Sequence |
|---|

37
DP37 16S rRNA
TGAAGAGTTTGATCATGGCTCAGATTGAACGCTGGCGGCAGGCCTAACACATGCAAGTCGAGCGG
TAGAGAGAAGCTTGCTTCTCTTGAGAGCGGCGGACGGGTGAGTAATGCCTAGGAATCTGCCTGGTAG
TGGGGGATAACGTTCGGAAACGAACGCTAATACCGCATACGTCCTACGGGAGAAAGCAGGGGACCTT
CGGGCCTTGCGCTATCAGATGAGCCTAGGTCGGATTAGCTAGTTGGTGGGGTAATGGCTCACCAAGG
CGACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGCCATTACCTAATACGTGATGGT
TTTGACGTTACCGACAGAATAAGCACCGGCTAACTCTGTGCCAGCAGCCGCGGTAATACAGAGGGTG
CAAGCGTTAATGGAATTACTGGGCGTAAAGCGCGCGTAGGTGGTTTGTTAAGTTGGATGTGAAATCC
CCGGGCTCAACCTGGGAACTGCATTCAAAACTGACTGACTAGAGTATGGTAGAGGGTGGTGGAATTT
CCTGTGTAGCGGTGAAATGCGTAGATATAGGAAGGAACACCAGTGGCGAAGGCGACCACCTGGACTG
ATACTGACACTGAGGTGCGAAAGCGTGGGGAGCAAACAGGATTAGATACCCTGGTAGTCCACGCCGT
AAACGATGTCAACTAGCCGTTGGGAGCCTTGAGCTCTTAGTGGCGCAGCTAACGCATTAAGTTGACC
GCCTGGGGAGTACGGCCGCAAGGTTAAAACTCAAATGAATTGACGGGGGCCCGCACAAGCGGTGGA
GCATGTGGTTTAATTCGAAGCAACGCGAAGAACCTTACCAGGCCTTGACATCCAATGAACTTTCTAGA
GATAGATTGGTGCCTTCGGGAACATTGAGACAGGTGCTGCATGGCTGTCGTCAGCTCGTGTCGTGAGA
TGTTGGGTTAAGTCCCGTAACGAGCGCAACCCTTGTCCTTAGTTACCAGCACGTAATGGTGGGCACTC
TAAGGAGACTGCCGGTGACAAACCGGAGGAAGGTGGGGATGACGTCAAGTCATCATGGCCCTTACGG
CCTGGGCTACACACGTGCTACAATGGTCGGTACAGAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGCGAATCAGAATGTCGCGGTGAATACGTTCCCGGGCCTTGTACACACCGCCCGTCACACCATGGG
AGTGGGTTGCACCAGAAGTAGCTAGTCTAACCTTCGGGGGGACGGTTACCACGGTGTGATTCATGAC
TGGGGTGAAGTCGTAACAAGGTAGCCGTAGGGGAACCTGCGGCTGGATCACCTCCTT

38
DP38 16S rRNA
TACGGAGAGTTTGATCCTGGCTCAGGACGAACGCTGGCGGCGTGCTTAACACATGCAAGTCGAGC
GGTAAGGCCTTTCGGGGTACACGAGCGGCGAACGGGTGAGTAACACGTGGGTGATCTGCCCTGCACT
CTGGGATAAGCTTGGGAAACTGGGTCTAATACCGGATATGACCACAGCATGCATGTGTTGTGGTGGA
AAGATTTATCGGTGCAGGATGGGCCCGCGGCCTATCAGCTTGTTGGTGGGGTAATGGCCTACCAAGG
CGACGACGGGTAGCCGACCTGAGAGGGTGACCGGCCACACTGGGACTGAGACACGGCCCAGACTCCT
ACGGGAGGCAGCAGTGGGGAATATTGCACAATGGGCGGAAGCCTGATGCAGCGACGCCGCGTGAGG
GATGAAGGCCTTCGGGTTGTAAACCTCTTTCAGCAGGGACGAAGCGTGAGTGACGGTACCTGCAGAA
GAAGCACCGGCTAACTACGTGCCAGCAGCCGCGGTAATACGTAGGGTGCGAGCGTTGTCCGGAATTA
CTGGGCGTAAAGAGTTCGTAGGCGGTTTGTCGCGTCGTTTGTGAAAACCCGGGGCTCAACTTCGGGCT
TGCAGGCGATACGGGCAGACTTGAGTGTTTCAGGGGAGACTGGAATTCCTGGTGTAGCGGTGAAATG
CGCAGATATCAGGAGGAACACCGGTGGCGAAGGCGGGTCTCTGGGAAACAACTGACGCTGAGGAAC
GAAAGCGTGGGTAGCAAACAGGATTAGATACCCTGGTAGTCCACGCCGTAAACGGTGGGCGCTAGGT
GTGGGTTCCTTCCACGGGATCTGTGCCGTAGCTAACGCATTAAGCGCCCCGCCTGGGGAGTACGGCCG
CAAGGCTAAAACTCAAAGGAATTGACGGGGGCCCGCACAAGCGGCGGAGCATGTGGATTAATTCGAT
GCAACGCGAAGAACCTTACCTGGGTTTGACATACACCGGAAAACCGTAGAGATACGGTCCCCCTTGT
GGTCGGTGTACAGGTGGTGCATGGCTGTCGTCAGCTCGTGTCGTGAGATGTTGGGTTAAGTCCCGCAA
CGAGCGCAACCCTTGTCTTATGTTGCCAGCACGTAATGGTGGGGACTCGTAAGAGACTGCCGGGGTC
AACTCGGAGGAAGGTGGGGACGACGTCAAGTCATCATGCCCCTTATGTCCAGGGCTTCACACATGCT
ACAATGGCCAGTACAGAGGGCTGCGAGACCGTGAGGTGGAGCGAATCCCTTAAAGCTGGTCTCAGTT
CGGATCGGGGTCTGCAACTCGACCCCGTGAAGTCGGAGTCGCTAGTAATCGCAGATCAGCAACGCTG
CGGTGAATACGTTCCCGGGCCTTGTACACACCGCCCGTCACGTCATGAAAGTCGGTAACACCCGAAG
CCGGTGGCCTAACCCCTTACGGGGAGGGAGCCGTCGAAGGTGGGATCGGCGATTGGGACGAAGTCGT
AACAAGGTAGCCGTACCGGAAGGTGCGGCTGGATCACCTCCTTT

39
DP39 16S rRNA
CTTGAGAGTTTGATCCTGGCTCAGAACGAACGCTGGCGGCAGGCTTAACACATGCAAGTCGAACG
CCCCGCAAGGGGAGTGGCAGACGGGTGAGTAACGCGTGGGAATCTACCGTGCCCTGCGGAATAGCTC
CGGGAAACTGGAATTAATACCGCATACGCCCTACGGGGGAAAGATTTATCGGGGTATGATGAGCCCG
CGTTGGATTAGCTAGTTGGTGGGGTAAAGGCCTACCAAGGCGACGATCCATAGCTGGTCTGAGAGGA
TGATCAGCCACATTGGGACTGAGACACGGCCCAAACTCCTACGGGAGGCAGCAGTGGGGAATATTGG
ACAATGGGCGCAAGCCTGATCCAGCCATGCCGCGTGAGTGATGAAGGCCTTAGGGTTGTAAAGCTCT
TTCACCGGAGAAGATAATGACGGTATCCGGAGAAGAAGCCCCGGCTAACTTCGTGCCAGCAGCCGCG
GTAATACGAAGGGGGCTAGCGTTGTTCGGAATTACTGGGCGTAAAGCGCACGTAGGCGGATATTTAA
GTCAGGGGTGAAATCCCAGAGCTCAACTCTGGAACTGCCTTTGATACTGGGTATCTTGAGTATGGAAG
AGGTAAGTGGAATTCCGAGTGTAGAGGTGAAATTCGTAGATATTCGGAGGAACACCAGTGGCGAAGG
CGGCTTACTGGTCCATTACTGACGCTGAGGTGCGAAAGCGTGGGGAGCAAACAGGATTAGATACCCT
GGTAGTCCACGCCGTAAACGATGAATGTTAGCCGTCGGGCAGTATACTGTTCGGTGGCGCAGCTAAC
GCATTAAACATTCCGCCTGGGGAGTACGGTCGCAAGATTAAAACTCAAAGGAATTGACGGGGGCCCG
CACAAGCGGTGGAGCATGTGGTTTAATTCGAAGCAACGCGCAGAACCTTACCAGCTCTTGACATTCG
GGGTTTGGGCAGTGGAGACATTGTCCTTCAGTTAGGCTGGCCCCAGAACAGGTGCTGCATGGCTGTCG
TCAGCTCGTGTCGTGAGATGTTGGGTTAAGTCCCGCAACGAGCGCAACCCTCGCCCTTAGTTGCCAGC
ATTTAGTTGGGCACTCTAAGGGGACTGCCGGTGATAAGCCGAGAGGAAGGTGGGGATGACGTCAAGT
CCTCATGGCCCTTACGGGCTGGGCTACACACGTGCTACAATGGTGGTGACAGTGGGCAGCGAGACAG
CGATGTCGAGCTAATCTCCAAAAGCCATCTCAGTTCGGATTGCACTCTGCAACTCGAGTGCATGAAGT
TGGAATCGCTAGTAATCGCAGATCAGCATGCTGCGGTGAATACGTTCCCGGGCCTTGTACACACCGCC

-continued

| SEQUENCE LISTING Seq ID No. Description Sequence |
|---|

CGTCACACCATGGGAGTTGGTTTTACCCGAAGGTAGTGCGCTAACCGCAAGGAGGCAGCTAACCACG
GTAGGGTCAGCGACTGGGGTGAAGTCGTAACAAGGTAGCCGTAGGGGAACCTGCGGCTGGATCACCT
CCTTT

40
DP40 16S rRNA
TTGACGTTACCCGCAGAAGAAGCACCGGCTAACTCCGTGCCAGCAGCCGCGGTAATACGGAGGGT
GCAAGCGTTAATCGGAATTACTGGGCGTAAAGCGCACGCAGGCGGTCTGTTAAGTCAGATGTGAAAT
CCCCGGGCTTAACCTGGGAACTGCATTTGAAACTGGCAGGCTTGAGTCTTGTAGAGGGGGGTAGAAT
TCCAGGTGTAGCGGTGAAATGCGTAGAGATCTGGAGGAATACCGGTGGCGAAGGCGGCCCCCTGGAC
AAAGACTGACGCTCAGGTGCGAAAGCGTGGGGAGCAAACAGGATTAGATACCCTGGTAGTCCACGCC
GTAAACGATGTCGACTTGGAGGTTGTTCCCTTGAGGAGTGGCTTCCGGAGCTAACGCGTTAAGTCGAC
CGCCTGGGGAGTACGGCCGCAAGGTTAAAACTCAAATGAATTGACGGGGGCCCGCACAAGCGGTGG
AGCATGTGGTTTAATTCGATGCAACGCGAAGAACCTTACCTACTCTTGACATCCAGAGAACTTTCCAG
AGATGGATTGGTGCCTTCGGGAACTCTGAGACAGGTGCTGCATGGCTGTCGTCAGCTCGTGTTGTGAA
ATGTTGGGTTAAGTCCCGCAACGAGCGCAACCCTTATCCTTTGTTGCCAGCGCGTGATGGCGGGAACT
CAAAGGAGACTGCCGGTGATAAACCGGAGGAAGGTGGGGATGACGTCAAGTCATCATGGCCCTTACG
AGTAGGGCTACACACGTGCTACAATGGCGCATACAAAGAGAAGCGACCTCGCGAGAGCAAGCGGAC
CTCACAAAGTGCGTCGTAGTCCGGATCGGAGTCTGCAACTCGACTCCGTGAAGTCGGAATCGCTAGT
AATCGTGGATCAGAATGCCACGGTGAATACGT

41
DP41 16S rRNA
GTGGAGAGTTTGATCCTGGCTCAGGATGAACGCTGGCGGCGTGCTTAACACATGCAAGTCGAACG
GAAAGGCCCAAGCTTGCTTGGGTACTCGAGTGGCGAACGGGTGAGTAACACGTGGGTGATCTGCCCT
GCACTTCGGGATAAGCCTGGGAAACTGGGTCTAATACCGGATAGGACGATGGTTTGGATGCCATTGT
GGAAAGTTTTTTCGGTGTGGGATGAGCTCGCGGCCTATCAGCTTGTTGGTGGGGTAATGGCCTACCAA
GGCGTCGACGGGTAGCCGGCCTGAGAGGGTGTACGGCCACATTGGGACTGAGATACGGCCCAGACTC
CTACGGGAGGCAGCAGTGGGGAATATTGCACAATGGGCGCAAGCCTGATGCAGCGACGCCGCGTGG
GGGATGACGGCCTTCGGGTTGTAAACTCCTTTCGCTAGGGACGAAGCGTTTTGTGACGGTACCTGGAG
AAGAAGCACCGGCTAACTACGTGCCAGCAGCCGCGGTAATACGTAGGGTGCGAGCGTTGTCCGGAAT
TACTGGGCGTAAAGAGCTCGTAGGTGGTTTGTCGCGTCGTTTGTGTAAGCCCGCAGCTTAACTGCGGG
ACTGCAGGCGATACGGGCATAACTTGAGTGCTGTAGGGGAGACTGGAATTCCTGGTGTAGCGGTGGA
ATGCGCAGATATCAGGAGGAACACCGATGGCGAAGGCAGGTCTCTGGGCAGTAACTGACGCTGAGG
AGCGAAAGCATGGGTAGCGAACAGGATTAGATACCCTGGTAGTCCATGCCGTAAACGGTGGGCGCTA
GGTGTGAGTCCCTTCCACGGGGTTCGTGCCGTAGCTAACGCATTAAGCGCCCCGCCTGGGGAGTACG
GCCGCAAGGCTAAAACTCAAAGGAATTGACGGGGGCCCGCACAAGCGGCGGAGCATGTGGATTAAT
TCGATGCAACGCGAAGAACCTTACCTGGGCTTGACATACACCAGATCGCCGTAGAGATACGGTTTCC
CTTTGTGGTTGGTGTACAGGTGGTGCATGGTTGTCGTCAGCTCGTGTCGTGAGATGTTGGGTTAAGTC
CCGCAACGAGCGCAACCCTTGTCTTATGTTGCCAGCACGTGATGGTGGGGACTCGTGAGAGACTGCC
GGGGTTAACTCGGAGGAAGGTGGGGATGACGTCAAATCATCATGCCCCTTATGTCCAGGGCTTCACA
CATGCTACAATGGTCGGTACAACGCGCATGCGAGCCTGTGAGGGTGAGCGAATCGCTGTGAAAGCCG
GTCGTAGTTCGGATTGGGGTCTGCAACTCGACCCCATGAAGTCGGAGTCGCTAGTAATCGCAGATCA
GCAACGCTGCGGTGAATACGTTCCCGGGCCTTGTACACACCGCCCGTCACACCATGGGAGTGGGTTG
CAAAAGAAGTAGGTAGCTTAACCTTCGGGAGGGCGCTTACCACTTTGTGAT

42
DP42 16S rRNA
TGAAGAGTTTGATCATGGCTCAGATTGAACGCTGGCGGCAGGCCTAACACATGCAAGTCGAGCGG
TAGAGAGGTGCTTGCACCTCTTGAGAGCGGCGGACGGGTGAGTAATACCTAGGAATCTGCCTGATAG
TGGGGGATAACGTTCGGAAACGGACGCTAATACCGCATACGTCCTACGGGAGAAAGCAGGGGACCTT
CGGGCCTTGCGCTATCAGATGAGCCTAGGTCGGATTAGCTAGTTGGTGAGGTAATGGCTCACCAAGG
CTACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGCATTAACCTAATACGTTAGTGT
CTTGACGTTACCGACAGAATAAGCACCGGCTAACTCTGTGCCAGCAGCCGCGGTAATACAGAGGGTG
CAAGCGTTAATCGGAATTACTGGGCGTAAAGCGCGCGTAGGTGGTTTGTTAAGTTGAATGTGAAATC
CCCGGGCTCAACCTGGGAACTGCATCCAAAACTGGCAAGCTAGAGTATGGTAGAGGGTAGTGGAATT
TCCTGTGTAGCGGTGAAATGCGTAGATATAGGAAGGAACACCAGTGGCGAAGGCGACTACCTGGACT
GATACTGACACTGAGGTGCGAAAGCGTGGGGAGCAAACAGGATTAGATACCCTGGTAGTCCACGCCG
TAAACGATGTCAACTAGCCGTTGGGAACCTTGAGTTCTTAGTGGCGCAGCTAACGCATTAAGTTGACC
GCCTGGGGAGTACGGCCGCAAGGTTAAAACTCAAATGAATTGACGGGGGCCCGCACAAGCGGTGGA
GCATGTGGTTTAATTCGAAGCAACGCGAAGAACCTTACCAGGCCTTGACATCCAATGAACTTTCCAGA
GATGGATTGGTGCCTTCGGGAACATTGAGACAGGTGCTGCATGGCTGTCGTCAGCTCGTGTCGTGAGA
TGTTGGGTTAAGTCCCGTAACGAGCGCAACCCTTGTCCTTAGTTACCAGCACGTAATGGTGGGCACTC
TAAGGAGACTGCCGGTGACAAACCGGAGGAAGGTGGGGATGACGTCAAGTCATCATGGCCCTTACGG
CCTGGGCTACACACGTGCTACAATGGTCGGTACAAAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGTGAATCAGAATGTCACGGTGAATACGTTCCCGGGCCTTGTACACACCGCCCGTCACACCATGGGA
GTGGGTTGCACCAGAAGTAGCTAGTCTAACCCTCGGGAGGACGGTTACCACGGTGTGATTCATGACT
GGGGTGAAGTCGTAACAAGGTAGCCGTAGGGGAACCTGCGGCTGGATCACCTCCTT

-continued

| SEQUENCE LISTING<br>Seq ID No.<br>Description<br>Sequence |
|---|

43
DP43 16S rRNA
CTGAGTTTGATCCTGGCTCAGATTGAACGCTGGCGGCATGCCTTACACATGCAAGTCGAACGGCAG
CACGGAGCTTGCTCTGGTGGCGAGTGGCGAACGGGTGAGTAATATATCGGAACGTACCCTGGAGTGG
GGGATAACGTAGCGAAAGTTACGCTAATACCGCATACGATCTAAGGATGAAAGTGGGGGATCGCAA
GACCTCATGCTCGTGGAGCGGCCGATATCTGATTAGCTAGTTGGTAGGGTAAAAGCCTACCAAGGCA
TCGATCAGTAGCTGGTCTGAGAGGACGACCAGCCACACTGGAACTGAGACACGGTCCAGACTCCTAC
GGGAGGCAGCAGTGGGGAATTTTGGACAATGGGCGAAAGCCTGATCCAGCAATGCCGCGTGAGTGA
AGAAGGCCTTCGGGTTGTAAAGCTCTTTTGTCAGGGAAGAAACGGTGAGAGCTAATATCTCTTGCTAA
TGACGGTACCTGAAGAATAAGCACCGGCTAACTACGTGCCAGCAGCCGCGGTAATACGTAGGGTGCA
AGCGTTAATCGGAATTACTGGGCGTAAAGCGTGCGCAGGCGGTTTTGTAAGTCTGATGTGAAATCCCC
GGGCTCAACCTGGGAATTGCATTGGAGACTGCAAGGCTAGAATCTGGCAGAGGGGGGTAGAATTCCA
CGTGTAGCAGTGAAATGCGTAGATATGTGGAGGAACACCGATGGCGAAGGCAGCCCCCTGGGTCAAG
ATTGACGCTCATGCACGAAAGCGTGGGGAGCAAACAGGATTAGATACCCTGGTAGTCCACGCCCTAA
ACGATGTCTACTAGTTGTCGGGTCTTAATTGACTTGGTAACGCAGCTAACGCGTGAAGTAGACCGCCT
GGGGAGTACGGTCGCAAGATTAAAACTCAAAGGAATTGACGGGGACCCGCACAAGCGGTGGATGAT
GTGGATTAATTCGATGCAACGCGAAAAACCTTACCTACCCTTGACATGGCTGGAATCCTTGAGAGATC
AGGGAGTGCTCGAAAGAGAACCAGTACACAGGTGCTGCATGGCTGTCGTCAGCTCGTGTCGTGAGAT
GTTGGGTTAAGTCCCGCAACGAGCGCAACCCTTGTCATTAGTTGCTACGAAAGGGCACTCTAATGAG
ACTGCCGGTGACAAACCGGAGGAAGGTGGGGATGACGTCAAGTCCTCATGGCCCTTATGGGTAGGGC
TTCACACGTCATACAATGGTACATACAGAGCGCCGCCAACCCGCGAGGGGGAGCTAATCGCAGAAAG
TGTATCGTAGTCCGGATTGTAGTCTGCAACTCGACTGCATGAAGTTGGAATCGCTAGTAATCGCGGAT
CAGCATGTCGCGGTGAATACGTTCCCGGGTCTTGTACACACCGCCCGTCACACCATGGGAGCGGGTTT
TACCAGAAGTAGGTAGCTTAACCGTAAGGAGGGCGCTTACCACGGTAGGATTCGTGACTGGGGTGAA
GTCGTAACAAGGTAGCCGTATCGGAAGGTGCGGCTGGATCACCTCCTTT

44
DP44 16S rRNA
TGGCGGCATGCCTTACACATGCAAGTCGAACGGCAGCATAGGAGCTTGCTCCTGATGGCGAGTGG
CGAACGGGTGAGTAATATATCGGAACGTGCCCTAGAGTGGGGGATAACTAGTCGAAAGACTAGCTAA
TACCGCATACGATCTACGGATGAAAGTGGGGGATCGCAAGACCTCATGCTCCTGGAGCGGCCGATAT
CTGATTAGCTAGTTGGTGGGGTAAAAGCTCACCAAGGCGACGATCAGTAGCTGGTCTGAGAGGACGA
CCAGCCACACTGGGACTGAGACACGGCCCAGACTCCTACGGGAGGCAGCAGTGGGGAATTTTGGACA
ATGGGGGCAACCCTGATCCAGCAATGCCGCGTGAGTGAAGAAGGCCTTCGGGTTGTAAAGCTCTTTT
GTCAGGGAAGAAACGGTTCTGGATAATACCTAGGACTAATGACGGTACCTGAAGAATAAGCACCGGC
TAACTACGTGCCAGCAGCCGCGGTAATACGTAGGGTGCAAGCGTTAATCGGAATTACTGGGCGTAAA
GCGTGCGCAGGCGGTTGTGTAAGTCAGATGTGAAATCCCCGGGCTCAACCTGGGAATTGCATTTGAG
ACTGCACGGCTAGAGTGTGTCAGAGGGGGGTAGAATTCCACGTGTAGCAGTGAAATGCGTAGATATG
TGGAGGAATACCGATGGCGAAGGCAGCCCCCTGGGATAACACTGACGCTCATGCACGAAAGCGTGG
GGAGCAAACAGGATTAGATACCCTGGTAGTCCACGCCCTAAACGATGTCTACTAGTTGTCGGGTCTTA
ATTGACTTGGTAACGCAGCTAACGCGTGAAGTAGACCGCCTGGGGAGTACGGTCGCAAGATTAAAAC
TCAAAGGAATTGACGGGGACCCGCACAAGCGGTGGATGATGTGGATTAATTCGATGCAACGCGAAAA
ACCTTACCTACCCTTGACATGGATGGAATCCCGAAGAGATTTGGGAGTGCTCGAAAGAGAACCATCA
CACAGGTGCTGCATGGCTGTCGTCAGCTCGTGTCGTGAGATGTTGGGTTAAGTCCCGCAACGAGCGCA
ACCCTTGTCATTAGTTGCTACGAAAGGGCACTCTAATGAGACTGCCGGTGACAAACCGGAGGAAGGT
GGGGATGACGTCAAGTCCTCATGGCCCTTATGGGTAGGGCTTCACACGTCATACAATGGTACATACA
GAGGGCCGCCAACCCGCGAGGGGGAGCTAATCCCAGAAAGTGTATCGTAGTCCGGATTGGAGTCTGC
AACTCGACTCCATGAAGTTGGAATCGCTAGTAATCGCGGATCAGCATGTCGCGGTGAATACGTTCCCG
GGTCTTGTACACACCGCCCGTCACACCATGGGAGCGGGTTTTACCAGAAGTGGGTAGCCTAACCGCA
AGGAGGGCGCTCACCACGGTAGGATTCGTGACTGGGGTGAAGTCGTAACAAGGTAGCCGTATCGGAA
GGTGCGGCTGGATCACCTCCTTT

45
DP45 16S rRNA
TACGGAGAGTTTGATCCTGGCTCAGGACGAACGCTGGCGGCGTGCTTAACACATGCAAGTCGAAC
GGTGACGCTAGAGCTTGCTCTGGTTGATCAGTGGCGAACGGGTGAGTAACACGTGAGTAACCTGCCC
TTGACTCTGGGATAACTCCGGGAAACCGGGGCTAATACCGGATACGAGACGCGACCGCATGGTCGGC
GTCTGGAAAGTTTTTCGGTCAAGGATGGACTCGCGGCCTATCAGCTTGTTGGTGAGGTAATGGCTCAC
CAAGGCGTCGACGGGTAGCCGGCCTGAGAGGGCGACCGGCCACACTGGGACTGAGACACGGCCCAG
ACTCCTACGGGAGGCAGCAGTGGGGAATATTGCACAATGGGCGAAAGCCTGATGCAGCGACGCCGC
GTGAGGGATGAAGGCCTTCGGGTTGTAAACCTCTTTCAGTAGGGAAGAAGCGAAAGTGACGGTACCT
GCAGAAGAAGCGCCGGCTAACTACGTGCCAGCAGCCGCGGTAATACGTAGGGCGCAAGCGTTGTCCG
GAATTATTGGGCGTAAAGAGCTCGTAGGCGGTTTGTCGCGTCTGGTGTGAAAACTCAAGGCTCAACCT
TGAGCTTGCATCGGGTACGGGCAGACTAGAGTGTGGTAGGGGTGACTGGAATTCCTGGTGTAGCGGT
GGAATGCGCAGATATCAGGAGGAACACCGATGGCGAAGGCAGGTCACTGGGCCACTACTGACGCTG
AGGAGCGAAAGCATGGGGAGCGAACAGGATTAGATACCCTGGTAGTCCATGCCGTAAACGTTGGGC
ACTAGGTGTGGGGCTCATTCCACGAGTTCCGCGCCGCAGCTAACGCATTAAGTGCCCCGCCTGGGGA
GTACGGCCGCAAGGCTAAAACTCAAAGGAATTGACGGGGGCCCGCACAAGCGGCGGAGCATGCGGA
TTAATTCGATGCAACGCGAAGAACCTTACCAAGGCTTGACATACACCGGAATCATGCAGAGATGTGT
GCGTCTTCGGACTGGTGTACAGGTGGTGCATGGTTGTCGTCAGCTCGTGTCGTGAGATGTTGGGTTAA
GTCCCGCAACGAGCGCAACCCTCGTCCTATGTTGCCAGCACGTTATGGTGGGGACTCATAGGAGACT
GCCGGGGTCAACTCGGAGGAAGGTGGGGATGACGTCAAATCATCATGCCCCTTATGTCTTGGGCTTC
ACGCATGCTACAATGGCCGGTACAAAGGGCTGCGATACCGCGAGGTGGAGCGAATCCCAAAAAGCC
GGTCTCAGTTCGGATTGGGGTCTGCAACTCGACCCCATGAAGTCGGAGTCGCTAGTAATCGCAGATCA

-continued

| SEQUENCE LISTING Seq ID No. Description Sequence |
|---|

GCAACGCTGCGGTGAATACGTTCCCGGGCCTTGTACACACCGCCCGTCAAGTCACGAAAGTCGGTAA
CACCCGAAGCCGGTGGCCTAACCCCTTGTGGGATGGAGCCGTCGAAGGTGGGATTGGCGATTGGGAC
TAAGTCGTAACAAGGTAGCCGTACCGGAAGGTGCGGCTGGATCACCTCCTTT

46
DP46 16S rRNA
TTGAAGAGTTTGATCATGGCTCAGATTGAACGCTGGCGGCAGGCCTAACACATGCAAGTCGGACG
GTAGCACAGAGGAGCTGCTCCTTGGGTGACGAGTGGCGGACGGGTGAGTAATGTCTGGGGATCTGCC
CGATAGAGGGGGATAACCACTGGAAACGGTGGCTAATACCGCATAACGTCGCAAGACCAAAGAGGG
GGACCTTCGGGCCTCTCACTATCGGATGAACCCAGATGGGATTAGCTAGTAGGCGGGGTAATGGCCC
ACCTAGGCGACGATCCCTAGCTGGTCTGAGAGGATGACCAGCCACACTGGAACTGAGACACGGTCCA
GACTCCTACGGGAGGCAGCAGTGGGGAATATTGCACAATGGGCGCAAGCCTGATGCAGCCATGCCGC
GTGTATGAAGAAGGCCTTCGGGTTGTAAAGTACTTTCAGCGGGGAGGAAGGCGACAGGGTTAATAAC
CCTGTCGATTGACGTTACCCGCAGAAGAAGCACCGGCTAACTCCGTGCCAGCAGCCGCGGTAATACG
GAGGGTGCAAGCGTTAATCGGAATTACTGGGCGTAAAGCGCACGCAGGCGGTCTGTTAAGTCAGATG
TGAAATCCCCGGGCTTAACCTGGGAACTGCATTTGAAACTGGCAGGCTTTAGTCTTGTAGAGTGGGGT
AGAATTCCAGGTGTAGCGGTGAAATGCGTAGAGATGTGGAGGAACACCAGTGGCGAAGGCGGCTTTT
TGGTCTGTAACTGACGCTGAGGCGCGAAAGCGTGGGGAGCAAACAGGATTAGATACCCTGGTAGTCC
ACGCCGTAAACGATGAGTGCTAAGTGTT

47
DP47 16S rRNA
AGGGTGCAAGCGTTAATCGGAATTACTGGGCGTAAAGCGCGCGTAGGTGGTTTGTTAAGTTGAAT
GTGAAATCCCCGGGCTCAACCTGGGAACTGCATTTGAAACTGGCAAGCTAGAGTCTCGTAGAGGGGG
GTAGAATTCCAGGTGTAGCGGTGAAATGCGTAGAGATCTGGAGGAATACCGGTGGCGAAGGCGGCCC
CCTGGACGAAGACTGACGCTCAGGTGCGAAAGCGTGGGGAGCAAACAGGATTAGATACCCTGGTAGT
CCACGCCGTAAACGATGTCAACTAGCCGTTGGAAGCCTTGAGCTTTTAGTGGCGCAGCTAACGCATTA
AGTTGACCGCCTGGGGAGTACGGCCGCAAGGTTAAAACTCAAATGAATTGACGGGGGCCCGCACAAG
CGGTGGAGCATGTGGTTTAATTCGAAGCAACGCGAAGAACCTTACCAGGCCTTGACATCCAATGAAC
TTTCTAGAGATAGATTGGTGCCTTCGGGAACATTGAGACAGGTGCTGCATGGCTGTCGTCAGCTCGTG
TCGTGAGATGTTGGGTTAAGTCCCGCAACGAGCGCAACCCTTGTCCTGTGTTGCCAGCGCGTAATGGC
GGGGACTCGCAGGAGACTGCCGGGGTCAACTCGGAGGAAGGTGGGGATGACGTCAAATCATCATGC
CCCTTATGTCTTGGGCTTCACGCATGCTACAATGGCCGGTACAAAGGGCTGCAATACCGTGAGGTGGA
GCGAATCCCAAAAAGCCGGTCCCAGTTCGGATTGAGGTCTGCAACTCGACCTCATGAAGTCGGAGTC
GCTAGTAATCGCAGATCAGCAACGCTGCGGTGAATACGTTCCCGGGTCTTGTACACACCGCCCGTCAA
GTCATGAAAGTCGGTAACACCTGAAGCCGGTGGCCCAACCCTTGTGGAGGGAGCCGTCGAAGGTGGG
ATCGGTAATTAGGACTAAGT

48
DP48 16S rRNA
CATGGAGAGTTTGATCCTGGCTCAGGACGAACGCTGGCGGCGTGCCTAATACATGCAAGTCGAGC
GGACAGATGGGAGCTTGCTCCCTGATGTTAGCGGCGGACGGGTGAGTAACACGTGGGTAACCTGCCT
GTAAGACTGGGATAACTCCGGGAAACCGGGGCTAATACCGGATGCTTGATTGAACCGCATGGTTCAA
TTATAAAAGGTGGCTTTTAGCTACCACTTACAGATGGACCCGCGGCGCATTAGCTAGTTGGTGAGGTA
ACGGCTCACCAAGGCAACGATGCGTAGCCGACCTGAGAGGGTGATCGGCCACACTGGGACTGAGAC
ACGGCCCAGACTCCTACGGGAGGCAGCAGTAGGGAATCTTCCGCAATGGACGAAAGTCTGACGGAGC
AACGCCGCGTGAGTGATGAAGGTTTTCGGATCGTAAAACTCTGTTGTTAGGGAAGAACAAGTACCGT
TCGAATAGGGCGGTACCTTGACGGTACCTAACCAGAAAGCCACGGCTAACTACGTGCCAGCAGCCGC
GGTAATACGTAGGTGGCAAGCGTTGTCCGGAATTATTGGGCGTAAAGCGCGCGCAGGCGGTTTCTTA
AGTCTGATGTGAAAGCCCCCGGCTCAACCGGGGAGGGTCATTGGAAACTGGGGAACTTGAGTGCAGA
AGAGGAGAGTGGAATTCCACGTGTAGCGGTGAAATGCGTAGAGATGTGGAGGAACACCAGTGGCGA
AGGCGACTCTCTGGTCTGTAACTGACGCTGAGGCGCGAAAGCGTGGGGAGCGAACAGGATTAGATAC
CCTGGTAGTCCACGCCGTAAACGATGAGTGCTAAGTGTTAGAGGGTTTCCGCCCTTTAGTGCTGCAGC
AAACGCATTAAGCACTCCGCCTGGGGAGTACGGTCGCAAGACTGAAACTCAAAGGAATTGACGGGG
GCCCGCACAAGCGGTGGAGCATGTGGTTTAATTCGAAGCAACGCGAAGAACCTTACCAGGTCTTGAC
ATCCTCTGACAACCCTAGAGATAGGGCTTCCCCTTCGGGGGCAGAGTGACAGGTGGTGCATGGTTGTC
GTCAGCTCGTGTCGTGAGATGTTGGGTTAAGTCCCGCAACGAGCGCAACCCTTGATCTTAGTTGCCAG
CATTCAGTTGGGCACTCTAAGGTGACTGCCGGTGACAAACCGGAGGAAGGTGGGGATGACGTCAAAT
CATCATGCCCCTTATGACCTGGGCTACACACGTGCTACAATGGGCAGAACAAAGGGCAGCGAAGCCG
CGAGGCTAAGCCAATCCCACAAATCTGTTCTCAGTTCGGATCGCAGTCTGCAACTCGACTGCGTGAAG
CTGGAATCGCTAGTAATCGCGGATCAGCATGCCGCGGTGAATACGTTCCCGGGCCTTGTACACACCGC
CCGTCACACCACGAGAGTTTGTAACACCCGAAGTCGGTGAGGTAACCTTTTGGAGCCAGCCGCCGAA
GGTGGGACAGATGATTGGGGTGAAGTCGTAACAAGGTAGCCGTATCGGAAGGTGCGGCTGGATCACC
TCCTTT

49
DP49 16S rRNA
TATGGAGAGTTTGATCCTGGCTCAGGACGAACGCTGGCGGCGTGCCTAATACATGCAAGTCGAGC
GGACGTTTTTGAAGCTTGCTTCAAAAACGTTAGCGGCGGACGGGTGAGTAACACGTGGGCAACCTGC
CTTATCGACTGGGATAACTCCGGGAAACCGGGGCTAATACCGGATAATATCTAGCACCTCCTGGTGC
AAGATTAAAAGAGGGCCTTCGGGCTCTCACGGTGAGATGGGCCCGCGGCGCATTAGCTAGTTGGAGA
GGTAATGGCTCCCCAAGGCGACGATGCGTAGCCGACCTGAGAGGGTGATCGGCCACACTGGGACTGA
GACACGGCCCAGACTCCTACGGGAGGCAGCAGTAGGGAATCTTCCGCAATGGACGAAAGTCTGACGG
AGCAACGCCGCGTGAGTGATGAAGGGTTTCGGCTCGTAAAGCTCTGTTATGAGGGAAGAACACGTAC

-continued

| SEQUENCE LISTING Seq ID No. Description Sequence |
|---|

CGTTCGAATAGGGCGGTACCTTGACGGTACCTCATCAGAAAGCCACGGCTAACTACGTGCCAGCAGC
CGCGGTAATACGTAGGTGGCAAGCGTTGTCCGGAATTATTGGGCGTAAAGCGCGCGCAGGCGGCCTT
TTAAGTCTGATGTGAAATCTTGCGGCTCAACCGCAAGCGGTCATTGGAAACTGGGAGGCTTGAGTAC
AGAAGAGGAGAGTGGAATTCCACGTGTAGCGGTGAAATGCGTAGATATGTGGAGGAACACCAGTGG
CGAAGGCGACTCTCTGGTCTGTAACTGACGCTGAGGCGCGAAAGCGTGGGGAGCAAACAGGATTAGA
TACCCTGGTAGTCCACGCCGTAAACGATGAGTGCTAGGTGTTAGGGGTTTCGATGCCCGTAGTGCCGA
AGTTAACACATTAAGCACTCCGCCTGGGGAGTACGGCCGCAAGGCTGAAACTCAAAGGAATTGACGG
GGGCCCGCACAAGCAGTGGAGCATGTGGTTTAATTCGAAGCAACGCGAAGAACCTTACCAGGTCTTG
ACATCCTTTGACCACTCTGGAGACAGAGCTTCCCCTTCGGGGGCAAAGTGACAGGTGGTGCATGGTTG
TCGTCAGCTCGTGTCGTGAGATGTTGGGTTAAGTCCCGCAACGAGCGCAACCCTTGACCTTAGTTGCC
AGCATTTAGTTGGGCACTCTAAGGTGACTGCCGGTGACAAACCGGAGGAAGGTGGGGATGACGTCAA
ATCATCATGCCCCTTATGACCTGGGCTACACACGTGCTACAATGGATGGTACAAAGGGTTGCGAAGC
CGCGAGGTGAAGCCAATCCCATAAAGCCATTCTCAGTTCGGATTGTAGGCTGCAACTCGCCTGCATGA
AGCTGGAATTGCTAGTAATCGCGGATCAGCATGCCGCGGTGAATACGTTCCCGGGCCTTGTACACACC
GCCCGTCACACCACGAGAGTTTGTAACACCCGAAGTCGGTGAGGTAACCTTTTGGAGCCAGCCGCCG
AAGGTGGGACAGATGATTGGGGTGAAGTCGTAACAAGGTAGCCGTATCGGAAGGTGCGGCTGGATC
ACCTCCTTT

50
DP50 16S rRNA
TTGAAGAGTTTGATCATGGCTCAGATTGAACGCTGGCGGCAGGCCTAACACATGCAAGTCGAACG
GTAGCACAGAGAGCTTGCTCTTGGGTGACGAGTGGCGGACGGGTGAGTAATGTCTGGGAAACTGCCC
GATGGAGGGGGATAACTACTGGAAACGGTAGCTAATACCGCATAACGTCGCAAGACCAAAGTGGGG
GACCTTCGGGCCTCACACCATCGGATGTGCCCAGATGGGATTAGCTAGTAGGTGGGGTAATGGCTCA
CCTAGGCGACGATCCCTAGCTGGTCTGAGAGGATGACCAGCCACACTGGAACTGAGACACGGTCCAG
ACTCCTACGGGAGGCAGCAGTGGGGAATATTGCACAATGGGCGCAAGCCTGATGCAGCCATGCCGCG
TGTATGAAGAAGGCCTTCGGGTTGTAAAGTACTTTCAGCGAGGAGGAAGGCATTGTGGTTAATAACC
GCAGTGATTGACGTTACTCGCAGAAGAAGCACCGGCTAACTCCGTGCCAGCAGCCGCGGTAATACGG
AGGGTGCAAGCGTTAATCGGAATTACTGGGCGTAAAGCGCACGCAGGCGGTCTGTCAAGTCGGATGT
GAAATCCCCGGGCTCAACCTGGGAACTGCATTCGAAACTGGCAGGCTAGAGTCTTGTAGAGGGGGGT
AGAATTCCAGGTGTAGCGGTGAAATGCGTAGAGATCTGGAGGAATACCGGTGGCGAAGGCGGCCCCC
TGGACAAAGACTGACGCTCAGGTGCGAAAGCGTGGGGAGCAAACAGGATTAGATACCCTGGTAGTCC
ACGCCGTAAACGATGTCGACTTGGAGGTTGTGCCCTTGAGGCGTGGCTTCCGGAGCTAACGCGTTAA
GTCGACCGCCTGGGGAGTACGGCCGCAAGGTTAAAACTCAAATGAATTGACGGGGGCCCGCACAAGC
GGTGGAGCATGTGGTTTAATTCGATGCAACGCGAAGAACCTTACCTACTCTTGACATCCACGGAATTT
AGCAGAGATGCTTTAGTGCCTTCGGGAACCGTGAGACAGGTGCTGCATGGCTGTCGTCAGCTCGTGTT
GTGAAATGTTGGGTTAAGTCCCGCAACGAGCGCAACCCTTATCCTTTGTTGCCAGCGGTTCGGCCGGG
AACTCAAAGGAGACTGCCAGTGATAAACTGGAGGAAGGTGGGGATGACGTCAAGTCATCATGGCCCT
TACGAGTAGGGCTACACACGTGCTACAATGGCATATACAAAGAGAAGCGACCTCGCGAGAGCAAGC
GGACCTCATAAAGTATGTCGTAGTCCGGATCGGAGTCTGCAACTCGACTCCGTGAAGTCGGAATCGCT
AGTAATCGTAGATCAGAATGCTACGGTGAATACGTTCCCGGGCCTTGTACACACCGCCCGTCACACCA
TGGGAGTGGGTTGCAAAAGAAGTAGGTAGCTTAACCTTCGGGAGGGCGCTTACCACTTTGTGATTCAT
GACTGGGGTGAAGTCGTAACAAGGTAACCGTAGGGGAACCTGCGGTTGGATCACCTCCTT

51
DP51 16S rRNA
TTGAAGAGTTTGATCATGGCTCAGATTGAACGCTGGCGGCAGGCCTAACACATGCAAGTCGAGCG
GTAGCACAGGGAGCTTGCTCCTGGGTGACGAGCGGCGGACGGGTGAGTAATGTCTGGGAAACTGCCT
GATGGAGGGGGATAACTACTGGAAACGGTAGCTAATACCGCATAACGTCGCAAGACCAAAGAGGGG
GACCTTCGGGCCTCTTGCCATCAGATGTGCCCAGATGGGATTAGCTAGTAGGTGAGGTAATGGCTCAC
CTAGGCGACGATCCCTAGCTGGTCTGAGAGGATGACCAGCCACACTGGAACTGAGACACGGTCCAGA
CTCCTACGGGAGGCAGCAGTGGGGAATATTGCACAATGGGCGCAAGCCTGATGCAGCCATGCCGCGT
GTATGAAGAAGGCCTTCGGGTTGTAAAGTACTTTCAGCGAGGAGGAAGGCATTAAGGTTAATAACCT
TGGTGATTGACGTTACTCGCAGAAGAAGCACCGGCTAACTCCGTGCCAGCAGCCGCGGTAATACGGG
GGGTGCAAGCGTTAATCGGAATTACTGGGCGTAAAGCGCACGCAGGCGGTTTGTCAAGTCGGATGTG
AAATCCCCGGGCTCAACCTGGGAACTGCATTCGAAACGGGCAAGCTAGAGTCTTGTAGAGGGGGGTA
GAATTCCAGGTGTAGCGGTGAAATGCGTAGAGATCTGGAGGAATACCGGTGGCGAAGGCGGCCCCCT
GGACAAAGACTGACGCTCAGGTGCGAAAGCGTGGGGAGCAAACAGGATTAGATACCCTGGTAGTCC
ACGCCGTAAACGATGTCGACTTGGAGGTTGTGCCCTTGAGGCGTGGCTTCCGGAGCTAACGCGTTAA
GTCGACCGCCTGGGGAGTACGGCCGCAAGGTTAAAACTCAAATGAATTGACGGGGGCCCGCACAAGC
GGTGGAGCATGTGGTTTAATTCGATGCAACGCGAAGAACCTTACCTACTCTTGACATCCAGAGAACTT
TCCAGAGATGGATTGGTGCCTTCGGGAACTCTGAGACAGGTGCTGCATGGCTGTCGTCAGCTCGTGTT
GTGAAATGTTGGGTTAAGTCCCGCAACGAGCGCAACCCTTATCCTTTGTTGCCAGCGAGTAATGTCGG
GAACTCAAAGGAGACTGCCAGTGACAAACTGGAGGAAGGTGGGGATGACGTCAAGTCATCATGGCC
CTTACGAGTAGGGCTACACACGTGCTACAATGGCATATACAAAGAGAAGCGACCTCGCGAGAGCAAG
CGGACCTCACAAAGTATGTCGTAGTCCGGATCGGAGTCTGCAACTCGACTCCGTGAAGTCGGAATCG
CTAGTAATCGTAGATCAGAATGCTACGGTGAATACGTTCCCGGGCCTTGTACACACCGCCCGTCACAC
CATGGGAGTGGGTTGCAAAAGAAGTAGGTAGCTTAACCTTCGGGAGGGCGCTTACCACTTTGTGATT
CATGACTGGGGTGAAGTCGTAACAAGGTAACCGTAGGGGAACCTGCGGTTGGATCACCTCCTT

52
DP52 16S rRNA
ACGGAGAGTTTGATCCTGGCTCAGGATGAACGCTGGCGGCGTGCTTAACACATGCAAGTCGAACG
ATGATCCCAGCTTGCTGGGGGATTAGTGGCGAACGGGTGAGTAACACGTGAGTAACCTGCCCTTGAC

-continued

SEQUENCE LISTING
Seq ID No.
Description
Sequence

TCTGGGATAAGCCTGGGAAACTGGGTCTAATACCGGATATGACTGTCTGACGCATGTCAGGTGGTGG
AAAGCTTTTGTGGTTTTGGATGGACTCGCGGCCTATCAGCTTGTTGGTGGGGTAATGGCCTACCAAGG
CGACGACGGGTAGCCGGCCTGAGAGGGTGACCGGCCACACTGGGACTGAGACACGGCCCAGACTCCT
ACGGGAGGCAGCAGTGGGGAATATTGCACAATGGGCGCAAGCCTGATGCAGCGACGCCGCGTGAGG
GATGACGGCCTTCGGGTTGTAAACCTCTTTCAGTAGGGAAGAAGCGAAAGTGACGGTACCTGCAGAA
GAAGCGCCGGCTAACTACGTGCCAGCAGCCGCGGTAATACGTAGGGCGCAAGCGTTATCCGGAATTA
TTGGGCGTAAAGAGCTCGTAGGCGGTTTGTCGCGTCTGCTGTGAAAGACCGGGGCTCAACTCCGGTTC
TGCAGTGGGTACGGGCAGACTAGAGTGCAGTAGGGGAGACTGGAATTCCTGGTGTAGCGGTGAAATG
CGCAGATATCAGGAGGAACACCGATGGCGAAGGCAGGTCTCTGGGCTGTAACTGACGCTGAGGAGC
GAAAGCATGGGGAGCGAACAGGATTAGATACCCTGGTAGTCCATGCCGTAAACGTTGGGCACTAGGT
GTGGGGGACATTCCACGTTTTCCGCGCCGTAGCTAACGCATTAAGTGCCCCGCCTGGGGAGTACGGCC
GCAAGGCTAAAACTCAAAGGAATTGACGGGGGCCCGCACAAGCGGCGGAGCATGCGGATTAATTCG
ATGCAACGCGAAGAACCTTACCAAGGCTTGACATGAACCGGTAATACCTGGAAACAGGTGCCCCGCT
TGCGGTCGGTTTACAGGTGGTGCATGGTTGTCGTCAGCTCGTGTCGTGAGATGTTGGGTTAAGTCCCG
CAACGAGCGCAACCCTCGTTCTATGTTGCCAGCGCGTTATGGCGGGGACTCATAGGAGACTGCCGGG
GTCAACTCGGAGGAAGGTGGGGACGACGTCAAATCATCATGCCCCTTATGTCTTGGGCTTCACGCATG
CTACAATGGCCGGTACAAAGGGTTGCGATACTGTGAGGTGGAGCTAATCCCAAAAAGCCGGTCTCAG
TTCGGATTGGGGTCTGCAACTCGACCCCATGAAGTCGGAGTCGCTAGTAATCGCAGATCAGCAACGC
TGCGGTGAATACGTTCCCGGGCCTTGTACACACCGCCCGTCAAGTCACGAAAGTTGGTAACACCCGA
AGCCGGTGGCCTAACCCTTGTGGGGGGAGCCGTCGAAGGTGGGACCGGCGATTGGGACTAAGTCGTA
ACAAGGTAGCCGTACCGGAAGGTGCGGCTGGATCACCTCCTTT

53
DP53 16S rRNA
TGAAGAGTTTGATCATGGCTCAGATTGAACGCTGGCGGCAGGCCTAACACATGCAAGTCGAGCGG
TAGAGAGAAGCTTGCTTCTCTTGAGAGCGGCGGACGGGTGAGTAATACCTAGGAATCTGCCTGATAG
TGGGGGATAACGTTCGGAAACGGACGCTAATACCGCATACGTCCTACGGGAGAAAGCAGGGGACCTT
CGGGCCTTGCGCTATCAGATGAGCCTAGGTCGGATTAGCTAGTTGGTGAGGTAATGGCTCACCAAGG
CTACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGCAGTTACCTAATACGTGATTGT
CTGACGTTACCGACAGAATAAGCACCGGCTAACTCTGTGCCAGCAGCCGCGGTAATACAGAGGGTGC
AAGCGTTAATCGGAATTACTGGGCGTAAAGCGCGCGTAGGTGGTTTGTTAAGTTGAATGTGAAATCC
CCGGGCTCAACCTGGGAACTGCATCCAAAACTGGCAAGCTAGAGTATGGTAGAGGGTAGTGGAATTT
CCTGTGTAGCGGTGAAATGCGTAGATATAGGAAGGAACACCAGTGGCGAAGGCGACTACCTGGACTG
ATACTGACACTGAGGTGCGAAAGCGTGGGGAGCAAACAGGATTAGATACCCTGGTAGTCCACGCCGT
AAACGATGTCAACTAGCCGTTGGGAGTCTTGAACTCTTAGTGGCGCAGCTAACGCATTAAGTTGACCG
CCTGGGGAGTACGGCCGCAAGGTTAAAACTCAAATGAATTGACGGGGGCCCGCACAAGCGGTGGAG
CATGTGGTTTAATTCGAAGCAACGCGAAGAACCTTACCAGGCCTTGACATCCAATGAACTTTCTAGAG
ATAGATTGGTGCCTTCGGGAACATTGAGACAGGTGCTGCATGGCTGTCGTCAGCTCGTGTCGTGAGAT
GTTGGGTTAAGTCCCGTAACGAGCGCAACCCTTGTCCTTAGTTACCAGCACGTAATGGTGGGCACTCT
AAGGAGACTGCCGGTGACAAACCGGAGGAAGGTGGGGATGACGTCAAGTCATCATGGCCCTTACGG
CCTGGGCTACACACGTGCTACAATGGTCGGTACAAAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGTGAATCAGAATGTCACGGTGAATACGTTCCCGGGCCTTGTACACACCGCCCGTCACACCATG

54
DP54 16S rRNA
CTTGAGAGTTTGATCCTGGCTCAGAGCGAACGCTGGCGGCAGGCTTAACACATGCAAGTCGAGCG
GGCACCTTCGGGTGTCAGCGGCAGACGGGTGAGTAACACGTGGGAACGTACCCTTCGGTTCGGAATA
ACGCTGGGAAACTAGCGCTAATACCGGATACGCCCTTTTGGGGAAAGGTTTACTGCCGAAGGATCGG
CCCGCGTCTGATTAGCTAGTTGGTGGGGTAACGGCCTACCAAGGCGACGATCAGTAGCTGGTCTGAG
AGGATGATCAGCCACACTGGGACTGAGACACGGCCCAGACTCCTACGGGAGGCAGCAGTGGGGAAT
ATTGGACAATGGGCGCAAGCCTGATCCAGCCATGCCGCGTGAGTGATGAAGGCCTTAGGGTTGTAAA
GCTCTTTTGTCCGGGACGATAATGACGGTACCGGAAGAATAAGCCCCGGCTAACTTCGTGCCAGCAG
CCGCGGTAATACGAAGGGGGCTAGCGTTGCTCGGAATCACTGGGCGTAAAGGGCGCGTAGGCGGCCA
TTCAAGTCGGGGGTGAAAGCCTGTGGCTCAACCACAGAATTGCCTTCGATACTGTTTGGCTTGAGTTT
GGTAGAGGTTGGTGGAACTGCGAGTGTAGAGGTGAAATTCGTAGATATTCGCAAGAACACCAGTGGC
GAAGGCGGCCAACTGGACCAATACTGACGCTGAGGCGCGAAAGCGTGGGGAGCAAACAGGATTAGA
TACCCTGGTAGTCCACGCCGTAAACGATGAATGCTAGCTGTTGGGGTGCTTGCACCTCAGTAGCGCAG
CTAACGCTTTAAGCATTCCGCCTGGGGAGTACGGTCGCAAGATTAAAACTCAAAGGAATTGACGGGG
GCCCGCACAAGCGGTGGAGCATGTGGTTTAATTCGAAGCAACGCGCAGAACCTTACCATCCCTTGAC
ATGTCGTGCCATCCGGAGAGATCCGGGGTTCCCTTCGGGGACGCGAACACAGGTGCTGCATGGCTGT
CGTCAGCTCGTGTCGTGAGATGTTGGGTTAAGTCCCGCAACGAGCGCAACCCACGTCCTTAGTTGCCA
TCATTTAGTTGGGCACTCTAGGGAGACTGCCGGTGATAAGCCGCGAGGAAGGTGTGGATGACGTC

55
DP55 16S rRNA
TCGGAGAGTTTGATCCTGGCTCAGGATGAACGCTGGCGGCGTGCCTAATACATGCAAGTCGAGCG
AACTGATTAGAAGCTTGCTTCTATGACGTTAGCGGCGGACGGGTGAGTAACACGTGGGCAACCTGCC
TGTAAGACTGGGATAACTTCGGGAAACCGAACTAATACCGGATAGGATCTTCTCCTTCATGGGAGAT
GATTGAAAGATGGTTTCGGCTATCACTTACAGATGGGCCCGCGGTGCATTAGCTAGTTGGTGAGGTAA
CGGCTCACCAAGGCAACGATGCATAGCCGACCTGAGAGGGTGATCGGCCACACTGGGACTGAGACAC
GGCCCAGACTCCTACGGGAGGCAGCAGTAGGGAATCTTCCGCAATGGACGAAAGTCTGACGGAGCA

-continued

| SEQUENCE LISTING<br>Seq ID No.<br>Description<br>Sequence |
|---|

ACGCCGCGTGAGTGATGAAGGCTTTCGGGTCGTAAAACTCTGTTGTTAGGGAAGAACAAGTACAAGA
GTAACTGCTTGTACCTTGACGGTACCTAACCAGAAAGCCACGGCTAACTACGTGCCAGCAGCCGCGG
TAATACGTAGGTGGCAAGCGTTATCCGGAATTATTGGGCGTAAAGCGCGCGCAGGCGGTTTCTTAAG
TCTGATGTGAAAGCCCACGGCTCAACCGTGGAGGGTCATTGGAAACTGGGGAACTTGAGTGCAGAAG
AGAAAAGCGGAATTCCACGTGTAGCGGTGAAATGCGTAGAGATGTGGAGGAACACCAGTGGCGAAG
GCGGCTTTTTGGTCTGTAACTGACGCTGAGGCGCGAAAGCGTGGGGAGCAAACAGGATTAGATACCC
TGGTAGTCCACGCCGTAAACGATGAGTGCTAAGTGTTAGAGGGTTTCCGCCCTTTAGTGCTGCAGCTA
ACGCATTAAGCACTCCGCCTGGGGAGTACGGTCGCAAGACTGAAACTCAAAGGAATTGACGGGGGCC
CGCACAAGCGGTGGAGCATGTGGTTTAATTCGAAGCAACGCGAAGAACCTTACCAGGTCTTGACATC
CTCTGACAACTCTAGAGATAGAGCGTTCCCCTTCGGGGGACAGAGTGACAGGTGGTGCATGGTTGTC
GTCAGCTCGTGTCGTGAGATGTTGGGTTAAGTCCCGCAACGAGCGCAACCCTTGATCTTAGTTGCCAG
CATTTAGTTGGGCACTCTAAGGTGACTGCCGGTGACAAACCGGAGGAAGGTGGGGATGACGTCAAAT
CATCATGCCCCTTATGACCTGGGCTACACACGTGCTACAATGGATGGTACAAAGGGCTGCAAGACCG
CGAGGTCAAGCCAATCCCATAAAACCATTCTCAGTTCGGATTGTAGGCTGCAACTCGCCTACATGAAG
CTGGAATCGCTAGTAATCGCGGATCAGCATGCT

56
DP56 16S rRNA
ATTGGAGAGTTTGATCCTGGCTCAGGACGAACGCTGGCGGCGTGCCTAATACATGCAAGTCGAGC
GGACCTGATGGAGTGCTTGCACTCCTGATGGTTAGCGGCGGACGGGTGAGTAACACGTAGGCAACCT
GCCCTCAAGACTGGGATAACTACCGGAAACGGTAGCTAATACCGGATAATTTATTTCACAGCATTGTG
GAATAATGAAAGACGGAGCAATCTGTCACTTGGGGATGGGCCTGCGGCGCATTAGCTAGTTGGTGGG
GTAACGGCTCACCAAGGCGACGATGCGTAGCCGACCTGAGAGGGTGAACGGCCACACTGGGACTGA
GACACGGCCCAGACTCCTACGGGAGGCAGCAGTAGGGAATCTTCCGCAATGGGCGAAAGCCTGACG
GAGCAACGCCGCGTGAGTGATGAAGGTTTTCGGATCGTAAAGCTCTGTTGCCAAGGAAGAACGTCTT
CTAGAGTAACTGCTAGGAGAGTGACGGTACTTGAGAAGAAAGCCCCGGCTAACTACGTGCCAGCAGC
CGCGGTAATACGTAGGGGGCAAGCGTTGTCCGGAATTATTGGGCGTAAAGCGCGCGCAGGCGGTTCT
TTAAGTCTGGTGTTTAAACCCGAGGCTCAACTTCGGGTCGCACTGGAAACTGGGGAACTTGAGTGCA
GAAGAGGAGAGTGGAATTCCACGTGTAGCGGTGAAATGCGTAGATATGTGGAGGAACACCAGTGGC
GAAGGCGACTCTCTGGGCTGTAACTGACGCTGAGGCGCGAAAGCGTGGGGAGCAAACAGGATTAGA
TACCCTGGTAGTCCACGCCGTAAACGATGAATGCTAGGTGTTAGGGGTTTCGATACCCTTGGTGCCGA
AGTTAACACATTAAGCATTCCGCCTGGGGAGTACGGTCGCAAGACTGAAACTCAAAGGAATTGACGG
GGACCCGCACAAGCAGTGGAGTATGTGGTTTAATTCGAAGCAACGCGAAGAACCTTACCAAGTCTTG
ACATCCCTCTGAATCCTCTAGAGATAGAGGCGGCCTTCGGGACAGAGGTGACAGGTGGTGCATGGTT
GTCGTCAGCTCGTGTCGTGAGATGTTGGGTTAAGTCCCGCAACGAGCGCAACCCTTGATTTTAGTTGC
CAGCACATCATGGTGGGCACTCTAGAATGACTGCCGGTGACAAACCGGAGGAAGGCGGGGATGACG
TCAAATCATCATGCCCCTTATGACTTGGGCTACACACGTACTACAATGGCTGGTACAACGGGAAGCG
AAGCCGCGAGGTGGAGCCAATCCTATAAAAGCCAGTCTCAGTTCGGATTGCAGGCTGCAACTCGCCT
GCATGAAGTCGGAATTGCTAGTAATCGCGGATCAGCATGCCGCGGTGAATACGTTCCCGGGTCTTGTA
CACACCGCCCGTCACACCACGAGAGTTTACAACACCCGAAGTCGGTGGGGTAACCCGCAAGGGAGCC
AGCCGCCGAAGGTGGGGTAGATGATTGGGGTGAAGTCGTAACAAGGTAGCCGTATCGGAAGGTGCG
GCTGGATCACCTCCTTT

57
DP57 16S rRNA
ATTGGAGAGTTTGATCCTGGCTCAGGATGAACGCTGGCGGCGTGCCTAATACATGCAAGTCGAGC
GAATGGATTAAGAGCTTGCTCTTATGAAGTTAGCGGCGGACGGGTGAGTAACACGTGGGTAACCTGC
CCATAAGACTGGGATAACTCCGGGAAACCGGGGCTAATACCGGATAACATTTTGCACCGCATGGTGC
GAAATTCAAAGGCGGCTTCGGCTGTCACTTATGGATGGACCCGCGTCGCATTAGCTAGTTGGTGAGGT
AACGGCTCACCAAGGCAACGATGCGTAGCCGACCTGAGAGGGTGATCGGCCACACTGGGACTGAGA
CACGGCCCAGACTCCTACGGGAGGCAGCAGTAGGGAATCTTCCGCAATGGACGAAAGTCTGACGGAG
CAACGCCGCGTGAGTGATGAAGGCTTTCGGGTCGTAAAACTCTGTTGTTAGGGAAGAACAAGTGCTA
GTTGAATAAGCTGGCACCTTGACGGTACCTAACCAGAAAGCCACGGCTAACTACGTGCCAGCAGCCG
CGGTAATACGTAGGTGGCAAGCGTTATCCGGAATTATTGGGCGTAAAGCGCGCGCAGGTGGTTTCTT
AAGTCTGATGTGAAAGCCCACGGCTCAACCGTGGAGGGTCATTGGAAACTGGGAGACTTGAGTGCAG
AAGAGGAAAGTGGAATTCCATGTGTAGCGGTGAAATGCGTAGAGATATGGAGGAACACCAGTGGCG
AAGGCGACTTTCTGGTCTGTAACTGACACTGAGGCGCGAAAGCGTGGGGAGCAAACAGGATTAGATA
CCCTGGTAGTCCACGCCGTAAACGATGAGTGCTAAGTGTTAGAGGGTTTCCGCCCTTTAGTGCTGAAG
TTAACGCATTAAGCACTCCGCCTGGGGAGTACGGCCGCAAGGCTGAAACTCAAAGGAATTGACGGGG
GCCCGCACAAGCGGTGGAGCATGTGGTTTAATTCGAAGCAACGCGAAGAACCTTACCAGGTCTTGAC
ATCCTCTGACAACCCTAGAGATAGGGCTTCCCCTTCGGGGGCAGAGTGACAGGTGGTGCATGGTTGTC
GTCAGCTCGTGTCGTGAGATGTTGGGTTAAGTCCCGCAACGAGCGCAACCCTTGATCTTAGTTGCCAT
CATTAAGTTGGGCACTCTAAGGTGACTGCCGGTGACAAACCGGAGGAAGGTGGGGATGACGTCAAAT
CATCATGCCCCTTATGACCTGGGCTACACACGTGCTACAATGGACGGTACAAAGAGCTGCAAGACCG
CGAGGTGGAGCTAATCTCATAAAACCGTTCTCAGTTCGGATTGTAGGCTGCAACTCGCCTACATGAAG
CTGGAATCGCTAGTAATCGCGGATCAGCATGCCGCGGTGAATACGTTCCCGGGCCTTGTACACACCGC
CCGTCACACCACGAGAGTTTGTAACACCCGAAGTCGGTGGGGTAACCTTTTTGGAGCCAGCCGCCTA
AGGTGGGACAGATGATTGGGGTGAAGTCGTAACAAGGTAGCCGTATCGGAAGGTGCGGCTGGATCAC
CTCCTTT

58
DP58 16S rRNA
AATGACGGTACCTGAAGAATAAGCACCGGCTAACTACGTGCCAGCAGCCGCGGTAATACGTAGGG
TGCAAGCGTTAATCGGAATTACTGGGCGTAAAGCGTGCGCAGGCGGTTTTGTAAGTCTGATGTGAAA

-continued

| SEQUENCE LISTING<br>Seq ID No.<br>Description<br>Sequence |
|---|

TCCCCGGGCTCAACCTGGGAATTGCATTGGAGACTGCAAGGCTAGAATCTGGCAGAGGGGGGTAGAA
TTCCACGTGTAGCAGTGAAATGCGTAGATATGTGGAGGAACACCGATGGCGAAGGCAGCCCCCTGGG
TCAAGATTGACGCTCATGCACGAAAGCGTGGGGAGCAAACAGGATTAGATACCCTGGTAGTCCACGC
CCTAAACGATGTCTACTAGTTGTCGGGTCTTAATTGACTTGGTAACGCAGCTAACGCGTGAAGTAGAC
CGCCTGGGGAGTACGGTCGCAAGATTAAAACTCAAAGGAATTGACGGGGACCCGCACAAGCGGTGG
ATGATGTGGATTAATTCGATGCAACGCGAAAAACCTTACCTACCCTTGACATGGCTGGAATCCTCGAG
AGATTGGGGAGTGCTCGAAAGAGAACCAGTACACAGGTGCTGCATGGCTGTCGTCAGCTCGTGTCGT
GAGATGTTGGGTTAAGTCCCGCAACGAGCGCAACCCTTGTCATTAGTTGCTACGAAAGGGCACTCTA
ATGAGACTGCCGGTGACAAACCGGAGGAAGGTGGGGATGACGTCAAGTCCTCATGGCCCTTATGGGT
AGGGCTTCACACGTCATACAATGGTACATACAGAGCGCCGCCAACCCGCGAGGGGGAGCTAATCGCA
GAAAGTGTATCGTAGTCCGGATTGTAGTCTGCAACTCGACTGCATGAAGTTGGAATCGCTAGTAATCG
CGGATCAGCATGTCGCGGTGAATACGTTCCCGGGTCTTGTACACACCGCCCGTCACACCATGGGAGC
GGGTTTTACCAGAAGTAGGTAGCTTAACCGTAAGGAGGGCGCTTACCACGGTAGGATTCGTGACTGG
GGTGAAGTCGTAACAAGGTAGCCGTATCGGAAGGTGCGGCTGGATCACCTCCTTT

59
DP59 16S rRNA
TTGAAGAGTTTGATCATGGCTCAGATTGAACGCTGGCGGCAGGCCTAACACATGCAAGTCGAACG
GTAACAGGAAGCAGCTTGCTGCTTTGCTGACGAGTGGCGGACGGGTGAGTAATGTCTGGGAAACTGC
CTGATGGAGGGGGATAACTACTGGAAACGGTAGCTAATACCGCATAACGTCGCAAGACCAAAGAGG
GGGACCTTCGGGCCTCTTGCCATCAGATGTGCCCAGATGGGATTAGCTAGTAGGTGGGGTAACGGCT
CACCTAGGCGACGATCCCTAGCTGGTCTGAGAGGATGACCAGCCACACTGGAACTGAGACACGGTCC
AGACTCCTACGGGAGGCAGCAGTGGGGAATATTGCACAATGGGCGCAAGCCTGATGCAGCCATGCCG
CGTGTATGAAGAAGGCCTTCGGGTTGTAAAGTACTTTCAGCGGGGAGGAAGGCGATGCGGTTAATAA
CCGCGTCGATTGACGTTACCCGCAGAAGAAGCACCGGCTAACTCCGTGCCAGCAGCCGCGGTAATAC
GGAGGGTGCAAGCGTTAATCGGAATTACTGGGCGTAAAGCGCACGCAGGCGGTCTGTCAAGTCGGAT
GTGAAATCCCCGGGCTCAACCTGGGAACTGCATCCGAAACTGGCAGGCTTGAGTCTCGTAGAGGGGG
GTAGAATTCCAGGTGTAGCGGTGAAATGCGTAGAGATCTGGAGGAATACCGGTGGCGAAGGCGGCCC
CCTGGACGAAGACTGACGCTCAGGTGCGAAAGCGTGGGGAGCAAACAGGATTAGATACCCTGGTAGT
CCACGCCGTAAACGATGTCGACTTGGAGGTTGTGCCCTTGAGGCGTGGCTTCCGGAGCTAACGCGTTA
AGTCGACCGCCTGGGGAGTACGGCCGCAAGGTTAAAACTCAAATGAATTGACGGGGGCCCGCACAA
GCGGTGGAGCATGTGGTTTAATTCGATGCAACGCGAAGAACCTTACCTGGTCTTGACATCCACAGAA
CTTGGCAGAGATGCCTTGGTGCCTTCGGGAACTGTGAGACAGGTGCTGCATGGCTGTCGTCAGCTCGT
GTTGTGAAATGTTGGGTTAAGTCCCGCAACGAGCGCAACCCTTATCCTTTGTTGCCAGCGGTTAGGCC
GGGAACTCAAAGGAGACTGCCAGTGATAAACTGGAGGAAGGTGGGGATGACGTCAAGTCATCATGG
CCCTTACGACCAGGGCTACACACGTGCTACAATGGCGCATACAAAGAGAAGCGATCTCGCGAGAGCC
AGCGGACCTCATAAAGTGCGTCGTAGTCCGGATTGGAGTCTGCAACTCGACTCCATGAAGTCGGAAT
CGCTAGTAATCGTGAATCAGAATGTCACGGTGAATACGTTCCCGGGCCTTGTACACACCGCCCGTCAC
ACCATGGGAGTGGGTTGCAAAAGAAGTAGGTAGCTTAACCTTCGGGAGGGCGCTTACCACTTTGTGA
TTCATGACTGGGGTGAAGTCGTAACAAGGTAACCGTAGGGGAACCTGCGGTTGGATCACCTCCTT

60
DP60 16S
rRNATCGGAGAGTTTGATCCTGGCTCAGGACGAACGCTGGCGGCGTGCCTAATACATGCAAGTCGAGC
GAATCGATGGGAGCTTGCTCCCTGAGATTAGCGGCGGACGGGTGAGTAACACGTGGGCAACCTGCCT
ATAAGACTGGGATAACTTCGGGAAACCGGAGCTAATACCGGATACGTTCTTTTCTCGCATGAGAGAA
GATGGAAAGACGGTTTTGCTGTCACTTATAGATGGGCCCGCGGCGCATTAGCTAGTTGGTGAGGTAAT
GGCTCACCAAGGCGACGATGCGTAGCCGACCTGAGAGGGTGATCGGCCACACTGGGACTGAGACAC
GGCCCAGACTCCTACGGGAGGCAGCAGTAGGGAATCTTCCGCAATGGACGAAAGTCTGACGGAGCA
ACGCCGCGTGAACGAAGAAGGCCTTCGGGTCGTAAAGTTCTGTTGTTAGGGAAGAACAAGTACCAGA
GTAACTGCTGGTACCTTGACGGTACCTAACCAGAAAGCCACGGCTAACTACGTGCCAGCAGCCGCGG
TAATACGTAGGTGGCAAGCGTTGTCCGGAATTATTGGGCGTAAAGCGCGCGCAGGTGGTTCCTTAAG
TCTGATGTGAAAGCCCACGGCTCAACCGTGGAGGGTCATTGGAAACTGGGGAACTTGAGTGCAGAAG
AGGAAAGTGGAATTCCAAGTGTAGCGGTGAAATGCGTAGAGATTTGGAGGAACACCAGTGGCGAAG
GCGACTTTCTGGTCTGTAACTGACACTGAGGCGCGAAAGCGTGGGGAGCAAACAGGATTAGATACCC
TGGTAGTCCACGCCGTAAACGATGAGTGCTAAGTGTTAGAGGGTTTCCGCCCTTTAGTGCTGCAGCTA
ACGCATTAAGCACTCCGCCTGGGGAGTACGGCCGCAAGGCTGAAACTCAAAGGAATTGACGGGGGCC
CGCACAAGCGGTGGAGCATGTGGTTTAATTCGAAGCAACGCGAAGAACCTTACCAGGTCTTGACATC
CTCTGACAACCCTAGAGATAGGGCGTTCCCCTTCGGGGGACAGAGTGACAGGTGGTGCATGGTTGTC
GTCAGCTCGTGTCGTGAGATGTTGGGTTAAGTCCCGCAACGAGCGCAACCCTTGATCTTAGTTGCCAG
CATTCAGTTGGGCACTCTAAGGTGACTGCCGGTGACAAACCGGAGGAAGGTGGGGATGACGTCAAAT
CATCATGCCCCTTATGACCTGGGCTACACACGTGCTACAATGGATGGTACAAAGGGCTGCAAACCTG
CGAAGGTAAGCGAATCCCATAAAGCCATTCTCAGTTCGGATTGTAGGCTGCAACTCGCCTACATGAA
GCCGGAATCGCTAGTAATCGCGGATCAGCATGCCGCGGTGAATACGTTCCCGGGCCTTGTACACACC
GCCCGTCACACCACGAGAGTTTGTAACACCCGAAGTCGGTGAGGTAACCTTTATGGAGCCAGCCGCC
TAAGGTGGGACAGATGATTGGGGTGAAGTCGTAACAAGGTAGCCGTATCGGAAGGTGCGGCTGGATC
ACCTCCTTT

61
DP61 16S rRNA
GGAAGGCGGTCTGTCAAGTCGGATGTGAAATCCCCGGGCTCAACCTGGGAACTGCATTCGAAACT
GGCAGGCTAGAGTCTTGTAGAGGGGGGTAGAATTCCAGGTGTAGCGGTGAAATGCGTAGAGATCTGG
AGGAATACCGGTGGCGAAGGCGGCCCCCTGGACAAAGACTGACGCTCAGGTGCGAAAGCGTGGGGA
GCAAACAGGATTAGATACCCTGGTAGTCCACGCCGTAAACGATGTCGACTTGGAGGTTGTTCCCTTGA

-continued

| SEQUENCE LISTING Seq ID No. Description Sequence |
| --- |

GGAGTGGCTTCCGGAGCTAACGCGTTAAGTCGACCGCCTGGGGAGTACGGCCGCAAGGTTAAAACTC
AAATGAATTGACGGGGGCCCGCACAAGCGGTGGAGCATGTGGTTTAATTCGATGCAACGCGAAGAAC
CTTACCTACTCTTGACATCCACGGAATTTAGCAGAGATGCTTTAGTGCCTTCGGGAACCGTGAGACAG
GTGCTGCATGGCTGTCGTCAGCTCGTGTTGTGAAATGTTGGGTTAAGTCCCGCAACGAGCGCAACCCT
TATCCTTTGTTGCCAGCGGTCCGGCCGGGAACTCAAAGGAGACTGCCAGTGATAAACTGGAGGAAGG
TGGGGATGACGTCAAGTCATCATGGCCCTTACGAGTAGGGCTACACACGTGCTACAATGGCGCATAC
AAAGAGAAGCGACCTCGCGAGAGCAAGCGGACCTCATAAAGTGCGTCGTAGTCCGGATCGGAGTCTG
CAACTCGACTCCGTGAAGTCGGAATCGCTAGTAATCGTAGATCAGAATGCTACGGTGAATACGTTCCC
GGGCCTTGTACACACCGCCCGTCACACCATGGGAGTGGGTTGCAAAAGAAGTAGGTAGCTTAACCTT
CGGGAGGGCGCTTACCACTTTGTGATTCATGACTGGGGTGAAGTCGTAACAAGGTAACCGTAGGGGA
ACCTGCGGTTGGATCACCTCCTT

62
DP62 16S rRNA
TGGCTCAGATTGAACGCTGGCGGCAGGCCTAACACATGCAAGTCGAACGGTAGCACAGAGGAGCT
TGCTCCTTGGGTGACGAGTGGCGGACGGGTGAGTAATGTCTGGGAAACTGCCCGATGGAGGGGGATA
ACTACTGGAAACGGTAGCTAATACCGCATAACGTCTTCGGACCAAAGTGGGGGACCTTCGGGCCTCA
CACCATCGGATGTGCCCAGATGGGATTAGCTAGTAGGTGGGGTAATGGCTCACCTAGGCGACGATCC
CTAGCTGGTCTGAGAGGATGACCAGCCACACTGGAACTGAGACACGGTCCAGACTCCTACGGGAGGC
AGCAGTGGGGAATATTGCACAATGGGCGCAAGCCTGATGCAGCCATGCCGCGTGTATGAAGAAGGCC
TTCGGGTTGTAAAGTACTTTCAGTGGGGAGGAAGGCGTTAAGGTTAATAACCTTGGCGATTGACGTTA
CCCGCAGAAGAAGCACCGGCTAACTCCGTGCCAGCAGCCGCGGTAATACGGAGGGTGCAAGCGTTAA
TCGGAATTACTGGGCGTAAAGCGCACGCAGGCGGTCTGTCAAGTCGGATGTGAAATCCCCGGGCTCA
ACCTGGGAACTGCATTCGAAACTGGCAGGCTAGAGTCTTGTAGAGGGGGGTAGAATTCCAGGTGTAG
CGGTGAAATGCGTAGAGATCTGGAGGAATACCGGTGGCGAAGGCGGCCCCCTGGACAAAGACTGAC
GCTCAGGTGCGAAAGCGTGGGGAGCAAACAGGATTAGATACCCTGGTAGTCCACGCCGTAAACGATG
TCGACTTGGAGGTTGTTCCCTTGAGGAGTGGCTTCCGGAGCTAACGCGTTAAGTCGACCGCCTGGGGA
GTACGG

63
DP63 16S rRNA
TGAAGAGTTTGATCATGGCTCAGATTGAACGCTGGCGGCAGGCCTAACACATGCAAGTCGAGCGG
TAGAGAGAAGCTTGCTTCTCTTGAGAGCGGCGGACGGGTGAGTAATGCCTAGGAATCTGCCTGGTAG
TGGGGGATAACGTTCGGAAACGGACGCTAATACCGCATACGTCCTACGGGAGAAAGCAGGGGACCTT
CGGGCCTTGCGCTATCAGATGAGCCTAGGTCGGATTAGCTAGTTGGTGAGGTAATGGCTCACCAAGG
CGACGATCCGTAACTGGTCTGAGAGGATGATCAGTCACACTGGAACTGAGACACGGTCCAGACTCCT
ACGGGAGGCAGCAGTGGGGAATATTGGACAATGGGCGAAAGCCTGATCCAGCCATGCCGCGTGTGTG
AAGAAGGTCTTCGGATTGTAAAGCACTTTAAGTTGGGAGGAAGGGTTGTAGATTAATACTCTGCAATT
TTGACGTTACCGACAGAATAAGCACCGGCTAACTCTGTGCCAGCAGCCGCGGTAATACAGAGGGTGC
AAGCGTTAATCGGAATTACTGGGCGTAAAGCGCGCGTAGGTGGTTTGTTAAGTTGGATGTGAAATCC
CCGGGCTCAACCTGGGAACTGCATTCAAAACTGACTGACTAGAGTATGGTAGAGGGTGGTGGAATTT
CCTGTGTAGCGGTGAAATGCGTAGATATAGGAAGGAACACCAGTGGCGAAGGCGACCACCTGGACTA
ATACTGACACTGAGGTGCGAAAGCGTGGGGAGCAAACAGGATTAGATACCCTGGTAGTCCACGCCGT
AAACGATGTCAACTAGCCGTTGGAAGCCTTGAGCTTTTAGTGGCGCAGCTAACGCATTAAGTTGACCG
CCTGGGGAGTACGGCCGCAAGGTTAAAACTCAAATGAATTGACGGGGGCCCGCACAAGCGGTGGAG
CATGTGGTTTAATTCGAAGCAACGCGAAGAACCTTACCAGGCCTTGACATCCAATGAACTTTCTAGAG
ATAGATTGGTGCCTTCGGGAACATTGAGACAGGTGCTGCATGGCTGTCGTCAGCTCGTGTCGTGAGAT
GTTGGGTTAAGTCCCGTAACGAGCGCAACCCTTGTTCTTAGTTACCAGCACGTTATGGTGGGCACTCT
AAGGAGACTGCCGGTGACAAACCGGAGGAAGGTGGGGATGACGTCAAGTCATCATGGCCCTTACGG
CCTGGGCTACACACGTGCTACAATGGTCGGTACAGAGGGTTGCCAAGCCGCGAGGTGGAGCTAATCC
CATAAAACCGATCGTAGTCCGGATCGCAGTCTGCAACTCGACTGCGTGAAGTCGGAATCGCTAGTAA
TCGCGAATCAGAATGTCGCGGTGAATACGTTCCCGGGCCTTGTACACACCGCCCGTCACACCATGGG
AGTGGGTTGCACCAGAAGTAGCTAGTCTAACCTTCGGGAGGACGGTTACCACGGTGTGATTCATGAC
TGGGGTGAAGTCGTAACAAGGTAGCCGTAGGGGAACCTGCGGCTGGATCACCTCCTT

64
DP64 ITS sequence
TCCGTAGGTGAACCTGCGGAAGGATCATTAAATAATCAATAATTTTGGCTTGTCCATTATTATCTAT
TTACTGTGAACTGTATTATTACTTGACGCTTGAGGGATGCTCCACTGCTATAAGGATAGGCGGTGGGG
ATGTTAACCGAGTCATAGTCAAGCTTAGGCTTGGTATCCTATTATTATTTACCAAAAGAATTCAGAAT
TAATATTGTAACATAGACCTAAAAAATCTATAAAACAACTTTTAACAACGGATCTCTTGGTTCTCGCA
TCGATGAAGAACGTAGCAAAGTGCGATAACTAGTGTGAATTGCATATTCAGTGAATCATCGAGTCTTT
GAACGCAACTTGCGCTCATTGGTATTCCAATGAGCACGCCTGTTTCAGTATCAAAACAAACCCTCTAT
TCAATATTTTTGTTGAATAGGAATACTGAGAGTCTCTTGATCTTTTCTGATCTCGAACCTCTTGAAATG
TACAAAGGCCTGATCTTGTTTGAATGCCTGAACTTTTTTTTAATATAAAGAGAAGCTCTTGCGGTAAA
CTGTGCTGGGGCCTCCCAAATAATACTCTTTTTAAATTTGATCTGAAATCAGGCGGGATTACCCGCTG
AACTTAAGCATATCAATAAGCGGAGGAAAAGAAAATAACAATGATTTCCCTAGTAACGGCGAGTGAA
GAGGAAAGAGCTCAAAGTTGGAAACTGTTTGGCTTAGCTAAACCGTATTGTAAACTGTAGAAACATT
TTCCTGGCACGCCGGATTAATAAGTCCTTTGGAACAAGGCATCATGGAGGGTGAGAATCCCGTCTTTG
ATCCGAGTAGTTGTCTTTTGTGATATGTTTTCAAAGAGTCAGGTTGTTTGGGAATGCAGCCTAAATTG
GGTGGTAAATCTCACCTAAAGCTAAATATTTGCGAGAGACCGATAGCGAACAAGTACCGTGAGGGAA
AGATGAAAAGAACTTTGAAAAGAGAGTTAAACAGTATGTGAAATTGTTAAAAGGGAACCGTTTGGAG
CCAGACTGGTTTGACTGTAATCAACCTAGAATTCGTTCTGGGTGCACTTGCAGTCTATACCTGCCAAC
AACAGTTTGATTTGGAGGAAAAAATTAGTAGGAATGTAGCCTCTCGAGGTGTTATAGCCTACTATCAT -continued

| SEQUENCE LISTING<br>Seq ID No.<br>Description<br>Sequence |
|---|

ACTCTGGATTGGACTGAGGAACGCAGCGAATGCCATTAGGCGAGATTGCTGGGTGCTTTCGCTAATA
AATGTTAGAATTTCTGCTTCGGGTGGTGCTAATGTTTAAAGGAGGAACACATCTAGTATATTTTTTATT
CGCTTAGGTTGTTGGCTTAATGACTCTAAATGACCCGTCTTGAAACACGGACCAAGGAGTCCACCATA
AGTGCAAGTATTTGAGTGACAAACTCATATGCGTAAGGAAACTGATTGATACGAAATCTTTTGATGGC
AGTATCACCCGGCGTTGACGTTTTATACTGAACTGACCGAGGTAAAGCACTTATGATGGGACCCGAA
AGATGGTGAACTATGCCTGAATAGGGTGAAGCCAGAGGAAACTCTGGTGGAGGCTCGTAGCGATTCT
GACGTGCAAATCGATCGTCAAATTTGGGTATAGGGGCGAAAGACTAATCGAACCATCTAGTAGCTGG
TTCCTGCCGAAGTTTCCCTCAGGA

65
DP65 ITS sequence
TCCGTAGGTGAACCTGCGGAAGGATCATTATTGAAAACAAGGGTGTCCAATTTAACTTGGAACCC
GAACTTCTCAATTCTAACTTTGTGCATCTGTATTATGGCGAGCAGTCTTCGGATTGTGAGCCTTCACTT
ATAAACACTAGTCTATGAATGTAAAATTTTTATAACAAATAAAAACTTTCAACAACGGATCTCTTGGC
TCTCGCATCGATGAAGAACGCAGCGAAATGCGATACGTAATGTGAATTGCAGAATTCAGTGAATCAT
CGAATCTTTGAACGCATCTTGCGCTCTCTGGTATTCCGGAGAGCATGTCTGTTTGAGTGTCATGAATTC
TTCAACCCAATCTTTTCTTGTAATCGATTGGTGTTTGGATTTTGAGCGCTGCTGGCTTCGGCCTAGCTC
GTTCGTAATACATTAGCATCCCTAATACAAGTTTGGATTGACTTGGCGTAATAGACTATTCGCTAAGG
ATTCGGTGGAAACATCGAGCCAACTTCATTAAGGAAGCTCCTAATTTAAAAGTCTACCTTTTGATTAG
ATCTCAAATCAGGCAGGATTACCCGCTGAACTTAAGCATATCAATAAGCGGAGGAAAAGAAACTAAC
AAGGATTCCCCTAGTAGCGGCGAGCGAAGCGGGAAAAGCTCAAATTTGTAATCTGGCGTCTTCGACG
TCCGAGTTGTAATCTCGAGAAGTGTTTTCCGTGATAGACCGCATACAAGTCTCTTGGAACAGAGCGTC
ATAGTGGTGAGAACCCAGTACACGATGCGGATGCCTATTACTTTGTGATACACTTTCGAAGAGTCGAG
TTGTTTGGGAATGCAGCTCAAATTGGGTGGTAAATTCCATCTAAAGCTAAATATTGGCGAGAGACCG
ATAGCGAACAAGTACCGTAAGGGAAAGATGAAAAGCACTTTGGAAAGAGAGTTAACAGTACGTGAA
ATTGTTGGAAGGGAAACACATGCAGTGATACTTGCTATTCGGGGCAACTCGATTGGCAGGCCCGCAT
CAGTTTTTCGGGGCGGAAAAGCGTAGAGAGAAGGTAGCAATTTCGGTTGTGTTATAGCTCTTTACTGG
ATTCGCCCTGGGGGACTGAGGAACGCAGCGTGCTTTTAGCAATTCCTTCGGGAATTCCACGCTTAGGA
TGCGGGTTTATGGCTGTATATGACCCGTCTTGAAACACGGACCAAGGAGTCTAACATGCTTGCGAGTA
TTTGGGTGTCAAACCCGGATGCGCAATGAAAGTGAATGGAGGTGGGAAGCGCAAGCTGCACCATCGA
CCGATCTGGATTTTTTAAGATGGATTTGAGTAAGAGCAAGTATGTTGGGACCCGAAAGATGGTGAAC
TATGCCTGAATAGGGCGAAGCCAGAGGAAACTCTGGTGGAGGCTCGTAGCGGTTCTGACGTGCAAAT
CGATCGTCAAATTTGGGTATAGGGGCGAAAGACTAATCGAACCATCTAGTAGCTGGTTCCTGCCGAA
GTTTCCCTCAGGA 66
DP66 ITS sequence
TCCGTAGGTGAACCTGCGGAAGGATCATTACTGTGATTTATCCACCACACTGCGTGGGCGACACGA
AACACCGAAACCGAACGCACGCCGTCAAGCAAGAAATCCACAAAACTTTCAACAACGGATCTCTTGG
TTCTCGCATCGATGAAGAGCGCAGCGAAATGCGATACCTAGTGTGAATTGCAGCCATCGTGAATCAT
CGAGTTCTTGAACGCACATTGCGCCCGCTGGTATTCCGGCGGGCATGCCTGTCTGAGCGTCGTTTCCT
TCTTGGAGCGGAGCTTCAGACCTGGCGGGCTGTCTTTCGGGACGGCGCGCCCAAAGCGAGGGGCCTT
CTGCGCGAACTAGACTGTGCGCGCGGGGCGGCCGGCGAACTTATACCAAGCTCGACCTCAGATCAGG
CAGGAGTACCCGCTGAACTTAAGCATATCAATAAGCGGAGGAAAAGAAACCAACAGGGATTGCCCC
AGTAGCGGCGAGTGAAGCGGCAAAAGCTCAGATTTGGAATCGCTTCGGCGAGTTGTGAATTGCAGGT
TGGCGCCTCTGCGGCGGCGGCGGTCCAAGTCCCTTGGAACAGGGCGCCATTGAGGGTGAGAGCCCCG
TGGGACCGTTTGCCTATGCTCTGAGGCCCTTCTGACGAGTCGAGTTGTTTGGGAATGCAGCTCTAAGC
GGGTGGTAAATTCCATCTAAGGCTAAATACTGGCGAGAGACCGATAGCGAACAAGTACTGTGAAGGA
AAGATGAAAAGCACTTTGAAAAGAGAGTGAAACAGCACGTGAAATTGTTGAAAGGGAAGGGTATTG
CGCCCGACATGGAGCGTGCGCACCGCTGCCCCTCGTGGGCGGCGCTCTGGGCGTGCTCTGGGCCAGC
ATCGGTTTTTGCCGCGGGAGAAGGGCGGCGGGCATGTAGCTCTTCGGAGTGTTATAGCCTGCCGCCG
GCGCCGCGAGCGGGGACCGAGGACTGCGACTTTTGTCTCGGATGCTGGCACAACGGCGCAACACCGC
CCGTCTTGAAACATGGACCAAGGAGTCTAACGTCTATGCGAGTGTTTGGGTGTGAAACCCCGGGCGC
GTAATGAAAGTGAACGTAGGTCGGACCGCTCCTCTCGGGGGGCGGGCACGATCGACCGATCCTGATG
TCTTCGGATGGATTTGAGTAAGAGCATAGCTGTTGGGACCCGAAAGATGGTGAACTATGCCTGAATA
GGGTGAAGCCAGAGGAAACTCTGGTGGAGGCTCGTAGCGGTTCTGACGTGCAAATCGATCGTCGAAT
TTGGGTATAGGGGCGAAAGACTAATCGAACCATCTAGTAGCTGGTTCCTGCCGAAGTTTCCCTCAGGA 67
DP53 Glutamine--tRNA ligase
ATGAGCAAGCCCACTGTCGACCCCACTCTGAATCCAAAGGCTGGCCCTGCTGTCCCGGCTAACTTC
CTGCGTCCAATCGTTCAGGCGGACCTAGACTCGGGTAAATACACACAGATCGTGACCCGCTTTCCGCC
GGAGCCAAACGGCTATCTGCACATCGGTCATGCCAAATCCATTTGTGTGAACTTTGGGCTGGCTCAAG
AGTTTGGCGGCGTGACGCATTTGCGTTTTGACGACACCAACCCGGCAAAAGAAGACCAGGAATACAT
CGACGCCATCGAAAGCGACGTCAAGTGGCTGGGCTTCGAGTGGGCCGGTGAAGTGCGTTACGCGTCG
CAATACTTCGATCAACTGCACGAGTGGGCGATTTACCTGATCAAAGAAGGCAAGGCCTACGTCTGCG
ACCTGACGCCCGAGCAAGCCAAGGAATACCGTGGCAGCCTGACCGAGCCCGGCAAGAACAGCCCGTT
CCGCGACCGTAGCGTTGAAGAGAACCTGGATCTGTTCGCCCGCATGACCGCCGGTGAGTTTGAAGAC
GGCAAGCGTGTGCTGCGCGCCAAGATCGACATGACCTCGCCGAACATGAACCTGCGCGACCCGATCA
TGTACCGCATCCGTCATGCCCATCACCACCAGACCGGTGACAAGTGGTGCATCTACCCCAACTATGAC
TTCACCCACGGTCAGTCGGATGCCATTGAAGGCATCACCCATTCGATCTGCACCCTGGAGTTCGAAAG
CCATCGTCCGCTGTACGAATGGTTCCTGGACAGCCTGCCAGTACCGGCGCGCCCGCGTCAGTACGAGT
TCAGCCGTCTGAACCTCAACTACACCATCACCAGCAAGCGCAAGCTCAAGCAGCTGGTCGATGAAAA
GCACGTCAACGGCTGGGATGACCCGCGCATGTCGACGCTGTCGGGTTTCCGCCGTCGCGGTTACACGC -continued

| SEQUENCE LISTING Seq ID No. Description Sequence |
|---|

CTAAATCGATTCGTAATTTCTGTGACATGGTCGGCACCAACCGTTCTGACGGTGTTGTTGACTTCGGC
ATGCTGGAATTCAGCATTCGTGACGATTTGGACCACAGCGCGCCGCGCGCCATGTGCGTGCTGCGTCC
ATTGAAGGTGATTATTACCAACTACCCGGAAGGTCAGGTCGAAAACCTCGAGCTGCCTTGCCACCCG
AAAGAAGACATGGGTGTGCGGGTGTTGCCGTTTGCCCGTGAAATCTACATCGACCGTGAAGACTTCA
TGGAAGAGCCGCCAAAAGGCTACAAGCGTCTTGAGCCTGCGGGCGAAGTGCGTTTGCGCGGCAGCTA
TGTGATCCGTGCCGACGAAGCGATCAAGGATGCCGATGGCAACATCGTTGAACTGCATTGCTCGTAC
GATCCGCTGACCCTGGGTAAAACCCTGAAGGTCGCAAGGTCAAGGGTGTTGTGCACTGGGTGCCGG
CGGCGGCCAGCGTCGAATGCGAAGTGCGTTTGTATGATCGTCTGTTCCGCTCGCCGAACCCTGAAAAG
GCCGAAGACGGCGCGGGCTTCCTGGAAAACATCAACCCTGACTCGCTGCAGGTACTGACCGGTTGTC
GTGCTGAACCCTCGCTGGGCAATGCACAGCCGGAAGACCGTTTCCAGTTCGAGCGCGAAGGCTACTT
CTGCGCAGATATCAAGGACTCGAAACCCGGTCACCCGGTATTCAACCGTACCGTGACCCTGCGTGATT
CGTGGGGCCAGTGA

68
DP53 DNA gyrase subunit B
TTGAGCGAAGAAAACACGTACGACTCAACGAGCATTAAAGTGCTGAAAGGCCTTGATGCCGTACG
CAAACGTCCCGGTATGTACATTGGTGATACTGACGATGGCAGCGGTCTGCACCACATGGTGTTCGAA
GTAGTCGACAACTCCATCGACGAAGCGCTGGCTGGCCATTGCGACGACATCACCATCACGATCCACC
CGGACGAGTCCATCACCGTGCGCGATAACGGCCGCGGTATTCCGGTTGACGTGCATAAAGAAGAAGG
CGTATCTGCAGCCGAGGTCATCATGACCGTGCTGCACGCCGGCGGTAAGTTCGATGACAACTCCTACA
AAGTATCCGGCGGCTTGCACGGTGTAGGTGTTTCGGTGGTAAACGCCCTGTCCGAACTGCTGGTCTTG
ACTGTACGCCGCAGCGGCAAGATCTGGGAACAGACCTACGTCCACGGTGTTCCTCAGGCGCCTATGG
CTATTGTGGGTGAAAGCGAAACCACGGGTACGCAGATCCACTTCAAGCCTTCGGCTGAAACCTTCAA
GAATATCCACTTTAGCTGGGACATCCTGGCCAAGCGGATTCGTGAACTGTCCTTCCTGAACTCCGGTG
TGGGTATCGTCCTCAAGGACGAGCGCAGCGGCAAGGAGGAGCTGTTCAAGTACGAAGGTGGCCTGCG
TGCATTCGTTGATTACCTGAACACCAACAAGAACGCTGTGAACCAGGTGTTCCACTTCAATGTTCAGC
GTGAAGACGGCATCGGCGTAGAAATCGCCCTGCAGTGGAACGACAGCTTCAACGAGAACCTGTTGTG
CTTCACCAACAACATTCCACAGCGCGATGGTGGCACGCACTTGGTGGGCTTCCGCTCTGCCCTGACGC
GTAACCTCAACACGTACATCGAAGCTGAAGGCCTGGCCAAGAAGCACAAGGTCGCCACCACCGGTGA
TGACGCCCGTGAAGGCTTGACCGCGATCATCTCGGTGAAAGTGCCGGATCCAAAGTTCAGCTCGCAG
ACTAAAGACAAGCTGGTGTCTTCCGAAGTGAAGACCGCTGTTGAACAGGAAATGGGCAAGTTCTTCT
CCGACTTCCTGCTGGAACACCCGAACGAAGCCAAGTTGATTGTCGGCAAGATGATCGACGCAGCCCG
TGCTCGTGAAGCTGCACGTAAAGCCCGTGAGATGACCCGTCGTAAAGGCGCGTTGGACATCGCGGGC
TTGCCGGGCAAGCTGGCTGACTGCCAGGAAAAAGACCCTGCTCTGTCCGAACTGTACCTGGTGGAAG
GTGACTCTGCTGGCGGCTCCGCCAAGCAGGGTCGCAACCGTCGTACCCAAGCCATCCTGCCGTTGAA
AGGTAAAATCCTCAACGTCGAGAAAGCCCGTTTTGACAAGATGATCTCTTCGCAAGAAGTCGGCACC
TTGATCACTGCGCTGGGCTGTGGCATCGGCCGCGAAGAGTACAACATCGACAAACTGCGCTATCACA
ACATCATCATCATGACCGATGCTGACGTTGACGGTTCGCACATCCGTACCCTGCTGCTGACCTTCTTCT
TCCGTCAGTTGCCGGAGCTGATCGAGCGTGGCTACATCTACATCGCCCAGCCACCGTTGTACAAAGTG
AAAAAGGGCAAGCAAGAGCAGTACATCAAAGACGACGAGGCCATGGAAGAGTACATGACCCAGTCG
GCTCTTGAAGATGCCAGCCTGCACTTGAACGAAGATGCCCCTGGCATCTCCGGTGAGGCACTGGAGC
GTCTGGTGTACGACTTCCGCATGGTGATGAAGACCCTCAAGCGTTTGTCGCGCCTGTACCCTCAGGAG
CTGACCGAGCACTTCATCTACCTGCCGGCTGTAAGCCTTGAGCAGTTGGGTGACCACGCTGCCATGCA
GGACTGGATGGCCAAGTTTGAAGAGCGTCTGCGTCTGGTTGAGAAATCGGGCCTGGTCTACAAAGCC
AGCCTGCGTGAAGACCGTGAGCGTAATGTCTGGTTGCCAGAGGTCGAACTGATCTCCCACGGCCACT
CGACGTTCATCACCTTCAACCGCGACTTCTTCGGCAGCAACGATTACAAAACCGTTGTGACCCTGGGC
GCTCAACTGAGCACCCTGCTGGATGAAGGCGCCTATATCCAGCGTGGCGAACGTCGCAAGCAAGTGA
CCGAGTTCAAAGAAGCACTGGACTGGTTGATGGCTGAAAGCACCAAGCGTCACACCATCCAGCGCTA
CAAAGGACTGGGTGAAATGAACCCGGATCAGCTCTGGGAAACCACGATGGACCCAAGCGTGCGTCGC
ATGCTGAAAGTCACCATCGAAGACGCGATCGGCGCCGATCAGATCTTCAACACCTTGATGGGCGATG
CTGTAGAACCACGTCGTGAATTCATCGAGAGCAACGCACTGGCAGTGTCCAACCTGGATTTCTGA 69
DP53 Isoleucine--tRNA ligase
ATGACCGACTACAAAGCCACGCTAAACCTCCCGGACACCGCCTTCCCAATGAAGGCCGGCCTGCC
ACAGCGCGAACCGCAAATTTTGCAGCGCTGGGACAGCATTGGCCTGTACGGGAAGTTGCGCGAGATT
GGCAAGGATCGTCCGAAGTTCGTACTTCACGACGGTCCTCCGTACGCCAACGGCACTATCCATATCGG
TCATGCGCTGAACAAGATTCTGAAAGACATGATCATCCGCTCCAAGACCCTGTCGGGTTTTGACGCGC
CGTATGTGCCGGGCTGGGATTGCCATGGTTTGCCGATTGAACACAAGGTCGAAGTGACCCACGGTAA
AAACCTGAGCGCGGATAAAACCCGCGAGCTGTGCCGTGCCTACGCCACCGAGCAGATCGAGGGGCA
GAAGTCCGAGTTCATCCGTCTGGGTGTGCTGGGTGATTTCGCCAACCCGTACAAGACCATGGACTTCA
AAAACGAAGCCGGTGAAATCCGTGCTTTGGCTGAGATCGTCAAGGGCGGTTTTGTGTTCAAGGGCCT
CAAGCCGGTGAACTGGTGCTTCGATTGCGGTTCGGCCCTGGCTGAAGCTGAAGTTGAATACCAGGAC
AAGAAGTCTGCGGCCATCGACGTTGCCTTCCCGGTTGCCGACGAGGCCAAGCTGGCCGAGGCCTTTG
GTCTGGCGGCACTGAGCAAACCTGCTTCGATCGTGATCTGGACCACCACCCCGTGGACCATTCCGGCC
AACCAGGCGCTTAACGTACACCCGGAATTCACCTACGCGCTGGTCGACGTGGGCGACAAGTTGCTGG
TACTGGCTGAAGAACTGGTCGAATCGAGTCTGGCGCGTTACAACCTGCAGGGTTCGGTCATCGCCACC
ACCACTGGCTCAGCGCTTGAACTAATCAACTTCCGTCACCCGTTCTATGACCGTCTGTCGCCTGTTTAT
CTGGCCGACTACGTTGAGCTGGGTGCTGGCACTGGTGTGGTTCACTCGGCTCCAGCCTACGGCGTAGA
CGACTTCGTGACCTGCAAAGCCTATGGCATGGTCAACGACGACATCATCAACCCGGTGCAAAGCAAT
GGCGTTTACGTGCCGTCGCTGGAGTTCTTCGGTGGCCAGTTCATCTGGAAGGCCAACCAGAACATCAT
CGACAAGCTGATCGAAGTCGGTTCGCTGATGTTCACCGAGACCATCAGCCACAGCTATATGCACTGCT
GGCGCCACAAGACGCCGCTGATCTACCGTGCCACCGCCCAGTGGTTTATCGGTATGGACAAGCAGCC
GACTGATGGCGATACCTTGCGCACCCGTGCGCTGCAAGCGATCGAAGACACCCAGTTCGTTCCGGCCT -continued

| SEQUENCE LISTING Seq ID No. Description Sequence |
|---|

GGGGTCAGGCGCGCCTGCACTCGATGATCGCCAACCGCCCGGACTGGTGCATCTCGCGTCAACGCAA
CTGGGGCGTGCCGATCCCGTTTTTCCTGAACAAGGAAAGCGGCGAGCTGCACCCGCGCACCGTCGAA
ATGATGGAAGAAGTGGCCAAGCGCGTTGAAGTCGAAGGCATCGAGGCGTGGTTCAAGCTGGATGCTG
CCGAGCTGCTGGGCGACGAAGCGCCGCTGTACGACAAGATCAGCGATACCCTCGACGTCTGGTTCGA
TTCGGGCACCACGCACTGGCATGTCCTTCGCGGTTCGCACCCGATGGGTCATGAAACCGGCCCACGCG
CTGATCTCTACCTTGAAGGCTCCGACCAGCACCGTGGCTGGTTCCACTCGTCGTTGCTGACCGGTTGC
GCCATCGACAACCACGCGCCGTACCGCGAGCTGCTGACCCACGGTTTTACCGTGGACGAAGCGGGCC
GCAAGATGTCCAAGTCGCTGGGCAACGTGATTGCACCGCAAAAGGTCAACGACACCCTGGGCGCCGA
CATCATGCGTCTGTGGGTTGCTTCGACCGACTACTCGGGCGAAATCGCGGTTTCCGACCAGATCCTGC
AGCGCAGTGCGGACGCCTACCGACGTATCCGCAATACCGCACGCTTCCTGCTGTCGAACCTGACCGGT
TTCAATCCAGCCACCGACATCCTGCCTGCCGAAGAAATGCTGGCACTGGACCGCTGGGCGGTGGATC
GTGCGTTGCTGCTGCAACGTGAGCTGGAGCTGCATTACGGCGAATACCGTTTCTGGAACGTGTACTCC
AAGGTGCACAACTTCTGCGTTCAGGAGCTGGGCGGTTTCTATCTCGACATCATCAAGGACCGCCAGTA
CACCACCGGCGCCAACAGCAAGGCTCGCCGTTCGTGCCAGACCGCGCTGTTCCACATCTCTGAAGCG
CTGGTGCGCTGGATCGCTCCGATCCTGGCGTTCACCGCTGATGAGTTGTGGCAGTACCTGCCGGGCGA
GCGCAACGAATCGGTCATGCTCAACACCTGGTACGAAGGCCTGACTGAACTGCCGGAAGGCACCGAA
CTGGATCGCGCCTACTGGGAGCGAATCATGGCGGTCAAGGTTGCGGTCAACAAGGAAATGGAAAACT
TGCGCGCAGCCAAGGCCATTGGCGGTAACTTGCAAGCAGAAGTGACCTTGTTCGCCGAAGATCAGCT
GGCTGCTGATTTGTCCAAGTTGAGCAACGAACTGCGTTTCGTGTTGATCACCTCCACTGCCAGCGTTG
CGCCTTTTGCGCAGGCTCCAGCAGATGCCGTGGTTACCGAAGTGGCTGGCCTCAAACTCAAGGTGGTC
AAGTCGGCCCATGCCAAGTGCGCCCGTTGCTGGCACTGCCGTGAAGACGTCGGCGTTAACCCCGAGC
ACCCTGAAATCTGCGGTCGTTGTGTAGACAATATCAGCGGCGCTGGTGAGGTACGTCACTATGCCTAA

70
DP53 NADH-quinone oxidoreductase subunit C/D
ATGACTGCAGGCTCCGCTCTGTACATCCCGCCTTACAAGGCTGACGACCAAGATGTGGTTGTCGAA
CTCAATACCCGTTTTGGCCCTGAGGCGTTCACCGCCCAGGCCACGCGCACCGGCATGCCGGTGCTTTG
GGTTAGCCGCGCAAAACTGGTCGAAGTACTGACCTTCCTGCGCAACCTGCCAAAACCCTACGTCATGC
TCTATGACCTGCACGGTGTGGACGAACGTCTGCGTACCAAGCGTCAGGGCCTGCCATCGGGTGCAGA
CTTCACCGTCTTCTACCACCTGATGTCGCTGGAACGTAACAGCGACGTCATGATCAAGGTGGCCCTGT
CTGAAAAAGACCTGAGTGTCCCTACCGTGACCGGTATCTGGCCGAACGCCAACTGGTACGAGCGTGA
AGTCTGGGACATGTTCGGCATCGATTTCAAAGGCCACCCGCACCTGTCGCGCATCATGATGCCGCCGA
CCTGGGAAGGTCACCCGCTGCGCAAGGACTTCCCGGCCCGTGCCACAGAGTTCGATCCGTACAGCCT
GACCCTGGCCAAGGTGCAGCTGGAAGAGGAAGCCGCGCGCTTCCGCCCGGAAGACTGGGGCATGAA
ACGCTCCGGTGAAAACGAGGACTACATGTTCCTCAACCTGGGCCCTAACCACCCTTCGGCTCACGGTG
CCTTCCGCATCATCCTGCAGCTGGACGGTGAAGAGATCGTCGACTGCGTGCCTGACGTCGGTTACCAC
CACCGTGGCGCCGAGAAAATGGCCGAACGCCAGTCCTGGCACAGTTTCATCCCGTACACCGACCGGA
TCGATTACCTCGGCGGAGTGATGAACAACCTGCCGTACGTGCTCTCGGTCGAGAAGCTGGCCGGTATC
AAAGTGCCGGATCGGGTCGACACCATCCGCATCATGATGGCCGAATTCTTCCGTATCACCAGCCACCT
GCTGTTCCTGGGTACCTATATCCAGGACGTGGGCGCCATGACCCCGGTGTTCTTCACGTTCACCGACC
GTCAGCGCGCTTACAAGGTGATCGAGGCCATCACCGGTTTCCGTCTGCACCCGGCCTGGTACCGCATC
GGCGGCGTTGCCCACGACCTGCCGAACGGCTGGGATCGCCTGGTCAAGGAATTCATCGACTGGATGC
CCAAGCGTCTGGACGAGTACCAGAAAGCCGCTCTGGACAACAGCATCCTGCGTGGTCGTACCATCGG
CGTTGCCGCCTACAACACCAAAGAGGCCCTGGAATGGGGCGTCACCGGTGCCGGCCTGCGCTCCACC
GGTTGTGACTTCGATATCCGCAAGGCGCGCCCGTATTCCGGCTACGAGAACTTCGAATTCGAAGTCCC
GCTGGCAGCCAACGGCGATGCCTACGATCGTTGCATCGTGCGCGTCGAAGAAATGCGCCAGAGCCTG
AAAATCATCGAGCAGTGCATGCGCAACATGCCGGCCGGCCCGTACAAGGCGGATCACCCGCTGACCA
CGCCGCCGCCTAAAGAACGCACGCTGCAGCATATCGAGACCTTGATCACGCACTTCCTGCAAGTTTCG
TGGGGCCCGGTGATGCCGGCCAACGAATCCTTCCAGATGATCGAAGCGACCAAGGGCATCAACAGTT
ATTACCTGACGAGCGATGGCGGCACCATGAGCTACCGCACCCGGATTCGCACCCCAAGCTTCCCGCA
CCTGCAACAGATCCCTTCGGTGATCAAAGGTGAAATGGTCGCGGACTTGATTGCGTACCTGGGTAGTA
TCGATTTCGTTATGGCCGACGTGGACCGCTAA 71
DP53 Protein RecA
ATGGACGACAACAAGAAGAAAGCCTTGGCTGCGGCCCTGGGTCAGATCGAACGTCAATTCGGCAA
GGGTGCCGTGATGCTGATGGGCGACCAGGAGCGTCAGGCAGTCCCGGCGATCTCCACCGGCTCCCTG
GGTCTGGACATCGCACTGGGCATTGGCGGTCTGCCAAAAGGCCGTATTGTTGAAATCTACGGCCCTGA
GTCGTCGGGTAAAACCACACTGACCCTGTCCGTGATTGCCCAGGCGCAAAAGGCCGGTGCTACCTGC
GCCTTCGTCGATGCCGAGCACGCCCTTGATCCTGAGTACGCTGCCAAACTGGGCGTAAACGTTGATGA
CCTGCTGGTTTCACAGCCTGACACCGGCGAACAGGCACTGGAAATCACCGATATGCTGGTGCGTTCCA
ATGCGGTTGACGTGATCATCATCGACTCCGTTGCTGCACTGACGCCAAAAGCTGAAATCGAAGGCGA
CATGGGCGATACCCACGTTGGCCTGCAAGCCCGTCTGATGTCGCAAGCGCTGCGTAAAATCACCGGT
AACATCAAGAACGCCAACTGCCTGGTTATCTTCATCAACCAGATCCGCATGAAAATCGGCGTGATGTT
CGGCAGCCCTGAAACCACCACCGGTGGTAACGCACTGAAGTTCTACGCTTCGGTACGTCTGGATATCC
GCCGCACCGGCGCCGTAAAAGAAGGCGATGTGGTGGTGGGTAGCGAAACCCGCGTGAAAGTGGTCA
AGAACAAGGTGGCACCACCGTTCCGTCAGGCTGAATTCCAGATCCTGTACGGCAAGGGTATCTACCT
GAACGGTGAAATGATTGACCTGGGCGTACTGCATGGCTTTGTTGAAAAAGCTGGCGCCTGGTACAGC
TACAACGGCAGCAAAATCGGTCAGGGCAAGGCCAACTCCGCCAAGTTCCTGGACGATAACCCGGACA
TCAAGGATGCGCTGGAGAAGCAGCTGCGTGAGAAGTTGCTCGGGCCAAAAACCGATGCCGAACTGGC
AGCGACGGACTGCAATGGACCTGCTCGCGCGACGCGAGCACGGTCGAGTCGAGCTGACGCGCAAGTT
GCGTCAGCGCGGCGCTTGCCCCGACATGATCGACGCTGCCCTTGA -continued

| SEQUENCE LISTING Seq ID No. Description Sequence |
|---|

72
DP53 RNA polymerase sigma factor RpoD
ATGTCCGGAAAAGCGCAACAGCAGTCTCGTATCAAAGAGTTGATCACCCTCGGCCGTGAGCAGAA
GTATCTGACTTACGCAGAGGTCAACGACCACCTGCCCGAAGATATTTCAGATCCGGAGCAAGTGGAA
GACATCATCCGCATGATTAATGACATGGGGATCCCCGTACACGAGAGTGCTCCGGATGCGGACGCCC
TTATGTTGGCCGATGCCGACACCGACGAAGCAGCAGCTGAAGAAGCGGCTGCAGCGTTGGCGGCAGT
AGAGACCGACATTGGTCGTACTACCGACCCTGTGCGCATGTATATGCGTGAAATGGGCACGGTAGAA
CTGCTGACACGTGAAGGCGAAATCGAAATCGCCAAGCGTATCGAAGAAGGCATCCGTGAAGTGATGG
GCGCAATCGCGCACTTCCCTGGCACGGTTGACCATATTCTCTCCGAGTACACTCGCGTCACCACCGAA
GGTGGCCGCCTGTCCGACGTTCTGAGCGGTTATATCGACCCGGACGACGGTATTGCGCCGCCCGCAGC
CGAAGTACCTCCTCCTGTCGACACCAAGGTGAAAGCCGAAGGTGATGACGAAGAGGACGACAAGGA
AGATTCCGGCGAAGACGAGGAAGAGGTCGAAAGCGGCCCTGATCCGATCATCGCGGCCCAGCGCTTT
GGCGCTGTTTTCGATCAGATGGAAATCGCTCGCAAGGCCCTGAAAAAGCACGGTCGCGGCAGCAAGC
AGGCAATTGCCGAGCTGGTTGCACTGGCTGAGCTGTTCATGCCGATCAAACTGGTTCCGAAGCAATTC
GAAGGCCTGGTTGAGCGTGTTCGCAGCGCCCTGGAGCGTCTGCGTGCACAAGAGCGCGCAATCATGC
AGCTGTGTGTACGTGATGCACGCATGCCGCGCACCGATTTCCTGCGTCTGTTCCCGGGCAACGAAGTC
GACGAAAGCTGGAGCGATGCGCTGGCCAAAGGCAAAAGCAAATATGCTGAAGCCATTGGTCGCCTGC
AACCGGACATCATCCGTTGCCAGCAAAAGCTCTCTGCTCTGGAAGCAGAAACCGGCTTGAAGATTGC
CGAGATCAAGGACATCAACCGTCGCATGTCGATCGGCGAGGCCAAGGCCCGCCGCGCGAAGAAAGA
AATGGTTGAAGCCAACTTGCGTCTGGTGATCTCCATCGCCAAGAAGTACACCAACCGTGGCCTGCAGT
TCCTCGATCTGATCCAGGAAGGCAACATCGGCTTGATGAAAGCGGTAGACAAGTTTGAATACCGCCG
CGGCTACAAATTCTCGACTTATGCCACCTGGTGGATCCGTCAGGCGATCACTCGCTCGATCGCCGACC
AGGCCCGCACCATCCGTATTCCGGTGCACATGATCGAGACGATCAACAAGCTCAACCGTATTTCCCGT
CAGATGTTGCAGGAAATGGGCCGTGAACCGACCCCGGAAGAGCTGGGCGAACGCATGGAAATGCCT
GAGGATAAAATCCGCAAGGTATTGAAGATCGCTAAAGAGCCGATCTCCATGGAAACCCCGATCGGTG
ATGACGAAGACTCCCATCTGGGTGACTTCATCGAAGACTCGACCATGCAGTCGCCAATCGATGTTGCT
ACCGTTGAGAGCCTTAAAGAAGCGACACGCGACGTACTCGGCGGCCTCACAGCCCGTGAAGCCAAGG
TACTGCGCATGCGTTTCGGTATCGACATGAATACCGACCACACCCTTGAGGAGGTTGGTAAACAGTTC
GACGTTACCCGTGAGCGGATTCGTCAGATCGAAGCCAAGGCGCTGCGCAAGCTGCGCCACCCGACGA
GAAGCGAGCATTTGCGCTCCTTCCTCGACGAGTGA 73
DP53 DNA-directed RNA polymerase subunit beta
ATGGCTTACTCATATACTGAGAAAAAACGTATCCGCAAGGACTTTAGCAAGTTGCCGGACGTCATG
GATGTGCCGTATCTCTTGGCAATCCAGCTGGATTCGTATCGTGAATTCTTGCAGGCGGGAGCGACTAA
AGATCAGTTCCGCGACGTGGGCCTGCATGCGGCCTTCAAATCCGTTTTCCCGATCATCAGCTACTCCG
GCAATGCTGCGCTGGAGTACGTCGGTTATCGCTTGGGCGAACCGGCATTTGATGTCAAAGAATGCGT
GTTGCGTGGCGTAACGTACGCCGTACCTTTGCGGGTAAAAGTTCGTTTGATCATTTTCGACAAAGAAT
CGTCGAACAAAGCGATCAAGGACATCAAAGAGCAAGAAGTCTACATGGGTGAAATCCCCCTGATGAC
TGAAAACGGTACCTTCGTAATCAACGGTACCGAGCGTGTAATTGTTTCCCAGCTGCACCGTTCCCCGG
GCGTGTTCTTTGCCACGACCGCGGCAAGACGCACAGCTCCGGTAAGCTGCTTTATTCCGCGCGTATCA
TTCCTTACCGTGGTTCGTGGCTCGACTTCGAGTTCGACCCGAAAGACTGCGTGTTCGTGCGTATTGAC
CGTCGTCGCAAGCTGCCTGCATCGGTATTGCTGCGCGCGCTGGGTTATACCACTGAGCAAGTGCTGGA
CGCGTTCTACACCACCAACGTGTTCCACGTTCAGGGTGAGAGCATCAGCCTGGAGCTGGTTCCACAGC
GTCTGCGCGGTGAAATCGCGGCCATCGACATTACCGATGACAAAGGCAAGGTGATTGTTGAGCAGGG
TCGTCGTATCACTGCTCGTCATATCAACCAGCTGGAAAAAGCCGGTGTCAAAGAGCTCGTTATGCCTC
TGGACTATGTCCTGGGTCGCACAACGGCCAAGGCTATCGTGCATCCGGCTACTGGCGAAATCATTGCT
GAGTGCAACACCGAGCTGACCACTGAAATCCTGGCAAAAGTTGCCAAGGGCCAGGTTGTTCGCATCG
AAACGTTGTACACCAACGATATCGACTGCGGTCCGTTCGTCTCCGACACGCTGAAGATCGACTCCACC
AGCAACCAACTGGAAGCGCTGGTCGAAATCTATCGCATGATGCGTCCAGGCGAGCCGCCAACCAAAG
ACGCTGCCGAGACTCTGTTCAACAACCTGTTCTTCAGCCCTGAGCGCTATGACCTGTCTGCGGTCGGC
CGGATGAAGTTCAACCGTCGTATCGGTCGTACCGAGATCGAAGGTTCGGGCGTGTTGTGCAAAGAAG
ACATCGTTGCCGTGCTGAAGACCCTGGTCGACATCCGTAACGGTAAAGGCATCGTCGATGACATCGA
CCACCTGGGTAACCGTCGTGTTCGCTGTGTAGGCGAAATGGCCGAGAACCAGTTCCGCGTTGGCCTGG
TACGTGTTGAGCGTGCGGTCAAAGAGCGTCTGTCGATGGCTGAAAGCGAAGGCCTGATGCCGCAAGA
CCTGATCAACGCCAAGCCTGTGGCTGCGGCGGTGAAAGAGTTCTTCGGTTCCAGCCAGCTGTCCCAGT
TCATGGACCAGAACAACCCTCTGTCCGAGATCACCCACAAGCGCCGTGTTTCTGCACTGGGCCCGGGC
GGTCTGACGCGTGAGCGTGCGGGCTTTGAAGTTCGTGACGTACACCCGACTCACTACGGCCGTGTTTG
CCCTATTGAGACGCCGGAAGGTCCGAACATCGGTCTGATCAACTCCCTGGCTGCCTATGCGCGCACCA
ACCAGTACGGCTTCCTCGAGAGCCCGTACCGTGTAGTGAAAGACGCACTGGTAACTGACGAGATCGT
TTTCCTGTCCGCCATCGAAGAAGCTGATCACGTGATCGCTCAGGCCTCGGCCACGATGAACGACAAG
AAAGTGCTGATCGACGAGCTGGTTGCTGTTCGTCACTTGAACGAATTCACCGTCAAGGCGCCGGAAG
ACGTCACCTTGATGGACGTTTCGCCGAAGCAGGTTGTTTCGGTTGCAGCGTCGCTGATCCCGTTCCTG
GAACACGATGACGCCAACCGTGCGTTGATGGGTTCCAACATGCAGCGTCAAGCTGTACCAACCCTGC
GCGCTGACAAGCCGCTGGTAGGTACCGGCATGGAGCGTAACGTAGCTCGTGACTCCGGCGTTTGCGT
CGTGGCTCGTCGTGGCGGCGTGATCGACTCTGTTGATGCCAGCCGTATCGTGGTTCGTGTTGCTGATG
ACGAAGTTGAAACTGGCGAAGCCGGTGTCGACATCTACAACCTGACCAAATACACCCGTTCCAACCA
GAACACTTGCATCAACCAGCGTCCGCTGGTGCGCAAGGGTGACCGTGTACAGCGTAGCGACATCATG
GCTGACGGCCCGTCCACCGATATGGGTGAACTGGCGCTGGGTCAAAACATGCGCATCGCGTTCATGG
CCTGGAACGGTTACAACTTCGAAGACTCCATCTGCTTGTCGGAACGAGTTGTTCAAGAAGACCGCTTT
ACCACGATCCACATTCAGGAACTGACCTGTGTGGCACGTGACACCAAGCTTGGGCCTGAAGAGATCA
CTGCAGACATCCCTAACGTGGGTGAAGCTGCACTGAACAAACTGGACGAAGCCGGTATCGTTTACGT
AGGTGCTGAAGTTGGCGCCGGCGACATTCTGGTAGGTAAGGTCACTCCGAAAGGCGAGACCCAGCTG
ACTCCGGAAGAGAAGCTGTTGCGTGCCATCTTCGGTGAAAAAGCCAGCGACGTTAAAGACACCTCCC -continued SEQUENCE LISTING
Seq ID No.
Description
Sequence TGCGCGTACCTACCGGTACCAAAGGTACTGTTATCGACGTGCAGGTCTTCACCCGTGACGGCGTTGAG
CGTGATGCTCGTGCACTGTCGATCGAGAAGACCCAGCTGGACGAGATCCGCAAGGATCTGAACGAAG
AGTTCCGTATCGTTGAAGGCGCTACCTTCGAACGTCTGCGCTCTGCTCTGGTTGGCCGCATTGCCGAA
GGTGGTGCCGGTCTGAAGAAAGGTCAGGAAATCACCAATGAAATCCTGGACGGTCTTGAGCATGGTC
AGTGGTTCAAACTGCGCATGGCTGAAGATGCTCTGAACGAGCAGCTTGAAAAGGCTCAGGCTTACAT
CATCGATCGCCGTCGTCTGCTGGACGACAAGTTCGAAGACAAGAAGCGCAAACTGCAGCAGGGCGAT
GACCTGGCTCCAGGCGTGCTGAAAATCGTCAAGGTTTACCTGGCAATCCGCCGTCGCATCCAGCCGG
GTGACAAGATGGCCGGTCGTCACGGTAACAAGGGTGTGGTCTCCGTGATCATGCCGGTTGAAGACAT
GCCGTACGATGCCAATGGCACCCCGGTTGATGTGGTCCTCAACCCGTTGGGCGTACCTTCGCGTATGA
ACGTTGGTCAGATTCTCGAAACTCACCTGGGCCTCGCGGCCAAAGGTCTGGGCGAGAAGATCAACCT
CATGATTGAAGAACAACGCAAGGTCGCTGACCTGCGTAAGTTCCTGCATGAGATCTACAACGAAATT
GGCGGTCGTCAAGAAAGCCTGGATGACTTCTCCGATCAGGAAATCCTGGATCTGGCGAAGAACCTTC
GCGGCGGTGTGCCAATGGCTACCCCGGTGTTCGACGGTGCCAAGGAAAGCGAAATCAAGGCAATGCT
TCGTTTGGCAGACCTGCCAGACAGCGGCCAGATGGTGCTGACTGATGGTCGTACCGGCAACAAGTTC
GAGCGTCCGGTTACCGTTGGCTACATGTACATGCTGAAGCTGAACCACTTGGTAGACGACAAGATGC
ACGCTCGTTCTACCGGTTCTTACAGCCTGGTTACCCAGCAGCCGCTGGGTGGTAAGGCGCAGTTCGGT
GGTCAGCGTTTCGGGGAGATGGAGGTCTGGGCGCTGGAAGCCTACGGCGCGGCATACACTCTGCAAG
AAATGCTCACAGTGAAGTCGGACGATGTGAACGGCCGTACCAAGATGTACAAAAACATCGTGGACGG
CGATCACCGTATGGAGCCGGGCATGCCCGAGTCCTTCAACGTGTTGATCAAAGAAATTCGTTCCCTCG
GCATCGATATCGATCTGGAAACCGAATAA 74
DP9 Glycine--tRNA ligase beta subunit
ATGGCACATAATTATTTACTAGAAATTGGATTGGAAGAAATTCCGGCCCATGTTGTAACTCCAAGT
ATCAAACAGTTAGTACAAAAAGTAACAGCCTTCTTAAAAGAAAATCGCTTAACATACGACTCAATTG
ATCATTTTTCAACTCCTCGTCGTTTGGCAATTCGAATCAATGGGTTAGGCGACCAACAACCTGATATT
GAAGAAGATGCTAAAGGCCCTGCTCGTAAAATTGCTCAAGATGCTGATGGAAATTGGACTAAGGCTG
CAATTGGCTTTACACGTGGACAAGGTCTTACGGTTGACGATATTACTTTTAAAACAATCAAAGGTACG
GACTATGTGTACGTCCATAAGTTAATCAAAGGAAAGATGACTAAGGAAATCCTTACGGGGATAAAAG
AAGTTGTTGAATCAATTAATTTCCCAACAATGATGAAGTGGGCTAACTTTGATTTTAAATATGTACGC
CCAATTCGTTGGCTGGTTTCTATTCTAGATGAAGAAGTCCTTCCTTTTAGTATCTTAGACGTAACTGCG
GGACGCCGAACAGAAGGACATCGTTTCTTAGGTGAAGCTGTCGAACTGGCTAATGCTGAAGAATATG
AAGCAAAATTACACGATCAATTTGTGATTGTTGATGCCGACGAGCGTAAACAATTAATTTCAAACCA
AATTAAAGCAATTGCTGAAAGCAATCGTTGGAACGTTACCCCTAACCCAGGTCTTTTAGAAGAGGTTA
ACAATTTGGTTGAGTGGCCAACCGCTTTTAATGGGGGATTTGATGAAAAGTATTTAGCTATTCCAGAA
GAGGTATTGATAACATCAATGCGTGACCACCAACGCTTCTTCTTTGTCCGCGACCAAGCTGGAAAGCT
ATTGCCAAACTTCATCTCCGTACGAAATGGGAATGAAGAATTTATTGAAAATGTTGTTCGTGGAAATG
AAAAAGTTTTAACTGCACGTTTAGAAGACGCTGCTTTCTTCTACGAAGAAGATCAAAAACATGATATT
AATTATTATGTTGACCGACTTAAAAAGGTTAGTTTCCATGATAAGATTGGTTCAATGTACGAAAAAAT
GCAACGAGTTAATTCTATTGCTAAAGTTATTGGAAACACCTTAAATCTTAATCAAACGGAACTTGATG
ATATCGATCGCGCTACAATGATTTATAAATTTGATTTGGTAACTGGTATGGTTGGTGAGTTCTCAGAA
TTACAAGGAGTAATGGGTGAAAAATATGCTCAACTTAATGGTGAAAACCAAGCAGTAGCCCAAGCCA
TTCGCGAACATTACATGCCAAATAGCGCAGAAGGTGATTTGCCTGAAAGTGTAACGGGCGCGGTAGT
CGCATTAGCTGATAAGTTTGATAACATCTTTAGTTTTTTCTCAGCTGGTATGATTCCAAGTGGTTCAAA
CGATCCATATGCATTACGCCGACATGCATATGGAATTGTTAGAATCTTAAATAGCCGTGATTGGCAAT
TAGATTTAAATCAATTCAAATCACAATTTAAGACTGAATTAGCGGAGAATGGCACAGCGTTTGGTGTG
GATGTCGATCAAAACTTTGACCAAGTACTTAACTTCTTTAATGACCGTATTAAACAATTGCTTGATCA
TCAAAAGATTAGTCATGATATCGTTGAAACGGTGCTTACAGGTAATAATCATGATGTTACGGAAATTA
TCGAAGCTGCCCAAGTACTAGCAGATGCTAAAGCGAGCTCTACATTTAAAGATGATATTGAAGCTTTA
ACACGAGTTCAAAGAATTGCTACAAAGAATGAAGAAAGTGGAGAACTTAATGTAGATCCACAATTAT
TTAATAATGCTTCTGAAGGCGAACTTTTTGATCAAATTATTAAAATTGAAGCTGCAAATAATTTGACA
ATGAGCCAACTATTTGCTAAATTATGCGAGTTGACTCCTGCGATTAGCAAGTACTTTGACGCAACGAT
GGTCATGGACAAAGACGAAAATATTAAGTGTAATCGTTTGAATATGATGAGTCGGTTAGCTAATTTA
ATTCTAAAAATTGGGGATCTAACTAACGTACTTGTAAAATAA 75
DP9 Glutamine synthetase
ATGGCAAAGAAAAATTATTCGCAAGCAGATATTCGTCAGATGGCAAAGGATGAAAATGTACGTTT
TCTCCGATTAATGTTTACAGATCTTTTTGGAATAATTAAGAACGTTGAAGTACCAATTAGTCAATTGG
ACAAACTATTAGATAATAAATTGATGTTTGATGGTTCCTCAATTGACGGGTTTGTTCGGATTGAAGAA
AGTGACATGTATTTATACCCAGATCTTTCTACTTGGATGGTTTTCCCATGGGGAAGCGAACATGGCAA
GGTGGCTCGCATTATTTGTGAAGTATACTCAAATGATCGTAAACCATTCGTGGGTGATCCACGTAACA
ATTTAATTCGAGTACTCCAAGAGATGAAGGATGCAGGATTTACTGATTTTAATATCGGACCTGAACCT
GAGTTTTTCTTGTTGAAATTAGATGAAAATGGTAAACCAACCACTAATTTAAATGATAAAGGTAGTTA
CTTTGATTTAGCTCCTGTTGATTTAGGTGAAAACTGCCGTCGTGATATTGTTTTGGAACTTGAAAATAT
GGGCTTTGATGTTGAAGCTTCTCATCATGAAGTTGCTCCAGGACAACACGAAATTGACTTTAAATACG
CCGATGCTTTGACCGCTGCCGATAACATTCAAACCTTTAAGTTGGTTGTTAAGACAGTTGCCCGTAAA
TATAACCTGCATGCTACATTTATGCCTAAACCTATGGATGGAATCAATGGTTCAGGGATGCATTTAAA
CATGTCACTTTTCAATAAGGAAGGCAATGCTTTCTATGACGAAAAGGGTGACTTACAACTTTCTCAAA
ATGCTTACTGGTTCCTTGGTGGACTATTGAAGCATGCTCGTAGTTATACGGCCGTATGTAACCCAATT
GTTAACTCGTACAAACGTTTAGTTCCTGGATATGAAGCTCCAGTATACGTTGCTTGGTCAGGTTCAAA
TCGTTCACCACTTATTCGCGTTCCTTCAAGTAAGGGACTCTCAACTCGTTTTGAAGTTCGAAGCGTCGA
TCCAGCTGCTAACCCATACTTAGCAATTGCATCAGTATTGGAAGCAGGCTTAGATGGCATTAGAAACA
AGATTGAACCAGAAGATTCCGTTGATCGTAATATCTATCGAATGAACATTCAAGAACGTAATGAAGA -continued

| SEQUENCE LISTING<br>Seq ID No.<br>Description<br>Sequence |
|---|
| GCATATTACAGATCTACCTTCAACATTACACAATGCTTTGAAGGAATTCCAAAATGATGATGTAATGC<br>GTAAGGCATTAGGAGATCACATTTTCCAAAGCTTCCTCGAAGCTAAGAAGTTAGAATGGGCTTCTTAC<br>CGTCAAGAAGTGACACAATGGGAACGTGATCAATATCTCGAAATGTTCTAG |
| 76<br>DP9 DNA gyrase subunit B<br>TTGGCAGACGAAAAAGAAACGAAAGCAGAATTAGCCAGAGAATATGATGCGAGTCAAATTCAGG<br>TTTTAGAGGGGCTCGAAGCAGTTCGTAAACGCCCAGGAATGTATATTGGGTCGACTAGTTCTCAAGG<br>ACTACACCATTTGGTTTGGGAAATTATTGATAATGGTATTGATGAAGCTCTTGCAGGATTTGCAGACA<br>AAATTGATGTGATCGTTGAAAAAGACAATAGTATTACCGTCACTGATAATGGACGTGGGATTCCGGTT<br>GATATCCAAAAGAAAACTGGAAAACCAGCTTTAGAAACAGTCTTTACGGTCCTACATGCCGGAGGTA<br>AATTCGGCGGTGGCGGTTATAAAGTTTCTGGAGGATTGCATGGTGTGGGCGCATCCGTTGTAAATGCG<br>TTATCAACGGAATTAGATGCGCGCGTCATGAAGGACGGTAAAATCTATTACATTGATTTTGCGCTAGG<br>AAAAGTAAAAACACCGATGAAAACGATTGGTGATACTGAACATCCTGACGATCATGGAACTATTGTT<br>CATTTCGTTCCAGATCCAGATATTTTCCAAGAAACTACCACATACGACATTAATATCTTAAAAACACG<br>AATTCGTGAATTAGCCTTTTTGAACAAAGGTCTACGGATTACTTTGAAGGATATGCGTCCTGAAAAGC<br>CAACTGAAGACGACTTCTTGTATGAAGGTGGGATTCGCCACTACGTTGAATATCTAAACGAAGGCAA<br>AGAAGTAATTTTCCCTGAACCTATCTATGTTGAAGGGGTTACAAAAGGTATCACTGTTGAAGTAGCTA<br>TGCAATATATCGAAGGTTATCAAAGTAAATTGTTAACTTTTACTAACAATATTCATACTTACGAAGGC<br>GGTACCCACGAAGAAGGTTTCAAACGTGCTTTAACACGAGTTATTAACGATTACGCTAAAAACAACA<br>ATATTTTAAAAGAAAATGATGATAAATTGTCTGGTGATGATGTTCGAGAAGGTTTGACGGCAGTAGTC<br>AGCGTTAAGCATCCTGATCCTCAATTCGAAGGACAAACGAAAACAAAATTGGGTAACTCAGATGCTC<br>GGACAGCTGTTAACGAAGTGTTTGCTGAAACTTTCAATAAATTCTTATTGGAAAATCCTAAGGTTGCA<br>CGTCAAATTGTTGATAAGGGAATCTTGGCAGCAAAAGCAAGAGTCGCCGCTAAACGAGCTCGTGAAG<br>TTACGCGTAAGAAGAGTGGCCTAGAACTCAATAATCTTCCTGGTAAATTAGCTGATAATACTTCTAAG<br>GATCCTTCAATTAGTGAATTATTCATTGTCGAGGGTGATTCTGCCGGTGGTAGTGCTAAGTCGGGACG<br>TTCGCGTCTCACACAAGCTATTTTGCCAATTCGTGGGAAGATTTTGAACGTTGAAAAAGCCACTTTGG<br>ATCGGGTTTTGGCCAATGAAGAAATTCGTTCACTCTTTACAGCGCTCGGAACTGGATTTGGTGAGGAC<br>TTTGATGTAAGTAAAGCCAACTATCATAAATTGATTATCATGACCGATGCCGATGTCGATGGTGCTCA<br>TATTCGGACACTATTATTGACGCTGTTCTATCGTTACATGCGTCCAATGATTGATGCAGGATTTGTTTA<br>CATTGCTCAACCACCGCTCTACCAAGTACGTCAAGGTAAGATGATTCAATATATCGATTCTGATGAAG<br>AATTAGAAACAGTACTTGGACAATTGTCACCATCACCAAAACCTGTAATTCAACGTTATAAAGGTCTT<br>GGTGAAATGGATGCTGAGCAACTTTGGGAAACAACCATGAATCCAGAAAATCGACGCTTGTTACGAG<br>TTTCAGCCGAAGATGCTGATGCTGCAAGTGGTGATTTTGAAATGTTGATGGGTGACAAGGTTGAACCA<br>CGTCGTAAATTCATTGAAGAGAACGCTGTGTTTGTTAAAAACTTGGATATCTAA |
| 77<br>DP9 Leucine--tRNA ligase<br>ATGGCTTATAATCATAAAGATATCGAACAGAAGTGGCAGCAATTCTGGAGCGACAATGAGACTTT<br>TAAGACGGTCGAAGATGCAGACAAACCCAAATATTATGCATTAGACATGTTCCCTTATCCATCAGGTC<br>AAGGACTCCATGTGGGCCATCCTGAAGGATATACAGCAACAGATATTATGTCACGAATGAAACGGAT<br>GCAAGGTTACAAAGTACTTCATCCAATGGGATGGGATGCTTTTGGTCTTCCAGCAGAACAATATGCGA<br>TGAAGACGGGTAACAATCCGCGTGATTTTACAGCTAAGAATATTCAAAACTTTAAGCGTCAAATCCA<br>ATCACTTGGTTTTTCTTATGACTGGTCGCGAGAAGTTAATACAACTGATCCAGCTTACTACAAGTGGA<br>CTCAATGGATTTTTGAGCAACTCTACAAGAAGGGCTTAGCTTATGAAAAAGAAACGCTGGTAAACTG<br>GGCTCCTGATTTAATGGGTGGAACGGTAGTTGCTAACGAAGAAGTTGTGGATGGTAAGACAGAACGT<br>GGTGGGTTCCCCGTTTATCGTAAACCAATGAAACAATGGATTCTTAAAATTACAGCTTACGCCGACCG<br>TTTGATTGACGATTTGGACCTGGTAGATTGGCCCGATAGTATTAAAGAAATGCAAAAAAACTGGATT<br>GGTCGTTCAGTGGGGGCTAGCGTCTTCTTTAATGTTGAAGATAGCGAAAAACAAATTGAAGTATTTAC<br>AACGCGTCCAGATACATTATTTGGCGCAACATACTTGGTAATTTCACCAGAACATGACCTCGTTGACC<br>AAATTACAACTCCAGAAAGTAAAGCTGCCGTTGAAGAATACAAGAAAGCTGTTGCAACTAAATCAGA<br>TCTTGAACGGACGGATTTGAGTAAAGATAAGACGGGAGTCTTTACGGGAGCATACGCGGTTAACCCT<br>GTTAATGGTAAGAAAATTCCAGTTTGGATTAGTGATTACGTATTGGCTTCATACGGAACTGGAGCAGT<br>GATGGCTGTTCCTGCTCATGATGGCCGTGACTACGAATTTGCTAAGAAATTCAAGATAGATATGGTGC<br>CAGTTTATGAAGGTGGCAATCTTGAAGATGGAGTATTGGACAGCGAAGGCGGGCTAATTAACTCTGG<br>ATTCCTAGATGGGATGGATAAGCAGACGGCTATTGATACCATGATTAGCTGGTTGGAAGAACATGGA<br>GTTGGTCATAAGAAGGTTAACTATCGTCTTCGTGACTGGGTCTTCTCTCGCCAACGCTACTGGGGTGA<br>ACCAATCCCTGTAATTCATTGGGAAGATGGAGAAACAACTTTGATTCCTGAAGATGAATTGCCATTGA<br>GACTCCCGGCTGCAACTGACATTCGTCCTTCCGGTACCGGAGAAAGCCCATTAGCTAACCTAGATGAT<br>TGGGTAAACGTAGTTGATGAAAATGGTCGTAAGGGTCGCCGGGAAACTAATACAATGCCACAATGGG<br>CGGGTAGTTCATGGTACTTCCTCCGTTACGTTGATCCTAAGAATGATCAAAAGATTGCTGACGAAGAT<br>TTACTTAAAGAATGGTTACCAGTCGACTTATATGTTGGTGGAGCTGAACATGCGGTACTTCATTTACT<br>TTATGCACGTTTCTGGCACAAAGTTTTATATGATCTAGGAGTTGTACCAACTAAGGAACCATTCCAAA<br>AATTGGTCAACCAAGGGATGATTCTCGGTAGCAATCATGAGAAGATGTCTAAGTCAAAAGGGAACGT<br>GGTTAATCCAGATGATATTGTTGAGCGCTTTGGAGCGGATACTTTACGATTATACGAAATGTTCATGG<br>GACCTCTGACAGAATCAGTCGCCTGGAGTGAAGATGGGCTTAACGGAAGTCGTAAGTGGATTGACCG<br>CGTCTGGCGCTTGATGATTGACGACGAAAACCAATTGCGTGATCATATTGTTACTGAAAATGATGGCA<br>GTTTGGATATGATTTATAACCAAACTGTTAAGAAGGTAACTGATGATTATGAAAACATGCGCTTTAAC<br>ACGGCTATTTCACAAATGATGGTCTTTGTTAATGAAGCATACAAGGCTGATAAACTTCCAGCAGTATA<br>TATGGAAGGATTAGTTAAGATGTTAGCTCCAATTATTCCGCACGTTGCTGAAGAACTTTGGAGTTTGC<br>TAGGTCACGAAGGTGGTATTTCATACGCTGAATGGCCAACATATGATGAAAGTAAGTTAGTAGAAGC<br>TACAGTTCAAGTCATTCTACAAGTTAATGGTAAAGTTCGGAGTAAAATTACCGTTGACAAGGATATCG<br>CCAAAGAAGAACTTGAAAAATTAGCGTTAGCTGATGCTAAGATTCAACAATGGACGGCAGATAAGAC<br>TGTTCGTAAGGTAATTGTTATTCCTAACAAGATTGTTAATATCGTAGTAGGCTAA |

-continued

SEQUENCE LISTING
Seq ID No.
Description
Sequence

78
DP9 Glucose-6-phosphate isomerase
ATGGCACATATTTCATTTGACAGTTCTAATGTTGCAGATTTTGTACATGAAAACGAACTTGCAGAA
ATCCAACCACTTGTTACAGCTGCTGATCAGATTTTACGTGATGGCTCTGGCGCTGGTAGTGATTTCCGT
GGATGGATCGATTTACCATCAAATTATGATAAGGACGAATTTGCCCGTATCAAGAAAGCCGCTGATA
AGATCCGCAATGACTCAGAAGTATTCGTTGCTATCGGTATTGGTGGTTCATATTTGGGTGCTCGTGCA
GCCATTGATTTCTTGAACAACACTTTCTACAATCTTCTTACTAAAGAACAACGTAATGGTGCTCCTCA
AGTAATCTTCGCTGGTAACTCAATTAGTTCAACTTACCTTGCTGACGTATTGAACTTAATCGGGGACC
GTGACTTCTCAATTAACGTAATTTCTAAGTCAGGTACAACTACAGAACCAGCTATTGCATTCCGTGTT
CTTAAAGAAAAACTAATCAAGAAGTACGGTGAAGAAGAAGCTAAGAAACGTATCTATGCAACAACT
GACCGTGCTAAAGGCGCCCTAAAGACAGAAGCTGATGCAGAAAACTATGAAGAATTCGTAGTTCCTG
ATGACATTGGTGGTCGTTTCTCTGTTCTTTCAGCTGTTGGTTTATTACCAATCGCGGTTGCCGGTGGCG
ATATTGACCAATTGATGAAGGGTGCTGAAGATGCAAGCAACGAATACAAGGATGCTGATGTTACAAA
GAACGAAGCATACAAGTACGCTGCTTTACGTAACATCCTTTATCGTAAGGGCTACACAACAGAACTTC
TTGAAAACTACGAACCAACACTTCAATACTTCGGCGAATGGTGGAAGCAATTGATGGGTGAATCAGA
AGGTAAAGATCAAAAGGGTATCTACCCATCTTCTGCTAACTTCTCAACTGACTTACATTCACTAGGAC
AATACATCCAAGAAGGTCGTCGCAATTTAATGGAAACAGTTATCAATGTTGAAAAGCCTAACCATGA
CATCGACATTCCTAAGGCTGACCAAGACCTTGATGGATTACGTTATCTCGAAGGTCGCACAATGGACG
AAGTTAACAAGAAAGCTTACCAAGGTGTAACTCTTGCTCATAACGACGGTGGTGTTCCAGTTATGACG
GTTAACATTCCTGATCAAACAGCTTACACATTAGGCTATATGATTTACTTCTTCGAAGCAGCTGTTGCT
GTATCTGGTTACTTGAACGGAATTAATCCATTCAACCAACCAGGTGTTGAAGCATACAAGTCAAATAT
GTTTGCATTACTTGGTAAACCAGGTTATGAAGATAAGACAGCTGAATTAAACGCTCGTCTATAA 79
DP9 Phosphoglucomutase
ATGAGTTGGGAAGATTCTGTCAAAGAATGGCAAGATTATGCAGATTTAGATTTTAATTTAAAAAAA
GAATTAGCAACTTTAGCTGAAGATAAAGATGCTTTAAAAGAAGCCTTTTATGCTCCAATGGAATTTGG
TACAGCAGGAATGCGTGGCGTAATGGGCCCTGGTATCAACCGGATGAATATCTATACGGTTCGTCAA
GCAACAGAAGGTTTAGCTAATTTTATGGATACCTTAGATTTTACTGATAAGAAACGGGGAGTGGCGA
TCAGTTTTGATTCCCGCTATCACTCACAAGAGTTTGCTTTAGCAGCAGCTGGTGTTTTAGGTAAGCATG
GTATTCCAAGTTTTGTTTTTGATAGTATGCGTCCCACTCCAGAATTATCATATACAGTACGTGAGTTAA
ACACTTATGCTGGAATCATGATTACTGCTAGTCATAATCCTAAACAATATAATGGATATAAGATTTAT
GGTCCTGATGGCGGACAAATGCCACCAATGGAATCTGATAAGATTACAGAATATATTCGCCAAGTAA
CTGACATCTTTGGTGTTGAAGCTCTTACTCAAAGTGAATTAAGAGCTAAGGGCTTAATGACCATTATT
GGTGAAGACATTGACCTCAAGTATCTTGAGGAAGTTAAGACGGTATCAATTAATCATGAACTAATCC
AGCGCTTTGGTGCAGACATGAAGTTGATCTACTCACCATTACATGGTACTGGAAAAGTAGTTGGTGGA
CGTGCGTTAGAAAATGCTGGTTTTAAGGATTACACTATGGTCCCTGAACAAGCAATTGCTGACCCAGA
ATTTATTACAACGCCATTCCCTAACCCAGAATTCCCACAAACTTTTGATTTGGCTATTGAATTAGGTAA
AAAGCAAGATGCTGACCTTTTGATTGCCACTGATCCGGATGCCGATCGTTTGGGAGCTGCCGTTCGTT
TACCAAATGGTGACTACAAATTATTGACAGGGAACCAAATTGCAGCCTTGATGTTAGAATACATCTTA
ACTGCGCATGATGCAGCAGGTGACTTGCCAGGTAACGCAGCTGCCGTTAAGTCAATTGTTTCTAGTGA
ACTAGCAACCAGAATTGCCGAAGCCCATCATGTAGAAATGATTAACGTTCTAACTGGGTTTAAGTAC
ATTGCTGACCAAATTAAACATTACGAAGAAAATGGCGACCATACCTTTATGTTTGGTTTCGAAGAAAG
TTATGGCTATCTTGTTCGGCCATTTGTTCGCGATAAAGATGCCATCCAAGGAATTGTCCTATTGGCTGA
AATTGCTGCTTATTATCGTAGTAAGGGGCAAACCTTATATGACGGTCTTCAAAACTTATTTACTACTTA
CGGATATCATGAAGAAAAGACCATTTCAAAAGATTTCCCTGGAGTTGACGGTAAAGAAAAAATGGCT
GCCATTATGGAAAAGGTTCGTGAAGAACGCCCAAGTCAATTTGATCAGTACAAGGTATTAGAAACTG
AAGACTTCTTAGCTCAAACTAAGTATGAAGCAGATGGATCTACCCAAGCTATCAAATTACCAAAAGC
GGATGTTTTGAAATTTACATTAGATGATGGTACTTGGATTGCAATTCGTCCTTCTGGAACAGAACCAA
AAATTAAATTCTATATTGGTACAGTTGGCGAAGATGAAAAAGATGCTTTGAATAAGATTGATGTTTTT
GAAACAGCTATTAATGAACTTATAAAATAA 80
DP9 2-oxoglutarate carboxylase small subunit
ATGCACCGTATTTTAATTGCCAACCGAGGCGAAATTGCGACCCGAATTATTCGGGCAACGCATGAA
CTCGGAAAAACAGCTGTAGCAATTTATGCTAAAGCGGATGAATTTTCTATGCATCGTTTTAAAGCAGA
TGAAGCTTACCAAGTTGGTGAAGATAGTGATCCAATTGGAGCATATTTAAATATTGATGACATTATTC
GTATTGCAAAAGAAAATAATATTGATGCAATTCACCCCGGCTATGGATTTTTGTCGGAAAATGCTGTA
TTTGCGCGAGCAGTTGAAGCAGCTGGGATTAAGTTCATTGGACCTCGACCCGAATTACTAGAAATGTT
TGGTGATAAATTACAAGCTAAAAATGCAGCCATTAAGGCCGGTGTACCAACTATTCCGGGAACGGAA
AAACCAGTTAAAGATGTCGATGACGCGCTAAATTTTGCAGAGCAATTTGGCTATCCTATATTTGTTAA
GTCAGCGGCAGGTGGCGGCGGAAAAGGGATGCGGATTGTACATCATCAACAAGAGATGCGCGAAGC
ATTTAAGATGGCTCAGTCAGAAGCTTCTTCGTCTTTTGGTGACGATGAAATTTACTTAGAACGTTACTT
AGTTGATCCAATCCATATTGAGGTTCAAGTAGTTGCGGATGAACACGGTGAGATGGTTCATTTGTATG
AACGAAATTCATCGATTCAGCGACGCCATCAAAAAATCATTGAATTTGCTCCAGCAGTGGGAATTTCT
GCCACCGTCCGTGATCAAATAAGAAAAGCTGCTTTAAAATTATTGAAGTCGGTCAATTATAGTAACGC
TGCAACCATTGAGTTTTTGGTAGAAGGTAATCAATTTTACTTTATGGAAGTGAATCCACGAATTCAGG
TTGAACATACAGTTACCGAAGAAGTCACGGGAATCGATATTGTGCAAACCCAAATTAAGGTTGCTGA
AGGTCAAAGATTACACGAAGAAATCGGTGTTCCTCAACAAGCCCAAATTGAAGCTGTGGGAGTGGCA
ATTCAAGCCCGAATTACCACTGAAGATCCAATGAATAACTTTATTCCAGATGTCGGTAGAATCCAGAC
GTATCGTTCACCTGGTGGAACAGGTGTGAGATTGGATGCTGGAAATGCCTTTGCTGGAGCCATTGTAA
CTCCGCATTATGATTCACTTCTGACCAAGGCAATTGTCCATGCGCCAACCTTTGACGAAGCCTTGGTA
AAGATGGATCGAGTGCTCAATGAATTTGTAATTGCTGGGGTTAAAACTAATATTCCATTTTTAAAGAA -continued

| SEQUENCE LISTING Seq ID No. Description Sequence |
|---|

ATTAATTCATCATCCTATTTTTAGATCGGAATTAGCTCCGACAACCTTTGTGGATGAGACACCAGAAC
TCTTTGATTTAAAAGCTGAAACTCCGGTAGTTACTCAACTTTTGAGTTACATTGCTAATACTACTATCA
ATGGTTATCCAGGCTTAGAAAAGCAGAATCCAGTAGTGTTAACTCGGCCAGTCCGTCCACATTTTGAA
GCACAAGTACCGCATGAAAATGCGAAACAGATCTTGGATAGTAAGGGACCTGATGCCATGATCAATT
GGCTGTTAAAACAAAAGCAGGTCTTGCTAACCGATACGACCATGCGGGATGCCCATCAATCATTATTT
GCTACGCGAATGCGGACCAAAGACATGGTAGAAATTGCCGATCAAGTCCAGAAAGGTCTGCCTAACC
TATTTTCAGCTGAAGTTTGGGGCGGTGCGACCTTTGATGTTGCTTATCGGTTCCTAGGTGAGGATCCAT
GGGAAAGACTCCAACAATTGCGGGCTAAAATGCCAAATACGATGCTCCAAATGCTTTTACGTGGGTC
AAATGCAGTAGGGTATCAAAATTATCCAGACAACGCCATTGACGAATTTATTCGATTGGCTGCCAAA
AATGGAATTGATGTTTTCCGAATCTTTGATTCTCTTAATTGGGTGCCACAGCTTGAAGAATCTATCCAA
CGGGTGCGTGATAATGGAAAAGTGGCTGAAGCAGCCATGGCATATACTGGCGATATTTTAGATACTA
ATCGTACTAAATATAATTTGAAATATTATGTGGATTTGGCTCAAGAACTCCAAGCAGCAGGTGCTCAT
ATTATTGGAATCAAAGATATGTCAGGAATTTTAAAACCACAAGCTGCTTATGCATTAATTTCAGAGTT
AAAAAATCATCTGGATGTGCCAATTCATTTGCATACGCACGATACTACAGGCAACGGCATTTTCTTAT
ATTCTGAAGCAATACGAGCTGGAGTTGATGTGGTCGACGTTGCCACTTCTGCGCTAGCGGGAACGACT
TCTCAGCCTTCAATGCAGTCTCTTTACTATGCGTTGTCTAATAACCAGCGCCAACCAGATTTAGATATT
CAAAAAGCAGAAAAACTAGATGAATATTGGGGCGGAATTCGACCATATTACGAAGGATTTGGCACCC
AATTAAATGGACCACAAACTGAAATTTATCGAATTGAAATGCCTGGTGGACAGTATACCAACCTTCG
CCAGCAAGCTAACGCAGTCCATTTGGGTAAGCGTTGGGATGAGATTAAGGAAATGTACGCAACCGTC
AATCAAATGTTTGGCGATATTCCAAAGGTTACGCCTTCTTCTAAAGTAGTTGGCGATATGGCACTATT
CATGGTCCAAAATGATTTGACGCCTGAAATGGTAATGAACGATAAGGGACAATTAAGTTTTCCCGAA
TCAGTGGTAAACTTTTTCCGTGGTGATTTAGGACAACCGGCGGGTGGTTTTCCAAAACAGCTCCAAAA
GGTGATTCTAAAAGAGCAAGCCCCATTGACAGTACGACCAGGAGCTTTAGCCGATCCAGTTGATTTTG
ATCAAGTTCGTAAACAGGCAACTAAGGTTTTAGGTCACCAAGCAAGTGATGAAGAAGTTATGTCGTT
TATTATGTATCCAGATGTGATGACCGAATACATTCAACGTCAAAATGAATATGGTCCAGTACCATTAT
TAGATACTCCAATCTTTTTCCAAGGCATGCATATTGGCCAACGCATTGATTTACAATTGGGACGCGGA
AAATCGGTCATTATTGTCCTTCGAGAAATTAGTGAAGCAGATGAGGCGGGCCAAAGGTCACTTTTCTT
TGATATAAATGGACAAAGTGAAGAAGTGATTGTTTATGATGTTAATGCGCAGGTAACGAAAGTAAAG
AAGATTAAAGCTGATCCGACTAAAGCCGAACAGATTGGCGCTACTATGGCGGGCTCGGTCATTGAAG
TCCAAGTAGAAGCGGGCCAAAAGGTCCAGCGAGGTGATAACTTAATTGTCACTGAGGCGATGAAAAT
GGAGACCGCGTTAAGAGCACCTTTCGACGCAACCATTAAGAAGATTTATGCTACCCCTGAAATGCAA
ATCGAGACGGGGGATTTATTGATTGAACTAGAAAAGGAGTAA

81
DP3 Glycine--tRNA ligase beta subunit
ATGTCAACATTTTTATTAGAAATTGGACTTGAAGAAATACCAGCTCATTTGGTAACCAGTTCAGAG
AATCAGTTAATTGAAAGAACTAAAAAGTTCTTATCAGAGCATCGTTTAACAGTAGGTGATATTAAACC
ATATTCAACACCGCGACGTCTGGCTGTCGTTTTGACAGATGTTGCTGAAACATCAGAAAGTTTAAGCG
AAGAAAAGCGTGGACCATCTGTTGACCGTGCACAAGACGAAAACGGTAATTGGACAAAGGCAGCAT
TAGGTTTTGCACGTGGTCAAGGTGCTAATCCTGAAGCATTTGAAATTAAAGATGGATATGTTTGGCTA
ACAAAACGTACTGCTGGTGTAGCCGCGAATGAAATTTTAGCTAAAATTGGTGATGAAGTTGTCGCCC
AAATGAAATTTTCAACTTATATGAAGTGGGCTAATCACAGCTTTTTGTATGTTCGACCTATTCGTTGGC
TCGTAGCACTTCTTGATAGTGAAGTCATTTCTTTCAACGTGTTAGATATTACCACAGATCGTTTCACAC
GTGGTCATCGTTTTTTGTCTTCAGAACATGTTGAAATATCTTCTGCAGATAATTATGTAACGACTTTGC
AGGGTGCTAACGTGGTTGTTGATGCTACAGTGCGCAAAAATGAAATTCGATCGCAGTTGAATGCAAT
TGCTGAAGCTAATGGTTGGGTTCTGCAACTTGAGACCGATGCGGCGCAAGATTTGTTGGAAGAAGTT
AATAACATTGTTGAGTGGCCAACAGCGTTTGCTGGCAGTTTCGATGAGAAATATTTAGAAATACCAG
ATGAAGTTTTGATTACATCAATGCGCGAACATCAGCGTTTCTTCTTTGTGACGAATGAAAAAGGACAA
TTATTGCCACACTTTTTGTCAATAAGAAATGGTAACCGTGAGCATCTAAACAACGTTATTGCTGGAAA
TGAAAAAGTATTGGTAGCAAGGTTAGAAGATGCCGAATTCTTCTATCATGAAGACCAAACCAAATCA
ATTTCTGATTACATGACTAAAGTTAAAAAGTTAGTCTTCCATGAAAAAATTGGTACGGTGTATGAACA
CATGCAACGCACTGGTGCTTTGGCTTCAGCAATGGCGGTGGTTTTGAAGTTTGATGAAGTACAACAGG
CTGATTTGACCCGTGCATCAGAAATTTATAAATTTGATTTGATGACCGGTATGGTTGGTGAATTTGAT
GAACTTCAAGGCATTATGGGTGAGCATTATGCCAAGCTTTTTGGCGAAGATGATGCGGTTGCAACAG
CCATTCGAGAGCATTATATGCCAACTTCAGCTAATGGTGAGGTTGCGCAATCTGAAATTGGTGCTTTG
TTGGCCGTTGCGGATAAACTTGATAGCATTGTGACGTTTTTTGCTGCTGGATTAATACCAAGTGGTTCT
AATGATCCTTATGGCTTACGACGTGCAGCTACTGGCATCGTGCGTACATTGGTGGATAAAAAAATGGCA
TATTGATTTGCGGCCTTTGCTAGCTGATTTTGTGCAACAGCAAGGTAAGGTAACTGACACCGATTTAA
CGACATTTGTTGATTTCATGTTGGATCGTGTTCGTAAATTATCGTTGGATGCTGGAATACGTCAAGAT
ATTGTCATTGCTGGATTAGGCAACGTTGATAGAGCTGATATCGTATATATTAGTCAGCGAGTCGAAGT
TTTGTCCCAACATAGTGGTGATGGCAATTTCCGAGATGTAATTGAGGCACTGACTCGTGTGGATCGCT
TAGCCGTAAAGCAAGTAACTAATGCAACGGTTGATCCTGCTAAGTTTGAAAATCAATCTGAAAAGGA
CCTATATCAAGCAACGTTAACGCTTGATTTAAATACTTTGATGCATGACGGTGCAGAAAATCTCTACA
TGGCCTTAGCAAATTTGCAAAAACCAATTGCGGCTTATTTTGATGAAACCATGGTTAACGCTGAAGAT
GAATCTGTTAAAGATAATCGATATGCGCAGCTGAACGTCATACAACGACTAACCAACGGATTAGGAG
ATTTGACGCAAATCGTCATTAAGTAA 82
DP3 Glutamine synthetase
ATGGCTCGTAAAACATTTACCAAAGAAGAAATTAAACAAATTGTTGTTGATGAAAATGTAGAATT
CATTCGTGTAACATTCACTGATGTCTTAGGTGCGATTAAAAACGTTGAAGTACCAACTTCTCAATTAG
ATAAGGTGCTTGACAACAATTTAATGTTTGACGGTTCATCAATCGAGGGATTTGTTCGTATCAATGAA
TCAGATATGTATCTTTACCCCGATTTATCAACATTTATGATTTTCCCATGGGCAACGGATGGTCATGGT
GGTAAAGTGGCCCGCTTGATTGCCGACATTTATACTGCTGATCGTGAGCCATTTGCTGGAGACCCCCG -continued

| SEQUENCE LISTING<br>Seq ID No.<br>Description<br>Sequence |
|---|

TCATGCGTTACGTTCGGTACTCGCTGACGCGCGTGAAGCTGGGTTTACGGCGTTTAATGTCGGGACAG
AACCTGAATTTTTCTTGTTTAAACTTGATGAAAAAGGCAACCCAACCACAGAGTTAAACGACAAAGG
TGGTTATTTTGACCTAGCACCATTGGATATGGGTGAAAATGTTCGTCGTGAAATTGTTTTGACTTTGGA
AAAAATGGGCTTTGAAATTGAAGCTGCTCACCACGAAGTTGCCGAAGGACAGCATGAAGTAGACTTT
AAATACGCTTCAGCTCTTGAAGCCGCTGACAACATTCAGACGTTTAAGTTGGTTGTTAAAACCATCGC
ACGCAAGAATGGTTACTATGCTACCTTTATGCCAAAGCCTGTTGCAGGTATTAACGGATCCGGTATGC
ACACAAACATGTCATTATTTACAAAAGATGGTAACGCATTTGTTGATACATCGGATGAAATGGGCTTG
TCAAAAACAGCATATAACTTCTTGGGTGGTATTTTAGAACATGCGACTGCGTTTACAGCGCTTGCAAA
CCCAACAGTTAACTCATACAAGCGCTTGACACCAGGATTCGAAGCACCTGTTTATGTTGCATGGTCAG
CATCAAATCGTTCACCAATGGTTCGAGTTCCGGCCTCACGTGGTAATTCAACACGTTTGGAACTTCGT
TCAGTTGACCCAACAGCTAATCCTTATACTGCATTGGCAGCCATTTTGGCTTCAGGACTGGATGGGAT
CAAGCGTGAATTAGAGCCTTTGGCCTCAGTTGATAAAAATATTTATTTGATGGATGAGGTCGAACGGG
AAAAGGCAGGCATTACAGACTTACCAGATACTCTGTTGGCTGCAGTTCGTGAGTTGGCGGCTGATGAT
GTTGTTCGTTCAGCTATTGGAGAACATATTGCTGATAAGTTTATTGAAGCAAAGAAGATTGAATACAC
ATCATATCGTCAGTTTGTTTCTGAATGGGAAACAGATTCTTATCTTGAAAATTACTAA

83
DP3 DNA gyrase subunit B
GTGTTCGCAGATTATATCTGTTCACACGCTAATAATATGGCAGAGAATATCGAAAATGAAGCATTG
GAGAACATTGATGGCATCGTAACCGATGATACCGAAATCCGTCAAGCAAGCACCGTTCATGCAGCAG
CAGGCGCTTACAATGCTGATCAGATTCAAGTTTTGGAAGGATTGGAAGCTGTCCGCAAACGCCCTGG
CATGTACATTGGTACGACCACAGCGCAAGGCTTGCACCATTTGGTATGGGAAATTGTTGATAACGGG
ATTGATGAGGCATTAGCAGGGTTTGCGTCACATATTACGGTCACAATCGAAAAGGATAACTCAATCA
CGGTAACCGATGACGGCCGTGGTATTCCTGTCGACATTCAAACTAAAACGGGTAAGCCAGCTCTTGA
AACTGTCTTTACGGTATTACACGCCGGTGGTAAATTTGGCGGTGGCGGTTATAAAGTATCTGGTGGAT
TACACGGTGTTGGAGCTTCTGTTGTCAATGCCTTGTCAACGGATTTGGACGTTAGAGTTGTTCGTGAT
AATACTGTTTATTACATGGACTTCAAAGTGGGACGCGTCAACACACCGATGAAACAATTGACGGAAA
AGCCCACTATTGAGCGTGGTACAATTGTTCATTTTAAGCCCGATGCAGATATTTTCCGTGAAACAACA
GTTTATAACTACAACACATTACTAACACGTGTGCGCGAATTGGCCTTTTTGAATAAAGGTTTGCGCAT
TTCGATTACAGATAATCGACCTGAAGAAGCTGTTTCTGAAAGCTTTCATTTTGAAGGTGGGATTAAAG
AATACGTCAGCTATTTGAATAAGGACAAGACTGCTATTTTCCCTGAACCTGTTTACGTTGAGGGTGAA
GAAAATGGCATTGTAGTGGAAGCTGCCTTACAGTACACTACCGATATTAAAGACAATCTGCGGACGT
TTACTAACAATATCAATACCTATGAAGGTGGGACGCACGAAACTGGCTTTAAAACAGCCTTAACACG
TGTAATCAATGATTACGCTCGTAAAAATGGTCAGCTCAAAGATAATGCAGAAAGTTTGACAGGGGAA
GATGTGCGCGAAGGCATGACTGCTATCGTGTCAATCAAGCACCCAGATCCACAATTTGAAGGACAAA
CCAAAACTAAATTAGGTAACTCCGATGCACGTCAAGCAACGGATCGGATGTTCTCAGAAACGTTCAG
TCGTTTCATGATGGAAAATCCAGCAGTTGCCAAGCAAATTGTTGAAAAAGGTGTCTTAGCCCAAAAA
GCACGATTGGCTGCCAAGCGTGCACGCGAAATGACACGCAAACAATCTGGTTTGGAAATTGGTAATT
TGCCAGGTAAATTAGCTGATAATACCTCAAATGATCCTGAAATTTCAGAATTATTTATTGTTGAGGGT
GATTCAGCCGGTGGTTCAGCTAAGCAAGGACGTAACCGTTTGACGCAAGCTATTTTGCCAATTCGAGG
CAAAATTTTAAATGTTGGGAAAGCCTCATTGGATCGGGTGTTAGCCAACGAAGAAATTCGATCATTGT
TTACAGCAATGGGAACTGGATTTGGTGAGGACTTTAATGTTGAAAAAGCCAATTATCACAAAGTCATT
ATTATGACAGATGCCGATGTCGATGGCGCCCATATTCGAACACTATTGTTAACGCTATTTTTATCGTTAT
ATGCGACCACTTGTTGACGCAGGCTATATTTATATTGCGCAGCCACCGCTTTACGGTGTTGCCTTAGG
CAATAATAAATCAATGACGTACATTGATTCTGATGAAGAACTTGAAGACTATTTGTCACAATTGCCAT
CTAATATTAAACCAAAAGTTCAACGTTATAAGGGACTAGGGGAAATGGATTACGATCAACTAGCAGA
TACAACCATGGATCCGCAGAATCGTCGTTTGCTACGTGTTGACCCAACTGATGCTGAAGAAGCCGAA
GCAGTTATTGATATGTTAATGGGTGGGGATGTACCACCACGTCGTAAGTTTATTGAAGACAATGCTGT
CTTTGTTGAGAACTTGGATATTTAA 84
DP3 Leucine--tRNA ligase
ATGATTTTCGTCAACGAAGCTTACAAAACCGATGCTGTGCCGAAAGCGGCGGCGGAAAACTTCGT
ACAGATGCTGTCCCCACTGGCACCGCATTTGGCAGAAGAACTGTGGGAACGACTTGGTCATACCGAT
ACGATTACGTATGAACCATGGCCAACGTACGATGAGGCTTGGACCATAGAATCCGAAGTGGAAATCG
TCGTGCAAGTGAACGGCAAAATCGTAGAACGCACGAAAATTTCCAAAGACCTGGATCAAGCAGCGAT
GCAAGAACACAGCTTAAGCCTGCCGAATGTTCAGCAGGCTGTGGCTGGGAAGACGATCCGCAAAGTG
ATTGCGGTGCCAGGCAAGCTGGTGAATATCGTCGTTGGATAA 85
DP3 Glucose-6-phosphate isomerase
ATGGCACACATTACATTTGACACAAAGAACATTGAGAATTTTGTTGCACCATACGAATTGGACGAA
ATGCAACCATTAATTACGATGGCTGACCAACAATTGCGCAATCGTACGGGCGCTGGTGCAGAATATT
CTGATTGGTTGACTCTACCTACTGATTACGACAAGGAAGAATTTGCACGTATTCAAAAGGCGGCGCA
ACAAATTCAATCTGATTCAAAGATTTTGGTTGTCATTGGTATTGGTGGTTCATATTTGGGCGCGAAGA
TGGCGGTTGATTTCTTGAATCCAATGTTTAATAATGAATTGTCGGATGACCAACGTCAAGGTGTTAAA
ATTTATTTTGCTGGTAACTCAACTTCTGCAGCTTACTTAAATGATTTAGTTCGTGTCATTGGTGATCAA
GACTTTTCTGTCAACGTTATCTCAAAGTCTGGCACAACAACGGAACCATCAATCGCTTTCCGTGTGTTT
AAACAATTGTTAGAGAAAAAGTATGGTTCTGATGCTGCTAAGAAGCGTATCTATGCCACAACAGATG
CCAATCGTGGTGCTTTGCACGATGAAGCAGCGGCTTCAGGTTATGAAACATTCACAATTCCTGATGGT
GTCGGTGGTCGCTTCTCTGTTTTGACAGCTGTTGGCTTGTTGCCAATTGCTGCTTCAGGCGCTGATATC
CAAAAATTGATGGACGGCGCTCGTGATGCGCAAAACGAATATACTGATTCTGATTTGAAAAAGAACG
AGGCATATAAATATGCAGCCGTTCGTCGTATTTTGTATGATAAGGGTTATACAACAGAATTGTTGATT
AACTGGGAACCTTCAATGCAATATTTGTCAGAGTGGTGGAAGCAATTGATGGGCGAGTCTGAAGGTA -continued

| SEQUENCE LISTING Seq ID No. Description Sequence |
|---|

AAAATCAAAAGGGTATCTATCCATCTTCAGCTAACTTCTCAACCGACTTGCACTCACTTGGACAATAT
ATTCAAGAAGGACGCCGTGATTTGTTTGAGACGGTGGTTAAGTTAGACAATCCTGTATCTAATTTGGA
CCTACCACATGAAGAAGGCAACAATGATGGTTTGCAATATTTGGAAGGTATCACGATCGATGAAGTG
AACACCAAAGCATCTCAAGGGGTTACTTTGGCTCACGTTGATGGTGGTGTGCCTAACTTGGCTGTTCA
CTTGCCAGCACAAGATGCTTATTCACTCGGTTACATGATTTACTTCTTTGAAATGGCTGTTGGGGCGTC
TGGTTATACGTTTGGTATTAACCCATTCAACCAACCGGGTGTCGAAGCCTATAAGACAGCTATGTTTG
CACTATTAGGTAAGCCTGGCTATGAGGAAGCGACAAAAGCATTCCGTGCCCGCTTAGACAAATAA

86
DP3 Beta-phosphoglucomutase
ATGACTAAATTTTCAGATATTAAAGGTTTTGCCTTTGATTTAGATGGGGTTATTGCTGATACGGCGC
GTTTCCATGGTGAAGCTTGGCATCAAACAGCTGATGAGGTTGGCACAACTTGGACACCAGAATTGGC
TGAAGGTTTGAAGGGCATTAGTCGTATGGCTTCCTTGCAAATGATTTTGGATGCTGGGGATCATGCCG
ATGATTTTTCGCAAGCAGATAAAGAAGCATTAGCAGAAAAGAAAAATCATAATTATCAACAACTTAT
TTCAACATTGACGGAAGATGATATTTTGCCTGGCATGAAAGATTTTATTCAATCAGCCAAGGCAGCCG
GCTATACAATGTCGGTGGCATCAGCTTCTAAAAACGCACCAATGATTCTAGATCATTTGGGATTGACC
AAGTATTTTGTCGGCATTGTTGATCCCGCCACTTTGACAAAGGGAAAACCTGATCCTGAAATCTTCGT
TCGTGCTGCGGAAGTCTTACATTTAAATCCAGAAAATGTTATTGGATTGGAAGATTCAGCTGCTGGTA
TTGTGTCAATCAATGGCGCAGGTGAGACATCACTAGCCATTGGTAACGCAGATGTTTTGTCAGGAGCG
GACTTGAATTTTGCGTCTACTTCAGAAGTGACCTTAGCAAATATTGAAGCTAAAATGCAATAG 87
DP3 2-oxoglutarate carboxylase small subunit
ATGTTTAAAAAAGTGCTTGTTGCTAATCGTGGTGAAATTGCGGTTCGCATCATTCGAACGCTCAAA
GAAATGGGGATTGCTTCAGTCGCTATTTACTCGACAGCCGATAAAGATAGTTTACACGTACAAATCGC
TGACGAAGCGATTGCTGTGGGGGGACCGAAACCTAAAGATTCATACTTAAATATGAAAAATATTTTA
AGTGCAGCCCTGCTGTCGGGAGCAGAGGCAATTCATCCAGGATATGGCTTTTTAGCTGAAAATACATT
GTTTGCTGAAATGGTTGGCGAAGTTGGTATTAAATGGATTGGGCCTAGGCCAGAAACAATTGAGTTA
ATGGGTAACAAAGCTAACGCACGTGAAGAAATGCGGCGTGCCGGCGTACCAGTAATTCCAGGTTCAG
AGGGATTTATCCGTGATTTTCATGAAGCAAAAACGGTTGCTGATAAAATTGGCTATCCTTTGTTGCTA
AAAGCTGCCGCTGGTGGTGGTGGTAAAGGCATGCGTTTTGTTTACGGTGAGGATGAGTTATCAGATA
AATTTGATGATGCTCAAAACGAAGCGCGTGCTTCGTTTGGCGATGATCACATGTATATTGAAAAAGTT
ATGTCACGTGTTCGCCACATTGAAATGCAAGTGTTTCGTGATGAGAATGGTCATGTTGTTTACTTGCC
AGAACGAAATTGCTCATTGCAACGCAATAATCAAAAGGTGATTGAAGAATCACCAGCTACGGGTGTA
ACGCCTGAAATGCGTGCGCATCTTGGCGAAATTGTTACTAAAGCCGCAAAAGCATTGGCGTATGAAA
ATACTGGAACCATTGAATTTTTGCAAGATCGCGATGGTCATTTCTACTTTATGGAAATGAACACACGT
ATTCAAGTAGAACATCCAGTTTCTGAAATGGTAACGGGATTAGATTTAATTAAGTTACAAATTCAAGT
TGCTGCAGGCTTAGATTTACCGGTGGTTCAAGATGACGTGATCGTTCAAGGCCACTCTATCGAAGTAC
GTTTGACGGCTGAGCAGCCAGAAAAACACTTTGCACCTAGTGCTGGAACGATTGATTTTGTTTTTTTG
CCAACTGGTGGACCGGGTGTTCGTATTGATTCAGCCTTATTTAATGGCGATAAAATTCAACCATTTTA
CGATTCTATGATTGGCAAATTAATTGTTAAGGCCGATGATCGTGAAACAGCCATGAGAAAGATTCAA
CGTGTGGTTGATGAAACTGTTGTACGTGGTGTAGCAACGAGCCGTAATTTTCAAAAGCTCTGTTAGC
TGATCCACAGGTTCAACGTGGCGAATTTGACACACGTTATTTGGAAACTGAATTTTTACCGAGATGGA
CACAAACATTGCCAGATAATCAATAA 88
DP1 Glutamine--tRNA ligase
ATGAGCAAGCCCACTGTCGACCCTACCTCGAATTCCAAGGCCGGACCTGCCGTCCCGGTCAATTTC
CTGCGCCCGATCATCCAGGCGGACCTGGATTCGGGCAAGCATACGCAGATCGTCACCCGCTTCCCGCC
AGAGCCCAACGGCTACCTGCACATCGGTCATGCCAAGTCGATTTGTGTGAACTTCGGCCTGGCTCAGG
AGTTCGGTGGCGTTACGCACCTGCGTTTCGACGACACCAACCCGGCCAAGGAAGACCAGGAATACAT
CGACGCCATCGAAAGCGACATCAAGTGGCTGGGCTTCGAATGGTCCGGTGAAGTGCGCTATGCATCC
AAGTATTTCGACCAGCTGTTCGACTGGGCCGTCGAGTTGATCAAGGCCGGCAAGGCCTACGTTGACG
ACCTGACCCCCGAGCAAGCCAAGGAATACCGTGGCAGCCTGACCGAGCCGGGCAAGAACAGCCCGTT
CCGCGACCGTTCGGTCGAAGAGAACCTCGACTGGTTCAACCGCATGCGCGCCGGTGAGTTCCCGGAC
GGCGCCCGCGTGCTGCGCGCCAAGATCGACATGGCCTCGCCGAACATGAACCTGCGCGACCCGATCA
TGTACCGCATTCGCCATGCCCATCACCACCAGACCGGTGACAAGTGGTGCATCTACCCCAACTACGAC
TTCACCCACGGTCAGTCGGACGCCATCGAAGGCATCACCCACTCCATCTGCACCCTGGAGTTCGAAAG
CCATCGCCCTCTGTACGAATGGTTCCTGGACAGCCTGCCGGTGCCGGCGCACCCGCGTCAGTACGAAT
TCAGCCGCCTGAACCTGAACTACACCATCACCAGCAAGCGCAAGCTCAAGCAACTGGTCGATGAAAA
GCACGTGCATGGCTGGGACGACCCGCGCATGTCGACGCTCTCGGGTTTCCGTCGTCGTGGCTACACCC
CGGCGTCGATCCGCAATTTCTGCGACATGGTCGGCACCAACCGTTCTGACGGTGTGGTCGATTACGGC
ATGCTTGAGTTCAGCATCCGTCAGGATCTGGACGCGAACGCGCCGCGCGCCATGTGCGTGCTGCGTCC
GTTGAAAGTCGTGATCACCAACTACCCGGAAGACAAGGTCGACCACCTTGAGCTGCCGCGTCACCCG
CAGAAAGAAGAGCTGGGCGTGCGCAAGCTGCCGTTCGCGCGCGAAATCTACATCGACCGTGACGACT
TCATGGAAGAGCCGCCGAAGGGTTACAAGCGCCTGGAGCCGAACGGCGAAGTGCGCCTGCGTGGCA
GCTACGTGATCCGCGCCGACGAAGCAATCAAGGACGCCGAAGGCAACATCGTCGAACTGCGCTGCTC
GTACGATCCGGAAACACTCGGCAAGAACCCTGAAGGCCGTAAGGTCAAGGGCGTGATCCACTGGGTG
CCGGCCGCTGCCAGCATCGAGTGCGAAGTGCGTCTGTACGATCGTCTGTTCCGATCGCCGAACCCGGA
GAAGGCCGAAGACAGCGCCAGCTTCCTGGACAACATCAACCCTGACTCGCTGCAAGTGCTTACAGGT
TGTCGTGCTGAGCCATCGCTTGGCGACGCACAGCCGGAAGACCGTTTCCAGTTCGAGCGCGAAGGTT
ACTTCTGCGCGGATATCAAGGACTCGAAACCCGGTGCTCCGGTATTCAACCGTACCGTGACCTTGCGT
GATTCGTGGGGCCAGTGA -continued

| SEQUENCE LISTING<br>Seq ID No.<br>Description<br>Sequence |
|---|

89
DP1 DNA gyrase subunit B
ATGAGCGAAGAAAACACGTACGACTCGACCAGCATTAAAGTGCTGAAAGGTTTGGATGCCGTACG
CAAACGTCCCGGTATGTACATCGGCGACACCGATGATGGTAGCGGTCTGCACCACATGGTGTTCGAG
GTGGTCGACAACTCCATCGACGAAGCTTTGGCCGGTCACTGCGACGACATCAGCATTATCATCCACCC
GGATGAGTCCATCACGGTGCGCGACAACGGTCGCGGCATTCCGGTCGATGTGCACAAAGAAGAAGGC
GTTTCGGCGGCTGAGGTCATCATGACCGTGCTGCACGCCGGCGGTAAGTTCGATGACAACTCTTATAA
AGTCTCCGGCGGTCTGCACGGTGTAGGTGTGTCGGTAGTGAACGCACTGTCCGAAGAGCTGATCCTG
ACCGTTCGCCGTAGCGGCAAGATTTGGGAGCAGACGTACGTCCATGGTGTGCCACAAGAGCCGATGA
AAATCGTTGGCGACAGTGAATCCACGGGTACGCAGATCCACTTCAAGCCATCGGCTGAAACCTTCAA
GAACATCCACTTTAGCTGGGACATCCTGGCCAAGCGGATTCGCGAACTGTCCTTCCTCAACTCCGGTG
TGGGTATCGTCCTCAAGGACGAGCGCAGCGGCAAGGAAGAACTGTTCAAGTACGAAGGCGGTCTGCG
CGCGTTCGTTGAATACCTGAACACCAATAAGACCGCGGTCAACCAGGTGTTCCACTTCAACATTCAGC
GTGAAGACGGCATCGGCGTGGAAATCGCCCTGCAGTGGAACGACAGCTTCAACGAGAACTTGTTGTG
CTTCACCAACAACATTCCACAGCGCGATGGCGGTACTCACTTGGTGGGTTTCCGTTCCGCACTGACGC
GTAACCTGAACACTTACATCGAAGCCGAAGGCTTGGCCAAGAAGCACAAAGTCGCCACCACCGGTGA
CGATGCGCGTGAAGGCCTGACCGCGATTATCTCGGTGAAAGTGCCGGATCCCAAGTTCAGCTCCCAG
ACCAAAGACAAGCTGGTTTCTTCCGAGGTGAAGACCGCCGTGGAACAGGAGATGGGCAAGTACTTCT
CCGACTTCCTGCTGGAGAACCCGAACGAAGCCAAGCTGGTCGTCGGCAAGATGATCGACGCTGCACG
TGCTCGCGAAGCGGCGCGTAAAGCCCGTGAGATGACCCGTCGTAAAGGCGCGCTGGATATTGCTGGC
TTGCCTGGCAAGTTGGCTGACTGCCAGGAGAAGGACCCAGCGCTCTCCGAGCTATATCTTGTGGAAG
GTGACTCTGCTGGCGGTTCCGCCAAGCAGGGTCGTAACCGTCGCACCCAGGCGATCCTGCCGTTGAA
AGGCAAGATTCTCAACGTAGAGAAGGCCCGCTTCGACAAGATGATTTCCTCCCAGGAAGTCGGCACC
TTGATTACGGCGTTGGGTTGCGGCATTGGCCGCGATGAGTACAACATCGACAAGCTGCGCTACCACA
ACATCATCATCATGACCGATGCTGACGTCGACGGTTCGCACATCCGTACCTTGCTGCTGACCTTCTTCT
TCCGTCAGTTGCCTGAGCTGATTGAGCGTGGCTACATCTATATCGCGCAGCCGCCGTTGTACAAAGTG
AAAAAGGGCAAGCAAGAGCAGTACATCAAAGACGACGACGCCATGGAAGAGTACATGACGCAGTCG
GCCCTGGAAGATGCAAGCCTGCACTTGAACGACGAAGCACCGGGTATCTCCGGTGAGGCGTTGGAGC
GTCTGGTTAACGACTTCCGTATGGTGATGAAGACCCTCAAGCGTCTATCGCGTCTGTACCCTCAGGAA
CTGACCGAGCACTTCATCTACCTGCCGGCCGTCAGTCTGGAGCAGTTGGGTGATCATGCAGCGATGCA
AGAGTGGCTGGCTCAGTACGAAGTACGCCTGCGCACTGTTGAGAAGTCTGGCCTGGTGTACAAAGCC
AGTCTGCGTGAAGACCGTGAACGTAACGTGTGGCTGCCGGAGGTTGAGTTGATCTCCCACGGCCTGTC
GAATTACGTCACCTTCAACCGCGACTTCTTCGGCAGTAATGACTACAAGACGGTCGTGACCCTCGGCG
CGCAGTTGAGCACCTTGCTGGATGATGGTGCTTACATTCAACGTGGCGAGCGTAAGAAAGCGGTCAA
GGAGTTCAAGGAAGCCTTGGACTGGCTGATGGCGGAAAGCACCAAGCGTCATACCATTCAGCGATAC
AAAGGTCTGGGCGAGATGAACCCTGATCAGTTGTGGGAAACCACCATGGATCCAGCACAGCGTCGCA
TGCTGCGCGTGACCATCGAAGACGCCATTGGCGCAGATCAGATCTTCAACACCCTGATGGGTGATGC
GGTCGAACCTCGCCGTGACTTCATCGAGAGCAATGCCTTGGCGGTGTCCAACCTGGACTTCTGA 90
DP1 Isoleucine--tRNA ligase
ATGACCGACTATAAAGCCACGCTAAACCTTCCGGACACCGCCTTCCCAATGAAGGCCGGCCTGCC
ACAGCGCGAACCGCAGATCCTGCAGCGCTGGGACAGTATTGGCCTGTACGGAAAGTTGCGCGAAATT
GGCAAGGATCGTCCGAAGTTCGTCCTGCACGACGGCCCTCCTTATGCCAACGGCACGATTCACATCGG
TCATGCGCTGAACAAAATTCTCAAGGACATGATCCTGCGCTCGAAAACCCTGTCGGGTTTTGACGCGC
CGTATGTCCCGGGCTGGGACTGCCATGGCCTGCCGATCGAACACAAAGTCGAAGTGACCTACGGCAA
AAACCTGGGCGCGGATAAAACCCGCGAACTGTGCCGTGCCTACGCCACTGAGCAGATCGAAGGGCAG
AAGTCCGAATTCATCCGCCTGGGCGTGCTGGGCGAGTGGGACAACCCGTACAAGACCATGAACTTCA
AGAACGAGGCCGGTGAAATCCGTGCCTTGGCTGAAATCGTCAAAGGCGGTTTTGTGTTCAAGGGCCT
CAAGCCCGTGAACTGGTGCTTCGACTGCGGTTCGGCCCTGGCTGAGGCGGAAGTCGAATACGAAGAC
AAGAAGTCCTCGACCATCGACGTGGCCTTCCCGATCGCCGACGACGCCAAGTTGGCCCAGGCTTTCG
GCCTGGCAAGCCTGAGCAAGCCGGCGGCCATCGTGATCTGGACCACCACCCCGTGGACCATCCCGGC
CAACCAGGCGCTGAACGTGCACCCGGAATTCACCTACGCCCTGGTGGACGTCGGTGATCGCCTGCTG
GTGCTGGCCGAGGAAATGGTCGAGGCCTGTCTGGCGCGCTACGAACTGCAAGGTTCGGTGATCGCCA
CCACCACCGGCTCCGCGCTGGAACTGATCAACTTCCGTCACCCGTTCTATGACCGCCTGTCGCCGGTT
TACCTGGCTGACTACGTCGAACTGGGTTCGGGTACGGGTGTGGTTCACTCCGCACCGGCCTACGGCGT
TGACGACTTCGTGACCTGCAAAGCCTACGGTATGGTCAACGATGACATCCTCAACCCGGTGCAGAGC
AATGGTGTGTACGCGCCATCGCTGGAGTTCTTCGGCGGCCAGTTCATCTTCAAGGCTAACGAGCCGAT
CATCGACAAACTGCGTGAAGTCGGTGCGCTGCTGCACACCGAAACCATCAAGCACAGCTACATGCAC
TGCTGGCGCCACAAAACCCCGCTGATCTACCGCGCCACCGCGCAGTGGTTTATCGGCATGGACAAAG
AGCCGACCAGCGGCGACACCCTGCGTGTGCGCTCGCTCAAAGCCATCGAAGACACCAAGTTCGTCCC
GGCCTGGGGCCAGGCGCGCCTGCACTCGATGATCGCCAATCGTCCGGACTGGTGCATCTCCCGCCAG
CGTAACTGGGGCGTACCGATCCCGTTCTTCCTGAACAAGGAAAGCGGCGAGCTGCACCCACGCACCG
TCGAGCTGATGGAAGCCGTGGCCTTGCGCGTTGAACAGGAAGGCATCGAAGCCTGGTTCAAGCTGGA
CGCCGCCGAGCTGCTGGGCGACGAAGCGCCGCTGTACGACAAGAAGGCTCGGACCAACACCGTGGCT
GGTTCCACTCGTCGCTGCTGA 91
DP1 NADH-quinone oxidoreductase subunit C/D
ATGACTACAGGCAGTGCTCTGTACATCCCGCCTTATAAGGCAGACGACCAGGATGTGGTTGTCGAA
CTCAATAACCGTTTTGGCCCTGACGCCTTTACCGCCCAGGCCACACGTACCGGCATGCCGGTGCTGTG
GGTGGCGCGCGCCAGGCTCGTCGAAGTCCTGACCTTCCTGCGCAACCTGCCCAAGCCGTACGTCATGC
TCTATGACCTGCATGGCGTGGACGAGCGTCTGCGGACCAAGCGCCAGGGCCTGCCGAGCGGCGCCGA
TTTCACCGTGTTCTATCACCTGCTGTCGATCGAACGTAACAGCGACGTGATGATCAAGGTCGCCCTCT -continued

| SEQUENCE LISTING Seq ID No. Description Sequence |
|---|

CCGAAAGCGACCTGAGCGTCCCGACCGTGACCGGCATCTGGCCCAACGCCAGTTGGTACGAGCGTGA
AGTCTGGGACATGTTCGGTATCGACTTCCCTGGCCACCCGCACCTGACGCGCATCATGATGCCGCCGA
CCTGGGAAGGTCACCCGCTGCGCAAGGACTTCCCTGCGCGCGCCACCGAATTCGACCCGTTCAGCCTG
AACCTCGCCAAGCAACAGCTTGAAGAAGAGGCTGCACGCTTCCGGCCGGAAGACTGGGGCATGAAA
CGCTCCGGCACCAACGAGGACTACATGTTCCTCAACCTGGGCCCGAACCACCCTTCGGCGCACGGTG
CCTTCCGTATCATCCTGCAACTGGACGGCGAAGAAATCGTCGACTGCGTGCCGGACATCGGTTACCAC
CACCGTGGTGCCGAGAAGATGGCCGAGCGCCAGTCGTGGCACAGCTTCATCCCGTACACCGACCGTA
TCGACTACCTCGGCGGCGTGATGAACAATCTGCCGTACGTGCTCTCGGTCGAGAAGCTGGCCGGTATC
AAGGTGCCGGACCGCGTCGACACCATCCGCATCATGATGGCCGAGTTCTTCCGGATCACCAGCCACCT
GCTGTTCCTGGGTACCTACATCCAGGACGTCGGCGCCATGACCCCGGTGTTCTTCACCTTCACCGACC
GTCAGCGCGCCTACAAGGTCATCGAAGCCATCACCGGCTTCCGCCTGCACCCGGCCTGGTACCGCATC
GGCGGTGTCGCGCACGACCTGCCAAATGGCTGGGAACGCCTGGTCAAGGAATTCATCGACTGGATGC
CCAAGCGTCTGGACGAGTACCAGAAAGCCGCCCTGGACAACAGCATCCTCAAGGGCCGGACCATTGG
GGTCGCGGCCTACAACACCAAAGAGGCCCTGGAATGGGGCGTCACCGGTGCTGGCCTGCGTTCCACC
GGTTGCGATTTCGACCTGCGTAAAGCGCGCCCGTACTCCGGCTACGAGAACTTCGAATTCGAAGTGCC
GTTGGCGGCCAATGGCGATGCCTACGACCGTTGCATCGTGCGCGTCGAAGAAATGCGCCAGAGCCTG
AAGATCATCGAGCAATGCATGCGCAACATCCGGCAGGCCCGTACAAGGCGGACCACCCGCTGACCAC
GCCGCCGCCGAAAGAGCGCACGCTGCAACACATCGAAACCCTGATCACGCACTTCCTGCAGGTTTCG
TGGGGCCCGGTGATGCCGGCCAACGAATCCTTCCAGATGATCGAAGCGACCAAGGGTATCAACAGTT
ATTACCTGACGAGCGATGGCGGCACCATGAGCTACCGCACCCGGATTCGCACTCCAAGCTTCCCGCA
CCTGCAGCAGATCCCTTCGGTGATCAAAGGTGAAATGGTCGCGGACTTGATTGCGTACCTGGGTAGTA
TCGATTTCGTTATGGCCGACGTGGACCGCTAA

92
DP1 Protein RecA
ATGGACGACAACAAGAAGAAAGCCTTGGCTGCGGCCCTGGGTCAGATCGAACGTCAATTCGGCAA
GGGTGCCGTAATGCGTATGGGCGATCACGACCGTCAGGCGATCCCGGCTATTTCCACTGGCTCTCTGG
GTCTGGACATCGCACTCGGCATTGGCGGCCTGCCAAAAGGCCGTATCGTTGAAATCTACGGCCCTGA
ATCTTCCGGTAAAACCACCCTGACCCTGTCGGTGATTGCCCAGGCGCAAAAAATGGGCGCCACTTGTG
CGTTCGTCGATGCCGAGCACGCTCTTGACCCTGAATACGCCGGCAAGCTGGGCGTCAACGTTGACGA
CCTGCTGGTTTCCCAACCGGACACCGGTGAGCAAGCCTTGGAAATCACCGACATGCTGGTGCGCTCCA
ACGCCATCGACGTGATCGTGGTCGACTCCGTGGCTGCCCTGGTGCCGAAAGCTGAAATCGAAGGCGA
AATGGGCGACATGCACGTGGGCCTGCAAGCCCGTCTGATGTCCCAGGCGCTGCGTAAAATCACCGGT
AACATCAAGAACGCCAACTGCCTGGTGATCTTCATCAACCAGATCCGTATGAAGATTGGCGTGATGTT
CGGCAGCCCGGAAACCACCACCGGTGGTAACGCGTTGAAGTTCTACGCTTCGGTCCGTCTGGATATCC
GCCGTACTGGCGCGGTGAAGGAAGGCGACGAGGTGGTGGGTAGCGAAACCCGCGTTAAAGTTGTGA
AGAACAAGGTGGCCCCGCCATTCCGTCAGGCTGAGTTCCAGATTCTCTACGGCAAGGGTATCTACCTG
AACGGCGAGATGATCGACCTGGGCGTACTGCACGGTTTCGTCGAGAAGTCCGGTGCCTGGTATGCCT
ACAACGGCAGCAAGATCGGTCAGGGCAAGGCCAACTCGGCCAAGTTCCTGGCGGACAACCCGGATAT
CGCTGCCACGCTTGAGAAGCAGATTCGCGACAAGCTGCTGACCCCGGCACCAGACGTGAAAGCTGCT
GCCAACCGCGAGCCGGTTGAAGAAGTAGAAGAAGTCGACACTGACATCTGA 93
DP1 RNA polymerase sigma factor RpoD
ATGGAAATCACCCGCAAGGCTCTGAAAAAGCACGGTCGCGGCAACAAGCTGGCAATTGCCGAGCT
GGTGGCCCTGGCTGAGCTGTTCATGCCAATCAAGCTGGTGCCGAAGCAATTTGAAGGCCTGGTTGAG
CGTGTGCGCAGTGCTCTTGAGCGTCTGCGTGCCCAAGAGCGCGCAATCATGCAGCTCTGCGTACGTGA
TGCACGCATGCCGCGTGCCGACTTCCTGCGCCAGTTCCCGGGCAACGAAGTGGATGAAAGCTGGACC
GACGCACTGGCCAAAGGCAAGGCGAAGTACGCCGAAGCCATTGGTCGCCTGCAGCCGGACATCATCC
GTTGCCAGCAGAAGCTGACCGCGCTTCAAACCGAAACCGGTCTGACGATTGCTGAGATCAAGGACAT
CAACCGTCGCATGTCGATCGGTGAGGCCAAGGCCCGCCGCGCGAAGAAAGAGATGGTTGAAGCGAA
CTTGCGTCTGGTGATCTCCATCGCCAAGAAGTACACCAACCGTGGCCTGCAATTCCTCGATCTGATCC
AGGAAGGCAACATCGGCTTGATGAAGGCTGTGGACAAGTTCGAATACCGTCGCGGCTACAAGTTCTC
GACTTATGCCACCTGGTGGATCCGTCAGGCGATCACTCGCTCGATCGCAGACCAGGCCCGCACCATCC
GTATTCCGGTGCACATGATCGAGACCATCAACAAGCTCAACCGTATTTCCCGGCAGATGTTGCAGGA
AATGGGTCGCGAACCGACGCCGGAAGAGCTGGGCGAACGCATGGAAATGCCTGAGGATAAAATCCG
TAAGGTATTGAAGATCGCTAAAGAGCCGATCTCCATGGAAACGCCGATTGGTGATGACGAAGACTCC
CATCTGGGTGACTTCATCGAAGACTCGACCATGCAGTCGCCCATCGATGTGGCTACCGTTGAGAGCCT
TAAAGAAGCGACTCGCGACGTACTGTCCGGCCTCACTGCCCGTGAAGCCAAGGTACTGCGCATGCGT
TTCGGCATCGACATGAATACCGACCACACCCTTGAGGAAGTCGGTAAGCAGTTTGACGTGACCCGTG
AACGGATCCGTCAGATCGAAGCCAAGGCACTGCGCAAGTTGCGCCACCCGACGCGAAGCGAGCATCT
ACGCTCCTTCCTCGACGAGTGA 94
DP1 DNA-directed RNA polymerase subunit beta
ATGGCTTACTCATATACTGAGAAAAAACGTATCCGCAAGGACTTTAGCAAGTTGCCGGACGTCATG
GATGTCCCGTACCTTCTGGCTATCCAGCTGGATTCGTATCGTGAATTCTTGCAAGCGGGAGCGACTAA
AGATCAGTTCCGCGACGTGGGCCTGCATGCGGCCTTCAAATCCGTTTTCCCGATCATCAGCTACTCCG
GCAATGCTGCGCTGGAGTACGTGGGTTATCGCCTGGGCGAACCGGCATTTGATGTCAAAGAATGCGT
GTTGCGCGGTGTTACGTACGCCGTACCTTTGCGGGTAAAAGTCCGTCTGATCATTTTCGACAAAGAAT
CGTCGAACAAAGCGATCAAGGACATCAAAGAGCAAGAAGTCTACATGGGCGAAATCCCATTGATGA
CTGAAAACGGTACCTTCGTTATCAACGGTACCGAGCGCGTTATCGTTTCCCAGCTGCACCGTTCCCCG
GGCGTGTTCTTCGACCACGACCGCGGCAAGACGCACAGCTCCGGTAAGCTCCTGTACTCCGCGCGGA
TCATTCCGTACCGCGGCTCGTGGTTGGACTTCGAGTTCGACCCGAAAGACTGCGTGTTCGTGCGTATC -continued SEQUENCE LISTING
Seq ID No.
Description
Sequence GACCGTCGTCGTAAGCTGCCGGCCTCGGTACTGCTGCGCGCGCTCGGCTATACCACTGAGCAAGTGCT
TGATGCTTTCTACACCACCAACGTATTCAGCCTGAAGGATGAAACCCTCAGCCTGGAACTGATTGCTT
CGCGTCTGCGTGGTGAAATTGCCGTCCTGGATATCCAGGATGAAAACGGCAAGGTCATCGTTGAAGC
TGGCCGCCGTATTACCGCGCGCCACATCAACCAGATCGAAAAAGCCGGTATCAAGTCGCTGGACGTG
CCGCTGGACTACGTCCTGGGTCGCACCACTGCCAAGGTCATCGTTCACCCGGCTACAGGCGAAATCCT
GGCTGAGTGCAACACCGAGCTGAACACCGAGATCCTGGCAAAAATCGCCAAGGCCCAGGTTGTTCGC
ATCGAGACCCTGTACACCAACGACATCGACTGCGGTCCGTTCATCTCCGACACGCTGAAGATCGACTC
CACCAGCAACCAATTGGAAGCGCTGGTCGAGATCTATCGCATGATGCGTCCTGGTGAGCCACCGACC
AAAGACGCTGCCGAGACCCTGTTCAACAACCTGTTCTTCAGCCCTGAGCGCTATGACCTGTCTGCGGT
CGGCCGGATGAAGTTCAACCGTCGTATCGGTCGTACCGAGATCGAAGGTTCGGGCGTGCTGTGCAAG
GAAGACATCGTCGCGGTACTGAAGACCTTGGTCGACATCCGTAACGGTAAAGGCATCGTCGATGACA
TCGACCACTTGGGTAACCGTCGTGTTCGCTGCGTAGGCGAAATGGCCGAGAACCAGTTCCGCGTTGGC
CTGGTACGTGTTGAGCGTGCGGTCAAAGAGCGTCTGTCGATGGCTGAAAGCGAAGGCCTGATGCCGC
AAGATCTGATCAACGCCAAGCCAGTGGCTGCGGCGGTGAAAGAGTTCTTCGGTTCCAGCCAGCTCTC
GCAGTTCATGGACCAGAACAACCCGCTCTCCGAGATCACCCACAAGCGCCGTGTTTCCGCACTGGGC
CCGGGCGGTCTGACCCGTGAGCGTGCAGGCTTTGAAGTTCGTGACGTACACCCAACGCACTACGGTC
GTGTTTGCCCGATCGAAACGCCGGAAGGTCCGAACATCGGTCTGATCAACTCCCTTGCCGCTTATGCA
CGCACTAACCAGTACGGCTTCCTCGAGAGCCCGTACCGTGTAGTGAAAGATGCACTGGTCACCGACG
AGATCGTGTTCCTGTCCGCCATCGAAGAAGCCGATCACGTGATCGCTCAGGCTTCGGCCACGATGAAC
GACAAGAAAGTCCTGATCGACGAGCTGGTAGCTGTTCGTCACTTGAACGAGTTCACCGTTAAGGCGC
CGGAAGACGTCACCTTGATGGACGTTTCGCCGAAGCAGGTAGTTTCGGTTGCAGCGTCGCTGATCCCG
TTCCTGGAGCACGATGACGCCAACCGTGCGTTGATGGGTTCCAACATGCAGCGTCAAGCTGTACCCAC
CCTGCGTGCCGACAAGCCGCTGGTAGGTACCGGCATGGAGCGTAACGTAGCCCGTGACTCCGGCGTT
TGCGTCGTGGCTCGTCGTGGCGGCGTGATCGACTCTGTTGATGCCAGCCGTATCGTGGTTCGTGTTGC
CGATGACGAAGTTGAGACTGGCGAAGCCGGTGTCGACATCTACAACCTGACCAAATACACCCGCTCG
AACCAGAACACCTGCATCAACCAGCGCCCGCTGGTGAGCAAGGGTGATCGCGTTCAGCGTAGCGACA
TCATGGCCGACGGCCCGTCCACCGATATGGGTGAGCTGGCACTGGGTCAGAACATGCGCATCGCGTT
CATGGCATGGAACGGCTTCAACTTCGAAGACTCCATCTGCCTGTCCGAGCGTGTTGTTCAAGAAGACC
GCTTCACCACGATCCACATTCAGGAGCTGACCTGTGTGGCGCGTGACACCAAGCTTGGGCCAGAGGA
AATCACTGCAGACATCCCGAACGTGGGTGAAGCTGCACTGAACAAACTGGACGAAGCCGGTATCGTT
TACGTAGGTGCTGAAGTTGGCGCAGGCGACATCCTGGTTGGTAAGGTCACTCCGAAAGGCGAGACCC
AACTGACTCCGGAAGAGAAGCTGTTGCGTGCCATCTTCGGTGAAAAAGCCAGCGACGTTAAAGACAC
TTCCCTGCGCGTACCTACCGGTACCAAGGGTACTGTCATCGACGTACAGGTCTTCACCCGTGACGGCG
TTGAGCGTGATGCTCGTGCACTGTCCATCGAGAAGACTCAACTCGACGAGATCCGCAAGGACCTGAA
CGAAGAGTTCCGTATCGTTGAAGGCGCGACCTTCGAACGTCTGCGTTCCGCTCTGGTAGGCCACAAGG
CTGAAGGCGGCGCAGGTCTGAAGAAAGGTCAGGACATCACCGACGAAATCCTCGACGGTCTTGAGCA
CGGCCAGTGGTTCAAACTGCGCATGGCTGAAGACGCTCTGAACGAGCAGCTCGAGAAGGCCCAGGCC
TATATCGTTGATCGCCGCCGTCTGCTGGACGACAAGTTCGAAGACAAGAAGCGCAAACTGCAGCAGG
GCGATGACCTGGCTCCAGGCGTGCTGAAAATCGTCAAGGTTTACCTGGCAATCCGTCGCCGCATTCAG
CCGGGCGACAAGATGGCCGGTCGTCACGGTAACAAGGGTGTGGTCTCCGTGATCATGCCGGTTGAAG
ACATGCCGCACGATGCCAATGGCACCCCGGTCGACGTCGTCCTCAACCCGTTGGGCGTACCTTCGCGT
ATGAACGTTGGTCAGATCCTTGAAACCCACCTGGGCCTCGCGGCCAAAGGTCTGGGCGAGAAGATCA
ACCGTATGATCGAAGAGCAGCGCAAGGTCGCAGACCTGCGTAAGTTCCTGCACGAGATCTACAACGA
GATCGGCGGTCGCAACGAAGAGCTGGACACCTTCTCCGACCAGGAAATCCTGGATCTGGCGAAGAAC
CTGCGCGGCGGCGTTCCAATGGCTACCCCGGTATTCGACGGTGCCAAGGAAAGCGAAATCAAGGCCA
TGCTGAAACTGGCAGACCTGCCGGAAAGTGGCCAGATGCAGCTGTTCGACGGCCGTACCGGCAACAA
GTTTGAGCGCCCGGTTACTGTTGGCTACATGTACATGCTGAAGCTGAACCACTTGGTAGACGACAAGA
TGCACGCTCGTTCTACCGGTTCGTACAGCCTGGTTACCCAGCAGCCGCTGGGTGGTAAGGCTCAGTTC
GGTGGTCAGCGTTTCGGGGAGATGGAGGTCTGGGCACTGGAAGCATACGGTGCTGCTTACACTCTGC
AAGAAATGCTCACAGTGAAGTCGGACGATGTGAACGGTCGGACCAAGATGTACAAAAACATCGTGG
ACGGCGATCACCGTATGGAGCCGGGCATGCCCGAGTCCTTCAACGTGTTGATCAAAGAAATTCGTTCC
CTCGGCATCGATATCGATCTGGAAACCGAATAA 95
DP22 Glutamine--tRNA ligase
ATGAGTGAGGCTGAAGCCCGCCCAACAAATTTTATCCGTCAGATTATTGATGAAGATCTGGCGACC
GGGAAACACAATACCGTTCATACCCGTTTCCCGCCTGAGCCAAATGGCTATCTGCATATCGGTCATGC
GAAATCTATCTGCCTGAACTTCGGCATTGCGCAAGACTATCAGGGGCAGTGCAACCTGCGTTTTGACG
ATACCAACCCGGCAAAAGAAGACATCGAATTCGTTGAGTCGATCAAACACGACGTCCAGTGGTTAGG
TTTCGACTGGAGCGGTGATATTCACTACTCTTCAGACTATTTTGATCAACTGCACGCTTATGCGCTGGA
ACTGATCAACAAAGGTCTGGCGTACGTTGACGAACTGTCACCGGATCAGATCCGTGAATACCGCGGC
TCGCTGACGTCTCCGGGCAAAAACAGCCCGTACCGTGACCGTTCAGTGGAAGAGAACATCGCGCTGT
TTGAGAAAATGCGTAACGGTGAATTTGCCGAAGGCGCTGCCTGTCTGCGTGCAAAAATCGATATGGC
GTCGCCTTTCTTCGTGATGCGCGATCCGGTTCTGTACCGTATTAAGTTTGCAGAACACCACCAGACCG
GCAAAAAATGGTGCATCTATCCGATGTACGATTTCACCCACTGCATTTCCGATGCGCTGGAAGGGATC
ACCCATTCGCTGTGTACGCTGGAATTCCAGGACAACCGCCGTCTGTACGACTGGGTTCTGGATAACAT
CTCCATTCCATGCCACCCGCGTCAGTACGAGTTCTCCCGTCTGAATCTCGAGTACTCCATCATGTCTAA
GCGTAAGCTGAACCAGCTGGTGACCGAGAAGATTGTGGAAGGCTGGGACGACCCGCGTATGCCGACT
GTTTCAGGTCTGCGTCGTCGTGGTTACACCGCCGCGTCTATCCGTGAATTCTGCCGTCGTATCGGCGTC
ACCAAGCAAGACAACAACGTCGAAATGATGGCGCTGGAATCCTGTATCCGTGACGATCTGAACGAAA
ATGCACCGCGCGCCATGGCGGTGATCAACCCGGTTAAAGTGATCATTGAAAACTTTACCGGTGATGA
CGTGCAGAGGGTGAAAATGCCGAACCACCCGAGCAAACCGGAAATGGGCACCCGCGAAGTGCCATT
TACCCGTGAGATTTATATCGATCAGGCAGATTTCCGCGAAGAAGCGAACAAGCAATACAAGCGTCTG
GTGCTCGGCAAAGAAGTGCGTCTGCGCAATGCGTATGTGATCAAAGCAGAACGTATCGAGAAAGATG -continued

| SEQUENCE LISTING<br>Seq ID No.<br>Description<br>Sequence |
|---|

CAGAAGGCAATATCACCACGATCTTCTGTTCTTACGATATCGATACACTGAGCAAAGATCCTGCCGAT
GGCCGCAAGGTGAAAGGCGTGATCCACTGGGTTTCGGCGTCAGAAGGCAAACCGGCGGAGTTCCGCC
TGTATGACCGTCTGTTCAGCGTCGCCAACCCGGGTCAGGCAGAAGATTTCCTGACCACCATCAACCCG
GAATCTCTGGTGATTTCCCACGGTTTCGTGGAGCCATCACTGGTGGCTGCACAGGCTGAAATCAGCCT
GCAGTTCGAGCGTGAAGGTTACTTCTGCGCCGACAGCCGCTACTCAAGCGCTGAACATCTGGTGTTTA
ACCGTACCGTTGGCCTGCGCGATACCTGGGAAAGCAAACCCGTCGTGTAA

96
DP22 DNA gyrase subunit B
ATGTCGAATTCTTATGACTCCTCAAGTATCAAGGTATTAAAAGGGCTGGACGCGGTGCGTAAGCGC
CCCGGCATGTATATCGGCGATACCGATGACGGCACTGGTCTGCACCACATGGTATTCGAGGTTGTGGA
CAACGCTATCGACGAAGCCCTCGCGGGCCACTGTAAAGAGATTCAGGTCACGATCCATGCGGATAAC
TCTGTGTCCGTACAGGATGATGGTCGTGGCATTCCGACCGGTATTCATGAAGAAGAGGGCGTTTCTGC
TGCTCAGGTCATCATGACCGTTCTTCACGCCGGCGGTAAATTTGACGATAACTCGTATAAAGTCTCCG
GCGGTCTGCATGGCGTGGGTGTTTCCGTCGTTAACGCCCTGTCAGAAAAACTGGAACTGGTTATCCGC
CGCGAAGGCAAAGTGCACACCCAGACTTACGTGCATGGCGAACCTCAGGATCCGCTGAAAGTGATTG
GCGATACTGACGTGACCGGTACCACGGTACGTTTCTGGCCAAGCTTCAACACCTTCACCAATCACACT
GAATTCGAGTATGACATTCTGGCGAAACGCCTGCGTGAACTGTCATTCCTGAACTCCGGCGTGGCGAT
CCGCCTGCTGGATAAACGTGATGGTAAAAACGATCACTTCCATTATGAAGGCGGTATCAAAGCTTTCG
TGGAATATCTGAACAAAAACAAAACCCCAATCCATCCGACCGTATTCTATTTCTCCACGGTCAAAGAT
GACATTGGCGTTGAAGTGGCGTTGCAGTGGAACGACGGTTTCCAGGAAAACATTTACTGCTTCACCA
ACAACATTCCACAGCGCGATGGCGGGACTCACTTAGCCGGTTTCCGTTCGGCAATGACCCGTACCCTG
AACGCGTACATGGATAAAGAAGGCTACAGCAAGAAATCCAAAATCAGCGCCACCGGTGATGATGCC
CGTGAAGGCCTGATTGCTGTGGTGTCGGTGAAGGTGCCGGATCCTAAGTTCTCTTCTCAGACCAAAGA
CAAACTGGTGTCTTCTGAAGTGAAAACAGCGGTTGAAACGCTGATGAACGAGAAGCTGGTGGATTAC
CTGATGGAAAACCCGTCAGACGCCAAAATCGTTGTCGGTAAAATCATCGACGCAGCGCGTGCCCGTG
AAGCAGCACGTAAAGCGCGTGAAATGACCCGCCGTAAAGGCGCGCTGGATCTGGCTGGCTTGCCAGG
CAAACTGGCGGACTGTCAGGAACGCGATCCGGCACATTCCGAACTGTACTTAGTGGAAGGGGACTCA
GCGGGCGGCTCTGCAAAACAAGGCCGTAACCGTAAGAACCAGGCGATTCTGCCGTTGAAAGGTAAAA
TCCTCAACGTGGAGAAAGCGCGCTTCGACAAAATGCTCTCTTCTCAGGAAGTGGCAACGCTGATTAC
AGCACTCGGTTGCGGCATTGGCCGTGACGAATACAACCCGGACAAACTGCGCTATCACAGCATCATC
ATCATGACCGATGCCGACGTCGATGGTTCGCACATCCGTACCCTGTTGCTGACATTCTTCTACCGTCA
GATGCCTGAAATTGTAGAACGTGGCCACGTGTTTATCGCCCAGCCGCCGTTGTACAAAGTGAAAAAA
GGCAAGCAGGAACAGTACATTAAAGATGACGAAGCGATGGATCAGTATCAGATTTCCATTGCGATGG
ACGGGGCAACGTTACACGCCAACGCTCATGCGCCAGCCCTGGCGGGTGAACCGCTGGAGAAACTGGT
CGCTGAACATCACAGCGTGCAGAAAATGATTGGCCGCATGGAACGTCGTTATCCGCGTGCGCTGCTG
AATAACCTGATCTATCAGCCGACCCTGCCGGGTGCAGATCTGGCCGATCAGGCGAAAGTGCAGGCCT
GGATGGAATCGCTGGTGGCGCGTCTCAACGAGAAAGAGCAGCACGGCAGTTCTTACAGCGCGATCGT
GCGTGAAAACCGCGAACATCAGCTGTTCGAACCGGTTCTGCGTATCCGCACCCACGGTGTTGATACCG
ATTACGATCTGGATGCCGACTTCATCAAAGGCGGCGAATACCGCAAAATCTGTGCGCTGGGTGAACA
GCTGCGCGGCCTGATCGAAGAAGATGCCTTCATCGAACGTGGCGAACGCCGTCAGCCCGTCACCAGC
TTCGAACAGGCGCTGGAATGGCTGGTGAAAGAGTCCCGTCGTGGTCTGTCGATTCAGCGATACAAAG
GTCTGGGTGAAATGAACCCTGAACAGCTGTGGGAAACCACCATGGATCCTGAGCAACGTCGCATGTT
ACGTGTGACCGTGAAGGATGCCATCGCCGCTGACCAGTTGTTCACGACGCTGATGGGCGATGCGGTT
GAACCGCGCCGCGCCTTTATCGAAGAGAACGCCCTGAAAGCCGCCAATATCGATATCTGA 97
DP22 Isoleucine--tRNA ligase
ATGAGTGACTACAAGAACACCCTGAATTTGCCGGAAACAGGGTTCCCGATGCGTGGCGATCTGGC
CAAGCGTGAACCTGACATGCTGAAAAATTGGTATGACCAGGATCTGTACGGGATTATTCGTGCTGCC
AAGAAAGGCAAAAAAACCTTTATTTTGCATGACGGCCCTCCGTATGCGAACGGCAGCATTCATATTG
GTCACTCAGTAAACAAAATTCTTAAAGACATGATTATCAAGTCCAAAGGACTTGCGGGCTTTGATGCG
CCGTATGTGCCGGGCTGGGATTGTCATGGTCTGCCGATCGAGCTGAAAGTCGAACAACTGATCGGTA
AGCCGGGCGAGAAAGTTACGGCGGCGGAATTCCGTGAAGCCTGCCGTAAATATGCCGCAGAACAGGT
TGAAGGCCAGAAGAAAGACTTCATCCGTCTGGGCGTGCTGGGCGACTGGGATCATCCGTACCTGACG
ATGGATTTCAAAACCGAAGCCAACATCATCCGTGCGCTGGGCAAAATCATCGGTAACGGCCACCTGC
ATAAAGGCGCCAAGCCGGTGCACTGGTGTACAGATTGCGGTTCGTCGCTGGCCGAAGCCGAAGTCGA
ATATTACGACAAAGCCTCGCCTTCTATTGATGTGGCGTTCAACGCGACGGATGCCGCAGCCGTGGCAG
CGAAATTTGGCGTTACTGCCTTTAATGGCCCGATCTCGCTGGTTATCTGGACCACAACACCGTGGACT
ATGCCCGCTAACCGCGCCATTTCACTGAATCCTGAGTTTGCTTATCAGCTGGTTCAGGTCGAAGGTCA
GTGTCTGATCCTGGCAACCGATCTGGTTGAAAGCGTCATGAAACGTGCCGGTATTGCCGGATGGACC
GTTCTGGGCGAGTGCAAAGGCGCAGACCTCGAACTGCTGCGCTTCAAACACCCGTTCCTCGGTTTCGA
CGTTCCGGCGATCCTGGGCGATCACGTGACGCTCGATGCGGGTACCGGTGCCGTGCATACCGCACCA
GGCCACGGCCCTGACGACTTTGTTATCGGCCAGAAATACGGTCTGGAAGTGGCGAATCCGGTAGGGC
CGAACGGTTGCTACCTGCCGGGCACTTACCCGACGCTGGACGGTAAATTTGTCTTTAAAGCCAACGAC
CTGATCGTTGAGTTGCTGCGTGAAAAAGGCGCATTGCTGCACGTTGAGAAAATCACGCACAGCTATC
CTTGCTGCTGGCGCCACAAAACGCCAATCATCTTCCGCGCGACGCCGCAATGGTTCATCAGCATGGAT
CAGAAGGGCCTGCGTCAGCAGTCGCTGGAAGAGATCAAAGGCGTGCAGTGGATCCCGGACTGGGGTC
AGGCACGTATCGAAAACATGGTCGCTAACCGTCCTGACTGGTGTATCTCCCGTCAGCGTACCTGGGGC
GTGCCGATGTCTCTGTTCGTTCACAAAGACACTGAGCAGCTGCATCCGCGCAGCCTTGAGCTGATGGA
AGAAGTGGCGAAACGTGTTGAGGTGGATGGCATTCAGGCGTGGTGGGATCTGAATCCGGAAGACATT
CTGGGTGCAGACGCCGCAGATTACGTCAAAGTACCGGACACGCTGGACGTCTGGTTTGACTCCGGTTC
AACGCATTCTTCCGTTGTGGATGTGCGTCCTGAGTTCAACGGGCATTCTCCTGATCTGTATCTGGAAG
GTTCTGACCAGCATCGCGGCTGGTTCATGTCTTCCCTGATGATTTCGACGGCAATGAAAGGCAAAGCG -continued

| SEQUENCE LISTING<br>Seq ID No.<br>Description<br>Sequence |
|---|

CCTTACAAACAAGTGCTGACTCACGGTTTCACCGTGGATGGTCAGGGCCGCAAAATGTCTAAATCCAT
CGGCAATACCATCGCGCCGCAAGACGTGATGAACAAGCTGGGTGGCGACATTCTGCGTCTGTGGGTC
GCGTCGACGGATTACACCGGCGAAATCGCCGTGTCCGACGAAATCCTCAAACGTGCTGCTGATTCTTA
CCGCCGTATCCGTAACACCGCGCGCTTCCTGCTGGCGAACCTTAACGGTTTCGATCCGGCGCTGCACA
GCGTGGCTCCGGAAGACATGGTGGTGCTGGACCGCTGGGCGGTTGGCCGTGCGAAAGCCGCTCAGGA
AGAAATCATTGCTGCGTATGAAGCCTATGATTTCCATGGCGTTGTTCAGCGTCTGATGCAGTTCTGCT
CGATCGAAATGGGTTCCTTCTATCTGGATATCATTAAAGATCGTCAGTACACCGCGAAAAGCGACAG
CGTTGCACGTCGCAGCTGTCAGACCGCGCTGTATCACATCAGTGAAGCGCTGGTTCGCTGGATGGCAC
CGATCATGTCGTTCACAGCCGATGAAATCTGGGCGGAACTGCCGGGAAGCCGTGAGAAATTCGTCTT
CACCGAAGAGTGGTACGACGGTCTGTTCGGTCTCGCAGGCAACGAATCCATGAACGATGCGTTCTGG
GATGAACTGCTGAAAGTGCGTGGCGAAGTGAACAAAGTGATCGAACAGGCGCGTGCGGATAAACGT
CTGGGCGGTTCTCTGGAAGCAGCGGTTACGCTGTTTGCTGATGATGCGCTGGCAACAGACCTGCGTTC
TCTGGGCAATGAACTGCGCTTTGTGCTGCTGACGTCAGGGGCGAAAGTTGCCGCACTGAGTGATGCA
GATGACGCGGCTCAGTCGAGTGAATTGCTGAAAGGCCTGAAGATTGGTCTGGCGAAAGCAGAAGGCG
ACAAGTGCCCGCGCTGCTGGCATTACACTACCGATTAA

98
DP22 NADH-quinone oxidoreductase subunit C/D
ATGACAGATTTGACGACGCAAGATTCCGCCCTGCCAGCATGGCATACCCGTGATCATCTCGATGAT
CCGGTTATCGGCGAATTGCGTAACCGTTTTGGGCCAGAGGCCTTTACTGTCCAGGCAACCCGCACCGG
AATTCCCGTGGTGTGGTTCAAGCGTGAACAGTTACTGGAAGCGATTACCTTTTTACGAAAACAGCCAA
AACCTTACGTCATGCTTTTCGATTTGCATGGCTTTGATGAGCGTTTACGTACACACCGCGACGGTTTAC
CGGCTGCGGATTTTTCCGTTTTCTACCACCTGATCTCCGTCGAGCGTAACCGCGACATCATGATCAAA
GTGGCGTTGTCAGAAAACGATCTTCATGTTCCGACGATCACCAAAGTGTTCCCGAACGCTAACTGGTA
CGAACGCGAAACATGGGAAATGTTCGGTATTACCTTCGACGGCCATCCGCACCTGACGCGCATCATG
ATGCCGCAGACCTGGGAAGGGCATCCGCTGCGTAAAGACTATCCGGCGCGCGCCACCGAGTTCGATC
CTTATGAGCTGACTAAGCAAAAAGAAGAACTCGAGATGGAATCGCTGACCTTCAAGCCGGAAGACTG
GGGCATGAAGCGCGGTACCGATAACGAGGACTTTATGTTCCTCAACCTCGGTCCTAACCACCCGTCAG
CGCATGGTGCATTCCGTATTATCCTGCAGCTGGATGGCGAAGAGATTGTCGACTGCGTGCCTGACGTC
GGTTACCACCACCGTGGTGCGGAGAAAATGGGCGAACGCCAGTCATGGCACAGCTACATTCCGTATA
CTGACCGTATCGAATATCTCGGCGGTTGTGTTAACGAAATGCCTTACGTGCTGGCTGTTGAAAAACTC
GCCGGTATCGTGACGCCGGATCGCGTTAACACCATCCGTGTGATGCTGTCTGAACTGTTCCGTATCAA
CAGCCATCTGCTGTACATCTCTACGTTTATTCAGGACGTGGGTGCGATGACGCCGGTATTCTTCGCCTT
TACCGATCGTCAGAAAATTTACGATCTGGTGGAAGCGATCACCGGTTTCCGTATGCACCCGGCCTGGT
TCCGTATCGGTGGCGTAGCGCATGACCTGCCGAAAGGCTGGGACCGCCTGCTGCGTGAATTCCTTGAC
TGGATGCCAGCCCGTTTGGATTCCTACGTCAAAGCGGCGCTGAGAAACACCATTCTGATTGGCCGTTC
CAAAGGCGTGGCCGCGTATAACGCCGACGACGCACTGGCCTGGGGCACCACCGGTGCTGGCCTGCGC
GCAACGGGTATCCCGTTCGATGTGCGTAAATGGCGTCCGTATTCAGGTTATGAAAACTTTGACTTTGA
AGTGCCGACCGGTGATGGCGTCAGTGACTGCTATTCCCGCGTGATGCTGAAAGTGGAAGAACTTCGT
CAGAGCCTGCGCATTCTGGAACAGTGCTACAAAAACATGCCGGAAGGCCCGTTCAAGGCGGATCACC
CGCTGACCACGCCGCCACCGAAAGAGCGCACGCTGCAACACATCGAGACCCTGATCACGCACTTCCT
GCAAGTGTCGTGGGGGCCGGTCATGCCTGCACAAGAATCTTTCCAGATGGTTGAAGCAACCAAAGGG
ATCAACAGCTACTACCTGACCAGTGACGGCAGCACCATGAGCTACCGCACCCGTGTCCGTACGCCGA
GCTTCCCGCATTTGCAGCAGATCCCGTCCGTAATCCGTGGCAGCCTGGTATCCGACCTGATCGTGTAT
CTGGGCAGTATCGATTTTGTAATGTCAGATGTGGACCGCTAA 99
DP22 Protein RecA
ATGGCTATTGATGAGAACAAGCAAAAAGCGTTAGCTGCAGCACTGGGCCAGATTGAAAAGCAATT
CGGTAAAGGCTCCATCATGCGTCTGGGTGAAGATCGCTCCATGGACGTTGAAACGATCTCTACCGGCT
CTTTGTCTCTGGATATCGCGTTAGGTGCCGGCGGTTTGCCAATGGGCCGTATCGTTGAGATCTATGGC
CCGGAATCTTCCGGTAAAACAACGCTGACCTTGCAAGTTATCGCGGCTGCACAGCGTGAAGGCAAAA
CCTGTGCGTTCATCGATGCAGAACACGCCCTGGACCCGATCTACGCTAAAAAACTGGGCGTGGATAT
CGATAACCTGCTGTGTTCTCAGCCAGATACCGGCGAACAGGCTCTGGAAATCTGTGACGCGCTGACCC
GTTCAGGCGCTGTTGACGTGATCATCGTTGACTCCGTTGCCGCACTGACACCGAAAGCGGAAATCGA
AGGCGAAATTGGTGACTCTCACATGGGCCTCGCGGCACGTATGATGAGCCAGGCGATGCGTAAGCTG
GCCGGTAACCTGAAAAACGCCAACACCTTGCTGATCTTCATCAACCAGATCCGTATGAAAATTGGTGT
GATGTTCGGTAACCCGGAAACCACCACCGGCGGTAACGCCCTGAAATTCTACGCTTCTGTGCGTCTGG
ATATCCGCCGTATCGGCGCGATCAAAGAAGGCGATGTGGTTGTCGGTAGCGAAACGCGTGTGAAAGT
GGTGAAGAACAAAATCGCTGCGCCATTTAAACAAGCTGAATTCCAGATCATGTACGGCGAAGGCATC
AATATCAACGGCGAGCTGATTGATCTCGGCGTGAAGCACAAGCTGATCGAAAAAGCCGGTGCATGGT
ATAGCTACAACGGTGAGAAGATTGGTCAGGGTAAAGCGAACTCCTGCAACTTCCTGAAAGAAAACCC
GAAAGTGGCTGCCGAGCTGGATAAAAAACTGCGTGATATGCTGTTGAGCGGTACCGGTGAACTGAGT
GCTGCGACCACGGCTGAAGATGCTGACGACAACATGGAAACCAGCGAAGAGTTTTAA 100
DP22 RNA polymerase sigma factor RpoD
ATGGAGCAAAACCCGCAGTCACAGCTTAAGCTACTTGTCACCCGTGGTAAGGAGCAAGGCTATCT
GACCTATGCTGAGGTCAATGACCATCTGCCGGAAGATATCGTCGATTCCGACCAGATCGAAGACATC
ATCCAGATGATTAACGACATGGGCATCCAGGTACTTGAAGAAGCACCGGACGCCGATGATTTGATGC
TGGCCGAAAACCGCCCTGATACCGATGAAGACGCTGCAGAAGCCGCGGCGCAGGTGCTTTCCAGCGT
TGAATCCGAAATTGGCCGTACCACCGACCCTGTGCGTATGTATATGCGCGAGATGGGTACCGTTGAGT
TGCTGACCCGTGAAGGCGAAATCGACATCGCCAAACGTATCGAAGACGGTATCAATCAGGTCCAGTG
CTCCGTTGCTGAATATCCTGAAGCTATCACTTATTTGTTAGAGCAATATGACCGTGTGGAAGCAGGCG -continued

| SEQUENCE LISTING<br>Seq ID No.<br>Description<br>Sequence |
|---|

AAGTACGTCTGTCTGACCTGATCACCGGTTTTGTTGACCCGAACGCCGAAGAAGAAATCGCACCAACT
GCGACTCACGTGGGTTCTGAACTGACCACTGAAGAGCAGAATGATGACGACGAAGACGAAGATGAA
GACGACGACGCTGAAGACGACAACAGCATCGATCCGGAACTGGCTCGCCAGAAGTTCACCGAACTGC
GTGAACAGCATGAAGCGACGCGTCTGGTCATCAAGAAAAACGGCCGTAGTCACAAGAGCGCAGCAG
AAGAAATCCTGAAGCTGTCCGATGTGTTCAAACAGTTCCGTCTGGTGCCAAAACAGTTCGATTTCCTG
GTTAACAGCATGCGTTCCATGATGGATCGCGTTCGTGCTCAGGAACGTCTGATCATGAAAGTGTGCGT
TGAACAGTGCAAAATGCCGAAGAAAAACTTCGTCAATCTGTTCGCCGGTAACGAAACCAGCGATACC
TGGTTTGATGCCGCTCTGGCAATGGGTAAACCATGGTCCGAGAAGCTGAAAGAAGTCACCGAAGACG
TGCAACGCGGCCTGATGAAACTGCGTCAGATCGAAGAAGAAACCGGCCTGACTATCGAACAGGTTAA
AGACATCAACCGTCGCATGTCGATCGGCGAAGCGAAAGCCCGTCGCGCGAAGAAAGAGATGGTTGA
AGCAAACTTACGTCTGGTTATTTCTATCGCCAAGAAATACACCAACCGTGGTCTGCAGTTCCTTGACC
TGATCCAGGAAGGTAACATCGGCCTGATGAAAGCCGTTGATAAGTTTGAATATCGCCGTGGTTATAA
GTTCTCAACTTATGCGACCTGGTGGATCCGTCAGGCTATCACCCGCTCCATCGCCGACCAGGCGCGTA
CCATCCGTATCCCGGTACATATGATTGAGACGATCAACAAACTCAACCGTATCTCCCGTCAGATGCTG
CAAGAGATGGGCCGCGAACCGACACCGGAAGAGCTGGCTGAGCGTATGTTGATGCCGGAAGACAAA
ATCCGCAAAGTGCTGAAAATTGCCAAAGAGCCAATCTCCATGGAAACGCCAATCGGCGACGATGAAG
ATTCGCATCTGGGCGATTTCATCGAGGATACCACCCTCGAGCTGCCACTGGATTCTGCGACGTCTGAA
AGCCTGCGTTCTGCAACGCATGACGTTCTGGCTGGCCTGACTGCACGTGAAGCGAAAGTTCTGCGTAT
GCGTTTCGGTATCGATATGAACACTGACCACACGCTGGAAGAAGTGGGCAAACAGTTCGACGTGACC
CGTGAGCGTATCCGTCAGATCGAAGCGAAAGCGTTGCGTAAACTGCGCCACCCGAGCCGCTCCGAAG
TACTGCGCAGCTTCCTGGACGATTAA

101
DP22 DNA-directed RNA polymerase subunit beta'
GTGAAAGACTTACTAAAGTTTCTGAAAGCGCAAACTAAGACCGAAGAGTTTGATGCGATCAAAAT
TGCTCTGGCATCGCCAGACATGATCCGTTCTTGGTCTTTTGGTGAAGTTAAGAAGCCAGAAACCATTA
ACTACCGTACGTTCAAACCAGAACGTGACGGCCTTTTCTGTGCCCGTATTTTCGGACCAGTAAAAGAC
TACGAATGCCTGTGCGGTAAGTACAAGCGTTTAAAACATCGCGGCGTGATCTGCGAGAAGTGCGGCG
TTGAAGTGACCCAGACTAAAGTACGCCGTGAGCGTATGGGCCACATCGAACTGGCTTCCCCGACTGC
ACACATCTGGTTCCTGAAATCGCTGCCATCGCGCATCGGTTTGCTGCTGGATATGCCACTGCGTGACA
TCGAACGTGTTCTGTACTTCGAATCCTATGTGGTTATCGAAGGCGGCATGACTAACCTCGAAAAACGC
CAGATCCTGACTGAAGAGCAGTATCTGGATGCGTTGGAAGAGTTTGGTGATGAGTTCGACGCGAAGA
TGGGTGCGGAAGCTATTCAGGCCCTGTTGAAAAACATGGATCTGGAAGCAGAGTGCGAGCAACTGCG
TGAAGAGTTGAACGAAACCAACTCCGAAACCAAACGTAAGAAGCTGACCAAGCGTATCAAGCTGCTG
GAAGCGTTCGTTCAGTCTGGTAACAAACCAGAGTGGATGATCCTGACTGTGCTGCCGGTACTGCCACC
AGACTTGCGTCCATTGGTTCCGTTGGACGGCGGCCGTTTCGCAACGTCGGATCTGAACGATCTGTATC
GTCGCGTGATCAACCGTAACAACCGTCTGAAACGCCTGCTGGATCTGGCTGCGCCAGACATCATCGTA
CGTAACGAAAAACGTATGCTGCAAGAAGCGGTAGATGCTTTGCTGGATAACGGCCGTCGCGGTCGTG
CTATCACCGGCTCTAACAAGCGTCCGCTGAAATCTCTGGCAGACATGATTAAAGGTAAACAGGGTCG
TTTCCGTCAGAACTTGCTGGGTAAACGTGTCGACTACTCTGGTCGTTCCGTTATCACCGTAGGTCCATA
CCTGCGTCTGCACCAGTGTGGTCTGCCGAAGAAAATGGCACTGGAACTGTTCAAACCGTTCATCTACG
GCAAGCTGGAACTGCGTGGCCTGGCCACCACCATCAAAGCCGCGAAGAAAATGGTTGAGCGCGAAG
AAGCTGTCGTTTGGGACATCCTGGACGAAGTTATCCGCGAACACCCGGTACTGCTGAACCGTGCACC
AACCCTGCACCGTTTGGGTATCCAGGCGTTTGAACCGGTTCTGATCGAAGGTAAAGCAATCCAGCTGC
ACCCGCTGGTTTGTGCGGCATATAACGCCGACTTCGATGGTGACCAGATGGCTGTTCACGTACCGTTG
ACGCTGGAAGCCCAGCTGGAAGCGCGTGCGTTGATGATGTCTACCAACAACATCCTGTCACCTGCGA
ACGGCGAGCCAATCATCGTTCCTTCTCAGGACGTTGTATTGGGTCTGTACTACATGACCCGTGACTGT
GTTAACGCCAAAGGCGAAGGCATGGTTCTGACCGGTCCTAAAGAAGCTGAGCGTATTTACCGCGCCG
GTTTGGCCTCTCTGCATGCGCGTGTCAAAGTGCGTATTACAGAAGAGATCAAAAATACCGAAGGCGA
AGTTACGCACAAGACGTCGATTATCGACACGACAGTTGGTCGCGCCATCCTTTGGATGATCGTACCTA
AAGGTCTGCCGTTCTCTATCGTCAACCAGCCTCTGGGCAAAAAAGCTATCTCCAAAATGCTGAACACC
TGTTACCGCATTTTGGGCCTGAAGCCGACCGTTATTTTTGCTGACCAGATCATGTACACCGGTTTTGCT
TACGCTGCCCGTTCAGGCGCGTCAGTAGGTATCGATGACATGGTAATCCCTGCGAAGAAAGCAGAGA
TCATCGAAGAAGCAGAAACCGAAGTTGCTGAAATCCAGGAACAGTTCCAGTCTGGTCTGGTCACTGC
TGGCGAACGCTATAACAAAGTGATCGACATCTGGGCTGCGGCCAACGAACGTGTTGCTAAGGCAATG
ATGGAAAACTTGTCTGTTGAAGACGTCGTCAACCGTGACGGTGTTGTTGAACAGCAGGTTTCCTTCAA
CAGTATCTTTATGATGGCCGACTCCGGTGCGCGTGGTTCTGCTGCACAGATTCGTCAGCTGGCCGGTA
TGCGTGGCCTGATGGCGAAACCAGATGGTTCCATCATTGAAACGCCAATCACCGCGAACTTCCGTGA
AGGTCTGAACGTACTCCAGTACTTCATCTCTACTCACGGTGCTCGTAAAGGTTTGGCGGATACCGCAC
TTAAAACGGCTAACTCCGGTTATCTGACCCGTCGTCTGGTTGACGTCGCGCAGGATCTGGTTGTGACC
GAAGACGACTGTGGGACTCACGAAGGCATCATGATGACTCCGGTCATCGAAGGTGGCGACGTTAAAG
AACCACTGCGTGAGCGTGTACTGGGTCGTGTGACTGCAGAAGATATCCTCAAGCCGGGTACGGCGGA
TATCCTGGTTCCACGTAACACCCTGCTTCACGAGAAGACGTGTGATCTGTTAGAAGAGAACTCAGTCG
ACAGCGTGAAAGTACGTTCAGTCGTAAGTTGCGAAACCGACTTTGGTGTGTGTGCAAACTGCTACGGT
CGCGACCTGGCACGTGGTCACATCATCAACAAAGGTGAAGCGATCGGTGTTATTGCAGCACAGTCCA
TCGGTGAGCCGGGTACCCAGCTGACGATGCGTACGTTCCACATCGGTGGTGCGGCATCTCGTGCGGC
AGCGGAATCCAGCATCCAGGTTAAGAACACTGGTACCATTAAACTGAGCAACCACAAGCACGTTAGC
AACTCTAACGGCAAACTGGTGATCACTTCCCGTAACACTGAGCTGAAATTGATCGACGAATTCGGTCG
TACCAAAGAAAGCTATAAAGTGCCTTACGGTTCCGTGATGGGCAAAGGCGATGGCGCATCAGTTAAC
GGCGGCGAAACCGTTGCTAACTGGGATCCGCACACCATGCCAGTTATCAGTGAAGTGAGTGGTTTCA
TTCGCTTTGCCGATATGGTGGATACTCAGACCATCACACGCCAGACCGACGACCTGACCGGTTTGTCT
TCTCTGGTTGTTCTGGACTCTGCAGAGCGTACCGGTAGCGGTAAAGACCTGCGTCCGGCACTGAAAAT
CGTTGACGCTAAAGGCGACGACGTATTGATTCCAGGTACTGATATGCCTGCTCAATACTTCCTGCCAG
GTAAAGCGATTGTTCAGCTGGAAGATGGTACTCAGATCCACTCTGGTGACACCCTGGCGCGTATTCCT -continued

| SEQUENCE LISTING<br>Seq ID No.<br>Description<br>Sequence |
|---|

CAGGAATCCGGCGGTACCAAGGACATCACCGGTGGTCTGCCACGCGTTGCTGACCTGTTCGAAGCAC
GTCGTCCGAAAGAGCCTGCAATCCTTGCTGAAATCAGCGGGATCATCTCCTTCGGTAAAGAAACCAA
AGGCAAACGTCGTCTGGTAATTTCTCCGTTAGATGGCAGCGATGCTTACGAAGAAATGATCCCTAAAT
GGCGTCAGCTGAACGTGTTCGAAGGCGAAGTTGTGGAACGTGGTGACGTCGTATCCGACGGCCCTGA
GTCTCCGCACGACATCTTGCGTTTACGTGGTGTTCACGCGGTTACCCGCTACATCACCAACGAAGTGC
AGGAAGTTTACCGTCTGCAAGGCGTTAAGATTAACGATAAGCACATCGAAGTTATCGTTCGTCAGAT
GTTGCGTAAAGGCACCATCGTTAGCGCTGGTGGCACTGACTTCCTGGAAGGCGAGCAGGCAGAAATG
TCTCGCGTTAAAATCGCTAACCGTAAGCTGGAAGCTGAAGGCAAAATCACGGCAACATTCAGCCGTG
ACCTGCTCGGTATCACCAAGGCATCCCTGGCGACCGAATCCTTCATCTCTGCAGCGTCGTTCCAGGAA
ACCACGCGTGTTCTTACCGAAGCGGCTGTTGCCGGTAAACGTGATGAACTGCGTGGCCTGAAAGAGA
ACGTTATCGTTGGCCGTCTGATCCCAGCCGGTACCGGTTACGCTTATCATCAGGATCGTGCACGCCGT
AAAGCACAAGGCGAAGTGCCAGTTGTACCGCAAGTCAGCGCGGATGAAGCAACGGCTAACCTGGCT
GAACTGCTGAACGCAGGTTTCGGTAACAGCGACGATTAA

102
DP67 Glutamine--tRNA ligase
ATGAGTGAGGCTGAAGCCCGCCCAACTAACTTTATTCGTCAGATTATCGACGAAGATCTGGCGAAC
GGTAAGCACAGTTCAGTGCACACCCGCTTCCCGCCTGAGCCGAATGGCTATCTGCATATTGGCCATGC
GAAATCAATCTGCCTGAACTTTGGTATCGCTCAGGATTATCAGGGGCAGTGTAACCTGCGCTTTGATG
ACACTAACCCGGTGAAAGAAGATCTGGAGTTTGTTGAATCAATCAAGCGTGATGTGCAGTGGCTGGG
CTTTAAGTGGAGTGGTGACGTACGCTACTCATCTGACTATTTCGAGCAACTGCACAATTATGCCGTTG
AGCTGATTAGTAAAGGGCTGGCGTACGTTGATGAACTGTCACCGGAGCAGATCCGTGAATACCGTGG
CAGCCTGACCTCAGCGGGTAAAAACAGCCCCTTCCGCGATCGCAGCGTGGACGAAAACCTTGCGCTC
TTTGCAAAAATGCGCGCGGGCGGCTTTGCCGAGGGCACCGCGTGTTTACGAGCCAAAATTGATATGG
CTTCCAACTTTATCGTTCTGCGCGATCCGGTGATCTACCGCATCAAATTTGCCGAACATCATCAGACC
GGCAATAAGTGGTGCATCTATCCGATGTATGACTTTACCCACTGCATCTCTGATGCGCTGGAAGGCAT
TACTCACTCACTGTGTACGCTGGAATTCCAGGATAACCGTCGCCTGTACGACTGGGTGCTGGATAACA
TCACCATTCCGGTTCATCCGCGTCAGTATGAATTCTCTCGCCTGAATCTTGAATATGCCATCATGTCCA
AGCGTAAGTTGAGTCAGTTGGTGACCGAGAACGTGGTGGAAGGTTGGGATGATCCCCGTATGCTGAC
TGTTTCGGGTTTGCGCCGCCGTGGCTACACTGCGGAATCCATCCGTGAATTCTGCCGCCGCATTGGGG
TGACCAAGCAGGACAATATTGTTGAAATGGCCGCTCTGGAATCCTGTATCCGTGACGACCTCAATGA
GAATGCCCCGCGTGCCATGGCAGTGATGGATCCGGTAAAAGTGGTGATAGAAAATCTGCCTGCGCAT
CACGATGAGGTGATCACCATGCCGAATCATCCGAGCAAGCCGGAAATGGGTACCCGCGAAGTCCCGT
TCAGTCGTGAGATCTACATCGATCGTGCTGACTTCCGTGAGGAAGCAAACAAGCAGTACAAGCGGCT
GGTGCTGGGCAAAGAAGTGCGTCTGCGTAACGCTTATGTGATCAAAGCCGAGCGCGTGGCAAAGGAC
GATGAAGGCAACATTACCTGCCTGTTCTGTACCTGTGATGTGGATACTCTGAGCAAGGATCCGGCCGA
CGGGCGTAAAGTGAAGGGCGTTATCCACTGGGTGTCAGCTGTTCATGCCCTTCCGGCAGAGTTCCGTC
TGTACGATCGGCTGTTCAGCGTACCGAATCCGGGGGCGGCAGAAGACTTCCTGGCCAGCATCAACCC
GGAATCTCTGGTGATCCGTCAGGGCTTCGTGGAGCCCGGGATGCAGCAGGCGGAGGCGTCAGCCCCG
TATCAGTTTGAGCGTGAAGGCTACTTCTGCGCTGACAGTGTCTACTCCAGTGCCAGCAATCTGGTGTT
CAACCGCACCGTTGGCCTGCGTGACACCTGGGCGAAAGTCGGCGAGTAA 103
DP67 DNA gyrase subunit B
ATGTCGAATTCTTATGACTCCTCCAGTATCAAAGTTCTGAAAGGGCTCGATGCTGTACGCAAACGC
CCGGGTATGTATATCGGCGATACGGATGACGGTACCGGTCTGCATCACATGGTATTTGAGGTCGTGGA
TAACGCCATTGACGAAGCGCTCGCCGGTCACTGTTCCGATATTCTTGTCACTATTCATGCCGATAACT
CTGTTTCCGTTGTGGATGATGGCCGTGGTATTCCGACCGGTATTCACGAAGAAGAAGGCATCTCAGCC
GCTGAAGTGATCATGACCGTGCTGCACGCCGGCGGTAAGTTCGACGATAACTCTTATAAAGTCTCCGG
CGGCCTGCACGGCGTGGGCGTGTCAGTGGTGAACGCCCTGTCGGAAAAACTGGAGCTGACCATTCGT
CGCGAAGGGAAAGTTCACCAGCAGACTTACGTCCACGGCGTGCCACAGGCCCCGTTGAGTGTGAGCG
GTGAAACTGACCTGACGGGAACGCGCGTGCGTTTCTGGCCCAGCCATCAGACGTTCACTAACGTCGT
GGAGTTCGAGTACGAAATTTTGGCAAAGCGCCTGCGTGAGCTGTCGTTCCTGAACTCCGGTGTATCAA
TCAAGCTGGAAGATAAGCGCGACGGTAAAAGCGACCATTACCACTATGAAGGTGGTATCAAGGCGTT
TGTTGAGTACCTCAACAAGAACAAAACCCCGATCCACCCGAATGTGTTCTATTTCTCAACCGAGAAAG
ACGGCATTGGTGTGGAAGTGGCGCTGCAGTGGAACGATGGTTTCCAGGAAAATATCTACTGCTTTACC
AACAACATCCCACAGCGGGATGGGGGCACGCACCTCGTTGGTTTCCGTACCGCGATGACCCGTACCC
TGAATGCCTACATGGATAAAGAAGGCTACAGCAAGAAAGCCAAAGTCAGCGCCACCGGTGACGACG
CGCGTGAAGGCCTGATTGCTGTGGTGTCGGTGAAAGTGCCGGATCCGAAATTCTCTTCACAGACCAA
AGATAAACTGGTCTCTTCTGAAGTGAAAACCGCCGTTGAGCAGCAGATGAACGAGCTGCTGGCAGAA
TACCTGCTGGAAAACCCGACCGATGCCAAAATCGTCGTCGGTAAAATCATTGATGCGGCCCGCGCCC
GTGAAGCGGCCCGTCGTGCACGTGAAATGACCCGCCGTAAAGGCGCGCTGGATCTGGCAGGCCTGCC
GGGCAAACTGGCGGACTGCCAGGAGCGTGATCCGGCTCTGTCCGAAATTTACCTGGTGGAAGGGGAC
TCTGCGGGCGGCTCTGCCAAGCAGGGACGTAACCGTAAAAACCAGGCCATCCTGCCGCTGAAGGGTA
AAATCCTCAACGTCGAGAAGGCGCGCTTTGACAAGATGCTCGCGTCGCAGGAAGTCGCTACGCTGAT
CACCGCGCTGGGCTGTGGTATCGGTCGTGATGAGTACAACCCCGACAAACTGCGCTATCACAGCATC
ATTATCATGACCGATGCCGACGTGGATGGCTCGCATATCCGTACCCTGCTGCTGACCTTCTTCTACCGT
CAGATGCCAGAAATCATTGAGCGTGGTCATGTCTATATTGCCCAGCCACCGCTGTACAAGGTGAAAA
AAGGCAAGCAGGAGCAGTATATTAAAGACGACGATGCGATGGATCAGTACCAGATCGCCATCGCGCT
GGACGGTGCCACGCTGCATGCGAACGCCAGCGCCCCGGCCCTTGGCGGTAAGCCACTGGAAGATCTG
GTGTCTGAGTTCAACAGCACGCGCAAGATGATCAAGCGCATGGAGCGCCGTTACCCGGTGGCCTTGC
TGAATGCGCTGGTCTACAACCCGACCCTGAGCGATTTGACCGCCGAAGCGCCGGTACAGAGCTGGAT
GGATGTGCTGGTGAAGTATCTGAACGACAACGACCAGCACGGCAGCACCTACAGCGGTCTGGTACGC
GAAAATCTGGAGCTGCATATCTTTGAGCCGGTACTGCGTATCAAAACCCACGGCGTGGATACCGATT -continued

| SEQUENCE LISTING<br>Seq ID No.<br>Description<br>Sequence |
|---|

ATCCGCTCGACAGCGAGTTTATGCTCGGCGGCGAATACCGTAAGCTCTGCGCGCTGGGTGAGAAGCT
GCGTGGCCTGATCGAAGAAGACGCGTTCATCGAACGTGGTGAGCGGCGTCAGCCGATTGCCAGCTTT
GAGCAGGCGATGGAGTGGCTGGTTAAAGAGTCACGCCGTGGCCTGACGGTTCAGCGTTATAAAGGTC
TGGGCGAGATGAACCCGGATCAGCTGTGGGAAACCACCATGGATCCGGACAGCCGCCGTATGCTGCG
CGTGACCATCAAAGATGCCGTGGCCGCCGACCAGCTGTTCACCACCCTGATGGGGGATGCGGTAGAG
CCCCGTCGTGCCTTTATTGAAGAGAACGCCCTGCGCGCGGCAAACATCGATATCTGA

104
DP67 Isoleucine--tRNA ligase
ATGAGTGACTATAAATCTACCCTGAATTTGCCGGAAACGGGGTTCCCGATGCGTGGCGATCTGGCC
AAACGCGAACCGGGTATGCTGCAACGTTGGTATGATGACAAGCTGTACGGCATCATTCGCGAAGCCA
AGAAAGGGAAAAAAACCTTTATCCTGCACGATGGCCCTCCTTACGCCAACGGCAGCATTCATATTGG
TCACTCCGTTAACAAGATTCTGAAAGACATTATCGTTAAGTCGAAAGGCATGGCGGGCTATGACTCGC
CTTATGTACCGGGTTGGGACTGCCACGGTCTGCCTATCGAGCATAAAGTTGAGCAGATGATCGGTAA
GCCGGGAGAGAGAAAGTCAGCGCCGCTGAGTTCCGTGCTGCCTGCCGCAAATACGCTGCCGAGCAGGTG
GAAGGGCAGAAAGCCGACTTTATCCGTCTGGGTGTGTTGGGTGACTGGGATCGTCCGTATCTGACAAT
GAACTTCCAGACCGAAGCCAATATTATCCGTGCGCTGGGTAAAATCATCGGTAACGGGCACCTGCAC
AAAGGGGCCAAGCCGGTACACTGGTGCCTGGACTGCCGTTCTGCCCTGGCTGAGGCGGAAGTGGAGT
ACTACGATAAAACCTCTCCGTCTATCGATGTCATGTTCAATGCGACTGATAAAGAGGGGGTACAGGC
CAAATTTGCGGCAACGAATGTTGACGGCCCGATCTCGCTGGTGATCTGGACTACCACGCCGTGGACC
ATGCCGGCTAACCGCGCTATCTCACTGCATCCTGAATTCGACTACCAGCTGGTACAGATTGAAGGCCG
TGCTCTGATCCTCGCCAAAGAGATGGTTGAGAGCGTGATGCAGCGCGTTGGTGTTGCCGCCTGGACCG
TGCTGGGCGAAGCGAAAGGGGCAGACCTGGAGCTGATGGGCTTCCAGCATCCGTTCCTCGACCATAC
CTCTCCGGTTGTGCTGGGTGAGCATGTCACGCTGGAAGCCGGTACCGGTGCGGTCCATACCGCACCAG
GCCATGGCCCGGACGACTATGTTATCGGTCAGAAATACGGTATCGAAGTGGCTAACCCGGTCGGCCC
GGATGGCTGCTACCTGCCGGGAACCTACCCGACGCTGGATGGTGTGAACGTCTTTAAAGCCAACGAT
ATGATCGTTGAACTGCTGCGTGAAAAGGGTGCTCTGCTGCACGTTGAGAAACTGTTCCACAGCTATCC
ACACTGCTGGCGTCATAAAACGCCCATCATCTTCCGCGCTACGCCACAGTGGTTTATCAGCATGGATC
AGAAGGGCCTGCGTGCGCAGTCGCTGAAAGAGATCAAGGGCGTGCAGTGGATCCCGGACTGGGGTC
AGGCACGTATTGAATCGATGGTCGCGAACCGTCCTGACTGGTGTATTTCCCGTCAGCGTACCTGGGGC
GTGCCGATGGCGCTGTTCGTCCATAAAGACACCGAACAGCTGCACCCGGATTCGCTGGAGCTGATGG
AGAAAGTGGCGAAGCGGGTTGAGCAGGACGGCATTCAGGCATGGTGGGATCTTGATGCCCGCGACCT
GATGGGCGCCGATGCTGACAACTACGTTAAAGTCCCGGATACCCTGGACGTCTGGTTTGACTCCGGTT
CAACCAGCTACTCGGTCGTCGATGCCCGCCCTGAATTTGACGGCAATGCCCCTGACCTGTATCTGGAA
GGATCGGATCAGCACCGCGGCTGGTTTATGTCCTCACTGATGATCTCGACCGCGATGAAAGGCAAAG
CGCCTTACCGTCAGGTACTGACGCACGGCTTCACCGTCGATGGTCAGGGCCGTAAGATGTCCAAGTCA
CTGGGCAATACTGTCAGCCCGCAGGATGTGATGAACAAACTGGGCGCCGATATTCTGCGCCTGTGGG
TCGCCTCTACGGACTACTCCGGTGAGATCGCCGTATCCGACGAGATCCTTAAACGCTCTGCCGACAGC
TATCGCCGCATCCGTAACACCGCACGTTTCCTGCTGGCAAACCTTGCCGGTTTTAATCCGGAAACCGA
TAGGGTGAAACCGGAAGAGATGGTGGTGGATCGCTGGGCCGTTGGCCGTGCGCTGGCGGCACAG
AATGATATCGTAGCCTCGTATGAAGCTTATGACTTCCATGAAGTCGTGCAGCGTCTGATGCAGTTCTG
TTCGGTTGAGATGGGCTCCTTCTACCTGGATATCATCAAGGATCGTCAGTACACCGCGAAGGCCGATG
GCCTGGCGCGTCGCAGCTGTCAGACGGCGCTGTGGTATATCGTGGAAGCGCTGGTGCGCTGGATGGC
ACCGATTATGTCCTTCACTGCCGATGAAATCTGGGGTTACCTGCCGGGTAAACGCAGCCAGTATGTCT
TTACCGAAGAGTGGTTTGACGGGCTGTTCAGCCTGGAGGACAATCAGCCGATGAACGACAGTTACTG
GGCAGAACTGCTGAAAGTACGCGGTGAAGTCAACAAGGTGATCGAGCAGGCCCGCGCTGATAAGCG
GATTGGCGGGTCTCTGGAAGCCAGCGTGACGCTGTATGCTGACGCAGACCTGGCCGCGAAGCTGACC
AGCCTGGGTGAGGAGCTGCGCTTTGTGTTGCTGACTTCCGGGGCGCAGGTTGCGGATTATGCGCAGGC
CACCGCTGATGCACAGCAAAGCGAAGGGGTAAAGGTCTGAAAATTGCCCTGAGCAAAGCGGAAGG
CGAGAAGTGCCCGCGCTGCTGGCATTACACTAACGATATCGGCCAGAATGCTGAACACGCTGACGTG
TGCGGCCGTTGTGTCACTAACGTCGCGGGCAGCGGCGAACAGCGTAAGTTTGCATGA 105
DP67 NADH-quinone oxidoreductase subunit C/D
GTGATCGGCGAGCTGCGTAATCGTTTTGGGCCTGATGCCTTTACAGTACAAGCGACCCGTACCGGC
GTGCCGGTGGTCTGGGTAAAACGTGAGCAGTTGCTTGAGATTATTGAGTTCCTGCGCAAGCTGCCTAA
ACCCTATGTGATGCTGTATGACCTGCATGGCATGGATGAGCGCCTGCGTACTCACCGTGCCGGTTTAC
CGGCGGCGGATTTTTCCGTTTTCTATCACTTCATCTCCATTGAACGTAACCGCGACATCATGCTCAAGG
TGGCGTTGTCTGAAAACGATTTGAATGTGCCCACCATCACCAAAATTTTCCCGAATGCCAACTGGTAT
GAGCGTGAAACCTGGGAGATGTTTGGTATCAATGTTGAAGGCCACCCGCACCTGACGCGCATTATGA
TGCCGCAGAGCTGGGAAGGGCATCCGCTGCGCAAAGATTACCCTGCGCGTGCGACCGAGTTCGATCC
GTTTGAACTGACCAAGCAGAAAGAAGATCTGGAGATGGAATCTCTGACCTTCAAGCCTGAAGACTGG
GGCATGAAGCGTTCGACCAACAATGAGGACTTCATGTTCCTCAACCTGGGCCCGAACCACCCTTCTGC
GCACGGCGCGTTCCGTATCATCCTGCAACTGGACGGTGAAGAGATCGTCGACTGCGTGCCGGATATC
GGATACCACCATCGTGGTGCCGAAAAAATGGGTGAACGCCAGTCCTGGCACAGCTACATTCCGTATA
CCGACCGTATTGAGTATCTCGGCGGCTGCGTAAACGAAATGCCGTACGTGCTGGCGGTAGAAAAGCT
GGCTGGTATCAAAGTCCCTGAGCGCGTGGAAGTCATTCGCGTGATGCTATCAGAGCTGTTCCGTATAA
ACAGCCACCTGCTGTACATCTCTACGTTTATCCAGGACGTCGGTGCTATGTCCCCGGTGTTCTTTGCCT
TTACTGACCGCCAGAAAATTTACGACGTGGTAGAAGCCATTACCGGCTTCCGTATGCATCCGGCCTGG
TTCCGCATTGGTGGCGTGGCGCATGATCTGCCTAAAGGCTGGGAGCGCCTGCTGCGTGAGTTCCTGGA
TTGGATGCCTAAGCGTCTGAAAGCCTATGAGCAGACCGCACTGAAAAACTCCGTGCTTATTGCCCGTT
CCAAAGGGGTTTCTGCCTATAACATGGAAGAAGCACTGGCCTGGGGCACGACGGGGGCTGGCCTGCG
TGGTACCGGTCTGGACTTTGATGTGCGTAAATGGCGTCCATATTCCGGTTATGAAAACTTCGATTTCG
AAGTGCCAATCGGAGATGGCGTAAGCTGTGCTTACACCCGTGTCATGCTGAAGATGGAAGAGATGCG -continued

| SEQUENCE LISTING<br>Seq ID No.<br>Description<br>Sequence |
|---|

CCAGAGTATGCGCATCCTGGAACAGTGCCTGAAGAACATGCCAGCAGGCCCGTTCAAGGCTGACCAT
CCGCTGACCACGCCGCCGCCGAAAGAGCGCACGCTGCAGCATATCGAAACCCTGATCACTCACTTCC
TGCAGGTTTCGTGGGGCCCGGTAATGCCGGCAAACGAATCCTTCCAGATGATTGAAGCGACCAAAGG
GATCAACAGTTACTACCTGACCAGTGATGGCAGCACGATGAGCTACCGCACCCGCGTGCGTACGCCG
AGCTTCCCGCATTTGCAACAGATCCCATCGGTGATCAACGGCAGCCTGGTATCCGATCTGATCGTATA
CCTCGGTAGTATCGATTTTGTTATGTCAGACGTGGACCGCTAA

106
DP67 Protein RecA
ATGGCTATCGACGAAAACAAGCAAAAAGCACTGGCAGCAGCGCTGGGCCAGATTGAAAAGCAGT
TTGGTAAAGGCTCCATCATGCGCCTGGGTGAAGACCGCACCATGGATGTGGAAACCATCTCAACCGG
TTCTTTATCACTGGATATCGCGCTGGGTGCCGGTGGTTTACCAATGGGCCGTATCGTTGAAATCTATG
GCCCGGAGTCTTCCGGTAAAACCACCCTGACGCTGCAGGTTATCGCTTCTGCACAGCGTAAAGGGAA
AACCTGTGCATTTATCGATGCCGAGCATGCTCTGGACCCGGTCTACGCTAAAAAACTGGGCGTGGATA
TCGATAACTTGCTGTGTTCTCAGCCGGATACCGGTGAGCAGGCGCTGGAAATCTGTGATGCGCTGGCC
CGTTCCGGTGCGGTTGACGTCATCATCGTCGACTCCGTAGCGGCGTTGACACCAAAAGCAGAAATCG
AAGGTGAAATCGGTGACTCTCATATGGGCCTTGCGGCACGTATGATGAGCCAGGCGATGCGTAAGCT
GGCCGGTAACCTGAAGAACTCCGGTACGCTGCTGATCTTTATCAACCAGATCCGTATGAAAATTGGCG
TGATGTTCGGTAACCCGGAAACCACTACCGGTGGTAACGCTCTGAAATTCTACGCTTCTGTCCGTCTG
GATATTCGCCGCATCGGCGCGATCAAAGAGGGTGATGAAGTGGTGGGTAGCGAAACCCGCGTTAAAG
TGGTGAAAAACAAAATCGCAGCACCGTTTAAACAGGCTGAGTTCCAGATCATGTACGGCGAAGGTAT
CAACGTTTACGGTGAGCTGGTCGACCTGGGCGTGAAGCACAAGCTGATCGAAAAAGCCGGTGCCTGG
TACAGCTATAACGGTGACAAGATTGGTCAGGGTAAAGCCAACTCAGGTAACTTCCTGAAAGAGAACC
CGGCTATCGCTAACGAAATCGAAGCAAAACTGCGTGAAATGCTGTTGAACAGCCCGGACGATAAGCC
TGATTTTGTTCCGGCTCCGCATGAAGCCGATAGTGAAGTTAACGAAGATATCTAA 107
RNA polymerase sigma factor RpoD
ATGGAGCAAAACCCGCAGTCACAGCTTAAGCTACTTGTCACCCGTGGTAAGGAGCAAGGCTATCT
GACCTATGCCGAGGTCAATGACCATCTGCCGGAAGATATCGTCGACTCCGATCAGATTGAAGACATC
ATTCAGATGATCAACGACATGGGCATTCAGGTTGTAGAAGAAGCGCCTGATGCCGATGATTTGATGC
TGAATGAGAACAACAACGACACGGACGAAGACGCTGCCGAAGCGGCTGCTCAGGTATTATCCAGCGT
AGAATCTGAAATCGGACGTACCACCGACCCGGTGCGCATGTACATGCGCGAAATGGGGACGGTTGAA
CTGCTGACGCGTGAAGGCGAGATCGATATCGCCAAACGCATCGAAGAGGGTATCAACCAGGTACAGT
GTTCCGTTGCTGAATATCCTGAAGCGATTACTTACCTGCTTGAGCAATATGACCGTGTTGAAGCGGGC
GAAGCGCGCCTGTCGGATCTGATCACCGGTTTTGTCGACCCGAATGCCGAAGCAGAGATCGCCCCTA
CTGCGACTCACGTGGGTTCAGAACTTTCCGCTGAAGAGCGTGATGACGAAGAAGAAGACGAAGAGTC
TGACGACGACAGCTCGGATGATGACAACAGCATCGATCCGGAACTGGCGCGGGAAAAATTCAACGA
CCTGCGCGTTCAGTACGAAACCACCCGTACCGTTATCAAAGCGAAAAGCCGCAGCCACGCTGATGCC
ATCGCTGAGATCCAGAATCTGTCCGACGTGTTCAAGCAGTTCCGCCTGGTGCCGAAGCAGTTCGACTT
CCTGGTGAACAGCATGCGCACCATGATGGATCGCGTCCGTACTCAGGAACGCCTGATCCTCAAGCTGT
GCGTAGAAATCTGTAAGATGCCGAAGAAGAACTTCATTACCCTGTTCACCGGTAATGAAACCAGCGA
AACCTGGTTCAAAGCGGCACTGGCAATGAATAAGCCGTGGTCAGAGAAGCTGAACGATGTGTCAGAT
GACGTACACCGTAGCCTGATGAAGCTGCAGCAGATCGAAACGGAAACTGGCCTGACGATTGAACAGG
TAAAAGACATCAACCGTCGTATGTCGATCGGCGAAGCGAAAGCGCGCCGTGCGAAGAAAGAGATGG
TTGAGGCTAACCTGCGTCTGGTTATCTCTATCGCCAAGAAGTACACCAACCGTGGCCTGCAGTTCCTG
GATCTGATTCAGGAAGGTAACATCGGTCTGATGAAAGCGGTGGATAAGTTTGAATATCGCCGTGGTT
ATAAGTTCTCGACTTATGCCACCTGGTGGATCCGTCAGGCGATCACCCGTTCAATCGCTGACCAGGCG
CGTACCATCCGTATTCCGGTGCACATGATTGAGACGATTAACAAGCTCAACCGTATTTCCCGCCAGAT
GCTGCAAGAGATGGGCCGTGAGCCGACGCCGGAAGAGCTGGCCGAGCGTATGCTGATGCCGGAAGA
TAAGATCCGTAAGGTGCTGAAAATTGCCAAAGAGCCGATCTCTATGGAGACGCCGATTGGTGATGAT
GAAGATTCACATCTGGGTGATTTTATCGAAGACACCACGCTGGAGCTGCCGCTGGACTCCGCGACGTC
AGAGAGCCTGCGTTCTGCCACGCACGACGTGCTGGCCGGTCTGACCGCGCGTGAAGCCAAAGTACTG
CGTATGCGTTTCGGTATCGATATGAATACCGACCACACGCTGGAAGAAGTGGGCAAACAGTTCGACG
TAACGCGTGAGCGTATTCGTCAGATTGAGGCGAAAGCGCTGCGTAAGCTGCGTCACCCAAGCCGCTC
TGAAGTGCTGCGCAGCTTCCTCGACGATTAA 108
DNA-directed RNA polymerase subunit beta
ATGGTTTACTCCTATACCGAGAAAAAACGTATTCGTAAGGATTTTGGAAAGCGTCCACAAGTTCTG
GACATTCCATATCTCCTTTCTATCCAGCTTGACTCGTTCCAGAAGTTCATCGAGCAAGATCCGGAAGG
TCAATATGGTCTGGAAGCAGCATTCCGCTCCGTATTTCCAATCCAAAGCTATAGCGGTAATTCTGAGC
TGCAGTACGTCAGCTACCGTTTAGGCGAACCCGTCTTTGATGTGAAAGAGTGTCAGATTCGTGGCGTC
ACGTATTCTGCTCCTCTGCGCGTAAAACTGCGCCTGGTGATCTACGAGCGCGAAGCGCCGGAAGGCA
CCGTTAAAGACATCAAAGAACAAGAAGTTTACATGGGCGAAATTCCGCTCATGACGGATAACGGTAC
CTTTGTTATCAACGGTACTGAGCGCGTTATCGTTTCTCAGCTCCACCGTAGTCCTGGTGTCTTCTTCGA
CAGCGATAAGGGTAAAACCCACTCGTCCGGTAAAGTGCTGTATAACGCACGTATCATCCCTTACCGTG
GTTCATGGCTGGACTTCGAGTTCGACCCGAAAGACAACCTGTTCGTCCGTATTGACCGTCGCCGTAAA
CTGCCAGCGACCATCATTCTGCGCGCGTTGAATTACACCACTGAACAGATCCTCGACCTGTTCTTCGA
TAAAGTGGTTTACCAAATTCGCGACAACAAGCTGCAGATGGAGCTTATTCCTGAGCGCCTGCGTGGTG
AGACCGCTTCATTTGATATTGAAGCGAACGGCACCGTTTACGTCGAAAAAGGCCGCCGTATTACTGCG
CGCCATATTCGCCAGCTTGAGAAAGATGCTGTTGCCCACATCGAAGTGCCGGTTGAGTATATTGCCGG
TAAAGTGGTCGCTAAAGACTACGTTGATGAGAGCACCGGTGAACTGCTGATCGCAGCGAACATGGAA
CTGTCACTGGATCTGCTGGCTAAACTCAGCCAGTCCGGTCACAAGCGCATTGAAACCCTGTTCACCAA -continued

| SEQUENCE LISTING<br>Seq ID No.<br>Description<br>Sequence |
|---|

CGATCTGGATCACGGTGCGTACATGTCTGAGACGGTACGTGTCGACCCAACCAGCGATCGCCTGAGC
GCTCTGGTTGAGATCTACCGCATGATGCGTCCTGGTGAGCCACCAACGCGTGAAGCGGCTGAAAACC
TGTTTGAGAACCTGTTCTTCTCTGAAGACCGCTATGATCTGTCTGCGGTTGGTCGTATGAAGTTCAACC
GTTCTCTGCTGCGCGACGAGATCGAAGGTTCCGGTATCCTGAGCAAAGACGACATCATTCAGGTGAT
GAAGAAGCTCATCGGTATCCGTAACGGTATTGGCGAAGTGGATGATATCGACCACCTCGGCAACCGT
CGTATCCGTTCCGTTGGCGAAATGGCTGAAAACCAGTTCCGTGTTGGCCTTGTGCGCGTAGAGCGTGC
GGTGAAAGAGCGTCTGTCCCTGGGCGATCTGGATACCCTGATGCCACAGGACATGATCAACGCCAAG
CCAATTTCTGCGGCAGTGAAAGAGTTCTTCGGCTCCAGCCAGCTGTCACAGTTTATGGACCAGAACAA
CCCGTTGTCTGAGATCACGCATAAGCGTCGTATCTCTGCACTGGGTCCGGGCGGTCTGACGCGTGAGC
GTGCAGGCTTCGAAGTTCGAGACGTACACCCGACGCACTACGGTCGCGTATGTCCAATCGAAACGCC
GGAAGGTCCAAACATCGGTCTGATCAACTCCTTGTCTGTGTATGCACAGACCAATGAGTACGGTTTCC
TGGAAACCCCATACCGTCGCGTTCGCGAAGGCGTGGTGACCGACGAAATTCATTACCTCTCTGCTATT
GAAGAGGGTAACTACGTTATCGCTCAGGCAAACACCAATCTCGACGACGAAGGTCACTTCGTAGACG
ACCTGGTCACCTGCCGTAGCAAAGGCGAATCGAGTCTCTTCAACCGCGATCAAGTTGACTACATGGA
CGTTTCCACCCAGCAGGTGGTTTCCGTCGGTGCGTCACTGATCCCGTTCCTGGAGCACGATGACGCCA
ACCGCGCATTGATGGGTGCAAACATGCAACGTCAGGCGGTTCCTACTCTGCGTGCTGATAAGCCGCTG
GTAGGTACCGGTATGGAGCGTGCGGTTGCGGTTGACTCCGGTGTTACTGCCGTAGCGAAACGTGGTG
GTACCGTGCAGTACGTGGATGCATCCCGTATCGTTATTAAAGTTAACGAAGACGAAATGTATCCGGG
CGAAGCCGGTATCGACATTTACAACCTGACCAAATATACCCGTTCTAACCAGAACACCTGCATCAACC
AGATGCCTTGCGTGAACCTGGGTGAGCCAATCGAACGTGGTGATGTGCTGGCTGATGGCCCTTCAACC
GATCTCGGCGAACTGGCACTCGGTCAGAACATGCGCGTCGCGTTCATGCCGTGGAACGGCTACAACT
TCGAAGACTCCATTCTGGTCTCGGAGCGCGTTGTTCAGGAAGATCGCTTCACCACTATCCACATTCAG
GAACTGGCGTGTGTGTCTCGTGACACCAAGCTGGGGCCAGAAGAGATCACCGCTGACATCCCTAACG
TGGGTGAAGCTGCGCTCTCTAAACTGGATGAGTCCGGTATCGTGTATATCGGTGCGGAAGTGACCGGT
GGGGACATTCTGGTTGGTAAGGTAACACCTAAAGGTGAAACCCAGCTGACGCCAGAAGAGAAACTGC
TGCGTGCGATCTTCGGTGAAAAAGCGTCTGACGTTAAAGACTCTTCTCTGCGCGTACCAAACGGTGTG
TCAGGGACAATCATCGACGTTCAGGTCTTTACCCGCGATGGCGTGGAAAAAGACAAGCGTGCGCTGG
AAATCGAAGAGATGCAGCTGAAGCAGGCGAAGAAAGACCTGTCTGAAGAATTGCAGATCCTCGAAG
CCGGCTTGTTCAGCCGTATTAACTACCTGCTGGTTGCCGGCGGTGTTGAAGCGGAAAAACTGGAGAA
GCTGCCACGTGAGCGCTGGCTCGAACTGGGCCTGACCGACGAAGAGAAGCAAAATCAGCTGGAACA
GCTGGCCGAGCAGTACGACGAGCTGAAGCACGAGTTTGAGAAAAAACTTGAAGCCAAGCGCCGTAA
AATCACTCAGGGCGATGACCTGGCACCTGGCGTGCTGAAAATCGTGAAAGTGTATCTGGCCGTTAAA
CGTCAGATCCAGCCTGGTGACAAAATGGCAGGTCGTCACGGGAACAAAGGTGTTATCTCCAAGATCA
ACCCGATCGAAGATATGCCATACGATGAGTTCGGTACGCCGGTCGACATCGTACTGAACCCGCTGGG
CGTTCCATCACGTATGAACATTGGTCAGATTCTTGAAACCCACCTGGGTATGGCTGCGAAAGGCATTG
GCGAGAAAATTAACGCTATGCTTAAGAAGCAGGAAGAAGTGTCCAAGCTGCGTGAATTCATTCAGCG
TGCTTACGATCTGGGCAGCGATCTGCGTCAGAAAGTTGACCTGAACACCTTCACCGATGACGAAGTG
CTGCGCCTGGCAGAGAATCTGAAAAAAGGTATGCCAATTGCAACACCAGTGTTTGACGGCGCGAAAG
AGAGCGAAATCAAAGAGCTGTTACAGCTCGGCGGCCTGCCTTCTTCTGGCCAGATCACGCTGTTTGAT
GGTCGTACCGGTGAGCAGTTCGAACGTCAGGTTACCGTTGGCTACATGTACATGCTGAAGCTGAACC
ACCTGGTTGATGACAAAATGCATGCGCGTTCTACCGGTTCTTACAGCCTCGTTACTCAGCAGCCGCTG
GGTGGTAAGGCGCAGTTCGGTGGTCAGCGCTTCGGTGAGATGGAAGTGTGGGCACTGGAAGCATACG
GTGCCGCGTATACCCTGCAGGAAATGCTGACCGTGAAGTCTGATGACGTTAACGGCCGTACCAAGAT
GTATAAAAACATCGTTGACGGCAACCATCAGATGGAACCGGGCATGCCGGAATCTTTCAACGTACTG
TTGAAAGAGATCCGCTCGCTGGGTATCAACATCGAGCTGGAAGACGAGTAA

109
DP68 Glutamine--tRNA ligase
ATGAGCAAGCCCACTGTCGACCCTACCTCGAATTCCAAGGCCGGACCTGCCGTCCCGGTCAATTTC
CTGCGCCCGATCATCCAGGCGGACCTGGATTCGGGCAAGCACACGCAGATCGTCACCCGCTTCCCGC
CAGAGCCCAACGGCTACCTGCACATCGGTCACGCCAAGTCGATCTGTGTGAACTTCGGCCTGGCCCA
GGAGTTCGGTGGCGTCACGCACCTGCGTTTCGACGACACCAACCCGGCCAAGGAAGACCAGGAATAC
ATCGACGCCATCGAAAGCGACATCAAGTGGCTGGGCTTCGAATGGTCCGGTGAAGTGCGCTATGCGT
CCAAGTATTTCGACCAGTTGTTCGACTGGGCCGTCGAGCTGATCAAGGCCGGCAAGGCCTACGTCGA
CGACCTGACCCCGGAGCAGGCCAAGGAATACCGTGGCACGCTGACCGAGCCGGGCAAGAACAGCCC
GTTCCGTGACCGTTCGGTAGAAGAGAACCTCGACTGGTTCAACCGCATGCGCGCCGGTGAGTTCCCG
GACGGCGCCCGCGTGCTGCGCGCCAAGATCGACATGGCCTCGCCGAACATGAACCTGCGCGACCCGA
TCATGTACCGCATCCGCCACGCCCATCACCACCAGACCGGTGACAAGTGGTGCATCTACCCGAACTAT
GACTTCACCCACGGTCAGTCGGACGCCATCGAAGGCATCACCCACTCCATCTGCACCCTGGAGTTCGA
AAGCCATCGCCCGCTGTATGAGTGGTTCCTCGACAGCCTGCCGGTTCCGGCGCACCCGCGTCAGTACG
AGTTCAGCCGCCTGAACCTGAACTACACCATCACCAGCAAGCGCAAGCTCAAGCAGTTGGTGGACGA
AAAGCACGTGCATGGCTGGGATGACCCGCGCATGTCCACCCTGTCGGGTTTCCGCCGTCGCGGCTACA
CCCCGGCGTCGATCCGCAGCTTCTGCGACATGGTCGGCACCAACCGCTCCGACGGCGTGGTCGATTAC
GGCATGCTCGAGTTCAGCATCCGTCAGGACCTGGACGCCAACGCGCCGCGTGCCATGTGCGTATTGC
GCCCGTTGAAAGTCGTGATCACCAACTATCCGGAAGACAAGGTCGACCACCTCGAACTGCCGCGTCA
CCCGCAGAAAGAAGAACTTGGCGTGCGCAAGCTGCCGTTCGCGCGTGAAATCTACATCGACCGTGAT
GACTTCATGGAAGAGCCGCCGAAAGGCTACAAGCGCCTGGAGCCTAACGGCGAAGTGCGCCTGCGCG
GCAGCTACGTGATCCGTGCCGATGAAGCGATCAAGGACGCCGATGGCAACATCGTCGAACTGCGATG
CTCCTACGACCCGGAAACCCTGGGCAAGAACCCTGAAGGCCGCAAGGTCAAAGGCGTCGTTCACTGG
GTGCCGGCTGCTGCCAGCATCGAGTGCGAAGTGCGCCTGTACGATCGTCTGTTCCGTTCGCCGAACCC
TGAGAAGGCTGAAGACAGCGCCAGCTTCCTGGACAACATCAACCCTGACTCCCTGCAAGTTCTCACG
GGTTGTCGTGCCGAGCCATCGCTTGGCGACGCACAGCCGGAAGACCGTTTCCAGTTCGAGCGCGAAG
GTTACTTCTGCGCGGATATCAAGGACTCCAAACCTGGTCATCCGGTCTTCAACCGTACCGTGACCTTG
CGTGATTCGTGGGGCCAGTG -continued

| SEQUENCE LISTING Seq ID No. Description Sequence |
|---|

110
DP68 DNA gyrase subunit B
ATGAGCGAAGAAAACACGTACGACTCGACCAGCATTAAAGTGCTGAAAGGTTTGGATGCCGTACG
CAAACGTCCCGGTATGTACATCGGCGACACCGATGATGGTAGCGGTCTGCACCACATGGTGTTCGAG
GTGGTCGACAACTCCATCGACGAAGCTTTGGCCGGTCACTGCGACGACATCAGCATTATCATCCACCC
GGATGAGTCCATCACCGTGCGCGACAACGGTCGCGGTATTCCGGTCGATGTGCACAAAGAAGAAGGC
GTATCGGCGGCAGAGGTCATCATGACCGTGCTTCACGCCGGCGGTAAGTTCGACGACAACTCCTATA
AAGTTTCCGGCGGTTTGCACGGTGTAGGTGTGTCGGTGGTGAACGCTCTGTCCGAAGAGCTTATCCTG
ACTGTTCGCCGTAGCGGCAAGATCTGGGAACAGACCTACGTGCATGGTGTTCCACAAGAACCGATGA
AAATCGTTGGCGACAGTGAATCCACCGGTACGCAGATCCACTTCAAGCCTTCGGCAGAAACCTTCAA
GAATATCCACTTCAGTTGGGACATCCTGGCCAAGCGTATTCGTGAACTGTCGTTCCTTAACTCCGGTG
TGGGTATCGTCCTCAAGGACGAGCGCAGCGGCAAGGAAGAGTTGTTCAAGTACGAAGGCGGCTTGCG
TGCGTTCGTTGAGTACCTGAACACCAACAAGACTGCGGTCAACCAGGTGTTCCACTTCAACATCCAGC
GTGAAGACGGTATCGGCGTTGAAATCGCCCTGCAGTGGAACGACAGCTTCAACGAGAACCTGTTGTG
CTTCACCAACAACATTCCACAGCGCGACGGCGGTACTCACTTGGTGGGTTTCCGTTCCGCACTGACGC
GTAACCTGAACACCTACATCGAAGCGGAAGGCTTGGCCAAGAAGCACAAAGTGGCCACTACCGGTGA
CGATGCGCGTGAAGGCCTGACGGCGATTATCTCGGTGAAAGTGCCGGATCCAAAGTTCAGCTCCCAG
ACCAAAGACAAGCTGGTGTCTTCCGAAGTGAAGACCGCAGTGGAACAGGAGATGGGCAAGTACTTCT
CCGACTTCCTGCTGGAAAACCCGAACGAAGCCAAGTTGGTTGTCGGCAAGATGATCGACGCGGCGCG
TGCCCGTGAAGCGGCGCGTAAAGCCCGTGAGATGACCCGCCGTAAAGGCGCGTTGGATATCGCCGGC
CTGCCGGGCAAACTGGCTGACTGCCAGGAGAAGGACCCTGCCCTCTCCGAACTGTACCTGGTGGAAG
GTGACTCTGCTGGCGGTTCCGCCAAGCAGGGTCGTAACCGTCGCACCCAGGCTATCCTGCCGTTGAAG
GGTAAGATCCTCAACGTCGAGAAGGCCCGCTTCGACAAGATGATTTCCTCTCAGGAAGTCGGCACCTT
GATCACGGCGTTGGGCTGCGGTATTGGCCGCGATGAGTACAACATCGACAAACTGCGTTACCACAAC
ATCATCATCATGACCGATGCTGACGTCGACGGTTCGCACATCCGTACCCTGCTGCTGACCTTCTTCTTC
CGTCAGTTGCCGGAGCTGATCGAGCGTGGCTACATCTACATCGCTCAGCCGCCGTTGTACAAAGTGAA
AAAGGGCAAGCAAGAGCAGTACATCAAAGACGACGACGCCATGGAAGAGTACATGACGCAGTCGGC
CCTGGAAGATGCCAGCCTGCACTTGAACGACGAAGCCCCGGGCATTTCCGGTGAGGCGCTGGAGCGT
TTGGTTAACGACTTCCGCATGGTAATGAAGACCCTCAAGCGTCTGTCGCGCCTGTACCCTCAGGAGCT
GACCGAGCACTTCATCTACCTGCCTTCCGTGAGCCTGGAGCAGTTGGGCGATCACGCCCACATGCAGA
ATTGGCTGGCTCAGTACGAAGTACGTCTGCGCACCGTCGAGAAGTCTGGCCTGGTTTACAAAGCCAG
CTTGCGTGAAGACCGTGAACGTAACGTGTGGCTGCCGGAGGTTGAACTGATCTCCCACGGCCTGTCG
AACTACGTCACCTTCAACCGCGACTTCTTCGGCAGCAACGACTACAAGACCGTGGTTACCCTCGGCGC
GCAATTGAGCACCCTGTTGGACGACGGTGCTTACATCCAGCGTGGCGAGCGTAAGAAAGCGGTCAAG
GAGTTCAAGGAAGCCCTGGACTGGTTGATGGCTGAAAGCACCAAGCGCCACACCATCCAGCGATACA
AAGGTCTGGGCGAGATGAACCCGGATCAACTGTGGGAAACCACCATGGATCCTGCTCAGCGTCGCAT
GCTACGCGTGACCATCGAAGACGCCATTGGCGCAGACCAGATCTTCAACACCCTGATGGGTGATGCG
GTCGAGCCTCGCCGTGACTTCATCGAGAGCAACGCCTTGGCGGTGTCTAACCTGGATTTCTGA 111
DP68 Isoleucine--tRNA ligase
ATGACCGACTATAAAGCCACGCTAAACCTTCCGGACACCGCCTTCCCAATGAAGGCCGGCCTGCC
ACAGCGCGAACCGCAGATCCTGCAGCGCTGGGACAGTATTGGCCTGTACGGAAAGTTGCGCGAAATT
GGCAAGGATCGTCCGAAGTTCGTCCTGCACGACGGCCCTCCTTATGCCAACGGCACGATTCACATCGG
TCATGCGCTGAACAAAATTCTCAAGGACATGATCCTGCGTTCGAAAACCCTGTCGGGCTTCGACGCGC
CTTATGTTCCGGGCTGGGACTGCCACGGCCTGCCGATCGAACACAAAGTCGAAGTGACCTACGGCAA
GAACCTGGGCGCGGATAAAACCCGCGAACTGTGCCGTGCCTACGCCACCGAGCAGATCGAAGGGCA
GAAGTCCGAATTCATCCGCCTGGGCGTGCTGGGCGAGTGGGACAACCCGTACAAGACCATGAACTTC
AAGAACGAGGCCGGTGAAATCCGTGCCTTGGCTGAAATCGTCAAAGGCGGTTTCGTGTTCAAGGGCC
TCAAGCCCGTGAACTGGTGCTTCGACTGCGGTTCGGCCCTGGCTGAAGCGGAAGTCGAGTACGAAGA
CAAGAAGTCCTCGACCATCGACGTGGCCTTCCCGATCGCCGACGACGACAAGCTGGCTCAAGCCTTT
GGCCTGTCCAGCCTGCCAAAGCCTGCAGCCATCGTGATCTGGACCACCACCCCGTGGACCATCCCGGC
CAACCAGGCGCTGAACGTGCACCCGGAATTCACCTACGCCCTGGTGGACGTCGGTGATCGCCTGCTG
GTGCTGGCTGAAGAAATGGTCGAGGCCTGCCTGGCGCGCTACGAGCTGCAAGGTTCGGTCATCGCCA
CCACCACCGGCACTGCGCTGGAGCTGATCAATTTCCGTCACCCGTTCTATGACCGTCTGTCGCCGGTG
TACCTGGCTGACTACGTAGAGCTGGGTTCGGGTACTGGTGTGGTTCACTCCGCGCCGGCCTACGGCGT
TGATGACTTTGTGACCTGCAAAGCCTACGGCATGGTCAACGATGACATCCTCAACCCGGTGCAGAGC
AATGGCGTGTACGCGCCGTCGCTGGAGTTCTTTGGCGGCCAGTTCATCTTCAAGGCCAACGAGCCGAT
CATCGACAAACTGCGTGAAGTCGGTTCGCTGCTGCACACCGAAACCATCAAGCACAGCTACATGCAC
TGCTGGCGTCACAAGACCCCGCTGATCTACCGCGCTACCGCGCAGTGGTTTATCGGCATGGACAAAG
AGCCGACCAGCGGCGACACCCTGCGTGTGCGCTCGCTCAAAGCGATCGAAGAGACCAAGTTTGTCCC
GGCCTGGGGCCAGGCGCGCCTGCACTCGATGATCGCCAACCGCCCGGACTGGTGCATCTCCCGCCAG
CGCAACTGGGGCGTGCCGATTCCGTTCTTCCTGAACAAGGAAAGCGGCGAGCTGCACCCACGTACCG
TTGAACTGATGGAAGCAGTGGCGCTGCGCGTTGAGCAGGAAGGCATCGAAGCCTGGTTCAAGCTGGA
CGCCGCCGAACTGCTGGGCGACGAAGCGCCGCTGTACGACAAGATCAGCGACACCCTCGACGTGTGG
TTCGACTCGGGTACCACCCACTGGCACGTGCTGCGCGGTTCGCACCCGATGGGTCACGCCACCGGCCC
GCGTGCCGACCTGTACCTGGAAGGCTCGGACCAACACCGTGGCTGGTTCCACTCGTCGTTGCTGACCG
GCTGCGCCATCGACAACCACGCGCCGTACCGCGAACTGCTGACCCACGGCTTCACCGTCGACGAGAC
GGGCCGCAAGATGTCCAAGTCGCTGAAAAACGTGATCGAGCCGAAAAAGATCAACGACACCCTGGG
CGCCGATATCATGCGTCTGTGGGTCGCCTCGACCGATTACTCGGGCGAAATCGCCGTGTCGGACCAGA
TCCTGGCCCGTAGCGCCGATGCCTACCGCCGTATCCGTAATACCGCACGCTTCCTGCTGTCGAACCTG
ACCGGTTTCAACCCGGCCACCGACATCCTGCCGGCCGAGGACATGCTCGCCCTGGACCGTTGGGCCGT
GGACCGTACGCTGTTGCTGCAGCGCGAGTTGCAGGAACACTACGGCGAATACCGTTTCTGGAACGTG -continued

| SEQUENCE LISTING Seq ID No. Description Sequence |
|---|

TACTCCAAGATCCACAACTTCTGCGTGCAGGAGCTGGGTGGTTTCTACCTCGATATCATCAAGGACCG
CCAGTACACCACCGGCGCCAACAGCAAGGCGCGCCGCTCGGCGCAGACCGCGCTGTACCACATCTCT
GAAGCGCTGGTGCGCTGGATCGCACCGATCCTGGCCTTCACCGCTGACGAACTGTGGGAATACCTGC
CGGGCGAGCGTAACGAATCGGTGATGCTCAACACCTGGTACGAAGGCCTGACCGAATTGCCGGCCAA
CTTCGAACTGGGCCGCGAGTACTGGGAAGGCGTGATGGCCGTCAAGGTTGCGGTGAACAAGGAGCTG
GAAGTTCAGCGCGCGGCCAAGGCCGTCGGTGGCAACCTGCAAGCCGAAGTCACCCTGTTTGCCGAGG
AAGGCCTGACCGCCGACCTGGCCAAGCTGAGCAACGAACTGCGCTTCGTACTGATCACCTCGACCGC
GAGCCTGGCACCGTTTGCCCAGGCACCTGCGGACGCAGTGGCCACCGAAGTGCCGGGCCTCAAGCTC
AAAGTGGTCAAGTCGGCCTTTCCTAAGTGCGCCCGTTGCTGGCACTGCCGTGAAGACGTCGGCGTGA
ACCCAGAGCATCCGGAAATCTGCGGTCGTTGCGTCGACAACATCAGCGGTGCTGGCGAGGTTCGCCA
CTATGCCTAA

112
DP68 NADH-quinone oxidoreductase subunit C/D
ATGACTACAGGCAGTGCTCTGTACATCCCGCCTTACAAGGCAGACGACCAGGATGTGGTTGTCGA
ACTCAATAACCGTTTTGGCCCTGACGCCTTCACCGCCCAGGCCACACGCACCGGTATGCCGGTGCTGT
GGGTGGCGCGCGCCAAGCTCGTCGAAGTCCTGAGCTTCCTGCGCAACCTGCCCAAGCCGTACGTCAT
GCTTTATGACCTGCATGGCGTGGACGAGCGTCTGCGCACCAAGCGTCAAGGTTTGCCGAGCGGTGCC
GATTTCACCGTGTTCTACCACTTGATGTCGCTGGAACGTAACAGCGACGTGATGATCAAGGTCGCGCT
GTCCGAAAGCGACTTGAGCATCCCGACCGTCACCGGTATCTGGCCGAATGCCAGCTGGTACGAGCGC
GAAGTTTGGGACATGTTCGGTATCGACTTCCCGGGCCACCCGCACCTGACGCGCATCATGATGCCGCC
GACCTGGGAAGGTCACCCGCTGCGCAAGGACTTTCCTGCCCGCGCAACCGAATTCGACCCGTTCAGC
CTCAACCTCGCCAAGCAGCAGCTTGAAGAAGAAGCTGCACGCTTCCGTCCGGAAGACTGGGGCATGA
AACGCTCCGGCACCAACGAGGACTACATGTTCCTCAACCTGGGCCCGAACCACCCTTCGGCTCACGGT
GCCTTCCGTATCATCCTGCAACTGGACGGCGAAGAAATCGTCGACTGTGTGCCGGACATCGGTTACCA
CCACCGTGGTGCCGAGAAGATGGCCGAGCGCCAGTCCTGGCACAGCTTCATCCCGTACACCGACCGT
ATCGACTACCTCGGCGGCGTGATGAACAACCTGCCGTACGTGCTGTCGGTCGAGAAGCTGGCCGGTA
TCAAGGTGCCGGACCGCGTCGACACCATCCGCATCATGATGGCCGAGTTCTTCCGCATCACCAGCCAC
CTGCTGTTCCTGGGTACCTATATCCAGGACGTTGGCGCCATGACCCCGGTGTTCTTCACCTTCACCGAC
CGTCAACGCGCCTACAAGGTGATCGAAGCCATCACCGGTTTCCGCCTGCACCCGGCCTGGTATCGCAT
CGGCGGCGTGGCGCACGACCTGCCGAACGGCTGGGAGCGCCTGGTCAAGGAATTCATCGACTGGATG
CCCAAGCGTCTGGACGAGTACCAAAAGGCTGCGCTGGACAACAGCATCCTCAAGGGTCGTACCATCG
GCGTCGCGCAGTACAACACCAAAGAAGCCCTGGAATGGGGCGTCACTGGTGCCGGCCTGCGTTCGAC
CGGCTGCGACTTCGACCTGCGTAAAGCACGGCCGTACTCGGGCTACGAGAACTTCGAGTTCGAAGTG
CCGCTGGCCGCCAATGGCGATGCCTACGACCGGTGCATCGTGCGCGTTGAAGAAATGCGCCAGAGCC
TGAAGATCATCGAGCAGTGCATGCGCAACATGCCGGCTGGCCCGTACAAGGCGGATCATCCGCTGAC
CACACCGCCGCCGAAAGAGCGCACGCTGCAGCACATCGAAACCCTGATCACGCACTTCCTGCAAGTT
TCGTGGGGCCCGGTGATGCCGGCCAACGAATCCTTCCAGATGATCGAAGCGACCAAGGGTATCAACA
GTTATTACCTGACGAGCGATGGCGGCACCATGAGCTACCGCACCCGGATTCGTACCCCAAGCTTTGCC
CACTTGCAGCAGATCCCTTCGGTGATCAAAGGCGAGATGGTCGCGGACTTGATTGCGTACCTGGGTA
GTATCGATTTCGTTATGGCCGACGTGGACCGCTAA 113
DP68 Protein RecA
ATGGACGACAACAAGAAGAAAGCCTTGGCTGCGGCCCTGGGTCAGATCGAACGTCAATTCGGCAA
GGGTGCCGTAATGCGTATGGGCGATCACGACCGTCAGGCGATCCCGGCTATTTCCACTGGCTCTCTGG
GTCTGGACATCGCACTCGGCATTGGCGGCCTGCCAAAAGGCCGTATCGTTGAAATCTACGGTCCTGAA
TCTTCCGGTAAAACCACCCTGACCCTGTCGGTGATTGCCCAGGCGCAAAAAATGGGCGCCACCTGTGC
GTTCGTCGACGCCGAGCACGCCCTGGACCCGGAATACGCCGGTAAGCTGGGCGTCAACGTTGACGAC
CTGCTGGTTTCCCAGCCGGACACCGGTGAGCAAGCCCTGGAAATCACCGACATGCTGGTGCGCTCCA
ACGCCATCGACGTGATCGTGGTCGACTCCGTGGCTGCCCTGGTACCGAAAGCTGAAATCGAAGGCGA
AATGGGCGACATGCACGTGGGCCTGCAAGCCCGCCTGATGTCCCAGGCGCTGCGTAAAATTACCGGT
AACATCAAGAACGCCAACTGCCTGGTGATCTTCATCAACCAGATCCGTATGAAGATCGGCGTAATGTT
CGGCAGCCCGGAAACCACTACCGGTGGTAACGCGCTGAAGTTCTACGCTTCGGTCCGTCTGGACATCC
GCCGTACCGGCGCGGTGAAGGAAGGTGACGAAGTTGTTGGTAGCGAAACTCGCGTTAAAGTCGTGAA
GAACAAGGTCGCTCCGCCTTTCCGTCAGGCAGAGTTCCAGATTCTCTACGGCAAGGGTATCTACCTGA
ACGGCGAGATGATTGACCTGGGCGTACTGCACGGTTTCGTCGAGAAGTCCGGTGCCTGGTATGCCTAC
AACGGCAGCAAGATCGGTCAGGGCAAGGCCAACTCGGCCAAGTTCCTGGCAGACAACCCGGATATCG
CTGCCACGCTTGAGAAGCAGATTCGCGACAAGCTGCTGACCCCAGCGCCAGACGTGAAAGCTGCCGC
CAACCGCGAGCCGGTTGAAGAAGTGGAAGAAGCTGACACTGATATCTGA 114
DP68 RNA polymerase sigma factor RpoD
ATGTCCGGAAAAGCGCAACAACAGTCTCGTATTAAAGAGTTGATCACCCTTGGTCGTGAGCAGAA
ATATCTGACTTACGCAGAGGTCAACGATCACCTGCCTGAGGATATTTCAGATCCTGAGCAGGTGGAA
GACATCATCCGCATGATTAATGACATGGGGATCCCCGTACACGAGAGTGCTCCGGATGCGGACGCCC
TTATGTTGGCCGACTCCGATACCGACGAGGCAGCTGCTGAAGAAGCGGCTGCTGCGCTGGCAGCGGT
GGAGACCGACATCGGTCGTACGACTGACCCTGTGCGCATGTATATGCGTGAAATGGGTACCGTCGAG
CTGCTGACACGTGAAGGCGAAATCGAAATCGCCAAACGTATTGAAGAGGGTATCCGTGAAGTGATGG
GCGCAATCGCGCACTTCCCTGGCACGGTTGACCACATTCTCTCCGAGTACACTCGCGTCACCACCGAA
GGTGGCCGCCTGTCTGACGTTCTGAGCGGCTACATCGACCCGGACGACGGCATTGCGCCGCCTGCCGC
CGAAGTACCGCCGCCCGTCGATGCGAAAGCCGCGAAGGCTGACGACGACACCGAAGACGACGATGC
TGAAGCCAGCAGCGACGACGAAGATGAAGTTGAAAGCGGCCCGGACCCGATCATCGCAGCCCAGCG
TTTCGGTGCGGTTTCCGATCAAATGGAAATCACCCGCAAGGCCCTGAAAAAGCACGGTCGCTCCAAC -continued

| SEQUENCE LISTING Seq ID No. Description Sequence |
|---|

AAGCTGGCGATTGCCGAGCTGGTGGCCCTGGCTGAGCTGTTCATGCCGATCAAGCTGGTACCGAAGC
AATTCGAAGGCTTGGTTGAGCGTGTTCGCAGTGCCCTTGAACGTCTGCGTGCGCAAGAACGCGCAATC
ATGCAGCTGTGTGTACGTGATGCACGTATGCCGCGGGCTGACTTCCTGCGCCAGTTCCCGGGCAACGA
AGTAGACGAAAGCTGGACCGACGCACTGGCCAAAGGCAAGGCGAAATACGCCGAAGCCATTGGTCG
CCTGCAGCCGGACATCATCCGTTGCCAGCAGAAGCTGACCGCGCTTGAGACCGAAACCGGTCTGACG
ATTGCTGAAATCAAAGACATCAACCGTCGCATGTCGATCGGTGAGGCCAAGGCCCGCCGCGCGAAGA
AAGAGATGGTTGAAGCGAACTTGCGTCTGGTGATCTCGATCGCCAAGAAGTACACCAACCGTGGTCT
GCAATTCCTCGATCTGATCCAGGAAGGCAACATCGGCTTGATGAAGGCGGTGGACAAGTTCGAATAC
CGTCGCGGCTACAAGTTCTCGACTTATGCCACCTGGTGGATCCGTCAGGCGATCACTCGCTCGATCGC
CGACCAGGCTCGCACCATCCGTATTCCGGTGCACATGATCGAGACGATCAACAAGCTCAACCGTATTT
CCCGGCAGATGTTGCAGGAAATGGGTCGCGAACCGACCCCGGAAGAGCTGGGCGAACGCATGGAAA
TGCCTGAGGATAAAATCCGCAAGGTATTGAAGATCGCTAAAGAGCCGATCTCCATGGAAACGCCGAT
TGGTGATGACGAAGACTCCCACCTGGGTGACTTCATCGAAGACTCGACCATGCAGTCGCCAATCGAT
GTCGCCACTGTTGAGAGCCTTAAAGAAGCGACTCGCGACGTACTGTCCGGCCTCACTGCCCGTGAAG
CCAAGGTACTGCGCATGCGTTTCGGCATCGACATGAATACCGACCACACCCTTGAGGAAGTCGGTAA
GCAGTTTGACGTGACCCGCGAGCGGATCCGTCAGATCGAAGCCAAGGCGCTGCGCAAGTTGCGCCAC
CCGACGCGAAGCGAGCATCTGCGCTCCTTCCTCGACGAGTGA

115
DP68 DNA-directed RNA polymerase subunit beta
ATGGCTTACTCATATACTGAGAAAAAACGTATCCGCAAGGACTTTAGCAAGTTGCCGGACGTCATG
GATGTCCCGTACCTTCTGGCTATCCAGCTGGATTCGTATCGTGAATTCTTGCAGGCGGGAGCGACCAA
AGATCAGTTCCGCGACGTGGGCCTGCATGCGGCCTTCAAATCCGTTTTCCCGATCATCAGCTACTCCG
GCAATGCTGCGCTGGAGTACGTGGGTTATCGCCTGGGCGAACCGGCATTTGATGTCAAAGAATGCGT
GTTGCGCGGTGTTACGTACGCCGTACCTTTGCGGGTAAAAGTCCGCCTGATCATTTTCGACAAAGAAT
CGTCGAACAAAGCGATCAAGGACATCAAAGAGCAAGAAGTCTACATGGGCGAAATCCCACTGATGA
CTGAAAACGGTACCTTCGTAATCAACGGTACCGAGCGTGTTATTGTTTCCCAGCTGCACCGTTCCCCG
GGCGTGTTCTTCGACCACGACCGCGGCAAGACGCACAGCTCCGGTAAACTCCTGTACTCCGCGCGGA
TCATTCCGTACCGCGGTTCGTGGTTGGACTTCGAGTTCGACCCGAAAGACTGCGTGTTCGTGCGTATC
GACCGTCGTCGCAAGCTGCCGGCCTCGGTACTGCTGCGCGCGCTCGGTTACACCACTGAGCAGGTGCT
GGACGCTTTCTACACCACCAACGTATTCAGCCTGAAGGATGAAACCCTCAGCCTGGAGCTGATTGCTT
CGCGTCTGCGTGGTGAAATTGCCGTTCTGGACATTCAGGACGAAAACGGCAAAGTGATCGTTGAAGC
GGGTCGTCGTATTACTGCGCGCCACATCAACCAGATCGAAAAAGCCGGCATCAAGTCGCTGGAAGTG
CCTCTGGACTACGTCCTGGGTCGCACCACCGCCAAGGTTATCGTTCACCCGGCTACAGGCGAAATCCT
GGCTGAGTGCAACACCGAGCTGAACACCGAAATCCTGGCAAAAATCGCCAAGGCCCAGGTTGTTCGC
ATCGAGACCCTGTACACCAACGACATCGACTGCGGTCCGTTCATCTCCGACACACTGAAGATCGACTC
CACCAGCAACCAATTGGAAGCGCTGGTCGAGATCTATCGCATGATGCGTCCTGGTGAGCCACCGACC
AAAGACGCTGCCGAGACCCTGTTCAACAACCTGTTCTTCAGCCCTGAGCGTTATGACCTGTCTGCGGT
CGGCCGGATGAAGTTCAACCGTCGTATCGGTCGTACCGAGATCGAAGGTTCGGGCGTGCTGTGCAAG
GAAGATATCGTCGCGGTACTGAAGACTCTGGTCGACATCCGTAACGGTAAAGGCATCGTCGATGACA
TCGACCACCTGGGTAACCGTCGTGTTCGCTGCGTAGGCGAAATGGCCGAAAACCAGTTCCGCGTTGG
CCTTGTGCGTGTTGAACGTGCGGTCAAAGAGCGTCTGTCGATGGCTGAAAGCGAAGGCCTGATGCCG
CAAGACCTGATCAACGCCAAGCCAGTGGCTGCGGCAGTGAAAGAGTTCTTCGGTTCCAGCCAGCTTT
CCCAGTTCATGGACCAGAACAACCCGCTCTCCGAGATCACCCACAAGCGCCGTGTTTCTGCACTGGGC
CCGGGCGGTCTGACCCGTGAGCGTGCTGGCTTTGAAGTTCGTGACGTACACCCGACGCACTACGGTCG
TGTTTGCCCGATCGAAACGCCGGAAGGTCCGAACATCGGTCTGATCAACTCCCTGGCCGCTTATGCGC
GCACCAACCAGTACGGCTTCCTCGAGAGCCCGTACCGCGTGGTGAAAGACGCTCTGGTCACCGACGA
GATCGTATTCCTGTCCGCCATCGAAGAAGCTGATCACGTGATCGCTCAGGCTTCGGCCACGATGAACG
ACAAGAAAGTCCTGATCGACGAGCTGGTAGCTGTTCGTCACTTGAACGAGTTCACCGTCAAGGCGCC
GGAAGACGTCACCTTGATGGACGTTTCGCCGAAGCAGGTAGTTTCGGTTGCAGCGTCGCTGATCCCGT
TCCTGGAACACGATGACGCCAACCGTGCGTTGATGGGTTCCAACATGCAGCGTCAAGCTGTACCAAC
CCTGCGCGCTGACAAGCCGCTGGTAGGTACCGGCATGGAGCGTAACGTAGCCCGTGACTCCGGCGTT
TGCGTCGTAGCCCGTCGTGGCGGCGTGATCGACTCCGTTGATGCCAGCCGTATCGTGGTTCGTGTTGC
CGATGATGAAGTTGAAACTGGCGAAGCCGGTGTCGACATCTACAACCTGACCAAATACACCCGCTCG
AACCAGAACACCTGCATCAACCAGCGTCCGCTGGTGAGCAAGGGTGACCGCGTTCAGCGTAGCGACA
TCATGGCCGACGGCCCGTCCACTGACATGGGTGAACTGGCTCTGGGTCAGAACATGCGCATCGCGTTC
ATGGCATGGAACGGCTTCAACTTCGAAGACTCCATCTGCCTGTCCGAGCGTGTTGTTCAAGAAGACCG
TTTCACCACGATCCACATTCAGGAACTGACCTGTGTGGCACGTGATACCAAGCTTGGGCCAGAGGAA
ATCACTGCAGACATCCCGAACGTGGGTGAAGCTGCACTGAACAAGCTGGACGAAGCCGGTATCGTTT
ACGTAGGTGCTGAAGTTGGCGCAGGCGACATCCTGGTAGGTAAGGTCACTCCGAAAGGCGAGACCCA
ACTGACTCCGGAAGAGAAGCTGCTGCGTGCCATCTTCGGTGAAAAAGCCAGCGACGTTAAAGACACC
TCCCTGCGTGTACCTACCGGTACCAAGGGTACTGTTATCGACGTACAGGTCTTCACCCGTGACGGCGT
TGAGCGTGATGCTCGTGCACTGTCCATCGAGAAGACTCAACTCGACGAGATCCGCAAGGACCTGAAC
GAAGAGTTCCGTATCGTTGAAGGCGCGACCTTCGAACGTCTGCGTTCCGCTCTGGTAGGCCACAAGGC
TGAAGGCGGCGCAGGTCTGAAGAAAGGTCAGGACATCACCGACGAAGTACTCGACGGTCTTGAGCAC
GGCCAGTGGTTCAAACTGCGCATGGCTGAAGATGCTCTGAACGAGCAGCTCGAGAAGGCCCAGGCCT
ACATCGTTGATCGCCGTCGTCTGCTGGACGACAAGTTCGAAGACAAGAAGCGCAAACTGCAGCAGGG
CGATGACCTGGCTCCAGGCGTGCTGAAAATCGTCAAGGTTTACCTGGCAATCCGTCGCCGCATCCAGC
CGGGCGACAAGATGGCCGGTCGTCACGGTAACAAAGGTGTGGTCTCCGTGATCATGCCGGTTGAAGA
CATGCCGCACGATGCCAATGGCACCCCGGTCGACGTCGTCCTCAACCCGTTGGGCGTACCTTCGCGTA
TGAACGTTGGTCAGATCCTCGAAACCCACCTGGGCCTCGCGGCCAAAGGTCTGGGCGAGAAGATCAA
CCGTATGATCGAAGAGCAGCGCAAGGTTGCTGACCTGCGTAAGTTCCTGCACGAGATCTACAACGAG
ATCGGCGGTCGCAACGAAGAGCTGGACACCTTCTCCGACCAGGAAATCCTGGACTTGGCGAAGAACC
TGCGCGGCGGCGTTCCAATGGCTACCCCGGTGTTCGACGGTGCCAAGGAAAGCGAAATCAAGGCCAT -continued

| SEQUENCE LISTING<br>Seq ID No.<br>Description<br>Sequence |
|---|

GCTGAAACTGGCAGACCTGCCGGAAAGCGGCCAGATGCAGCTGTTCGACGGCCGTACCGGCAACAAG
TTTGAGCGCCCGGTTACTGTTGGCTACATGTACATGCTGAAGCTGAACCACTTGGTAGACGACAAGAT
GCACGCTCGTTCTACCGGTTCGTACAGCCTGGTTACCCAGCAGCCGCTGGGTGGTAAGGCTCAGTTCG
GTGGTCAGCGTTTCGGGGAGATGGAGGTCTGGGCACTGGAAGCATACGGTGCTGCATACACTCTGCA
AGAAATGCTCACAGTGAAGTCGGACGATGTGAACGGTCGGACCAAGATGTACAAAAACATCGTGGA
CGGCGATCACCGTATGGAGCCGGGCATGCCCGAGTCCTTCAACGTGTTGATCAAAGAAATTCGTTCCC
TCGGCATCGATATCGATCTGGAAACCGAATAA

116
DP69 Glutamine--tRNA ligase
GTGCGCGAGGACCTGGCCAGCGGAAAGCACCAGGCGATCAAGACCCGCTTCCCGCCGGAGCCGAA
CGGCTACCTGCACATCGGCCACGCCAAGTCGATCTGCCTGAACTTCGGCATCGCCGGTGAGTTCAGCG
GCGTCTGCAACCTGCGTTTCGACGACACCAATCCGGCCAAGGAAGACCCGGAGTACGTGGCCGCGAT
CCAGGACGACGTGCGCTGGCTGGGCTTTGAATGGAACGAGCTGCGCCACGCCTCGGACTACTTCCAG
ACCTATTACCTGGCCGCCGAGAAGCTGATCGAACAGGGCAAGGCCTACGTCTGCGACCTGTCGGCCG
AGGAAGTGCGCGCCTACCGCGGCACCCTGACCGAGCCGGGCCGCCCGTCGCCGTGGCGTGACCGCAG
CGTCGAGGAGAACCTCGACCTGTTCCGCCGCATGCGTGCCGGTGAATTCCCCGATGGCGCGCGCACC
GTGCGCGCCAAGATCGACATGGCCAGCGGCAACATCAACCTGCGTGATCCGGCGCTGTACCGCATCA
AGCACGTCGAGCACCAGAACACCGGCAACGCGTGGCCGATCTACCCGATGTACGACTTCGCCCATGC
GCTGGGCGATTCGATCGAGGGCATCACCCACTCGCTGTGCACGCTGGAATTCGAAGACCACCGCCCG
CTGTACGACTGGTGCGTGGACAACGTCGACTTCGCCCACGATGACGCGCTGACCCAGCCGCTGGTCG
ACGCCGGCCTGCCGCGCGAAGCGGCCAAACCGCGCCAGATCGAGTTCTCGCGCCTGAACATCAACTA
CACGGTGATGAGCAAGCGCAAGCTGATGGCGCTGGTCACCGAACAGCTGGTGGACGGCTGGGAAGA
CCCGCGCATGCCGACCCTGCAGGGCCTGCGTCGCCGTGGCTACACCCCGGCAGCGATGCGCCTGTTCG
CCGAGCGCGTGGGCATCAGCAAGCAGAATTCGCTGATCGATTTCAGCGTGCTGGAAGGCGCGCTGCG
CGAAGACCTGGACAGCGCCGCACCGCGCCGCATGGCCGTGGTCGACCCGGTCAAGCTGGTGCTGACC
AACCTGGCCGAAGGCCACGAAGAGCAGCTGACCTTCAGCAACCACCCGAAGGACGAGAGCTTCGGT
ACCCGCGAAGTGCCGTTCGCACGTGAAGTGTGGATCGACCGCGAGGACTTCGCCGAAGTGCCGCCGA
AGGGCTGGAAGCGCCTGGTTCCCGGTGGTGAAGTGCGCCTGCGCGGCGCCGGCATCATCCGCTGCGA
CGACGTGATCAAGGATGCCGACGGCACCATCACCGAGCTGCGCGGCTGGCTGGATCCGGAATCGCGC
CCGGGCATGGAAGGCGCCAACCGCAAGGTCAAGGGCACCATCCACTGGGTCAGCGCGGTGCACGGT
GTGCCGGCCGAGATCCGCCTGTATGACCGCCTGTTCTCGGTGCCGAACCCGGACGATGAATCGGAAG
GCAAGACCTACCGCGACTACCTCAATCCGGACTCGCGCCGCACCGTCACCGGCTATGTCGAGCCGGC
GGCTGCCAGCGCTGCGCCGGAACAGTCGTTCCAGTTCGAGCGCACCGGCTACTTCGTTGCCGACCGCC
GCGACCACACCGAAGCCAAGCCGGTGTTCAACCGCAGCGTGACCCTGCGCGACACCTGGTCGGCCTG
A 117
DP69 DNA gyrase subunit B
ATGACCGACGAACAGAACACCCCGGCAAACAACGGCAACTACGACGCCAACAGCATTACGGCCCT
GGAAGGCCTGGAGGCTGTCCGCAAGCGCCCAGGCATGTACATCGGCGACGTCCATGACGGCACCGGC
CTGCATCACATGGTGTTCGAGGTCGTCGACAACTCAATCGACGAAGCCCTCGCCGGCCATGCCGACC
ACGTCTCGGTGACGATCCATGCCGATGGCTCGGTAGGCGTGTCCGACAACGGTCGCGGCATCCCGAC
GGGCAAGCACGAGCAGATGAGCAAGAAGCTCGACCGCGATGTGTCTGCAGCCGAAGTGGTGATGAC
GGTCCTGCACGCAGGCGGCAAGTTCGACGACAACAGCTACAAGGTTTCCGGCGGCCTGCACGGCGTG
GGCGTCAGCGTGGTCAACGCGCTGTCGCAGAAGCTGGTCCTGGATATCTACCAGGGTGGCTTCCACTA
CCAGCAGGAGTACGCCGACGGCGCAGCACTGCATCCGCTGAAGCAGATCGGCCCCAGCACCAAGCGC
GGGACCACCCTGCGCTTCTGGCCCTCGGTAAAGGCTTTCCACGACAACGTGGAATTCCACTACGACAT
CCTGGCCCGGCGCCTGCGCGAACTGTCCTTCCTCAATTCCGGCGTCAAGATCGTGCTGGTGGACGAGC
GTGGTGATGGCCGCCGCGACGACTTCCATTACGAGGGCGGCATCCGCAGCTTCGTGGAGCATCTGGC
GCAGTTGAAGACGCCGTTGCACCCGAACGTGATCTCGGTGACCGGCGAATCCAATGGCATCACCGTG
GAAGTGGCGCTGCAGTGGACCGACTCCTACCAGGAGACGATGTACTGCTTCACCAACAACATTCCGC
AGAAGGACGGCGGTACCCACCTGGCCGGCTTCCGTGGCGCATTGACCCGCGTGCTCAACAACTACAT
CGAGCAGAACGGCATCGCCAAGCAGGCCAAGATCAACCTGACCGGCGATGACATGCGCGAAGGCAT
GATCGCGGTGCTGTCGGTGAAGGTGCCGGATCCCAGCTTCTCCAGCCAGACCAAGGAAAAGCTGGTC
AGCTCGGATGTGCGCCCGGCCGTGGAAAGCGCGTTCGGCCAGCGCCTGGAAGAGTTCCTGCAGGAAA
ACCCGAACGAAGCCAAGGCCATCGCCGGCAAGATCGTCGACGCTGCCCGTGCCCGCGAAGCGGCGCG
CAAGGCCCGCGACCTGACCCGCCGCAAGGGTGCGCTGGATATCGCCGGCCTGCCGGGCAAGCTGGCC
GACTGCCAGGAAAAGGATCCGGCGCTGTCCGAACTGTTCATCGTCGAGGGTGACTCGGCAGGTGGTT
CGGCCAAGCAGGGTCGCAACCGCAAGAACCAGGCGGTGCTGCCGCTGCGCGGCAAGATCCTCAACGT
GGAACGTGCGCGCTTCGACCGCATGCTGGCGTCCGACCAGGTGGGTACGCTGATCACCGCGCTGGGT
ACCGGCATCGGTCGTGACGAGTACAACCCGGACAAGCTGCGGTACCACAAGATCATCATCATGACCG
ACGCCGACGTCGACGGCGCGCACATCCGCACCCTGCTGCTGACGTTCTTCTACCGTCAGATGCCGGAG
CTGATCGAGCGCGGTTATGTCTATATCGGCCTGCCGCCGTTGTACAAGATCAAGCAGGGCAAGCAGG
AGCTGTACCTGAAGGACGACCCGGCGCTGGACAGCTATCTGGCCAGCAGCGCGGTGGAGAACGCTGG
GCTGGTGCCGGCCAGCGGCGAGCCGCCGATCGACGGCGTGGCACTGGAAAAGCTGCTGCTCGCCTAC
GCTGCCGCGCAGGACACGATCAACCGCAATACCCACCGCTACGACCGCAACCTGCTCGAAGCGCTGG
TCGACTTCATGCCGCTGGAGCTGGAAAACCTGCGCACTGCAGGTCCTGGCGAAGGTCTGGACGCGTT
GGCCAAGCACCTCAACCAGGGCAACCTCGGCAGCGCCCGCTTCACCCTGGAACTGCAGGAACCCAAC
GAGCAGCGTCCGGCGGCCGTACTGGTGACCCGCAGCCACATGGGCGAACAGCACATCCAGGTGCTGC
CGCTGTCCGCGCTGGAAAGCGGCGAACTGCGCGGCATCCATCAGGCAGCGCAGCTGCTGCACGGTCT
GGTCCGCGAAGGCGCGGTCATCACCCGTGGCGCCAAGTCGATCGAGATCGACTCGTTCGCACAGGCC
CGCAACTGGCTGTTGGACGAAGCCAAGCGCGGCCGGCAGATCCAGCGATTCAAGGGTCTGGGCGAAA
TGAATCCGGAACAGCTGTGGGATACCACCGTCAATCCCGATACCCGTCGCCTGCTGCAGGTGCGCATC -continued

| SEQUENCE LISTING<br>Seq ID No.<br>Description<br>Sequence |
|---|

GAAGACGCGGTGGCCGCTGACCAGATCTTCAGCACCCTGATGGGTGATGTGGTCGAACCGCGTCGTG
ACTTCATCGAAGACAACGCGTTGAAGGTCGCCAACCTGGATATCTGA

118
DP69 Isoleucine--tRNA ligase
GTGAGCCAGGACTACAAGACCACCCTCAACCTGCCGGCCACCGAATTCCCGATGCGCGGCGACCT
GCCCAAGCGCGAGCCGGGCATTCTGGCGCGCTGGGAAGAGCAGGGGCTCTACCAGCAGCTGCGCGAC
AACGCCGCCGGCCGCCCGCTGTTCGTGCTGCATGACGGCCCGCCGTACGCCAATGCGCGCATCCACCT
GGGCCATGCGGTCAACAAGATCCTCAAGGACATCATCGTCAAGTCGCGCTACCTGGCCGGCTTCGAT
GCGCCCTACGTGCCGGGCTGGGACTGCCATGGCCTGCCGATCGAAATCGCGGTGGAAAAGAAGTGGG
GCAAGGTCGGGGTGAAGCTCGATGCGGTCGAGTTCCGGCAGAAGTGCCGCGAGTTCGCCGAAGAACA
GATCGACATCCAGCGTGCCGACTTCAAGCGCCTGGGCGTCACCGGCGACTGGGACAACCCGTACAAG
ACCCTAAGCTTCGATTTCGAGGCCAACGAGATCCGTGCGCTGTCCAAGATCGTGGCCAACGGCCATCT
GCTGCGTGGCGCCAAGCCGGTCTACTGGTGCTTCGACTGCGGCTCGGCACTGGCCGAGGCCGAGATC
GAGTACCACGAGAAGACCTCGCCGGCGATCGACGTGGCCTACACCGCGCGTGATCCGCAGGCGGTGG
CGCAGGCGTTCGGCGTCAGCCTGCCGGCCGATGTCGAAGTGGCGGTGCCGATCTGGACCACCACTCC
GTGGACGCTGCCGGCTTCGCTGGCGGTGTCGCTGGGCGCGGACATCCGCTACGTGCTGGCCGAAGGC
CCGGCGCACAACGGCAAGCGCCGTTGGCTGGTGCTGGCTGCTGCGCTGGCCGAACGGTCGCTGCAGC
GCTACGGCGTGGACGCGGTGGTGCTGCACGGTGAAGCCGAAGGTTCGGCGCTGGAAAACCAGCTGCT
GGCGCACCCGTTCTACCCGGAGCGCGAGATCCCCGTGCTCAACGGCGAACACGTGTCCGACGAGGAC
GGTACCGGTGCGGTGCACACTGCCCCCGGCCACGGCCAGGAAGACTACGTGGTCAGCCAGAAGTACG
GCCTGCTGGAGAAGTACAACGCCGGCCAGATCAATCCGGTCGACGGTGCGGGCGTGTACCTGGCGTC
CACCCCGCCCGCCGGTGACCTGGTGCTGGCCGGTACCCACATCTGGAAGGCGCAGCAGCCGATCATC
GAAGTGCTGGCCGCCAGCGGCGCGCTGCTCAAGGCCGTGGAGATCGTGCACAGTTATCCGCATTGTT
GGCGCCACAAGAAGACCCCGCTGGTGTTCCGCGCCACCCCGCAGTGGTTCATTTCGATGGACAAGGC
CAACCTGCGCAACGATGCGCTGGCCGCGATCGATACCGTCGGCTGGTTCCCGAGCTGGGGCAAGGCG
CGCATCCAAAGCATGATCGACGGCCGCCCGGACTGGACCATCTCGCGCCAGCGCACCTGGGGCGTGC
CGATCGCGCTGTTCACCCACCGCCAGACCGGCGAGATCCACCCGCGTTCGGTGGAGCTGATGCAGCA
GGTGGCCGACCGCGTTGAAGCCGAAGGCATCGACGTGTGGTACTCGCTGGATGCGGCTGAACTGCTG
GGCGCTGAAGCGGCCGACTACGAGAAGGTCACCGACATCCTCGATGTCTGGTTCGATTCCGGCGTGA
CCCACGAAGCCGTGCTGGCTGCCCGTGGCTTCGGCAAGCCGGCCGATCTGTACCTGGAAGGTTCGGA
CCAGCATCGCGGCTGGTTCCAGTCCTCGCTGCTGACCGGCGTGGCCATCGACAAGCGCGCGCCGTAC
AAGCAGTGCCTCACCCACGGTTTCACCGTGGACGAGCACGGCCGCAAGATGTCCAAGTCGCTGGGCA
ACGGCATCGAACCGCAGGAAATCATGAACAAGCTGGGCGCGGACATCCTGCGCCTGTGGATCGCCTC
GGCCGACTACAGCAACGAGATGTCGCTGTCGCAGGAAATCCTCAAGCGCACCGCCGACGCCTACCGC
CGCCTGCGCAACACCGCCCGCTTCCTGCTGGGCAACCTGGACGGTTTCGATCCGGCCCAGCACCTGCG
CCCGCTCAACGAGATGGTCGCGCTGGACCGCTGGATCGTGCATCGCGCCTGGGAGCTGCAGGAGAAG
ATCAAGGCGGCGTATGACAACTACGACATGGCCGAGATCGTGCAGTTGCTGCTGAACTTCTGCAGCG
TGGACCTGGGCTCGCTGTACCTGGACGTGACCAAGGATCGCCTGTATACGATGCCGACCGATTCGGAT
GGTCGTCGTTCGGCGCAGAGCGCGATGTACCACATCGCCGAAGCGTTCACCCGCTGGGTGGCGCCGA
TCCTGACCTTCACCGCCGACGAGCTGTGGGGCTACCTGCCGGGCGATCGTGCCGGCCACGTGCTGTTC
ACTACCTGGTACGAGGGCCTGGCACCGCTGCCGACCGATGCACAGCTCAACGCTGCCGACTTCGATC
AGCTGCTGGCCGTGCGCGAGCAGGTGGCCAAGGTGCTGGAGCCGATGCGCGCCAATGGTGCGATCGG
TGCCGCGCTGGAAGCGGAGATCACCATCGCCGCCAGCGAAGAGCAGGCCGCGCGCTGGCAGCCGCTG
GCCGATGAACTGCGTTTCCTGTTCATCAGTGGTGACGTGCAGGTGCGTCCGGCGACCACCGACGAGGT
GTTCGTCAGCGCGCAGCCGACGCAGAAGTCCAAGTGCGTGCGCTGCTGGCACCACCGTGCCGACGTT
GGCAGCAATGCCGACCACCCGGAACTGTGCGGCCGCTGCGTGACCAACATCGCCGGTGCCGGCGAAG
CGCGGAGCTGGTTCTGA 119
DP69 Glycine--tRNA ligase beta subunit
ATGAGCCACTTGTCTCCCCTGCTGATTGAACTGGGCACCGAAGAGTTGCCGGTCAAGGCGCTGCCG
GGCCTGGCCCAGGCCTTCTTCGACGGTGTTGTCGATGGCCTGCGCAAGCGCGGCGTCGAACTGGAGCT
GGGCGATGCCCGCCCGCTGTCGACCCCGCGCCGCCTGGCCGTGCTGCTGCCGGGCGTTGGCCTGGAA
CAGCCGGAACAACACAGCGAAGTGCTGGGCCCGTACCTGAACATCGCGCTGGACGCCGAAGGCCAG
CCGACCAAGGCGCTGCAGGGTTTCGCGGCCAAGGCCGGGATCGACTGGACCGCGCTGGAGAAGACC
ACCGACAACAAGGGTGAGCGCTTCGTGCACCGTGCGGTGACTCCGGGCGCGCGCACCGCTGCGCTGC
TGCCGGAGATCCTGCGCGAGGCCATCGCCGGCATGCCGATTCCCAAGCCGATGCGCTGGGGCGACCA
CAGCTGGGGCTTCGCCCGCCCGGTGCACTGGCTGGTGCTGCTGCATGGCGGCGACGTGGTCGAGGCC
GAACTGTTTGGCCTGAAGGCCGACCGCATGAGCCGCGGCCACCGCTTCCTGCACGACAAGACCGTGT
GGCTGACCCAGCCGCAGGACTATGTCGAATCGCTGCGCGCCGCCTTCGTGCTGGTCGATCCGGCCGA
GCGCCGCCGGCGCATCGTTGCCGAAGTGGAAGCCGCTGCCGCCACCGCCGGTGGCAGCGCACGCATC
ACCGAGGACAACCTGGAGCAGGTGGTGAACCTGGTCGAGTGGCCGGCGGCAGTGTTGTGCAGCTTCG
AGCGCGCGTTCCTGGCGGTACCGCAGGAAGCGCTGATCGAGACGATGGAGATCAACCAGAAGTTCTT
CCCGGTGCTGGATGACGGCGGCAAGCTGACCGAGAAGTTCATCGGCATCGCCAACATCGAGTCCAAG
GACGTGGCCGAAGTGGCCAAGGGCTACGAGCGCGTGATCCGCCCGCGCTTCGCCGATGCCAAGTTCT
TCTTCGACGAAGACCTGAAGCAGGGCCTGCAGGCGATGGGCGAGGGCCTGAAGACGGTGACCTACCA
GGCCAAGCTGGGCAGCGTGGCCGACAAGGTCGCGCGCGTGGCGGCGCTGGCCGAGGTGATCGCTGCG
CAGGTGGGGGCCGACCCGGTGCTGGCCAAGCGTGCCGCGCAGCTGGCCAAGAACGACCTGCAGTCGC
GCATGGTCAATGAGTTCCCGGAACTGCAGGGCATCGCTGGCCGCCACTACGCGGTGGCCGGTGGCGA
GTCGCCGGAGGTGGCGCTGGCCATCGACGAGGCCTACCAGCCGCGCTTCGGTGGCGATGACATCGCG
CTGTCGCCGCTGGGCAAGGTGCTGGCGATCGCCGAGCGTGTGGACACGCTGGCCGGCGGTTTCGCCG
CGGGCCTGAAGCCGACCGGCAACAAGGACCCGTTCGCCCTGCGCCGCAACGCGCTGGGCCTGGCCCG
CACGATTATCGAAAGTGGCTTCGAGCTGGACCTGCGCGCGCTGCTGGCCAGCGCCAATGCCGGGCTG -continued

| SEQUENCE LISTING Seq ID No. Description Sequence |
| --- |

ACCGTGCGCAACGTGCAGGCCGACGTGGCTGAGCTGTACGACTTCATCCTCGACCGCCTGAAGGGCT
ACTACAGCGACAAGGGCGTGCCGGCCAGCCACTTCAATGCGGTGGCTGAGCTGAAGCCGGTCTCGCT
GTACGATTTCGACCGTCGCCTGGACGCCATCGGTATCTTCGCGGCGCTGCCGGAGGCCGAGGCGCTG
GCAGCGGCCAACAAGCGCATCCGCAACATCCTGCGCAAGGCCGAAGGCGATATTCCGGGCCAGATCG
ATGCGGCCCTGTTGCAGGAAGATGCCGAGCGCGCGCTGGCGGAAGCCGTGACTGCAGCCATCGACGA
CACCGGCGCCAGCCTGCACCAGAAGGACTACGTGGCCGTGCTGGCGCGCCTGGCCCGCCTGCGTCCG
CAGGTCGATGCGTTCTTCGATGGGGTGATGGTCAATGCCGAGGATCCGGCACTGCGCGGCAACCGCC
TGGCGCTGCTGACGATGCTGGGCGAGCGCTTGGGCAAGGTCGCGGCGATCGAGCATCTGTCGAGCTG
A

120
DP69 Glutamine synthetase
ATGTCCGTGGAAACCGTAGAGAAGCTGATCAAGGACAACCAGATCGAGTTCGTCGATCTGCGCTT
CGTCGACATGCGTGGTGTCGAACAGCATGTGACCTTCCCGGTCAGCATCGTCGAGCCGTCGCTGTTTG
AAGAAGGCAAGATGTTCGATGGCAGCTCGATCGCCGGCTGGAAGGGCATCAACGAGTCGGACATGGT
GCTGCTGCCGGACACCGCCAGCGCCTACGTCGACCCGTTCTACGCCGATCCGACCATCGTGATCAGCT
GCGACATCCTCGACCCGGCCACCATGCAGCCGTATGGCCGTTGCCCGCGCGGCATCGCCAAGCGCGC
CGAGTCCTACCTGAAGTCCTCGGGCATCGCCGAAACCGCGTTCTTCGGCCCGGAGCCGGAGTTCTTCA
TCTTCGACTCGGTGCGTTTCGCCAATGAAATGGGCAACACCTTCTTCAAGGTCGACTCGGAAGAAGCG
GCGTGGAACAGCGGCGCCAAGTACGACGGCGCCAACAGCGGCTACCGTCCGGGCGTGAAGGGCGGT
TATTTCCCCGTTCCGCCGACCGACACCCTGCACGACCTGCGTGCGGAGATGTGCAAGACCCTGGAACA
GGTCGGCATCGAAGTGGAAGTGCAGCACCACGAAGTGGCCACCGCCGGCCAGTGCGAGATCGGCAC
CAAGTTCAGCACCCTGGTGCAGAAGGCCGACGAACTGCTGCGGATGAAGTACGTCATCAAGAACGTC
GCCCACCGCAACGGCAAGACCGTCACCTTCATGCCCAAGCCGATCGTCGGCGACAACGGCAGCGGCA
TGCACGTGCACCAGTCGCTGTCCAAGGGCGGCACCAACCTGTTCTCCGGTGACGGCTACGGTGGCCTG
AGCCAGATGGCGCTGTGGTACATCGGCGGCATCTTCAAGCATGCCAAGGCGATCAACGCCTTTGCCA
ACTCGGGTACCAACAGCTACAAGCGCCTGGTGCCGGGCTTCGAAGCCCCGGTGATGCTGGCCTACTC
GGCGCGCAACCGTTCGGCCTCGTGCCGCATTCCGTGGGTGTCCAACCCGAAGGCGCGTCGCATTGAA
ATGCGCTTCCCCGATCCGATCCAGTCGGGCTACCTGACCTTCACCGCGCTGATGATGGCCGGCCTGGA
CGGCATCAAGAACCAGATCGACCCGGGCGCACCGAGCGACAAGGATCTGTACGACCTGCCGCCGGA
AGAAGAGAAGCTGATTCCGCAGGTCTGCTCCTCGCTGGACCAGGCCCTGGAAGCGCTGGACAAGGAC
CGTGAGTTCCTCAAGGCCGGTGGCGTGATGAGCGATGACTTCATCGACGGCTACATCGCGCTGAAGA
TGCAGGAAGTGACCAAGTTCCGCGCGGCGACCCACCCGCTGGAATACCAGTTGTACTACGCCAGCTG
A 121
DP69 Glucose-6-phosphate isomerase
ATGACAACGAACAACGGATTCGACTCGCTGCATTCCCACGCCCAGCGCCTGAAGGGCGCAAGCAT
CCCCAGCCTGCTCGCCGCCGAACCCGGCCGCGTACAGGACCTGGCGCTGCGGGTCGGTCCGTTGTATG
TCAACTTCGCCCGGCAGAAATACGATGCCGCGGCGTTGCAGGCGCTGTTGGCGCTGGCTGCCGAACG
TGATGTCGGCGGCGCCATCACGCGCCTGTTCCGTGGCGAGCAGGTCAATCTGACCGAAGGCCGCGCC
GCACTGCACACCGCACTGCGCGGCGACGTGGTCGATGCGCCGGTTGCCGCCGAGGCCTATGCCACGG
CCCGCGAAATCCGCCAGCGCATGGGCGTGCTGGTGCGCGCACTGGAAGACAGTGGCGTGACCGATGT
GGTCAGTGTCGGCATCGGCGGTTCCGATCTCGGTCCGCGTCTGGTCGCCGACGCACTGCGTCCAGTCA
CTGGCGCTCGCCTGCGCGTGCATTTCGTGTCTAACGTGGACGGCGCTGCCATGCAGCGCACGCTGGCC
ACGCTGGATCCGGCGAAGACCGCCGGCATCCTCATTTCCAAGACCTTCGGTACCCAGGAAACCCTGCT
CAACGGCCAGATCCTGCACGATTGGCTGGGTGGCAGCGAGCGCCTGTACGCGGTCAGCGCCAATCCG
GAACGCGCCGCCAAGGCCTTCGCCATCGCCGCCGAGCGCGTGCTGCCGATGTGGGACTGGGTAGGGG
GGCGCTATTCGCTGTGGTCGGCCGTCGGTTTCCCGATCGCACTGGCCATCGGCTTCGAGCGTTTCGAG
CAGTTGCTGGAAGGCGCCGCGCAGATGGATGCGCATGCGCTGGACGCGCCGCTGGAGCGCAACCTGC
CGGTGCTGCACGGCCTGACCGACATCTGGAACCGCAATCTGCTGGGCTCTGCCACGCATGCGGTGAT
GACCTACGACCAGCGCTTGGCGCTGCTGCCGGCCTACCTGCAGCAGCTGGTGATGGAAAGCCTGGGC
AAGCGCGTGCAGCGCGATGGCCAGCCGGTCACCACCGACACCGTGCCGGTGTGGTGGGGCGGTGCCG
GCACCGATGTGCAGCACAGCTTCTTCCAGGCCCTGCACCAGGGCACCAGCATCATTCCGGCCGATTTC
ATCGGCTGCGTGCACAACGACGATCCGTATACGGTCAACCACCAGGCGTTGATGGCCAACCTGCTGG
CGCAGACCGAAGCGCTGGCCAACGGCCAGGGCAGTGACGATCCGCACCGCGATTATCCGGGTGGCCG
CCCGAGCACGATGATCCTGCTCGACGCGCTCACCCCGCAGGCGCTGGGCGCCTTGATCGCGATGTAC
GAACACGCCGTGTACGTGCAGTCGGTGATCTGGAACATCAACGCCTTCGACCAGTTCGGTGTCGAGCT
GGGCAAGCAGCTGGCCAGTGGCCTGCTGCCCGCTCTGCAGGGTGAGGATGTCGAGGTCAACGACCCG
CTGACCCGTGAGCTGCTGGCCCAGCTGAAGGGCTGA 122
DP69 Leucine--tRNA ligase
ATGACCAGCGTCGAACCCAACGTTTACGATCCGCAGCAGGTTGAATCCGCCGCCCAGAAGTACTG
GGACGCTACCCGTGCCTTCGAGGTCGATGAAGCCTCGGACAAGCCGAAGTACTACTGCCTGTCGATG
CTTCCGTATCCGTCCGGTGCGCTGCACATGGGCCACGTGCGCAATTACACGATCGGCGACGTGATCAG
CCGCTACAAGCGCATGACCGGCCACAACGTGCTGCAGCCGATGGGCTGGGACGCGTTTGGCCTGCCG
GCGGAAAACGCTGCGATCAAGAACAAGACCGCGCCGGCCGCCTGGACCTACAAGAACATCGACCAC
ATGCGCAGCCAGCTGCAGTCGCTGGGCTATGCCATCGACTGGTCGCGCGAGTTCGCCACCTGCCGCCC
GGACTATTACGTCCACGAGCAGCGCATGTTCACCCGCCTGATGCGCAAGGGCCTGGCCTACCGCCGC
AACGCGGTGGTGAACTGGGACCCGGTCGACCAGACCGTGCTGGCCAACGAGCAGGTCATCGACGGCC
GTGGCTGGCGCTCCGGCGCGCTTGTGGAAAAGCGCGAGATCCCGCAGTGGTTCCTGCGCATCACCGA
CTACGCCCAGGAACTGCTGGACGGCCTGGATGAGCTGGACGGCTGGCCGGAGTCGGTCAAGACCATG
CAGCGCAACTGGATCGGCCGCTCCGAAGGGCTGGAAATCCAGTTCGACGTGCGCGACGTCGATGGTG -continued SEQUENCE LISTING
Seq ID No.
Description
Sequence CCGCACTGGATCCGCTGCGCGTGTTCACCACCCGCCCGGACACCGTGATGGGCGTGACTTTCGTGTCG
ATCGCGGCCGAACATCCGCTGGCGCTGCATGCCGCGAAGAACAACCCGGAACTGGCTGCGCTGCTGT
CGGAAATGAAGCAGGGCGGCGTGTCCGAGGCCGAGCTGGAGACCCAGGAAAAGCGCGGCATGGATA
CCGGCCTGCGCGCCGTGCATCCGGTTACCGGTGCCCAGGTGCCGGTGTGGGTCGCCAACTTCGTGCTG
ATGGGCTACGGCACTGGCGCGGTGATGGCCGTACCGGGCCACGACCAGCGCGACAATGAATTCGCCA
ACAAGTACAACCTGCCGATCCGCCAGGTCATCGCGCTGAAGTCGCTGCGCAAGGACGAAGGCGCCTA
CGACGCGACGCGCTGGCAGGACTGGTACGGCGACAAGACCCGCGAGACCGAACTGGTCAACTCCGA
AGAGTTCGACGGCCTGGACTTCCAGGGCGCTTTCGAGGCGCTGGCCGAACGGTTCGAGCGCAAGGCC
CAGGGACAGCGCCGGGTGAACTACCGCCTGCGCGACTGGGGCGTGAGCCGCCAGCGCTACTGGGGCT
GCCCGATTCCGGTGATCTACTGCGACAAGTGTGGCGCGGTACCGGTGCCGGAAGACCAGCTGCCGGT
GGTGCTGCCGGAAGACGTGGCGTTCGCCGGTACCGGTTCGCCGATCAAGACCGATCCGGAATGGCGC
AAGACCACCTGCCCGGACTGCGGCGGTGCGGCCGAGCGTGAGACCGACACCTTCGACACCTTCATGG
AGTCGAGCTGGTACTACGCCCGCTACACCTCGCCGGGCGCCCGCGATGCGGTCGACAAGCGCGGCAA
CTACTGGCTGCCGGTGGACCAGTACATCGGTGGCATCGAACACGCGATCCTGCACCTGATGTATTTCC
GCTTCTACCACAAGCTGCTGCGCGACGCGCGGATGGTGGACAGCAACGAACCCGCGCGGAACCTGCT
GTGCCAGGGCATGGTGATCGCTGAGACCTACTACCGCCCGAACCCGGACGGCTCGAAGGACTGGATC
AACCCGGCCGATGTGGAAGTGCAGCGCGACGAGCGCGGCCGCATCACCGGCGCCACCCTGATCGCCG
ACGGTCAGCCGGTGGTGGTCGGTGGTACCGAGAAGATGTCCAAGTCGAAGAACAACGGCGTGGACCC
GCAGGCGATGGTCGGCAAGTACGGCGCCGATACCGTGCGCCTGTTCTCGATGTTCGCTGCACCGCCG
GAACAGTCGCTGGAATGGAACGAAGCCGGCGTGGACGGCATGGCCCGCTTCCTGCGCCGCCTGTGGG
CACAGGTGCAGAAGCACGCTGCCGAGGGTGCCGCACCGGCGCTCGACGCGGCCGCGCTGGATGCCGG
CCAGAAGGCCCTGCGCCGCAAGACCCACGAGACCATCGGCAAGGTCGGCGACGACTACGGCCGCCG
CCACAGCTTCAACACCGCCATTGCCGCGGTGATGGAGCTGATGAACGCGCTGGCCAAGTTCGAGGAC
GGCAGTGAACAGGGGCGCGCCGTGCGCCAGGAAGCACTGCAGGCCATCGTGCTGCTGCTCAACCCGA
TCACCCCGCATGCCAGCCACGCCCTGTGGCAGGTACTGGGCCATGGCGAAACGCTGCTGGAAGATCA
GCCGTTCCCGCAGGCCGACAGCAGTGCGCTGGTGCGCGATGCGCTGACTTTGGCCGTGCAGGTCAAT
GGCAAGCTGCGTGGCACCATCGAGGTCGCCGCCGATGCCGCGCGCGAGCAGATCGAAGCGCTGGCCC
TGGCCGAGCCGAACGCGGCCAAGTTCCTGGAAGGCCTGACGGTGCGCAAGATCATCATCGTTCCCGG
CAAGATCGTGAACATCGTCGCTGCCTGA 123
DP70 Glycine--tRNA ligase beta subunit
ATGTCTAAACATACAGTATTGTTCGAATTGGGCTGTGAAGAACTTCCACCTAAAAGCCTCAAAAAA
TTACGTGATGCACTGCATGCTGAAACGGTAAAAGGCTTAAAAGATGCAGGCTTAGCATTCGACTCAA
TCGAAGCTTATGCAGCACCGCGTCGTTTGGCACTTAAAATTGTGAATATCGATGGCGCTCAGCCTGAT
ACACAAAAACGCTTTGACGGCCCTGCAAAAGAAGCGGCTTATGATGCTGAAGGCAAACCAAGCAAA
GCATTAGAAGGCTTTATGCGTGGTCAAGGCATCACTGCGGATCAAGTCACCACGTTCCAAGCGGGTA
AAGTTGAAAAGGTTTGCTATTTAAAAGATGTTAAAGGTCAAAGCCTTGAGGTTTTACTGCCACAAATT
CTACAAGCAGCTTTGGACAATCTTCCAATTGCAAAACGTATGCGTTCAGCGGCAAGCCGTACTGAATT
CGTGCGTCCTGTAAAATGGGTGGTGTTGCTCAAAGACAATGATGTGATTGCAGCCACTATTCAAGATC
ACAAAGCAGGCAATGTGACTTATGGTCATCGTTTCCATGCCCCTGAAGCGATTACTTTGGCTCATGCA
GATGAATATCTTGCCAAGTTAAAAGCGGCTTATGTGGTTGCTGACTTTGCAGAACGCCAAGCCATCAT
TGACCAACAAGTCAAAGCGTTGGCTGATGAAGTTAATGCGATTGCGATTGTACCAAGCGACCTGCGT
GATGAAGTGACCGCATTGGTGGAATGGCCTGTTGCGCTACGTGCCAGCTTTGAGGAGCGTTTCCTTGC
TGTACCGCAAGAAGCTTTGATTACCACGATGCAAGACAACCAAAAATACTTCTGTTTGGTGAATAGTG
ATAACAAGCTACAGCCTTATTTCATTACTGTTTCAAATATTGAGTCTAAAGATCCGATTCAAATTATTG
AAGGCAATGAAAAAGTGGTTCGTCCACGTTTGTCGGATGCTGAATTCTTCTTCTTGCAAGATCAAAAG
CAACCACTAGCTTCTCGTAAAGAAAAACTGGCTAACATGGTGTTCCAAGCACAATTGGGTACGCTGT
GGGATAAGTCACAACGTATTGCAAAATTGGCTGTGGCTTTATCGAACATCACGGGTGCAACTGCGGC
TGATGCTGAAAAAGCAGCATTGCTGGCAAAATGTGACTTAACCTCTGAATTGGTGGGTGAATTCCCTG
AACTTCAAGGCATTGCGGGAACCTATTACGCACGCATTGAAGGTGAAAACCATGAAGTGGCTGAAGC
TTTAGGCGAACAGTATTTACCTAAATTTGCAGGCGATGTTTTACCGCAAACAAAAACAGGCACAACC
ATTGCCCTTGCCGACCGTTTAGACACGCTCACGGGTATTTTTGGTATTGGTCAAGCACCTACAGGTTCT
AAAGATCCGTTTGCATTACGTCGTTCTGCAATCGGTATTTTACGTTTGGTGACTGAAAACAATCTTGAT
GTGTCGATTGAAGATTTAATCCAGCTGGCATTAAACGCTTATGGCGATGTTGTAGCGGATCATGCGAA
GACTTTAGCGGATGCTGTTGCATTCCTTGAAGGTCGTTACCGTGCCAAGTATGAAGACCAAGGCGTTG
CAGTTGATGTGATTCAAGCGGTTCAAGCATTATCACCAAAATCACCTTTAGATTTTGATAAGCGTGTG
ACTGCGGTAAATCATTTCCGTGCATTGCCTGAAGCTGCTGCACTGGCTGCTGCAAATAAGCGTGTTGC
CAACATTCTTGCCAAAGAAGCAGAACTAACAGGCGCAGTGGTTGAAGCAAACTTGGTTGAAGAGGCT
GAAAAAGCATTATTCGCTGTACTTGCTAAAATTACGCCTGAAGTTGAACCATTATTTGCTGCCAAAGA
TTACACCACTGCATTGTCTAAGCTTGCTGCTTTACGTGCGCCTGTGGATGCATTCTTTGAAGGCGTCAT
GGTCATGGCAGATGATGCAGAATTGAAAGCCAACCGTTTACGTTTATTGGCTCAATTACGTGGTTTGT
TTACAAGTGTTGCGGATATTTCGGTGTTGCAGCACTAA 124
DP70 DNA gyrase subunit B
ATGAGTTCAGAAGATCAAGCTGCTTCTCAAACAGAACAAACCAATGAAAAGGCTTATGATTCCTCT
AGTATCAAAGTATTACGTGGCCTAGATGCTGTTCGTAAGCGTCCGGGTATGTATATTGGTGATACGGA
CGATGGTTCAGGTTTACATCACATGGTGTTTGAGGTGGTCGATAATGCGATTGATGAAGCCTTAGCGG
GTCACTGTGATGAAATCTTAGTCACCATCCATGAAGATGAGTCTGTAAGTGTTGCAGATAACGGTCGT
GGGATTCCAACGGATATTCACCCTGAAGAAGGGGTATCTGCCGCTGAAGTGATTTTAACCATTTTGCA
TGCTGGCGGTAAGTTTGATGATAATAGCTATAAAGTTTCCGGTGGTTTACACGGGGTAGGTGTTTCTG
TTGTAAATGCCTTGTCGAGTAAATTATTACTAAATATTCGTCGTGCAGGAAAAGTATATGAACAGGAA
TATCACCATGGTGATCCTGTCTATCCATTACGCGCGATTGGTGATACTGAAGAAACCGGTACCACCGT -continued

| SEQUENCE LISTING<br>Seq ID No.<br>Description<br>Sequence |
|---|
| TCGTTTCTATCCGAGTGAATTAACCTTCTCTCAAACGATTTTTAATGTTGATATTTTAGCGCGTCGTTT<br>GCGCGAACTTTCATTCTTAAATGCAGGGGTTCGTATTGTATTACGTGATGAACGTATCAATGCTGAAC<br>ATGTATTTGATTATGAAGGTGGTTTGTCTGAATTTGTAAAATATATCAATCAAGGTAAAACCCACTTG<br>AATGAGATTTTTCATTTTACCAGTGAAGTTGTGGAAACAGGAATTACTGTTGAAGTAGCATTACAGTG<br>GAATGATACTTATCAAGAAAATGTCCGTTGCTTTACCAATAACATCCCACAAAAAGATGGTGGTACG<br>CATTTAGCCGGTTTCCGTGCCGCGTTAACACGGGGTTTAAACCAGTATCTTGATAGTGAAAATATTCT<br>TAAGAAAGAAAAAGTTGCTGTCACAGGTGATGATGCCCGTGAAGGTTTAACGGCGATTGTTTCAGTG<br>AAAGTGCCTGATCCAAAATTCTCATCACAAACCAAAGAAAAATTGGTTTCCAGTGAAGTGAAAACTG<br>CTGTAGAGCAGGCGATGAACAAGTCTTTTTCTGAATATCTTTTAGAAAATCCACAAGCGGCTAAATCG<br>ATTGCCGGCAAAATTATTGATGCTGCACGTGCACGTGATGCTGCGCGTAAAGCACGTGAAATGACAC<br>GTCGTAAGAGTGCATTAGATATTGCTGGTCTGCCTGGTAAACTGGCGGATTGCCAAGAAAAAGATCC<br>AGCATTGTCTGAACTTTACTTGGTCGAAGGTGACTCGGCGGGCGGTTCTGCAAAACAGGGTCGTAACC<br>GTAAGATGCAAGCTATTCTGCCGCTTAAAGGTAAAATCTTAAACGTAGAACGTGCACGTTTTGACAA<br>AATGATTTCATCGCAAGAAGTGGGCACGCTGATTACTGCACTGGGCTGTGGTATTGGTCGTGAGGAAT<br>ACAATCCTGATAAATTGCGTTATCACAAAATCATTATCATGACCGATGCCGACGTCGATGGTTCGCAC<br>ATTCGTACGCTCCTGTTGACCTTCTTCTTCCGTCAAATGCCAGAACTTGTGGAACGTGGTTATATTTAT<br>ATTGCACAGCCACCGTTGTATAAGTTGAAAAAAGGTAAGCAAGAGCAATATCTTAAAGATAATGATG<br>CTTTAGAAACCTATCTTATTTCGAATGCCATTGATGAGCTTGAACTGCATATTAGTGCTGAGGCACCT<br>GCGATTCGTGGTGAATCTTTGGCTAAAGTGATTGCTGATTATCAAACCTCACAAAAAAGTTTAAATCG<br>TTTAACGCTACGTTATCCTGCAAGCTTGCTGGATGGTTTACTTGGTTTGGATGCATTTAAACTTGATCA<br>AAATCATGATGAAGATTATGTAAAACAATGGTCTGAACAATTGCGTGCAGCAATTGAACAACACCAA<br>CCAAGTTTGCGTCCTGAAATCACCTTAGAAGCTTTTGAAAAAGAGCATGCAGATGGTGAGAAAGTGA<br>CGCATTATTGGCCACGTGTAACGGTCTATGTACATAACTTGCCGCATCATTATTTACTTGATTCTGGAT<br>TATTGGCTTCAAGTGAATACAAGCGTTTACTGCAAAATTCGAAGAGTTGGTTCACATTGCTTGAAGAT<br>GGCGCTTATTTGCAAAAAGGTGAGCGTAAAATTCATGTCGCCACTTTCCATCAAGTTTGGCAACATAT<br>TTTATCCGACTCGCGTCGTGGCATGATGATCCAGCGCTATAAAGGTTTGGGTGAGATGAACGCGGAA<br>CAGCTTTGGGAAACCACCATGGATCCTGAAAACCGTAACATGTTGCAAGTCACCATTAATGATGCGA<br>TTGAAGCGGATCGTATGTTCTCTTGTTTGATGGGAGATGATGTGGAACCACGTCGTGCCTTCATTGAA<br>GAAAATGCTTTAAATGCGGATATTGACGCTTAA |
| 125<br>DP70 Leucine--tRNA ligase<br>ATGACTACTTCTCACATTGACCCTGAATATCAAGCGAGCGCGATTGAATCCACTGTCCAACAAGAC<br>TGGGAAACTCGCAAAGCCTTTAAAGTTGCCGACACTGTAGAAGGTAAACATCGTTATATCCTCTCGAT<br>GTTCCCTTATCCAAGTGGCAAGCTGCATATGGGTCATGTGCGTAACTACACCATTGGCGACGTGATTA<br>GCCGTTTCCACCGTCTCAAAGGTGAAACTGTCCTACAACCGATGGGTTGGGATGCTTTTGGTCTGCCT<br>GCGGAAAATGCAGCGATTGCACACCAAGTTGCCCCTGCAAAATGGACCTTTGAAAACATCGCGTACA<br>TGCGTGACCAGTTAAAAAAATTGGGTCTGTCAGTCGATTGGGATCGTGAATTTGCGACCTGTACGCCA<br>GAGTATTATCACTGGGAACAATGGTTATTTGTACAGCTGTATAAAAAAGGGCTGATTTATCGCAAACT<br>TTCAACGGTAAACTGGGATCCTGTCGATCAGACTGTACTTGCTAATGAACAAGTTGAAAATGGTCGTG<br>GTTGGCGTTCGGGTGCATTGGTTGAAAAACGTGATATTCCAATGTATTACTTCCGTATTACCGATTAT<br>GCACAAGAATTATTAGACGATTTAGATTCGCTTAAAGATGGTTGGCCGCAACAAGTCTTGACCATGCA<br>ACGCAACTGGATTGGTCGTTCACAAGGCATGGAAATCACCTTTCCATCTGCGAACCCTGAAATCTATG<br>CAGATGATTTAACGGTTTATACCACACGTGGTGACACCTTGATGGGCGTGACGTATGTTGCGGTTGCC<br>GCTGAACATCCAATGGCGCTTAAAGCGGCTGAAACAAATCCCGAATTGGCTGCATTTATTGAAGAAT<br>GCCGTATGGGTTCAGTGGCTGAAGCAGATCTTGCCACTGCCGAGAAAAAAGGCATGGCCACTGGTTT<br>GTCTGTGAAGCATCCTGTAACGGGTGAAGTGGTTCCAGTGTGGATTGCGAACTATGTATTGATGTCAT<br>ACGGTTCAGGTGCGGTGATGGCAGTTCCAGCACACGACGAACGTGATTTCGAATTTGCCAACAAATA<br>TGGTTTAACCCTCCAGCAAGTGATTGATGCCAAAGGTGCAGACGATGCTGAATTTTCTGCAACTGAAT<br>GGCAGGAATGGTATGGCTCGAAAGAAGGCAAACTGGTTAATTCTGGCGAATTTGACGGTTTAGACTT<br>CCAAGCTGCATTTGATGCATTCATTGCAAAATTAGAACCACAAAAACTGGCAAATACGAAAGTTCAG<br>TTCCGTCTACGTGACTGGGGTGTTTCGCGTCAGCGTTATTGGGGTTGTCCAATTCCAATGATCAACTGT<br>GAAACTTGTGGTCAAGTACCTGTACCTGAAGAACAACTTCCAGTAATTTTACCAACTGACGTGGTGCC<br>AGATGGTTCAGGCAATCCGTTAAATAAAATGCCTGAATTTTATGAAACCCAATGTCCATGTTGTGGTG<br>CAGGTGCACGCCGTGAAACCGATACTTTGGATACGTTCGTAGAGTCATCTTGGTACTATGCACGTTAT<br>GCATCTCCAGATTTCACTGGCGGTTTAGTTAAACCTGAAGCTGCAAAATCATGGCTACCAGTCAACCA<br>ATATATTGGCGGTGTGGAACATGCAATTTTGCATTTATTGTATGCCCGTTTCTTCCATAAATTGATGCG<br>TGATGAAGGCGTCGTTGAAGGCAATGAACCTTTCGCTAACTTACTGACTCAAGGTATGGTTTTAGCTG<br>ATACCTTCTACCGTGAAGCCGAATCAGGTAAGAAAACATGGTTTAATCCTGCGGATATTGAATTAGA<br>AAAAGACGAAAAAGGTCGTGTTCTTTCTGCTAAATACACAGGTGATGGCCAAGAAGTTGTGGTTGGC<br>GGTCAAGAAAAAATGTCGAAATCGAAAAATAATGGCATCGACCCGCAATCGATTATTGATCAATACG<br>GCGCAGATACTGCACGTGTATTTATGATGTTTGCGGCCCCACCCGATCAATCGCTTGAATGGTCTGAT<br>GCCGGTGTGGAAGGTGCAAACCGTTTCTTGAAACGTGTATGGCGTTTAACCCACAGGTTTCTTAGAAAA<br>AGGCAACCATGCTGCTGTAATTGATGTTGCGAATTTGTCATCAGCGGCACAAGACTTACGTCGTAAAA<br>CCCACGAAACCATTCAAAAAGTCGGTGATGACATTGAACGTCGTCATGCCTTCAATACTGCCATTGCA<br>GCGCAAATGGAATTATTGAATGCTTGCAATAAATTTGAAGCCAAAGATGATAATGACGTTGCGGTTG<br>AACGCGATGCTATTGTTAGCTTACTCACTTTACTTGCACCATTTGCACCACATTTAAGTCAGACCCTAT<br>TGGCTCAATTCGGTATTGAGTTAACTGAAACCTTGTTCCCTACTGTGGATGAGTCTGCGCTAACCCGC<br>AACACACAAACTATTGTGGTACAGGTCAATGGTAAACTTCGTGGCAAGTTGGAAGTGTCTGTTGATCT<br>CTCTAAAGAAGATATTTTGGATCAAGCCAAAGCATTGCCTGAAGTACAACAATTCTTAACCGGTCCAA<br>CCAAGAAAGAAATTGTGGTGCCGAATAAATTGGTCAATTTGGTGGTTTAA |

-continued

| SEQUENCE LISTING<br>Seq ID No.<br>Description<br>Sequence |
|---|

126
DP70 Glucose-6-phosphate isomerase
ATGAATAGTATTGAAAAATTTCCCTTGCATGATACGGATCTGATTCAGGAAAAACTAAAAAGTTTT
GCCCAACAAGAGCAAGAGATTAATTTAAATTATTTATTTAAAAAAAATAAAAAACGTTTTGATGAAT
ATTCCGTTCATGCGGGTCAGTTATGTTTTGATTATAGTAAGCACCGTGTTGATGAGCGTATTATTAACG
AGCTTATTTGTTATGCGGAATCACAACATTTGGGTAACTGGATTCAGCGCTTATTTTCTTTAGAAAAA
ATTAATTACACTGAAAATCGCGCAGCGATGCATTGGGCTTTGCGTTTGCCGAAGCAAGATAGTACAC
ATGCAGATTTGGCAGCGCAGGTACATAGTCAGCTTGATCGTATGTATCAATTGGTCGAGAAAATTCAT
CAGGGGCAGTATCGAGGAGCTACAGGTGAGGTCATCCATGATGTGGTCAATATTGGTGTCGGTGGAT
CAGATCTTGGTCCTTTAATGGTGTCTCAAGCGCTGACTGATTTTAAAGTTCAAACGGCTCAAAAATTA
AAAGTCCATTTTGTTTCGACGATGGATGGCAGCCAACTTTCAGATCTTTTACATCAGTTTCGCCCAGA
AACCACCTTGTTTATTATTTCATCCAAGTCTTTTGGCACCATTGATACGCTTTCCAATGCACAAACGGC
AAAATGCTGGCTTGAGCAATCTTTAGGAACGTCGAAATCAGTTCTAAGATGTCACTTTGTTGGTGTTT
CAACCAAGCCCGATAAGATGACCGAGTGGGGAATCAGCACTGAAAATCAATTCTTATTGTGGGATTG
GGTCGGTGGGCGCTATTCACTATGGTCGTGTATTGGTTTGCCTATTGCATTAAGTATTGGGGTCGAGG
GCTTTAAACAGTTGCTTGCTGGTGCTTATGAAATGGATCAGCATTTTCAGAACACACCACTTGAACAA
AATATTCCTGTGTTGATGGGTTTACTGGGAATATGGAATAACAACTTCCTGAATATTCAAACTCATGC
GGTACTTCCTTATGATGGTCGGCTGAAATATTTTGCGGCTTATTTACAGCAATTGGAAATGGAGTCGA
ATGGTAAGTCGATTCAGCGTTCTGGTGAAAAAGTCGTATTAGATACCTGCCCAATTTTATGGGGTGAA
GTTGGACCAAATGCACAACATGCTTTTTATCAGCTGCTGCATCAAGGTACACATGCTGTGAGTTGTGA
CTTTATTGCACCTGTGAAACGCTATAATGCCAATCAATTTACCTATGTTGAAAATGCAGAGGCTTTAG
TTGAACAACACCATTTAGCCTTATCGAATTGTTTGGCACAATCACGTCTATTGGCCTTTGGTAATCATG
TTCTAGATCCGAAAGAAGTAGAAAGTTCACCGAAATATAAACAATATGCAGGCAACCAACCGACCAC
AACAATTTTGTTAAAAGAGTTGAATCCGCGCAGTTTAGGTATGCTCATTGCGATGTATGAGCACAAGG
TATTTGTGCAATCCGTGATGTGGAATATTAATCCATTTGACCAATGGGGCGTAGAAAAAGGTAAAGA
AATTGCCAATCAACTGTTACCGATTCTCAATCAAGAGCAAGCTGATGTTTCTGATCTTGATTCTTCAAC
GCAAGGTCTATTAAGAATTTTACTGGGAAAAGCTGATGGCTAA 127
DP70 NADH-quinone oxidoreductase subunit C/D
ATGGCTGAAACTGACATTGCTATGCCAGAATCAACGCCTGTTGATTCACGCCCAGCATTTGCAATT
GTAGAAGAGCTCAAAGCCAAATTTGGTGAGAACTTCTATGTGCAAGCGACTTTTGAAGATTTTCCAAC
GGTCTGGGTTGAGCGCGCGCGCGTACAAGATGTTTTAATGTTCTTGCGTAAAGTATCACGTCCATACG
TGATGCTGTTCGACTTGTCTGCGGTAGATGAGCGTTTACGTACCCACCGTGACGGTTTACCTGCATCA
GACTTCACTGTGTTTTATCATTTGTTGTCGCTAGAGCGCAACAGTGATATTCGTATTAAAGTTGCGTTG
AGTGAGAGTGATCTCAATCTTCCAACCGCAACCAACATTTGGCCAAATGCCAACTGGTACGAACGTG
AAGCTTACGATATGTTCGGGATCAATTTCGAAGGGCATCCAATGCTCCGTCGTATTTTGTTGCCAACC
TATTGGGAAGGTCACCCACTGCGTAAAGAATATTCTGCACGTGCGACTGAATATACACCGTATATGCA
GAACCAAGCGAAGCAGGATTTCGAGCAAGAACATTTACGTTTTGTTCCTGAAGATTGGGGTCTATCAC
GCGGTAATGCCGATGAAGATTTCATGTTCTTGAACTTAGGTCCAAACCATCCATCTGCGCACGGTGCA
TTCCGTATCATTTTGCAGTTGGACGGTGAAGAAGTGAAAGACTGTGTGCCTGATATTGGCTATCACCA
CCGTGGTGTGGAAAAGATGGCTGAACGTCAAACTTGGCATTCATTCATTCCATATACCGACCGTGTTG
ACTACTTGGGTGGTTGTGCGCAAAACATGCCTTATGTGATGGGTGTGGAGCAAATGGCAGGAATTAC
TGTTCCTGACCGTGCACAATGTATCCGTGTCATGATGTCTGAATTATTCCGTATCAATAACCATTTATT
GTTTATTGGTACTGCAATTCAAGATGCCGGCGGTATGACGCCAGTCTTCTATATGTTTGCCGATCGTC
AAAAGATCTATGATGCGATTGAAGCGATTACAGGCTACCGTATGCATCCAGCATGGTTCCGTATTGGC
GGGACTGCGCACGACCTTCCAAACAATTGGCAACATCTGATTCGTGAAATTCTCGAATGGATGCCGA
AGCGTATGAATGAATACTATACAGCTGCACTACGCAACTCAGTATTTATTGGTCGTACCCGTAATGTT
GCACAATACGATGCAAAATCTGCATTGGCTTGGGGTGTAACAGGTACAGGTCTACGCGCGACAGGGA
TTGATTTCGACGTGCGTAAATACCGTCCGTATAGCGGTTATGAAAACTACGACTTCGACGTGCCTTTA
GAATACGAAGGCGATGCTTACGCTCGTGTGATGGTTCACTTCCGTGAAATTGAAGAATCACTGAAAA
TTGTGAAGCAGTGCTTGGATAACATGCCATCTGGTCCATATAAAGCGGATCATCCTTTGGCTGTTCCA
CCACCAAAAGACAAGACATTACAAGATATTGAAACTTTGATTACGCACTTCTTGAGCGTGTCATGGG
GTCCTGTGATGCCTGCGGGTGAAGCGTCTGTAATGGCTGAAGTGGTAAAAGGTGCATCGAACTACTA
CTTGACTTCAGACAAGTCAACCATGAGTTATCGTACCCGTATTCGTACACCAACTTTCACGCACTTAC
AGCAAATGCCTTCTGTGATTAATGGCAGTCTTGTATCTGACTTGATCATTTATTTAGCGACCATTGACG
TCGTAATGGCTGACGTGGATCGCTAG 128
DP70 Protein RecA
ATGGATGATAATAAAAGTAAGGCGCTTAATGCTGCCCTAAGCCAGATTGAAAAACAATTTGGTAA
AAATACCGTAATGCGTCTTGGTGATAATACCGTATTGGCCGTTGAAGCGGTCTCTACAGGTTCTTTAA
CACTAGACATTGCACTTGGTATTGGTGGCTTACCAAAAGGTCGTATCGTTGAAATTTACGGTCCTGAA
TCTTCTGGTAAAACCACAATGACATTGCAAGCGATTGCACAATGTCAAAAAGCCGGTGGTACTTGTGC
TTTTATCGATGCAGAACATGCACTCGATCCTCAGTATGCACGTAAGCTTGGTGTCGACCTTGACAACC
TGTTGGTTTCTCAACCAGACCACGGTGAACAAGCCCTTGAAATTGCAGACATGTTAGTCCGCTCTGGT
GCTATTGACATGATCGTTGTCGATTCCGTGGCTGCACTGACACCTCGCGCTGAAATTGAAGGTGAAAT
GGGCGACTCACATATGGGCTTACAAGCACGTTTGATGAGTCAGGCATTACGTAAAATTACTGGTAAT
GCAAAACGCTCAAACTGTATGGTGATCTTCATTAACCAAATCCGTATGAAGATTGGTGTAATGTTTGG
TAGCCCTGAAACCACAACAGGTGGTAATGCACTCAAATTCTACGCTTCTGTACGTTTGGATATCCGTC
GTATTGGTCAAGTGAAAGAAGGCGATGAAATTGTCGGTTCAGAAACCCGCGTTAAAGTCGTAAAAAA
TAAAATGGCACCTCCTTTTAAGGAAGCGTTATTCCAAATTTTATATGGCAAAGGTGTCAATCAACTGG
GTGAACTGGTTGATCTTGCTGTTGCGCAAGAACTGGTACAAAAAGCAGGTGCTTGGTATTCATATCAA
GGCAATAAAATTGGTCAAGGTAAAAACAACGTGATCCGCCATTTAGAGGAAAATCCTCAAATTGCAC -continued

| SEQUENCE LISTING Seq ID No. Description Sequence |
|---|

AAGAACTTGATCGCCTGATTCGTGAAAAATTGTTGACACCAACGACCACGCCTATTGAAGAAAAAGA
TGAAGTAGAACCAGACTTTCTAGATGCTTAA

129
DP70 RNA polymerase sigma factor RpoD
ATGAGCGATATGACTTCCCCTACTTCGCAAGTAGCGGCTCTGATTAGCCGAGGCAAAGAGCAAGG
TTACTTAACTTACGCTGAGGTTAACGATCATCTCCCAGACTCGATCACGGAAAGCGAACAGATTGAA
GACATTATTCAAATGCTTCAAGATGTCGGCATTCCAGTGCATGAACGTGCGCCTGAATCTGATGACAC
CATGTTCGACGGTAACAATGCAGAAGCAACCGATGAAGTCGCTGAAGAAGAAGCGGCAGCTGTTCTT
GCTTCAGTTGAAAGCGAACCTGGTCGTACCACCGATCCAGTACGTATGTACATGCGTGAAATGGGAA
CGGTTGAACTATTAACGCGTGAAGGCGAAATTAGCATTGCAAAACGCATTGAAGAAGGTATTCGTGA
CGTTCTTCATTCGATTGCGTACTGGCCAAATGCAGTTGAAGTTGTATTAAAAGAATATAGCGATGTTG
CTGAAGGCGAACGTCGTCTTGCTGATATTTTATCTGGTTATTTAGACCCAGAATCTGACGAAGAAATT
CCAGAAGTTTTAGAAGAAGAAGCTGAAATTGTTGAAGATGATGAAGCGACGACTAAAACCACTAAA
GATGTAAAATTGGACGATGACGAAGAAGAAGAATCTGAAAGTGATGATGATTCTGAAGGTGAGTCTG
GTCCAGATCCAGAAATTGCACGTGTTCGTTTCACTGAATTAGAAGATGCGTGGAAAGTAACCAAAGC
CACCATTGAAAAGCATGGCCGTAACAGCAAACAAGCAGATGAAGCGCTTGAAGCTCTTGCAACTGTG
TTTATGATGTTCAAATTTACACCACGTTTATTTGAAATCATTTCAGAAATGATTCGTGGCACGCATGA
ACAAATTCGTACAGCAGAACGTGAAGTGATGCGTTACGCAGTTCGTCGTGGTCGTATGGACCGTACC
CAATTCCGTACATCGTTCCCAGGCCAAGAGTCAAATCCAGCTTGGTTAGATGAACAAATTGCTAAAGC
ACCTGCGGATCAAAAAGGTTATTTAGAAAAAGTACGTCCAGATGTTGTTGCATTCCAGCAAAAGATT
GCCGATATCGAAAAAGAATTGGGCTTAGATGTTAAAGACATCAAAGACATTTCTAAACGTATGGCTG
TGGGTGAAGCGAAAGCACGTCGCGCGAAAAAAGAAATGGTTGAAGCAAACTTACGTTTGGTGATTTC
GATTGCGAAAAAATATACCAACCGTGGTTTACAATTCCTTGACTTGATTCAAGAAGGTAACATCGGTT
TGATGAAAGCCGTAGACAAGTTTGAATACCGTCGTGGTTATAAATTCTCGACTTATGCAACTTGGTGG
ATTCGTCAGGCGATTACCCGTTCGATTGCCGATCAAGCACGTACCATCCGTATTCCAGTACACATGAT
CGAAACCATTAACAAGATCAACCGTGTATCTCGTCAACTTCTTCAAGAAATGGGCCGTGAGCCTACCC
CTGAAGAATTAGGCGAACGTCTGGAAATGGACGAAGTTAAAGTACGTAAAGTGCTGAAAATTGCCAA
AGAACCGATTTCGATGGAAACACCGATTGGTGATGACGAAGATTCGCATCTTGGTGACTTCATTGAA
GATGGTAACATTACCTCTCCAATTGATGCCGCGACTTCTGAAGGCTTAAAAGAAGCAACACGTGAAG
TGCTGGAAAACTTGACCGAACGTGAAGCGAAAGTCTTAAAAATGCGTTTTGGTATTGATATGCCAAC
CGACCATACTTTAGAAGAAGTGGGTAAACAATTTGATGTAACACGTGAACGTATTCGTCAGATTGAA
GCCAAAGCTTTACGTAAATTACGTCACCCTTCTCGTTCTGAACACTTACGTTCATTCCTAGAAAATGA
CTAA 130
DP71 Glutamine--tRNA ligase
ATGAGTGAGGCTGAAGCCCGCCCAACAAATTTTATCCGTCAGATTATTGATGAAGATCTGGCGACC
GGGAAACACAATACCGTTCACACCCGTTTCCCGCCTGAGCCTAATGGCTATTTGCATATCGGCCATGC
GAAGTCTATCTGCCTGAATTTCGGCATTGCGCAAGACTACCAGGGTCAGTGCAATCTGCGTTTTGACG
ATACTAACCCGGCAAAAGAAGACATCGAATTCGTTGAGTCGATCAAATACGACGTCCAGTGGCTGGG
CTTCGACTGGAGCGGTGATATTCACTACTCCTCAGACTATTTCGATCAACTGCACGCATACGCGCTGG
AGCTAATCAACAAAGGTCTGGCGTACGTTGACGAACTGTCTCCCGATCAAATTCGCGAATACCGTGGT
TCGCTGACCGCACCGGGCAAAAACAGCCCGTATCGCGATCGCAGCGTGGAAGAAAATATCGCGCTGT
TTGAAAAAATGCGTAACGGTGAATTCGCCGAAGGTGCCGCTTGCCTGCGTGCCAAAATCGATATGGC
GTCGCCATTCTTCGTGATGCGCGATCCGGTCATCTACCGTATTAAGTTTGCCGAACATCATCAGACTG
GCACAAAATGGTGCATCTACCCGATGTACGATTTCACTCACTGCATTTCCGATGCGCTGGAAGGGATC
ACCCATTCACTGTGTACGCTGGAATTCCAGGACAACCGCCGTCTGTACGACTGGGTACTGGATAACAT
CACTATTCCATGCCATCCGCGTCAGTATGAGTTCTCCCGTCTGAATCTTGAATACTCCATCATGTCCAA
GCGTAAGCTGAACCTGCTGGTGACGGATAAGATTGTAGAAGGTTGGGACGATCCGCGTATGCCGACG
GTTTCCGGTCTGCGTCGCCGTGGTTATACCGCCGCGTCTATCCGCGAATTCTGCCGTCGTATCGGCGTG
ACCAAGCAGGACAACAACGTTGAAATGATGGCGCTGGAATCCTGTATTCGTGACGATCTGAACGAAA
ACGCACCGCGCGCCATGGCCGTTATTAACCCGGTTAAAGTTGTCATTGAGAACTTCACCGGTGATGAC
GTGCAAATGGTGAAAATGCCGAATCATCCGAGCAAACCGGAAATGGGCACCCGCGAAGTGCCGTTCA
CCCGTGAGATTTACATCGATCAGGCTGATTTCCGCGAAGAAGCGAACAAACAGTACAAACGTCTGGT
GCTGGGCAAAGAAGTTCGCCTGCGCAATGCGTATGTGATCAAAGCGGAACACATCGAGAAAGACGC
GGAAGGGAATATCACCACCATCTTCTGTTCTTACGATATCGATACGCTGAGCAAAGATCCCGCTGATG
GCCGTAAGGTGAAAGGCGTGATTCACTGGGTTTCTGCTTCTGAAGGTAAACCGGCAGAATTTCGCCTG
TATGACCGTCTGTTCAGTGTTGCGAACCCTGGCCAGGCTGAAGATTTCCTGACCACCATCAACCCGGA
ATCTCTGGTGATTGCTCAGGGCTTCGTTGAGCCGTCTCTGGTCGCTGCTCAGGCAGAAGTCAGTGTGC
AGTTCGAACGTGAAGGTTACTTCTGTGCCGACAGCCGCTATTCAAGTGCTGAGCATCTGGTGTTCAAC
CGCACCGTCGGCCTTCGCGACACCTGGGAAAGCAAACCCGTCGCCTGA 131
DP71 DNA gyrase subunit B
ATGTCGAATTCTTATGACTCCTCAAGTATCAAGGTATTAAAAGGGCTGGACGCGGTGCGTAAGCGC
CCCGGCATGTATATCGGCGATACCGATGACGGCACTGGTCTGCACCACATGGTATTCGAGGTTGTGGA
CAACGCTATCGACGAAGCCCTCGCGGGCCACTGTAAAGAGATTCAGGTCACGATCCATGCGGATAAC
TCTGTTTCCGTACAGGATGATGGTCGTGGTATTCCTACCGGCATTCACGAAGAAGAGGGCGTTTCTGC
TGCTCAGGTCATCATGACCGTACTTCATGCCGGCGGTAAATTTGACGATAACTCGTACAAAGTCTCCG
GCGGTCTGCATGGCGTGGGTGTTTCCGTCGTTAACGCCCTGTCGGAAAAACTGGAGCTGGTTATCCGC
CGTGAAGGCAAAGTGCACACCCAGACTTACGTCCACGGTGAGCCGCAGGATCCGCTGAAAGTGGTTG
GCGATACCGAGGCGACCGGTACGACCGTGCGCTTCTGGCCAAGCTACGCCACCTTCACCAATCAAAC
AGAATTCGAGTATGACATTCTGGCGAAACGCCTCCGTGAGCTGTCATTCCTGAACTCTGGTGTGGCGA -continued

| SEQUENCE LISTING<br>Seq ID No.<br>Description<br>Sequence |
|---|

TCCGCCTGCTCGACAAACGCGATGGCAAGAACGATCACTTCCATTATGAAGGCGGTATCAAAGCTTTC
GTGGAATACCTGAACAAAAACAAAACCCCAATCCACCCAACCGTGTTCTATTTCTCCACCGTGAAAG
ACGATATCGGTGTGGAAGTGGCGTTGCAGTGGAATGATGGTTTCCAGGAAAATATTTACTGCTTTACC
AACAATATCCCTCAGCGCGACGGCGGCACCCATCTGGTAGGCTTCCGTTCTGCGATGACCCGTACGCT
TAACGCGTATATGGATAAAGAAGGCTACAGCAAGAAATCCAAAATCAGCGCCACCGGTGATGATGCC
CGTGAAGGCCTGATCGCCGTGGTTTCGGTAAAAGTGCCGGATCCTAAGTTCTCCTCTCAGACCAAAGA
CAAACTGGTTTCTTCCGAAGTGAAGACCGCCGTTGAGTCTCTGATGAACGAGAAGCTGGTTGATTATC
TGATGGAAAACCCGGCCGACGCGAAAATCGTTGTCGGTAAAATCATCGATGCAGCCCGTGCGCGTGA
AGCCGCGCGTAAAGCACGTGAAATGACCCGTCGTAAAGGCGCGCTCGATCTGGCCGGTCTGCCAGGC
AAACTGGCTGACTGTCAGGAACGCGACCCGGCACATTCCGAACTGTACTTAGTGGAAGGGGACTCAG
CGGGCGGCTCTGCAAAACAAGGCCGTAACCGTAAGAACCAGGCGATTCTGCCGTTGAAAGGGAAAAT
CCTCAACGTTGAGAAAGCGCGCTTCGACAAAATGCTCTCTTCTCAGGAAGTGGCGACGCTGATTACCG
CGCTCGGTTGCGGTATCGGCCGTGACGAATACAACCCGGATAAACTGCGTTATCACAGCATCATCATC
ATGACCGATGCCGACGTCGATGGTTCGCACATCCGTACCCTGTTACTGACATTCTTCTACCGTCAGAT
GCCTGAAATTGTAGAGCGTGGCCACGTGTTTATCGCGCAGCCTCCGCTGTACAAAGTGAAAAAAGGC
AAACAGGAACAGTACATTAAAGATGATGAAGCGATGGATCAGTATCAAATCTCTATCGCGATGGACG
GGGCAACGTTACACGCCAACGCCCATGCACCAGCACTGGCGGGCGAACCGCTGGAGAAACTGGTGGC
TGAACATCACAGCGTGCAGAAAATGATTGGCCGTATGGAACGTCGTTATCCGCGTGCGCTGCTGAAT
AATCTGGTCTATCAGCCAACGCTGGCGGGTGCTGAACTTGCCGACGAAGCGAAAGTGAAGGAATGGA
TTGAAACGCTGGTGTCTCGTCTGAACGAGAAAGAGCAGCACGGCAGCAGCTACAGTGCGATCGTGCG
CGAAAATCTTGAACACCAGCTGTTCGAGCCAATCCTGCGCATTCGTACTCACGGTGTGGATACCGACT
ACGATCTCGATGCAGACTTCATTCAGGGCGGCGAATACCGCAAAATCTGTACCCTGGGTGAAAAACT
GCGCGGCCTGATCGAAGAAGATGCTTACATCGAACGTGGCGAACGCCGTCAGCCAGTGACCAGCTTC
GAGCAGGCGCTGGAATGGCTGGTGAAAGAGTCGCGTCGCGGTCTGTCGATTCAGCGTTATAAAGGTC
TGGGTGAAATGAACCCTGAGCAATTGTGGGAAACCACGATGGATCCGACACAACGCCGCATGCTGCG
CGTGACGGTGAAAGATGCTATCGCGGCGGACCAGCTGTTCACCACGCTGATGGGCGATGCGGTTGAA
CCGCGCCGCGCCTTCATCGAAGAGAACGCCCTTAAAGCTGCCAATATCGATATCTGA

132
DP71 Isoleucine--tRNA ligase
ATGAGTGACTACAAGAACACCCTGAATTTGCCGGAAACAGGGTTCCCGATGCGTGGCGATCTGGC
CAAGCGTGAACCTGACATGCTGAAGAATTGGTATGACCAGGATCTGTACGGGATTATTCGTGCTGCC
AAGAAAGGCAAGAAAACCTTTATCTTGCATGACGGCCCTCCGTATGCGAACGGCAGCATTCATATTG
GTCACTCAGTAAACAAAATTCTTAAAGACATGATCGTTAAGTCCAAAGGACTGGCGGGCTTTGATGC
GCCGTATGTTCCGGGCTGGGATTGTCATGGTCTGCCGATTGAACTGAAAGTTGAACAGCTGATCGGTA
AGCCGGGCGAAAAAGTCACGGCGGCGGAATTCCGTGAAGCCTGCCGCAAGTACGCTGCTGAACAGGT
TGAAGGTCAGAAGAAAGACTTCATCCGTCTGGGCGTGCTCGGTGACTGGGATCATCCGTACCTGACC
ATGGACTTCAAAACAGAAGCCAACATCATTCGTGCCCTGGGTAAAATCATCGGCAACGGTCACCTGC
ATAAAGGTGCGAAACCTGTTCACTGGTGTACCGATTGCGGATCTTCACTGGCTGAAGCCGAAGTCGA
ATATTACGACAAAGTGTCTCCGTCTATCGACGTGACGTTTAATGCGACGGATGCCGCCGCTGTTGCTG
CGAAATTCGGTGCCACTGCTTTCAATGGCCCGGTTTCTCTGGTCATCTGGACCACCACCCCGTGGACC
ATGCCAGCTAACCGCGCGATTTCACTCAACGCTGAGTTCTCTTATCAGCTGGTGCAGATTGAAGGTCA
GTGCCTGATCCTGGCTACCGATCTGGTAGAAAGCGTGATGAATCGCGCCGGTATCGCTGAGTGGACT
GTGCTGGGCGAATGTAAAGGTGCGGATCTTGAATTGCTTCGATTCCAGCATCCGTTCCTCGGTTTCGA
TGTTCCGGCGATCCTCGGCGATCACGTTACTCTCGATGCCGGTACCGGTGCTGTACATACCGCACCTG
GCCACGGTCCTGATGACTTTGTCATTGGCCAGAAATACGGTCTGGAAGTCGCAAACCCGGTTGGACC
GAACGGCTGCTACCTGCCGGGCACTTATCCGACGCTGGATGGCAAATTCGTCTTTAAAGCGAATGATC
TGATCGTTGAATTGCTGCGTGAGAAGGGCGCACTGCTGCACGTTGAGAAAATGAACCACAGCTATCC
GTGCTGCTGGCGTCACAAAACGCCGATCATCTTCCGCGCTACGCCACAATGGTTCATCAGCATGGATC
AGAAAGGTTTGCGTCAGAAGTCTCTGGAAGAGATCAAAGGCGTGCAGTGGATCCCTGACTGGGGTCA
GGCGCGTATCGAAAACATGGTCGCTAACCGTCCTGACTGGTGTATCTCCCGCCAGCGTACGTGGGGC
GTACCGATGTCTCTGTTCGTGCATAAAGATACCGAACAGCTTCATCCGCGCAGCCTTGAGCTGATGGA
AGAAGTGGCAAAACGCGTGGAAGCCGATGGCATTCAGGCATGGTGGGATCTGAACCCTGAAGAGATT
TTGGGTGCAGACGCTGCCGATTACGTCAAAGTGCCGGATACGCTGGACGTCTGGTTTGACTCCGGTTC
CACGCACTCCTCCGTTGTGGATGTGCGCCCTGAGTTCAACGGTCATTCACCGGATCTGTATCTGGAAG
GTTCTGACCAGCATCGCGGCTGGTTCATGTCTTCTCTGATGATTTCTACGGCGATGAAAGGCAAAGCG
CCTTACAAACAAGTACTGACTCACGGTTTCACCGTCGATGGTCAGGGCCGTAAAATGTCTAAATCCAT
CGGTAACACCATCGCGCCTCAGGATGTGATGAATAAGCTGGGTGGCGACATCCTGCGTTTGTGGGTG
GCATCTACGGATTACACCGGCGAAATCGCCGTGTCCGACGAAATCCTCAAACGTGCTGCCGATTCTTA
TCGCCGTATCCGTAACACCGCGCGCTTCCTGCTGGCGAACCTTAACGGTTTCGATCCGGCGCTGCACA
GCGTGGCACCGGAAGAGATGGTTGTGCTGGATCGCTGGGCGGTTGGCCGCGCGAAAGCTGCACAAGA
CGAGATCATTGCTGCGTACGAAGCCTATGATTTCCACGGCGTTGTTCAGCGTCTGATGCAGTTCTGCT
CGATCGAAATGGGTTCGTTCTATCTGGATATCATTAAAGATCGCCAGTACACCGCGAAGAGCGACAG
CGTTGCGCGCCGCAGCTGCCAGACCGCGCTGTATCACATCTGCGAAGCACTGGTTCGCTGGATGGCGC
CAATCATGTCCTTCACTGCCGATGAAATCTGGGCTGAACTGCCAGGTCATCGCGAGAAGTTCGTCTTT
ACTGAAGAATGGTACGACGGTCTGTTTGGCCTGATCGGTAACGAATCCATGAACGATGCGTTCTGG
ATGAGCTGCTGAAAGTGCGTGGTGAAGTGAACAAAGTGATCGAACAGGCGCGTGCTGATAAACGTCT
GGGCGGTTCTCTGGAAGCAGCCGTGACCTTATATGCAGACGACGCGCTGGCAACAGACCTGCGTTCT
CTGGGTAACGAACTGCGCTTTGTGCTCCTGACTTCCGGTGCGAAAGTCGCCGCGCTGTCTGAAGCTGA
TGACTCAGCGCAGGCCAGCGAATTGTTGAAAGGACTGAAAATTGGTCTGGCGAAAGCAGAAGGCGA
GAAGTGCCCGCGCTGCTGGCATTTCACCACTGATATCGGCCAGAATGCGGAACACAGTGACATCTGT
GGCCGTTGTGTGACTAACATTGCCGGTGACGGCGAAGAGCGTAAGTTTGCATAA -continued

| SEQUENCE LISTING Seq ID No. Description Sequence |
|---|

133
DP71 NADH-quinone oxidoreductase subunit C/D
ATGTCAGAACTTACTCATATTAATGCTTCCGGCGACGCCCACATGGTGGATGTCTCCGGTAAAGAC
GACACCGTTCGTGAAGCCCGTGCCGAAGCCTTTGTTGAAATGGCCGAAAGCACGCTGGCGATGATCA
TCGGCGGTAATCACCATAAGGGTGACGTGTTCGCGACCGCGCGGATTGCCGGTATTCAGGCAGCGAA
GAAAACCTGGGATCTGATCCCGCTGTGTCATCCGCTGTTGCTGACCAAGGTGGAAGTGAATCTTGAAG
CGCAGCCAGAATTTAATCGTGTACGTATTGAATCCCGCTGCCGCCTGAGCGGTAAAACCGGCGTCGA
GATGGAAGCGCTGACCTTCAAGCCTGAAGACTGGGGAATGAAGCGCGGCACCGAAAACGAGGACTT
CATGTTCCTCAACCTCGGACCTAACCATCCGTCTGCGCACGGTGCGTTCCGCATCATCCTGCAGCTTG
ATGGCGAAGAAATTGTCGACTGTGTACCGGACGTCGGTTACCACCACCGTGGTGCTGAGAAGATGGG
CGAGCGCCAGTCATGGCACAGCTACATTCCATACACGGACCGTATCGAATACCTCGGCGGTTGCGTTA
ACGAGATGCCATACGTACTGGCTGTTGAAAAACTGGCGGGTATCGTCGTGCCGGATCGCGTTAACAC
CATCCGCGTGATGCTGTCTGAACTGTTCCGTATCAACAGCCACCTGCTGTACATCTCTACGTTTATTCA
GGACGTGGGCGCGATGACGCCAGTGTTCTTCGCCTTTACCGATCGTCAGAAAATTTACGATCTGGTGG
AAGCGATCACCGGTTTCCGTATGCACCCGGCCTGGTTCCGTATTGGTGGCGTTGCACACGACCTGCCG
AAAGGCTGGGAGCGTCTGCTGCGTGAATTCCTTGACTGGATGCCAGCCCGTCTGGATTCCTACGTCAA
GGCAGCGCTGAAAAACACCATTCTGATTGGACGTTCCAAAGGCGTAGCAGCATACAACGCCGATGAT
GCGCTGGCGTGGGGCACCACCGGTGCTGGCCTGCGTGCGACCGGGATCGACTTCGATGTCCGCAAAT
GGCGTCCATATTCAGGTTACGAAAACTTCGATTTTGAAGTGCCGGTCGGCGATGGCGTCAGTGATTGC
TATTCCCGCGTGATGCTAAAAGTGGAAGAGCTTCGTCAGAGCCTGCGCATTCTGGAACAGTGCTACA
AAAACATGCCGGAAGGCCCGTTCAAGGCGGATCACCCGCTGACCACGCCGCCACCGAAAGAGCGTAC
GCTGCAACACATCGAAACCCTGATCACTCACTTCCTGCAAGTGTCGTGGGGTCCGATCATGCCTGCGC
AAGAATCTTTCCAGATGGTTGAAGCCACCAAAGGGATCAACAGCTACTACCTGACCAGTGACGGCAG
CACCATGAGCTACCGCACGCGCGTCCGTACGCCAAGCTTCCCGCATTTGCAGCAGATCCCGTCCGTAA
TCCGTGGCAGCCTGGTATCCGACCTGATCGTGTATCTGGGCAGTATCGATTTTGTAATGTCAGATGTG
GACCGCTAA 134
DP71 Protein RecA
ATGGCTATTGATGAGAACAAGCAAAAAGCGTTAGCTGCAGCACTGGGCCAGATTGAAAAGCAATT
CGGTAAAGGCTCCATCATGCGTCTGGGTGAAGATCGCTCTATGGACGTGGAAACGATCTCTACCGGCT
CTTTGTCTCTGGATATCGCGTTAGGCGCCGGTGGTTTGCCGATGGGCCGTATCGTTGAGATTTATGGC
CCGGAATCCTCCGGTAAAACTACGCTGACCCTTCAGGTTATTGCTGCCGCACAGCGCGAAGGCAAAA
CCTGTGCGTTCATCGATGCGGAACATGCACTTGACCCTATCTACGCGAAGAAATTGGGCGTAGATATC
GACAACCTGTTGTGTTCTCAGCCGGATACCGGCGAACAGGCTCTGGAAATCTGTGACGCGCTGACCC
GTTCAGGCGCGGTCGACGTTATCATCGTCGACTCCGTTGCTGCACTGACGCCAAAAGCAGAAATCGA
AGGCGAAATCGGTGACTCTCACATGGGCCTTGCGGCACGTATGATGAGCCAGGCAATGCGTAAGCTT
GCCGGTAACCTGAAAAACGCCAACACCTTGCTGATCTTCATCAACCAGATCCGTATGAAAATCGGTGT
GATGTTCGGTAACCCGGAAACCACCACCGGTGGTAACGCCCTGAAATTCTACGCCTCTGTGCGTCTGG
ATATCCGCCGCATCGGCGCTATCAAAGAAGGCGACGTGGTGATCGGCAGTGAAACGCGCGTGAAAGT
TGTGAAGAACAAAATCGCTGCGCCTTTCAAACAGGCTGAATTCCAGATCCTATACGGCGAAGGCATC
AACATTAACGGCGAGCTGATCGATTTGGGCGTTAAGCACAAACTGGTCGAAAAAGCCGGTGCATGGT
ACAGCTACAACGGCGAGAAGATTGGTCAGGGTAAATCTAACTCCTGCAACTATCTGAAAGAAAACCC
GAAAATCGCTGCTGAACTGGATAAAAAACTGCGTGATATGTTGTTGAGTGGCACTGGTGAACTGGCC
GCTGCAACCACAGCAGAACTTGCAGACGACGATATGGAAACCAGCGAAGAGTTTTAA 135
DP71 RNA polymerase sigma factor RpoD
GGTAAGGAGCAAGGCTATCTGACCTTTGCTGAGGTCAATGACCATCTGCCGGAAGATATCGTCGA
CTCCGACCAGATCGAAGACATCATCCAGATGATTAACGACATGGGCATCCAGGTTCTTGAAGAAGCG
CCGGACGCCGATGATTTGATGCTGGCCGAAAACCGCCCTGATACCGATGAAGATGCTGCAGAAGCAG
CGGCTCAGGTGCTTTCCAGCGTTGAATCTGAAATTGGCCGTACCACCGACCCTGTGCGTATGTATATG
CGCGAAATGGGTACCGTTGAGCTCCTGACCCGTGAAGGCGAAATCGACATCGCCAAACGTATCGAAG
ACGGTATCAATCAGGTCCAGTGCTCCGTTGCTGAATATCCTGAAGCTATCACCTATTTGTTAGAGCAA
TATGACCGTGTTGAAGCAGGCGAAGCACGTCTGTCTGATTTGATCACCGGTTTTGTTGATCCGAACGC
CGAAGAAGAAATCGCGCCGACTGCGACTCACGTGGGTTCTGAACTGACCACTGAAGAGCAAAATGAT
ACCGACGACGATGAAGAAGACGACGACGATGCTGAAGACGACAACAGCATCGACCCGGAACTGGCG
CGTCAGAAGTTCACCGATCTGCGTGAGCAACATGAAGCGACCCGTGCCGTCATCAAGAAAAATGGCC
GTAGCCACAAAAGCGCCGCAGAAGAAATTCTGAAGCTGTCCGATGTGTTTAAACAGTTCCGTCTGGT
ACCAAAACAGTTCGATTTCCTGGTGAACAGCATGCGCTCCATGATGGATCGCGTCCGTACTCAGGAAC
GTCTGATCATGAAAGTGTGCGTTGAACAGTGCAAAATGCCGAAGAAAAACTTCGTCAATCTGTTCGC
CGGTAACGAAACCAGCAGTACCTGGTTTGATGCTGCTCTGGCAATGGGTAAACCATGGTCTGAGAAG
CTGAAAGAAGTGACCGAAGACGTGCAGCGCGGCCTGATGAAACTGCGCCAAATCGAAGAAGAAACT
GGCCTGACTATCGAACAGGTAAAAGACATTAACCGTCGCATGTCGATCGGCGAAGCGAAAGCACGCC
GCGCGAAGAAAGAGATGGTTGAAGCGAACTTACGTCTGGTTATCTCTATCGCGAAGAAATACACCAA
CCGTGGCTTGCAGTTCCTTGACCTGATTCAGGAAGGTAACATCGGCCTGATGAAAGCCGTTGATAAGT
TTGAATATCGCCGTGGTTATAAGTTCTCTACTTATGCGACCTGGTGGATCCGTCAGGCTATCACCCGCT
CCATCGCCGACCAGGCACGTACCATCCGTATTCCGGTGCATATGATTGAGACCATCAACAAACTCAAC
CGTATTTCGCGCCAGATGTTGCAGGAGATGGGCCGTGAGCCGACGCCGGAAGAGCTGGCTGAACGCA
TGCTGATGCCGGAAGACAAGATCCGTAAAGTGCTGAAAATTGCTAAAGAGCCAATCTCCATGGAAAC -continued

| SEQUENCE LISTING<br>Seq ID No.<br>Description<br>Sequence |
|---|
| GCCAATCGGCGACGATGAAGATTCGCATCTGGGTGATTTCATCGAGGATACTACCCTCGAGCTGCCGC<br>TGGATTCTGCGACCTCTGAAAGCCTGCGTTCTGCAACGCACGACGTTCTGGCTGGCCTGACCGCACGT<br>GAAGCGAAAGTTCTGCGTATGCGTTTCGGTATCGATATGAACACTGACCACACTCTGGAAGAAGTGG<br>GCAAACAGTTCGACGTAACCCGTGAACGTATCCGTCAGATCGAAGCCAAAGCGTTGCGTAAACTACG<br>CCACCCAAGCCGCTCCGAAGTGCTGCGCAGCTTCCTCGACGACTAG |
| 136<br>DP71 DNA-directed RNA polymerase subunit beta<br>ATGGACCAGAACAACCCGTTGTCTGAGATCACGCACAAACGTCGTATCTCTGCACTGGGCCCGGG<br>CGGTTTGACCCGTGAACGTGCTGGCTTTGAAGTTCGAGACGTACACCCGACGCACTACGGTCGCGTAT<br>GTCCAATCGAAACGCCAGAAGGTCCAAACATCGGTCTGATCAACTCATTATCTGTCTATGCACAGACA<br>AATGAGTATGGTTTCCTGGAAACCCCTTACCGCCGTGTGCGTGAAGGTATGGTTACCGATGAAATTAA<br>CTACCTGTCTGCCATCGAAGAAGGCAACTTTGTTATCGCTCAGGCGAACTCCAACCTGGATGACGAAG<br>GCCACTTCCTGGAAGATTTAGTCACTTGTCGTAGCAAAGGCGAATCAAGCCTGTTCAGCCGCGACCAG<br>GTTGACTACATGGACGTTTCTACCCAGCAGATCGTATCCGTTGGTGCTTCACTGATTCCATTCCTGGAA<br>CACGATGACGCCAACCGTGCATTGATGGGTGCGAACATGCAACGTCAGGCAGTTCCTACTCTGCGTG<br>CTGATAAGCCGCTGGTAGGTACTGGTATGGAACGTGCTGTTGCGGTTGACTCCGGTGTTACTGCCGTT<br>GCCAAACGTGGTGGTACTGTTCAGTACGTAGATGCATCCCGTATCGTTATTCGTGTTAACGAAGAAGA<br>GATGAATCCAGGCGAAGCAGGTATCGACATTTATAACCTGACTAAGTACACCCGTTCTAACCAGAAC<br>ACCTGCATCAACCAGATGCCGTGTGTGAATCTGGGCGAGCCAATCGAGCGCGGCGACGTGCTGGCAG<br>ATGGTCCGTCAACAGATCTGGGCGAACTGGCACTGGGTCAGAACATGCGTGTCGCGTTCATGCCTTGG<br>AACGGTTACAACTTCGAAGACTCCATCTTGGTCTCCGAACGTGTTGTGCAGGAAGATCGCTTCACGAC<br>CATCCATATCCAGGAACTGGCATGTGTGTCCCGTGACACAAAGTTAGGGCCTGAAGAGATCACTGCT<br>GATATCCCTAACGTGGGTGAAGCTGCGCTCTCCAAACTGGATGAGTCCGGTATTGTGTATATCGGTGC<br>TGAAGTGACCGGTGGTGACATTCTGGTCGGTAAAGTTACGCCTAAAGGCGAAACCCAGCTGACTCCA<br>GAAGAGAAACTGCTGCGTGCGATCTTCGGTGAGAAAGCGTCTGACGTTAAAGATTCTTCTCTGCGTGT<br>ACCAAACGGCGTTTCCGGTACGATTATTGACGTGCAAGTCTTTACCCGCGATGGCGTGGAAAAAGAT<br>AAGCGTGCGTTAGAAATCGAAGAAATGCAGCTGAAACAGGCTAAGAAAGACCTGACTGAAGAGCTG<br>CAAATTCTGGAAGCTGGTCTGTTTGCACGTATCCAGTCCGCGCTGGTTGCTGGCGGTGTTGAAGCCGA<br>TAAGCTGGGCAAATTGCCACGCGATCGTTGGCTTGAACTGTCACTGACTGACGAAGACAAACAGAAT<br>CAGTTGGAACAGCTTGCTGAACAGTACGACGAACTGAAATCCGAGTTTGAGAAAAAACTCGAAGCTA<br>AACGTCGTAAAATCACTCAGGGCGATGACCTAGCACCAGGTGTGCTGAAAATCGTTAAAGTGTACCT<br>GGCCGTTAAACGTCAGATCCAACCTGGTGACAAAATGGCAGGCCGCCACGGTAACAAAGGTGTTATC<br>TCCAAGATCAACCCGATCGAAGATATGCCTTACGATGAAAACGGGACTCCTGTTGACATCGTACTGA<br>ACCCGCTGGGCGTTCCATCACGTATGAACATTGGTCAGATTTTAGAAACCCACCTGGGTATGGCCGCG<br>AAAGGTATTGGTGAAAAAATCAATGCCATGCTTAAGAAACATGAAGAAGTTTCTAAGCTGCGCGAGT<br>TCATCCAGCGTGCCTATGATCTGGGCGACGACGTACGTCAGAAAGTTGATCTGACCACCTTCACCGAT<br>GATGAAGTATTGCGTTTGGCTGAAAACCTGAAAAAGGGTATGCCAATTGCAACACCAGTCTTCGACG<br>GTGCGAAAGAGACAGAGATCAAGCAACTGCTTGAAATGGGCGGCGTCCCAACCTCTGGCCAGATCAC<br>ACTGTTTGACGGCCGTACCGGCGAGCAATTCGAGCGCCAGGTTACCGTCGGCTACATGTACATGCTGA<br>AACTGAACCACCTGGTTGACGATAAGATGCATGCGCGTTCTACCGGTTCTTACAGCCTTGTTACTCAG<br>CAGCCGCTGGGTGGTAAAGCTCAGTTCGGTGGTCAGCGCTTCGGTGAGATGGAAGTGTGGGCACTGG<br>AAGCATACGGTGCCGCTTATACCCTGCAGGAAATGCTGACTGTTAAGTCCGATGACGTGAACGGCCG<br>TACTAAGATGTATAAAAACATCGTAGATGGCGATCACCGGATGGAACCAGGCATGCCGGAATCATTC<br>AACGTACTGTTGAAAGAAATCCGCTCTCTGGGTATCAACATCGAGCTGGAAGACGAGTAA |

The invention claimed is:

1. A pharmaceutical composition comprising a mixture of a plurality of purified, viable microbes, wherein at least two microbes have at least 99 percent identity to any of Seq ID Nos. 1, 2, 3, 5, 9, 22, or 53 at the 16S rRNA or fungal ITS locus, and wherein the pharmaceutical composition is formulated in an oral dosage form selected from the group consisting of powder, tablet, capsule, caplet, granules, pellets, emulsion, and syrup.

2. The pharmaceutical composition of claim 1, wherein the at least two microbes have 100 percent identity to one of Seq ID Nos. 1, 2, 3, 5, 9, 22, or 53 at the 16S rRNA or fungal ITS locus.

3. The pharmaceutical composition of claim 1, wherein a first microbe of the at least two microbes has at least 99 percent identity at the 16S rRNA or fungal ITS locus to Seq ID No. 1 and a second microbe of the at least two microbes has at least 99 percent identity at the 16S rRNA or fungal ITS locus to a Seq ID No. 22.

4. The pharmaceutical composition of claim 1, wherein a first microbe of the at least two microbes has at least 99 percent identity at the 16S rRNA or fungal ITS locus to Seq ID No. 2 and a second microbe of the at least two microbes has at least 99 percent identity at the 16S rRNA or fungal ITS locus to a Seq ID No. selected from the group consisting of Seq ID Nos. 3 and 9.

5. The pharmaceutical composition of claim 1, wherein a first microbe of the at least two microbes has at least 99 percent identity at the 16S rRNA or fungal ITS locus to Seq ID No. 9 and a second microbe of the at least two microbes has at least 99 percent identity at the 16S rRNA or fungal ITS locus to a Seq ID No. selected from the group consisting of Seq ID Nos. 2, 3, 5, and 53.

6. The pharmaceutical composition of claim 1, further comprising an anti-diabetic drug.

7. The pharmaceutical composition of claim 1, further comprising a prebiotic.

8. The pharmaceutical composition of claim 7, wherein the prebiotic is oligofructose or fructooligosaccharide.

9. A pharmaceutical composition comprising a defined microbial mixture comprising purified, viable microbial populations, which when combined with an anti-diabetic therapy, improves at least one selected from the group consisting of fasting blood glucose, glucose tolerance, insulin sensitivity, hemoglobin A1c (HbA1c) levels, and homeostatic model assessment of insulin resistance (HOMA-IR) levels compared to levels found in a subject treated with said anti-diabetic therapy alone, wherein at least two of the microbes in said microbial populations have at least 99 percent identity at the 16S rRNA locus or the ITS locus to any of Seq ID Nos. 1, 2, 3, 5, 9, 22, or 53, and wherein the pharmaceutical composition is formulated in an oral dosage form selected from the group consisting of powder, tablet, capsule, caplet, granules, pellets, emulsion and syrup.

10. The pharmaceutical composition of claim 9, wherein at least three of the microbes have at least 99 percent identity at the 16S rRNA locus or the ITS locus to any of Seq ID Nos. 1, 2, 3, 5, 9, 22, or 53.

11. The pharmaceutical composition of claim 9, wherein at least one of the microbes has 100 percent identity at the 16S rRNA locus or the ITS locus to any of Seq ID Nos. 1, 2, 3, 5, 9, 22, or 53.

12. The pharmaceutical composition of claim 9, further comprising a prebiotic.

13. The pharmaceutical composition of claim 12, wherein the prebiotic is oligofructose or fructooligosaccharide.

14. A method of treating type-2 diabetes in a subject, comprising orally administering to the subject a therapeutically effective amount of the pharmaceutical composition as set forth in claim 9.

15. The method of claim 14, wherein at least two of the microbes have 100 percent identity to any of SEQ ID Nos. 1, 2, 3, 5, 9, 22, or 53, at the 16S rRNA or fungal ITS locus.

16. The method of claim 14, wherein the pharmaceutical composition is administered in combination with an anti-diabetic therapy.

17. The method of claim 14, wherein the pharmaceutical composition further comprises a prebiotic.

18. The method of claim 17, wherein the prebiotic is oligofructose or fructooligosaccharide.

19. A pharmaceutical composition comprising a synthetic consortium of purified, viable microbes comprising a mixture of at least two microbial entities, selected from bacteria and fungi, whose genomes are defined, such that it is possible to predict production of short chain fatty acids by unconstrained genome-wide metabolic models, based upon genes contained in the genomes of said microbial entities, and wherein said models predict a synergistic interaction and/or higher short chain fatty acid production when said microbial entities are combined and/or grown on prebiotic polysaccharides, as compared to short chain fatty acid production of the microbial entities grown in isolation and/or grown in rich medium, wherein the predictions of the genome-wide metabolic model are tested and validated by experimentally quantifying the production of short chain fatty acids of the at least two microbial entities in isolation and/or grown in rich medium and grown together and/or grown on prebiotic polysaccharides, and wherein the pharmaceutical composition is formulated to be orally administered to an animal in an amount effective to improve at least one of fasting blood glucose, glucose tolerance, insulin sensitivity, hemoglobin A1c (HbA1c) levels, and/or homeostatic model assessment of insulin resistance (HOMA-IR) levels compared to levels found in a subject treated with an anti-diabetic therapy alone and wherein the at least two microbial entities have at least 99 percent identity at the 16S rRNA locus or the ITS locus to any of Seq ID Nos. 1, 2, 3, 5, 9, 22, or 53, and wherein the pharmaceutical composition is formulated in an oral dosage form selected from the group consisting of powder, tablet, capsule, caplet, granules, pellets, emulsion and syrup.

20. The pharmaceutical composition of claim 1, wherein the plurality of purified, viable microbes synergize to produce an increased amount of short chain fatty acid (SCFA) when grown together relative to the amount of SCFA produced by each distinct microbe grown in isolation.

21. The pharmaceutical composition of claim 20, wherein the SCFA is selected from the group consisting of: acetate, propionate, butyrate, and isomers thereof.

22. A pharmaceutical composition comprising a mixture of a plurality of purified, viable microbes, wherein at least two microbes have at least 99 percent identity at the 16S rRNA locus or the ITS locus to any of Seq ID No. 1, 2, 3, 5, 9, 22 or 53, wherein the pharmaceutical composition is formulated in an oral dosage form selected from the group consisting of powder, tablet, capsule, caplet, granules, pellets, emulsion and syrup, and wherein the plurality of purified, viable microbes synergize to produce an increased amount of short chain fatty acid (SCFA) when grown together relative to the amount of SCFA produced by each distinct microbe grown in isolation.

23. The pharmaceutical composition of claim 22, wherein the SCFA is selected from the group consisting of: acetate, propionate, butyrate, and isomers thereof.

24. The pharmaceutical composition of claim 22, wherein a first microbe of the at least two microbes has at least 99 percent identity at the 16S rRNA or fungal ITS locus to Seq ID No. 1 and a second microbe of the at least two microbes has at least 99 percent identity at the 16S rRNA or fungal ITS locus to a Seq ID No. 22.

25. The pharmaceutical composition of claim 22, wherein a first microbe of the at least two microbes has at least 99 percent identity at the 16S rRNA or fungal ITS locus to Seq ID No. 2 and a second microbe of the at least two microbes has at least 99 percent identity at the 16S rRNA or fungal ITS locus to a Seq ID No. selected from the group consisting of Seq ID Nos. 3 and 9.

26. The pharmaceutical composition of claim 22, wherein a first microbe of the at least two microbes has at least 99 percent identity at the 16S rRNA or fungal ITS locus to Seq ID No. 9 and a second microbe of the at least two microbes has at least 99 percent identity at the 16S rRNA or fungal ITS locus to a Seq ID No. selected from the group consisting of Seq ID Nos. 2, 3, 5, and 53.

27. The pharmaceutical composition of claim 22, wherein at least two microbes have 100 percent identity to one of Seq ID Nos. 1, 2, 3, 5, 9, 22, or 53 at the 16S rRNA or fungal ITS locus.

28. The pharmaceutical composition of claim 22, further comprising a prebiotic.

* * * * *